(12) United States Patent
Li et al.

(10) Patent No.: US 10,927,125 B2
(45) Date of Patent: Feb. 23, 2021

(54) SUBSTITUTED CINNOLINES AS INHIBITORS OF KRAS G12C

(71) Applicant: Araxes Pharma LLC, San Diego, CA (US)

(72) Inventors: Liansheng Li, San Diego, CA (US); Jun Feng, San Diego, CA (US); Tao Wu, Carlsbad, CA (US); Pingda Ren, San Diego, CA (US); Yi Liu, San Diego, CA (US); Yuan Liu, San Diego, CA (US); Yun Oliver Long, San Diego, CA (US)

(73) Assignee: ARAXES PHARMA LLC, San Diego, CA (US)

( * ) Notice: Subject to any disclaimer, the term of this patent is extended or adjusted under 35 U.S.C. 154(b) by 0 days.

(21) Appl. No.: 16/449,967

(22) Filed: Jun. 24, 2019

(65) Prior Publication Data

US 2020/0102321 A1 Apr. 2, 2020

Related U.S. Application Data

(62) Division of application No. 15/805,716, filed on Nov. 7, 2017, now Pat. No. 10,370,386, which is a division of application No. 14/511,425, filed on Oct. 10, 2014, now Pat. No. 9,840,516.

(60) Provisional application No. 62/052,366, filed on Sep. 18, 2014, provisional application No. 62/034,619, filed on Aug. 7, 2014, provisional application No. 61/889,460, filed on Oct. 10, 2013.

(51) Int. Cl.

| | |
|---|---|
| *A61K 31/502* | (2006.01) |
| *C07D 237/28* | (2006.01) |
| *C07D 495/04* | (2006.01) |
| *C07D 239/94* | (2006.01) |
| *C07D 401/12* | (2006.01) |
| *C07D 217/22* | (2006.01) |
| *C07D 215/46* | (2006.01) |
| *C07D 215/54* | (2006.01) |
| *C07D 239/84* | (2006.01) |
| *C07D 487/04* | (2006.01) |
| *C07D 239/95* | (2006.01) |
| *C07D 403/04* | (2006.01) |
| *C07D 241/44* | (2006.01) |
| *C07D 401/04* | (2006.01) |
| *C07D 409/04* | (2006.01) |

(52) U.S. Cl.
CPC ........ *C07D 495/04* (2013.01); *C07D 215/46* (2013.01); *C07D 215/54* (2013.01); *C07D 217/22* (2013.01); *C07D 239/84* (2013.01); *C07D 239/94* (2013.01); *C07D 239/95* (2013.01); *C07D 241/44* (2013.01); *C07D 401/04* (2013.01); *C07D 401/12* (2013.01); *C07D 403/04* (2013.01); *C07D 409/04* (2013.01); *C07D 487/04* (2013.01)

(58) Field of Classification Search
CPC ............................ A61K 31/502; C07D 237/28
USPC .......................................... 514/248; 544/235
See application file for complete search history.

(56) References Cited

U.S. PATENT DOCUMENTS

| | | |
|---|---|---|
| 3,702,849 A | 11/1972 | Cronin et al. |
| 3,752,660 A | 8/1973 | Little |
| 4,439,606 A | 3/1984 | Du et al. |
| 4,649,219 A | 3/1987 | Itoh et al. |
| 4,656,181 A | 4/1987 | Sunkel et al. |

(Continued)

FOREIGN PATENT DOCUMENTS

| | | |
|---|---|---|
| CN | 104 418 860 B | 9/2016 |
| EP | 0 094 498 A2 | 11/1983 |

(Continued)

OTHER PUBLICATIONS

Adibekian et al., "Optimization and characterization of a triazole urea dual inhibitor for lysophospholipase 1 (LYPLA1) and lysophospholipase 2 (LYPLA2)," *Probe Reports from the NIH Molecular Libraries Program*, 2011, 42 pages.

Al-Muhammed et al., "In-vivo studies on dexamethasone sodium phosphate liposomes," *J. Microencapsulation* 13(3):293-306, 1996.

Appel et al., "Supramolecular Cross-Linked Networks via Host-Guest Complexation with Cucurbit[8]uril," *J. Am. Chem. Soc.* 132(40):14251-14260, Jul. 2010.

(Continued)

*Primary Examiner* — Douglas M Willis
(74) *Attorney, Agent, or Firm* — Seed Intellectual Property Law Group LLP

(57) ABSTRACT

Compounds having activity as inhibitors of G12C mutant KRAS protein are provided. The compounds have the following structure (I):

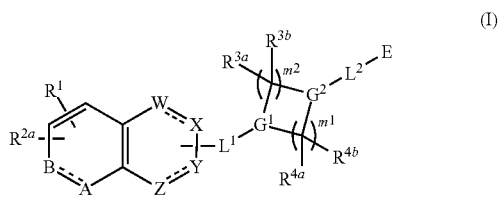

or a pharmaceutically acceptable salt, tautomer, prodrug or stereoisomer thereof, wherein $R^1$, $R^{2a}$, $R^{3a}$, $R^{3b}$, $R^{4a}$, $R^{4b}$, $G^1$, $G^2$, $L^1$, $L^2$, $m^1$, $m^2$, A, B, W, X, Y, Z and E are as defined herein. Methods associated with preparation and use of such compounds, pharmaceutical compositions comprising such compounds and methods to modulate the activity of G12C mutant KRAS protein for treatment of disorders, such as cancer, are also provided.

29 Claims, 3 Drawing Sheets

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Köster |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,002,008 A | 12/1999 | Wissner et al. |
| 6,017,696 A | 1/2000 | Heller |
| 6,043,031 A | 3/2000 | Köster et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,511,993 B1 | 1/2003 | Dack et al. |
| 6,689,779 B2 | 2/2004 | Lee et al. |
| 6,903,118 B1 | 6/2005 | Biedermann et al. |
| 7,074,801 B1 | 7/2006 | Yoshida et al. |
| 7,595,397 B2 | 9/2009 | Zindell et al. |
| 7,879,863 B2 | 2/2011 | Tokumasu et al. |
| 8,399,454 B2 | 3/2013 | Bian et al. |
| 8,426,401 B2 | 4/2013 | Bian et al. |
| 8,466,288 B2 | 6/2013 | Aronov et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,126,952 B2 | 9/2015 | Mederski et al. |
| 9,227,978 B2 | 1/2016 | Ren et al. |
| 9,273,057 B2 | 3/2016 | Purandare et al. |
| 9,376,559 B2 | 6/2016 | Holtcamp et al. |
| 9,745,319 B2 | 8/2017 | Ren et al. |
| 9,810,690 B2 | 11/2017 | Patricelli et al. |
| 9,840,516 B2 | 12/2017 | Li et al. |
| 9,862,701 B2 | 1/2018 | Li et al. |
| 9,926,267 B2 | 3/2018 | Ren et al. |
| 9,938,292 B2 | 4/2018 | Wu et al. |
| 9,988,357 B2 | 6/2018 | Mani et al. |
| 10,023,588 B2 | 7/2018 | Ostrem et al. |
| 10,111,874 B2 | 10/2018 | Janes et al. |
| 10,144,724 B2 | 12/2018 | Li et al. |
| 10,246,424 B2 | 4/2019 | Li et al. |
| 10,273,207 B2 | 4/2019 | Ren et al. |
| 10,280,172 B2 | 5/2019 | Li et al. |
| 10,351,550 B2 | 7/2019 | Li et al. |
| 10,370,386 B2 | 8/2019 | Li et al. |
| 10,377,743 B2 | 8/2019 | Li et al. |
| 10,414,757 B2 | 9/2019 | Li et al. |
| 10,428,064 B2 | 10/2019 | Li et al. |
| 10,556,906 B2 | 2/2020 | Kuramoto et al. |
| 10,646,488 B2 | 5/2020 | Liu et al. |
| 10,647,703 B2 | 5/2020 | Li et al. |
| 10,689,356 B2 | 6/2020 | Li et al. |
| 10,723,738 B2 | 7/2020 | Li et al. |
| 10,730,867 B2 | 8/2020 | Li et al. |
| 10,736,897 B2 | 8/2020 | Li et al. |
| 10,745,385 B2 | 8/2020 | Li et al. |
| 2002/0169300 A1 | 11/2002 | Waterman et al. |
| 2003/0022344 A1 | 1/2003 | Williams et al. |
| 2003/0078277 A1 | 4/2003 | Hibi et al. |
| 2003/0166620 A1 | 9/2003 | Lee et al. |
| 2003/0171400 A1 | 9/2003 | Pikul et al. |
| 2004/0106634 A1 | 6/2004 | Satoh et al. |
| 2005/0012070 A1 | 1/2005 | Inoue et al. |
| 2005/0119266 A1 | 6/2005 | Shi et al. |
| 2005/0227997 A1 | 10/2005 | Noe et al. |
| 2006/0167044 A1 | 7/2006 | Arnaiz et al. |
| 2007/0249648 A1 | 10/2007 | Bladh et al. |
| 2008/0004285 A1 | 1/2008 | De Jonghje et al. |
| 2008/0004348 A1 | 1/2008 | Yous et al. |
| 2008/0039450 A1 | 2/2008 | Jensen et al. |
| 2008/0070892 A1 | 3/2008 | Harris et al. |
| 2009/0036430 A1 | 2/2009 | De Jonghje et al. |
| 2009/0054402 A1 | 2/2009 | Wang et al. |
| 2009/0124636 A1 | 5/2009 | Barber et al. |
| 2009/0298075 A1 | 12/2009 | Travers et al. |
| 2010/0331300 A1 | 12/2010 | Bian et al. |
| 2011/0046370 A1 | 2/2011 | Sim et al. |
| 2011/0217309 A1 | 9/2011 | Buck et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2012/0083476 A1 | 4/2012 | Breitenbucher et al. |
| 2013/0012489 A1 | 1/2013 | Mederski |
| 2013/0029964 A1 | 1/2013 | Aoki et al. |
| 2013/0203768 A1 | 8/2013 | Berger et al. |
| 2013/0274252 A1 | 10/2013 | Pandey et al. |
| 2013/0302407 A1 | 11/2013 | Rao et al. |
| 2014/0315886 A1 | 10/2014 | Suzuki et al. |
| 2015/0087628 A1 | 3/2015 | Ostrem et al. |
| 2016/0368930 A1 | 12/2016 | Ostrem et al. |
| 2017/0131278 A1 | 5/2017 | Patricelli et al. |
| 2017/0247376 A1 | 8/2017 | Li et al. |
| 2018/0015087 A1 | 1/2018 | Liu et al. |
| 2018/0141927 A1 | 5/2018 | Li et al. |
| 2018/0246102 A1 | 8/2018 | Patricelli et al. |
| 2018/0273515 A1 | 9/2018 | Li et al. |
| 2018/0273523 A1 | 9/2018 | Li et al. |
| 2018/0282307 A1 | 10/2018 | Li et al. |
| 2018/0282308 A1 | 10/2018 | Li et al. |
| 2018/0319775 A1 | 11/2018 | Li et al. |
| 2019/0055211 A1 | 2/2019 | Li et al. |
| 2019/0092767 A1 | 3/2019 | Li et al. |
| 2019/0262342 A1 | 8/2019 | Janes et al. |
| 2019/0284144 A1 | 9/2019 | Li et al. |
| 2019/0343838 A1 | 11/2019 | Allen et al. |
| 2019/0345158 A1 | 11/2019 | Li et al. |
| 2019/0367489 A1 | 12/2019 | Li et al. |
| 2019/0375743 A1 | 12/2019 | Hudson et al. |
| 2019/0382377 A1 | 12/2019 | Li et al. |
| 2019/0389796 A1 | 12/2019 | Ren et al. |
| 2019/0389851 A1 | 12/2019 | Li et al. |
| 2020/0010454 A1 | 1/2020 | Li et al. |
| 2020/0115363 A1 | 4/2020 | Li et al. |
| 2020/0181123 A1 | 6/2020 | Li et al. |

FOREIGN PATENT DOCUMENTS

| | | |
|---|---|---|
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |
| EP | 1 004 578 A1 | 5/2000 |
| EP | 0 655 442 B1 | 5/2001 |
| EP | 1 348 434 A1 | 10/2003 |
| EP | 1 736 465 A1 | 12/2006 |
| EP | 2 133 334 A1 | 12/2009 |
| EP | 2 270 002 A1 | 1/2011 |
| EP | 2 889 291 A1 | 7/2015 |
| GB | 939516 A | 10/1963 |
| GB | 9912961.1 | 6/1999 |
| JP | 2002-371078 A | 12/2002 |
| JP | 2007-016011 A | 1/2007 |
| JP | 2013-107855 A | 6/2013 |
| WO | 90/05719 A1 | 5/1990 |
| WO | 91/19735 A1 | 12/1991 |
| WO | 92/00091 A1 | 1/1992 |
| WO | 93/20242 A1 | 10/1993 |

(56) References Cited

FOREIGN PATENT DOCUMENTS

| | | |
|---|---|---|
| WO | 96/05309 A2 | 2/1996 |
| WO | 96/13262 A1 | 5/1996 |
| WO | 96/27583 A1 | 9/1996 |
| WO | 96/33172 A1 | 10/1996 |
| WO | 97/00271 A1 | 1/1997 |
| WO | 97/30992 A1 | 8/1997 |
| WO | 98/03516 A1 | 1/1998 |
| WO | 98/07697 A1 | 2/1998 |
| WO | 98/30566 A1 | 8/1998 |
| WO | 98/33496 A1 | 8/1998 |
| WO | 98/33768 A1 | 8/1998 |
| WO | 98/34915 A1 | 8/1998 |
| WO | 98/35951 A2 | 8/1998 |
| WO | 98/43960 A1 | 10/1998 |
| WO | 98/57948 A1 | 12/1998 |
| WO | 99/07675 A1 | 2/1999 |
| WO | 99/29667 A1 | 2/1999 |
| WO | 99/31063 A1 | 6/1999 |
| WO | 99/52910 A1 | 6/1999 |
| WO | 99/52889 A1 | 10/1999 |
| WO | 99/67641 A1 | 12/1999 |
| WO | 00/39587 A1 | 7/2000 |
| WO | 00/74681 A1 | 12/2000 |
| WO | 01/68186 A2 | 9/2001 |
| WO | 02/04420 A1 | 1/2002 |
| WO | 02/080928 A1 | 10/2002 |
| WO | 03/004480 A2 | 1/2003 |
| WO | 03/053958 A1 | 7/2003 |
| WO | 2004/033427 A1 | 4/2004 |
| WO | 2004/074283 A1 | 9/2004 |
| WO | 2004/080976 A1 | 9/2004 |
| WO | 2005/070891 A2 | 8/2005 |
| WO | 2005/082892 A2 | 9/2005 |
| WO | 2005/092894 A1 | 10/2005 |
| WO | 2006/066948 A1 | 6/2006 |
| WO | 2006/095014 A1 | 9/2006 |
| WO | 2006/097261 A1 | 9/2006 |
| WO | 2006/135993 A1 | 12/2006 |
| WO | 2007/047146 A2 | 4/2007 |
| WO | 2007/095588 A1 | 8/2007 |
| WO | 2007/113226 A1 | 10/2007 |
| WO | 2007/144394 A2 | 12/2007 |
| WO | 2008/009078 A2 | 1/2008 |
| WO | 2008/028691 A1 | 3/2008 |
| WO | 2008/112440 A1 | 9/2008 |
| WO | 2010/027746 A2 | 3/2010 |
| WO | 2011/002816 A1 | 1/2011 |
| WO | 2011/031896 A2 | 3/2011 |
| WO | 2011/082285 A1 | 7/2011 |
| WO | 2011/093524 A1 | 8/2011 |
| WO | 2011/148922 A1 | 12/2011 |
| WO | 2011/153553 A2 | 12/2011 |
| WO | 2012/016082 A1 | 2/2012 |
| WO | 2012/041872 A1 | 4/2012 |
| WO | 2012/054716 A1 | 4/2012 |
| WO | 2012/061557 A2 | 5/2012 |
| WO | 2012/174489 A2 | 12/2012 |
| WO | 2013/096151 A1 | 6/2013 |
| WO | 2013/096455 A1 | 6/2013 |
| WO | 2013/140148 A1 | 9/2013 |
| WO | 2013/155223 A1 | 10/2013 |
| WO | 2013/184757 A1 | 12/2013 |
| WO | 2014/011900 A2 | 1/2014 |
| WO | 2014/071109 A1 | 5/2014 |
| WO | 2014/143659 A1 | 9/2014 |
| WO | 2014/152588 A1 | 9/2014 |
| WO | 2014/159837 A1 | 10/2014 |
| WO | 2014/201435 A1 | 12/2014 |
| WO | 2015/003166 A1 | 1/2015 |
| WO | 2015/017502 A1 | 2/2015 |
| WO | 2015/054572 A1 | 4/2015 |
| WO | 2015/108992 A1 | 7/2015 |
| WO | 2015/132799 A2 | 9/2015 |
| WO | 2015/143148 A1 | 9/2015 |
| WO | 2015/184349 A2 | 12/2015 |
| WO | 2020/028706 A1 | 2/2020 |
| WO | 2020/086739 A1 | 4/2020 |
| WO | 2020/113071 A1 | 6/2020 |

OTHER PUBLICATIONS

Arkin et al., "Binding of small molecules to an adaptive protein-protein interface," *PNAS* 100(4):1603-1608, Feb. 2003.

Bachovchin et al., "Identification of selective inhibitors of uncharacterized enzymes by high-throughput screening with fluorescent activity-based probes," *Nat. Biotechnol* 27(7):387-394, 2009.

Banker et al. (eds.),*Modern Pharmaceutics*, New York, Marcel Dekker, Inc., 1996, pp. 451 and 596. (3 pages).

Barbe et al., "Highly Chemoselective Metal-Free Reduction of Tertiary Amides," *J. Am. Chem. Soc.* 130:18-19, 2008.

Bégué et al., "Ions α-Cetocarbenium. Influence De La Structure Sur L'Evolution Des Ions α-Cetocyclohexylcarbenium," *Tetrahedron* 31(20):2505-2511, 1975. (English Abstract Only).

Berge et al., "Pharmaceutical Salts," *Journal of Pharmaceutical Sciences* 66(1):1-19, 1977.

Cho et al., "An Unnatural Biopolymer," *Science* 261:1303-1305, Sep. 1993.

Chonn et al., "Recent advances in liposomal drug-delivery systems," *Current Opinion in Biotechnology* 6:698-708, 1995.

Choong et al., "Identification of Potent and Selective Small-Molecule Inhibitors of Caspase-3 through the Use of Extended Tethering and Structure-Based Drug Design,"*J. Med. Chem.* 45:5005-5022, 2002.

Cox et al., "Drugging the undruggable RAS: Mission Possible?," *Nat. Rev. Drug Discov.* 13(11):828-851, 2014.

DeWitt et al., ""Diversomers": An approach to nonpeptide, nonoligomeric chemical diversity," *Proc. Natl. Acad. Sci.* 90:6909-6913, Aug. 1993.

Duncan et al., "N-Dialkylaminoalkybiphenylamines as Antimalarial and Atischistosomal Agents," *Journal of Medicinal Chemistry* 12:25-29, Jan. 1969.

Erlanson et al., "Site-directed ligand discovery," *Proc. Natl Acad. Sci. U.S.A.* 97(17):9367-9372, Aug. 2000.

Forbes et al., "COSMIC 2005," *British Journal of Cancer* 94:318-322, 2006.

Gorfe et al., "Mapping the Nucleotide and Isoform-Dependent Structural and Dynamical Features of Ras Proteins," *Structure* 16:885-896, Jun. 2008.

Hall et al., "The Effect of $Mg^{2+}$ on Guanine Nucleotide Exchange Rate of $p21^{N\text{-}ras}$," *The Journal of Biological Chemistry* 261(24):10963-10965, 1986.

Hall et al., "The structural basis for the transition from Ras-GTP to Ras-GDP," *PNAS* 99(19):12138-12142, Sep. 2002.

Hardy et al., "Discovery of an allosteric site in the caspases," *PNAS* 101(34):12461-12466, Aug. 2004.

Hattori et al., "Neutralizing monoclonal antibody against ras oncogene product p21 which impairs guanine nucleotide exchange," *Mol. Cell. Biol.* 7(5):1999-2002, May 1987.

Ito et al., "Regional Polysterism in the GTP-Bound Form of the Human c-Ha-Ras Protein," *Biochemistry* 36(30):9109-1119, Jul. 1997.

Johnson et al., "The Chemistry of β-Bromopropionyl Isocyanate. I. Synthesis of 1-Aryldihydrouracils," *The Journal of Organic Chemistry* 24(9):1391-1392, Sep. 1959.

Jones et al., "Increased frequency of the k-ras G12C mutation in MYH polyposis colorectal adenomas," *British Journal of Cancer* 90:1591-1593, 2004.

Jordan, "Tamoxifen: A most unlikely pioneering medicine," *Nature Reviews* 2:205-213, Mar. 2003.

Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinal Chemistry* 6(6):673-686, Jun. 1998.

Knochel et al., "Functionalization of heterocyclic compounds using polyfunctional magnesium and zinc reagents," *Beilstein Journal of Organic Chemistry* 7:1261-1277, 2011.

(56) References Cited

OTHER PUBLICATIONS

Kraulis et al., "Solution Structure and Dynamics of Ras p21-GDP Determined by Heteronuclear Three- and Four-Dimensional NMR Spectroscopy," *Biochemistry* 33:3515-3531, 1994.
Le Picard et al., "Design and Synthesis of Naphthalenic Derivatives as Potential Inhibitors of Hydroxyindole-O-methyltransferase," *Pharm. Pharmacol. Commun.* 5:183-188, 1999.
Lee et al., "Preparation of (S)-3-(pyrimidinyl- or pyridinylphenyl)-5-(acetylaminomethyl)-2-oxazolidinones as antibacterial agents," *Chemical Abstracts* 136(37590), 2001. (8 pages).
Lee et al., "The mutation spectrum revealed by paired genome sequences from a lung cancer patient," *Nature* 465:473-477, May 2010.
Lenzen et al., "[10] Analysis of Intrinsic and CDC25-Stimulated Guanine Nucleotide Exchange of $p21^{ras}$—Nucleotide Complexes by Fluorescence Measurements," *Methods in Enzymology* 255:95-109, 1995.
Liang et al., "Parallel Synthesis and Screening of a Solid Phase Carbohydrate Library," *Science* 274:1520-1522, Nov. 1996.
Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.
Loboda et al., "A gene expression signature of RAS pathway dependence predicts response to PI3K and RAS pathway inhibitors and expands the population of RAS pathway activated tumors," *BMC Medical Genomics* 3(26):1-11, 2010.
Lone et al., "A substrate-free activity-based protein profiling screen for the discovery of selective PREPL inhibitors," *J. Am Chem Soc.* 133(30):11665-11674, Aug. 2011, 20 pages.
Malani et al., "Synthesis, characterization and in vitro screening on bacterial, fungal and malarial strain of piprazinyl cyano biphenyl based compounds," *Bioorganic Chemistry* 51:16-23, 2013.
Margarit et al., "Structural Evidence for Feedback Activation by Ras•GTP of the Ras-Specific Nucleotide Exchange Factor SOS," *Cell* 112:685-695, Mar. 2003.
Mattos et al., "Multiple Binding Modes," in Kubinyi (ed.), *3D QSAR in Drug Design—Theory Methods and Applications*, vol. 2-3, Springer, Boston, Massachusetts, USA, 1998, pp. 243-244. (6 Pages).
Maurer et al., "Small-molecule ligands bind to a distinct pocket in Ras and inhibit SOS-mediated nucleotide exchange activity," *PNAS* 109(14):5299-5304, 2012.
McMahon, "VEGF Receptor Signaling in Tumor Angiogenesis," *The Oncologist* 5(suppl. 1):3-10, 2000.
Milburn et al., "Molecular switch for signal transduction: structural differences between active and inactive forms of protooncogenic ras proteins," *Science* 247(4945):939-945, Feb. 1990.
Minto et al., "Pharmacokinetics and Pharmacodynamics of Nandrolone Esters in Oil Vehicle: Effects of Ester, Injection Site and Injection Volume," *The Journal of Pharmacology and Experimental Therapeutics* 281(1):93-102, 1997.
Mirguet et al., "From ApoA1 upregulation to BET family bromodomain inhibition: Discovery of I-BET151," *Bioorganic & Medicinal Chemistry Letters* 22:2963-2967, 2012.
Noe et al., "Selective Inhibition of Aggrecanase in Osteoarthritis Treatment," U.S. Appl. No. 60/148,464, filed Aug. 12, 1999, 92 pages.
Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 1971.
Ostrem et al., "K-Ras(G12C) inhibitors allosterically control GTP affinity and effector interactions," *Nature* 503(7477):548-551, 2013. (14 pages).
Pacold et al., "Crystal structure and functional analysis of Ras binding to its effector phosphoinositide 3-kinase gamma," *Cell* 103(6):931-943, Dec. 2000.
Palmioli et al., "First experimental identification of Ras-inhibitor binding interface using a water-soluble Ras ligand," *Bioorganic and Medicinal Chemistry Letters* 19:4217-4222, 2009.
Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.
Pardin et al., "Synthesis and evaluation of peptidic irreversible inhibitors of tissue transglutaminase," *Bioorg Med Chem* 14(24):8379-8385, 2006.
Pautsch et al., "Crystal structure of the C3bot-RaIA complex reveals a novel type of action of a bacterial exoenzyme," *The EMBO Journal* 24:3670-3680, 2005.
Pédeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.
Peri et al., "Arabinose-derived bicyclic amino acids: synthesis, conformational analysis and construction of an $α_vβ_3$-selective RGD peptide," *J. Am. Chem. Soc., Perkins Trans* 1(5):638-644, Feb. 2002.
Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.
Peri et al., "Synthesis of bicyclic sugar azido acids and their incorporation in cyclic peptides," *Chem. Commun.* 23:2303-2304, Jan. 2000.
Pinedo et al., "Aggressive combination therapy to cure patients with metastatic cancer," *The Lancet Oncology* 1:72-73, Oct. 2000.
Pinedo et al., "Translational Research: The Role of VEGF in Tumor Angiogenesis," *The Oncologist* 5(suppl. 1):1-2, 2000.
Polinsky, "High-Speed Chemistry Libraries: Assessment of Drug-Likeness," in Wermuth (ed.), *The Practice of Medicinal Chemistry*, 2nd Ed., Academic Press, Cambridge, Massachusetts, USA, 2003, pp. 147-157.
PubChem Compound "(Z)-1-(4-(5-(5-(Trifluoromethyl)-1,2,4-oxadiazol-3-yl)pyridin-2-yl)piperazin-1-yl)but-2-en-1-one" CID: 49702158, Create: Nov. 27, 2010, 4 pages.
PubChem Compound, "AKOS024742141," Nov. 27, 2010, retrieved from http://pubchem.ncbi.nih.gov/compound/49702158#x304 on Nov. 20, 2015, 12 pages.
PubChem Compound, "SCHEMBL6674271," Dec. 1, 2012, retrieved from http://pubchem.ncbi.nim.nih.gov/compound/69861127#x304, CID 69861127, 12 pages.
PubChem Compound, "SCHEMBL6797439," Dec. 1, 2012, retrieved from http://pubchem.ncbi.nim.nih.gov/compound/69898605#x304, CID 69898605, 12 pages.
Rensland et al., "Substrate and Product Structural Requirements for Binding of Nucleotides to H-ras p21: The Mechanism of Discrimination between Guanosine and Adenosine Nucleotides," *Biochemistry* 34(2):593-599, 1995.
Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.
Schubbert et al., "Biochemical and Functional Characterization of Germ Line KRAS Mutations," *Molecular and Cellular Biology* 27(22):7765-7770, Nov. 2007.
Shima et al., "Discovery of small molecule Ras inhibitors that display antitumor activity by interfering with Ras, GTP-effector interaction," *Enzymes* 34(pt. b):1-23, 2013.
Singh et al., "A Gene Expression Signature Associated with "K-Ras Addiction" Reveals Regulators of EMT and Tumor Cell Survival," *Cancer Cell* 15:489-500, Jun. 2009.
Spiegel et al., "Small-molecule modulation of Ras signaling," *Nature Chemical Biology* 10:613-622, Aug. 2014.
Stefanachi et al., "1-, 3-, and 8-substituted-9-deazaxanthines as potent and selective antagonists at the human A2B adenosine receptor," *Bioorg Med Chem* 16(6):2852-2869, 2008.
Streuff et al., "First asymmetric aminohydroxylation of acrylamides," *Tetrahedron: Asymmetry* 16(21):3492-3496, Oct. 2005.
Sun et al., "Discovery of small molecules that bind to K-Ras and inhibit Sos-mediated activation," *Angew Chem Int Ed Engl.* 51(25):6140-6143, 2012.
Sunaga et al., "Knockdown of Oncogenic KRAS in Non-Small Cell Lung Cancers Suppresses Tumor Growth and Sensitizes Tumor Cells to Targeted Therapy," *Molecular Cancer Therapeutics* 10(2):336-346, Feb. 2011.

(56) References Cited

OTHER PUBLICATIONS

Sundberg et al., "The O-Styrylnitrene Route to 2-Substituted Indoles. Pyrolysis of O-Azidostyrenes," *Journal of Organic Chemistry* 37(5):719-724, 1972.

Sydor et al., "Transient Kinetic Studies on the Interaction of Ras and the Ras-Binding Domain of c-Raf-1 Reveal Rapid Equilibration of the Complex," *Biochemistry* 37:14292-14299, 1998.

Taveras et al., "Ras Oncoprotein Inhibitors: The Discovery of Potent, Ras Nucleotide Exchange Inhibitors and the Structural Determination of a Drug-Protein Complex," *Bioorganic and Medicinal Chemistry* 5(1):125-133, 1997.

Terfloth et al., "Electronic Screening: Lead Finding from Database Mining," in Wermuth (ed.), *The Practice of Medicinal Chemistry*, 2nd Ed., Academic Press, Cambridge, Massachusetts, USA, 2003, pp. 131-145.

Tsubaki et al., "Reduction of metastasis, cell invasion, and adhesion in mouse osteosarcoma by YM529/ONO-5920-induced blockade of the Ras/MEK/ERK and Ras/PI3K/Akt pathway," *Toxicology and Applied Pharmacology* 259(3):402-410, Jan. 2012.

Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.

Vetter et al., "The Guanine Nucleotide-Binding Switch in Three Dimensions," *Science* 294(5545): 1299-1304, Nov. 2001.

Vippagunta et al., "Crystalline solids," *Advanced Drug Delivery Reviews* 48:3-26, 2001.

Wolff, (ed.), *Burger's Medicinal Chemistry and Drug Discovery, Fifth Edition*, vol. 1: *Principles and Practice*, San Diego, California, John Wiley & Sons, 1994, pp. 975-977.

Wu et al., "Stereoselective synthesis of dioxabicycles from 1-C-allyl-2-O-benzyl-glycosides—An intramolecular cyclization between 2-O-benzyl oxygen and the allyl double bond," *Can. J. Chem.* 84(1):597-602, Jan. 2006.

Xu et al., "Design, Synthesis, and Biological Evaluation of 2-Oxo-3,4-dihydropyrimido[4,5-d]pyrimidinyl Derivatives as New Irreversible Epidermal Growth Factor Receptor Inhibitors with Improved Pharmacokinetic Properties," *Journal of Medicinal Chemistry* 56:8803-8813, 2013.

Yang et al., "Fragment-Based Discovery of Nonpeptidic BACE-1 Inhibitors Using Tethering," *Biochemistry* 48:4488-4496, 2009.

Young et al., "Oncogenic and Wild-type Ras Play Divergent Roles in the Regulation of Mitogen-Activated Protein Kinase Signaling," *Cancer Discovery* 3(1):112-123, Jan. 2013.

Boys et al., "Discovery of a series of 2-(1H-pyrazol-1-yl)pyridines as ALK5 inhibitors with potential utility in the prevention of dermal scarring," *Bioorganic & Medicinal Chemistry Letters* 22:3392-3397, 2012.

Canon et al., "The Clinical KRAS (G12C) Inhibitor AMG 510 Drives Anti-Tumor Immunity," *Nature* 575:217-223, 2019 (26 Pages).

Horig et al., "From bench to clinic and back: perspective on the 1st IQPC translational research conference," *Journal of Translational Medicine* 2(44):1-8, 2004.

Jayanthi et al., "Biological Activities of Few Nitrogen Heterocyles using Pass and Lipophilicity using Adme Boxes," *Pharma Science Monitor: An International Journal of Pharmaceutical Sciences* 3(3, Suppl-1) 2012 (13 Pages).

Keith et al., "Heteroarylureas with spirocyclic diamine cores as inhibitors of fatty acid amide hydrolase," *Bioogranic & Medicinal Chemistry Letters* 24:737-741, 2014.

Liu et al., "Targeting the untargetable KRAS in cancer therapy," *Acta Pharmaceutica Sinica B* 9(5):871-879, 2019.

Reilly et al., "Examination of Diazaspiro Cores as Piperazine Bioisosteres in the Olaparib Framework Shows Reduced DNA Damage and Cytotoxicity," *J. Med. Chem.* 61:5367-5379, 2018.

Schafer et al., "Failure is an option: learning from unsuccessful proof-of-concept trials," *Drug Discovery Today* 13(21/22):913-916, 2008.

Silverman, "Prodrugs and Drug Delivery Systems," *The Organic Chemistry of Drug Design and Drug Action*, p. 352-399, 1992.

STN Registry No. 1027262-22-1, "Pentanoic acid, 5-fluoro-4-oxo-3-[[(2S)-1-oxo-2-(4-oxo-6-phenyl-3(4H)-quinazolinyl)butyl]amino]-," Jun. 11, 2008, 1 page.

STN Registry Nos. 1179043-51-6; 1156698-93-9; 1156156-36-3; 1070748-55-8; 1; 1070685-77-6; 1070667-53-6; 1070315-89-7; 1069961-90-5; 1069566-58-0; 1065560-16-8; 1065554-88-2; 1061025-62-4; 1060435-61-1; 958948-04-4; 958839-16-2, 6 pages.

Zheng et al., "The use of spirocyclic scaffolds in drug discovery," *Bioorganic & Medicinal Chemistry Letters* 24:3673-3682, 2014.

U.S. Appl. No. 10,646,488, filed May 12, 2020.
U.S. Appl. No. 10,647,703, filed May 12, 2020.
U.S. Appl. No. 10,689,356, filed Jun. 23, 2020.
U.S. Appl. No. 10,723,738, filed Jul. 28, 2020.
U.S. Appl. No. 10,730,867, filed Aug. 4, 2020.
U.S. Appl. No. 10,736,897, filed Aug. 11, 2020.
U.S. Appl. No. 10,745,385, filed Aug. 18, 2020.
U.S. Appl. No. 16/915,942, filed Jun. 29, 2020.
U.S. Appl. No. 16/374,356, filed Apr. 3, 2019.
U.S. Appl. No. 16/421,186, filed May 23, 2019.
U.S. Appl. No. 16/445,683, filed Jun. 19, 2019.
U.S. Appl. No. 16/480,205, filed Jul. 23, 2019.
U.S. Appl. No. 16/480,849, filed Jul. 25, 2019.
U.S. Appl. No. 16/514,675, filed Jul. 17, 2019.
U.S. Appl. No. 16/535,999, filed Aug. 8, 2019.
U.S. Appl. No. 16/616,066, filed Nov. 22, 2019.

| Oncogene | Tumor Type | Cumulative Mutation Frequency (All Tumors) |
|---|---|---|
| Bcr-Abl | 90% CML | <1% |
| EGFR | 10% NSCLC | <5% |
| ALK | 5% NSCLC | <1% |
| B-Raf | 66% Melanoma | <5% |
| Flt3 | 25% AML | <1% |
| PI3kα | 25% Breast; 25% Endometrial; 15% CRC | 15-20% |
| K-Ras | >80% Pancreatic; >40% colon >20% lung | ~20% |

FIG. 3

SUBSTITUTED CINNOLINES AS INHIBITORS OF KRAS G12C

BACKGROUND

Technical Field

The present invention is generally directed to novel compounds and methods for their preparation and use as therapeutic or prophylactic agents, for example for treatment of cancer.

Description of the Related Art

RAS represents a group of closely related monomeric globular proteins of 189 amino acids (21 kDa molecular mass) which are associated with the plasma membrane and which bind either GDP or GTP. RAS acts as a molecular switch. When RAS contains bound GDP, it is in the resting or off position and is "inactive". In response to exposure of the cell to certain growth promoting stimuli, RAS is induced to exchange its bound GDP for a GTP. With GTP bound, RAS is "switched on" and is able to interact with and activate other proteins (its "downstream targets"). The RAS protein itself has a very low intrinsic ability to hydrolyze GTP back to GDP, thus turning itself into the off state. Switching RAS off requires extrinsic proteins termed GTPase-activating proteins (GAPs) that interact with RAS and greatly accelerate the conversion of GTP to GDP. Any mutation in RAS which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer.

Structurally, RAS proteins contain a G domain which is responsible for the enzymatic activity of RAS—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the RAS subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. About 30% of all human tumors are found to carry some mutation in RAS genes. Remarkably, KRAS mutations are detected in 25-30% of tumors. By comparison, the rates of oncogenic mutation occurring in the NRAS and HRAS family members are much lower (8% and 3% respectively). The most common KRAS mutations are found at residue G12 and G13 in the P-loop and at residue Q61.

G12C is a frequent mutation of KRAS gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge.

Accordingly, while progress has been made in this field, there remains a need in the art for improved compounds and methods for treatment of cancer, for example by inhibition of KRAS, HRAS or NRAS. The present invention fulfills this need and provides further related advantages.

BRIEF SUMMARY

In brief, the present invention provides compounds, including stereoisomers, pharmaceutically acceptable salts, tautomers and prodrugs thereof, which are capable of modulating G12C mutant KRAS, HRAS and/or NRAS proteins. In some instances, the compounds act as electrophiles which are capable of forming a covalent bond with the cysteine residue at position 12 of a KRAS, HRAS or NRAS G12C mutant protein. Methods for use of such compounds for treatment of various diseases or conditions, such as cancer, are also provided.

In one embodiment, compounds having the following structure (I) are provided:

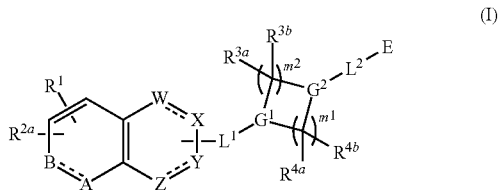

or a pharmaceutically acceptable salt, tautomer, stereoisomer or prodrug thereof, wherein $R^1$, $R^{2a}$, $R^{3a}$, $R^{3b}$, $R^{4a}$, $R^{4b}$, $G^1$, $G^2$, $L^1$, $L^2$, $m^1$, $m^2$, A, B, W, X, Y, Z and E are as defined herein. Pharmaceutical compositions comprising one or more of the foregoing compounds of Structure (I) and a pharmaceutically acceptable carrier are also provided in various other embodiments.

In other embodiments, the present invention provides a method for treatment of cancer, the method comprising administering an effective amount of a pharmaceutical composition comprising any one or more of the compounds of structure (I) to a subject in need thereof.

Other provided methods include a method for regulating activity of a KRAS, HRAS or NRAS G12C mutant protein, the method comprising reacting the KRAS, HRAS or NRAS G12C mutant protein with any one of the compounds of structure (I). In other embodiments, a method for inhibiting proliferation of a cell population, the method comprising contacting the cell population with any one of the compounds of structure (I) is also provided.

In other embodiments, the invention is directed to a method for treating a disorder mediated by a KRAS, HRAS or NRAS G12C mutation in a subject in need thereof, the method comprising:

determining if the subject has a KRAS, HRAS or NRAS G12C mutation; and if the subject is determined to have the KRAS, HRAS or NRAS G12C mutation, then administering to the subject a therapeutically effective amount of a pharmaceutical composition comprising any one or more compounds of structure (I).

In still more embodiments, the invention is directed to a method for preparing a labeled KRAS, HRAS or NRAS G12C mutant protein, the method comprising reacting the KRAS, HRAS or NRAS G12C mutant with a compound of structure (I), to result in the labeled KRAS, HRAS or NRAS G12C protein.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility.

Further, the particular shapes of the elements as drawn are not intended to convey any information regarding the actual shape of the particular elements, and have been solely selected for ease of recognition in the figures.

FIG. 3 shows some common oncogenes, their respective tumor type and cumulative mutation frequencies (all tumors).

DETAILED DESCRIPTION

Figure 1:
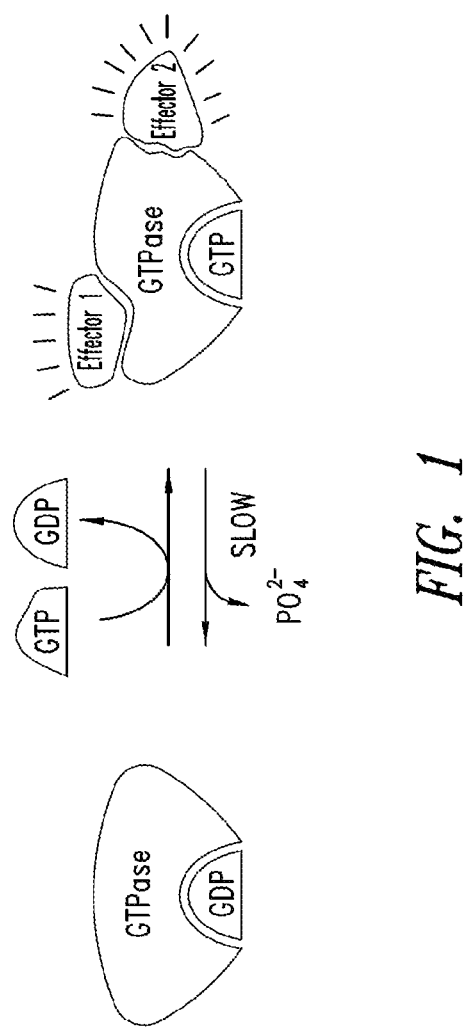
FIG. 1 illustrates the enzymatic activity of RAS.
Figure 2:
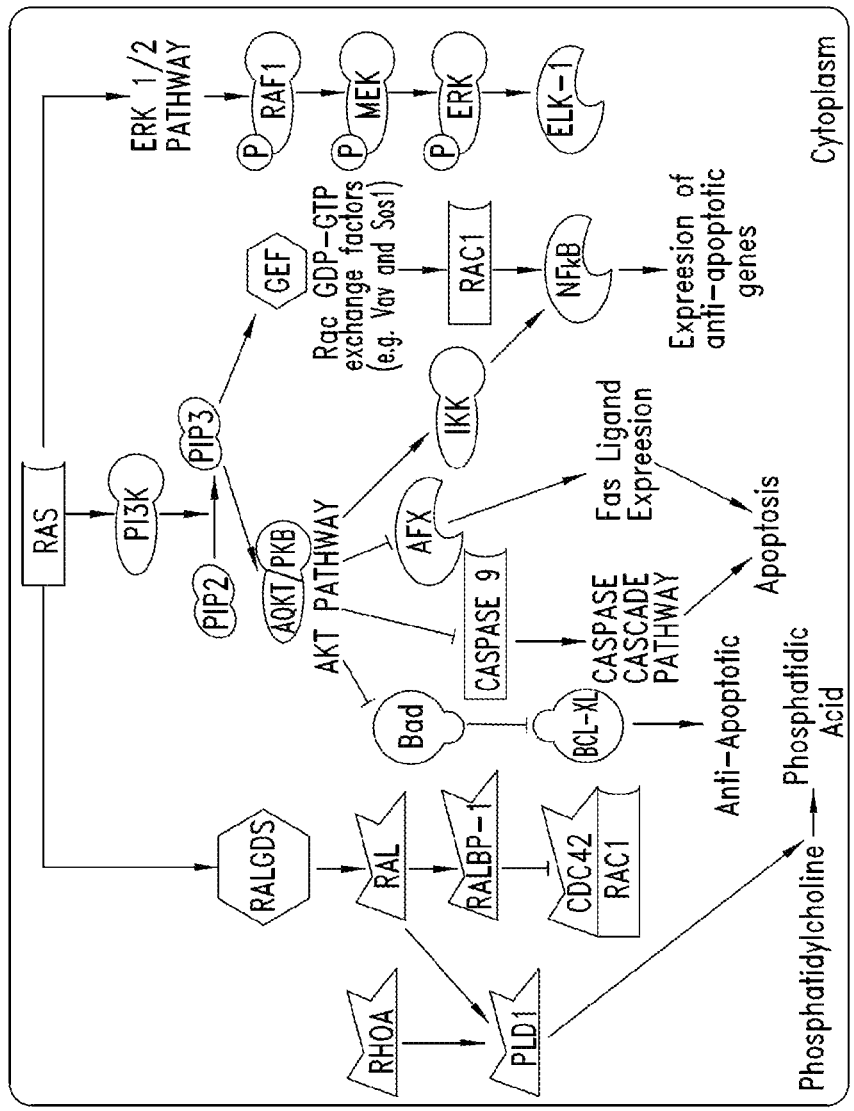
FIG. 2 depicts a signal transduction pathway for RAS.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

"Amidinyl" refers to a radical of the form —(C=NR$_a$)NR$_b$R$_c$, wherein R$_a$, R$_b$ and R$_c$ are each independently H or C$_1$-C$_6$ alkyl.

"Amino" refers to the —NH$_2$ radical.

"Aminylsulfone" refers to the —S(O)$_2$NH$_2$ radical.

"Carboxy" or "carboxyl" refers to the —CO$_2$H radical.

"Cyano" refers to the —CN radical.

"Guanidinyl" refers to a radical of the form —NR$_d$(C=NR$_a$)NR$_b$R$_c$, wherein R$_a$, R$_b$, R$_c$ and R$_d$ are each independently H or C$_1$-C$_6$ alkyl.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). "Amidinylalkyl" refers to an alkyl group comprising at least one amidinyl substituent. "Guanidinylalkyl" refers to an alkyl group comprising at least one guanidinyl substituent. Unless stated otherwise specifically in the specification, an alkyl, amidinylalkyl and/or guanidinylalkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkylcycloalkyl" refers to a radical of the formula —R$_b$R$_d$ where R$_b$ is cycloalkyl chain as defined herein and R$_d$ is an alkyl radical as defined above. Unless stated otherwise specifically in the specification, a alkylcycloalkyl group is optionally substituted.

"Alkoxy" refers to a radical of the formula —OR$_a$ where R$_a$ is an alkyl radical as defined above containing one to twelve carbon atoms. "Amidinylalkyloxy" refers to an alkoxy group comprising at least one amidinyl substituent on the alkyl group. "Guanidinylalkyloxy" refers to an alkoxy group comprising at least one guanidinyl substituent on the alkyl group. "Alkylcarbonylaminylalkyloxy" refers to an alkoxy group comprising at least one alkylcarbonylaminyl substituent on the alkyl group. "Heterocyclylalkyloxy" refers to an alkoxy group comprising at least one heterocyclyl substituent on the alkyl group. "Heteroarylalkyloxy" refers to an alkoxy group comprising at least one heteroaryl substituent on the alkyl group. "Aminylalkyloxy" refers to an alkoxy group comprising at least one substituent of the form —$NR_aR_b$, where $R_a$ and $R_b$ are each independently H or $C_1$-$C_6$ alkyl, on the alkyl group. Unless stated otherwise specifically in the specification, an alkoxy, amidinylalkyloxy, guanidinylalkyloxy, alkylcarbonylaminyl, heterocyclylalkyloxy, heteroarlyalkyloxy and/or aminylalkyloxy group is optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above containing one to twelve carbon atoms. Unless stated otherwise specifically in the specification, an alkoxyalkyl group is optionally substituted.

"Alkoxycarbonyl" refers to a radical of the formula —$C(O)OR_a$ where $R_a$ is an alkyl radical as defined above containing one to twelve carbon atoms. Unless stated otherwise specifically in the specification, an alkoxycarbonyl group is optionally substituted.

"Aryloxy" refers to a radical of the formula —$OR_a$ where $R_a$ is an aryl radical as defined herein. Unless stated otherwise specifically in the specification, an aryloxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. A "haloalkylaminyl" group is an alkylaminyl group comprising at least one halo substitutent on the alkyl group. A "hydroxylalkylaminyl" group is an alkylaminyl group comprising at least one hydroxyl substitutent on the alkyl group. A "amidinylalkylaminyl" group is an alkylaminyl group comprising at least one amidinyl substitutent on the alkyl group. A "guanidinylalkylaminyl" group is an alkylaminyl group comprising at least one guanidinyl substitutent on the alkyl group. Unless stated otherwise specifically in the specification, an alkylaminyl, haloalkylaminyl, hydroxylalkylaminyl, amidinylalkylaminyl and/or guanidinylalkylaminyl group is optionally substituted.

"Aminylalkyl" refers to an alkyl group comprising at least one aminyl substituent (—$NR_aR_b$ wherein $R_a$ and $R_b$ are each independently H or $C_1$-$C_6$ alkyl). The aminyl substituent can be on a tertiary, secondary or primary carbon. Unless stated otherwise specifically in the specification, an aminylalkyl group is optionally substituted.

"Aminylalkylaminyl" refers to a radical of the formula —$NR_b$ wherein $R_a$ is H or $C_1$-$C_6$ alkyl and $R_b$ is aminylalkyl. Unless stated otherwise specifically in the specification, an aminylalkylaminyl group is optionally substituted.

"Aminylalkoxy" refers to a radical of the formula —$OR_aNH_2$ wherein $R_a$ is alkylene. Unless stated otherwise specifically in the specification, an aminylalkoxy group is optionally substituted.

"Alkylaminylalkoxy" refers to a radical of the formula —$OR_aNR_bR_c$ wherein $R_a$ is alkylene and $R_b$ and $R_c$ are each independently H or $C_1$-$C_6$ alkyl, provided one of $R_b$ or $R_c$ is $C_1$-$C_6$ alkyl. Unless stated otherwise specifically in the specification, an alkylaminylalkoxy group is optionally substituted.

"Alkylcarbonylaminyl" refers to a radical of the formula —$NH(C=O)R_a$ where $R_a$ is an alkyl radical as defined above containing one to twelve carbon atoms. Unless stated otherwise specifically in the specification, an alkylcarbonylaminyl group is optionally substituted. An alkenylcarbonylaminyl is an alkylcarbonylaminyl containing at least one carbon-carbon double bond. An alkenylcarbonylaminyl group is optionally substituted.

"Alkylcarbonylaminylalkoxy" refers to a radical of the formula —$OR_bNH(C=O)R_a$ where $R_a$ is an alkyl radical as defined above containing one to twelve carbon atoms and $R_b$ is alkyelene. Unless stated otherwise specifically in the specification, an alkylcarbonylaminylalkoxy group is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Aminylcarbonyl" refers to a radical of the formula —$C(=O)NR_aR_b$ where $R_a$ and $R_b$ are each independently H or alkyl. Unless stated otherwise specifically in the specification, an aminylcarbonyl group is optionally substituted.

"Alkylaminylcarbonyl" refers to a radical of the formula —$C(=O)NR_aR_b$, where $R_a$ and $R_b$ are each independently H or alkyl, provided at least one of $R_a$ or $R_b$ is alkyl. Unless stated otherwise specifically in the specification, an alkylaminylcarbonyl group is optionally substituted.

"Aminylcarbonylalkyl" refers to a radical of the formula —$R_cC(=O)NR_aR_b$, where $R_a$ and $R_b$ are each independently H or alkyl and $R_c$ is alkylene. Unless stated otherwise specifically in the specification, an aminylcarbonylalkyl group is optionally substituted.

"Aminylcarbonycycloalkylalkyl" refers to a radical of the formula —$R_cC(=O)NR_aR_b$, where $R_a$ and $R_b$ are each independently H or alkyl and $R_c$ is cycloalkyl. Unless stated otherwise specifically in the specification, an aminylcarbonylcycloalkyl group is optionally substituted.

"Aryl" refers to a hydrocarbon ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group is optionally substituted.

"Arylalkyloxy" refers to a radical of the formula —$OR_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aryllkyloxy group is optionally substituted.

"Arylalkylaminyl" refers to a radical of the formula —$N(R_a)R_b$—$R_c$ where $R_a$ is H or $C_1$-$C_6$ alkyl, $R_b$ is an alkylene chain as defined above and $R_c$ is one or more aryl radicals as defined above, for example, benzyl, diphenylmethyl and the like. Unless stated otherwise specifically in the specification, an arylalkylaminyl group is optionally substituted.

"Carboxyalkyl" refers to a radical of the formula —$R_b$—$R_c$ where $R_b$ is an alkylene chain as defined above and $R_c$ is a carboxy group as defined above. Unless stated otherwise specifically in the specification, carboxyalkyl group is optionally substituted.

"Cyanoalkyl" refers to a radical of the formula —$R_b$—$R_c$ where $R_b$ is an alkylene chain as defined above and $R_d$ is a cyano group as defined above. Unless stated otherwise specifically in the specification, a cyanoalkyl group is optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

"Cyanocycloalkyl" refers to a radical of the formula —$R_b$—$R_c$ where $R_b$ is cycloalkylene chain and $R_c$ is a cyano group as defined above. Unless stated otherwise specifically in the specification, a cyanocycloalkyl group is optionally substituted.

"Cycloalkylaminylcarbonyl" refers to a radical of the formula —C(=O)$NR_aR_b$, where $R_a$ and $R_b$ are each independently H or cycloalkyl, provided at least one of $R_a$ or $R_b$ is cycloalkyl. Unless stated otherwise specifically in the specification, n cycloalkylaminylcarbonyl group is optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Halolkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification. "Heterocyclyloxy" refers to a heterocyclyl group bound to the remainder of the molecule via an oxygen bond (—O—). "Heterocyclylaminyl" refers to a heterocyclyl group bound to the remainder of the molecule via a nitrogen bond (—$NR_a$—, where $R_a$ is H or $C_1$-$C_6$ alkyl). Unless stated otherwise specifically in the specification, a heterocyclyl, heterocyclyloxy and/or hetercyclylaminyl group is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group is optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heterocyclylalkyloxy" refers to a radical of the formula —$OR_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyloxy group is optionally substituted.

"Heterocyclylalkylaminyl" refers to a radical of the formula —N($R_c$)$R_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom, $R_c$ is H or $C_1$-$C_6$ alkyl. Unless stated otherwise specifically in the specification, a heterocyclylalkyloxy group is optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). "Heteroaryloxy" refers to a heteroaryl group bound to the remainder of the molecule via an oxygen bond (—O—). "Heteroarylaminyl" refers to a heteroaryl group bound to the remainder of the molecule via a nitrogen bond (—NR$_a$—, where R$_a$ is H or C$_1$-C$_6$ alkyl). Unless stated otherwise specifically in the specification, a heteroaryl, heteroaryloxy and/or heteroarylaminyl group is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —R$_b$R$_f$ where R$_b$ is an alkylene chain as defined above and R$_f$ is a heteroaryl radical as defined above. Unless stated otherwise specifically in the specification, a heteroarylalkyl group is optionally substituted.

"Heteroarylalkyloxy" refers to a radical of the formula —OR$_b$R$_f$ where R$_b$ is an alkylene chain as defined above and R$_f$ is a heteroaryl radical as defined above, and if the heteroaryl is a nitrogen-containing heterocyclyl, the heterocyclyl is optionally attached to the alkyl radical at the nitrogen atom. Unless stated otherwise specifically in the specification, a heteroarylalkyloxy group is optionally substituted.

"Heteroarylalkylaminyl" refers to a radical of the formula —NR$_c$R$_b$R$_f$ where R$_b$ is an alkylene chain as defined above and R$_f$ is a heteroaryl radical as defined above, and if the heteroaryl is a nitrogen-containing heterocyclyl, the heterocyclyl is optionally attached to the alkyl radical at the nitrogen atom, and R$_c$ is H or C$_1$-C$_6$ alkyl. Unless stated otherwise specifically in the specification, a heteroarylalkyloxy group is optionally substituted. "Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted. "Hydroxylalkylaminyl" is an alkylaminyl groups comprising at least one —OH substituent, which is on a primary, secondary or tertiary carbon. Unless stated otherwise specifically in the specification, a hydroxylalkylaminyl group is optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group is optionally substituted.

The term "substituted" used herein means any of the above groups (e.g., alkyl, alkylene, alkylcycloalkyl, alkoxy, amidinylalkyloxy, guanidinylalkyloxy, alkylcarbonylaminylalkyloxy, heterocyclylalkyloxy, heteroarylalkyloxy, aminylalkyloxy, alkoxyalkyl, alkoxycarbonyl, haloalkylaminyl, hydroxylalkylaminyl, amidinylalkylaminyl, guanidinylalkylaminyl, aminylalkyl, aminylalkylaminyl, aminylalkoxy, alkylaminylalkoxy aryloxy, alkylaminyl, alkylcarbonylaminyl, alkylaminylalkyl, aminylcarbonyl, alkylaminylcarbonyl, alkylcarbonylaminylalkoxy, aminylcarbonylalkyl, aminylcarbonycycloalkylalkyl, thioalkyl, aryl, aralkyl, arylalkyloxy, arylalkylaminyl, carboxyalkyl, cyanoalkyl, cycloalkyl, cycloalkyloxy, cycloalkylaminyl, cyanocycloalkyl, cycloalkylaminylcarbonyl, cycloalkylalkyl, haloalkyl, haloalkoxy, heterocyclyl, heterocyclyloxy, heterocyclylaminyl, N-heterocyclyl, heterocyclylalkyl, heterocyclylalkyloxy, heterocyclylalkylaminyl, heteroaryl, N-heteroaryl, heteroarylalkyl, heteroarylalkyloxy, heteroarylalkylaminyl, hydroxylalkylaminyl and/or hydroxylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrohiles typically are electron poor or comprise atoms which are electron poor. In certain embodiments an electrohile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as KRAS, HRAS or NRAS G12C. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent ise water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the invention may exist as mixtures of atropisomers or purified or enriched for the presence of one atropisomer. Non-limiting examples of compounds which exist as atropisomers include the following compounds:

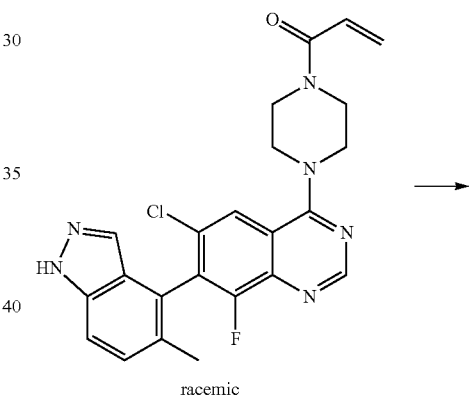

racemic

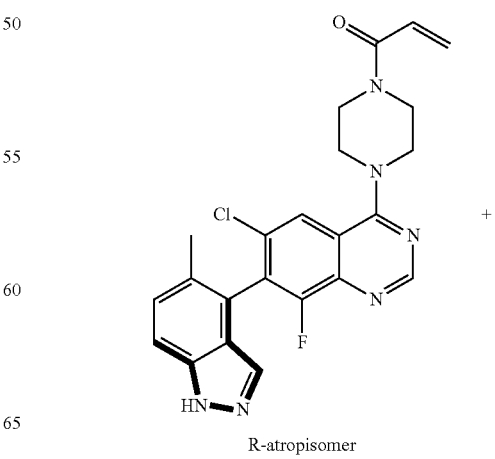

R-atropisomer

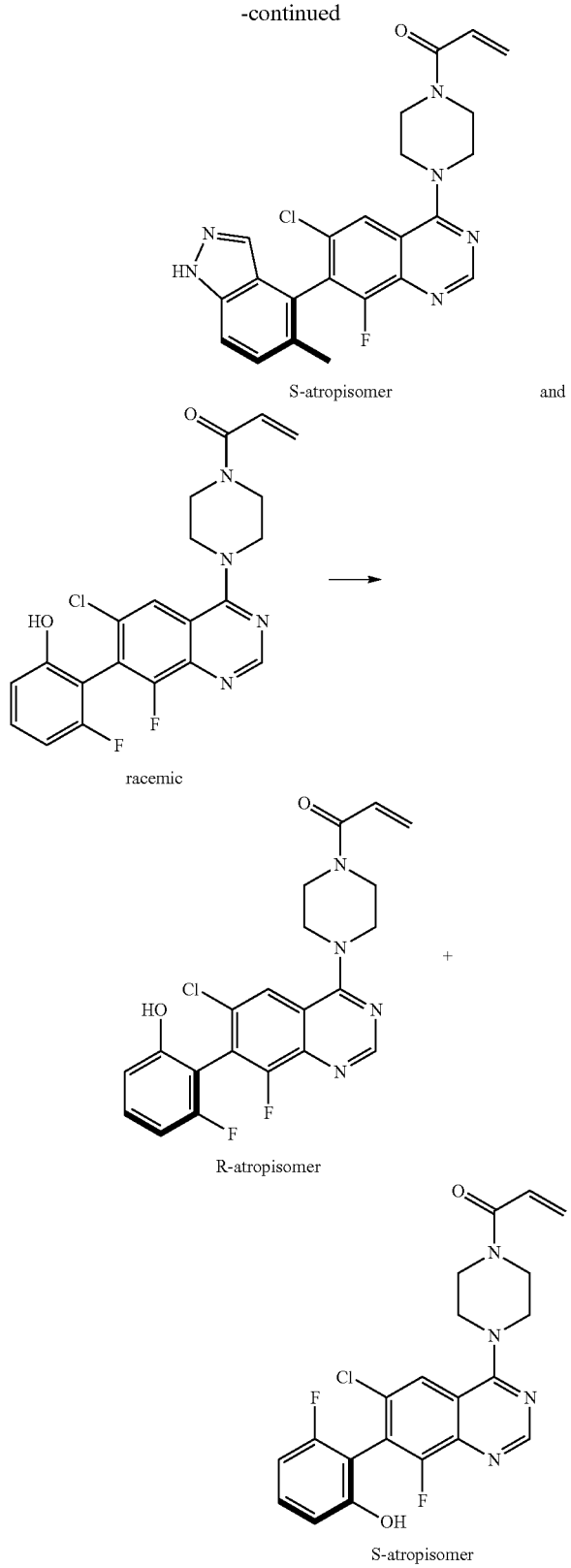

and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the invention provides compounds which are capable of selectively binding to and/or modulating a G12C mutant KRAS, HRAS or NRAS protein. The compounds may modulate the G12C mutant KRAS, HRAS or NRAS protein by reaction with an amino acid. While not wishing to be bound by theory, the present applicants believe that, in some embodiments, the compounds of the invention selectively react with the G12C mutant KRAS, HRAS or NRAS proteins by forming a covalent bond with the cysteine at the 12 position of a G12C mutant KRAS, HRAS or NRAS protein. By binding to the Cystine 12, the compounds of the invention may lock the switch II of the G12C mutant KRAS, HRAS or NRAS into an inactive stage. This inactive stage may be distinct from those observed for GTP and GDP bound KRAS, HRAS or NRAS. Some compounds of the invention may also be able to perturb the switch I conformation. Some compounds of the invention may favor the binding of the bound KRAS, HRAS or NRAS to GDP rather than GTP and therefore sequester the KRAS, HRAS or NRAS into an inactive KRAS, HRAS or NRAS GDP state. Because effector binding to KRAS, HRAS or NRAS is highly sensitive to the conformation of switch I and II, the irreversible binding of these compounds may disrupt KRAS, HRAS or NRAS downstream signaling.

As noted above, in one embodiment of the present invention, compounds having activity as modulators of a G12C mutant KRAS, HRAS or NRAS protein are provided, the compounds have the following structure (I):

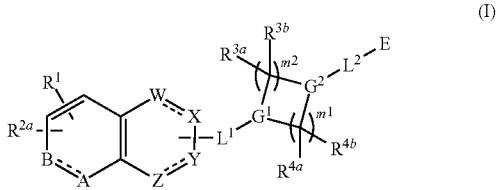

(I)

or a pharmaceutically acceptable salt, tautomer, prodrug or stereoisomer thereof, wherein:

A is $CR^1$, $CR^{2b}$, $NR^7$ or S;
B is a bond, $CR^1$ or $CR^{2c}$
$G^1$ and $G^2$ are each independently N or CH;
W, X and Y are each independently N, $NR^5$ or $CR^6$;
Z is a bond, N or $CR^6$, or Z is NH when Y is C=O;
$L^1$ is a bond or $NR^7$;
$L^2$ is a bond or alkylene;

A "stereoisomer" refers to a compound made up of the same atoms bonded by the same bonds but having different three-dimensional structures, which are not interchangeable. The present invention contemplates various stereoisomers $R^1$ is H, cyano, halo, $CF_3$, $C_1$-$C_6$alkyl, $C_1$-$C_6$alkylaminyl, $C_3$-$C_8$ cycloalkyl, $C_1$-$C_6$alkenyl or $C_3$-$C_8$cycloalkenyl, heterocyclyl, heteroaryl, aryloxy, heteroaryloxy or aryl;

$R^{2a}$, $R^{2b}$ and $R^{2c}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl, heteroaryl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl or a bond to $L^1$;

$R^6$ is, at each occurrence, independently H, oxo, cyano, cyanoalkyl, amino, aminylalkyl, aminylalkylaminyl, aminylcarbonyl, aminylsulfonyl, —CO$_2$NR$^a$R$^b$, wherein R$^a$ and R$^b$, are each independently H or C1-C6 alkyl or R$^a$ and R$^b$ join to form a carbocyclic or heterocyclic ring, alkylaminyl, haloalkylaminyl, hydroxylalkyaminyl, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl, heteroarylalkylaminyl, aryl, aryloxy, arylaminyl, arylalkylaminyl, arylalkyloxy or a bond to $L^1$;

$R^7$ is H or $C_1$-$C_6$ alkyl;

$m^1$ and $m^2$ are each independently 1, 2 or 3;

==== indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X, Y or Z is CR$^6$ where R$^6$ is a bond to $L^1$, and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some other embodiments of compound (I):

A is CR$^1$, CR$^{2b}$, NR$^7$ or S;

B is a bond, CR$^1$ or CR$^{2c}$ $G^1$ and $G^2$ are each independently N or CH;

W, X and Y are each independently N, NR$^5$ or CR$^6$;

Z is a bond, N or CR$^{6a}$ or Z is NH when Y is C=O;

$L^1$ is a bond or NR$^7$;

$L^2$ is a bond or alkylene;

$R^1$ is heterocyclyl, heteroaryl or aryl;

$R^{2a}$, $R^{2b}$ and $R^{2c}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl, heteroaryl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl or a bond to $L^1$;

$R^6$ is, at each occurrence, independently H, oxo, cyano, cyanoalkyl, amino, aminylalkyl, aminylalkylaminyl, aminylcarbonyl, aminylsulfonyl, —CO$_2$NR$^a$R$^b$, wherein R$^a$ and R$^b$, are each independently H or $C_1$-$C_6$ alkyl or R$^a$ and R$^b$ join to form a carbocyclic or heterocyclic ring, alkylaminyl, haloalkylaminyl, hydroxylalkyaminyl, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylaminylalkoxy alkylcarbonylaminylalkoxy, $C_1$-$C_6$ alkyl, heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl, heteroarylalkylaminyl, aryl, aryloxy, arylaminyl, arylalkylaminyl, arylalkyloxy or a bond to $L^1$;

$R^{6a}$ is H, alkyl or a bond to $L^1$;

$R^7$ is H or $C_1$-$C_6$ alkyl $m^1$ and $m^2$ are each independently 1, 2 or 3;

==== indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X, Y or Z is CR$^6$ where R$^6$ is a bond to $L^1$ or at least one of W, X or Y is NR$^5$, wherein $R^5$ is a bond to $L^1$, and provided that least one of $R^{2a}$, $R^{2b}$ or $R^{2c}$ is not H when $R^1$ is pyridyl.

In some of the foregoing embodiments, $R^1$ is aryl. In other embodiments, $R^1$ is heterocyclyl. In still other embodiments, $R^1$ is heteroaryl, provided that least one of $R^{2a}$, $R^{2b}$ or $R^{2c}$ is not H when $R^1$ is pyridyl. In some other embodiments, $C_1$-$C_6$ haloalkyl is $CF_3$.

In some embodiments of the compound of structure (I), the bond between W and X is a double bond. In other embodiments, the bond between Y and Z is a double bond. In more embodiments, the bond between A and B is a double bond. In still more embodiments, the bonds between W and X, Y and Z and A and B are each double bonds.

In some embodiments, Z is a bond, N or CR$^6$. In some embodiments, Z is a bond, N or CR$^{6a}$, wherein R$^{6a}$ is H, alkyl or a bond to $L^1$. In other embodiments Z is NH when Y is C=O In some more embodiments of the foregoing compound of structure (I):

A is $CR^1$, $CR^{2b}$, $NR^7$ or S;
B is a bond, $CR^1$ or $CR^{2c}$
$G^1$ and $G^2$ are each independently N or CH;
W, X and Y are each independently N, $NR^5$ or $CR^6$;
Z is a bond, N or $CR^6$;
$L^1$ is a bond or $NR^7$;
$L^2$ is a bond or alkylene;
$R^1$ is H, cyano, halo, heterocyclyl, heteroaryl, aryloxy or aryl;
$R^{2a}$, $R^{2b}$ and $R^{2C}$ are each independently H, halo, hydroxyl, $C_1$-$C_6$ alkyl, $C_1$-$C_6$ haloalkyl $C_3$-$C_8$ cycloalkyl or aryl;
$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;
$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;
$R^5$ and $R^7$ are each independently H or $C_1$-$C_6$ alkyl;
$R^6$ is, at each occurrence, independently H, oxo, cyano, cyanoalkyl, amino, aminylcarbonyl, alkylaminyl, $C_1$-$C_6$ alkoxy, $C_1$-$C_6$ alkyl or a bond to $L^1$;
$m^1$ and $m^2$ are each independently 1, 2 or 3;
==== indicates a single or double bond such that all valences are satisfied; and
E is an electrophilic moiety capable of forming a covalent bond with the cysteine residue at position 12 of a KRAS, HRAS or NRAS G12C mutant protein,
wherein at least one of W, X, Y or Z is $CR^6$ where $R^6$ is a bond to $L^1$, and
provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some other embodiments of the foregoing compound of structure (I):

A is $CR^{2b}$, $NR^7$ or S;
B is a bond or $CR^{2c}$
$G^1$ and $G^2$ are each independently N or CH;
W, X and Y are each independently N, $NR^5$ or $CR^6$;
Z is a bond, N or $CR^6$;
$L^1$ is a bond or $NR^7$;
$L^2$ is a bond or alkylene;
$R^1$ is cyano, $C_1$-$C_6$alkyl, $C_1$-$C_6$alkylaminyl, $C_3$-$C_8$ cycloalkyl, $C_1$-$C_6$alkenyl or $C_3$-$C_8$ cycloalkenyl, heterocyclyl or aryl;
$R^{2a}$, $R^{2b}$ and $R^{2c}$ are each independently H, halo, $C_1$-$C_6$alkyl or $C_3$-$C_8$ cycloalkyl;
$R^{3a}$ and $R^{3b}$ are, at each occurrence, independently H, —OH, —$NH_2$, —$CO_2H$, halo, cyano, hydroxylalkly, aminylalkyl, cyanoalkyl, carboxyalkyl or aminylcarbonyl; or $R^{3a}$ and $R^{3b}$ join to form a carbocyclic or heterocyclic ring; or $R^{3a}$ is H, —OH, —$NH_2$, —$CO_2H$, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;
$R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl; or $R^{4a}$ and $R^{4b}$ join to form a carbocyclic or heterocyclic ring; or $R^{4a}$ is H, —OH, —$NH_2$, —$CO_2H$, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring;
$R^5$ and $R^7$ are each independently H or $C_1$-$C_6$alkyl;
$R^6$ is, at each occurrence, independently H, cyano, amino, alkylaminyl, $C_1$-$C_6$alkoxy, $C_1$-$C_6$alkyl or a bond to $L^1$;
$m^1$ and $m^2$ are each independently 1, 2 or 3;
==== indicates a single or double bond such that all valences are satisfied; and
E is an electrophilic moiety capable of forming a covalent bond with the cysteine residue at position 12 of a KRAS, HRAS or NRAS G12C mutant protein,
wherein at least one of W, X or Y is $CR^6$ where $R^6$ is a bond to $L^1$.

In still other embodiments of the foregoing compound of structure (I), $R^1$ is H, cyano, halo, heterocyclyl, heteroaryl, aryloxy or aryl.

The structure of E is not particularly limited provided it is capable of forming a covalent bond with a nucleophile, such as the cysteine residue at position 12 of a KRAS, HRAS or NRAS G12C mutant protein. Accordingly, moieties which are capable of reaction with (e.g., by covalent bond formation) a nucleophile are preferred. In certain embodiments, E is capable of reacting in a conjugate addition manner (e.g., 1,4-conjugate addition) with an appropriately reactive nucleophile. In some embodiments, E comprises conjugated pi bonds such that delocalization of electrons results in at least one atom (e.g., a carbon atom) having a positive charge, partial positive charge or a polarized bond. In other embodiments, E comprises one or more bonds wherein the electronegativity of the two atoms forming the bonds is sufficiently different such that a partial positive charge (e.g., by polarization of the bond) resides on one of the atoms, for example on a carbon atom. E moieties comprising carbon-halogen bonds, carbon-oxygen bonds or carbon bonds to various leaving groups known in the art are examples of such E moieties.

In certain embodiments of the foregoing, E has the following structure:

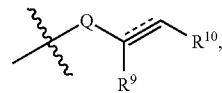

wherein:
≡ represents a double or triple bond;
Q is —C(=O)—, —C(=$NR^{8'}$)—, —$NR^8$C(=O)—, —S(=O)$_2$— or —$NR^8$S(=O)$_2$—;
$R^8$ is H, $C_1$-$C_6$alkyl or hydroxylalkyl;
$R^{8'}$ is H, —OH, —CN or $C_1$-$C_6$alkyl; and
when ≡ is a double bond then $R^9$ and $R^{10}$ are each independently H, cyano, carboxyl, $C_1$-$C_6$alkyl, alkoxycarbonyl, aminylalkyl, alkylaminylalkyl, or hydroxylalkyl or $R^9$ and $R^{10}$ join to form a carbocyclic or heterocyclic ring;

when ≡ is a triple bond; then $R^9$ is absent and $R^{10}$ is H, $C_1$-$C_6$alkyl, aminylalkyl, alkylaminylalkyl or hydroxylalkyl.

In certain embodiments when ≡ is a double bond then $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is —C(=O)—, —NR$^8$C(=O)—, —S(=O)$_2$— or —NR$^8$S(=O)$_2$—.

In some other of the foregoing embodiments, Q is —C(=NR$^{8'}$)—, wherein R$^{8'}$ is H, —OH, —CN or $C_1$-$C_6$alkyl. For example, in some embodiments R$^{8'}$ is H. In other embodiments, R$^{8'}$ is —CN. In other embodiments, R$^{8'}$ is —OH.

In some embodiments, the compound has the following structure (I'):

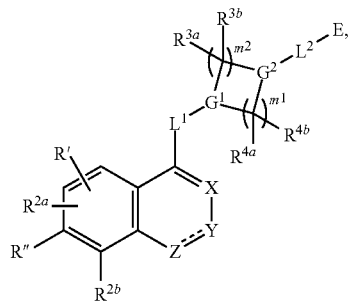

(I')

wherein R' is $R^1$ and R" is $R^{2c}$ or R' is H and R" is $R^1$.

In other embodiments, the compound has the following structure (I'a):

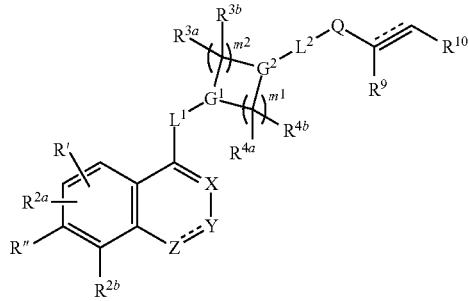

(I'a)

wherein:
≡ represents a double or triple bond;
Q is —C(=O)—, —C(=NR$^{8'}$)—, —NR$^8$C(=O)—, —S(=O)$_2$— or —NR$^8$S(=O)$_2$—;
$R^8$ is H, $C_1$-$C_6$alkyl or hydroxylalkyl;
$R^{8'}$ is H, —OH, —CN or $C_1$-$C_6$alkyl;
when ≡ is a double bond then $R^9$ and $R^{10}$ are each independently H, cyano, carboxyl, $C_1$-$C_6$alkyl, alkoxycarbonyl, aminylalkyl, alkylaminylalkyl, heteroaryl or hydroxylalkyl or $R^9$ and $R^{10}$ join to form a carbocyclic or heterocyclic ring;
when ≡ is a triple bond then $R^9$ is absent and $R^{10}$ is H, $C_1$-$C_6$alkyl, aminylalkyl, alkylaminylalkyl or hydroxylalkyl; and
R' is $R^1$ and R" is $R^{2c}$ or R' is H and R" is $R^1$.

In some of the foregoing embodiments of compound (I'a), Q is —C(=O)—, —NR$^8$C(=O)—, —S(=O)$_2$— or —NR$^8$S(=O)$_2$—.

In some other of the foregoing embodiments of compound (I'a), Q is —C(=NR$^{8'}$)—, wherein R$^{8'}$ is H, —OH, —CN or $C_1$-$C_6$alkyl. For example, in some embodiments R$^{8'}$ is H. In other embodiments, R$^{8'}$ is —CN. In other embodiments, R$^{8'}$ is —OH.

In still more embodiments of the foregoing compounds, the compound has one of the following structures (I'b), (I'c), (I'd) or (I'e):

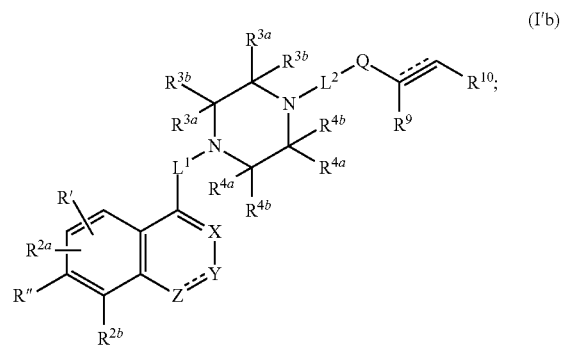

(I'b)

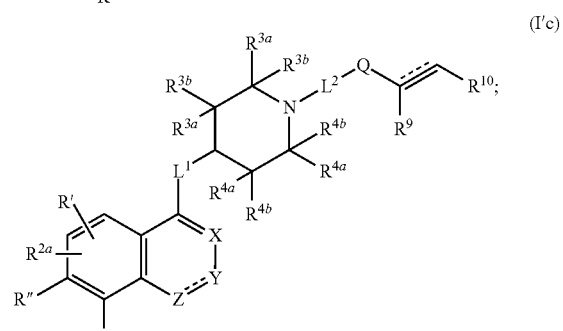

(I'c)

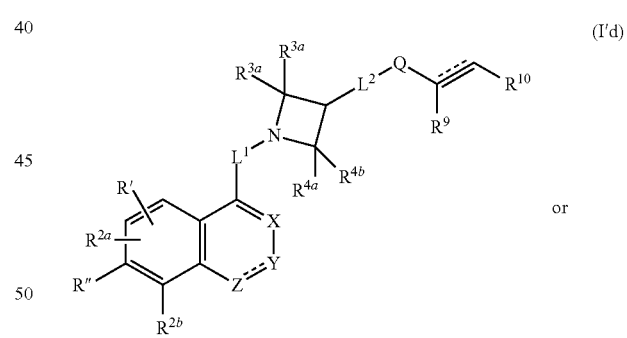

(I'd)

or

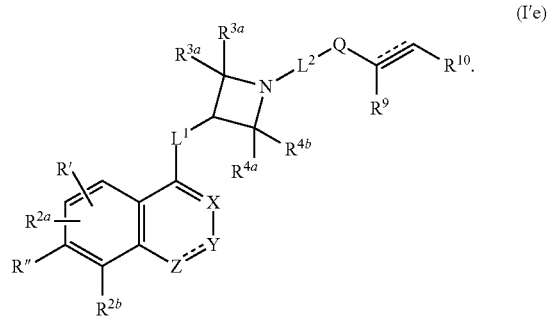

(I'e)

In still more embodiments, the compound has one of the following structures (I'f), (I'g), (I'h) or (I'i):

In different embodiments, the compound has one of the following structures (I'j), (I'k), (I'l) or (I'm):

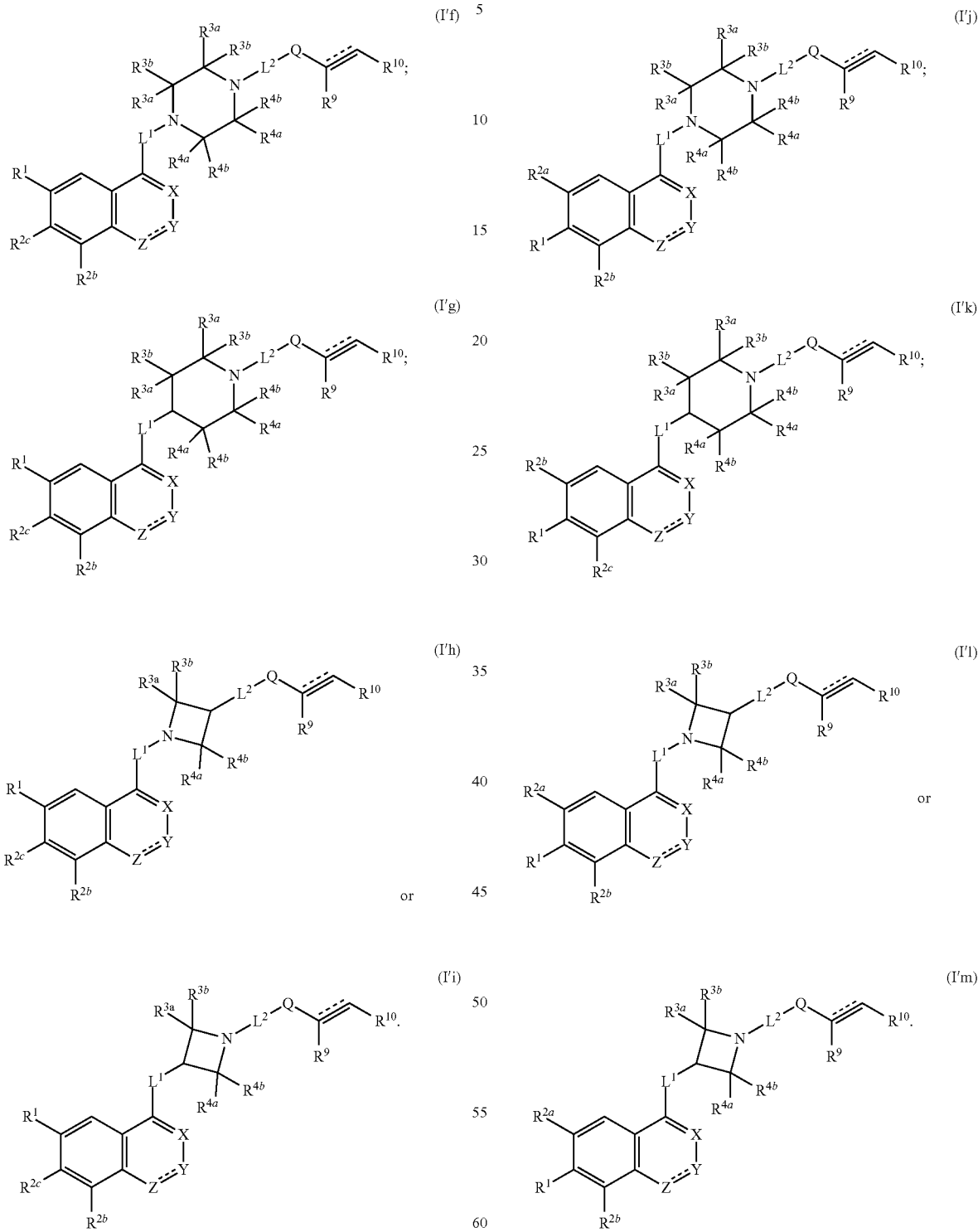

In some embodiments of the compounds of structures (I'f), (I'g), (I'h) or (I'i), $R^1$ is aryl and $R^{2c}$ and $R^{2b}$ are independently selected from H and halo, for example in some further embodiments $R^1$ is aryl and $R^{2c}$ and $R^{2b}$ are independently selected from halo.

In some embodiments of the compounds of structures (I'j), (I'k), (I'l) or (I'm), $R^1$ is aryl and $R^{2a}$ and $R^{2b}$ are independently selected from H and halo, for example in some further embodiments $R^1$ is aryl and $R^{2a}$ and $R^{2b}$ are independently selected from halo.

In other embodiments, the compound has the following structure (I″):

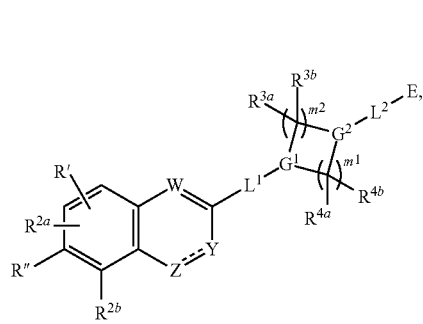
(I″)

wherein R' is R¹ and R" is R$^{2c}$ or R' is H and R" is R¹. For example, in some embodiments the compound has the following structure (I″a):

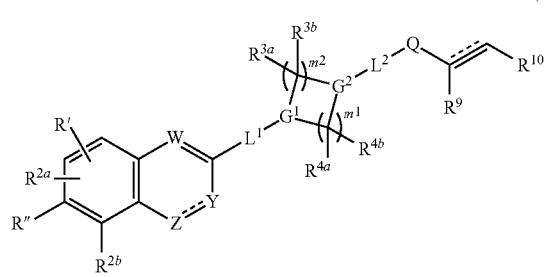
(I″a)

wherein:

≡ represents a double or triple bond;

Q is —C(=O)—, —C(=NR$^8$)—, —NR$^8$C(=O)—, —S(=O)$_2$— or —NR$^8$S(=O)$_2$—;

R$^8$ is H, C$_1$-C$_6$alkyl or hydroxylalkyl;

R$^{8'}$ is H, —OH, —CN or C$_1$-C$_6$alkyl;

when ≡ is a double bond then R$^9$ and R$^{10}$ are each independently H, cyano, carboxyl, C$_1$-C$_6$alkyl, alkoxycarbonyl, aminylalkyl, alkylaminylalkyl, heteroaryl or hydroxylalkyl or R$^9$ and R$^{10}$ join to form a carbocyclic or heterocyclic ring;

when ≡ is a triple bond then R$^9$ is absent and R$^{10}$ is H, C$_1$-C$_6$alkyl, aminylalkyl, alkylaminylalkyl or hydroxylalkyl; and R' is R¹ and R" is R$^{2c}$ or R' is H and R" is R¹.

In some of the foregoing embodiments of compound (I″a), Q is Q is —C(=O)—, —NR$^8$C(=O)—, —S(=O)$_2$— or —NR$^8$S(=O)$_2$—.

In some other of the foregoing embodiments of compound (I″a), Q is —C(=NR$^{8'}$)—, wherein R$^{8'}$ is H, —OH, —CN or C$_1$-C$_6$alkyl. For example, in some embodiments R$^{8'}$ is H. In other embodiments, R$^{8'}$ is —CN. In other embodiments, R$^{8'}$ is —OH.

In other embodiments, the compound has one of the following structures (I″b), (I″c), (I″d) or (I″e):

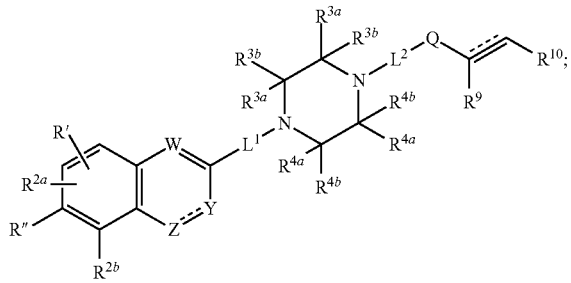
(I″b)

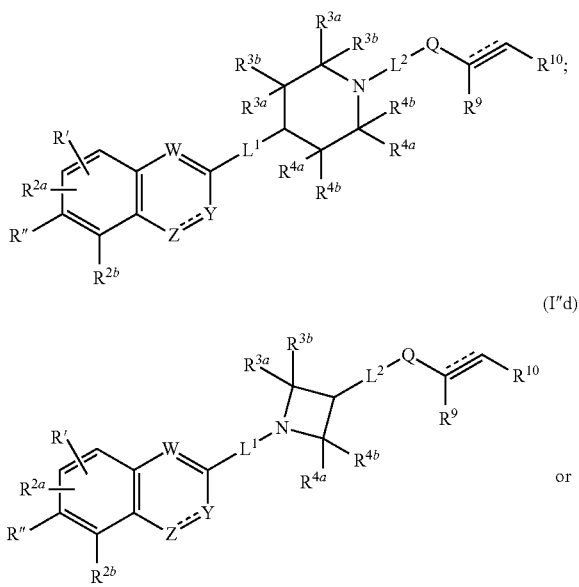
(I″c)

(I″d)

or (I″e)

In other embodiments, the compound has one of the following structures (I″f), (I″g), (I″h) or (I″i):

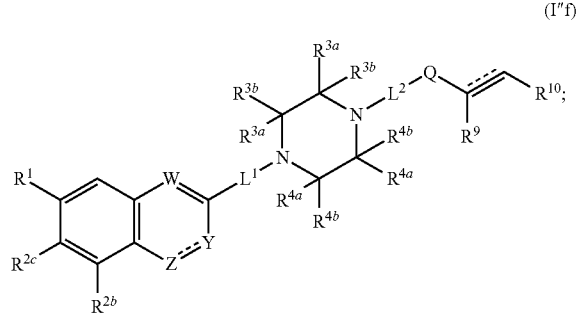
(I″f)

-continued

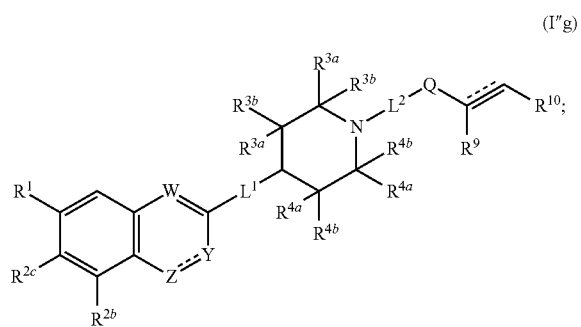
(I″g)

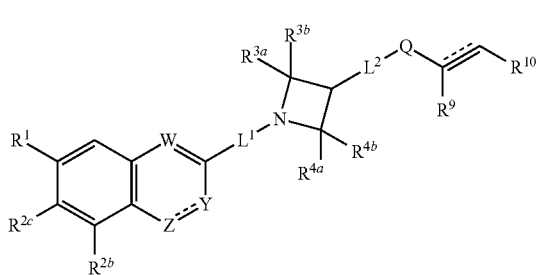
(I″h)

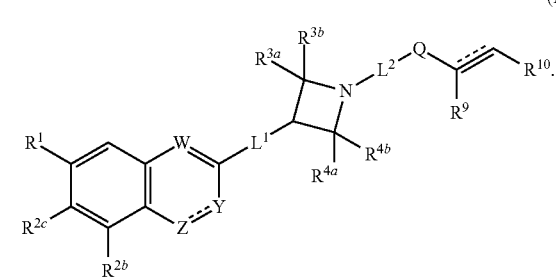
(I″i)

In some different embodiments, the compound has one of the following structures (I″j), (I″k), (I″l) or (I″m):

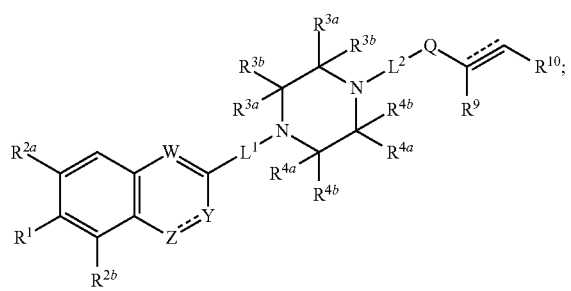
(I″j)

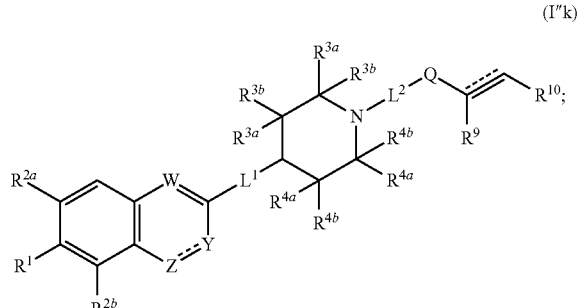
(I″k)

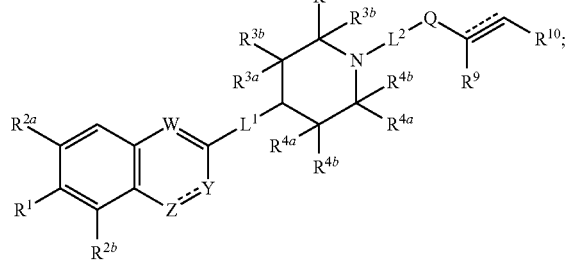
(I″l)

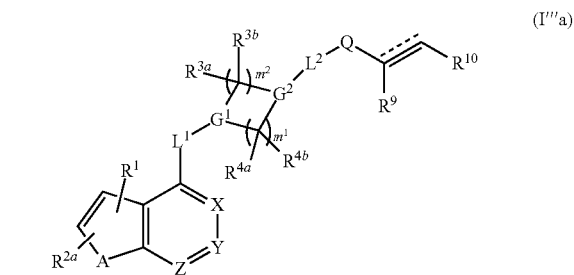
(I″m)

In other various embodiments, the compound has the following structure (I‴):

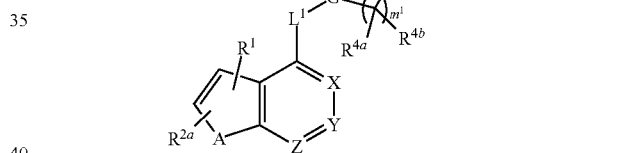
(I‴)

wherein A is NH or S.

For example, in some embodiments, the compound has the following structure (I‴a):

(I‴a)

wherein:
$\equiv$ represents a double or triple bond;
Q is —C(=O)—, —C(=NR$^8$')—, —NR$^8$C(=O)—, —S(=O)$_2$— or —NR$^8$S(=O)$_2$—;
R$^8$ is H, C$_1$-C$_6$alkyl or hydroxylalkyl;
R$^8$ is H, —OH, —CN or C$_1$-C$_6$alkyl; and
when $\equiv$ is a double bond then R$^9$ and R$^{10}$ are each independently H, cyano, carboxyl, C$_1$-C$_6$alkyl, alkoxycarbonyl, aminylalkyl, alkylaminylalkyl, heteroaryl or hydroxylalkyl or $R^9$ and $R^{10}$ join to form a carbocyclic or heterocyclic ring;

when ≡ is a triple bond then $R^9$ is absent and $R^{10}$ is H, $C_1$-$C_6$alkyl, aminylalkyl, alkylaminylalkyl or hydroxylalkyl; and A is NH or S.

In some of the foregoing embodiments of compound (I'''a), Q is Q is —C(=O)—, —NR$^8$C(=O)—, —S(=O)$_2$— or —NR$^8$S(=O)$_2$—.

In some other of the foregoing embodiments of compound (I'''a), Q is —C(=NR$^{8'}$)—, wherein R$^{8'}$ is H, —OH, —CN or $C_1$-$C_6$alkyl. For example, in some embodiments R$^{8'}$ is H. In other embodiments, R$^{8'}$ is —CN. In other embodiments, R$^{8'}$ is —OH.

In other embodiments, the compound has one of the following structures (I'''b), (I'''c), (I'''d) or (I'''e):

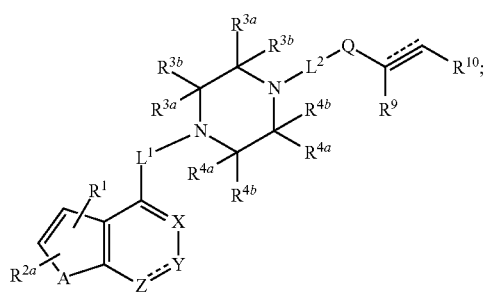

(I'''b)

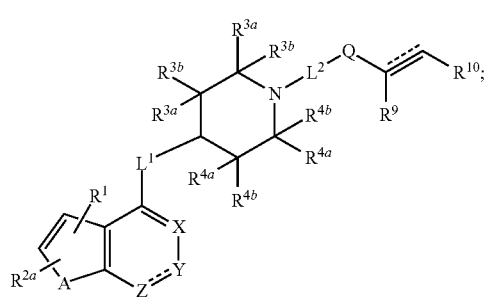

(I'''c)

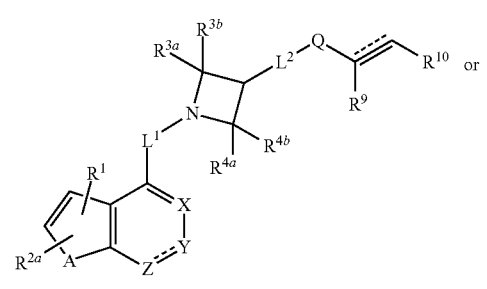

(I'''d)

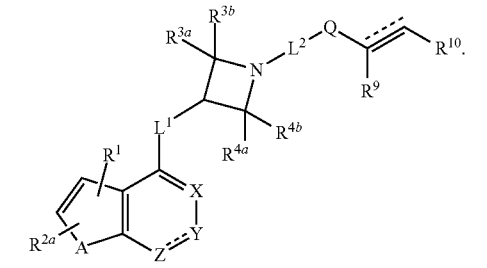

(I'''e)

In still more embodiments, the compound has one of the following structures (I'''f), (I'''g), (I'''h) or (I'''i):

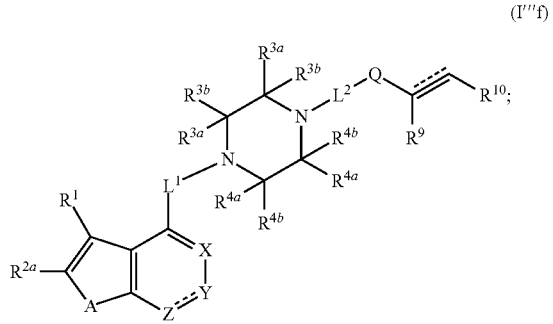

(I'''f)

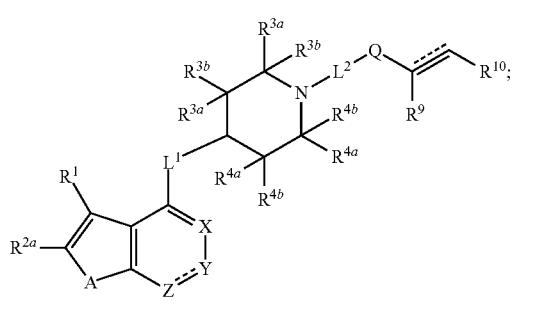

(I'''g)

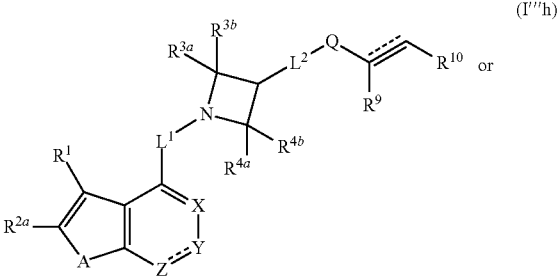

(I'''h)

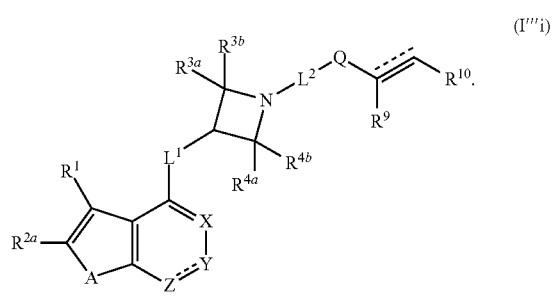

(I'''i)

In certain embodiments of any of the foregoing, at least one of $G^1$ or $G^2$ is N. In other embodiments, at least one of W, X or Y is N or NR$^5$. In other embodiments, at least one of W, X or Y is N and at least one of W, X or Y is CR$^6$. For example, in some embodiments two of W, X and Y are N and one of W, X and Y is CR$^6$.

In some embodiments, at least one of W, X or Y is N or NR$^5$, wherein R$^5$ is a bond to L$^1$. In some other embodiments, at least one of W, X or Y is N or CR$^6$, wherein R$^6$ is a bond to L$^1$.

For example, in some different embodiments, the compound has one of the following structures:

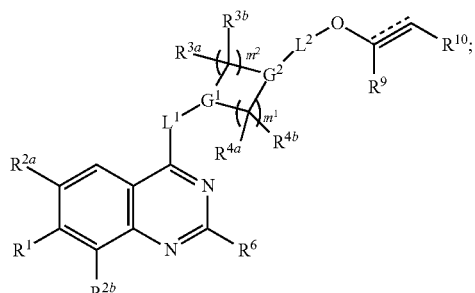
(I'n)

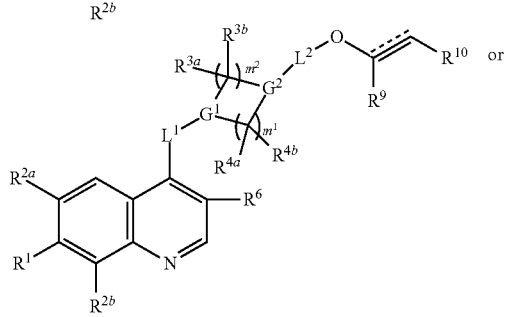
or

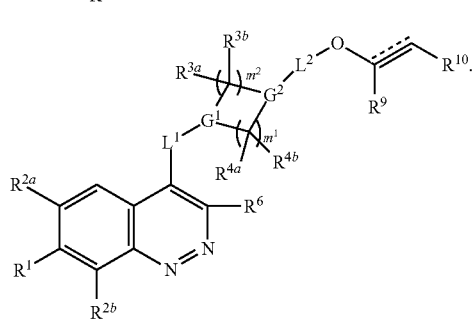
(I'p)

wherein:
≡ represents a double or triple bond;
Q is —C(=O)—, —C(=NR$^{8'}$)—, —NR$^8$C(=O)—, —S(=O)$_2$— or —NR$^8$S(=O)$_2$—;
R$^8$ is H, C$_1$-C$_6$alkyl or hydroxylalkyl;
R$^{8'}$ is H, —OH, —CN or C$_1$-C$_6$alkyl;
when ≡ is a double bond then R$^9$ and R$^{10}$ are each independently H, cyano, carboxyl, C$_1$-C$_6$alkyl, alkoxycarbonyl, aminylalkyl, alkylaminylalkyl, heteroaryl or hydroxylalkyl or R$^9$ and R$^{10}$ join to form a carbocyclic or heterocyclic ring; and
when ≡ is a triple bond then R$^9$ is absent and R$^{10}$ is H, C$_1$-C$_6$alkyl, aminylalkyl, alkylaminylalkyl or hydroxylalkyl.

In some embodiments of the compounds of structures (I'n), (I'o) or (I'p), R$^1$ is aryl or heteroaryl and R$^{2a}$ and R$^{2b}$ are independently selected from H and halo, for example in some further embodiments R$^1$ is aryl or heteroaryl and R$^{2a}$ and R$^{2b}$ are independently selected from halo, such as chloro and fluoro. In some embodiments, R$^1$ is aryl or heteroaryl, R$^{2a}$ is chloro and R$^{2b}$ is fluoro. In other embodiments R$^1$ is aryl or heteroaryl, one of R$^{2a}$ or R$^{2b}$ is halo, such as chloro or fluoro, and the other one of R$^{2a}$ or R$^{2b}$ is H. In other embodiments of the foregoing, R$^6$ is H, cyano, cyanoalkyl, amino, or C$_1$-C$_6$ alkyl.

In other different embodiments, the bond between W and X Y and Z are both single bonds. For example, in some embodiments the compound has one of the following structures (I''''a) or (I''''b):

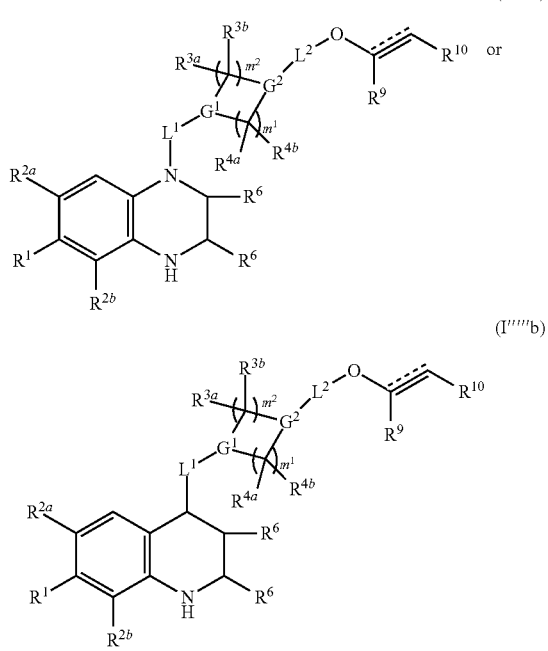
(I''''a)

(I''''b)

wherein:
≡ represents a double or triple bond;
Q is —C(=O)—, —C(=NR$^{8'}$)—, —NR$^8$C(=O)—, —S(=O)$_2$— or —NR$^8$S(=O)$_2$—;
R$^8$ is H, C$_1$-C$_6$alkyl or hydroxylalkyl;
R$^{8'}$ is H, —OH, —CN or C$_1$-C$_6$alkyl;
when ≡ is a double bond then R$^9$ and R$^{10}$ are each independently H, cyano, carboxyl, C$_1$-C$_6$alkyl, alkoxycarbonyl, aminylalkyl, alkylaminylalkyl, heteroaryl or hydroxylalkyl or R$^9$ and R$^{10}$ join to form a carbocyclic or heterocyclic ring; and
when ≡ is a triple bond then R$^9$ is absent and R$^{10}$ is H, C$_1$-C$_6$alkyl, aminylalkyl, alkylaminylalkyl or hydroxylalkyl.

In some embodiments of the compounds of structures (I''''a) or (I''''b), R$^1$ is aryl or heteroaryl and R$^{2a}$ and R$^{2b}$ are independently selected from H and halo, for example in some further embodiments R$^1$ is aryl or heteroaryl and R$^{2a}$ and R$^{2b}$ are independently selected from halo, such as chloro and fluoro. In some embodiments, R$^1$ is aryl or heteroaryl, R$^{2a}$ is chloro and R$^{2b}$ is fluoro. In other embodiments R$^1$ is aryl or heteroaryl, one of R$^{2a}$ or R$^{2b}$ is halo, such as chloro or fluoro, and the other one of R$^{2a}$ or R$^{2b}$ is H. In other embodiments of the foregoing, R$^6$ is H, cyano, cyanoalkyl, amino, or C$_1$-C$_6$ alkyl.

In yet more of any of the foregoing embodiments, E has the following structure:

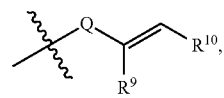

wherein:
Q is —C(=O)—, —C(=NR$^{8'}$)—, —NR$^8$C(=O)—, —S(=O)$_2$— or —NR$_8$S(=O)$_2$—;
R$^8$ is H, C$_1$-C$_6$alkyl or hydroxylalkyl;
R$^{8'}$ is H, —OH, —CN or C$_1$-C$_6$alkyl; and $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is Q is —C(=O)—, —NR$^8$C(=O)—, —S(=O)$_2$— or —NR$^8$S(=O)$_2$—.

In some other of the foregoing embodiments, Q is —C(=NR$^{8'}$)—, wherein R$^{8'}$ is H, —OH, —CN or $C_1$-$C_6$alkyl. For example, in some embodiments R$^{8'}$ is H. In other embodiments, R$^{8'}$ is —CN. In other embodiments, R$^{8'}$ is —OH.

In still other of any of the foregoing embodiments, E has the following structure:

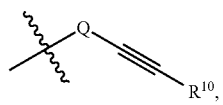

wherein:

Q is —C(=O)—, —NR$^8$C(=O)—, —S(=O)$_2$— or —NR$^8$S(=O)$_2$—;

R$^8$ is H, $C_1$-$C_6$alkyl or hydroxylalkyl; and

R$^{10}$ is H, $C_1$-$C_6$alkyl, aminylalkyl, alkylaminylalkyl or hydroxylalkyl.

In some embodiments of any of the compounds described herein, $C_1$-$C_6$ haloalkyl is $CF_3$ (e.g., when one or more of $R^{2a}$, $R^{2b}$ or $R^{2c}$ is $C_1$-$C_6$ haloalkyl).

In some embodiments $m^1$ is 1. In other embodiments $m^1$ is 2. In still more embodiments, $m^1$ is 3. In different embodiments, $m^2$ is 1. In some other embodiments, $m^2$ is 2. In yet still more embodiments, $m^2$ is 3.

In some other particular embodiments of any of the foregoing compounds, $m^1$ is 1, and $m^2$ is 1. In other embodiments, $m^1$ is 1 and, $m^2$ is 2. In still other embodiments $m^1$ is 2, and $m^2$ is 2. In more embodiments, $m^1$ is 1, and $m^2$ is 3.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

Without wishing to be bound by theory, Applicants believe correct selection of the R$^1$ substituent may play a part in the compounds' inhibitory activity (e.g., against KRAS, HRAS or NRAS G12C). In some embodiments, R$^1$ is aryl or hetercyclyl (e.g., heteroaryl or aliphatic heterocyclyl), each of which is optionally substituted with one or more substituents. In some embodiments, R$^1$ is capable of reversible interaction with KRAS, HRAS or NRAS G12C mutant protein. In some embodiments R$^1$ has high affinity towards KRAS, HRAS or NRAS and is highly specific towards G12C KRAS, HRAS or NRAS. In some embodiments R$^1$ is capable of hydrophobic interaction with KRAS, HRAS or NRAS G12C. In some embodiments R$^1$ is able to form hydrogen bonds with various residues of G12C KRAS, HRAS or NRAS protein.

In other of the foregoing embodiments, R$^1$ is heterocyclyl, heteroaryl or aryl.

In certain embodiments of any of the foregoing, R$^1$ is aryl. For example, in some embodiments R$^1$ is phenyl. In other embodiments, R$^1$ is napthyl. In some of these embodiments, R$^1$ is unsubstituted aryl, such as unsubstituted phenyl or unsubstituted napthyl. In other embodiments, R$^1$ is substituted with one or more substituents. In some of these embodiments, the substituents are selected from halo, cyano, hydroxyl, $C_1$-$C_6$alkyl, $C_1$-$C_6$alkoxy and $C_3$-$C_8$cycloalkyl. In other more specific embodiments, the substituents are selected from fluoro, chloro, bromo, hydroxyl, methoxy and cyclopropyl.

In other embodiments, the R$^1$ substituents are selected from halo, cyano, cyano$C_1$-$C_6$alkyl, cyano$C_3$-$C_8$cycloalkyl, hydroxyl, $C_1$-$C_6$alkyl, $C_1$-$C_6$alkylcycloalky, $C_2$-$C_6$alkynyl, $C_1$-$C_6$alkoxy, $C_1$-$C_6$haloalkoxy, $C_1$-$C_6$alkylaminyl, $C_1$-$C_6$ alkylcarbonylaminyl, $C_1$-$C_6$hydroxylalkyl, $C_1$-$C_6$haloalkyl, $C_1$-$C_6$alkoxyalkyl, aminylsulfone, aminylcarbonyl, aminylcarbonyl$C_1$-$C_6$alkyl, aminylcarbonyl$C_3$-$C_8$cycloalkyl, $C_1$-$C_6$alkylaminylcarbonyl, $C_3$-$C_8$cycloalkylaminyl- carbonyl, $C_3$-$C_8$cycloalkylalkyl and $C_3$-$C_8$cycloalkyl, $C_3$-$C_8$fused cycloalkyl and heteroaryl.

In still other embodiments, the R$^1$ substituents are selected from fluoro, chloro, bromo, cyano, hydroxyl, hydroxylmethyl, methoxy, methoxymethyl, ethyl, isopropyl, trifluoromethyl, aminylcarbonyl and cyclopropyl.

In still more embodiments, the R$^1$ substituents are selected from fluoro, chloro, bromo, cyano, hydroxyl, hydroxylmethyl, methoxy, methoxymethyl, methyl, ethyl, isopropyl, difluoromethyl, trifluoromethyl, aminylcarbonyl and cyclopropyl.

In certain embodiments, R$^1$ has one of the following structures:

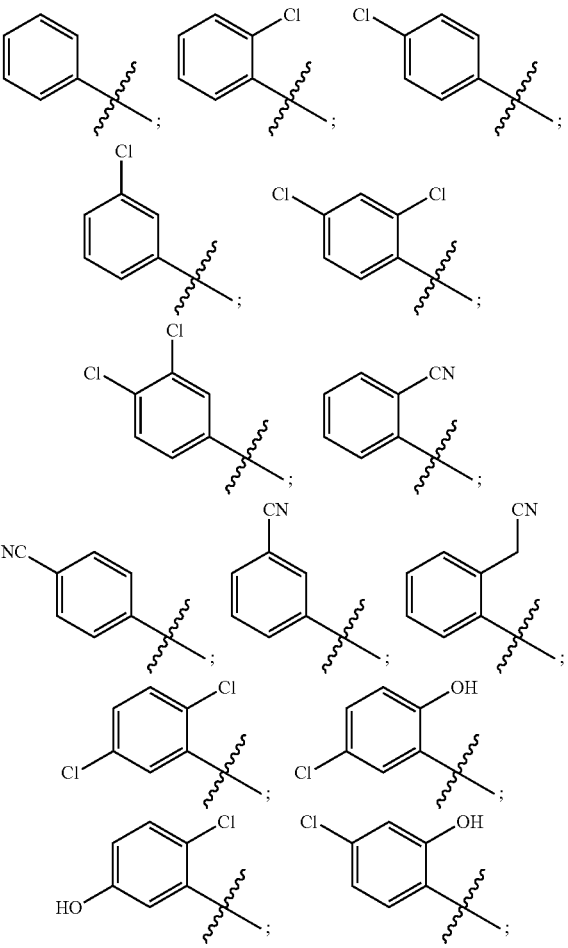

-continued
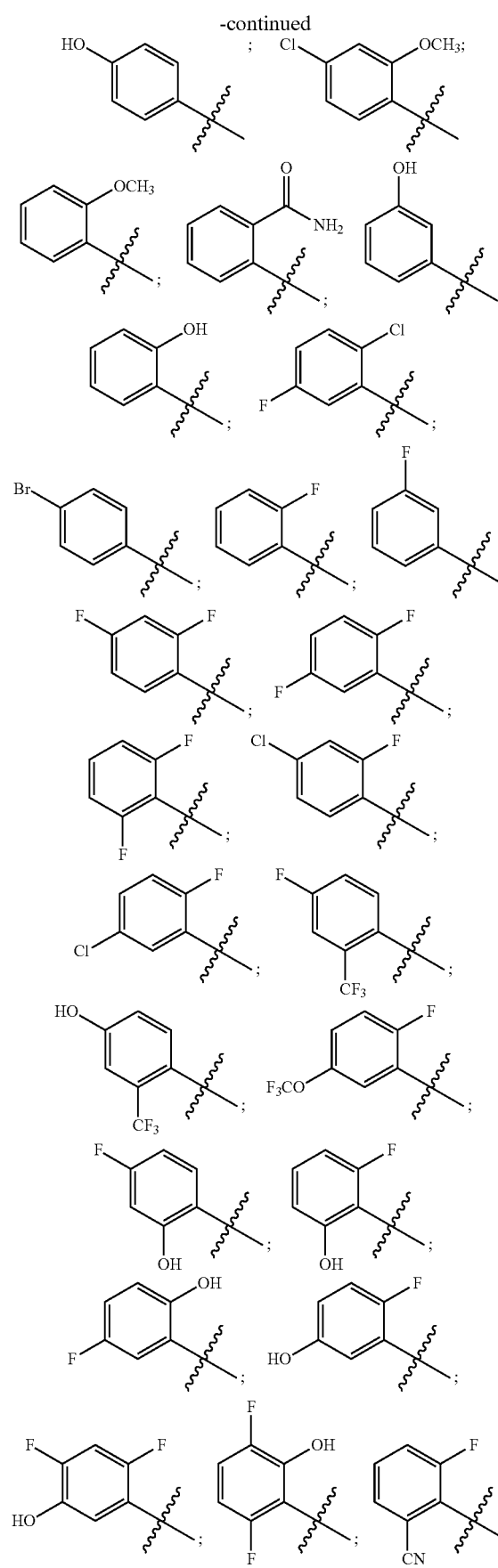
-continued
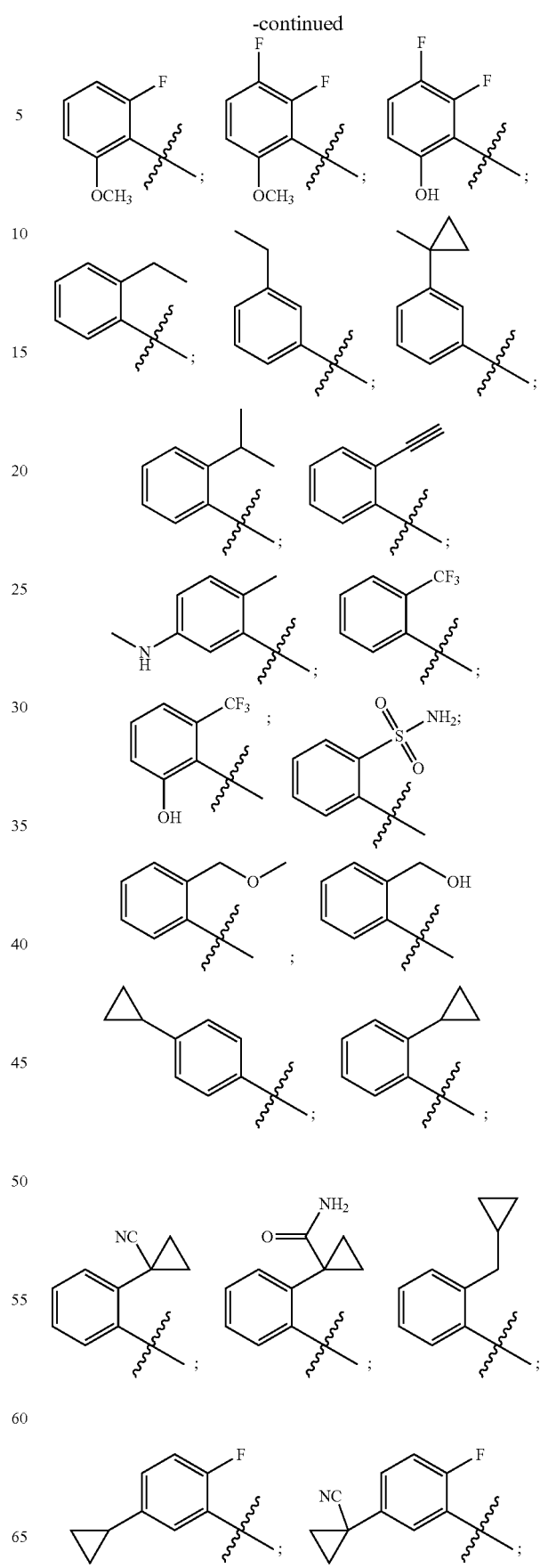

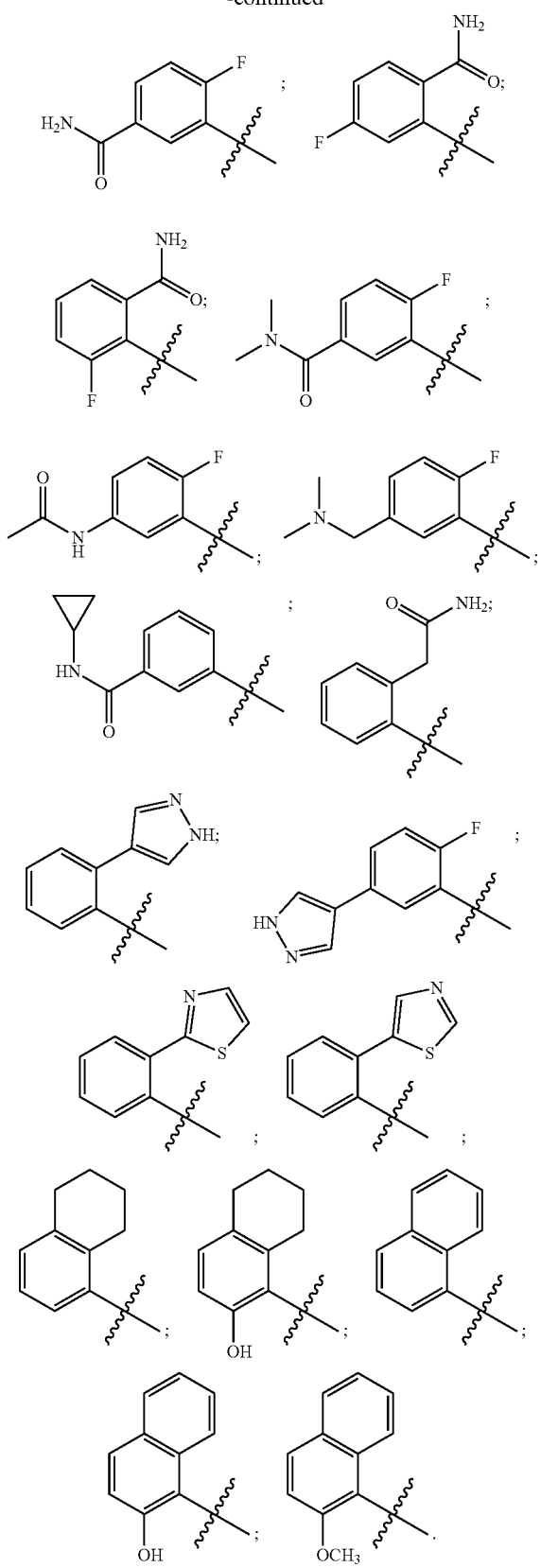
In other of the foregoing embodiments, R¹ has one of the following structures:
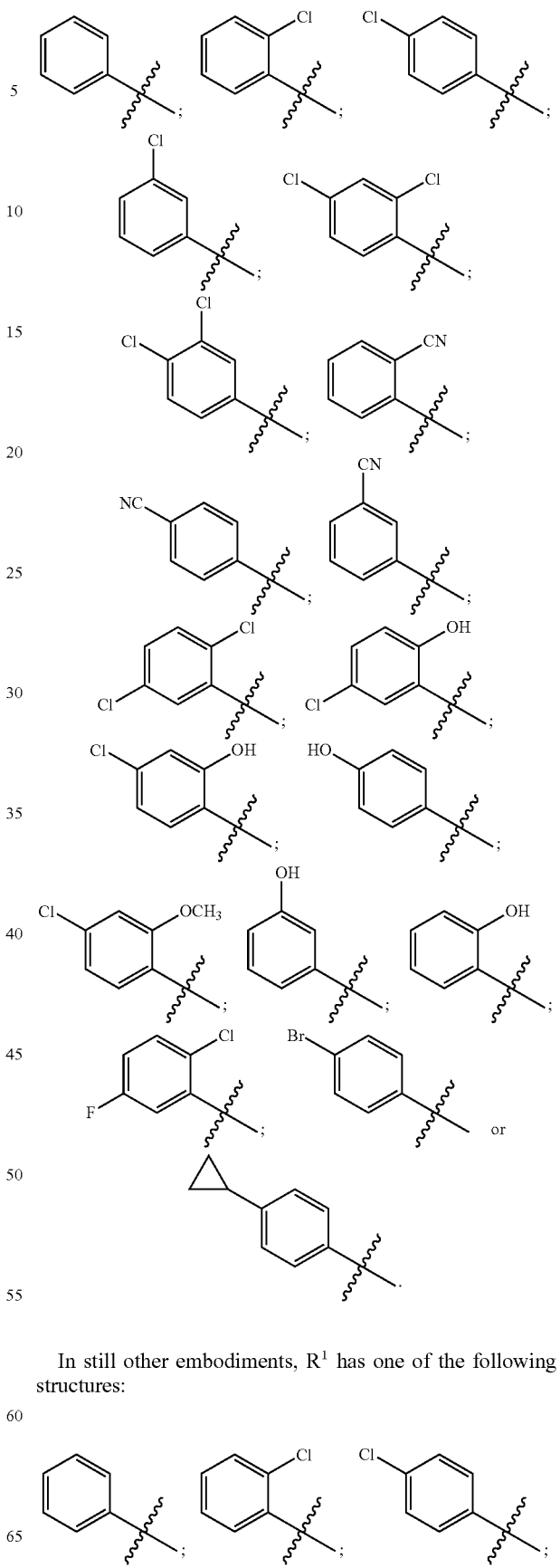
In still other embodiments, R¹ has one of the following structures:

-continued
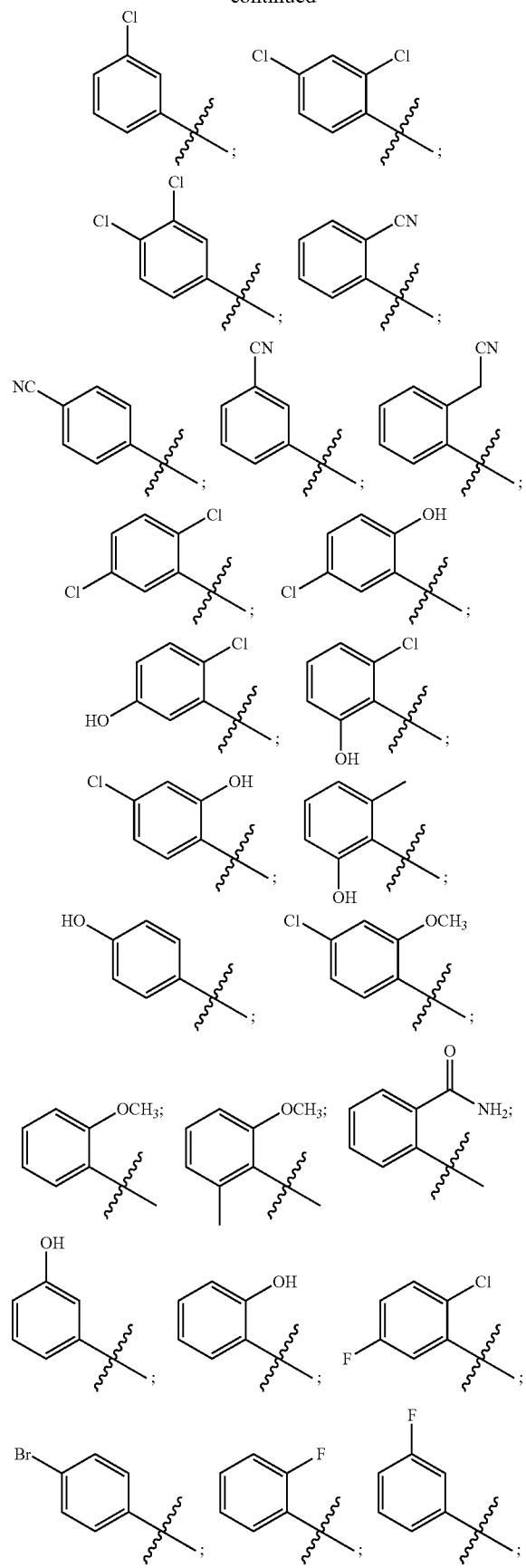
-continued
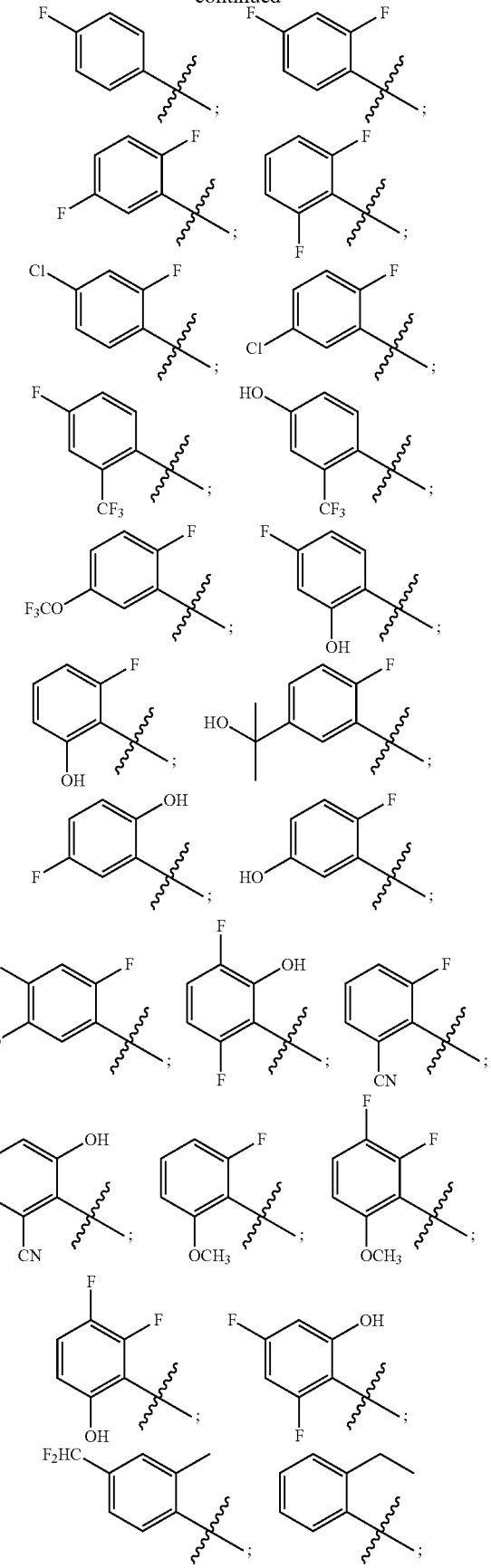

-continued
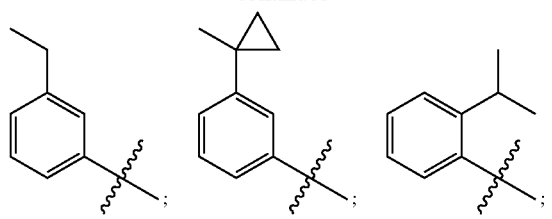
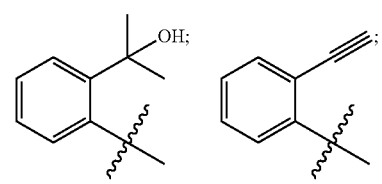
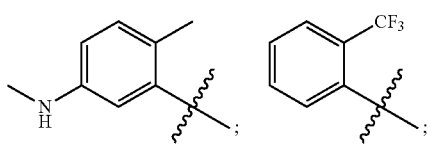
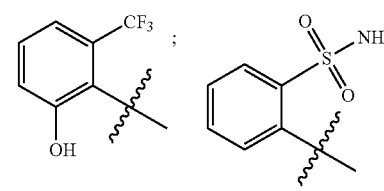
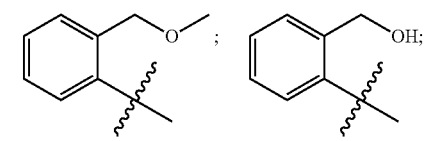
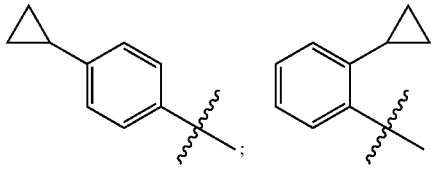
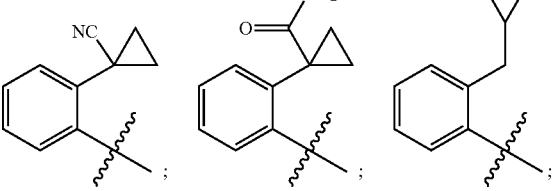
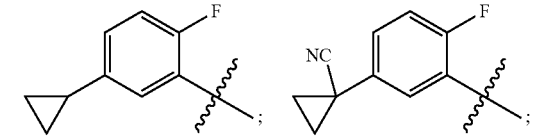
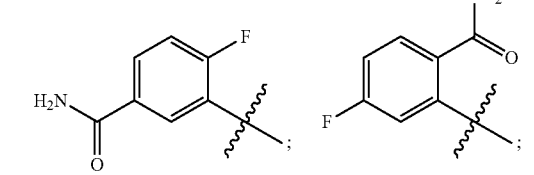
-continued
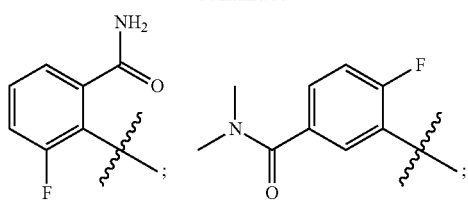
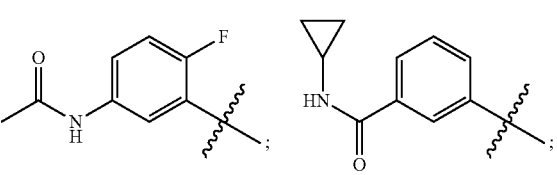
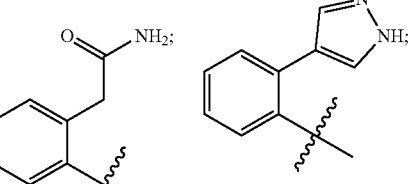
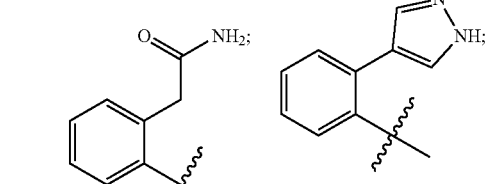
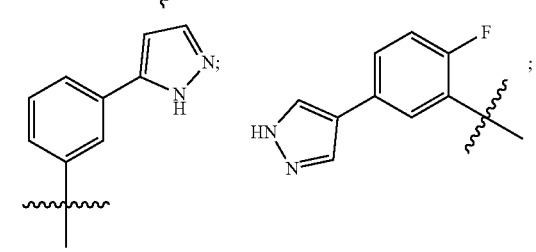
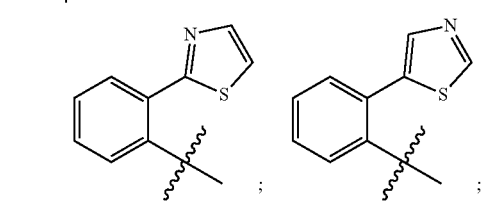
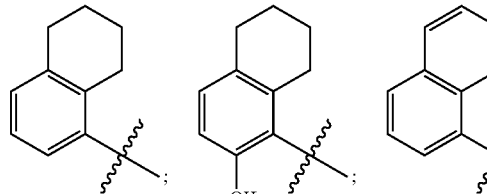
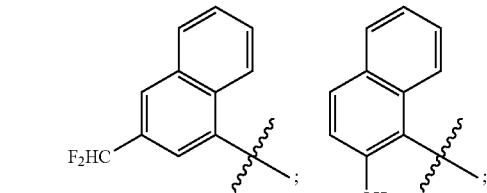
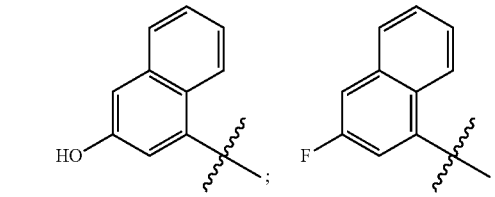

-continued

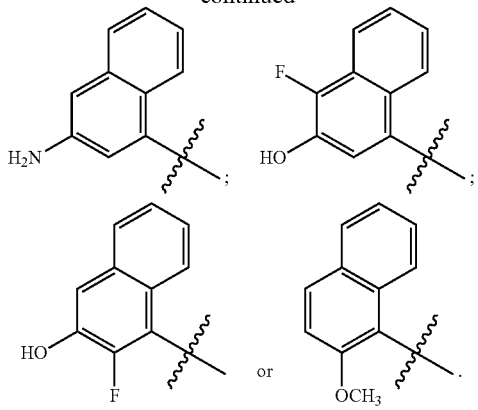

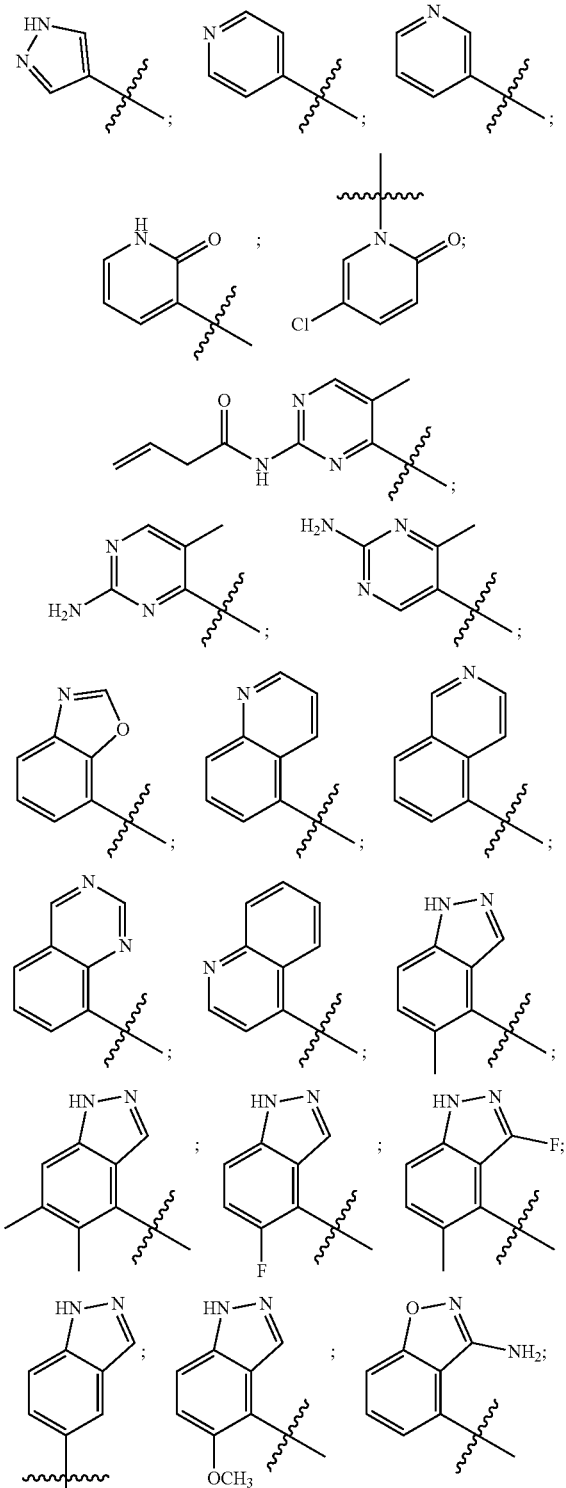

In some different embodiments of any of the foregoing, $R^1$ is heteroaryl. In certain embodiments, $R^1$ comprises oxygen, sulfur, nitrogen or combinations thereof. In some of these embodiments, $R^1$ comprises sulfur or nitrogen. In certain embodiments, $R^1$ is thiophenyl, pyridinyl, pyridinonyl, pyrimidinyl, benzooxazolyl, benzoisoxazolyl, benzodioxazolyl, benzoimidazolyl, quinolinyl, quinolinonyl, dihydroquinolinonyl, tetrahydroquinolinyl, quinazolinyl, indazolyl, indolinonyl, benzothiophenyl or dihydrobenzodioxinyl.

In some embodiments, $R^1$ is substituted or unsubstituted indazolyl. In some of these embodiments the indazolyl is substituted with one or more $C_1$-$C_6$ alkyl, $C_1$-$C_6$ alkoxy and/or halo groups. For example, in some embodiments, the indazolyl is substituted with one or more methyl, methoxy, chloro and/or fluoro groups.

For example, in some embodiments $R^1$ is pyridinyl. In some embodiments $R^1$ is unsubstituted pyridinyl, for example unsubstituted pyridin-4-yl or unsubstituted pyridin-3-yl. In other embodiments $R^1$ is thiophenyl. In some embodiments $R^1$ is unsubstituted thiophenyl, for example unsubstituted thiophen-2-yl.

In other embodiments, $R^1$ is substituted with one or more substituents. For example, in some embodiments, the substituents are selected from halo, $C_1$-$C_6$alkyl, $C_1$-$C_6$alkoxy, or $C_2$-$C_6$alkenylcarbonylaminyl. In some of these embodiments, the substituents are selected from halo and $C_1$-$C_6$alkyl. In other embodiments, the substituents are selected from fluoro, chloro, amino and methyl. For example, in more specific embodiments, the substituents are selected from chloro and methyl. In other embodiments at least one R1 substituent is fluoro.

In some embodiments, $R^1$ has one of the following structures:

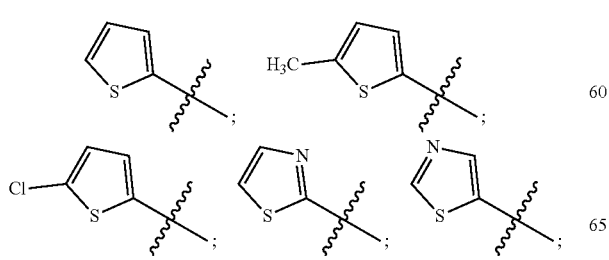

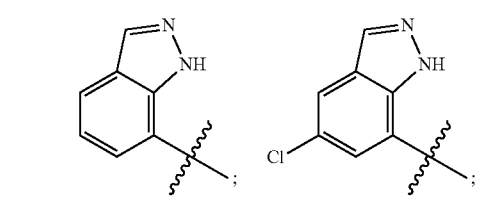

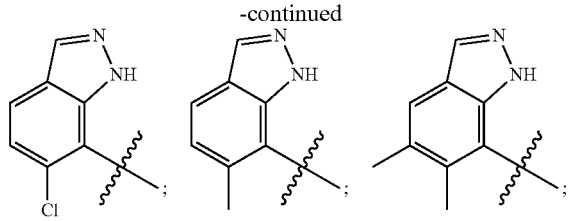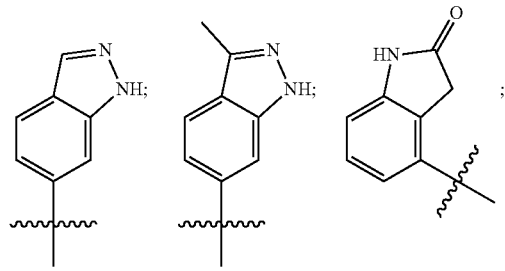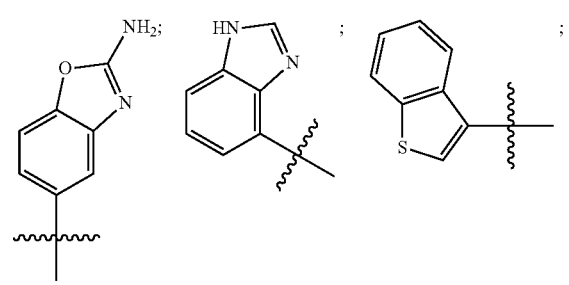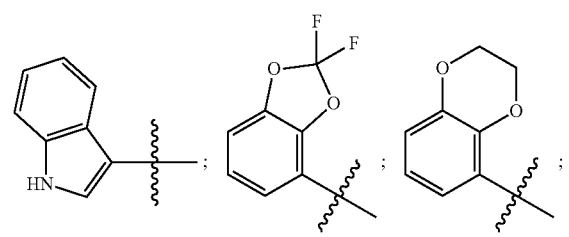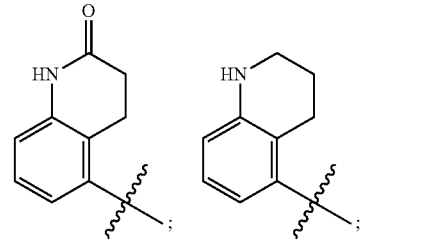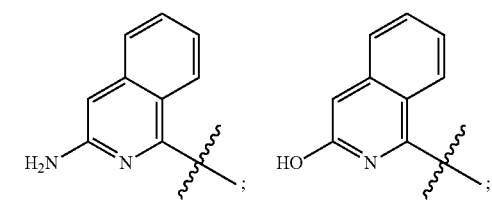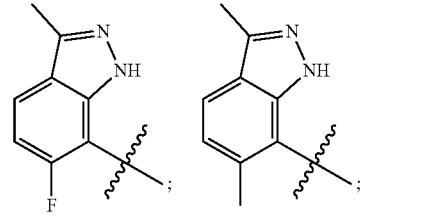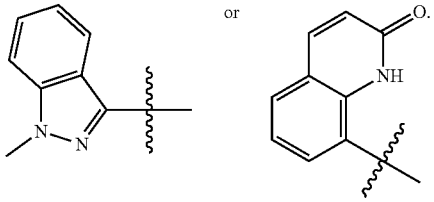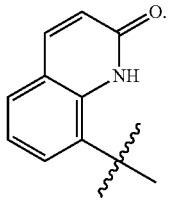
In certain embodiments. R[1] has one of the following structures:
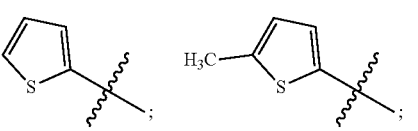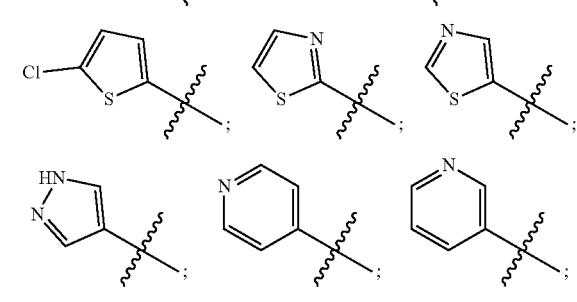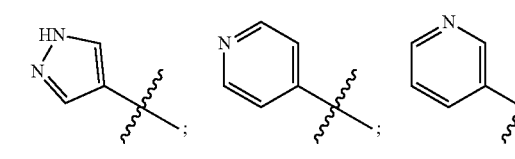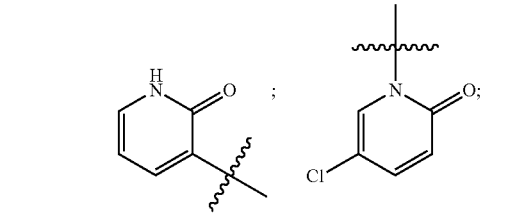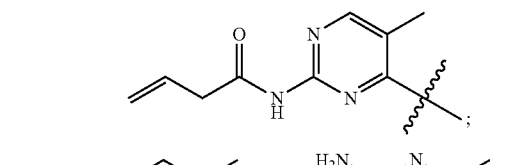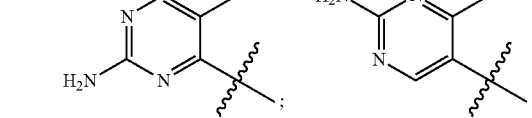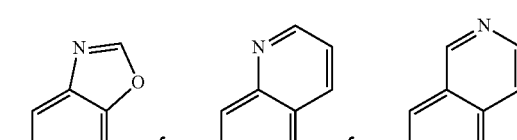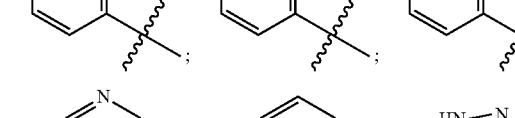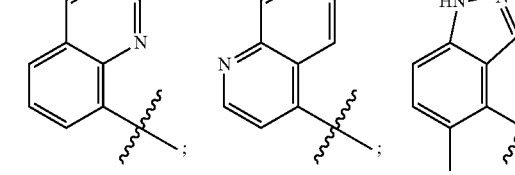

-continued

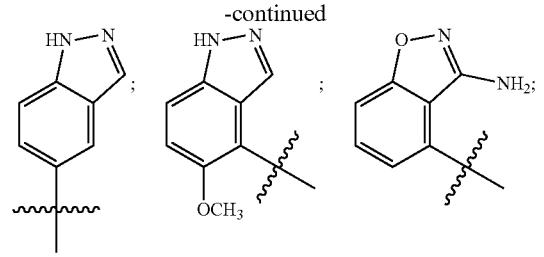

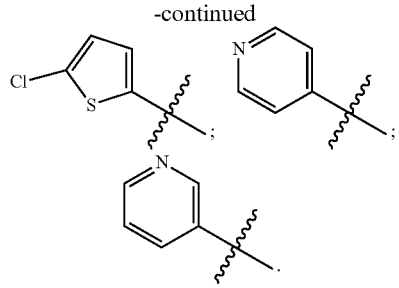

In still other embodiments, $R^1$ is aliphatic heterocyclyl. In some embodiments the aliphatic heterocyclyl comprises oxygen and/or nitrogen. In some further embodiments, $R^1$ is morpholinyl. For example, in some embodiments $R^1$ has the following structure:

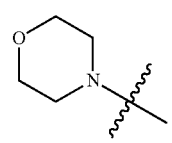 [SMILES: *N1CCOCC1]

In various embodiments of the foregoing, $R^1$ is unsubstituted.

In some of the foregoing embodiments, $R^{2a}$ is H. In other embodiments, $R^{2a}$ is halo, for example in some embodiments $R^{2a}$ is chloro or fluoro. In still other embodiments of the foregoing, $R^{2a}$ is $C_1$-$C_6$alkyl. For example, in some embodiments $R^{2a}$ is $C_3$-$C_8$ cycloalkyl, such as cyclopropyl.

In other embodiments of the foregoing compounds, $R^{2b}$ and $R^{2c}$, when present, are H. In different embodiments, $R^{2b}$ and $R^{2c}$, when present, are each independently halo. In yet other embodiments, $R^{2b}$, when present, is halo. In more embodiments, $R^{2c}$, when present, is halo. In certain of the foregoing embodiments, halo is chloro or fluoro.

The Q moiety is typically selected to optimize the reactivity (i.e., electrophilicity) of E. In certain of the foregoing embodiments, Q is —C(=O)—. In other embodiments, Q is —S(=O)$_2$—. In still more embodiments, Q is —NR$_8$C(=O)—. In still more different embodiments, Q is —NR$^8$S(=O)$_2$—.

In some of the immediately foregoing embodiments, $R^8$ is H. In other of these embodiments, $R^8$ is hydroxylalkyl, for example in some embodiments the hydroxylalkyl is 2-hydroxylalkyl.

In some embodiments, Q is —C(=NR$^{8'}$)—, wherein $R^{8'}$ is H, —OH, —CN or $C_1$-$C_6$alkyl. For example, in some embodiments $R^{8'}$ is H. In other embodiments, $R^{8'}$ is —CN. In other embodiments, $R^{8'}$ is —OH.

In some of any one of the foregoing embodiments, at least one of $R^9$ or $R^{10}$ is H. For example, in some embodiments each of $R^9$ and $R^{10}$ are H.

In other of the foregoing embodiments, $R^{10}$ is alkylaminylalkyl. In some of these embodiments, $R^{10}$ has the following structure:

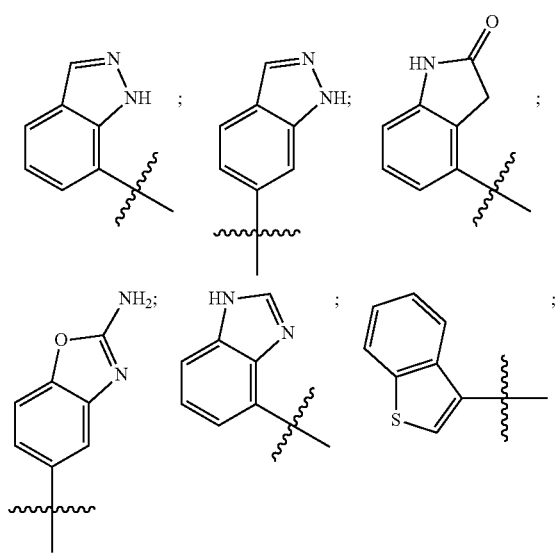

In some of the foregoing embodiments, $R^1$ has one of the following structures:

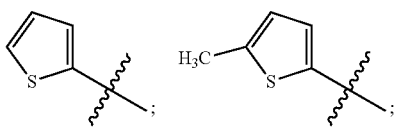

In other embodiments, $R^{10}$ is hydroxylalkyl, such as 2-hydroxylalkyl.

In some other different embodiments of the foregoing embodiments, $R^9$ and $R^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

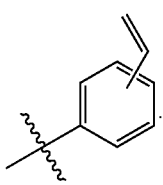

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

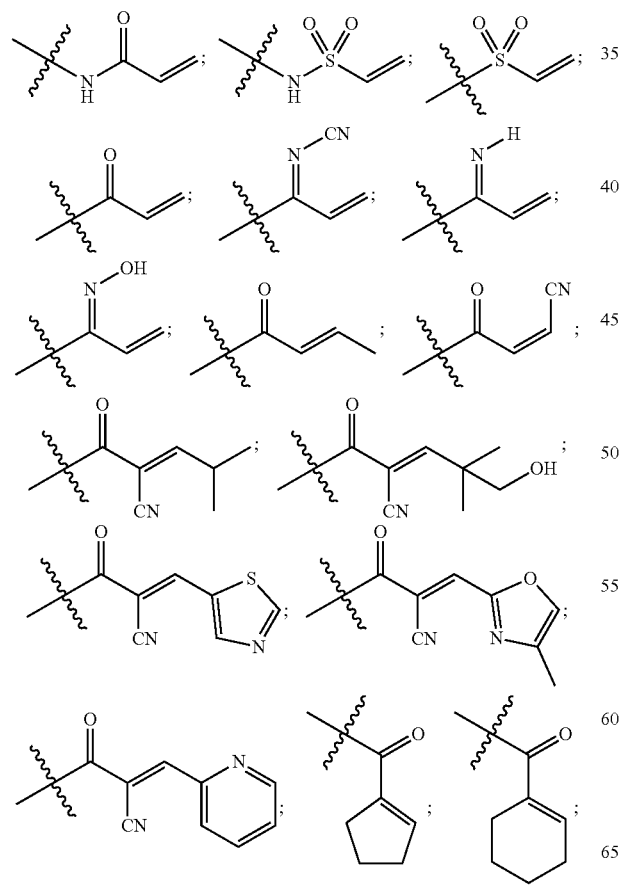

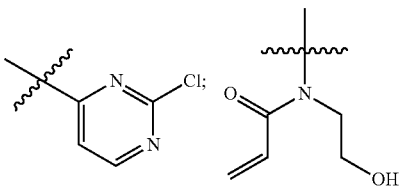

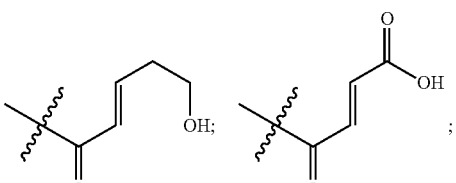

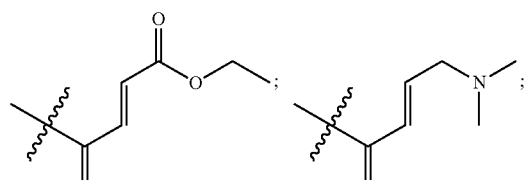

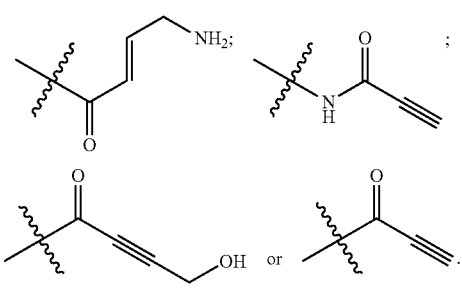

In other embodiments of any of the foregoing, E has one of the following structures:

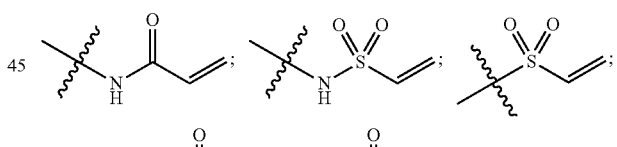

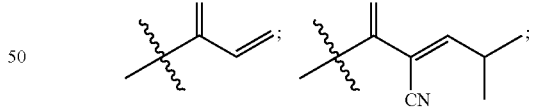

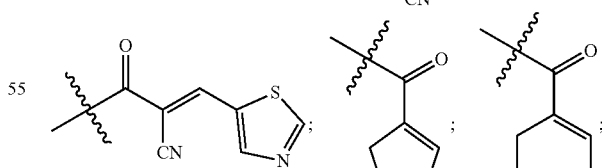

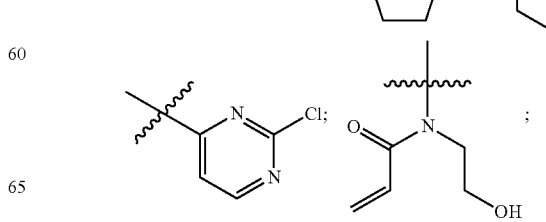

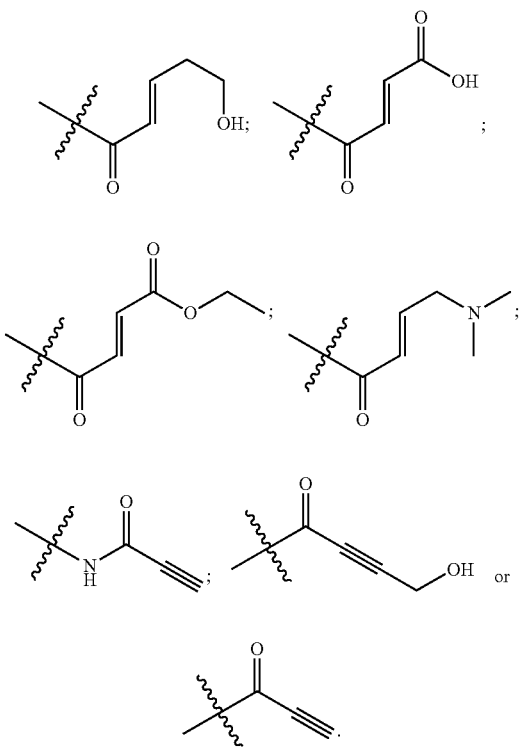

In different embodiments E has one of the following structures:

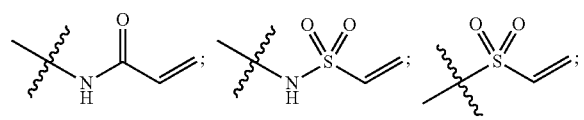

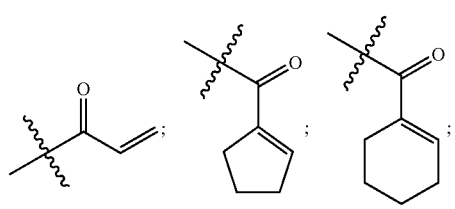

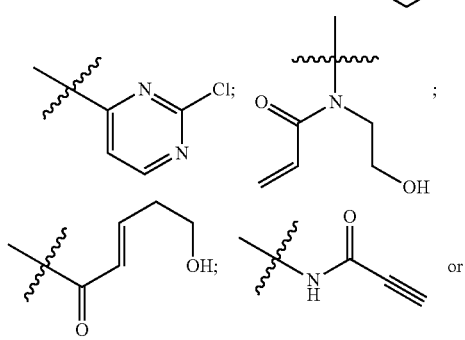

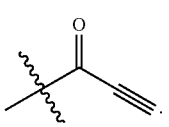

In some cases E has one of the following structures:

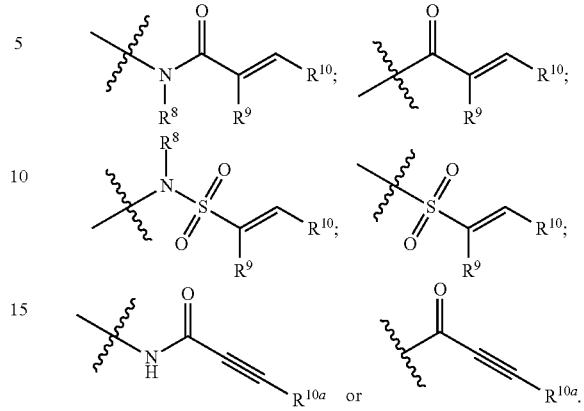

wherein:
$R^8$ is H or $C_1$-$C_6$alkyl;
$R^9$ is H, cyano or $C_1$-$C_6$alkyl, or $R^9$ joins with $R^{10}$ to form a carbocycle;
$R^{10}$ is H or $C_1$-$C_6$alkyl or $R^{10}$ joins with $R^9$ to form a carbocycle and
$R^{10a}$ is H or $C_1$-$C_6$alkyl.

In some embodiments E is

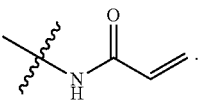 [SMILES: *NC(=O)C=C]

In some embodiments E is

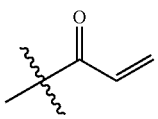 [SMILES: *C(=O)C=C]

In some embodiments E is

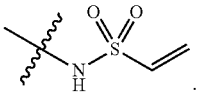 [SMILES: *NS(=O)(=O)C=C]

In some of any of the foregoing embodiments, $L^1$ is a bond. In other embodiments, $L^1$ is $NR^7$. For example, in some of these embodiments, $R^7$ is $C_1$-$C_6$alkyl. In other embodiments, $L^1$ is NH.

$L^2$ can be selected to provide proper spacing and/or orientation for the E group to form a bond with the KRAS, HRAS or NRAS protein. In some of the foregoing embodiments, $L^2$ is a bond. In other of the foregoing embodiments, $L^2$ is alkylene. In some embodiments, the alkylene is substituted/In other embodiments the alkylene is unsubstituted. For example, in some embodiments $L^2$ is $CH_2$ or $CH_2CH_2$.

In certain embodiments, $R^{3a}$ and $R^{3b}$ are, at each occurrence, independently H, —OH, —$NH_2$, —$CO_2H$, halo, cyano, hydroxylalkly, aminylalkyl, cyanoalkyl, carboxyalkyl or aminylcarbonyl, and $R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl.

In other of the foregoing embodiments, $R^{3a}$ and $R^{4a}$ are, at each occurrence, independently H, —OH, hydroxylalkly, cyano, or aminylcarbonyl and $R^{3b}$ and $R^{4b}$ are H.

In certain other embodiments, $R^{3a}$ and $R^{4a}$ are H and $R^{3b}$ and $R^{4b}$ are, at each occurrence, independently H, —OH, —NH$_2$, —CO$_2$H, halo, cyano, hydroxylalkly, aminylalkyl, cyanoalkyl, carboxyalkyl or aminylcarbonyl.

In any of the foregoing embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ are H.

In some embodiments, $R^{3a}$ is —OH, —NH$_2$, —CO$_2$H, halo, cyano, hydroxylalkly, aminylalkyl, cyanoalkyl, carboxyalkyl or aminylcarbonyl, and $R^{3b}$, $R^{4a}$ and $R^{4b}$ are H.

In other embodiments, $R^{4a}$ is —OH, —NH$_2$, —CO$_2$H, halo, cyano, hydroxylalkly, aminylalkyl, cyanoalkyl, carboxyalkyl or aminylcarbonyl, and $R^{3a}$, $R^{3b}$ and $R^{4b}$ are H.

In other embodiments, $R^{3a}$ is H, —OH, —NH$_2$, —CO$_2$H, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;

In still more embodiments, $R^{4a}$ is H, —OH, —NH$_2$, —CO$_2$H, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring.

In still other embodiments, $R^{3a}$ or $R^{4a}$ is aminylcarbonyl. For example, in certain embodiments, the aminylcarbonyl is

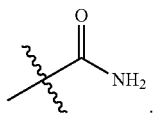 [SMILES: *C(N)=O]

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some embodiments, $R^6$ is, at each occurrence, independently H, oxo, cyano, cyanoalkyl, aminyl, aminylalkyl, aminylalkylaminyl, aminylcarbonyl, aminylsulfonyl, —CO$_2$NR$^a$R$^b$, wherein R$^a$ and R$^b$, are each independently H or C1-C6 alkyl or R$^a$ and R$^b$ join to form a carbocyclic or heterocyclic ring, alkylaminyl, haloalkylaminyl, hydroxylalkyaminyl, amindinylalkyl, amidinylalkoxy, amindinylalkyaminyl, guanidinylalkyl, guanidinylalkoxy, guanidinylalkylaminyl, C$_1$-C$_6$ alkoxy, aminylalkoxy, alkylcarbonylaminylalkoxy, C$_1$-C$_6$ alkyl, heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl, heteroarylalkylaminyl, aryl, aryloxy, arylaminyl, arylalkylaminyl, arylalkyloxy or a bond to L$^1$.

Each of the foregoing R$^6$ moieties may be substituted with one or more substituents. For example, in some embodiments the one or more substituents are aminyl (e.g., substituted or substituted), alkylcarbonyl aminyl, hydroxyl, haloalkyl or heterocycyclyl (e.g., substituted or substituted aliphatic heterocycle or substituted or substituted heteroaryl). For example, in some embodiments, the R$^6$ moiety is C$_1$-C$_6$ alkyl, C$_1$-C$_6$ alkoxy or alkylaminyl, which is further substituted with alkylcarbonylaminyl, hydroxyl, —CN or haloalkyl. For example, in some embodiments, R$^6$ has one of the following structures:

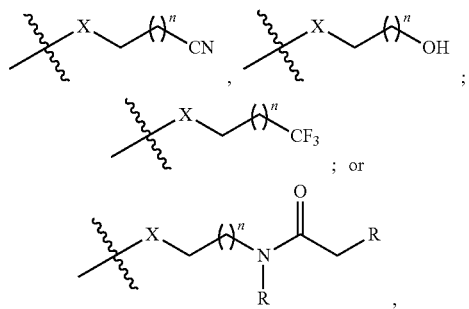

wherein X is a bond, —O— or —NR—; each R is independently H or C$_1$-C$_6$alkyl and n is an integer from 0 to 6.

Various different R$^6$ moities are included in the scope of the compounds. For example, in various embodiments, R$^6$ is H. In other embodiments, R$^6$ is —CN. In more embodiments, R$^6$ is methoxy.

In various other embodiments, R$^6$ is aminylalkyl, aminylalkyloxy or aminylalkyaminyl. For example, in some embodiments R$^6$ has the following structures:

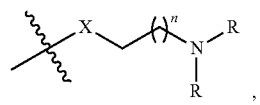

wherein X is a bond, —O— or —NR—; each R is independently H or C$_1$-C$_6$alkyl and n is an integer from 0 to 6.

In other embodiments, R$^6$ is amindinylalkyl, amidinylalkoxy, amindinylalkylaminyl, guanidinylalkyl, guanidinylalkoxy or guanidinylalkylaminyl. For example, in some embodiments R$^6$ has one of the following structures:

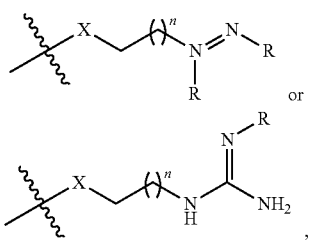

wherein X is a bond, —O— or —NR—; each R is independently H or C$_1$-C$_6$alkyl and n is an integer from 0 to 6.

In other embodiments, R$^6$ is heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl or heteroarylalkylaminyl. For example, in some embodiments R$^6$ has one of the following structures:

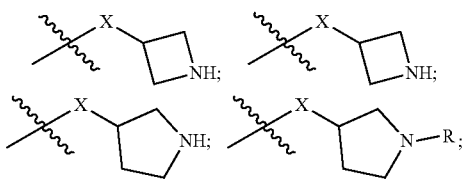

-continued

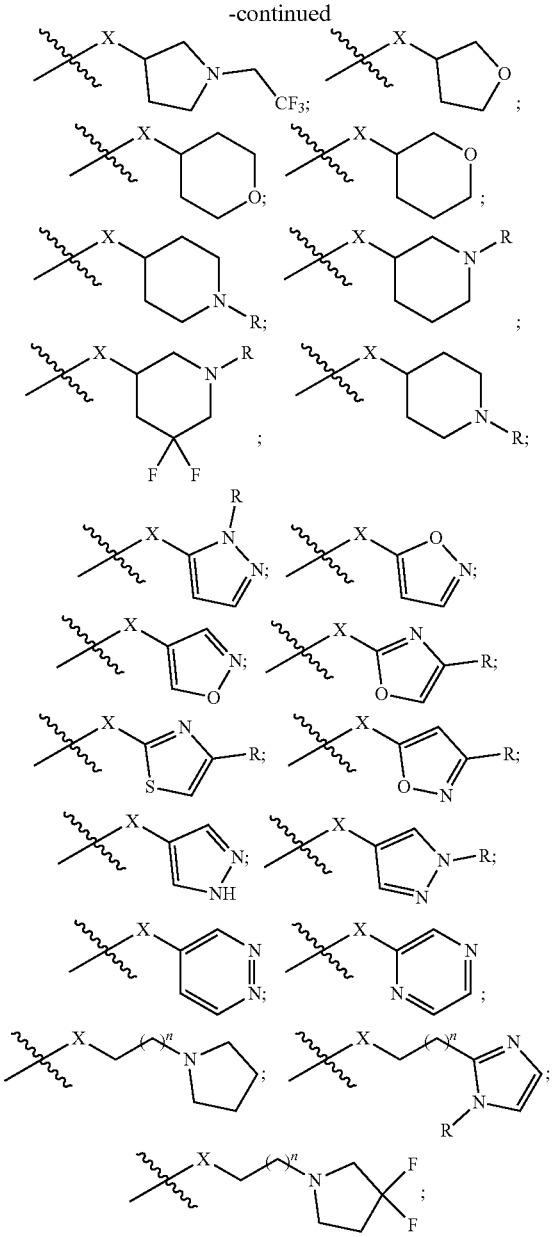

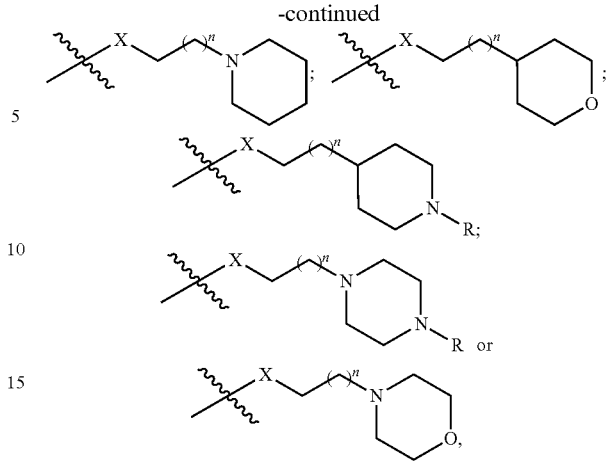

wherein X is a bond, —O— or —NR—; each R is independently H or $C_1$-$C_6$alkyl and n is an integer from 0 to 6.

In some of the foregoing embodiments, X is N. in other of the foregoing embodiments, X is N. In other of the foregoing embodiments, Z is N. In still more embodiments, X is N and Z is N.

In some embodiments, Z is N and Y is N. In other embodiments, X is N, Z is N, Y is $CR^6$, wherein $R^6$ is H and W is $CR^6$, wherein $R^6$ is a bond to $L^1$. In different embodiments, Z is N and Y is $CR^6$, wherein $R^6$ is H, W is $CR^6$, wherein $R^6$ is a bond to $L^1$ and X is $CR^6$, wherein $R^6$ is cyano, methoxy or amino.

In other embodiments, Z is N, X is $CR^6$ and $R^6$ is cyano, Y is $CR^6$, wherein $R^6$ is H and W is $CR^6$, wherein $R^6$ is a bond to $L^1$.

In other embodiments, Y is N, Z is N, W is $CR^6$, wherein $R^6$ is a bond to $L^1$ and X is $CR^6$, wherein $R^6$ is H.

In other of the foregoing embodiments, Z is a bond.

In certain embodiments, Y is $NR^5$. In some of these embodiments, $R^5$ is $C_1$-$C_6$alkyl. In other embodiments, $R^5$ is H.

In still other embodiments, X or Y is $CR^6$. In some of these embodiments, $R^6$ is, at each occurrence, independently H, cyano, amino, $C_1$-$C_6$alkoxy or a bond to $L^1$. In some other of these embodiments, $R^6$ is H. In other embodiments, $R^6$ is $C_1$-$C_6$alkoxy. In other embodiments, $R^6$ is cyano. In more embodiments, $R^6$ is methoxy. In other embodiments, $R^6$ is amino.

In various different embodiments, the compound has one of the structures set forth in Table 1 below:

TABLE 1

Representative Compounds

| No. | Structure | Name | Method | [M + H]⁺ |
|---|---|---|---|---|
| 1 | 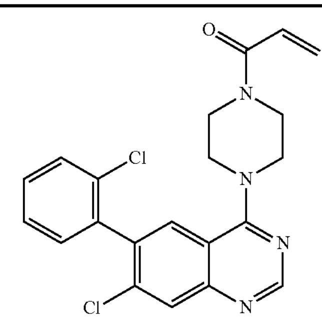 | 1-(4-(7-chloro-6-(2-chlorophenyl)quinazolin-4-yl)piperazin-1-yl)prop-2-en-1-one | A | 413.20 |

TABLE 1-continued

Representative Compounds

| No. | Structure | Name | Method | [M + H]+ |
|---|---|---|---|---|
| 2 | 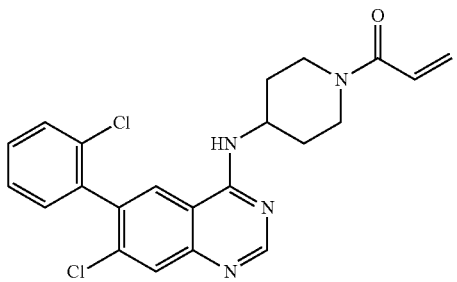 [SMILES: C=CC(=O)N1CCC(Nc2ncnc3cc(Cl)c(-c4ccccc4Cl)cc23)CC1] | 1-(4-(7-chloro-6-(2-chlorophenyl)quinazolin-4-ylamino)piperidin-1-yl)prop-2-en-1-one | A | 427.25 |
| 3 | 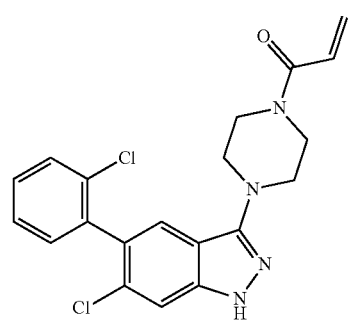 [SMILES: C=CC(=O)N1CCN(c2n[nH]c3cc(Cl)c(-c4ccccc4Cl)cc23)CC1] | 1-(4-(6-chloro-5-(2-chlorophenyl)-1H-indazol-3-yl)piperazin-1-yl)prop-2-en-1-one | C | 401.20 |
| 4 | 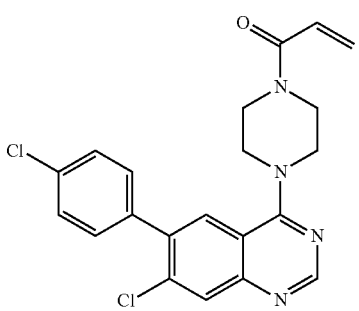 | 1-(4-(7-chloro-6-(4-chlorophenyl)quinazolin-4-yl)piperazin-1-yl)prop-2-en-1-one | B | 413.25 |
| 5 | 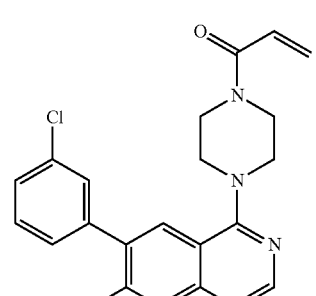 | 1-(4-(7-chloro-6-(3-chlorophenyl)quinazolin-4-yl)piperazin-1-yl)prop-2-en-1-one | B | 413.20 |
| 6 | 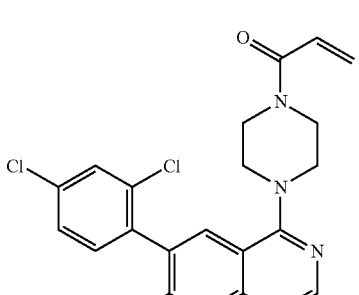 | 1-(4-(7-chloro-6-(2,4-dichlorophenyl)quinazolin-4-yl)piperazin-1-yl)prop-2-en-1-one | B | 447.20# |

TABLE 1-continued

Representative Compounds

| No. | Structure | Name | Method | [M + H]+ |
|---|---|---|---|---|
| 7 | 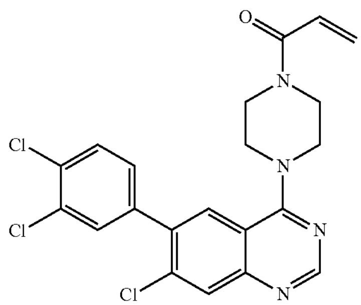 [SMILES: C=CC(=O)N1CCN(c2ncnc3cc(Cl)c(-c4ccc(Cl)c(Cl)c4)cc23)CC1] | 1-(4-(7-chloro-6-(3,4-dichlorophenyl)quinazolin-4-yl)piperazin-1-yl)prop-2-en-1-one | B | 449.15 |
| 8 | 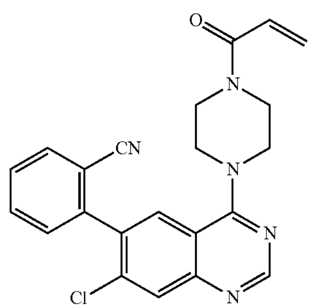 | 2-(4-(4-acryloylpiperazin-1-yl)-7-chloroquinazolin-6-yl)benzonitrile | B | 404.1 |
| 9 | 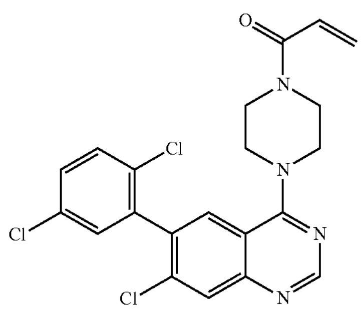 [SMILES: C=CC(=O)N1CCN(c2ncnc3cc(Cl)c(-c4cc(Cl)ccc4Cl)cc23)CC1] | 1-(4-(7-chloro-6-(2,5-dichlorophenyl)quinazolin-4-yl)piperazin-1-yl)prop-2-en-1-one | B | 448.45 |
| 10 | 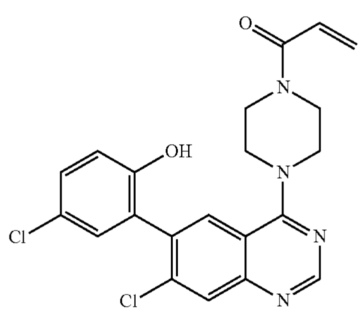 [SMILES: C=CC(=O)N1CCN(c2ncnc3cc(Cl)c(-c4cc(Cl)ccc4O)cc23)CC1] | 1-(4-(7-chloro-6-(5-chloro-2-hydroxyphenyl)quinazolin-4-yl)piperazin-1-yl)prop-2-en-1-one | B | 429.25 |
| 11 | 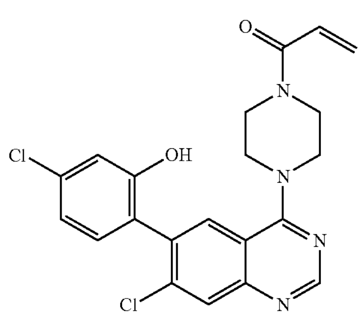 [SMILES: C=CC(=O)N1CCN(c2ncnc3cc(Cl)c(-c4ccc(Cl)cc4O)cc23)CC1] | 1-(4-(7-chloro-6-(4-chloro-2-hydroxyphenyl)quinazolin-4-yl)piperazin-1-yl)prop-2-en-1-one | B | 429.25 |

TABLE 1-continued

Representative Compounds

| No. | Structure | Name | Method | [M + H]+ |
|---|---|---|---|---|
| 12 | 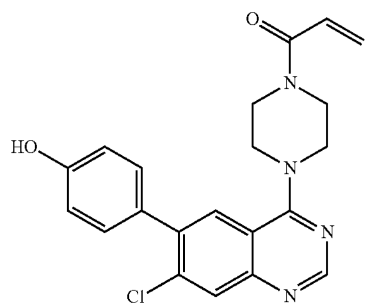 | 1-(4-(7-chloro-6-(4-hydroxyphenyl)quinazolin-4-yl)piperazin-1-yl)prop-2-en-1-one | B | 395.25 |
| 13 | 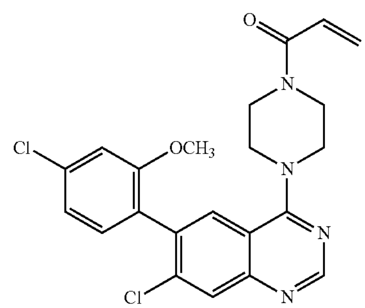 [SMILES: C=CC(=O)N1CCN(c2ncnc3cc(Cl)c(-c4ccc(Cl)cc4OC)cc23)CC1] | 1-(4-(7-chloro-6-(4-chloro-2-methoxyphenyl)quinazolin-4-yl)piperazin-1-yl)prop-2-en-1-one | B | 443.30 |
| 14 | 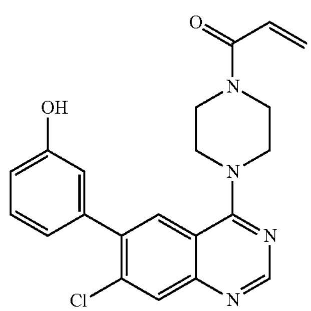 [SMILES: C=CC(=O)N1CCN(c2ncnc3cc(Cl)c(-c4cccc(O)c4)cc23)CC1] | 1-(4-(7-chloro-6-(3-hydroxyphenyl)quinazolin-4-yl)piperazin-1-yl)prop-2-en-1-one | B | 395.25 |
| 15 | 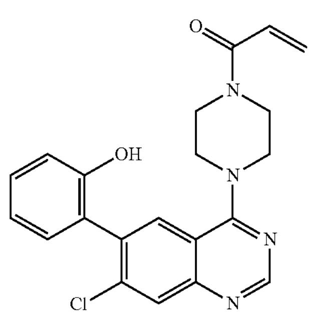 [SMILES: C=CC(=O)N1CCN(c2ncnc3cc(Cl)c(-c4ccccc4O)cc23)CC1] | 1-(4-(7-chloro-6-(2-hydroxyphenyl)quinazolin-4-yl)piperazin-1-yl)prop-2-en-1-one | B | 395.25 |
| 16 | 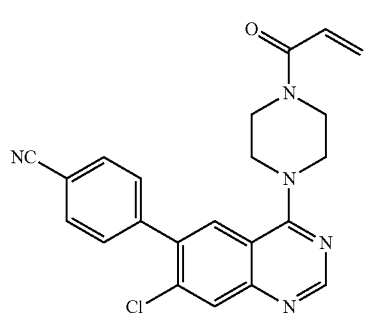 [SMILES: C=CC(=O)N1CCN(c2ncnc3cc(Cl)c(-c4ccc(C#N)cc4)cc23)CC1] | 4-(4-(4-acryloylpiperazin-1-yl)-7-chloroquinazolin-6-yl)benzonitrile | B | 404.3 |

TABLE 1-continued

Representative Compounds

| No. | Structure | Name | Method | [M + H]+ |
|---|---|---|---|---|
| 17 | 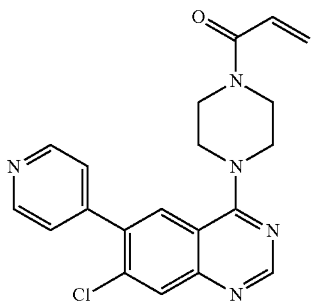 [SMILES: C=CC(=O)N1CCN(c2ncnc3cc(Cl)c(-c4ccncc4)cc23)CC1] | 1-(4-(7-chloro-6-(pyridin-4-yl)quinazolin-4-yl)piperazin-1-yl)prop-2-en-1-one | B | 380.25 |
| 18 | 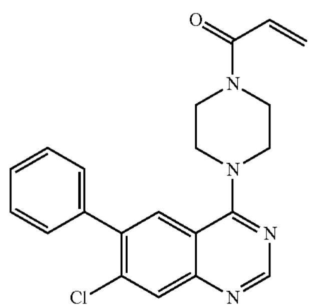 [SMILES: C=CC(=O)N1CCN(c2ncnc3cc(Cl)c(-c4ccccc4)cc23)CC1] | 1-(4-(7-chloro-6-phenylquinazolin-4-yl)piperazin-1-yl)prop-2-en-1-one | B | 379.25 |
| 19 | 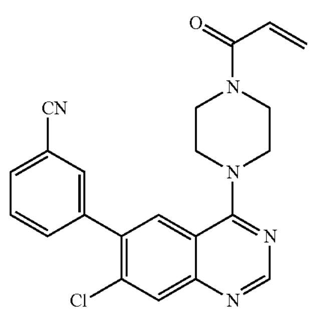 | 3-(4-(4-acryloylpiperazin-1-yl)-7-chloroquinazolin-6-yl)benzonitrile | B | 404.25 |
| 20 | 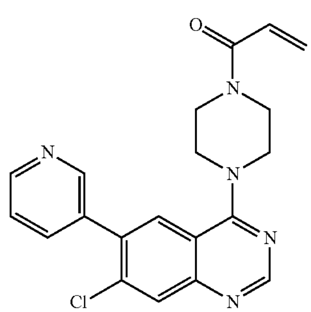 [SMILES: C=CC(=O)N1CCN(c2ncnc3cc(Cl)c(-c4cccnc4)cc23)CC1] | 1-(4-(7-chloro-6-(pyridin-3-yl)quinazolin-4-yl)piperazin-1-yl)prop-2-en-1-one | B | 380.25 |
| 21 | 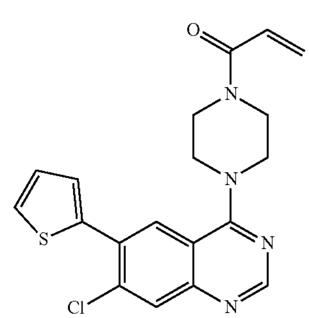 [SMILES: C=CC(=O)N1CCN(c2ncnc3cc(Cl)c(-c4cccs4)cc23)CC1] | 1-(4-(7-chloro-6-(thiophen-2-yl)quinazolin-4-yl)piperazin-1-yl)prop-2-en-1-one | B | 385.25 |

TABLE 1-continued

Representative Compounds

| No. | Structure | Name | Method | [M + H]⁺ |
|---|---|---|---|---|
| 22 | 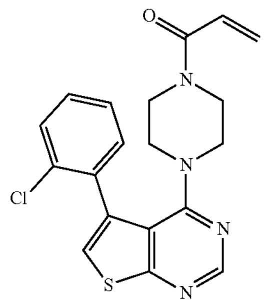 [SMILES: C=CC(=O)N1CCN(c2ncnc3scc(-c4ccccc4Cl)c23)CC1] | 1-(4-(5-(2-chlorophenyl)-4a,7a-dihydrothieno[2,3-d]pyrimidin-4-yl)piperazin-1-yl)prop-2-en-1-one | H | 385.20 |
| 23 | 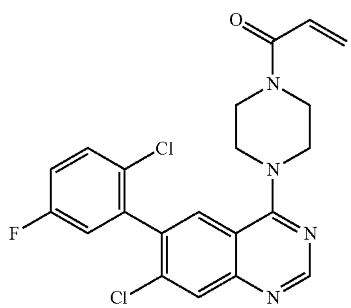 [SMILES: C=CC(=O)N1CCN(c2ncnc3cc(Cl)c(-c4cc(F)ccc4Cl)cc23)CC1] | 1-(4-(7-chloro-6-(2-chloro-5-fluorophenyl)quinazolin-4-yl)piperazin-1-yl)prop-2-en-1-one | B | 431.20 |
| 24 | 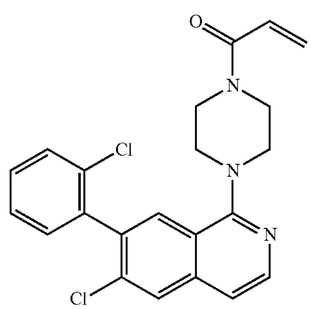 [SMILES: C=CC(=O)N1CCN(c2nccc3cc(Cl)c(-c4ccccc4Cl)cc23)CC1] | 1-(4-(6-chloro-7-(2-chlorophenyl)isoquinolin-1-yl)piperazin-1-yl)prop-2-en-1-one | D | 412.20 |
| 25 | 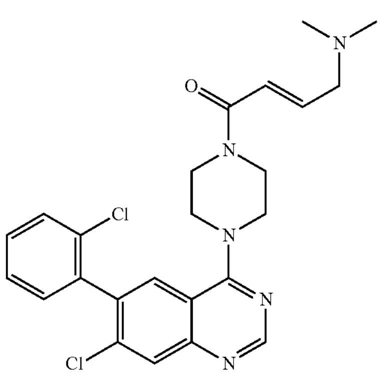 [SMILES: CN(C)C/C=C/C(=O)N1CCN(c2ncnc3cc(Cl)c(-c4ccccc4Cl)cc23)CC1] | (E)-1-(4-(7-chloro-(2-chlorophenyl)quinazolin-4-yl)piperazin-1-yl)-4-(dimethylamino)but-2-en-1-one | A | 470.35 |

TABLE 1-continued

Representative Compounds

| No. | Structure | Name | Method | [M + H]+ |
|---|---|---|---|---|
| 26 | 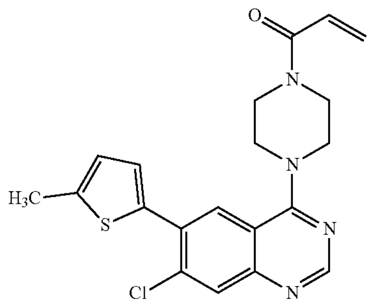 [SMILES: C=CC(=O)N1CCN(c2ncnc3cc(Cl)c(-c4ccc(C)s4)cc23)CC1] | 1-(4-(7-chloro-6-(5-methylthiophen-2-yl)quinazolin-4-yl)piperazin-1-yl)prop-2-en-1-one | B | 399.20 |
| 27 | 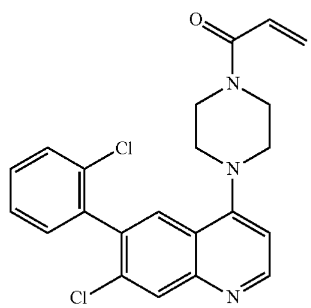 [SMILES: C=CC(=O)N1CCN(c2ccnc3cc(Cl)c(-c4ccccc4Cl)cc23)CC1] | 1-(4-(7-chloro-6-(2-chlorophenyl)quinolin-4-yl)piperazin-1-yl)prop-2-en-1-one | E | 412.20 |
| 28 | 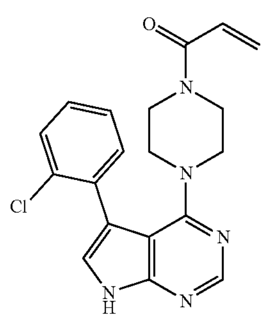 [SMILES: C=CC(=O)N1CCN(c2ncnc3[nH]cc(-c4ccccc4Cl)c23)CC1] | 1-(4-(5-(2-chlorophenyl)-7,7a-dihydro-4aH-pyrrolo[2,3-d]pyrimidin-4-yl)piperazin-1-yl)prop-2-en-1-one | J | 368.25 |
| 29 | 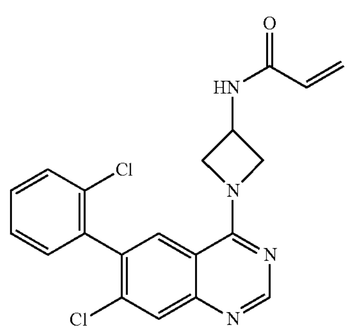 [SMILES: C=CC(=O)NC1CN(c2ncnc3cc(Cl)c(-c4ccccc4Cl)cc23)C1] | N-(1-(7-chloro-6-(2-chlorophenyl)quinazolin-4-yl)azetidin-3-yl)acrylamide | B | 399.20 |
| 30 | 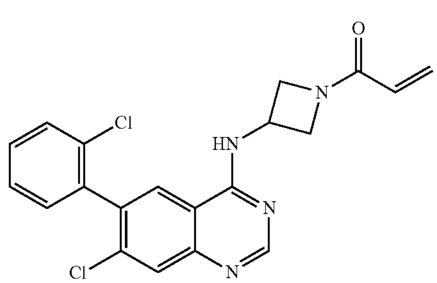 [SMILES: C=CC(=O)N1CC(Nc2ncnc3cc(Cl)c(-c4ccccc4Cl)cc23)C1] | 1-(3-(7-chloro-6-(2-chlorophenyl)quinazolin-4-ylamino)azetidin-1-yl)prop-2-en-1-one | B | 399.20 |

TABLE 1-continued

| No. | Structure | Name | Method | [M + H]+ |
|---|---|---|---|---|
| 31 | 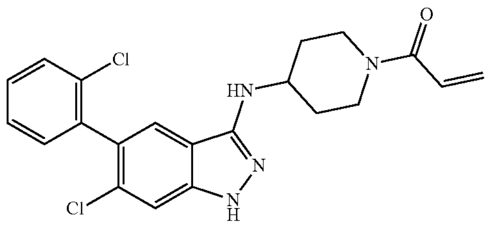 [SMILES: C=CC(=O)N1CCC(Nc2n[nH]c3cc(Cl)c(-c4ccccc4Cl)cc23)CC1] | 1-(4-(6-chloro-5-(2-chlorophenyl)-1H-indazol-3-ylamino)piperidin-1-yl)prop-2-en-1-one | C | 413.40+ |
| 32 | 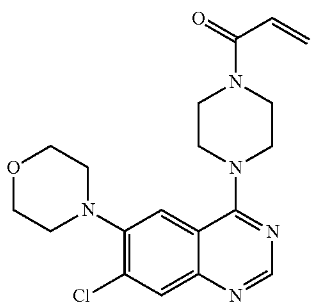 [SMILES: C=CC(=O)N1CCN(c2ncnc3cc(Cl)c(N4CCOCC4)cc23)CC1] | 1-(4-(7-chloro-6-morpholinoquinazolin-4-yl)piperazin-1-yl)prop-2-en-1-one | L | 388.25 |
| 33 | 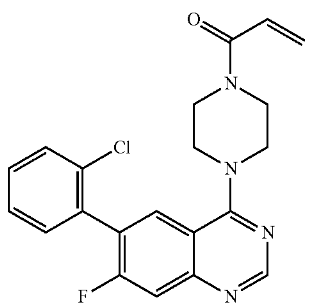 [SMILES: C=CC(=O)N1CCN(c2ncnc3cc(F)c(-c4ccccc4Cl)cc23)CC1] | 1-(4-(6-(2-chlorophenyl)-7-fluoroquinazolin-4-yl)piperazin-1-yl)prop-2-en-1-one | B | 397.20 |
| 34 | 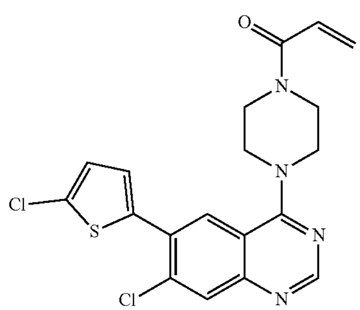 [SMILES: C=CC(=O)N1CCN(c2ncnc3cc(Cl)c(-c4ccc(Cl)s4)cc23)CC1] | 1-(4-(7-chloro-6-(5-chlorothiophen-2-yl)quinazolin-4-yl)piperazin-1-yl)prop-2-en-1-one | B | 419.15 |
| 35 | 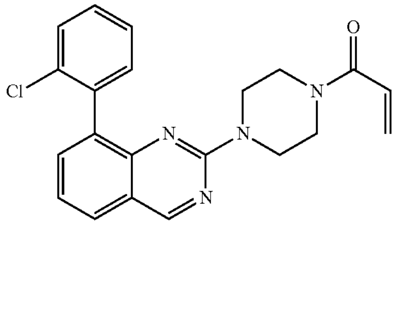 [SMILES: C=CC(=O)N1CCN(c2ncc3cccc(-c4ccccc4Cl)c3n2)CC1] | 1-(4-(8-(2-chlorophenyl)quinazolin-2-yl)piperazin-1-yl)prop-2-en-1-one | I | 379.1 |

TABLE 1-continued

Representative Compounds

| No. | Structure | Name | Method | [M + H]+ |
|---|---|---|---|---|
| 36 | 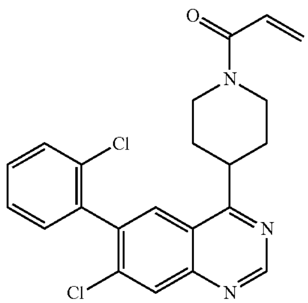 [SMILES: C=CC(=O)N1CCC(c2ncnc3cc(Cl)c(-c4ccccc4Cl)cc23)CC1] | 1-(4-(7-chloro-6-(2-chlorophenyl)quinazolin-4-yl)piperidin-1-yl)prop-2-en-1-one | K | 410.35+ |
| 37 | 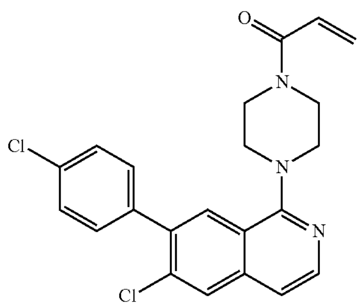 [SMILES: C=CC(=O)N1CCN(c2nccc3cc(Cl)c(-c4ccc(Cl)cc4)cc23)CC1] | 1-(4-(6-chloro-7-(4-chlorophenyl)isoquinolin-1-yl)piperazin-1-yl)prop-2-en-1-one | D | 412.20 |
| 38 | 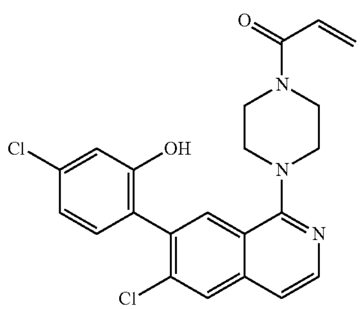 | 1-(4-(6-chloro-7-(4-chloro-2-hydroxyphenyl)isoquinolin-1-yl)piperazin-1-yl)prop-2-en-1-one | D | 428.25 |
| 39 | 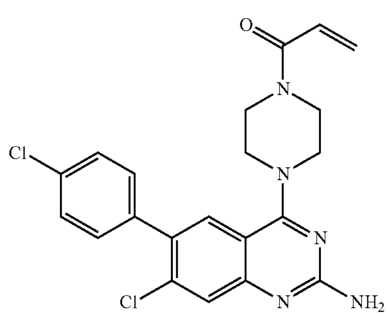 [SMILES: C=CC(=O)N1CCN(c2nc(N)nc3cc(Cl)c(-c4ccc(Cl)cc4)cc23)CC1] | 1-(4-(2-amino-7-chloro-6-(4-chlorophenyl)quinazolin-4-yl)piperazin-1-yl)prop-2-en-1-one | F | 428.3 |
| 40 | 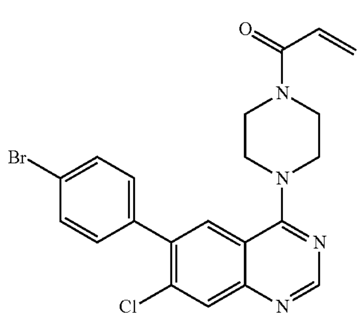 | 1-(4-(6-(4-bromophenyl)-7-chloroquinazolin-4-yl)piperazin-1-yl)prop-2-en-1-one | B | 459.25 |

TABLE 1-continued

Representative Compounds

| No. | Structure | Name | Method | [M + H]+ |
|---|---|---|---|---|
| 41 | 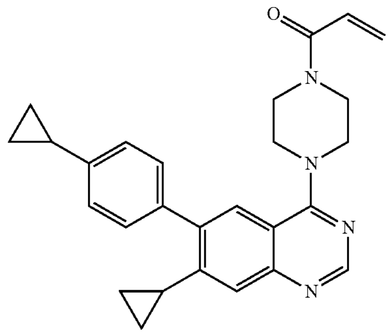 [SMILES: C=CC(=O)N1CCN(c2ncnc3cc(C4CC4)c(-c4ccc(C5CC5)cc4)cc23)CC1] | 1-(4-(7-cyclopropyl-6-(4-cyclopropylphenyl)quinazolin-4-yl)piperazin-1-yl)prop-2-en-1-one | B | 425.25 |
| 42 | 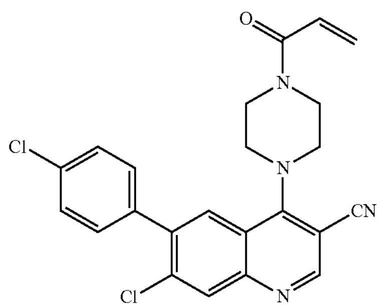 [SMILES: C=CC(=O)N1CCN(c2c(C#N)cnc3cc(Cl)c(-c4ccc(Cl)cc4)cc23)CC1] | 4-(4-acryloylpiperazin-1-yl)-7-chloro-6-(4-chlorophenyl)quinoline-3-carbonitrile | G | 437.25 |
| 43 | 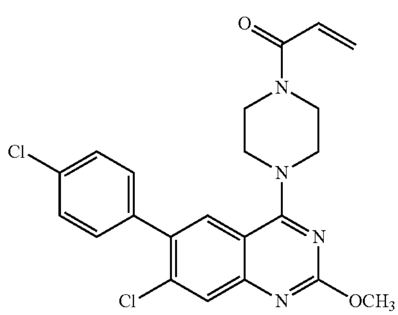 [SMILES: C=CC(=O)N1CCN(c2nc(OC)nc3cc(Cl)c(-c4ccc(Cl)cc4)cc23)CC1] | 1-(4-(7-chloro-6-(4-chlorophenyl)-2-methoxyquinazolin-4-yl)piperazin-1-yl)prop-2-en-1-one | F | 465.30* |
| 44 | 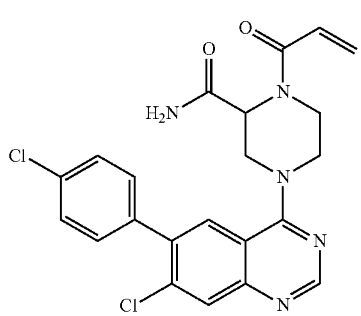 [SMILES: C=CC(=O)N1CCN(c2ncnc3cc(Cl)c(-c4ccc(Cl)cc4)cc23)CC1C(N)=O] | 1-acryloyl-4-(7-chloro-6-(4-chlorophenyl)quinazolin-4-yl)piperazine-2-carboxamide | A | 454.35+ |

TABLE 1-continued

Representative Compounds

| No. | Structure | Name | Method | [M + H]+ |
|---|---|---|---|---|
| 45 | 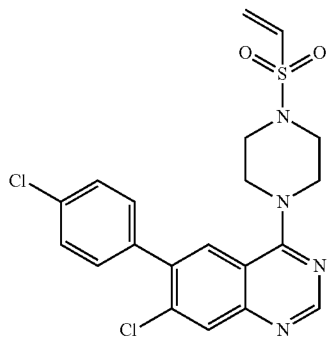 [SMILES: C=CS(=O)(=O)N1CCN(c2ncnc3cc(Cl)c(-c4ccc(Cl)cc4)cc23)CC1] | 7-chloro-6-(4-chlorophenyl)-4-(4-(vinylsulfonyl)piperazin-1-yl)quinazoline | A | 449.25 |
| 46 | 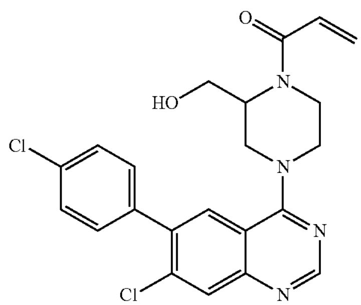 [SMILES: C=CC(=O)N1CCN(c2ncnc3cc(Cl)c(-c4ccc(Cl)cc4)cc23)CC1CO] | 1-(4-(7-chloro-6-(4-chlorophenyl)quinazolin-4-yl)-2-(hydroxymethyl)piperazin-1-yl)prop-2-en-1-one | A | 443.30 |
| 47 | 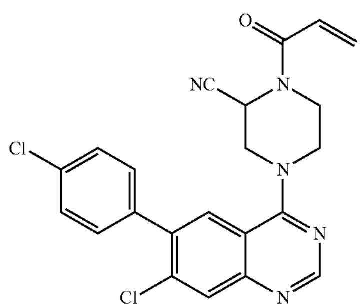 [SMILES: C=CC(=O)N1CCN(c2ncnc3cc(Cl)c(-c4ccc(Cl)cc4)cc23)CC1C#N] | 1-acryloyl-4-(7-chloro-6-(4-chlorophenyl)quinazolin-4-yl)piperazine-2-carbonitrile | A | 438.25 |
| 48 | 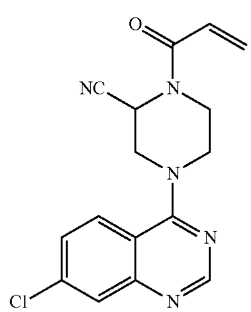 [SMILES: C=CC(=O)N1CCN(c2ncnc3cc(Cl)ccc23)CC1C#N] | 1-acryloyl-4-(7-chloroquinazolin-4-yl)piperazine-2-carbonitrile | A | 328.2 |
| 49 | 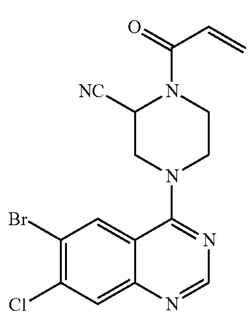 [SMILES: C=CC(=O)N1CCN(c2ncnc3cc(Cl)c(Br)cc23)CC1C#N] | 1-acryloyl-4-(6-bromo-7-chloroquinazolin-4-yl)piperazine-2-carbonitrile | A | 408.20 |

TABLE 1-continued

Representative Compounds

| No. | Structure | Name | Method | [M + H]+ |
|---|---|---|---|---|
| 50 | 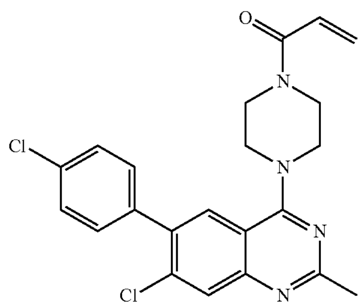 [SMILES: C=CC(=O)N1CCN(c2nc(C)nc3cc(Cl)c(-c4ccc(Cl)cc4)cc23)CC1] | 1-(4-(7-chloro-6-(4-chlorophenyl)-2-methylquinazolin-4-yl)piperazin-1-yl)prop-2-en-1-one | M | 427.35 |
| 51 | 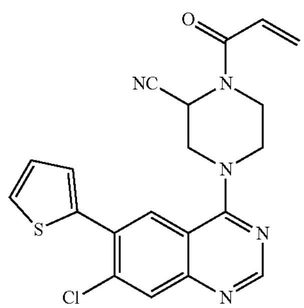 [SMILES: C=CC(=O)N1CCN(c2ncnc3cc(Cl)c(-c4cccs4)cc23)CC1C#N] | 1-acryloyl-4-(7-chloro-6-(thiophen-2-yl)quinazolin-4-yl)piperazine-2-carbonitrile | A | 410.30 |
| 52 | 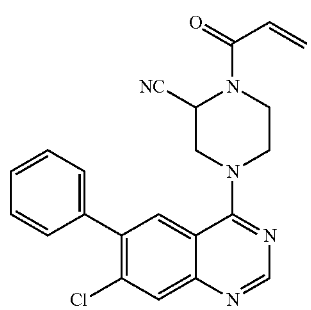 [SMILES: C=CC(=O)N1CCN(c2ncnc3cc(Cl)c(-c4ccccc4)cc23)CC1C#N] | 1-acryloyl-4-(7-chloro-6-phenylquinazolin-4-yl)piperazine-2-carbonitrile | A | 404.35 |
| 53 | 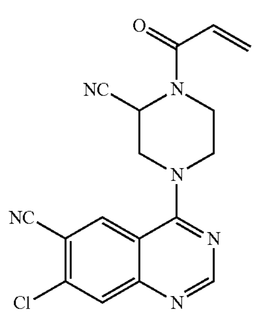 [SMILES: C=CC(=O)N1CCN(c2ncnc3cc(Cl)c(C#N)cc23)CC1C#N] | 4-(4-acryloyl-3-cyanopiperazin-1-yl)-7-chloroquinazoline-6-carbonitrile | B | 353.20 |
| 54 | 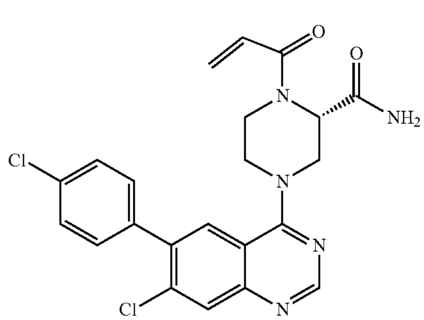 [SMILES: C=CC(=O)N1CCN(c2ncnc3cc(Cl)c(-c4ccc(Cl)cc4)cc23)C[C@H]1C(N)=O] | (S)-1-acryloyl-4-(7-chloro-6-(4-chlorophenyl)quinazolin-4-yl)piperazine-2-carboxamide | A | 456.30 |

TABLE 1-continued

Representative Compounds

| No. | Structure | Name | Method | [M + H]+ |
|---|---|---|---|---|
| 55 | 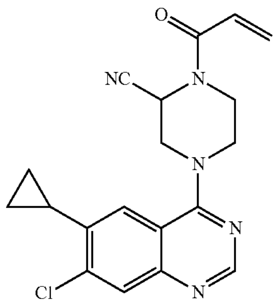 [SMILES: C=CC(=O)N1CCN(c2ncnc3cc(Cl)c(C4CC4)cc23)CC1C#N] | 1-acryloyl-4-(7-chloro-6-cyclopropylquinazolin-4-yl)piperazine-2-carbonitrile | B | 368.25 |
| 56 | 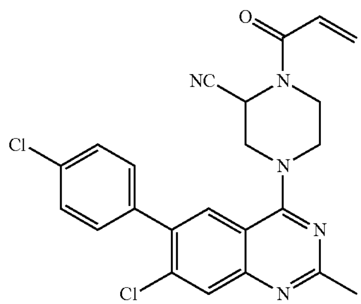 [SMILES: C=CC(=O)N1CCN(c2nc(C)nc3cc(Cl)c(-c4ccc(Cl)cc4)cc23)CC1C#N] | 1-acryloyl-4-(7-chloro-6-(4-chlorophenyl)-2-methylquinazolin-4-yl)piperazine-2-carbonitrile | M | 452.30 |
| 57 | 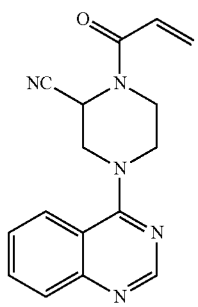 [SMILES: C=CC(=O)N1CCN(c2ncnc3ccccc23)CC1C#N] | 1-acryloyl-4-(quinazolin-4-yl)piperazine-2-carbonitrile | A | 294.20 |
| 58 | 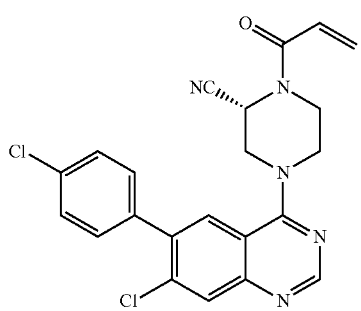 [SMILES: C=CC(=O)N1CCN(c2ncnc3cc(Cl)c(-c4ccc(Cl)cc4)cc23)C[C@@H]1C#N] | (R)-1-acryloyl-4-(7-chloro-6-(4-chlorophenyl)quinazolin-4-yl)piperazine-2-carbonitrile | A | 438.20 |
| 59 | 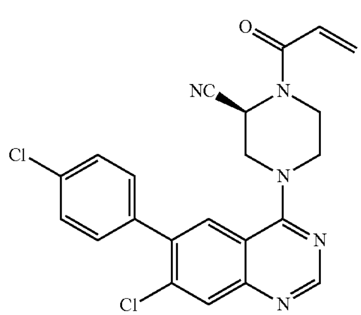 [SMILES: C=CC(=O)N1CCN(c2ncnc3cc(Cl)c(-c4ccc(Cl)cc4)cc23)C[C@H]1C#N] | (S)-1-acryloyl-4-(7-chloro-6-(4-chlorophenyl)quinazolin-4-yl)piperazine-2-carbonitrile | A | 438.25 |

TABLE 1-continued

Representative Compounds

| No. | Structure | Name | Method | [M + H]+ |
|---|---|---|---|---|
| 60 | 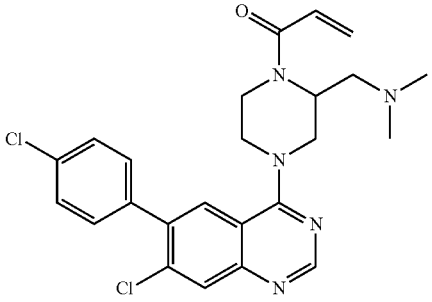 [SMILES: C=CC(=O)N1CCN(c2ncnc3cc(Cl)c(-c4ccc(Cl)cc4)cc23)CC1CN(C)C] | 1-(4-(7-chloro-6-(4-chlorophenyl)quinazolin-4-yl)-2-((dimethylamino)methyl)piperazin-1-yl)prop-2-en-1-one | A | 470.35 |
| 61 | 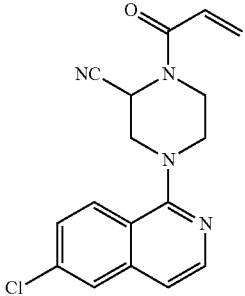 | 1-acryloyl-4-(6-chloroisoquinolin-1-yl)piperazine-2-carbonitrile | D | 327.20 |
| 62 | 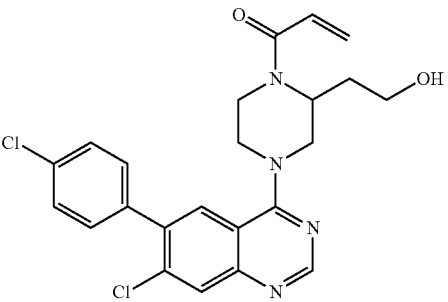 [SMILES: C=CC(=O)N1CCN(c2ncnc3cc(Cl)c(-c4ccc(Cl)cc4)cc23)CC1CCO] | 1-(4-(7-chloro-6-(4-chlorophenyl)quinazolin-4-yl)-2-(2-hydroxyethyl)piperazin-1-yl)prop-2-en-1-one | A | 457.35 |
| 63 | 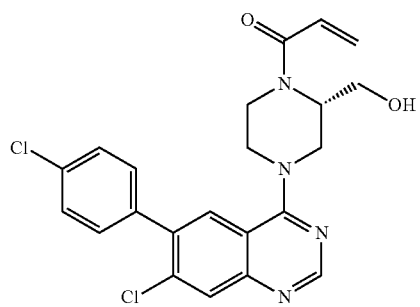 | (S)-1-(4-(7-chloro-6-(4-chlorophenyl)quinazolin-4-yl)-2-(hydroxymethyl)piperazin-1-yl)prop-2-en-1-one | A | 443.30 |
| 64 | 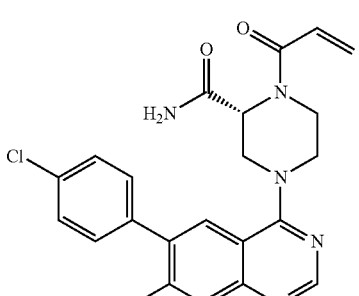 | (R)-1-acryloyl-4-(7-chloro-6-(4-chlorophenyl)quinazolin-4-yl)piperazine-2-carboxamide | A | 456.30 |

TABLE 1-continued

Representative Compounds

| No. | Structure | Name | Method | [M + H]+ |
|---|---|---|---|---|
| 65 | 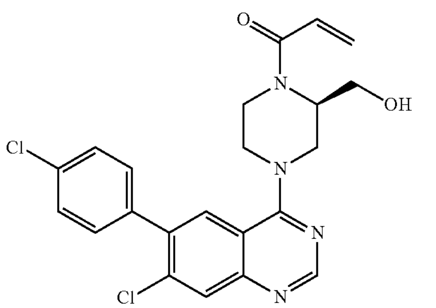 [SMILES: C=CC(=O)N1CCN(c2ncnc3cc(Cl)c(-c4ccc(Cl)cc4)cc23)C[C@@H]1CO] | (R)-1-(4-(7-chloro-6-(4-chlorophenyl)quinazolin-4-yl)-2-(hydroxymethyl)piperazin-1-yl)prop-2-en-1-one | A | 443.35 |
| 66 | 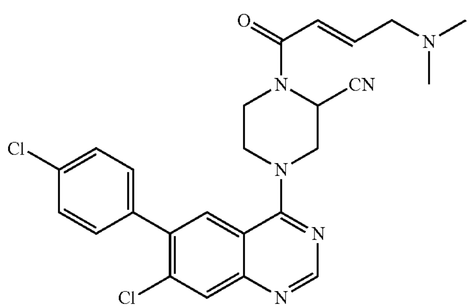 [SMILES: CN(C)C/C=C/C(=O)N1CCN(c2ncnc3cc(Cl)c(-c4ccc(Cl)cc4)cc23)CC1C#N] | (E)-4-(7-chloro-6-(4-chlorophenyl)quinazolin-4-yl)-1-(4-(dimethylamino)but-2-enoyl)piperazine-2-carbonitrile | A | 495.40 |
| 67 | 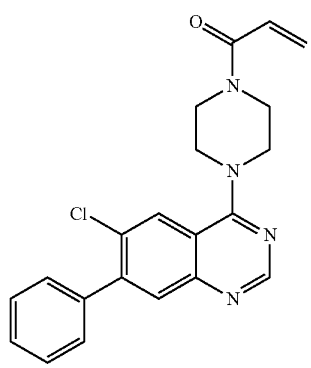 [SMILES: C=CC(=O)N1CCN(c2ncnc3cc(-c4ccccc4)c(Cl)cc23)CC1] | 1-(4-(6-chloro-7-phenylquinazolin-4-yl)piperazin-1-yl)prop-2-en-1-one | B | 379.30 |
| 68 | 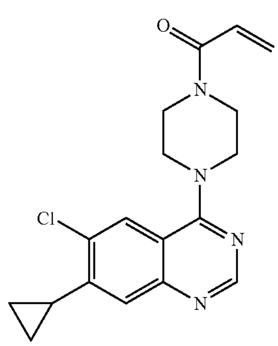 [SMILES: C=CC(=O)N1CCN(c2ncnc3cc(C4CC4)c(Cl)cc23)CC1] | 1-(4-(6-chloro-7-cyclopropylquinazolin-4-yl)piperazin-1-yl)prop-2-en-1-one | A | 343.25 |

TABLE 1-continued

Representative Compounds

| No. | Structure | Name | Method | [M + H]+ |
|---|---|---|---|---|
| 69 | 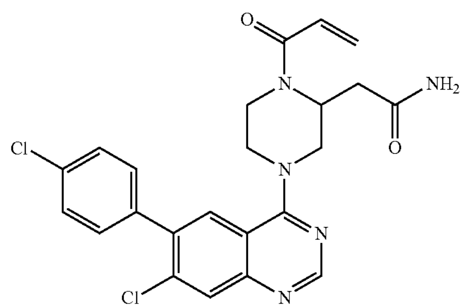 [SMILES: C=CC(=O)N1CCN(c2ncnc3cc(Cl)c(-c4ccc(Cl)cc4)cc23)CC1CC(N)=O] | 2-(1-acryloyl-4-(7-chloro-6-(4-chlorophenyl)quinazolin-4-yl)piperazin-2-yl)acetamide | A | 470.35 |
| 70 | 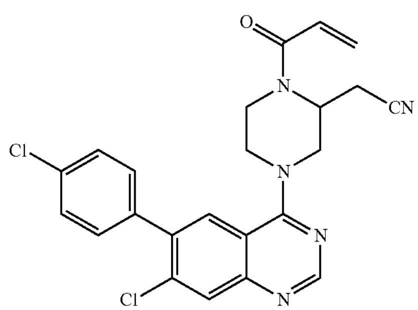 | 2-(1-acryloyl-4-(7-chloro-6-(4-chlorophenyl)quinazolin-4-yl)piperazin-2-yl)acetonitrile | A | 452.35 |
| 71 | 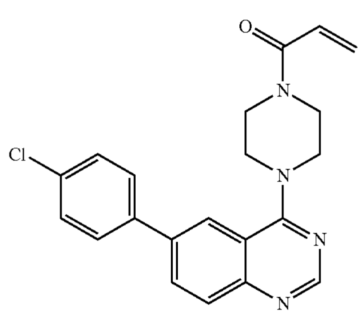 [SMILES: C=CC(=O)N1CCN(c2ncnc3ccc(-c4ccc(Cl)cc4)cc23)CC1] | 1-(4-(6-(4-chlorophenyl)quinazolin-4-yl)piperazin-1-yl)prop-2-en-1-one | A | 379.30 |
| 72 | 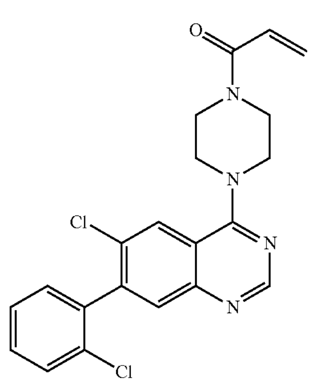 [SMILES: C=CC(=O)N1CCN(c2ncnc3cc(-c4ccccc4Cl)c(Cl)cc23)CC1] | 1-(4-(6-chloro-7-(2-chlorophenyl)quinazolin-4-yl)piperazin-1-yl)prop-2-en-1-one | A | 413.25 |

TABLE 1-continued

Representative Compounds

| No. | Structure | Name | Method | [M + H]+ |
|---|---|---|---|---|
| 73 | 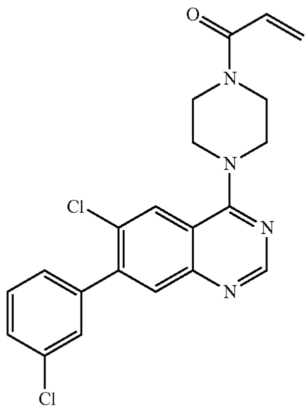 [SMILES: C=CC(=O)N1CCN(c2ncnc3cc(-c4cccc(Cl)c4)c(Cl)cc23)CC1] | 1-(4-(6-chloro-7-(3-chlorophenyl)quinazolin-4-yl)piperazin-1-yl)prop-2-en-1-one | A | 413.3 |
| 74 | 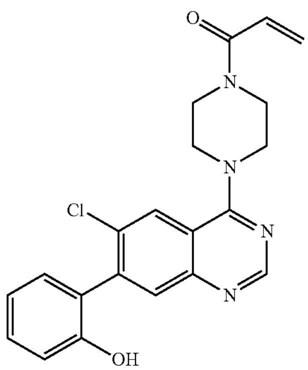 | 1-(4-(6-chloro-7-(2-hydroxyphenyl)quinazolin-4-yl)piperazin-1-yl)prop-2-en-1-one | A | 395.25 |
| 75 | 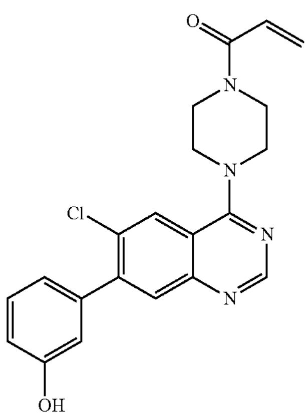 | 1-(4-(6-chloro-7-(3-hydroxyphenyl)quinazolin-4-yl)piperazin-1-yl)prop-2-en-1-one | A | 395.25 |
| 76 | 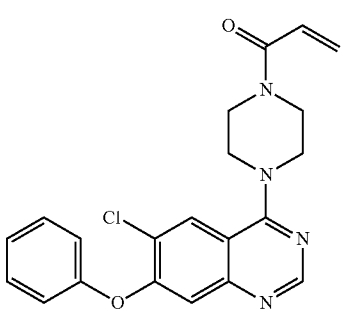 [SMILES: C=CC(=O)N1CCN(c2ncnc3cc(Oc4ccccc4)c(Cl)cc23)CC1] | 1-(4-(6-chloro-7-phenoxyquinazolin-4-yl)piperazin-1-yl)prop-2-en-1-one | L | 395.25 |

TABLE 1-continued

Representative Compounds

| No. | Structure | Name | Method | [M + H]+ |
|---|---|---|---|---|
| 77 | 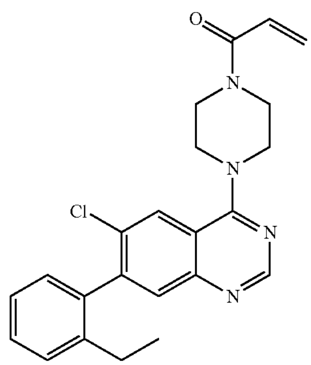 [SMILES: C=CC(=O)N1CCN(c2ncnc3cc(-c4ccccc4CC)c(Cl)cc23)CC1] | 1-(4-(6-chloro-7-(2-ethylphenyl)quinazolin-4-yl)piperazin-1-yl)prop-2-en-1-one | A | 407.75 |
| 78 | 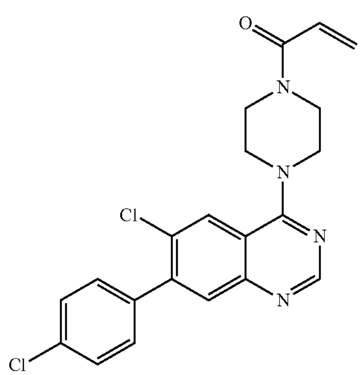 [SMILES: C=CC(=O)N1CCN(c2ncnc3cc(-c4ccc(Cl)cc4)c(Cl)cc23)CC1] | 1-(4-(6-chloro-7-(4-chlorophenyl)quinazolin-4-yl)piperazin-1-yl)prop-2-en-1-one | A | 413.25 |
| 79 | 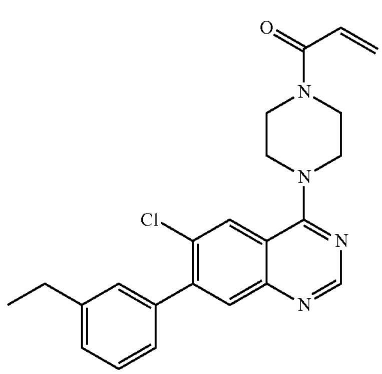 [SMILES: C=CC(=O)N1CCN(c2ncnc3cc(-c4cccc(CC)c4)c(Cl)cc23)CC1] | 1-(4-(6-chloro-7-(3-ethylphenyl)quinazolin-4-yl)piperazin-1-yl)prop-2-en-1-one | A | 407.30 |
| 80 | 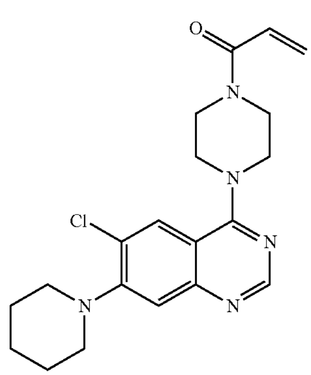 [SMILES: C=CC(=O)N1CCN(c2ncnc3cc(N4CCCCC4)c(Cl)cc23)CC1] | 1-(4-(6-chloro-7-(piperidin-1-yl)quinazolin-4-yl)piperazin-1-yl)prop-2-en-1-one | L | 387.25 |

TABLE 1-continued

Representative Compounds

| No. | Structure | Name | Method | [M + H]+ |
|---|---|---|---|---|
| 81 | 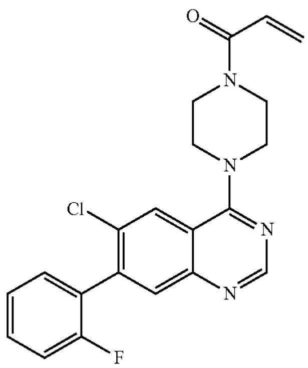 | 1-(4-(6-chloro-7-(2-fluorophenyl)quinazolin-4-yl)piperazin-1-yl)prop-2-en-1-one | A | 397.25 |
| 82 | 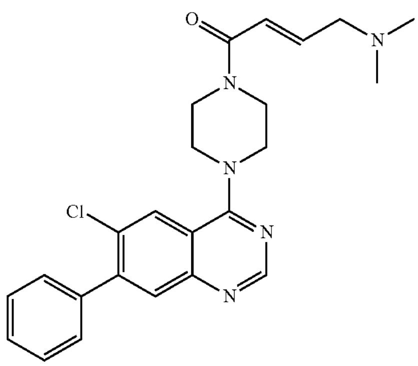 [SMILES: CN(C)C/C=C/C(=O)N1CCN(c2ncnc3cc(-c4ccccc4)c(Cl)cc23)CC1] | (E)-1-(4-(6-chloro-7-phenylquinazolin-4-yl)piperazin-1-yl)-4-(dimethylamino)but-2-en-1-one | A | 436.40 |
| 83 | 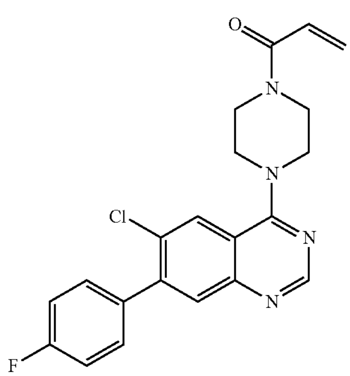 [SMILES: C=CC(=O)N1CCN(c2ncnc3cc(-c4ccc(F)cc4)c(Cl)cc23)CC1] | 1-(4-(6-chloro-7-(4-fluorophenyl)quinazolin-4-yl)piperazin-1-yl)prop-2-en-1-one | A | 397.25 |
| 84 | 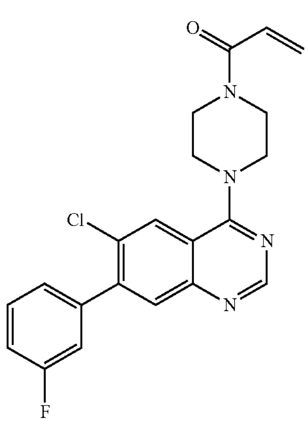 [SMILES: C=CC(=O)N1CCN(c2ncnc3cc(-c4cccc(F)c4)c(Cl)cc23)CC1] | 1-(4-(6-chloro-7-(3-fluorophenyl)quinazolin-4-yl)piperazin-1-yl)prop-2-en-1-one | A | 397.25 |

TABLE 1-continued

Representative Compounds

| No. | Structure | Name | Method | [M + H]⁺ |
|---|---|---|---|---|
| 85 | 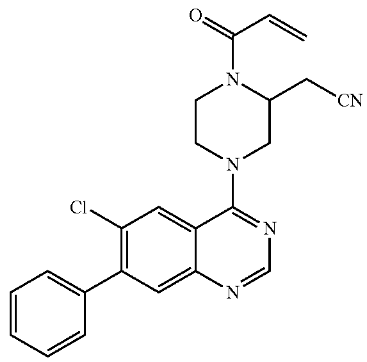 [SMILES: C=CC(=O)N1CCN(c2ncnc3cc(-c4ccccc4)c(Cl)cc23)CC1CC#N] | 2-(1-acryloyl-4-(6-chloro-7-phenylquinazolin-4-yl)piperazin-2-yl)acetonitrile | A | 418.30 |
| 86 | 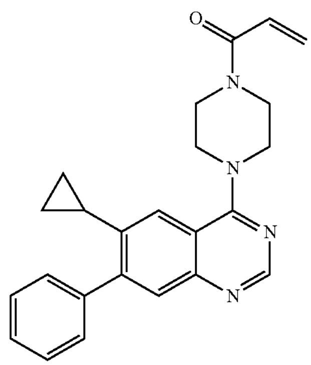 [SMILES: C=CC(=O)N1CCN(c2ncnc3cc(-c4ccccc4)c(C4CC4)cc23)CC1] | 1-(4-(6-cyclopropyl-7-phenylquinazolin-4-yl)piperazin-1-yl)prop-2-en-1-one | B | 385.75 |
| 87 | 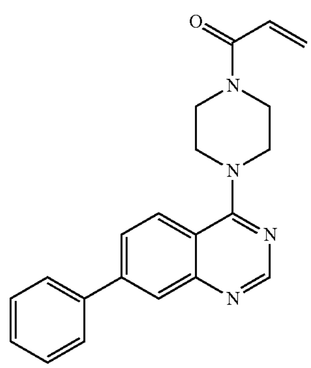 | 1-(4-(7-phenylquinazolin-4-yl)piperazin-1-yl)prop-2-en-1-one | B | 345.20 |
| 88 | 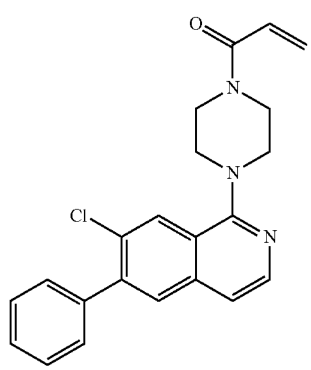 | 1-(4-(7-chloro-6-phenylisoquinolin-1-yl)piperazin-1-yl)prop-2-en-1-one | D | 378.20 |

TABLE 1-continued

Representative Compounds

| No. | Structure | Name | Method | [M + H]+ |
|---|---|---|---|---|
| 89 | 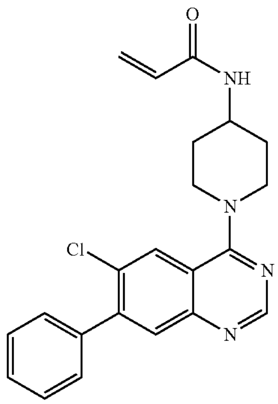 [SMILES: C=CC(=O)NC1CCN(c2ncnc3cc(-c4ccccc4)c(Cl)cc23)CC1] | N-(1-(6-chloro-7-phenylquinazolin-4-yl)piperidin-4-yl)acrylamide | B | 393.25 |
| 90 | 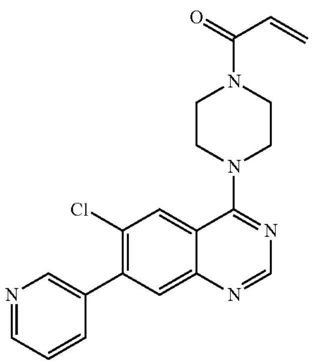 [SMILES: C=CC(=O)N1CCN(c2ncnc3cc(-c4cccnc4)c(Cl)cc23)CC1] | 1-(4-(6-chloro-7-(pyridin-3-yl)quinazolin-4-yl)piperazin-1-yl)prop-2-en-1-one | B | 380.25 |
| 91 | 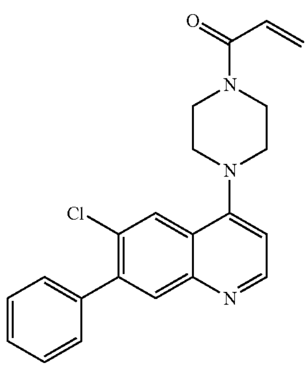 [SMILES: C=CC(=O)N1CCN(c2ccnc3cc(-c4ccccc4)c(Cl)cc23)CC1] | 1-(4-(6-chloro-7-phenylquinolin-4-yl)piperazin-1-yl)prop-2-en-1-one | E | 378.20 |
| 92 | 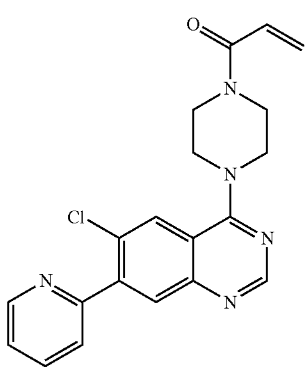 | 1-(4-(6-chloro-7-(pyridin-2-yl)quinazolin-4-yl)piperazin-1-yl)prop-2-en-1-one | B | 380.25 |

TABLE 1-continued

| No. | Structure | Name | Method | [M + H]⁺ |
|---|---|---|---|---|
| 93 | 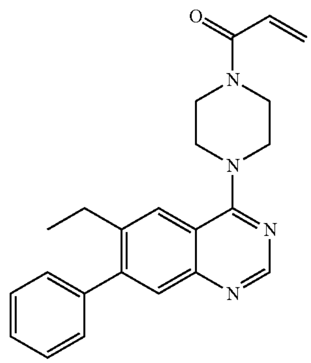 [SMILES: C=CC(=O)N1CCN(c2ncnc3cc(-c4ccccc4)c(CC)cc23)CC1] | 1-(4-(6-ethyl-7-phenylquinazolin-4-yl)piperazin-1-yl)prop-2-en-1-one | B | 373.75 |
| 94 | 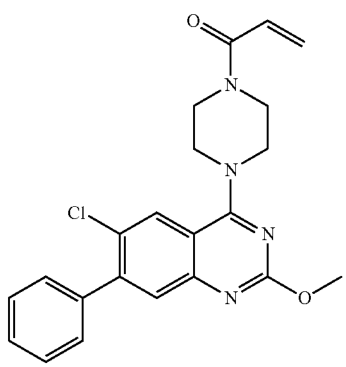 [SMILES: C=CC(=O)N1CCN(c2nc(OC)nc3cc(-c4ccccc4)c(Cl)cc23)CC1] | 1-(4-(6-chloro-2-methoxy-7-phenylquinazolin-4-yl)piperazin-1-yl)prop-2-en-1-one | F | 409.30 |
| 95 | 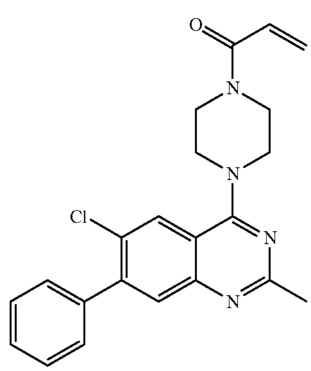 [SMILES: C=CC(=O)N1CCN(c2nc(C)nc3cc(-c4ccccc4)c(Cl)cc23)CC1] | 1-(4-(6-chloro-2-methyl-7-phenylquinazolin-4-yl)piperazin-1-yl)prop-2-en-1-one | M | 393.70 |
| 96 | 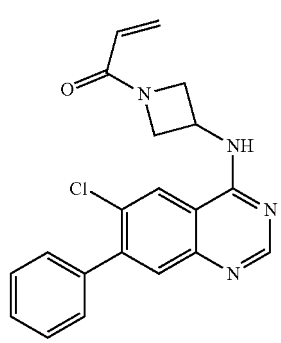 [SMILES: C=CC(=O)N1CC(Nc2ncnc3cc(-c4ccccc4)c(Cl)cc23)C1] | 1-(3-(6-chloro-7-phenylquinazolin-4-ylamino)azetidin-1-yl)prop-2-en-1-one | A | 365.20 |

TABLE 1-continued

Representative Compounds

| No. | Structure | Name | Method | [M + H]⁺ |
|---|---|---|---|---|
| 97 | 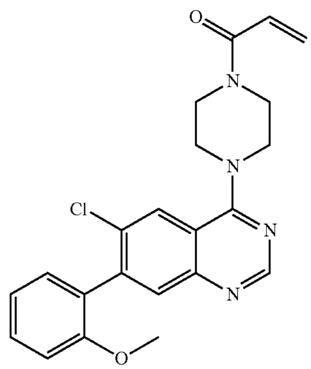 [SMILES: C=CC(=O)N1CCN(c2ncnc3cc(-c4ccccc4OC)c(Cl)cc23)CC1] | 1-(4-(6-chloro-7-(2-methoxyphenyl)quinazolin-4-yl)piperazin-1-yl)prop-2-en-1-one | B | 409.7 |
| 98 | 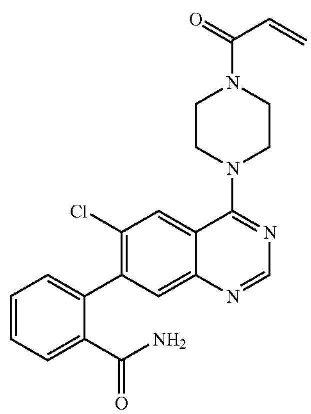 [SMILES: C=CC(=O)N1CCN(c2ncnc3cc(-c4ccccc4C(N)=O)c(Cl)cc23)CC1] | 2-(4-(4-acryloylpiperazin-1-yl)-6-chloroquinazolin-7-yl)benzamide | B | 422.30 |
| 99 | 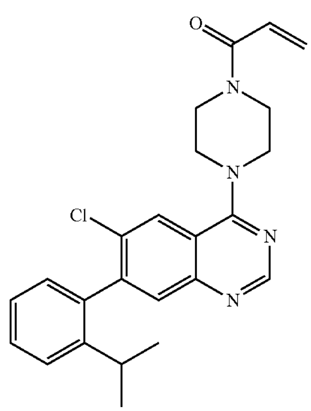 [SMILES: C=CC(=O)N1CCN(c2ncnc3cc(-c4ccccc4C(C)C)c(Cl)cc23)CC1] | 1-(4-(6-chloro-7-(2-isopropylphenyl)quinazolin-4-yl)piperazin-1-yl)prop-2-en-1-one | B | 421.35 |
| 100 | 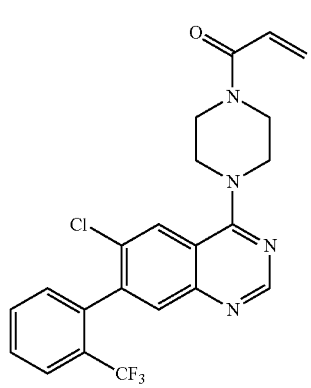 [SMILES: C=CC(=O)N1CCN(c2ncnc3cc(-c4ccccc4C(F)(F)F)c(Cl)cc23)CC1] | 1-(4-(6-chloro-7-(2-(trifluoromethyl)phenyl)quinazolin-4-yl)piperazin-1-yl)prop-2-en-1-one | B | 447.80 |

TABLE 1-continued

Representative Compounds

| No. | Structure | Name | Method | [M + H]+ |
|---|---|---|---|---|
| 101 | 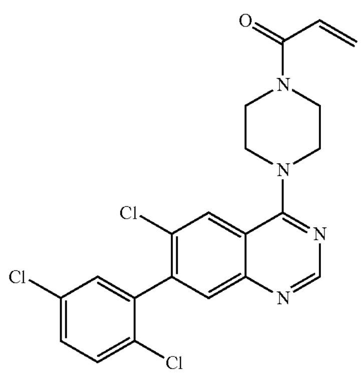 [SMILES: C=CC(=O)N1CCN(c2ncnc3cc(-c4cc(Cl)ccc4Cl)c(Cl)cc23)CC1] | 1-(4-(6-chloro-7-(2,5-dichlorophenyl)quinazolin-4-yl)piperazin-1-yl)prop-2-en-1-one | B | 447.25 |
| 102 | 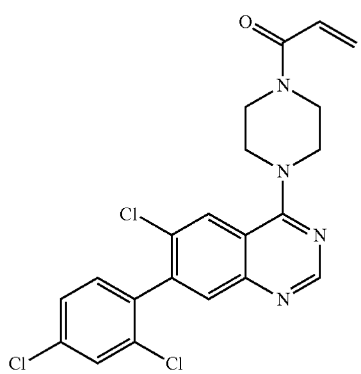 [SMILES: C=CC(=O)N1CCN(c2ncnc3cc(-c4ccc(Cl)cc4Cl)c(Cl)cc23)CC1] | 1-(4-(6-chloro-7-(2,4-dichlorophenyl)quinazolin-4-yl)piperazin-1-yl)prop-2-en-1-one | B | 447.30 |
| 103 | 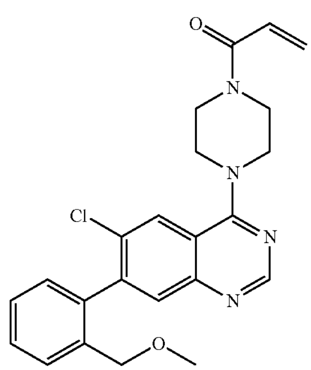 [SMILES: C=CC(=O)N1CCN(c2ncnc3cc(-c4ccccc4COC)c(Cl)cc23)CC1] | 1-(4-(6-chloro-7-(2-(methoxymethyl)phenyl)quinazolin-4-yl)piperazin-1-yl)prop-2-en-1-one | B | 423.35 |
| 104 | 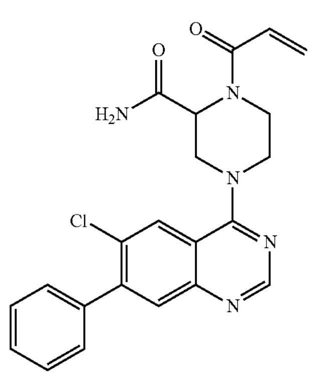 [SMILES: C=CC(=O)N1CCN(c2ncnc3cc(-c4ccccc4)c(Cl)cc23)CC1C(N)=O] | 1-acryloyl-4-(6-chloro-7-phenylquinazolin-4-yl)piperazine-2-carboxamide | B | 422.35 |

TABLE 1-continued

Representative Compounds

| No. | Structure | Name | Method | [M + H]⁺ |
|---|---|---|---|---|
| 105 | 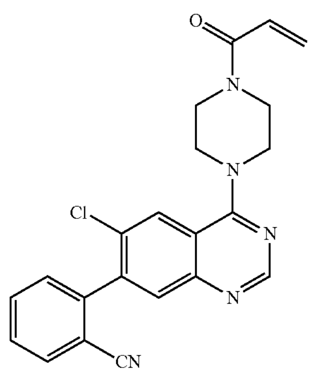 [SMILES: C=CC(=O)N1CCN(c2ncnc3cc(-c4ccccc4C#N)c(Cl)cc23)CC1] | 2-(4-(4-acryloylpiperazin-1-yl)-6-chloroquinazolin-7-yl)benzonitrile | B | 405.20 |
| 106 | 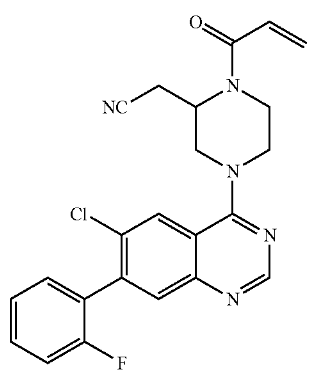 | 2-(1-acryloyl-4-(6-chloro-7-(2-fluorophenyl)quinazolin-4-yl)piperazin-2-yl)acetonitrile | B | 437.30 |
| 107 | 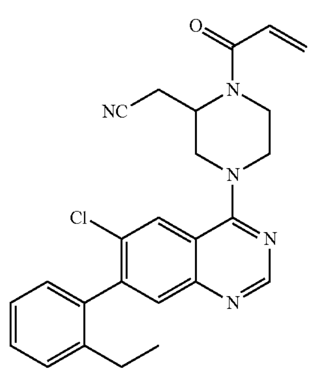 [SMILES: C=CC(=O)N1CCN(c2ncnc3cc(-c4ccccc4CC)c(Cl)cc23)CC1CC#N] | 2-(1-acryloyl-4-(6-chloro-7-(2-ethylphenyl)quinazolin-4-yl)piperazin-2-yl)acetonitrile | B | 446.35 |
| 108 | 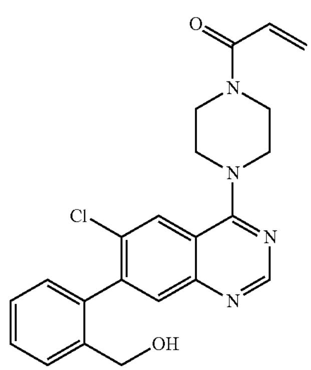 | 1-(4-(6-chloro-7-(2-(hydroxymethyl)phenyl)quinazolin-4-yl)piperazin-1-yl)prop-2-en-1-one | B | 409.30 |

TABLE 1-continued

Representative Compounds

| No. | Structure | Name | Method | [M + H]+ |
|---|---|---|---|---|
| 109 | 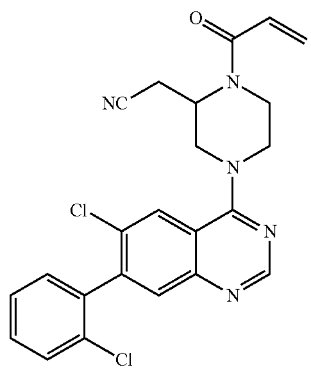 [SMILES: C=CC(=O)N1CCN(c2ncnc3cc(-c4ccccc4Cl)c(Cl)cc23)CC1CC#N] | 2-(1-acryloyl-4-(6-chloro-7-(2-chlorophenyl)quinazolin-4-yl)piperazin-2-yl)acetonitrile | B | 452.30 |
| 110 | 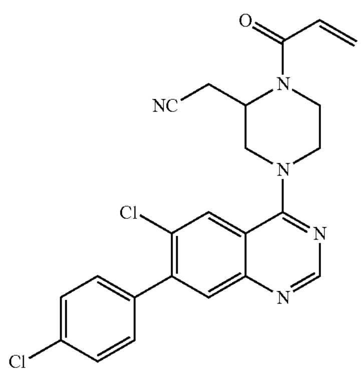 [SMILES: C=CC(=O)N1CCN(c2ncnc3cc(-c4ccc(Cl)cc4)c(Cl)cc23)CC1CC#N] | 2-(1-acryloyl-4-(6-chloro-7-(4-chlorophenyl)quinazolin-4-yl)piperazin-2-yl)acetonitrile | B | 452.25 |
| 111 | 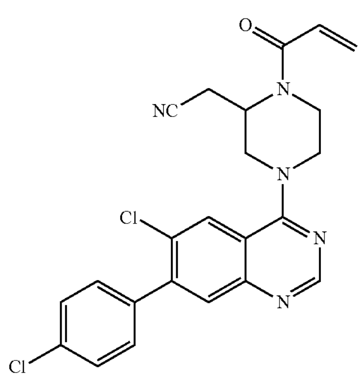 [SMILES: C=CC(=O)N1CCN(c2ncnc3cc(-c4ccc(Cl)cc4)c(Cl)cc23)CC1CC#N] | 2-(1-acryloyl-4-(6-chloro-7-(4-chlorophenyl)quinazolin-4-yl)piperazin-2-yl)acetonitrile | B | 452.25 |
| 112 | 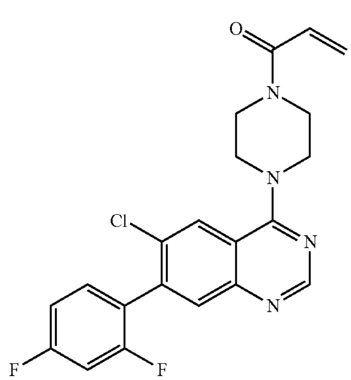 [SMILES: C=CC(=O)N1CCN(c2ncnc3cc(-c4ccc(F)cc4F)c(Cl)cc23)CC1] | 1-(4-(6-chloro-7-(2,4-difluorophenyl)quinazolin-4-yl)piperazin-1-yl)prop-2-en-1-one | B | 415.0 |

TABLE 1-continued

Representative Compounds

| No. | Structure | Name | Method | [M + H]⁺ |
|---|---|---|---|---|
| 113 | 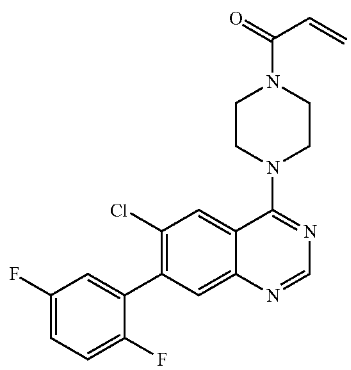 [SMILES: C=CC(=O)N1CCN(c2ncnc3cc(-c4cc(F)ccc4F)c(Cl)cc23)CC1] | 1-(4-(6-chloro-7-(2,5-difluorophenyl)quinazolin-4-yl)piperazin-1-yl)prop-2-en-1-one | B | 415.10 |
| 114 | 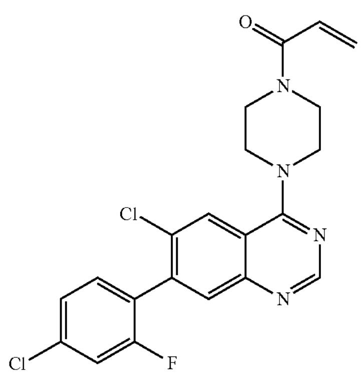 [SMILES: C=CC(=O)N1CCN(c2ncnc3cc(-c4ccc(Cl)cc4F)c(Cl)cc23)CC1] | 1-(4-(6-chloro-7-(4-chloro-2-fluorophenyl)quinazolin-4-yl)piperazin-1-yl)prop-2-en-1-one | B | 431.05 |
| 115 | 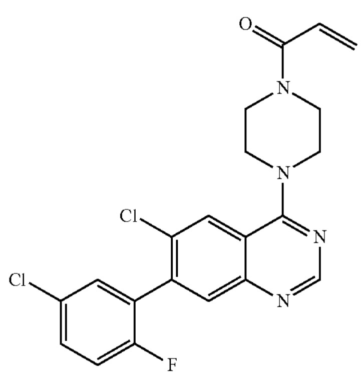 [SMILES: C=CC(=O)N1CCN(c2ncnc3cc(-c4cc(Cl)ccc4F)c(Cl)cc23)CC1] | 1-(4-(6-chloro-7-(5-chloro-2-fluorophenyl)quinazolin-4-yl)piperazin-1-yl)prop-2-en-1-one | B | 431.05 |
| 116 | 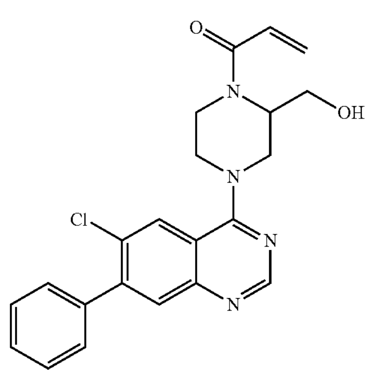 | 1-(4-(6-chloro-7-phenylquinazolin-4-yl)-2-(hydroxymethyl)piperazin-1-yl)prop-2-en-1-one | B | 409.25 |

TABLE 1-continued

Representative Compounds

| No. | Structure | Name | Method | [M + H]+ |
|---|---|---|---|---|
| 117 | 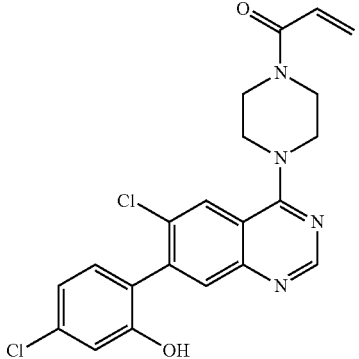 | 1-(4-(6-chloro-7-(4-chloro-2-hydroxyphenyl)quinazolin-4-yl)piperazin-1-yl)prop-2-en-1-one | B | 429.35 |
| 118 | 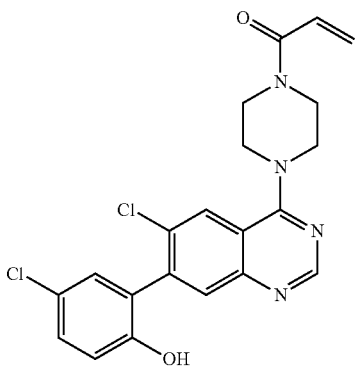 [SMILES: C=CC(=O)N1CCN(c2ncnc3cc(-c4cc(Cl)ccc4O)c(Cl)cc23)CC1] | 1-(4-(6-chloro-7-(5-chloro-2-hydroxyphenyl)quinazolin-4-yl)piperazin-1-yl)prop-2-en-1-one | B | 429.30 |
| 119 | 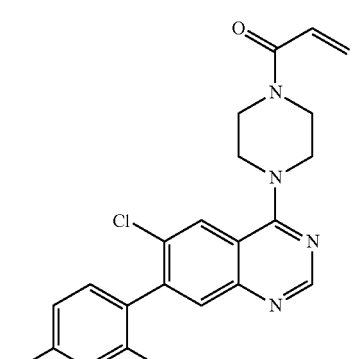 | 1-(4-(6-chloro-7-(4-fluoro-2-(trifluoromethyl)phenyl)quinazolin-4-yl)piperazin-1-yl)prop-2-en-1-one | B | 465.35 |
| 120 | 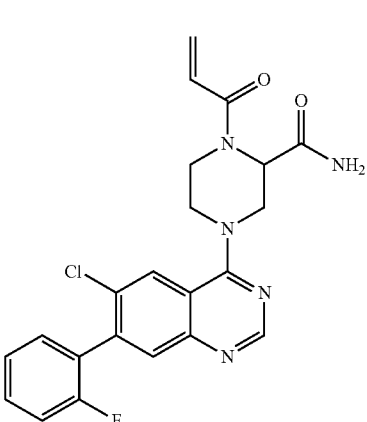 | 1-acryloyl-4-(6-chloro-7-(2-fluorophenyl)quinazolin-4-yl)piperazine-2-carboxamide | B | 440.30 |

TABLE 1-continued

Representative Compounds

| No. | Structure | Name | Method | [M + H]+ |
|---|---|---|---|---|
| 121 | 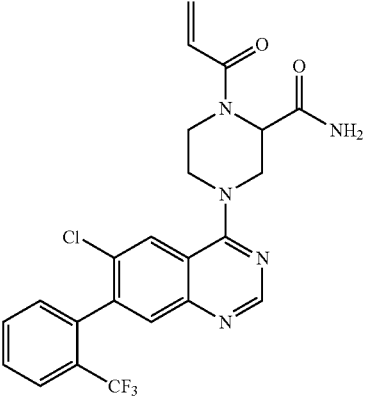 [SMILES: C=CC(=O)N1CCN(c2ncnc3cc(-c4ccccc4C(F)(F)F)c(Cl)cc23)CC1C(N)=O] | 1-acryloyl-4-(6-chloro-7-(2-(trifluoromethyl)phenyl)quinazolin-4-yl)piperazine-2-carboxamide | B | 490.40 |
| 122 | 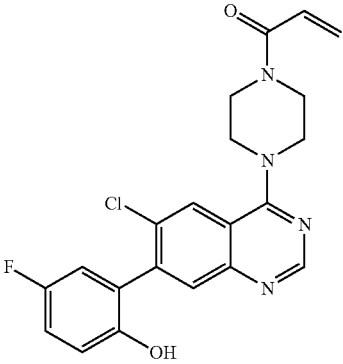 [SMILES: C=CC(=O)N1CCN(c2ncnc3cc(-c4cc(F)ccc4O)c(Cl)cc23)CC1] | 1-(4-(6-chloro-7-(5-fluoro-2-hydroxyphenyl)quinazolin-4-yl)piperazin-1-yl)prop-2-en-1-one | B | 413.30 |
| 123 | 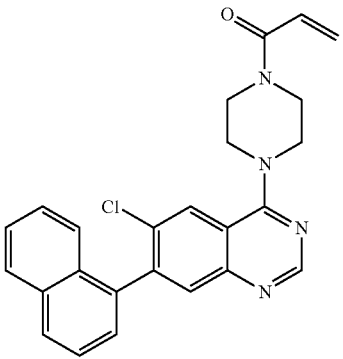 [SMILES: C=CC(=O)N1CCN(c2ncnc3cc(-c4cccc5ccccc45)c(Cl)cc23)CC1] | 1-(4-(6-chloro-7-(naphthalen-1-yl)quinazolin-4-yl)piperazin-1-yl)prop-2-en-1-one | B | 429.35 |
| 124 | 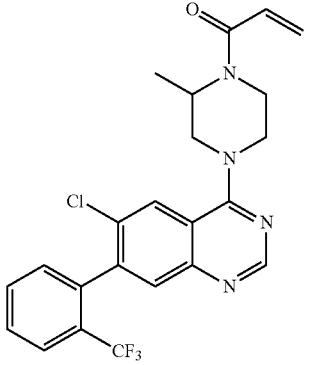 [SMILES: C=CC(=O)N1CCN(c2ncnc3cc(-c4ccccc4C(F)(F)F)c(Cl)cc23)CC1C] | 1-(4-(6-chloro-7-(2-(trifluoromethyl)phenyl)quinazolin-4-yl)-2-methylpiperazin-1-yl)prop-2-en-1-one | B | 461.35 |

TABLE 1-continued

Representative Compounds

| No. | Structure | Name | Method | [M + H]+ |
|---|---|---|---|---|
| 125 | 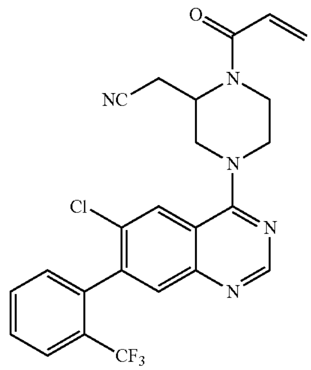 [SMILES: C=CC(=O)N1CCN(c2ncnc3cc(-c4ccccc4C(F)(F)F)c(Cl)cc23)CC1CC#N] | 2-(1-acryloyl-4-(6-chloro-7-(2-(trifluoromethyl)phenyl)quinazolin-4-yl)piperazin-2-yl)acetonitrile | B | 486.40 |
| 126 | 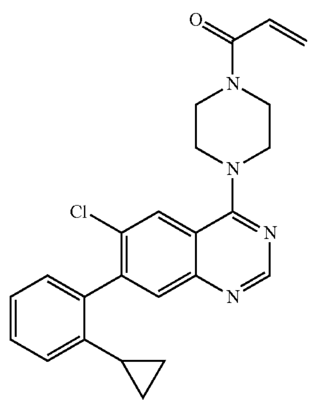 [SMILES: C=CC(=O)N1CCN(c2ncnc3cc(-c4ccccc4C4CC4)c(Cl)cc23)CC1] | 1-(4-(6-chloro-7-(2-cyclopropylphenyl)quinazolin-4-yl)piperazin-1-yl)prop-2-en-1-one | B | 419.20 |
| 127 | 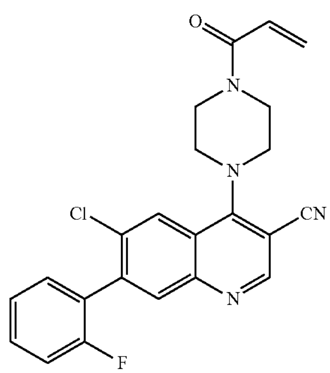 [SMILES: C=CC(=O)N1CCN(c2c(C#N)cnc3cc(-c4ccccc4F)c(Cl)cc23)CC1] | 4-(4-acryloylpiperazin-1-yl)-6-chloro-7-(2-fluorophenyl)quinoline-3-carbonitrile | G | 421.30 |
| 128 | 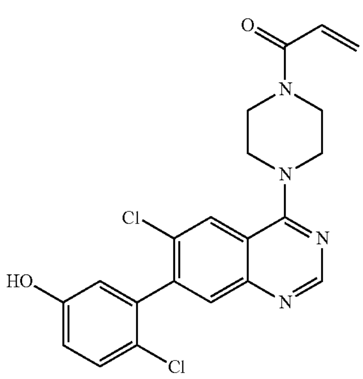 [SMILES: C=CC(=O)N1CCN(c2ncnc3cc(-c4cc(O)ccc4Cl)c(Cl)cc23)CC1] | 1-(4-(6-chloro-7-(2-chloro-5-hydroxyphenyl)quinazolin-4-yl)piperazin-1-yl)prop-2-en-1-one | B | 430.10 |

TABLE 1-continued
Representative Compounds
| No. | Structure | Name | Method | [M + H]+ |
|---|---|---|---|---|
| 129 | 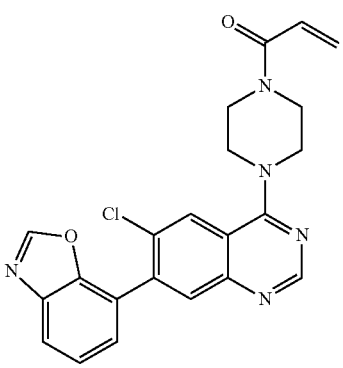 [SMILES: C=CC(=O)N1CCN(c2ncnc3cc(-c4cccc5ncoc45)c(Cl)cc23)CC1] | 1-(4-(7-(benzo[d]oxazol-7-yl)-6-chloroquinazolin-4-yl)piperazin-1-yl)prop-2-en-1-one | B | 420.10 |
| 130 | 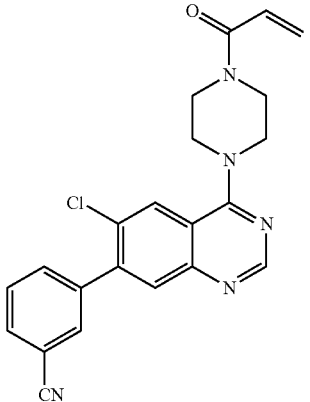 [SMILES: C=CC(=O)N1CCN(c2ncnc3cc(-c4cccc(C#N)c4)c(Cl)cc23)CC1] | 3-(4-(4-acryloylpiperazin-1-yl)-6-chloroquinazolin-7-yl)benzonitrile | B | 404.10 |
| 131 | 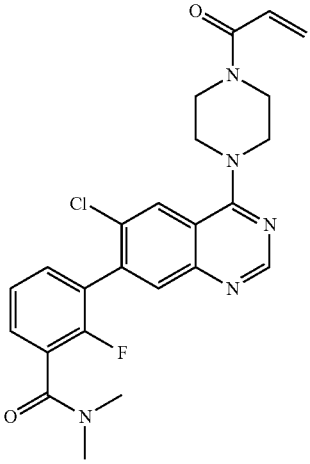 [SMILES: C=CC(=O)N1CCN(c2ncnc3cc(-c4cccc(C(=O)N(C)C)c4F)c(Cl)cc23)CC1] | 3-(4-(4-acryloylpiperazin-1-yl)-6-chloroquinazolin-7-yl)-2-fluoro-N,N-dimethylbenzamide | B | 468.10 |

TABLE 1-continued

Representative Compounds

| No. | Structure | Name | Method | [M + H]+ |
|---|---|---|---|---|
| 132 | 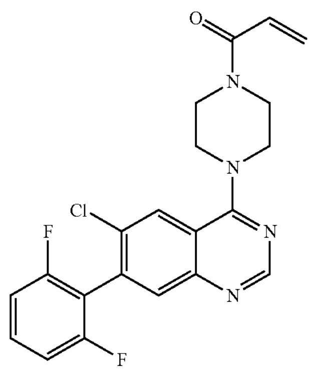 [SMILES: C=CC(=O)N1CCN(c2ncnc3cc(-c4c(F)cccc4F)c(Cl)cc23)CC1] | 1-(4-(6-chloro-7-(2,6-difluorophenyl)quinazolin-4-yl)piperazin-1-yl)prop-2-en-1-one | B | 415.3 |
| 133 | 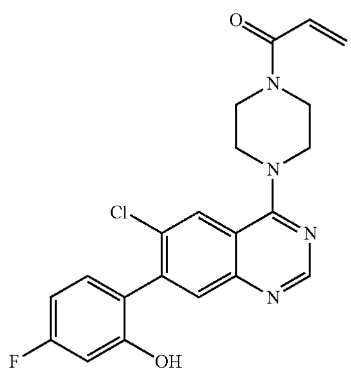 [SMILES: C=CC(=O)N1CCN(c2ncnc3cc(-c4ccc(F)cc4O)c(Cl)cc23)CC1] | 1-(4-(6-chloro-7-(4-fluoro-2-hydroxyphenyl)quinazolin-4-yl)piperazin-1-yl)prop-2-en-1-one | B | 413.30 |
| 134 | 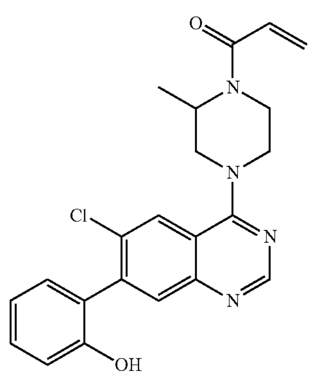 | 1-(4-(6-chloro-7-(2-hydroxyphenyl)quinazolin-4-yl)-2-methylpiperazin-1-yl)prop-2-en-1-one | B | 409.30 |
| 135 | 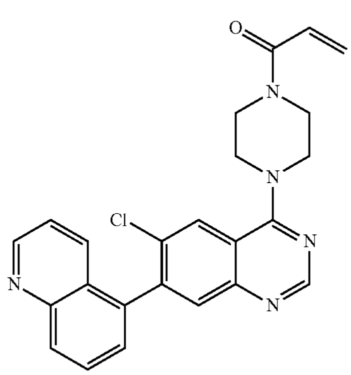 [SMILES: C=CC(=O)N1CCN(c2ncnc3cc(-c4cccc5ncccc45)c(Cl)cc23)CC1] | 1-(4-(6-chloro-7-(quinolin-5-yl)quinazolin-4-yl)piperazin-1-yl)prop-2-en-1-one | B | 430.30 |

TABLE 1-continued

Representative Compounds

| No. | Structure | Name | Method | [M + H]+ |
|---|---|---|---|---|
| 136 | 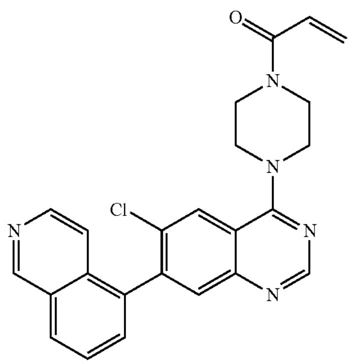 [SMILES: C=CC(=O)N1CCN(c2ncnc3cc(-c4cccc5cnccc45)c(Cl)cc23)CC1] | 1-(4-(6-chloro-7-(isoquinolin-5-yl)quinazolin-4-yl)piperazin-1-yl)prop-2-en-1-one | B | 430.35 |
| 137 | 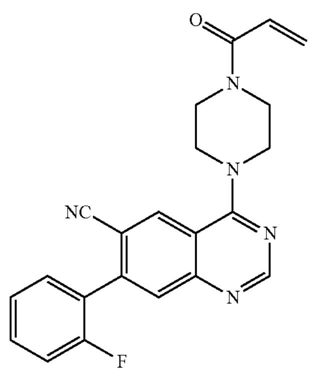 [SMILES: C=CC(=O)N1CCN(c2ncnc3cc(-c4ccccc4F)c(C#N)cc23)CC1] | 4-(4-acryloylpiperazin-1-yl)-7-(2-fluorophenyl)quinazoline-6-carbonitrile | B | 388.30 |
| 138 | 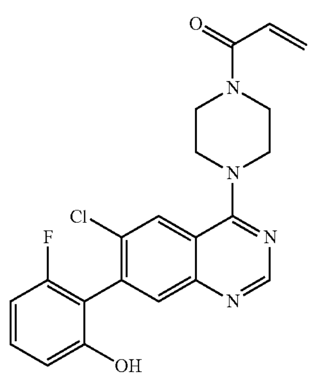 [SMILES: C=CC(=O)N1CCN(c2ncnc3cc(-c4c(O)cccc4F)c(Cl)cc23)CC1] | 1-(4-(6-chloro-7-(2-fluoro-6-hydroxyphenyl)quinazolin-4-yl)piperazin-1-yl)prop-2-en-1-one | B | 413.25 |
| 139 | 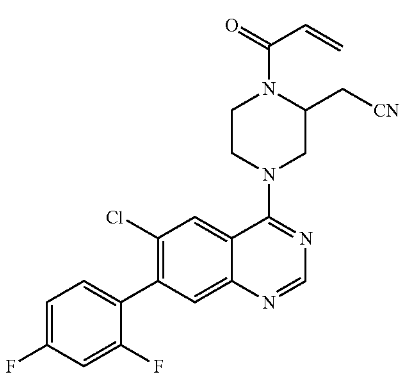 [SMILES: C=CC(=O)N1CCN(c2ncnc3cc(-c4ccc(F)cc4F)c(Cl)cc23)CC1CC#N] | 2-(1-acryloyl-4-(6-chloro-7-(2,4-difluorophenyl)quinazolin-4-yl)piperazin-2-yl)acetonitrile | B | 454.30 |

TABLE 1-continued

Representative Compounds

| No. | Structure | Name | Method | [M + H]+ |
|---|---|---|---|---|
| 140 | 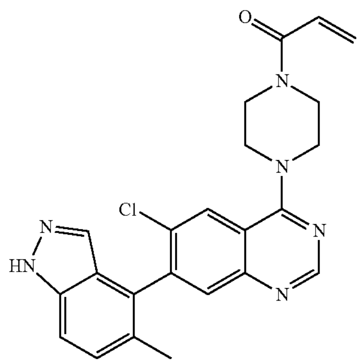 [SMILES: C=CC(=O)N1CCN(c2ncnc3cc(-c4c(C)ccc5[nH]ncc45)c(Cl)cc23)CC1] | 1-(4-(6-chloro-7-(5-methyl-1H-indazol-4-yl)quinazolin-4-yl)piperazin-1-yl)prop-2-en-1-one | Q | 433.15 |
| 141 | 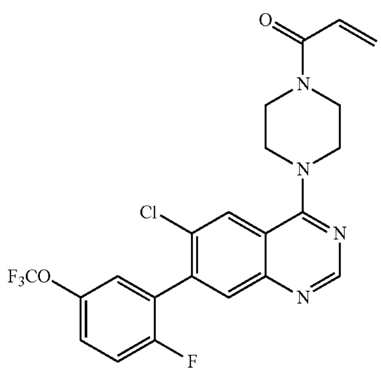 [SMILES: C=CC(=O)N1CCN(c2ncnc3cc(-c4cc(OC(F)(F)F)ccc4F)c(Cl)cc23)CC1] | 1-(4-(6-chloro-7-(2-fluoro-5-(trifluoromethoxy)phenyl)quinazolin-4-yl)piperazin-1-yl)prop-2-en-1-one | B | 481.10 |
| 142 | 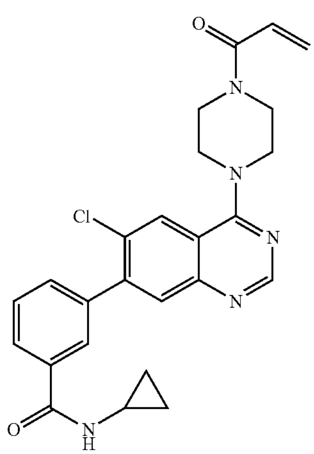 [SMILES: C=CC(=O)N1CCN(c2ncnc3cc(-c4cccc(C(=O)NC5CC5)c4)c(Cl)cc23)CC1] | 3-(4-(4-acryloylpiperazin-1-yl)-6-chloroquinazolin-7-yl)-N-cyclopropylbenzamide | B | 462.20 |
| 143 | 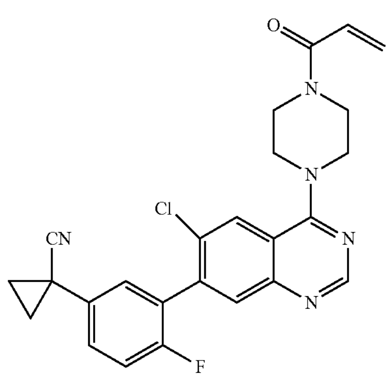 [SMILES: C=CC(=O)N1CCN(c2ncnc3cc(-c4cc(C5(C#N)CC5)ccc4F)c(Cl)cc23)CC1] | 1-(3-(4-(4-acryloylpiperazin-1-yl)-6-chloroquinazolin-7-yl)-4-fluorophenyl)cyclopropaecarbonitrile | B | 462.10 |

TABLE 1-continued

Representative Compounds

| No. | Structure | Name | Method | [M + H]+ |
|---|---|---|---|---|
| 144 | 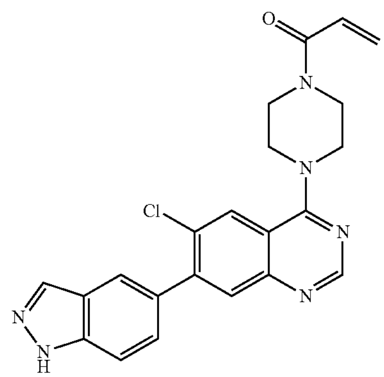 [SMILES: C=CC(=O)N1CCN(c2ncnc3cc(-c4ccc5[nH]ncc5c4)c(Cl)cc23)CC1] | 1-(4-(6-chloro-7-(1H-indazol-5-yl)quinazolin-4-yl)piperazin-1-yl)prop-2-en-1-one | B | 419.25 |
| 145 | 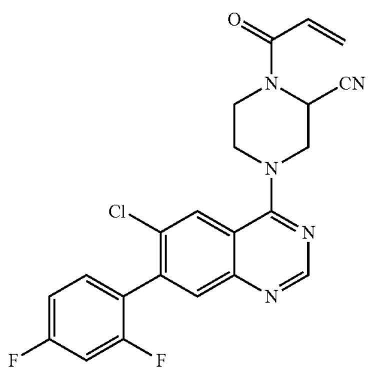 [SMILES: C=CC(=O)N1CCN(c2ncnc3cc(-c4ccc(F)cc4F)c(Cl)cc23)CC1C#N] | 1-acryloyl-4-(6-chloro-7-(2,4-difluorophenyl)quinazolin-4-yl)piperazine-2-carbonitrile | B | 440.30 |
| 146 | 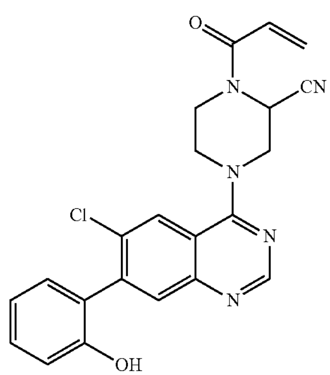 [SMILES: C=CC(=O)N1CCN(c2ncnc3cc(-c4ccccc4O)c(Cl)cc23)CC1C#N] | 1-acryloyl-4-(6-chloro-7-(2-hydroxyphenyl)quinazolin-4-yl)piperazine-2-carbonitrile | B | 420.25 |
| 147 | 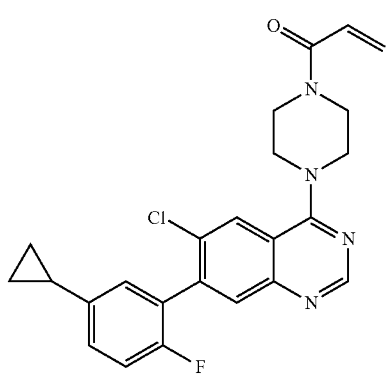 [SMILES: C=CC(=O)N1CCN(c2ncnc3cc(-c4cc(C5CC5)ccc4F)c(Cl)cc23)CC1] | 1-(4-(6-chloro-7-(5-cyclopropyl-2-fluorophenyl)quinazolin-4-yl)piperazin-1-yl)prop-2-en-1-one | B | 437.10 |

TABLE 1-continued
Representative Compounds
| No. | Structure | Name | Method | [M + H]+ |
|---|---|---|---|---|
| 148 | 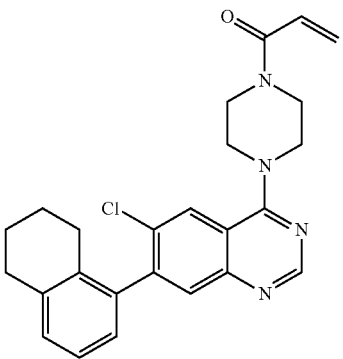 [SMILES: C=CC(=O)N1CCN(c2ncnc3cc(-c4cccc5c4CCCC5)c(Cl)cc23)CC1] | 1-(4-(6-chloro-7-(5,6,7,8-tetrahydronaphthalen-1-yl)quinazolin-4-yl)piperazin-1-yl)prop-2-en-1-one | B | 433.20 |
| 149 | 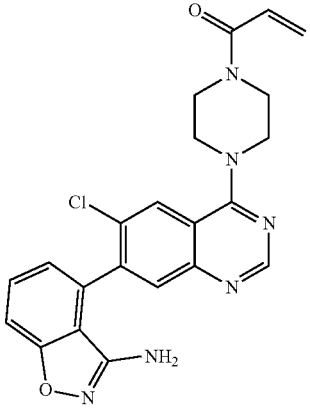 [SMILES: C=CC(=O)N1CCN(c2ncnc3cc(-c4cccc5onc(N)c45)c(Cl)cc23)CC1] | 1-(4-(7-(3-aminobenzo[d]isoxazol-4-yl)-6-chloroquinazolin-4-yl)piperazin-1-yl)prop-2-en-1-one | B | 435.30 |
| 150 | 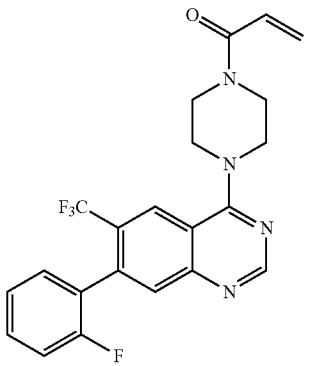 [SMILES: C=CC(=O)N1CCN(c2ncnc3cc(-c4ccccc4F)c(C(F)(F)F)cc23)CC1] | 1-(4-(7-(2-fluorophenyl)-6-(trifluoromethyl)quinazolin-4-yl)piperazin-1-yl)prop-2-en-1-one | R | 431.30 |
| 151 | 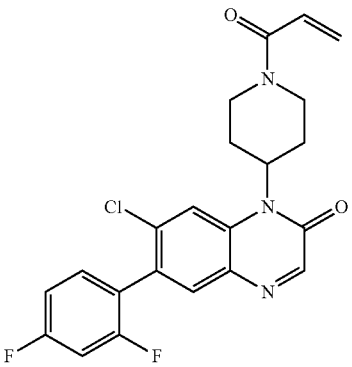 [SMILES: C=CC(=O)N1CCC(n2c(=O)cnc3cc(-c4ccc(F)cc4F)c(Cl)cc32)CC1] | 1-(1-acryloylpiperidin-4-yl)-7-chloro-6-(2,4-difluorophenyl)quinoxalin-2(1H)-one | S | 430.30 |

TABLE 1-continued

Representative Compounds

| No. | Structure | Name | Method | [M + H]+ |
|---|---|---|---|---|
| 152 | 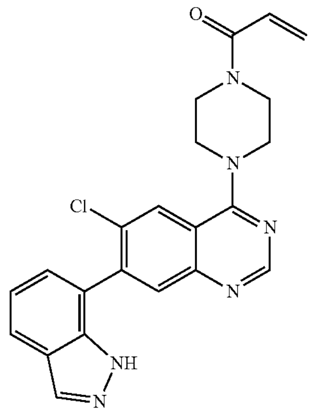 [SMILES: C=CC(=O)N1CCN(c2ncnc3cc(-c4cccc5cn[nH]c45)c(Cl)cc23)CC1] | 1-(4-(6-chloro-7-(1H-indazol-7-yl)quinazolin-4-yl)piperazin-1-yl)prop-2-en-1-one | B | 419.30 |
| 153 | 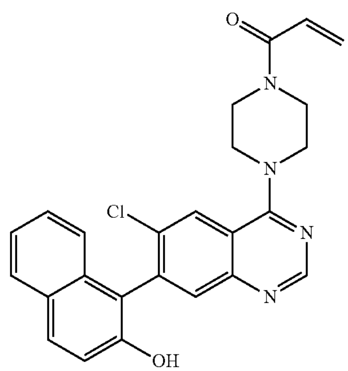 [SMILES: C=CC(=O)N1CCN(c2ncnc3cc(-c4c(O)ccc5ccccc45)c(Cl)cc23)CC1] | 1-(4-(6-chloro-7-(2-hydroxynaphthalen-1-yl)quinazolin-4-yl)piperazin-1-yl)prop-2-en-1-one | Q | 445.10 |
| 154 | 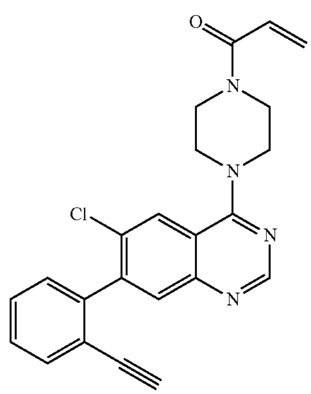 [SMILES: C#Cc1ccccc1-c1cc2ncnc(N3CCN(C(=O)C=C)CC3)c2cc1Cl] | 1-(4-(6-chloro-7-(2-ethynylphenyl)quinazolin-4-yl)piperazin-1-yl)prop-2-en-1-one | B | 403.25 |
| 155 | 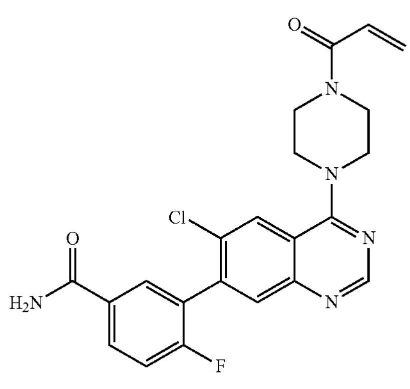 [SMILES: C=CC(=O)N1CCN(c2ncnc3cc(-c4cc(C(N)=O)ccc4F)c(Cl)cc23)CC1] | 3-(4-(4-acryloylpiperazin-1-yl)-6-chloroquinazolin-7-yl)-4-fluorobenzamide | B | 440.25 |

TABLE 1-continued

Representative Compounds

| No. | Structure | Name | Method | [M + H]+ |
|---|---|---|---|---|
| 156 | 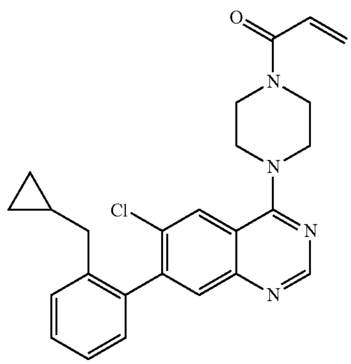 [SMILES: C=CC(=O)N1CCN(c2ncnc3cc(-c4ccccc4CC4CC4)c(Cl)cc23)CC1] | 1-(4-(6-chloro-7-(2-(cyclopropylmethyl)phenyl)quinazolin-4-yl)piperazin-1-yl)prop-2-en-1-one | B | 433.35 |
| 157 | 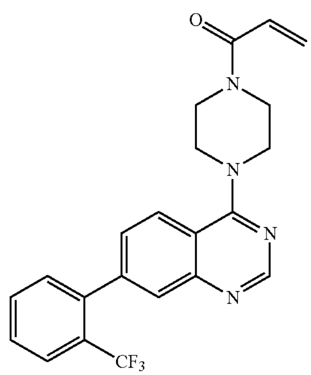 [SMILES: C=CC(=O)N1CCN(c2ncnc3cc(-c4ccccc4C(F)(F)F)ccc23)CC1] | 1-(4-(7-(2-(trifluoromethyl)phenyl)quinazolin-4-yl)piperazin-1-yl)prop-2-en-1-one | B | 413.10 |
| 158 | 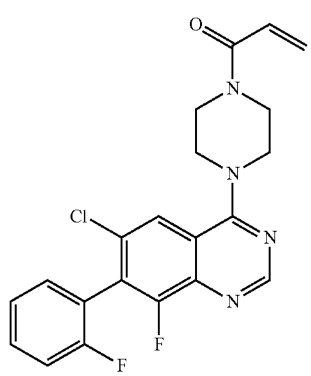 [SMILES: C=CC(=O)N1CCN(c2ncnc3c(F)c(-c4ccccc4F)c(Cl)cc23)CC1] | 1-(4-(6-chloro-8-fluoro-7-(2-fluorophenyl)quinazolin-4-yl)piperazin-1-yl)prop-2-en-1-one | O | 415.25 |
| 159 | 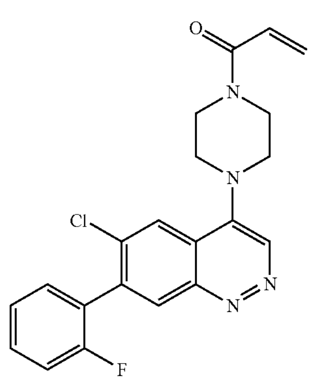 [SMILES: C=CC(=O)N1CCN(c2cnnc3cc(-c4ccccc4F)c(Cl)cc23)CC1] | 1-(4-(6-chloro-7-(2-fluorophenyl)cinnolin-4-yl)piperazin-1-yl)prop-2-en-1-one | N | 397.25 |

TABLE 1-continued

Representative Compounds

| No. | Structure | Name | Method | [M + H]+ |
|---|---|---|---|---|
| 160 | 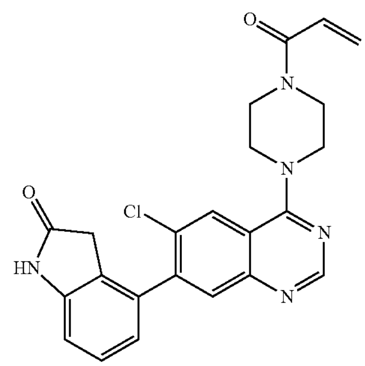 [SMILES: C=CC(=O)N1CCN(c2ncnc3cc(-c4cccc5c4CC(=O)N5)c(Cl)cc23)CC1] | 4-(4-(4-acryloylpiperazin-1-yl)-6-chloroquinazolin-7-yl)indolin-2-one | B | 434.25 |
| 161 | 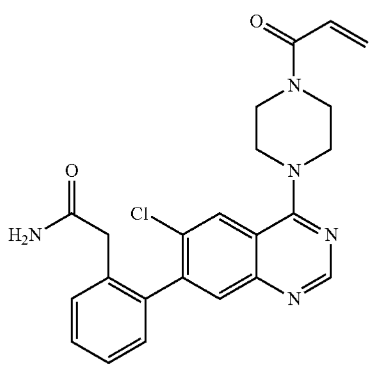 [SMILES: C=CC(=O)N1CCN(c2ncnc3cc(-c4ccccc4CC(N)=O)c(Cl)cc23)CC1] | 2-(2-(4-(4-acryloylpiperazin-1-yl)-6-chloroquinazolin-7-yl)phenyl)acetamide | B | 436.1 |
| 162 | 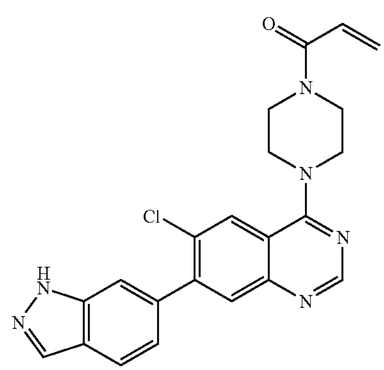 [SMILES: C=CC(=O)N1CCN(c2ncnc3cc(-c4ccc5cn[nH]c5c4)c(Cl)cc23)CC1] | 1-(4-(6-chloro-7-(1H-indazol-6-yl)quinazolin-4-yl)piperazin-1-yl)prop-2-en-1-one | B | 419.3 |
| 163 | 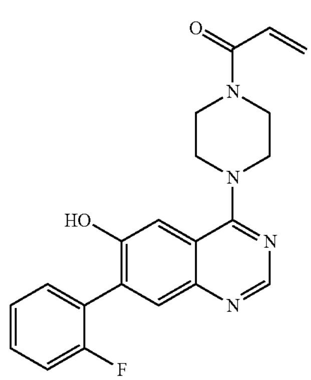 | 1-(4-(7-(2-fluorophenyl)-6-hydroxyquinazolin-4-yl)piperazin-1-yl)prop-2-en-1-one | A | 379.25 |

TABLE 1-continued

| No. | Structure | Name | Method | [M + H]+ |
|---|---|---|---|---|
| 164 | 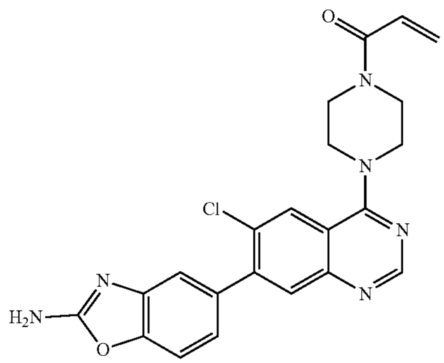 [SMILES: C=CC(=O)N1CCN(c2ncnc3cc(-c4ccc5oc(N)nc5c4)c(Cl)cc23)CC1] | 4-(4-(7-(2-aminobenzo[d]oxazol-5-yl)-6-chloroquinazolin-4-yl)piperazin-1-yl)prop-2-en-1-one | B | 435.25 |
| 165 | 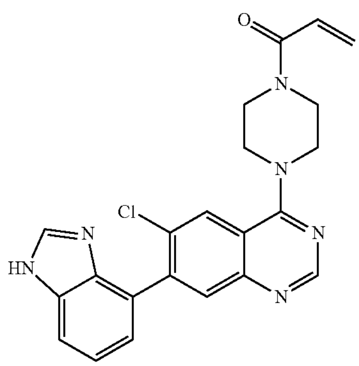 [SMILES: C=CC(=O)N1CCN(c2ncnc3cc(-c4cccc5[nH]cnc45)c(Cl)cc23)CC1] | 1-(4-(7-(1H-benzo[d]imidazol-4-yl)-6-chloroquinazolin-4-yl)piperazin-1-yl)prop-2-en-1-one | B | 419.30 |
| 166 | 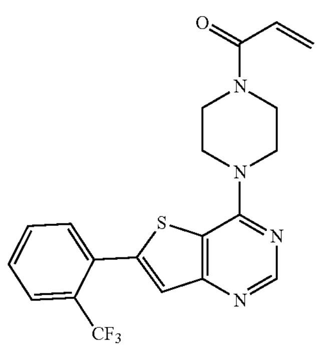 [SMILES: C=CC(=O)N1CCN(c2ncnc3cc(-c4ccccc4C(F)(F)F)sc23)CC1] | 1-(4-(6-(2-(trifluoromethyl)phenyl)thieno[3,2-d]pyrimidin-4-yl)piperazin-1-yl)prop-2-en-1-one | H | 419.10 |
| 167 | 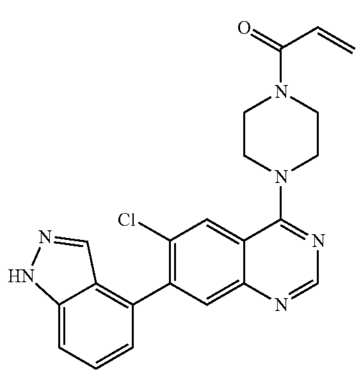 [SMILES: C=CC(=O)N1CCN(c2ncnc3cc(-c4cccc5[nH]ncc45)c(Cl)cc23)CC1] | 1-(4-(6-chloro-7-(1H-indazol-4-yl)quinazolin-4-yl)piperazin-1-yl)prop-2-en-1-one | B | 419.30 |

TABLE 1-continued

Representative Compounds

| No. | Structure | Name | Method | [M + H]+ |
|---|---|---|---|---|
| 168 | 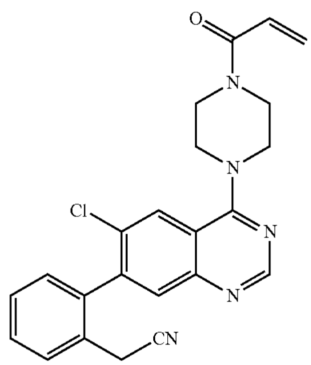 [SMILES: C=CC(=O)N1CCN(c2ncnc3cc(-c4ccccc4CC#N)c(Cl)cc23)CC1] | 2-(2-(4-(4-acryloylpiperazin-1-yl)-6-chloroquinazolin-7-yl)phenyl)acetonitrile | B | 418.1 |
| 169 | 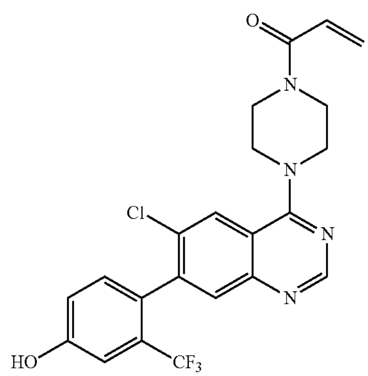 [SMILES: C=CC(=O)N1CCN(c2ncnc3cc(-c4ccc(O)cc4C(F)(F)F)c(Cl)cc23)CC1] | 1-(4-(6-chloro-7-(4-hydroxy-2-(trifluoromethyl)phenyl)quinazolin-4-yl)piperazin-1-yl)prop-2-en-1-one | B | 463.30 |
| 170 | 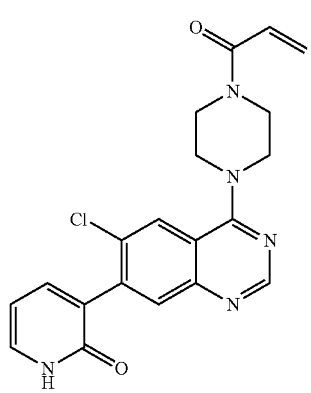 [SMILES: C=CC(=O)N1CCN(c2ncnc3cc(-c4ccc[nH]c4=O)c(Cl)cc23)CC1] | 3-(4-(4-acryloylpiperazin-1-yl)-6-chloroquinazolin-7-yl)pyridin-2(1H)-one | B | 396.25 |
| 171 | 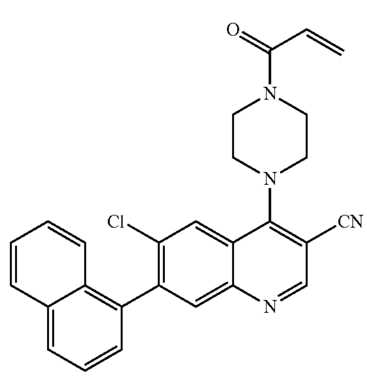 [SMILES: C=CC(=O)N1CCN(c2c(C#N)cnc3cc(-c4cccc5ccccc45)c(Cl)cc23)CC1] | 4-(4-acryloylpiperazin-1-yl)-6-chloro-7-(naphthalen-1-yl)quinoline-3-carbonitrile | P | 453.30 |

TABLE 1-continued

Representative Compounds

| No. | Structure | Name | Method | [M + H]+ |
|---|---|---|---|---|
| 172 | 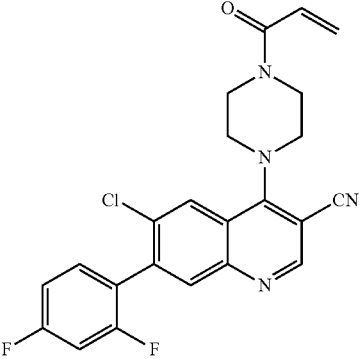 [SMILES: C=CC(=O)N1CCN(c2c(C#N)cnc3cc(-c4ccc(F)cc4F)c(Cl)cc23)CC1] | 4-(4-acryloylpiperazin-1-yl)-6-chloro-7-(2,4-difluorophenyl)quinoline-3-carbonitrile | P | 439.25 |
| 173 | 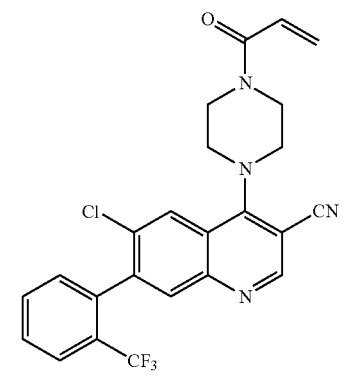 [SMILES: C=CC(=O)N1CCN(c2c(C#N)cnc3cc(-c4ccccc4C(F)(F)F)c(Cl)cc23)CC1] | 4-(4-acryloylpiperazin-1-yl)-6-chloro-7-(2-(trifluoromethyl)phenyl)quinoline-3-carbonitrile | P | 471.35 |
| 174 | 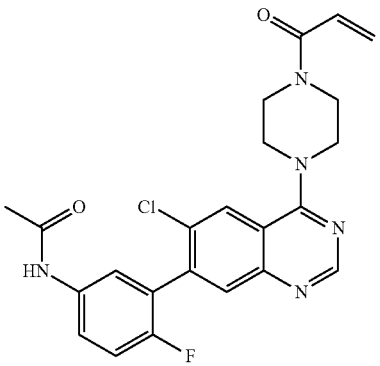 [SMILES: C=CC(=O)N1CCN(c2ncnc3cc(-c4cc(NC(C)=O)ccc4F)c(Cl)cc23)CC1] | N-(3-(4-(4-acryloylpiperazin-1-yl)-6-chloroquinazolin-7-yl)-4-fluorophenyl)acetamide | B | 454.10 |
| 175 | 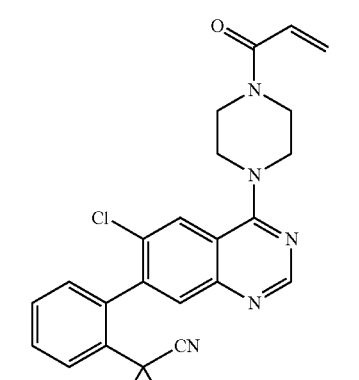 | 1-(2-(4-(4-acryloylpiperazin-1-yl)-6-chloroquinazolin-7-yl)phenyl)cyclopropanecarbonitrile | B | 444.1 |

TABLE 1-continued

Representative Compounds

| No. | Structure | Name | Method | [M + H]+ |
|---|---|---|---|---|
| 176 | 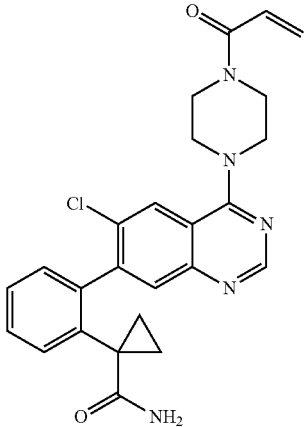 [SMILES: C=CC(=O)N1CCN(c2ncnc3cc(-c4ccccc4C4(C(N)=O)CC4)c(Cl)cc23)CC1] | 1-(2-(4-(4-acryloylpiperazin-1-yl)-6-chloroquinazolin-7-yl)phenyl)cyclopropanecarboxamide | B | 462.2 |
| 177 | 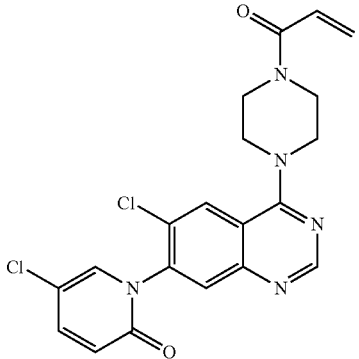 [SMILES: C=CC(=O)N1CCN(c2ncnc3cc(-n4cc(Cl)ccc4=O)c(Cl)cc23)CC1] | 1-(4-(4-acryloylpiperazin-1-yl)-6-chloroquinazolin-7-yl)-5-chloropyridin-2(1H)-one | T | 430.20 |
| 178 | 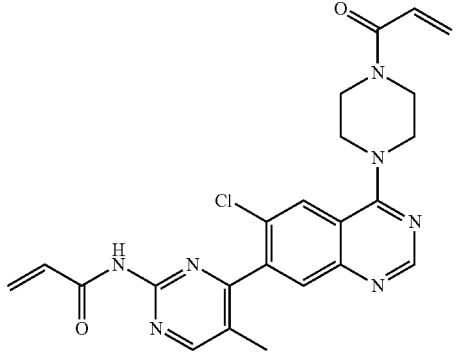 [SMILES: C=CC(=O)Nc1ncc(C)c(-c2cc3ncnc(N4CCN(C(=O)C=C)CC4)c3cc2Cl)n1] | N-(4-(4-(4-acryloylpiperazin-1-yl)-6-chloroquinazolin-7-yl)-5-methylpyrimidin-2-yl)acrylamide | B | 464.10 |
| 179 | 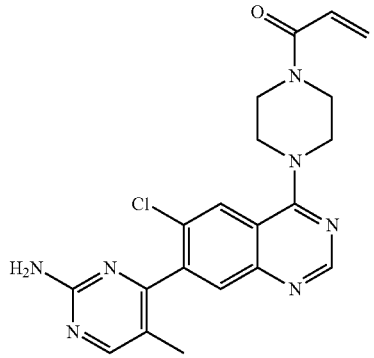 [SMILES: C=CC(=O)N1CCN(c2ncnc3cc(-c4nc(N)ncc4C)c(Cl)cc23)CC1] | 1-(4-(7-(2-amino-5-methylpyrimidin-4-yl)-6-chloroquinazolin-4-yl)piperazin-1-yl)prop-2-en-1-one | B | 410.10 |

TABLE 1-continued
Representative Compounds
| No. | Structure | Name | Method | [M + H]+ |
|---|---|---|---|---|
| 180 | 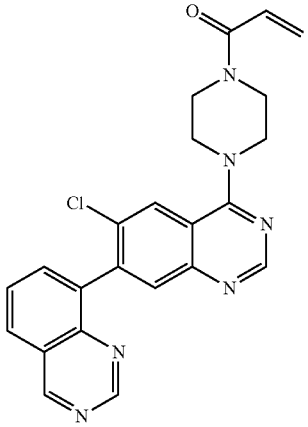 [SMILES: C=CC(=O)N1CCN(c2ncnc3cc(-c4cccc5cncnc45)c(Cl)cc23)CC1] | 1-(4-(6-chloro-7,8'-biquinazolin-4-yl)piperazin-1-yl)prop-2-en-1-one | B | 431.10 |
| 181 | 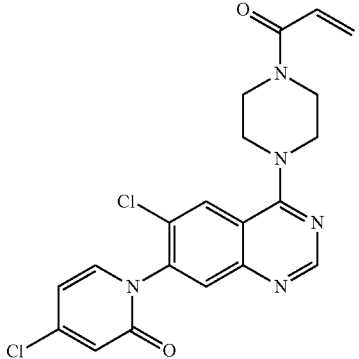 [SMILES: C=CC(=O)N1CCN(c2ncnc3cc(-n4ccc(Cl)cc4=O)c(Cl)cc23)CC1] | 1-(4-(4-acryloylpiperazin-1-yl)-6-chloroquinazolin-7-yl)-4-chloropyridin-2(1H)-one | T | 430.10 |
| 182 | 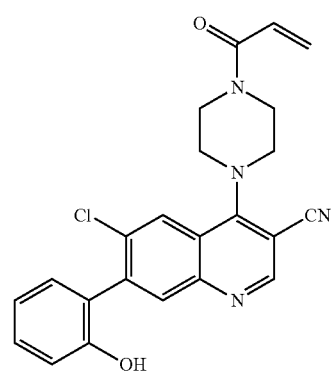 [SMILES: C=CC(=O)N1CCN(c2c(C#N)cnc3cc(-c4ccccc4O)c(Cl)cc23)CC1] | 4-(4-acryloylpiperazin-1-yl)-6-chloro-7-(2-hydroxyphenyl)quinoline-3-carbonitrile | P | 419.15 |

TABLE 1-continued

Representative Compounds

| No. | Structure | Name | Method | [M + H]+ |
|---|---|---|---|---|
| 183 | 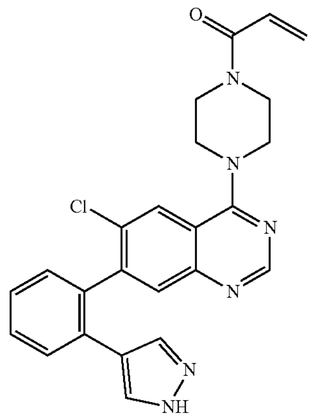 [SMILES: C=CC(=O)N1CCN(c2ncnc3cc(-c4ccccc4-c4cn[nH]c4)c(Cl)cc23)CC1] | 1-(4-(7-(2-(1H-pyrazol-4-yl)phenyl)-6-chloroquinazolin-4-yl)piperazin-1-yl)prop-2-en-1-one | B | 445.20 |
| 184 | 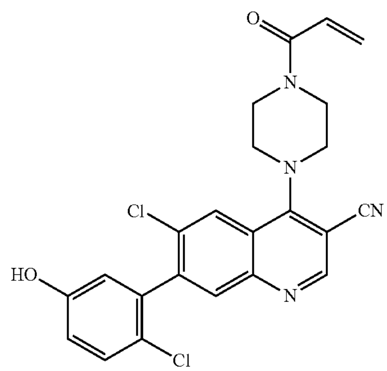 [SMILES: C=CC(=O)N1CCN(c2c(C#N)cnc3cc(-c4cc(O)ccc4Cl)c(Cl)cc23)CC1] | 4-(4-acryloylpiperazin-1-yl)-6-chloro-7-(2-chloro-5-hydroxyphenyl)quinoline-3-carbonitrile | P | 453.15 |
| 185 | 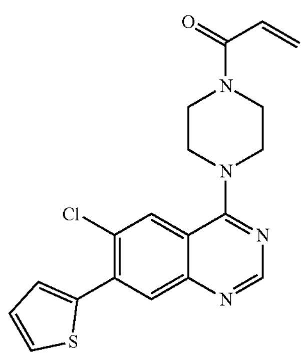 [SMILES: C=CC(=O)N1CCN(c2ncnc3cc(-c4cccs4)c(Cl)cc23)CC1] | 1-(4-(6-chloro-7-(thiophen-2-yl)quinazolin-4-yl)piperazin-1-yl)prop-2-en-1-one | B | 385.10 |
| 186 | 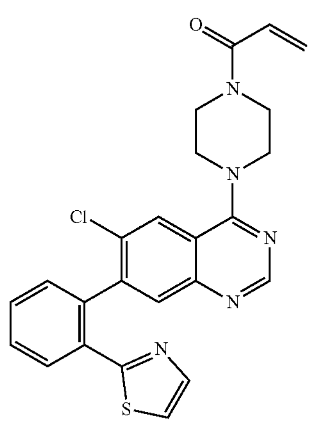 [SMILES: C=CC(=O)N1CCN(c2ncnc3cc(-c4ccccc4-c4nccs4)c(Cl)cc23)CC1] | 1-(4-(6-chloro-7-(2-(thiazol-2-yl)phenyl)quinazolin-4-yl)piperazin-1-yl)prop-2-en-1-one | U | 462.25 |

TABLE 1-continued

Representative Compounds

| No. | Structure | Name | Method | [M + H]+ |
|---|---|---|---|---|
| 187 | 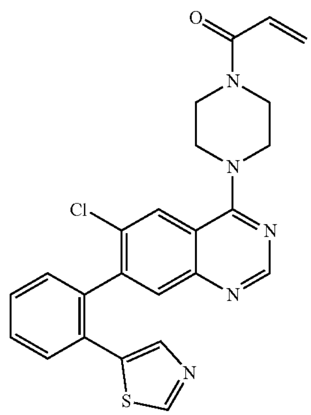 [SMILES: C=CC(=O)N1CCN(c2ncnc3cc(-c4ccccc4-c4cncs4)c(Cl)cc23)CC1] | 1-(4-(6-chloro-7-(2-(thiazol-5-yl)phenyl)quinazolin-4-yl)piperazin-1-yl)prop-2-en-1-one | U | 462.25 |
| 188 | 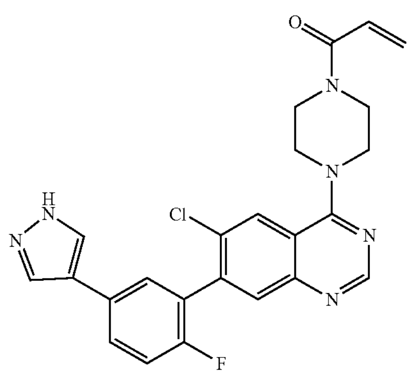 [SMILES: C=CC(=O)N1CCN(c2ncnc3cc(-c4cc(-c5cn[nH]c5)ccc4F)c(Cl)cc23)CC1] | 1-(4-(6-chloro-7-(2-fluoro-5-(1H-pyrazol-4-yl)phenyl)quinazolin-4-yl)piperazin-1-yl)prop-2-en-1-one | B | 463.20 |
| 189 | 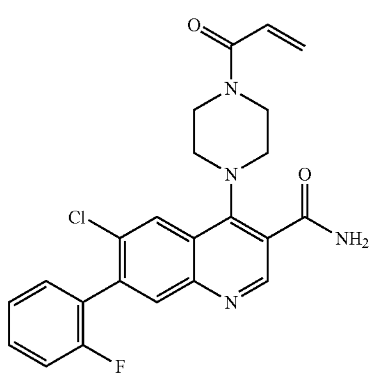 [SMILES: C=CC(=O)N1CCN(c2c(C(N)=O)cnc3cc(-c4ccccc4F)c(Cl)cc23)CC1] | 4-(4-acryloylpiperazin-1-yl)-6-chloro-7-(2-fluorophenyl)quinoline-3-carboxamide | P | 439.60 |
| 190 | 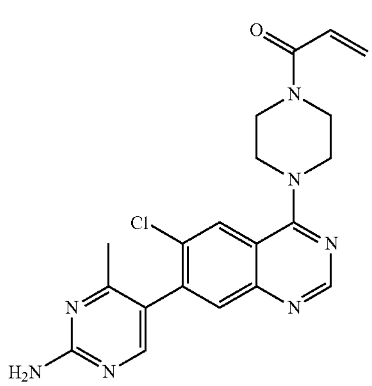 [SMILES: C=CC(=O)N1CCN(c2ncnc3cc(-c4cnc(N)nc4C)c(Cl)cc23)CC1] | 1-(4-(7-(2-amino-4-methylpyrimidin-5-yl)-6-chloroquinazolin-4-yl)piperazin-1-yl)prop-2-en-1-one | B | 410.10 |

TABLE 1-continued
Representative Compounds
| No. | Structure | Name | Method | [M + H]+ |
|---|---|---|---|---|
| 191 | 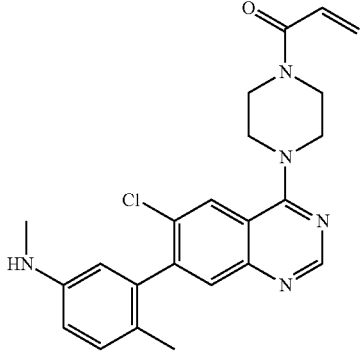 [SMILES: C=CC(=O)N1CCN(c2ncnc3cc(-c4cc(NC)ccc4C)c(Cl)cc23)CC1] | 1-(4-(6-chloro-7-(2-methyl-5-(methylamino)phenyl)quinazolin-4-yl)piperazin-1-yl)prop-2-en-1-one | B | 422.20 |
| 192 | 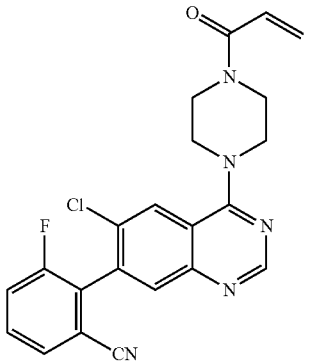 [SMILES: C=CC(=O)N1CCN(c2ncnc3cc(-c4c(F)cccc4C#N)c(Cl)cc23)CC1] | 2-(4-(4-acryloylpiperazin-1-yl)-6-chloroquinazolin-7-yl)-3-fluorobenzonitrile | B | 422.10 |
| 193 | 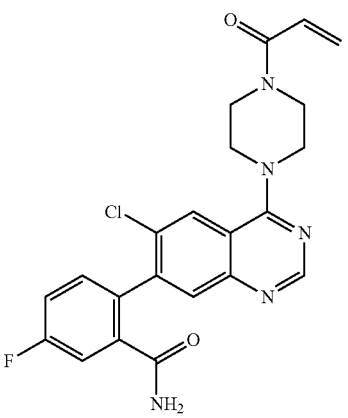 [SMILES: C=CC(=O)N1CCN(c2ncnc3cc(-c4ccc(F)cc4C(N)=O)c(Cl)cc23)CC1] | 2-(4-(4-acryloylpiperazin-1-yl)-6-chloroquinazolin-7-yl)-5-fluorobenzamide | B | 440.20 |
| 194 | 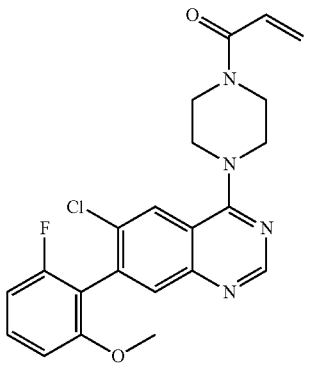 [SMILES: C=CC(=O)N1CCN(c2ncnc3cc(-c4c(F)cccc4OC)c(Cl)cc23)CC1] | 1-(4-(6-chloro-7-(2-fluoro-6-methoxyphenyl)quinazolin-4-yl)piperazin-1-yl)prop-2-en-1-one | B | 427.15 |

TABLE 1-continued

Representative Compounds

| No. | Structure | Name | Method | [M + H]+ |
|---|---|---|---|---|
| 195 | 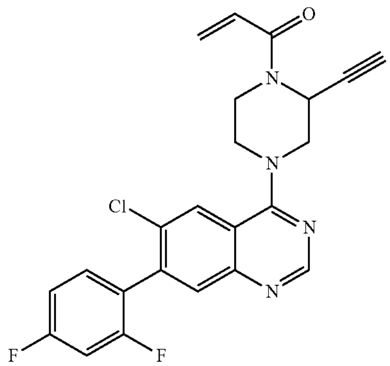 [SMILES: C#CC1CN(c2ncnc3cc(-c4ccc(F)cc4F)c(Cl)cc23)CCN1C(=O)C=C] | 1-(4-(6-chloro-7-(2,4-difluorophenyl)quinazolin-4-yl)-2-ethynylpiperazin-1-yl)prop-2-en-1-one | B | 439.15 |
| 196 | 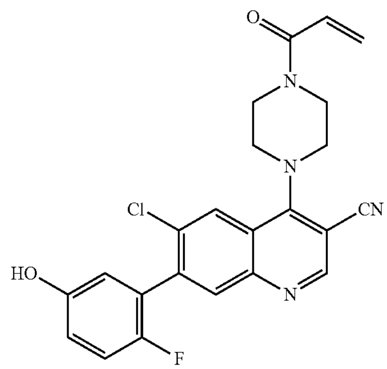 [SMILES: C=CC(=O)N1CCN(c2c(C#N)cnc3cc(-c4cc(O)ccc4F)c(Cl)cc23)CC1] | 4-(4-acryloylpiperazin-1-yl)-6-chloro-7-(2-fluoro-5-hydroxyphenyl)quinoline-3-carbonitrile | P | 437.15 |
| 197 | 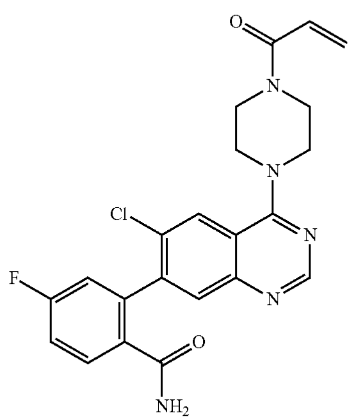 [SMILES: C=CC(=O)N1CCN(c2ncnc3cc(-c4cc(F)ccc4C(N)=O)c(Cl)cc23)CC1] | 2-(4-(4-acryloylpiperazin-1-yl)-6-chloroquinazolin-7-yl)-4-fluorobenzamide | B | 440.20 |
| 198 | 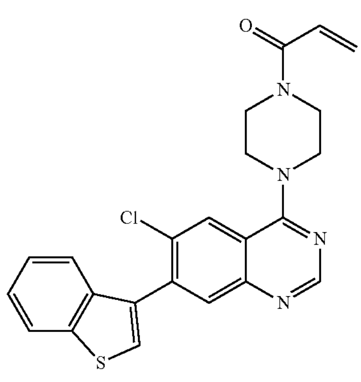 [SMILES: C=CC(=O)N1CCN(c2ncnc3cc(-c4csc5ccccc45)c(Cl)cc23)CC1] | 1-(4-(7-(benzo[b]thiophen-3-yl)-6-chloroquinazolin-4-yl)piperazin-1-yl)prop-2-en-1-one | B | 435.15 |

TABLE 1-continued

Representative Compounds

| No. | Structure | Name | Method | [M + H]⁺ |
|---|---|---|---|---|
| 199 | 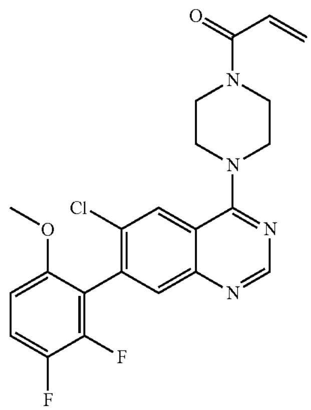 [SMILES: C=CC(=O)N1CCN(c2ncnc3cc(-c4c(OC)ccc(F)c4F)c(Cl)cc23)CC1] | 1-(4-(6-chloro-7-(2,3-difluoro-6-methoxyphenyl)quinazolin-4-yl)piperazin-1-yl)prop-2-en-1-one | B | 445.1 |
| 200 | 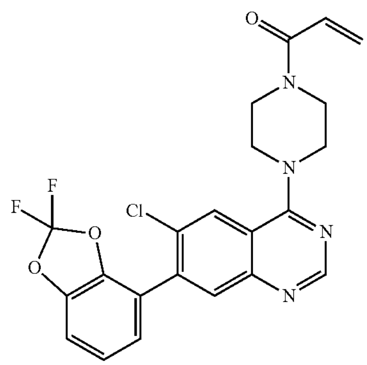 [SMILES: C=CC(=O)N1CCN(c2ncnc3cc(-c4cccc5c4OC(F)(F)O5)c(Cl)cc23)CC1] | 1-(4-(6-chloro-7-(2,2-difluorobenzo[d][1,3]dioxol-4-yl)quinazolin-4-yl)piperazin-1-yl)prop-2-en-1-one | B | 459.10 |
| 201 | 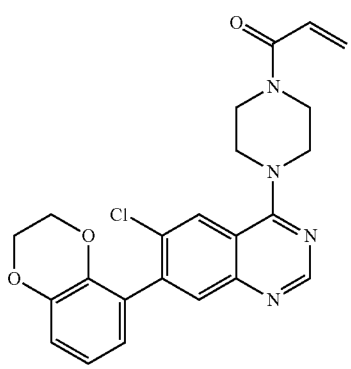 [SMILES: C=CC(=O)N1CCN(c2ncnc3cc(-c4cccc5c4OCCO5)c(Cl)cc23)CC1] | 1-(4-(6-chloro-7-(2,3-dihydrobenzo[b][1,4]dioxin-5-yl)quinazolin-4-yl)piperazin-1-yl)prop-2-en-1-one | B | 437.1 |
| 202 | 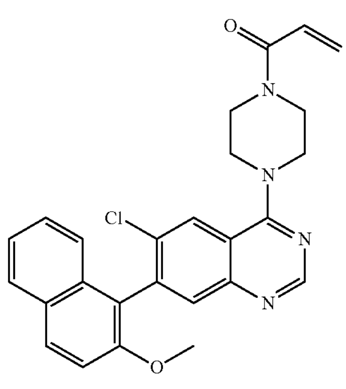 [SMILES: C=CC(=O)N1CCN(c2ncnc3cc(-c4c(OC)ccc5ccccc45)c(Cl)cc23)CC1] | 1-(4-(6-chloro-7-(2-methoxynaphthalen-1-yl)quinazolin-4-yl)piperazin-1-yl)prop-2-en-1-one | O | 459.15 |

TABLE 1-continued

Representative Compounds

| No. | Structure | Name | Method | [M + H]+ |
|---|---|---|---|---|
| 203 | 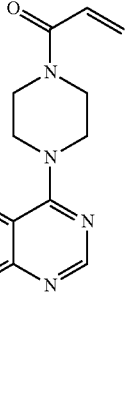 | 1-(4-(6-chloro-7-(2,3-difluoro-6-hydroxyphenyl)quinazolin-4-yl)piperazin-1-yl)prop-2-en-1-one | B | 431.10 |
| 204 | 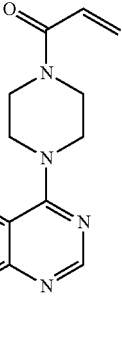 | 1-(4-(7-(2,4-difluorophenyl)-6-(trifluoromethyl)quinazolin-4-yl)piperazin-1-yl)prop-2-en-1-one | B | 449.15 |
| 205 | 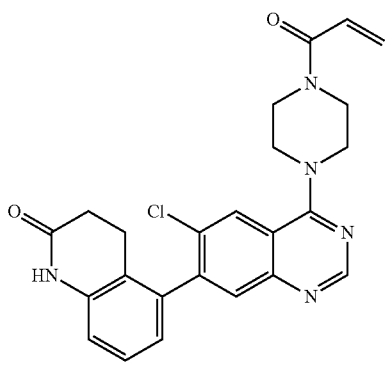 [SMILES: C=CC(=O)N1CCN(c2ncnc3cc(-c4cccc5c4CCC(=O)N5)c(Cl)cc23)CC1] | 5-(4-(4-acryloylpiperazin-1-yl)-6-chloroquinazolin-7-yl)-3,4-dihydroquinolin-2(1H)-one | B | 448.15 |
| 206 | 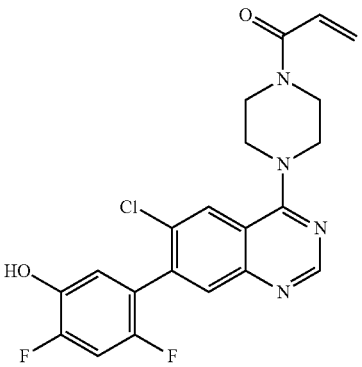 [SMILES: C=CC(=O)N1CCN(c2ncnc3cc(-c4cc(O)c(F)cc4F)c(Cl)cc23)CC1] | 1-(4-(6-chloro-7-(2,4-difluoro-5-hydroxyphenyl)quinazolin-4-yl)piperazin-1-yl)prop-2-en-1-one | U | 431.10 |

TABLE 1-continued

Representative Compounds

| No. | Structure | Name | Method | [M + H]+ |
|---|---|---|---|---|
| 207 | 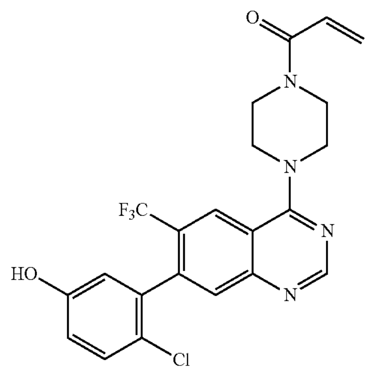 [SMILES: C=CC(=O)N1CCN(c2ncnc3cc(-c4cc(O)ccc4Cl)c(C(F)(F)F)cc23)CC1] | 1-(4-(7-(2-chloro-5-hydroxyphenyl)-6-(trifluoromethyl)quinazolin-4-yl)piperazin-1-yl)prop-2-en-1-one | R | 463.15 |
| 208 | 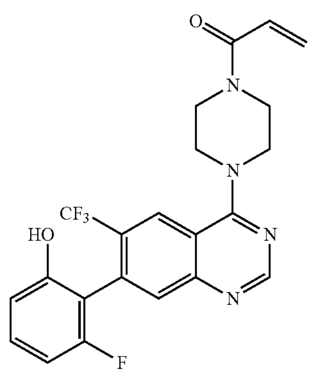 [SMILES: C=CC(=O)N1CCN(c2ncnc3cc(-c4c(O)cccc4F)c(C(F)(F)F)cc23)CC1] | 1-(4-(7-(2-fluoro-6-hydroxyphenyl)-6-(trifluoromethyl)quinazolin-4-yl)piperazin-1-yl)prop-2-en-1-one | R | 447.20 |
| 209 | 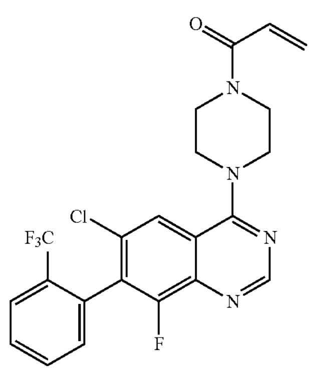 [SMILES: C=CC(=O)N1CCN(c2ncnc3c(F)c(-c4ccccc4C(F)(F)F)c(Cl)cc23)CC1] | 1-(4-(6-chloro-8-fluoro-7-(2-(trifluoromethyl)phenyl)quinazolin-4-yl)piperazin-1-yl)prop-2-en-1-one | O | 465.15 |
| 210 | 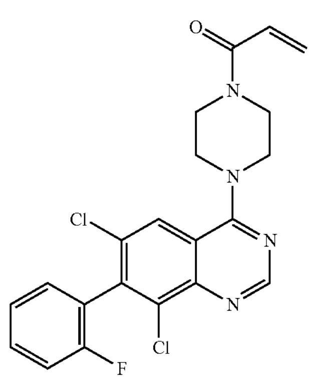 [SMILES: C=CC(=O)N1CCN(c2ncnc3c(Cl)c(-c4ccccc4F)c(Cl)cc23)CC1] | 1-(4-(6,8-dichloro-7-(2-fluorophenyl)quinazolin-4-yl)piperazin-1-yl)prop-2-en-1-one | R | 431.10 |

TABLE 1-continued

Representative Compounds

| No. | Structure | Name | Method | [M + H]+ |
|---|---|---|---|---|
| 211 | 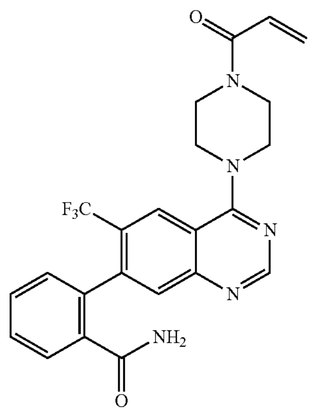 [SMILES: C=CC(=O)N1CCN(c2ncnc3cc(-c4ccccc4C(N)=O)c(C(F)(F)F)cc23)CC1] | 2-(4-(4-acryloylpiperazin-1-yl)-6-(trifluoromethyl)quinazolin-7-yl)benzamide | R | 456.15 |
| 212 | 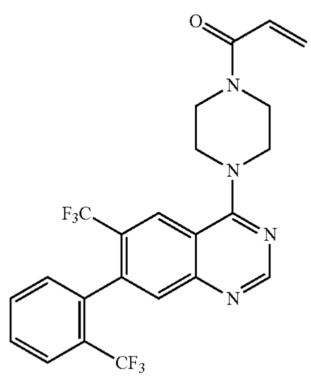 [SMILES: C=CC(=O)N1CCN(c2ncnc3cc(-c4ccccc4C(F)(F)F)c(C(F)(F)F)cc23)CC1] | 1-(4-(6-(trifluoromethyl)-7-(2-(trifluoromethyl)phenyl)quinazolin-4-yl)piperazin-1-yl)prop-2-en-1-one | R | 481.20 |
| 213 | 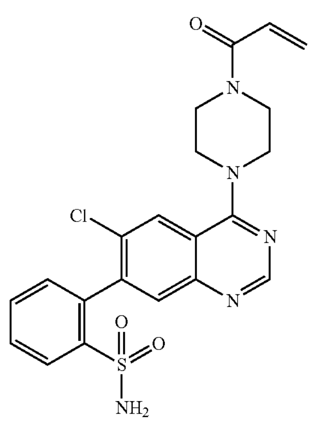 [SMILES: C=CC(=O)N1CCN(c2ncnc3cc(-c4ccccc4S(N)(=O)=O)c(Cl)cc23)CC1] | 2-(4-(4-acryloylpiperazin-1-yl)-6-chloroquinazolin-7-yl)benzenesulfonamide | B | 458.10 |
| 214 | 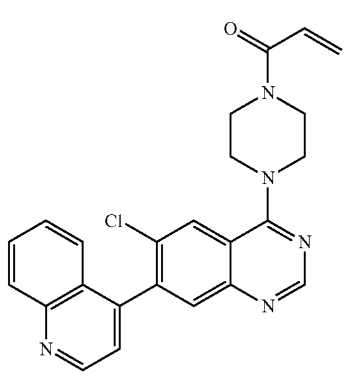 [SMILES: C=CC(=O)N1CCN(c2ncnc3cc(-c4ccnc5ccccc45)c(Cl)cc23)CC1] | 1-(4-(6-chloro-7-(quinolin-4-yl)quinazolin-4-yl)piperazin-1-yl)prop-2-en-1-one | Q | 430.10 |

TABLE 1-continued

Representative Compounds

| No. | Structure | Name | Method | [M + H]+ |
|---|---|---|---|---|
| 215 | 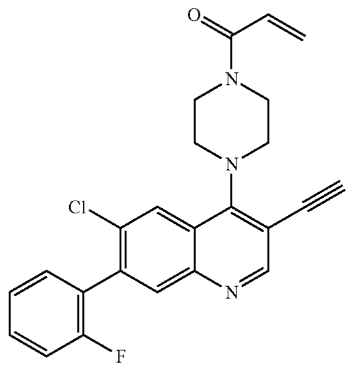 [SMILES: C#Cc1cnc2cc(-c3ccccc3F)c(Cl)cc2c1N1CCN(C(=O)C=C)CC1] | 1-(4-(6-chloro-3-ethynyl-7-(2-fluorophenyl)quinolin-4-yl)piperazin-1-yl)prop-2-en-1-one | G | 430.10 |
| 216 | 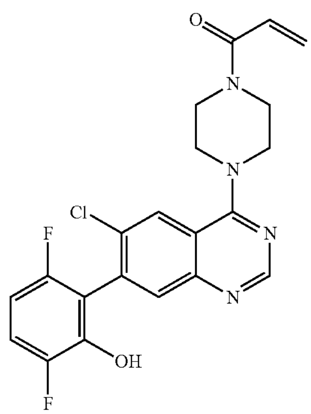 [SMILES: C=CC(=O)N1CCN(c2ncnc3cc(-c4c(F)ccc(F)c4O)c(Cl)cc23)CC1] | 1-(4-(6-chloro-7-(3,6-difluoro-2-hydroxyphenyl)quinazolin-4-yl)piperazin-1-yl)prop-2-en-1-one | U | 431.15 |
| 217 | 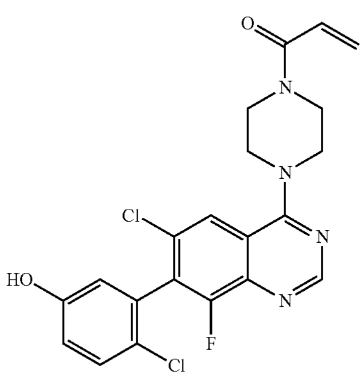 [SMILES: C=CC(=O)N1CCN(c2ncnc3c(F)c(-c4cc(O)ccc4Cl)c(Cl)cc23)CC1] | 1-(4-(6-chloro-7-(2-chloro-5-hydroxyphenyl)-8-fluoroquinazolin-4-yl)piperazin-1-yl)prop-2-en-1-one | O | 447.05 |
| 218 | 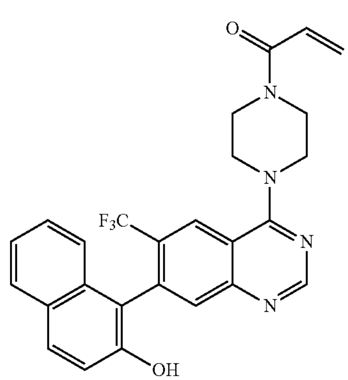 [SMILES: C=CC(=O)N1CCN(c2ncnc3cc(-c4c(O)ccc5ccccc45)c(C(F)(F)F)cc23)CC1] | 1-(4-(7-(2-hydroxynaphthalen-1-yl)-6-(trifluoromethyl)quinazolin-4-yl)piperazin-1-yl)prop-2-en-1-one | R | 479.20 |

TABLE 1-continued

Representative Compounds

| No. | Structure | Name | Method | [M + H]+ |
|---|---|---|---|---|
| 219 | 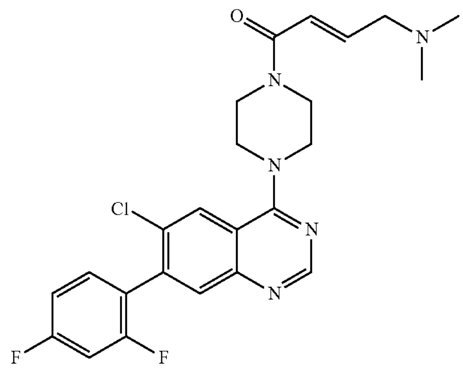 [SMILES: CN(C)C/C=C/C(=O)N1CCN(c2ncnc3cc(-c4ccc(F)cc4F)c(Cl)cc23)CC1] | (E)-1-(4-(6-chloro-7-(2,4-difluorophenyl)quinazolin-4-yl)piperazin-1-yl)-4-(dimethylamino)but-2-en-1-one | O | 472.10 |
| 220 | 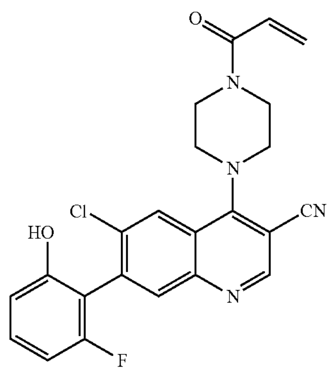 [SMILES: C=CC(=O)N1CCN(c2c(C#N)cnc3cc(-c4c(O)cccc4F)c(Cl)cc23)CC1] | 4-(4-acryloylpiperazin-1-yl)-6-chloro-7-(2-fluoro-6-hydroxyphenyl)quinoline-3-carbonitrile | P | 437.15 |
| 221 | 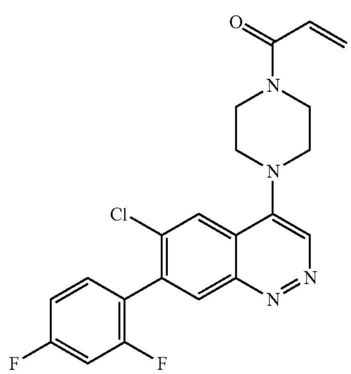 [SMILES: C=CC(=O)N1CCN(c2cnnc3cc(-c4ccc(F)cc4F)c(Cl)cc23)CC1] | 1-(4-(6-chloro-7-(2,4-difluorophenyl)cinnolin-4-yl)piperazin-1-yl)prop-2-en-1-one | N | 415.10 |
| 222 | 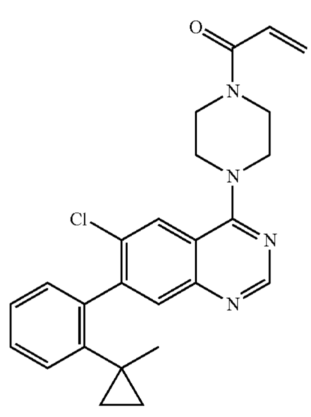 [SMILES: C=CC(=O)N1CCN(c2ncnc3cc(-c4ccccc4C4(C)CC4)c(Cl)cc23)CC1] | 1-(4-(6-chloro-7-(2-(1-methylcyclopropyl)phenyl)quinazolin-4-yl)piperazin-1-yl)prop-2-en-1-one | B | 433.20 |

TABLE 1-continued

Representative Compounds

| No. | Structure | Name | Method | [M + H]⁺ |
|---|---|---|---|---|
| 223 | 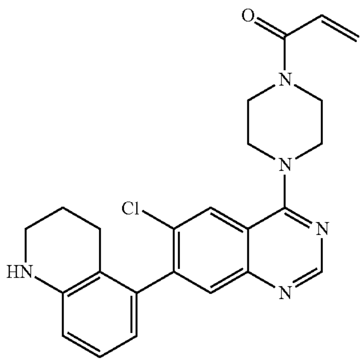 [SMILES: C=CC(=O)N1CCN(c2ncnc3cc(-c4cccc5c4CCCN5)c(Cl)cc23)CC1] | 1-(4-(6-chloro-7-(1,2,3,4-tetrahydroquinolin-5-yl)quinazolin-4-yl)piperazin-1-yl)prop-2-en-1-one | B | 434.15 |
| 224 | 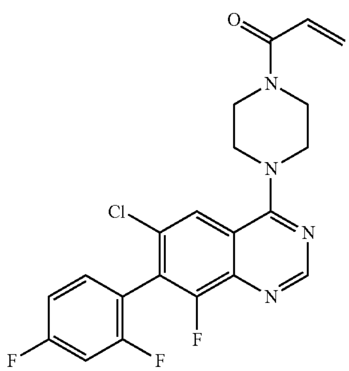 [SMILES: C=CC(=O)N1CCN(c2ncnc3c(F)c(-c4ccc(F)cc4F)c(Cl)cc23)CC1] | 1-(4-(6-chloro-7-(2,4-difluorophenyl)-8-fluoroquinazolin-4-yl)piperazin-1-yl)prop-2-en-1-one | O | 433.10 |
| 225 | 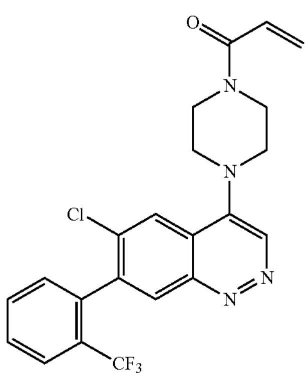 [SMILES: C=CC(=O)N1CCN(c2cnnc3cc(-c4ccccc4C(F)(F)F)c(Cl)cc23)CC1] | 1-(4-(6-chloro-7-(2-(trifluoromethyl)phenyl)cinnolin-4-yl)piperazin-1-yl)prop-2-en-1-one | N | 447.05 |
| 226 | 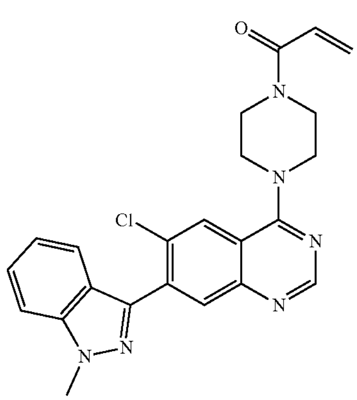 [SMILES: C=CC(=O)N1CCN(c2ncnc3cc(-c4nn(C)c5ccccc45)c(Cl)cc23)CC1] | 1-(4-(6-chloro-7-(1-methyl-1H-indazol-3-yl)quinazolin-4-yl)piperazin-1-yl)prop-2-en-1-one | B | 433.05 |

TABLE 1-continued

Representative Compounds

| No. | Structure | Name | Method | [M + H]+ |
|---|---|---|---|---|
| 227 | 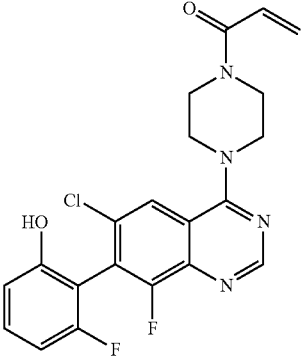 [SMILES: C=CC(=O)N1CCN(c2ncnc3c(F)c(-c4c(O)cccc4F)c(Cl)cc23)CC1] | 1-(4-(6-chloro-8-fluoro-7-(2-fluoro-6-hydroxyphenyl)quinazolin-4-yl)piperazin-1-yl)prop-2-en-1-one | O | 431.05 |
| 228 | 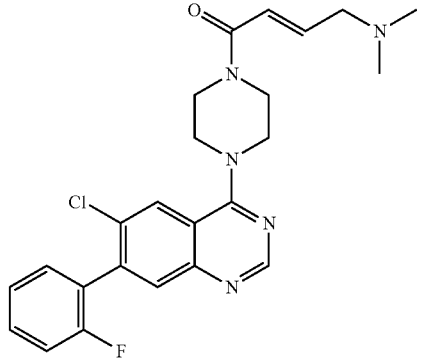 [SMILES: CN(C)C/C=C/C(=O)N1CCN(c2ncnc3cc(-c4ccccc4F)c(Cl)cc23)CC1] | (E)-1-(4-(6-chloro-7-(2-fluorophenyl)quinazolin-4-yl)piperazin-1-yl)-4-(dimethylamino)but-2-en-1-one | B | 454.15 |
| 229 | 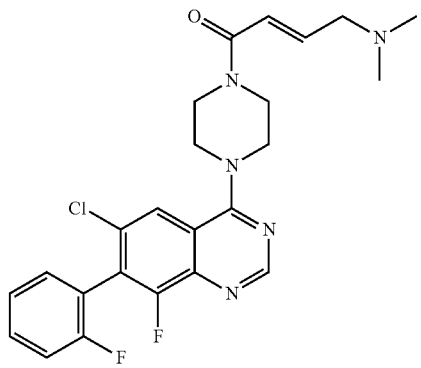 [SMILES: CN(C)C/C=C/C(=O)N1CCN(c2ncnc3c(F)c(-c4ccccc4F)c(Cl)cc23)CC1] | (E)-1-(4-(6-chloro-8-fluoro-7-(2-fluorophenyl)quinazolin-4-yl)piperazin-1-yl)-4-(dimethylamino)but-2-en-1-one | O | 472.15 |
| 230 | 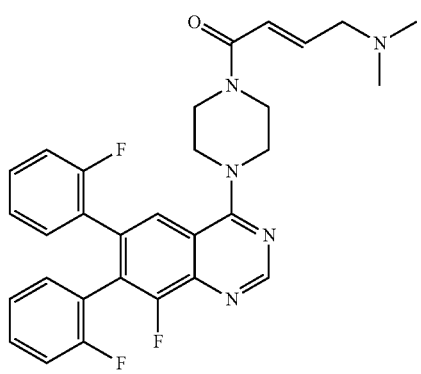 [SMILES: CN(C)C/C=C/C(=O)N1CCN(c2ncnc3c(F)c(-c4ccccc4F)c(-c4ccccc4F)cc23)CC1] | (E)-4-(dimethylamino)-1-(4-(8-fluoro-6,7-bis(2-fluorophenyl)quinazolin-4-yl)piperazin-1-yl)but-2-en-1-one | O | 532.25 |

TABLE 1-continued
Representative Compounds
| No. | Structure | Name | Method | [M + H]+ |
|---|---|---|---|---|
| 231 | 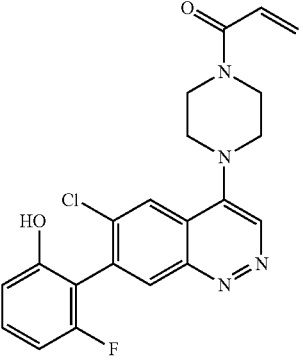 [SMILES: C=CC(=O)N1CCN(c2cnnc3cc(-c4c(O)cccc4F)c(Cl)cc23)CC1] | 1-(4-(6-chloro-7-(2-fluoro-6-hydroxyphenyl)cinnolin-4-yl)piperazin-1-yl)prop-2-en-1-one | N | 413.10 |
| 232 | 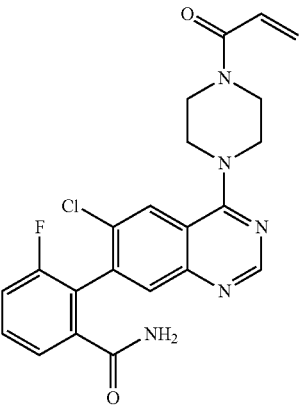 [SMILES: C=CC(=O)N1CCN(c2ncnc3cc(-c4c(F)cccc4C(N)=O)c(Cl)cc23)CC1] | 2-(4-(4-acryloylpiperazin-1-yl)-6-chloroquinazolin-7-yl)-3-fluorobenzamide | Q | 440.10 |
| 233 | 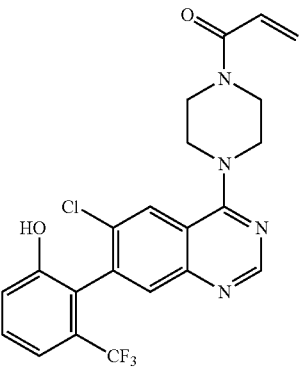 [SMILES: C=CC(=O)N1CCN(c2ncnc3cc(-c4c(O)cccc4C(F)(F)F)c(Cl)cc23)CC1] | 1-(4-(6-chloro-7-(2-hydroxy-6-(trifluoromethyl)phenyl)quinazolin-4-yl)piperazin-1-yl)prop-2-en-1-one | B | 463.10 |
| 234 | 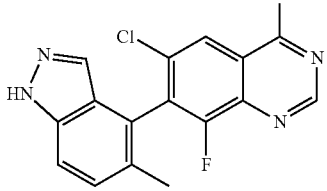 | 1-(4-(6-chloro-8-fluoro-7-(5-methyl-1H-indazol-4-yl)quinazolin-4-yl)piperazin-1-yl)prop-2-en-1-one | O | 451.1 |

TABLE 1-continued
Representative Compounds
| No. | Structure | Name | Method | [M + H]+ |
|---|---|---|---|---|
| 235 | 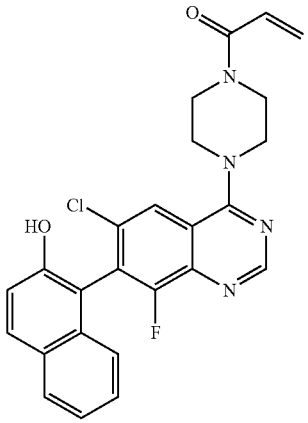 [SMILES: C=CC(=O)N1CCN(c2ncnc3c(F)c(-c4c(O)ccc5ccccc45)c(Cl)cc23)CC1] | 1-(4-(6-chloro-8-fluoro-7-(2-hydroxynaphthalen-1-yl)quinazolin-4-yl)piperazin-1-yl)prop-2-en-1-one | O | 463.10 |
| 236 | 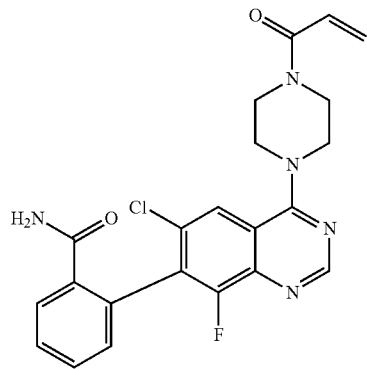 [SMILES: C=CC(=O)N1CCN(c2ncnc3c(F)c(-c4ccccc4C(N)=O)c(Cl)cc23)CC1] | 2-(4-(4-acryloylpiperazin-1-yl)-6-chloro-8-fluoroquinazolin-7-yl)benzamide | O | 440.10 |
| 237 | 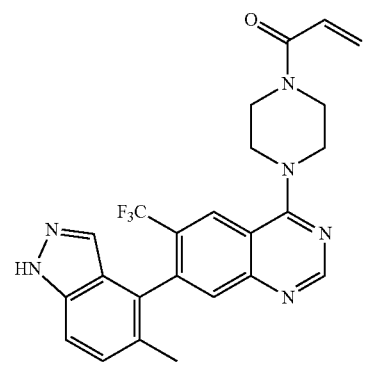 [SMILES: C=CC(=O)N1CCN(c2ncnc3cc(-c4c(C)ccc5[nH]ncc45)c(C(F)(F)F)cc23)CC1] | 1-(4-(7-(5-methyl-1H-indazol-4-yl)-6-(trifluoromethyl)quinazolin-4-yl)piperazin-1-yl)prop-2-en-1-one | R | 467.20 |
| 238 | 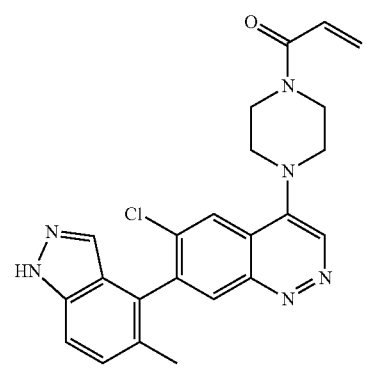 [SMILES: C=CC(=O)N1CCN(c2cnnc3cc(-c4c(C)ccc5[nH]ncc45)c(Cl)cc23)CC1] | 1-(4-(6-chloro-7-(5-methyl-1H-indazol-4-yl)cinnolin-4-yl)piperazin-1-yl)prop-2-en-1-one | N | 433.10 |

TABLE 1-continued
Representative Compounds
| No. | Structure | Name | Method | [M + H]+ |
|---|---|---|---|---|
| 239 | 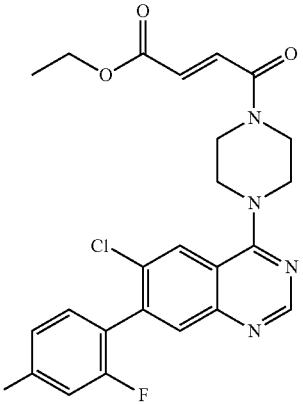 | (E)-ethyl 4-(4-(6-chloro-7-(2,4-difluorophenyl)quinazolin-4-yl)piperazin-1-yl)-4-oxobut-2-enoate | O | 487.10 |
| 240 | 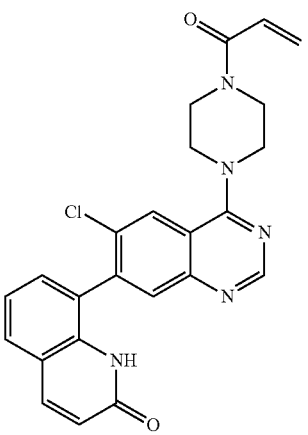 [SMILES: C=CC(=O)N1CCN(c2ncnc3cc(-c4cccc5ccc(=O)[nH]c45)c(Cl)cc23)CC1] | 8-(4-(4-acryloylpiperazin-1-yl)-6-chloroquinazolin-7-yl)quinolin-2(1H)-one | U | 446.10 |
| 241 | 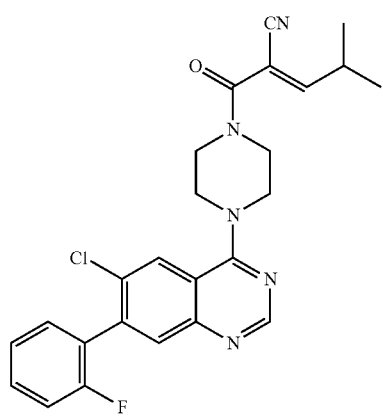 [SMILES: CC(C)/C=C(\C#N)C(=O)N1CCN(c2ncnc3cc(-c4ccccc4F)c(Cl)cc23)CC1] | (E)-2-(4-(6-chloro-7-(2-fluorophenyl)quinazolin-4-yl)piperazine-1-carbonyl)-4-methylpent-2-enenitrile | B | 464.10 |

TABLE 1-continued

Representative Compounds

| No. | Structure | Name | Method | [M + H]+ |
|-----|-----------|------|--------|----------|
| 242 | 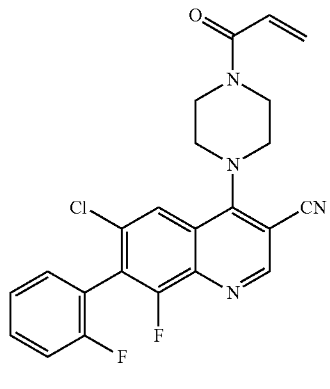 [SMILES: C=CC(=O)N1CCN(c2c(C#N)cnc3c(F)c(-c4ccccc4F)c(Cl)cc23)CC1] | 4-(4-acryloylpiperazin-1-yl)-6-chloro-8-fluoro-7-(2-fluorophenyl)quinoline-3-carbonitrile | P | 439.10 |
| 243 | 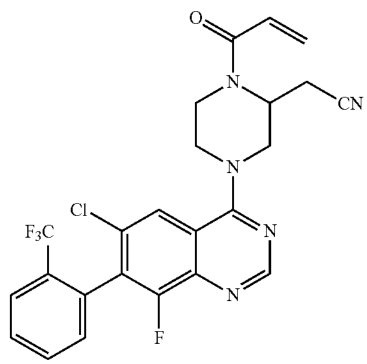 [SMILES: C=CC(=O)N1CCN(c2ncnc3c(F)c(-c4ccccc4C(F)(F)F)c(Cl)cc23)CC1CC#N] | 2-(1-acryloyl-4-(6-chloro-8-fluoro-7-(2-(trifluoromethyl)phenyl)quinazolin-4-yl)piperazin-2-yl)acetonitrile | O | 504.10 |
| 244 | 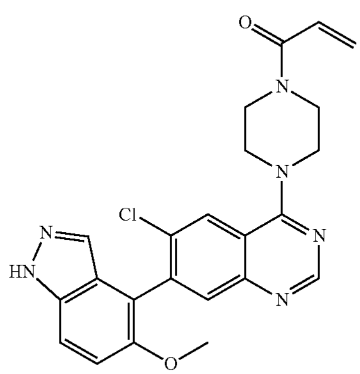 [SMILES: C=CC(=O)N1CCN(c2ncnc3cc(-c4c(OC)ccc5[nH]ncc45)c(Cl)cc23)CC1] | 1-(4-(6-chloro-7-(5-methoxy-1H-indazol-4-yl)quinazolin-4-yl)piperazin-1-yl)prop-2-en-1-one | B | 449.10 |
| 245 | 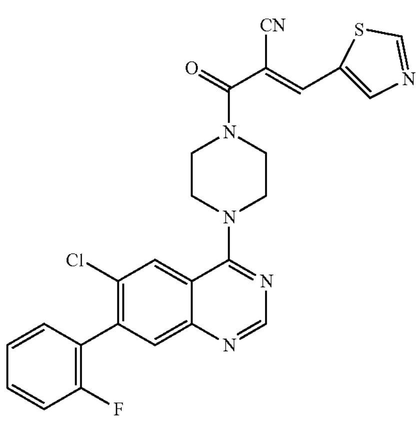 [SMILES: N#C/C(=C\c1cncs1)C(=O)N1CCN(c2ncnc3cc(-c4ccccc4F)c(Cl)cc23)CC1] | (E)-2-(4-(6-chloro-7-(2-fluorophenyl)quinazolin-4-yl)piperazine-1-carbonyl)-3-(thiazol-5-yl)acrylonitrile | B | 505.10 |

TABLE 1-continued
Representative Compounds
| No. | Structure | Name | Method | [M + H]+ |
|---|---|---|---|---|
| 246 | 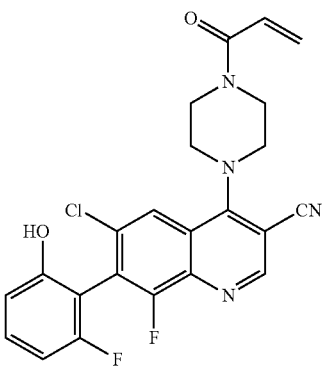 [SMILES: C=CC(=O)N1CCN(c2c(C#N)cnc3c(F)c(-c4c(O)cccc4F)c(Cl)cc23)CC1] | 4-(4-acryloylpiperazin-1-yl)-6-chloro-8-fluoro-7-(2-fluoro-6-hydroxyphenyl)quinoline-3-carbonitrile | P | 455.15 |
| 247 | 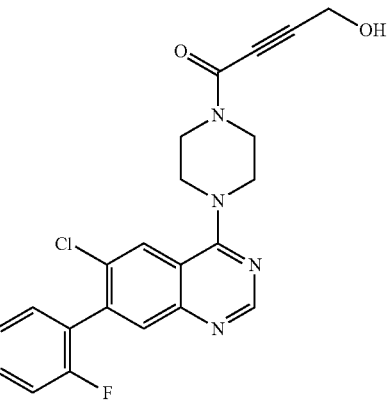 | 1-(4-(6-chloro-7-(2,4-difluorophenyl)quinazolin-4-yl)piperazin-1-yl)-4-hydroxybut-2-yn-1-one | B | 443.1 |
| 248 | 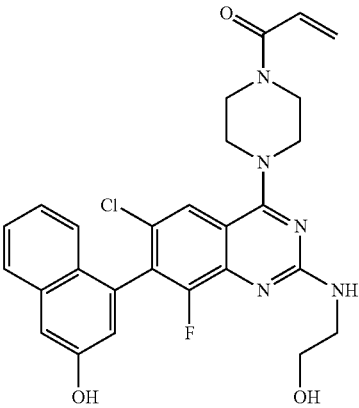 [SMILES: C=CC(=O)N1CCN(c2nc(NCCO)nc3c(F)c(-c4cc(O)cc5ccccc45)c(Cl)cc23)CC1] | 1-(4-(6-chloro-8-fluoro-2-(2-hydroxyethylamino)-7-(3-hydroxynaphthalen-1-yl)quinazolin-4-yl)piperazin-1-yl)prop-2-en-1-one | AC | 522.30 |

TABLE 1-continued

Representative Compounds

| No. | Structure | Name | Method | [M + H]+ |
|---|---|---|---|---|
| 249 | 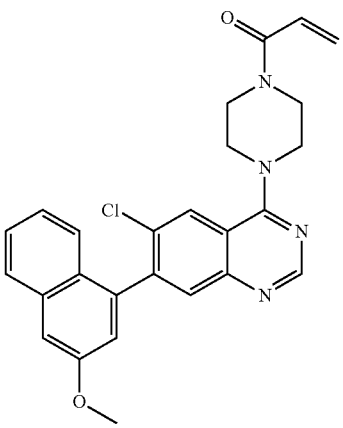 [SMILES: C=CC(=O)N1CCN(c2ncnc3cc(-c4cc(OC)cc5ccccc45)c(Cl)cc23)CC1] | 1-(4-(6-chloro-7-(3-methoxynaphthalen-1-yl)quinazolin-4-yl)piperazin-1-yl)prop-2-en-1-one | B | 459.1 |
| 250 | 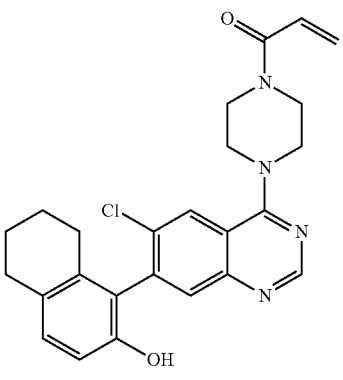 [SMILES: C=CC(=O)N1CCN(c2ncnc3cc(-c4c(O)ccc5c4CCCC5)c(Cl)cc23)CC1] | 1-(4-(6-chloro-7-(2-hydroxy-5,6,7,8-tetrahydronaphthalen-1-yl)quinazolin-4-yl)piperazin-1-yl)prop-2-en-1-one | AF | 449.10 |
| 251 | 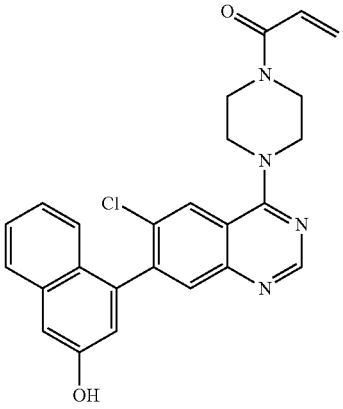 [SMILES: C=CC(=O)N1CCN(c2ncnc3cc(-c4cc(O)cc5ccccc45)c(Cl)cc23)CC1] | 1-(4-(6-chloro-7-(3-hydroxynaphthalen-1-yl)quinazolin-4-yl)piperazin-1-yl)prop-2-en-1-one | P | 445.10 |
| 252 | 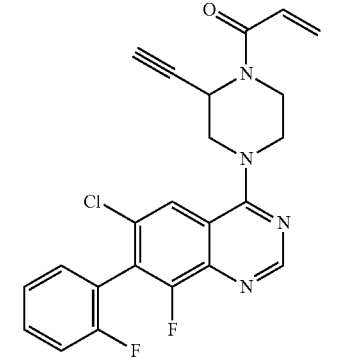 [SMILES: C#CC1CN(c2ncnc3c(F)c(-c4ccccc4F)c(Cl)cc23)CCN1C(=O)C=C] | 1-(4-(6-chloro-8-fluoro-7-(2-fluorophenyl)quinazolin-4-yl)-2-ethynylpiperazin-1-yl)prop-2-en-1-one | O | 439.10 |

TABLE 1-continued

Representative Compounds

| No. | Structure | Name | Method | [M + H]+ |
|---|---|---|---|---|
| 253 | 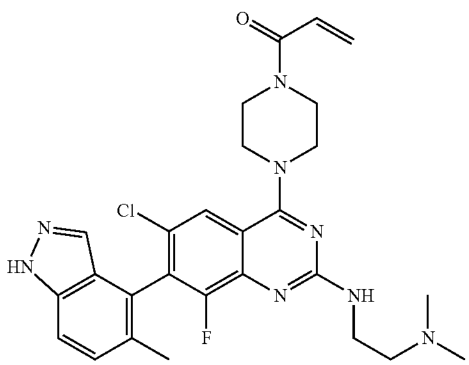 [SMILES: C=CC(=O)N1CCN(c2nc(NCCN(C)C)nc3c(F)c(-c4c(C)ccc5[nH]ncc45)c(Cl)cc23)CC1] | 1-(4-(6-chloro-2-(2-(dimethylamino)ethylamino)-8-fluoro-7-(5-methyl-1H-indazol-4-yl)quinazolin-4-yl)piperazin-1-yl)prop-2-en-1-one | AC | 537.4 |
| 254 | 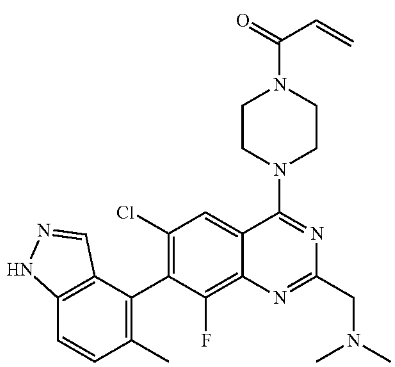 [SMILES: C=CC(=O)N1CCN(c2nc(CN(C)C)nc3c(F)c(-c4c(C)ccc5[nH]ncc45)c(Cl)cc23)CC1] | 1-(4-(6-chloro-2-((dimethylamino)methyl)-8-fluoro-7-(5-methyl-1H-indazol-4-yl)quinazolin-4-yl)piperazin-1-yl)prop-2-en-1-one | AD | 508.3 |
| 255 | 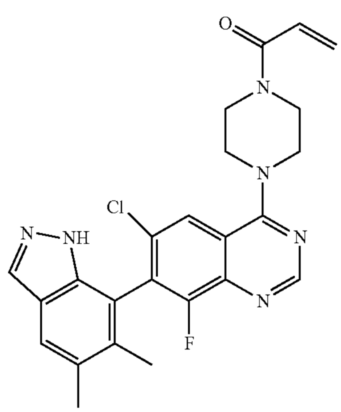 [SMILES: C=CC(=O)N1CCN(c2ncnc3c(F)c(-c4c(C)c(C)cc5cn[nH]c45)c(Cl)cc23)CC1] | 1-(4-(6-chloro-7-(5,6-dimethyl-1H-indazol-7-yl)-8-fluoroquinazolin-4-yl)piperazin-1-yl)prop-2-en-1-one | Q | 465.1 |
| 256 | 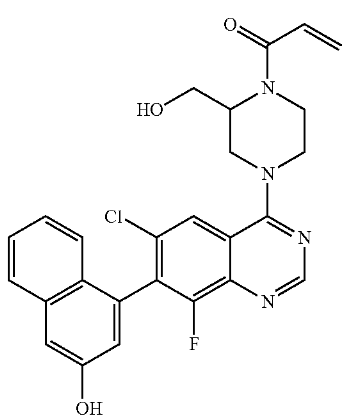 [SMILES: C=CC(=O)N1CCN(c2ncnc3c(F)c(-c4cc(O)cc5ccccc45)c(Cl)cc23)CC1CO] | 1-(4-(6-chloro-8-fluoro-7-(3-hydroxynaphthalen-1-yl)quinazolin-4-yl)-2-(hydroxymethyl)piperazin-1-yl)prop-2-en-1-one | O | 493.3 |

TABLE 1-continued

Representative Compounds

| No. | Structure | Name | Method | [M + H]+ |
|---|---|---|---|---|
| 257 | 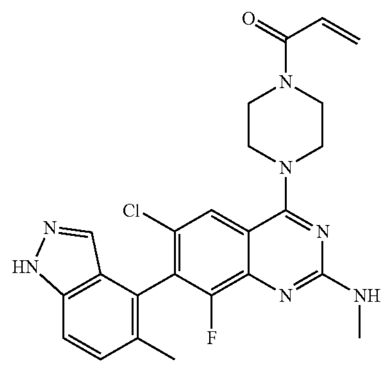 [SMILES: C=CC(=O)N1CCN(c2nc(NC)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(methylamino)quinazolin-4-yl)piperazin-1-yl)prop-2-en-1-one | AC | 480.2 |
| 258 | 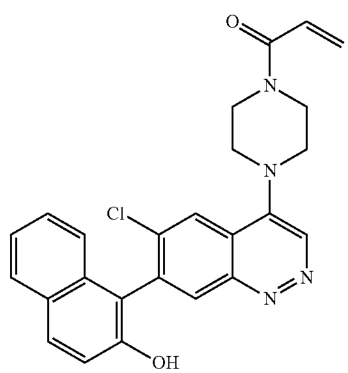 [SMILES: C=CC(=O)N1CCN(c2cnnc3cc(-c4c(O)ccc5ccccc45)c(Cl)cc23)CC1] | 1-(4-(6-chloro-7-(2-hydroxynaphthalen-1-yl)cinnolin-4-yl)piperazin-1-yl)prop-2-en-1-one | N | 445.1 |
| 259 | 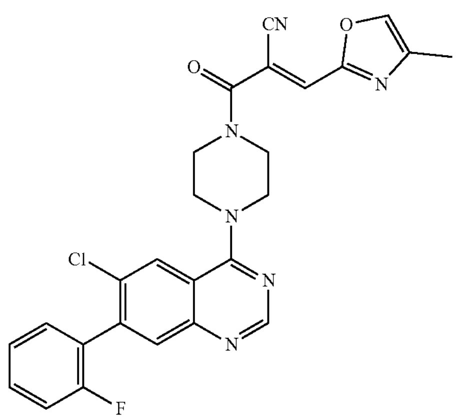 [SMILES: Cc1coc(/C=C(\C#N)C(=O)N2CCN(c3ncnc4cc(-c5ccccc5F)c(Cl)cc34)CC2)n1] | (E)-2-(4-(6-chloro-7-(2-fluorophenyl)quinazolin-4-yl)piperazine-1-carbonyl)-3-(4-methyloxazol-2-yl)acrylonitrile | B | 503.2 |
| 260 | 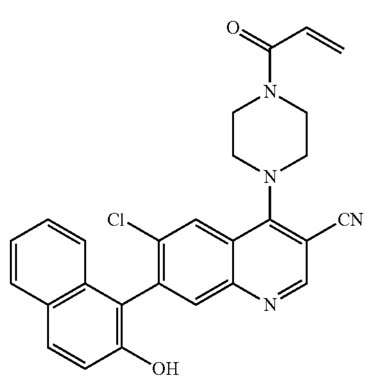 [SMILES: C=CC(=O)N1CCN(c2c(C#N)cnc3cc(-c4c(O)ccc5ccccc45)c(Cl)cc23)CC1] | 4-(4-acryloylpiperazin-1-yl)-6-chloro-7-(2-hydroxynaphthalen-1-yl)quinoline-3-carbonitrile | P | 469.1 |

TABLE 1-continued
Representative Compounds
| No. | Structure | Name | Method | [M + H]+ |
|---|---|---|---|---|
| 261 | 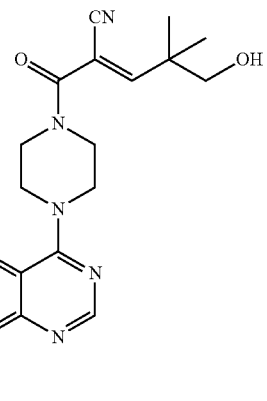 | (E)-2-(4-(6-chloro-7-(2-fluorophenyl)quinazolin-4-yl)piperazine-1-carbonyl)-5-hydroxy-4,4-dimethylpent-2-enenitrile | B | 494.4 |
| 262 | 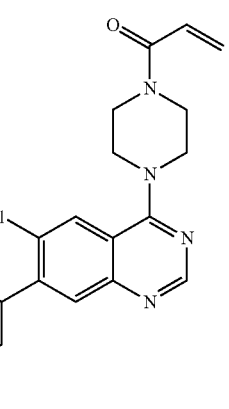 | 1-(4-(6-chloro-7-(6-methyl-1H-indazol-4-yl)quinazolin-4-yl)piperazin-1-yl)prop-2-en-1-one | AF | 494.3 |
| 263 | 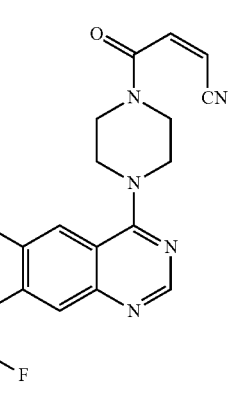 | (Z)-4-(4-(6-chloro-7-(2,4-difluorophenyl)quinazolin-4-yl)piperazin-1-yl)-4-oxobut-2-enenitrile | B | 440.1 |

TABLE 1-continued

Representative Compounds

| No. | Structure | Name | Method | [M + H]+ |
|---|---|---|---|---|
| 264 | 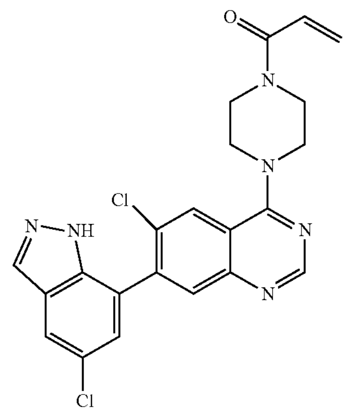 [SMILES: C=CC(=O)N1CCN(c2ncnc3cc(-c4cc(Cl)cc5cn[nH]c45)c(Cl)cc23)CC1] | 1-(4-(6-chloro-7-(5-chloro-1H-indazol-7-yl)quinazolin-4-yl)piperazin-1-yl)prop-2-en-1-one | AF | 454.1 |
| 265 | 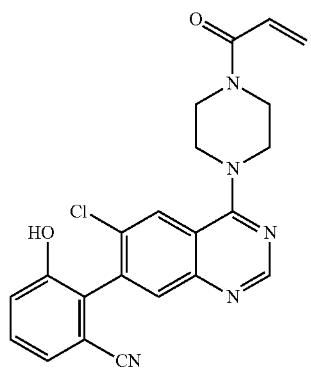 [SMILES: C=CC(=O)N1CCN(c2ncnc3cc(-c4c(O)cccc4C#N)c(Cl)cc23)CC1] | 2-(4-(4-acryloylpiperazin-1-yl)-6-chloroquinazolin-7-yl)-3-hydroxybenzonitrile | AF | 420.1 |
| 266 | 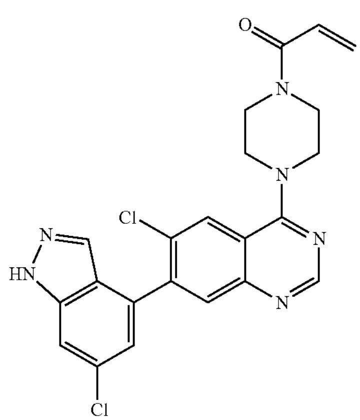 [SMILES: C=CC(=O)N1CCN(c2ncnc3cc(-c4cc(Cl)cc5[nH]ncc45)c(Cl)cc23)CC1] | 1-(4-(6-chloro-7-(6-chloro-1H-indazol-4-yl)quinazolin-4-yl)piperazin-1-yl)prop-2-en-1-one | B | 453.1 |
| 267 | 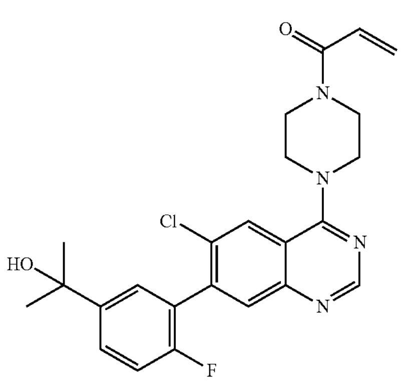 [SMILES: C=CC(=O)N1CCN(c2ncnc3cc(-c4cc(C(C)(C)O)ccc4F)c(Cl)cc23)CC1] | 1-(4-(6-chloro-7-(2-fluoro-5-(2-hydroxypropan-2-yl)phenyl)quinazolin-4-yl)piperazin-1-yl)prop-2-en-1-one | B | 455.1 |

TABLE 1-continued

Representative Compounds

| No. | Structure | Name | Method | [M + H]+ |
|---|---|---|---|---|
| 268 | 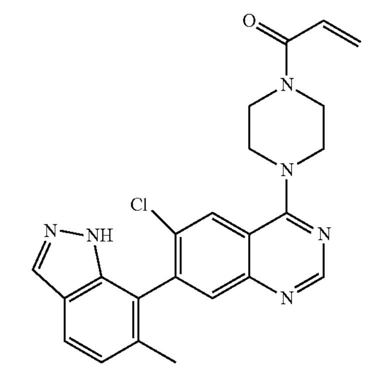 [SMILES: C=CC(=O)N1CCN(c2ncnc3cc(-c4c(C)ccc5cn[nH]c45)c(Cl)cc23)CC1] | 1-(4-(6-chloro-7-(6-methyl-1H-indazol-7-yl)quinazolin-4-yl)piperazin-1-yl)prop-2-en-1-one | AF | 433.2 |
| 269 | 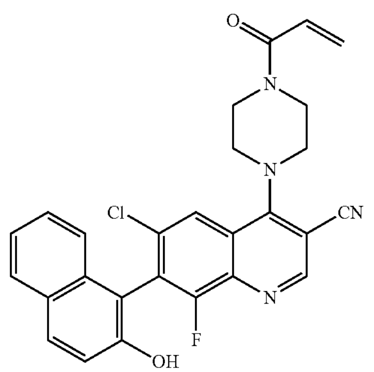 [SMILES: C=CC(=O)N1CCN(c2c(C#N)cnc3c(F)c(-c4c(O)ccc5ccccc45)c(Cl)cc23)CC1] | 4-(4-acry4oylpiperazin-1-yl)-6-chloro-8-fluoro-7-(2-hydroxynaphthalen-1-yl)quinoline-3-carbonitrile | P | 487.1 |
| 270 | 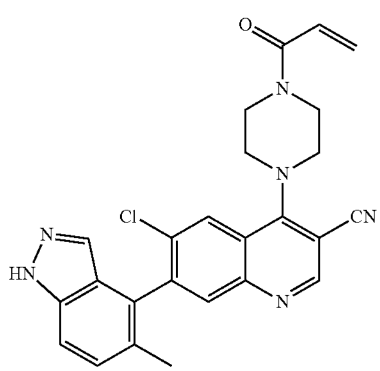 [SMILES: C=CC(=O)N1CCN(c2c(C#N)cnc3cc(-c4c(C)ccc5[nH]ncc45)c(Cl)cc23)CC1] | 4-(4-acryloylpiperazin-1-yl)-6-chloro-7-(5-methyl-1H-indazol-4-yl)quinoline-3-carbonitrile | P | 457.1 |
| 271 | 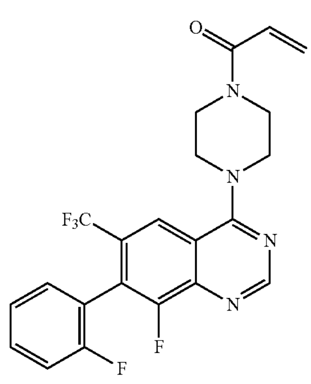 [SMILES: C=CC(=O)N1CCN(c2ncnc3c(F)c(-c4ccccc4F)c(C(F)(F)F)cc23)CC1] | 1-(4-(8-fluoro-7-(2-fluorophenyl)-6-(trifluoromethyl)quinazolin-4-yl)piperazin-1-yl)prop-2-en-1-one | W | 449.2 |

TABLE 1-continued

Representative Compounds

| No. | Structure | Name | Method | [M + H]+ |
|---|---|---|---|---|
| 272 | 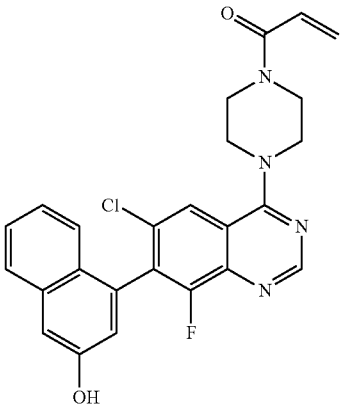 [SMILES: C=CC(=O)N1CCN(c2ncnc3c(F)c(-c4cc(O)cc5ccccc45)c(Cl)cc23)CC1] | 1-(4-(6-chloro-8-fluoro-7-(3-hydroxynaphthalen-1-yl)quinazolin-4-yl)piperazin-1-yl)prop-2-en-1-one | Q | 463.2 |
| 273 | 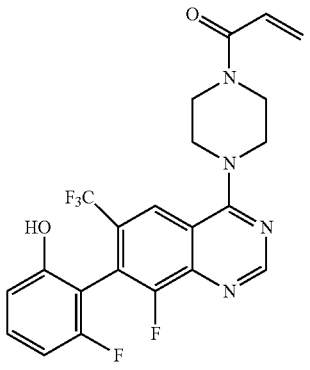 [SMILES: C=CC(=O)N1CCN(c2ncnc3c(F)c(-c4c(O)cccc4F)c(C(F)(F)F)cc23)CC1] | 1-(4-(8-fluoro-7-(2-fluoro-6-hydroxyphenyl)-6-(trifluoromethyl)quinazolin-4-yl)piperazin-1-yl)prop-2-en-1-one | W | 465.2 |
| 274 | 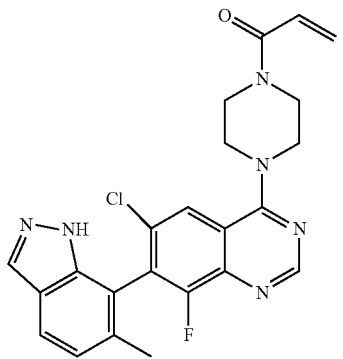 [SMILES: C=CC(=O)N1CCN(c2ncnc3c(F)c(-c4c(C)ccc5cn[nH]c45)c(Cl)cc23)CC1] | 1-(4-(6-chloro-8-fluoro-7-(6-methyl-1H-indazol-7-yl)quinazolin-4-yl)piperazin-1-yl)prop-2-en-1-one | O | 451.2 |
| 275 | 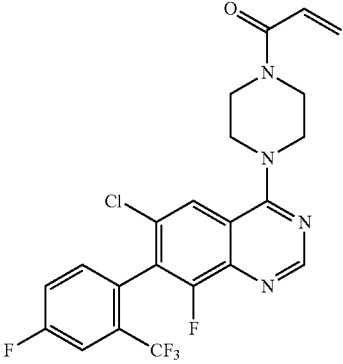 [SMILES: C=CC(=O)N1CCN(c2ncnc3c(F)c(-c4ccc(F)cc4C(F)(F)F)c(Cl)cc23)CC1] | 1-(4-(6-chloro-8-fluoro-7-(4-fluoro-2-(trifluoromethyl)phenyl)quinazolin-4-yl)piperazin-1-yl)prop-2-en-1-one | O | 483.2 |

TABLE 1-continued
Representative Compounds
| No. | Structure | Name | Method | [M + H]+ |
|---|---|---|---|---|
| 276 | 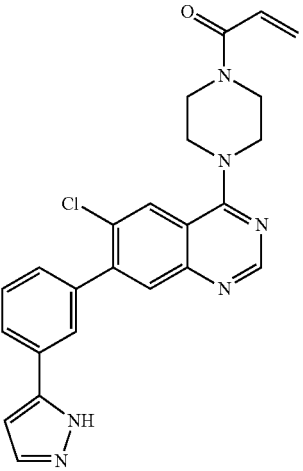 [SMILES: C=CC(=O)N1CCN(c2ncnc3cc(-c4cccc(-c5ccn[nH]5)c4)c(Cl)cc23)CC1] | 1-(4-(7-(3-(1H-pyrazol-5-yl)phenyl)-6-chloroquinazolin-4-yl)piperazin-1-yl)prop-2-en-1-one | Q | 445.2 |
| 277 | 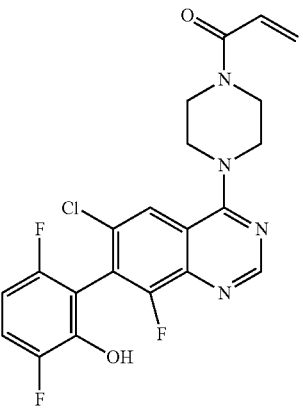 [SMILES: C=CC(=O)N1CCN(c2ncnc3c(F)c(-c4c(F)ccc(F)c4O)c(Cl)cc23)CC1] | 1-(4-(6-chloro-7-(3,6-difluoro-2-hydroxyphenyl)-8-fluoroquinazolin-4-yl)piperazin-1-yl)prop-2-en-1-one | O | 449.1 |
| 278 | 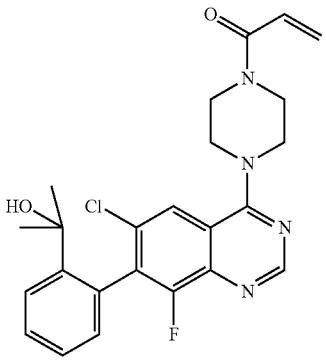 [SMILES: C=CC(=O)N1CCN(c2ncnc3c(F)c(-c4ccccc4C(C)(C)O)c(Cl)cc23)CC1] | 1-(4-(6-chloro-8-fluoro-7-(2-(2-hydroxypropan-2-yl)phenyl)quinazolin-4-yl)piperazin-1-yl)prop-2-en-1-one | O | 455.2 |

TABLE 1-continued

Representative Compounds

| No. | Structure | Name | Method | [M + H]+ |
|---|---|---|---|---|
| 279 | 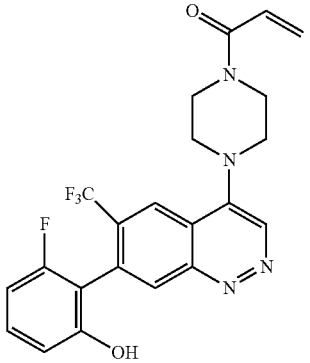 [SMILES: C=CC(=O)N1CCN(c2cnnc3cc(-c4c(O)cccc4F)c(C(F)(F)F)cc23)CC1] | 1-(4-(7-(2-fluoro-6-hydroxyphenyl)-6-(trifluoromethyl)cinnolin-4-yl)piperazin-1-yl)prop-2-en-1-one | X | 447.2 |
| 280 | 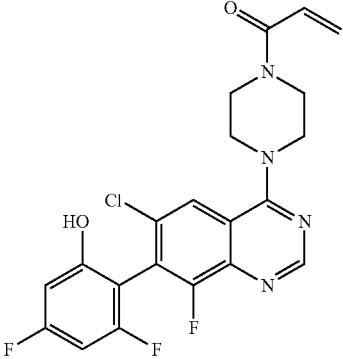 [SMILES: C=CC(=O)N1CCN(c2ncnc3c(F)c(-c4c(O)cc(F)cc4F)c(Cl)cc23)CC1] | 1-(4-(6-chloro-7-(2,4-difluoro-6-hydroxyphenyl)-8-fluoroquinazolin-4-yl)piperazin-1-yl)prop-2-en-1-one | O | 449.1 |
| 281 | 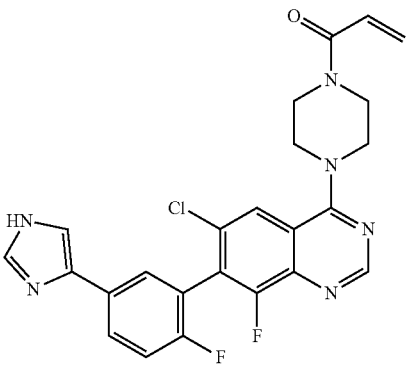 [SMILES: C=CC(=O)N1CCN(c2ncnc3c(F)c(-c4cc(-c5c[nH]cn5)ccc4F)c(Cl)cc23)CC1] | 1-(4-(6-chloro-8-fluoro-7-(2-fluoro-5-(1H-imidazol-4-yl)phenyl)quinazolin-4-yl)piperazin-1-yl)prop-2-en-1-one | O | 481.2 |
| 282 | 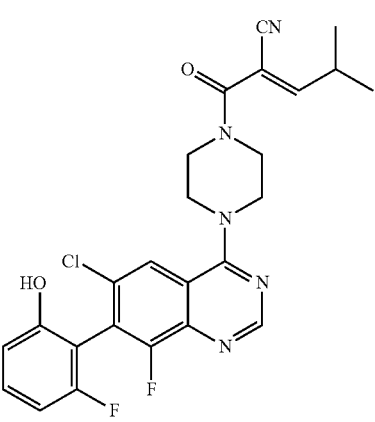 [SMILES: CC(C)/C=C(\C#N)C(=O)N1CCN(c2ncnc3c(F)c(-c4c(O)cccc4F)c(Cl)cc23)CC1] | (E)-2-(4-(6-chloro-8-fluoro-7-(2-fluoro-6-hydroxyphenyl)quinazolin-4-yl)piperazine-1-carbonyl)-4-methylpent-2-enenitrile | O | 498.2 |

TABLE 1-continued

Representative Compounds

| No. | Structure | Name | Method | [M + H]+ |
|---|---|---|---|---|
| 283 | 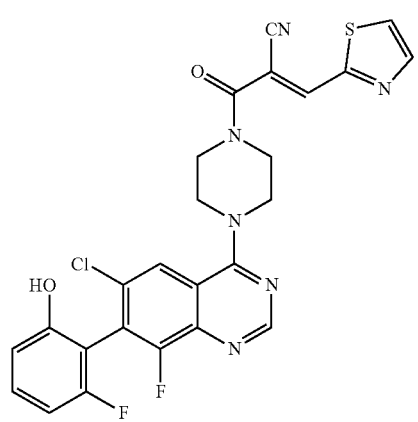 [SMILES: N#C/C(=C\c1nccs1)C(=O)N1CCN(c2ncnc3c(F)c(-c4c(O)cccc4F)c(Cl)cc23)CC1] | (E)-2-(4-(6-chloro-8-fluoro-7-(2-fluoro-6-hydroxyphenyl)quinazolin-4-yl)piperazine-1-carbonyl)-3-(thiazol-5-yl)acrylonitrile | O | 539.2 |
| 284 | 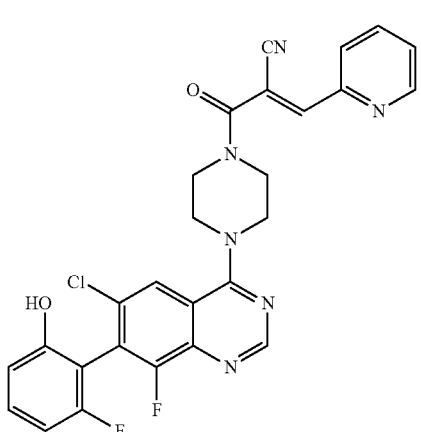 | (E)-2-(4-(6-chloro-8-fluoro-7-(2-fluoro-6-hydroxyphenyl)quinazolin-4-yl)piperazine-1-carbonyl)-3-(pyridin-2-yl)acrylonitrile | O | 533.2 |
| 285 | 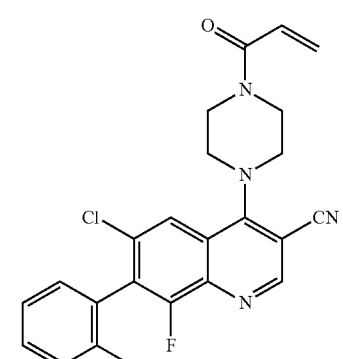 | 4-(4-acryloylpiperazin-1-yl)-6-chloro-8-fluoro-7-(2-(trifluoromethyl)phenyl)quinoline-3-carbonitrile | P | 489.2 |

TABLE 1-continued

Representative Compounds

| No. | Structure | Name | Method | [M + H]+ |
|---|---|---|---|---|
| 286 | 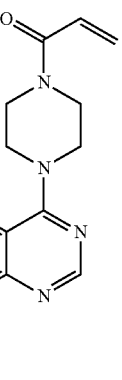 | 1-(4-(6,8-dichloro-7-(2-methoxynaphthalen-1-yl)quinazolin-4-yl)piperazin-1-yl)prop-2-en-1-one | V | 494.1 |
| 287 | 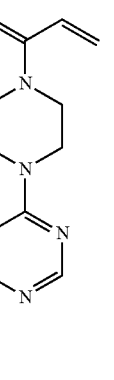 | 1-(4-(6-chloro-8-fluoro-7-(2-methoxy-6-methylphenyl)quinazolin-4-yl)piperazin-1-yl)prop-2-en-1-one | Q | 441.2 |
| 288 | 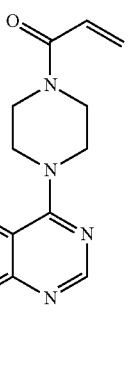 | 1-(4-(6-chloro-8-fluoro-7-(1H-indol-3-yl)quinazolin-4-yl)piperazin-1-yl)prop-2-en-1-one | Q | 436.1 |
| 289 | 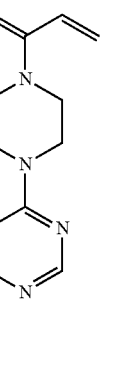 | 1-(4-(6-chloro-7-(2-chloro-6-hydroxyphenyl)-8-fluoroquinazolin-4-yl)piperazin-1-yl)prop-2-en-1-one | O | 448.0 |

TABLE 1-continued

Representative Compounds

| No. | Structure | Name | Method | [M + H]+ |
|---|---|---|---|---|
| 290 | 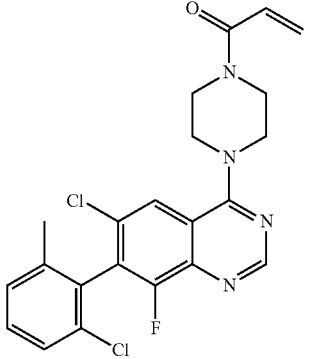 [SMILES: C=CC(=O)N1CCN(c2ncnc3c(F)c(-c4c(C)cccc4Cl)c(Cl)cc23)CC1] | 1-(4-(6-chloro-7-(2-chloro-6-methylphenyl)-8-fluoroquinazolin-4-yl)piperazin-1-yl)prop-2-en-1-one | Q | 427.1 |
| 291 | 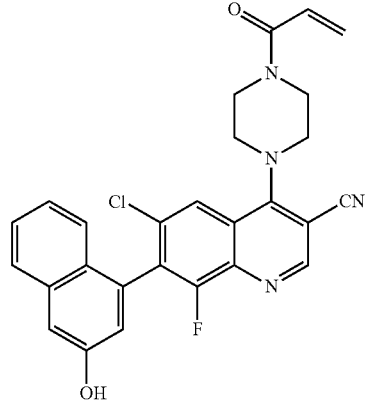 [SMILES: C=CC(=O)N1CCN(c2c(C#N)cnc3c(F)c(-c4cc(O)cc5ccccc45)c(Cl)cc23)CC1] | 4-(4-acryloylpiperazin-1-yl)-6-chloro-8-fluoro-7-(3-hydroxynaphthalen-1-yl)quinoline-3-carbonitrile | P | 487.1 |
| 292 | 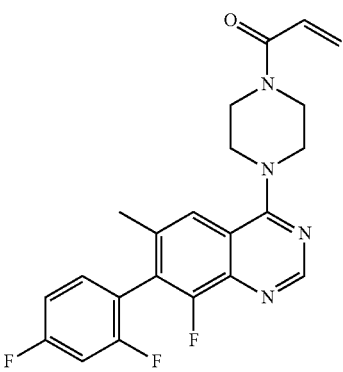 [SMILES: C=CC(=O)N1CCN(c2ncnc3c(F)c(-c4ccc(F)cc4F)c(C)cc23)CC1] | 1-(4-(7-(2,4-difluorophenyl)-8-fluoro-6-methylquinazolin-4-yl)piperazin-1-yl)prop-2-en-1-one | AJ | 413.2 |
| 293 | 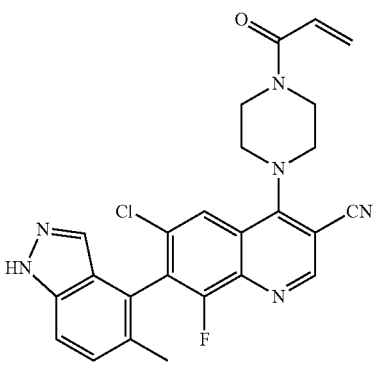 | 4-(4-acryloylpiperazin-1-yl)-6-chloro-8-fluoro-7-(5-methyl-1H-indazol-4-yl)quinoline-3-carbonitrile | P | 475.2 |

TABLE 1-continued

Representative Compounds

| No. | Structure | Name | Method | [M + H]+ |
|---|---|---|---|---|
| 294 | 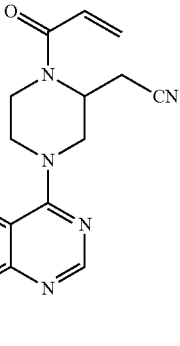 | 2-(1-acryloyl-4-(6-chloro-8-fluoro-7-(5-methyl-1H-indazol-4-yl)quinazolin-4-yl)piperazin-2-yl)acetonitrile | O | 490.2 |
| 295 | 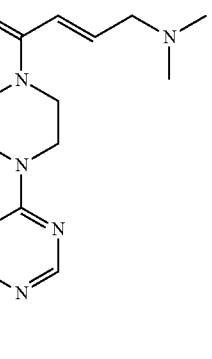 | (E)-1-(4-(6-chloro-8-fluoro-7-(5-methyl-1H-indazol-4-yl)quinazolin-4-yl)piperazin-1-yl)-4-(dimethylamino)but-2-en-1-one | O | 508.2 |
| 296 | 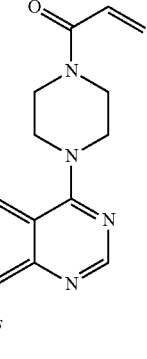 | 1-(4-(7-(2,4-difluorophenyl)-6,8-difluoroquinazolin-4-yl)piperazin-1-yl)prop-2-en-1-one | Y | 417.22 |
| 297 | 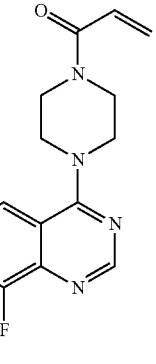 | 1-(4-(6,8-difluoro-7-(5-methyl-1H-indazol-4-yl)quinazolin-4-yl)piperazin-1-yl)prop-2-en-1-one | Y | 435.3 |

TABLE 1-continued

Representative Compounds

| No. | Structure | Name | Method | [M + H]⁺ |
|---|---|---|---|---|
| 298 | 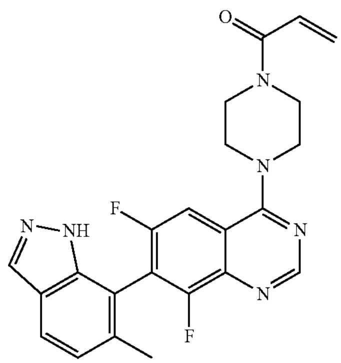 [SMILES: C=CC(=O)N1CCN(c2ncnc3c(F)c(-c4c(C)ccc5cn[nH]c45)c(F)cc23)CC1] | 1-(4-(6,8-difluoro-7-(6-methyl-1H-indazol-7-yl)quinazolin-4-yl)piperazin-1-yl)prop-2-en-1-one | Y | 435.3 |
| 299 | 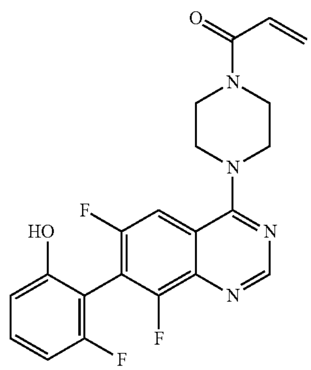 [SMILES: C=CC(=O)N1CCN(c2ncnc3c(F)c(-c4c(O)cccc4F)c(F)cc23)CC1] | 1-(4-(6,8-difluoro-7-(2-fluoro-6-hydroxyphenyl)quinazolin-4-yl)piperazin-1-yl)prop-2-en-1-one | Y | 415.3 |
| 300 | 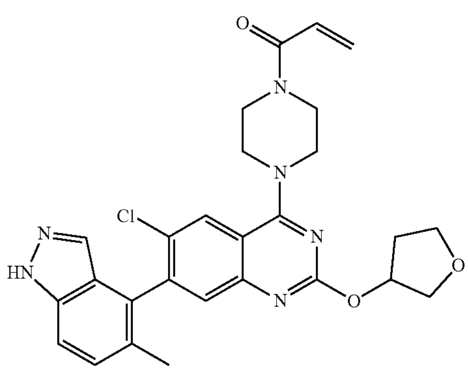 [SMILES: C=CC(=O)N1CCN(c2nc(OC3CCOC3)nc3cc(-c4c(C)ccc5[nH]ncc45)c(Cl)cc23)CC1] | 1-(4-(6-chloro-7-(5-methyl-1H-indazol-4-yl)-2-(tetrahydrofuran-3-yloxy)quinazolin-4-yl)piperazin-1-yl)prop-2-en-1-one | F | 519.3 |
| 301 | 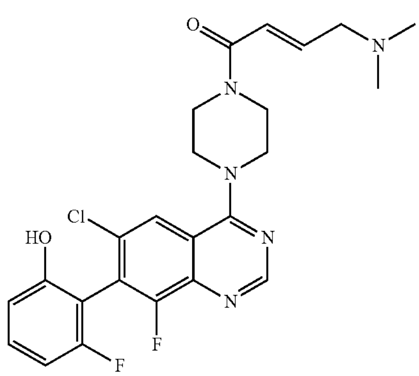 [SMILES: CN(C)C/C=C/C(=O)N1CCN(c2ncnc3c(F)c(-c4c(O)cccc4F)c(Cl)cc23)CC1] | (E)-1-(4-(6-chloro-8-fluoro-7-(2-fluoro-6-hydroxyphenyl)quinazolin-4-yl)piperazin-1-yl)-4-(dimethylamino)but-2-en-1-one | O | 488.2 |

TABLE 1-continued

Representative Compounds

| No. | Structure | Name | Method | [M + H]⁺ |
|---|---|---|---|---|
| 302 | 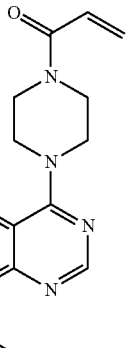 | 1-(4-(6-chloro-8-methoxy-7-(5-methyl-1H-indazol-4-yl)quinazolin-4-yl)piperazin-1-yl)prop-2-en-1-one | Z | 463.3 |
| 303 | 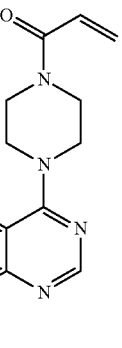 | 1-(4-(6,8-dichloro-7-(2-hydroxynaphthalen-1-yl)quinazolin-4-yl)piperazin-1-yl)prop-2-en-1-one | V | 479.1 |
| 304 | 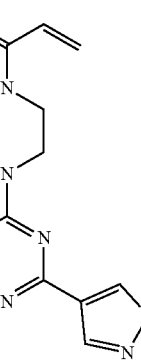 | 1-(4-(6-chloro-8-fluoro-7-(5-methyl-1H-indazol-4-yl)-2-(1H-pyrazol-4-yl)quinazolin-4-yl)piperazin-1-yl)prop-2-en-1-one | AG | 517.0 |
| 305 | 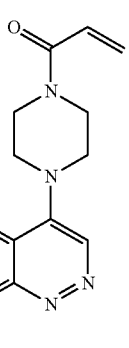 | 1-(4-(7-(5-methyl-1H-indazol-4-yl)-6-(trifluoromethyl)cinnolin-4-yl)piperazin-1-yl)prop-2-en-1-one | X | 467.2 |

TABLE 1-continued

Representative Compounds

| No. | Structure | Name | Method | [M + H]+ |
|---|---|---|---|---|
| 306 | 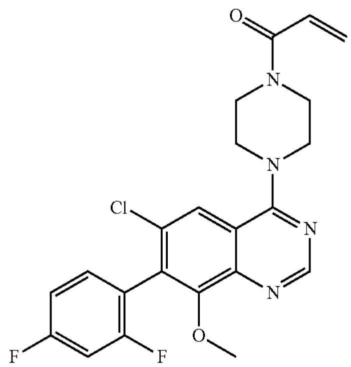 [SMILES: C=CC(=O)N1CCN(c2ncnc3c(OC)c(-c4ccc(F)cc4F)c(Cl)cc23)CC1] | 1-(4-(6-chloro-7-(2,4-difluorophenyl)-8-methoxyquinazolin-4-yl)piperazin-1-yl)prop-2-en-1-one | Z | 445.2 |
| 307 | 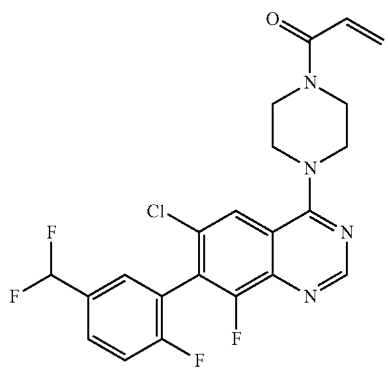 [SMILES: C=CC(=O)N1CCN(c2ncnc3c(F)c(-c4cc(C(F)F)ccc4F)c(Cl)cc23)CC1] | 1-(4-(6-chloro-7-(5-(difluoromethyl)-2-fluorophenyl)-8-fluoroquinazolin-4-yl)piperazin-1-yl)prop-2-en-1-one | O | 461.2 |
| 308 | 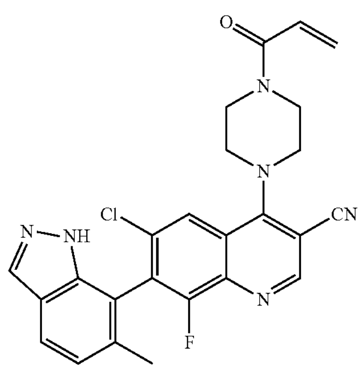 [SMILES: C=CC(=O)N1CCN(c2c(C#N)cnc3c(F)c(-c4c(C)ccc5cn[nH]c45)c(Cl)cc23)CC1] | 4-(4-acryloylpiperazin-1-yl)-6-chloro-8-fluoro-7-(6-methyl-1H-indazol-7-yl)quinoline-3-carbonitrile | P | 475.1 |
| 309 | 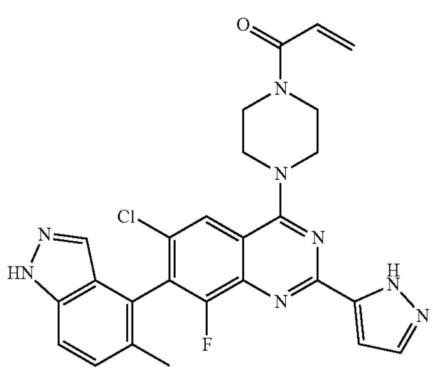 [SMILES: C=CC(=O)N1CCN(c2nc(-c3ccn[nH]3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1H-pyrazol-5-yl)quinazolin-4-yl)piperazin-1-yl)prop-2-en-1-one | AG | 517.1 |

TABLE 1-continued

Representative Compounds

| No. | Structure | Name | Method | [M + H]+ |
|---|---|---|---|---|
| 310 | 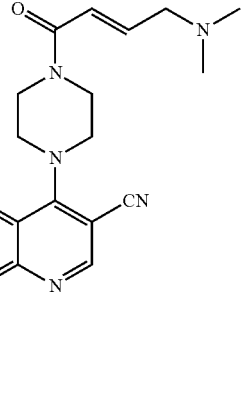 | (E)-6-chloro-4-(4-(4-(dimethylamino)but-2-enoyl)piperazin-1-yl)-8-fluoro-7-(3-hydroxynaphthalen-1-yl)quinoline-3-carbonitrile | P | 544.2 |
| 311 | 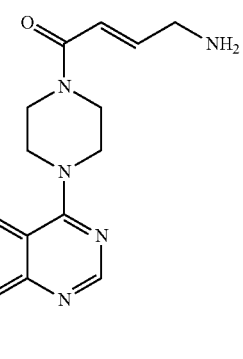 | (E)-4-amino-1-(4-(6-chloro-8-fluoro-7-(5-methyl-1H-indazol-4-yl)quinazolin-4-yl)piperazin-1-yl)but-2-en-1-one | O | 480.2 |
| 312 | 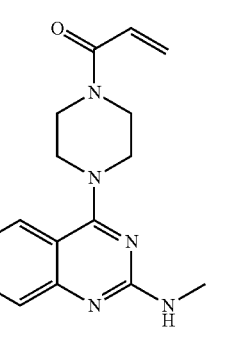 | 1-(4-(6-chloro-7-(5-methyl-1H-indazol-4-yl)-2-(methylamino)quinazolin-4-yl)piperazin-1-yl)prop-2-en-1-one | F | 462.3 |
| 313 | 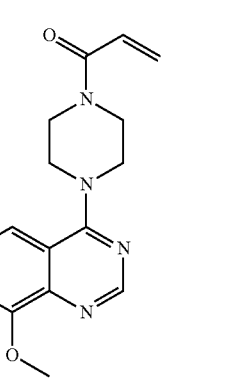 | 1-(4-(6-chloro-7-(2-fluoro-6-hydroxyphenyl)-8-methoxyquinazolin-4-yl)piperazin-1-yl)prop-2-en-1-one | Z | 443.2 |

TABLE 1-continued

Representative Compounds

| No. | Structure | Name | Method | [M + H]+ |
|---|---|---|---|---|
| 314 | 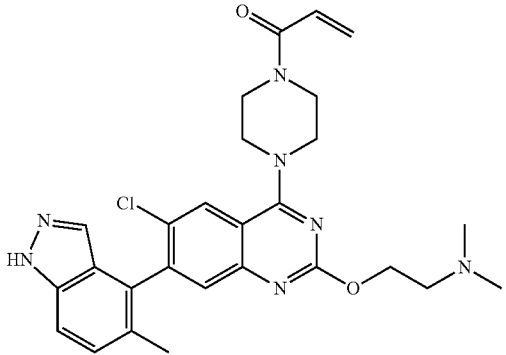 [SMILES: C=CC(=O)N1CCN(c2nc(OCCN(C)C)nc3cc(-c4c(C)ccc5[nH]ncc45)c(Cl)cc23)CC1] | 1-(4-(6-chloro-2-(2-(dimethylamino)ethoxy)-7-(5-methyl-1H-indazol-4-yl)quinazolin-4-yl)piperazin-1-yl)prop-2-en-1-one | F | 520.4 |
| 315 | 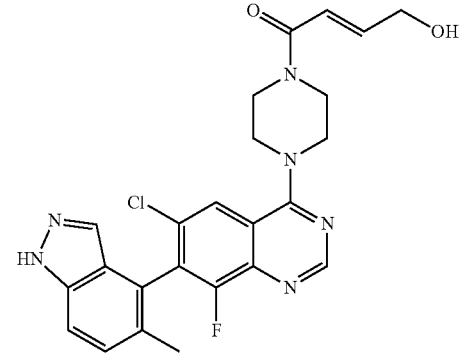 [SMILES: Cc1ccc2[nH]ncc2c1-c1c(Cl)cc2c(N3CCN(C(=O)/C=C/CO)CC3)ncnc2c1F] | (E)-1-(4-(6-chloro-8-fluoro-7-(5-methyl-1H-indazol-4-yl)quinazolin-4-yl)piperazin-1-yl)-4-hydroxybut-2-en-1-one | O | 481.3 |
| 316 | 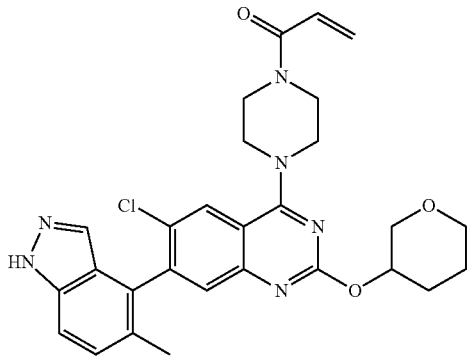 [SMILES: C=CC(=O)N1CCN(c2nc(OC3CCCOC3)nc3cc(-c4c(C)ccc5[nH]ncc45)c(Cl)cc23)CC1] | 1-(4-(6-chloro-7-(5-methyl-1H-indazol-4-yl)-2-(tetrahydro-2H-pyran-3-yloxy)quinazolin-4-yl)piperazin-1-yl)prop-2-en-1-one | F | 533.3 |
| 317 | 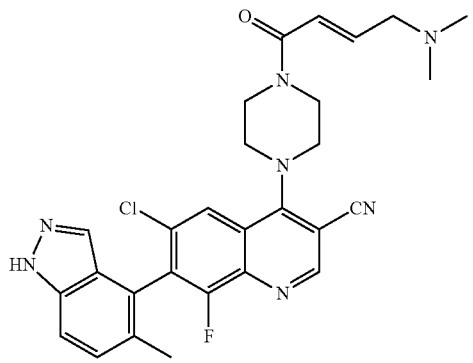 [SMILES: Cc1ccc2[nH]ncc2c1-c1c(Cl)cc2c(N3CCN(C(=O)/C=C/CN(C)C)CC3)c(C#N)cnc2c1F] | (E)-6-chloro-4-(4-(4-(dimethylamino)but-2-enoyl)piperazin-1-yl)-8-fluoro-7-(5-methyl-1H-indazol-4-yl)quinoline-3-carbonitrile | P | 532.3 |

TABLE 1-continued

Representative Compounds

| No. | Structure | Name | Method | [M + H]+ |
|---|---|---|---|---|
| 318 | 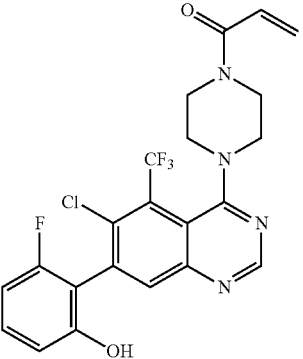 | 1-(4-(6-chloro-7-(2-fluoro-6-hydroxyphenyl)-5-(trifluoromethyl)quinazolin-4-yl)piperazin-1-yl)prop-2-en-1-one | AA | 481.1 |
| 319 | 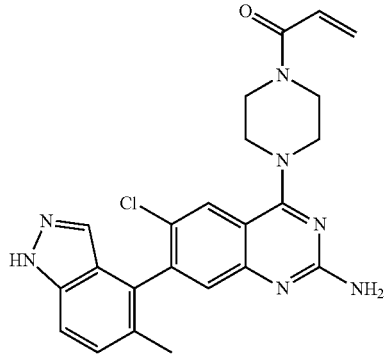 [SMILES: C=CC(=O)N1CCN(c2nc(N)nc3cc(-c4c(C)ccc5[nH]ncc45)c(Cl)cc23)CC1] | 1-(4-(2-amino-6-chloro-7-(5-methyl-1H-indazol-4-yl)quinazolin-4-yl)piperazin-1-yl)prop-2-en-1-one | F | 448.2 |
| 320 | 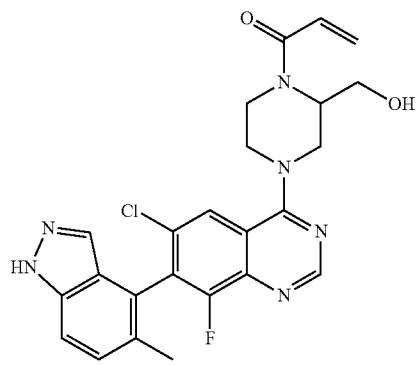 | 1-(4-(6-chloro-8-fluoro-7-(5-methyl-1H-indazol-4-yl)quinazolin-4-yl)-2-(hydroxymethyl)piperazin-1-yl)prop-2-en-1-one | O | 481.2 |
| 321 | 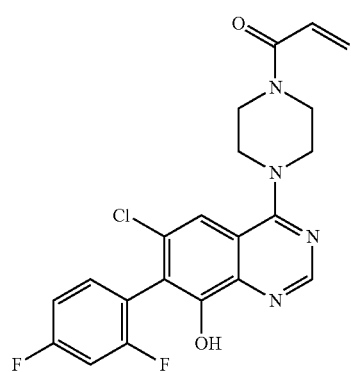 [SMILES: C=CC(=O)N1CCN(c2ncnc3c(O)c(-c4ccc(F)cc4F)c(Cl)cc23)CC1] | 1-(4-(6-chloro-7-(2,4-difluorophenyl)-8-hydroxyquinazolin-4-yl)piperazin-1-yl)prop-2-en-1-one | Z | 431.1 |

TABLE 1-continued

Representative Compounds

| No. | Structure | Name | Method | [M + H]+ |
|---|---|---|---|---|
| 322 | 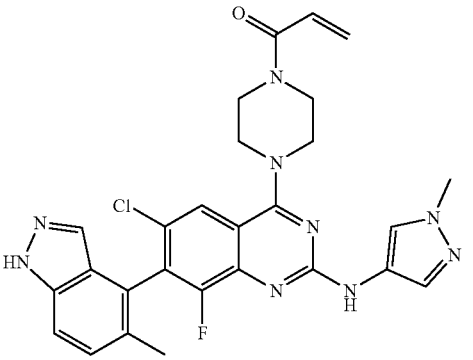 [SMILES: C=CC(=O)N1CCN(c2nc(Nc3cnn(C)c3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methyl-1H-pyrazol-4-ylamino)quinazolin-4-yl)piperazin-1-yl)prop-2-en-1-one | F | 546.2 |
| 323 | 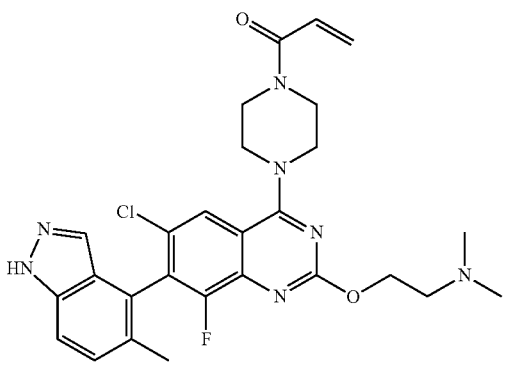 [SMILES: C=CC(=O)N1CCN(c2nc(OCCN(C)C)nc3c(F)c(-c4c(C)ccc5[nH]ncc45)c(Cl)cc23)CC1] | 1-(4-(6-chloro-2-(2-(dimethylamino)ethoxy)-8-fluoro-7-(5-methyl-1H-indazol-4-yl)quinazolin-4-yl)piperazin-1-yl)prop-2-en-1-one | F | 538.2 |
| 324 | 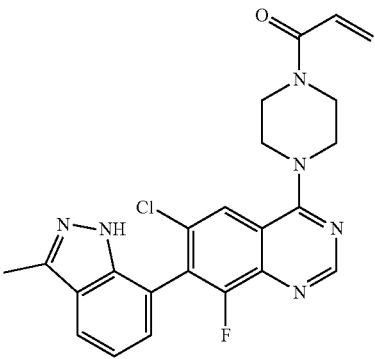 [SMILES: C=CC(=O)N1CCN(c2ncnc3c(F)c(-c4cccc5c(C)n[nH]c45)c(Cl)cc23)CC1] | 1-(4-(6-chloro-8-fluoro-7-(3-methyl-1H-indazol-7-yl)quinazolin-4-yl)piperazin-1-yl)prop-2-en-1-one | B | 451.1 |
| 325 | 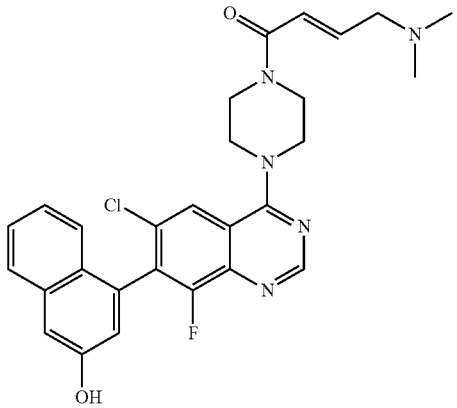 [SMILES: CN(C)C/C=C/C(=O)N1CCN(c2ncnc3c(F)c(-c4cc(O)cc5ccccc45)c(Cl)cc23)CC1] | (E)-1-(4-(6-chloro-8-fluoro-7-(3-hydroxynaphthalen-1-yl)quinazolin-4-yl)piperazin-1-yl)-4-(dimethylamino)but-2-en-1-one | O | 520.3 |

TABLE 1-continued

Representative Compounds

| No. | Structure | Name | Method | [M + H]+ |
|---|---|---|---|---|
| 326 | 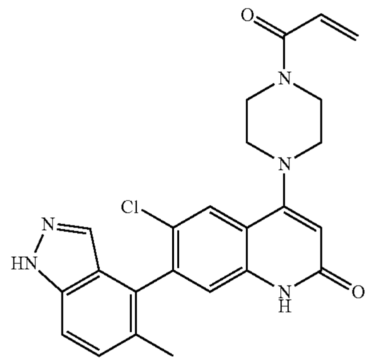 [SMILES: C=CC(=O)N1CCN(c2cc(=O)[nH]c3cc(-c4c(C)ccc5[nH]ncc45)c(Cl)cc23)CC1] | 4-(4-acryloylpiperazin-1-yl)-6-chloro-7-(5-methyl-1H-indazol-4-yl)quinolin-2(1H)-one | AB | 448.2 |
| 327 | 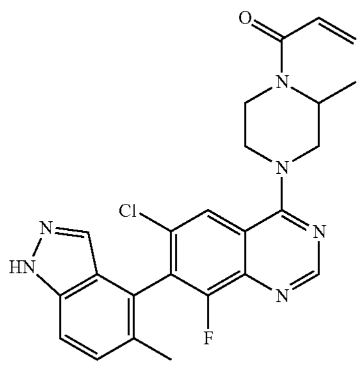 [SMILES: C=CC(=O)N1CCN(c2ncnc3c(F)c(-c4c(C)ccc5[nH]ncc45)c(Cl)cc23)CC1C] | 1-(4-(6-chloro-8-fluoro-7-(5-methyl-1H-indazol-4-yl)quinazolin-4-yl)-2-methylpiperazin-1-yl)prop-2-en-1-one | O | 465.2 |
| 328 | 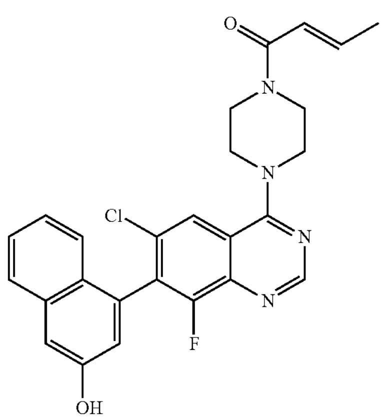 [SMILES: C/C=C/C(=O)N1CCN(c2ncnc3c(F)c(-c4cc(O)cc5ccccc45)c(Cl)cc23)CC1] | (E)-1-(4-(6-chloro-8-fluoro-7-(3-hydroxynaphthalen-1-yl)quinazolin-4-yl)piperazin-1-yl)but-2-en-1-one | O | 477.2 |
| 329 | 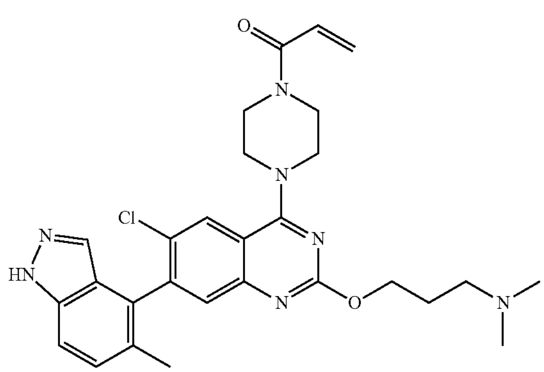 [SMILES: C=CC(=O)N1CCN(c2nc(OCCCN(C)C)nc3cc(-c4c(C)ccc5[nH]ncc45)c(Cl)cc23)CC1] | 1-(4-(6-chloro-2-(3-(dimethylamino)propoxy)-7-(5-methyl-1H-indazol-4-yl)quinazolin-4-yl)piperazin-1-yl)prop-2-en-1-one | F | 534.3 |

TABLE 1-continued

Representative Compounds

| No. | Structure | Name | Method | [M + H]+ |
|---|---|---|---|---|
| 330 | 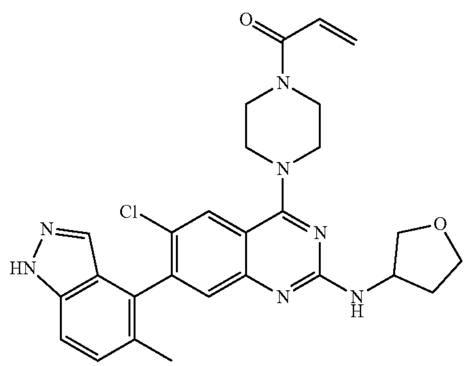 [SMILES: C=CC(=O)N1CCN(c2nc(NC3CCOC3)nc3cc(-c4c(C)ccc5[nH]ncc45)c(Cl)cc23)CC1] | 1-(4-(6-chloro-7-(5-methyl-1H-indazol-4-yl)-2-(tetrahydrofuran-3-ylamino)quinazolin-4-yl)piperazin-1-yl)prop-2-en-1-one | F | 518.3 |
| 331 | 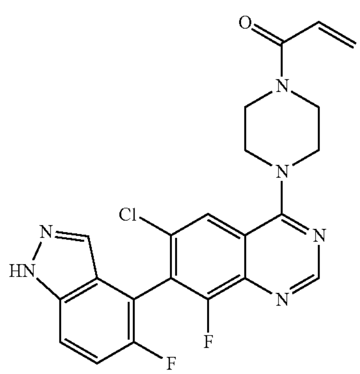 [SMILES: C=CC(=O)N1CCN(c2ncnc3c(F)c(-c4c(F)ccc5[nH]ncc45)c(Cl)cc23)CC1] | 1-(4-(6-chloro-8-fluoro-7-(5-fluoro-1H-indazol-4-yl)quinazolin-4-yl)piperazin-1-yl)prop-2-en-1-one | Q | 455.1 |
| 332 | 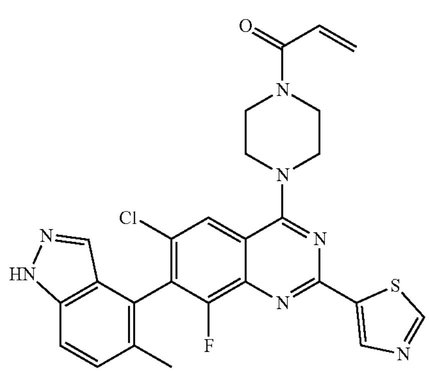 [SMILES: C=CC(=O)N1CCN(c2nc(-c3cncs3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(thiazol-5-yl)quinazolin-4-yl)piperazin-1-yl)prop-2-en-1-one | AG | 534.1 |
| 333 | 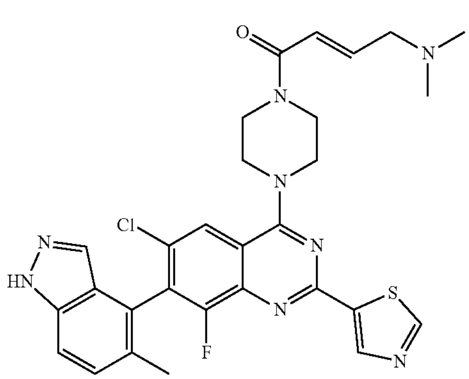 [SMILES: Cc1ccc2[nH]ncc2c1-c1c(Cl)cc2c(N3CCN(C(=O)/C=C/CN(C)C)CC3)nc(-c3cncs3)nc2c1F] | (E)-1-(4-(6-chloro-8-fluoro-7-(5-methyl-1H-indazol-4-yl)-2-(thiazol-5-yl)quinazolin-4-yl)piperazin-1-yl)-4-(dimethylamino)but-2-en-1-one | AG | 591.1 |

TABLE 1-continued
Representative Compounds
| No. | Structure | Name | Method | [M + H]+ |
|---|---|---|---|---|
| 334 | 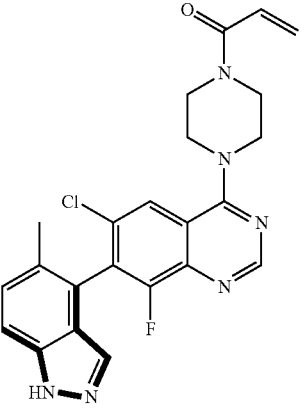 | (R)-1-(4-(6-chloro-8-fluoro-7-(5-methyl-1H-indazol-4-yl)quinazolin-4-yl)piperazin-1-yl)prop-2-en-1-one | O | 451.2 |
| 335 | 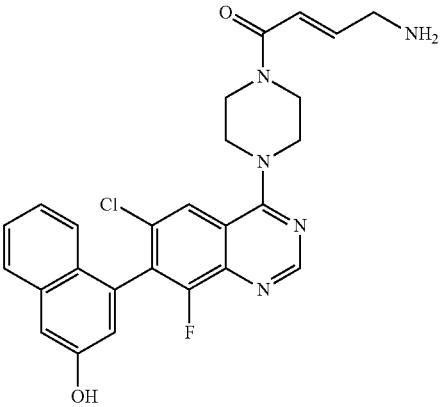 [SMILES: NC/C=C/C(=O)N1CCN(c2ncnc3c(F)c(-c4cc(O)cc5ccccc45)c(Cl)cc23)CC1] | (E)-4-amino-1-(4-(6-chloro-8-fluoro-7-(3-hydroxynaphthalen-1-yl)quinazolin-4-yl)piperazin-1-yl)but-2-en-1-one | O | 492.2 |
| 336 | 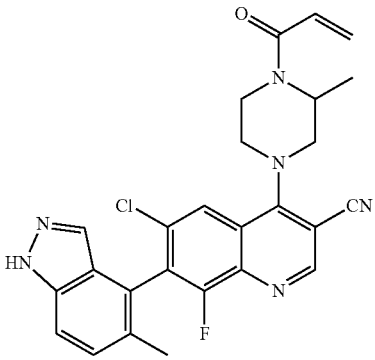 [SMILES: C=CC(=O)N1CCN(c2c(C#N)cnc3c(F)c(-c4c(C)ccc5[nH]ncc45)c(Cl)cc23)CC1C] | 4-(4-acryloyl-3-methylpiperazin-1-yl)-6-chloro-8-fluoro-7-(5-methyl-1H-indazol-4-yl)quinoline-3-carbonitrile | P | 489.2 |

TABLE 1-continued

Representative Compounds

| No. | Structure | Name | Method | [M + H]+ |
|---|---|---|---|---|
| 337 | 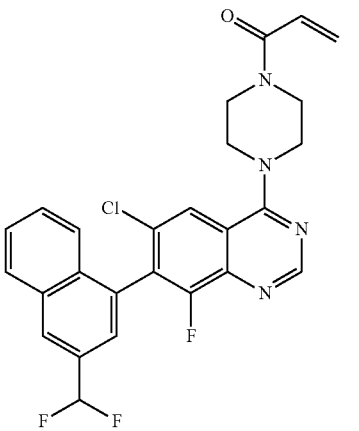 [SMILES: C=CC(=O)N1CCN(c2ncnc3c(F)c(-c4cc(C(F)F)cc5ccccc45)c(Cl)cc23)CC1] | 1-(4-(6-chloro-7-(3-(difluoromethyl)naphthalen-1-yl)-8-fluoroquinazolin-4-yl)piperazin-1-yl)prop-2-en-1-one | O | 497.2 |
| 338 | 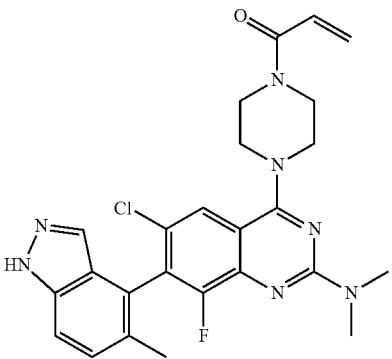 [SMILES: C=CC(=O)N1CCN(c2nc(N(C)C)nc3c(F)c(-c4c(C)ccc5[nH]ncc45)c(Cl)cc23)CC1] | 1-(4-(6-chloro-2-(dimethylamino)-8-fluoro-7-(5-methyl-1H-indazol-4-yl)quinazolin-4-yl)piperazin-1-yl)prop-2-en-1-one | AC | 494.4 |
| 339 | 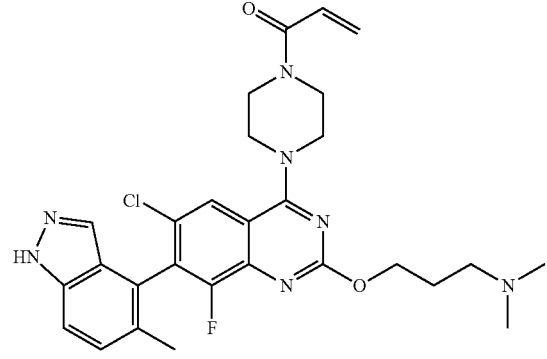 [SMILES: C=CC(=O)N1CCN(c2nc(OCCCN(C)C)nc3c(F)c(-c4c(C)ccc5[nH]ncc45)c(Cl)cc23)CC1] | 1-(4-(6-chloro-2-(3-(dimethylamino)propoxy)-8-fluoro-7-(5-methyl-1H-indazol-4-yl)quinazolin-4-yl)piperazin-1-yl)prop-2-en-1-one | B | 552.2 |
| 340 | 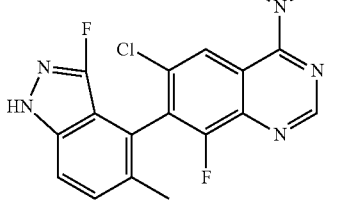 | 1-(4-(6-chloro-8-fluoro-7-(3-fluoro-5-methyl-1H-indazol-4-yl)quinazolin-4-yl)piperazin-1-yl)prop-2-en-1-one | AH | 469.1 |

TABLE 1-continued

Representative Compounds

| No. | Structure | Name | Method | [M + H]+ |
|---|---|---|---|---|
| 341 | 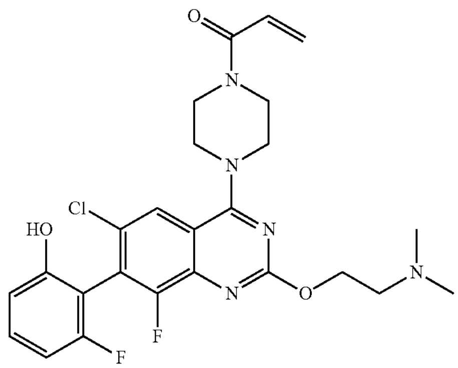 [SMILES: C=CC(=O)N1CCN(c2nc(OCCN(C)C)nc3c(F)c(-c4c(O)cccc4F)c(Cl)cc23)CC1] | 1-(4-(6-chloro-2-(2-(dimethylamino)ethoxy)-8-fluoro-7-(2-fluoro-6-hydroxyphenyl)quinazolin-4-yl)piperazin-1-yl)prop-2-en-1-one | F | 518.2 |
| 342 | 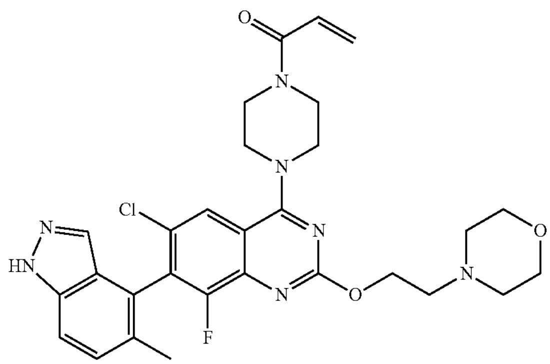 [SMILES: C=CC(=O)N1CCN(c2nc(OCCN3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2-morpholinoethoxy)quinazolin-4-yl)piperazin-1-yl)prop-2-en-1-one | F | 580.2 |
| 343 | 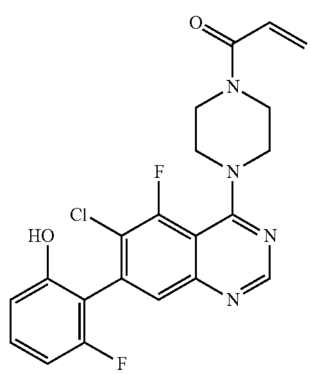 [SMILES: C=CC(=O)N1CCN(c2ncnc3cc(-c4c(O)cccc4F)c(Cl)c(F)c23)CC1] | 1-(4-(6-chloro-5-fluoro-7-(2-fluoro-6-hydroxyphenyl)quinazolin-4-yl)piperazin-1-yl)prop-2-en-1-one | AD | 431.2 |
| 344 | 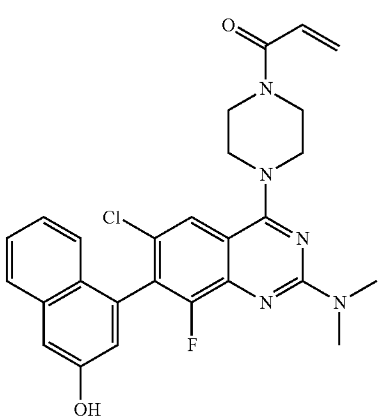 [SMILES: C=CC(=O)N1CCN(c2nc(N(C)C)nc3c(F)c(-c4cc(O)cc5ccccc45)c(Cl)cc23)CC1] | 1-(4-(6-chloro-2-(dimethylamino)-8-fluoro-7-(3-hydroxynaphthalen-1-yl)quinazolin-4-yl)piperazin-1-yl)prop-2-en-1-one | AC | 506.3 |

TABLE 1-continued

Representative Compounds

| No. | Structure | Name | Method | [M + H]+ |
|---|---|---|---|---|
| 345 | 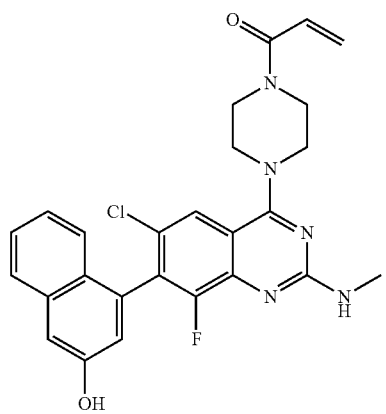 [SMILES: C=CC(=O)N1CCN(c2nc(NC)nc3c(F)c(-c4cc(O)cc5ccccc45)c(Cl)cc23)CC1] | 1-(4-(6-chloro-8-fluoro-7-(3-hydroxynaphthalen-1-yl)-2-(methylamino)quinazolin-4-yl)piperazin-1-yl)prop-2-en-1-one | AC | 492.2 |
| 346 | 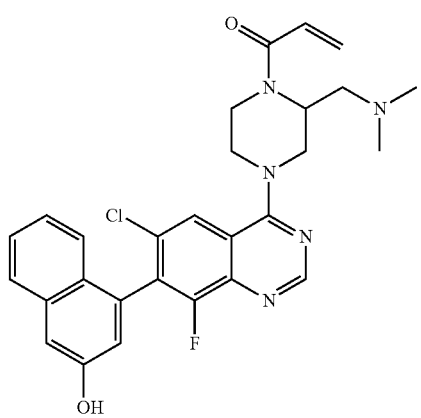 [SMILES: C=CC(=O)N1CCN(c2ncnc3c(F)c(-c4cc(O)cc5ccccc45)c(Cl)cc23)CC1CN(C)C] | 1-(4-(6-chloro-8-fluoro-7-(3-hydroxynaphthalen-1-yl)quinazolin-4-yl)-2-((dimethylamino)methyl)piperazin-1-yl)prop-2-en-1-one | O | 520.2 |
| 347 | 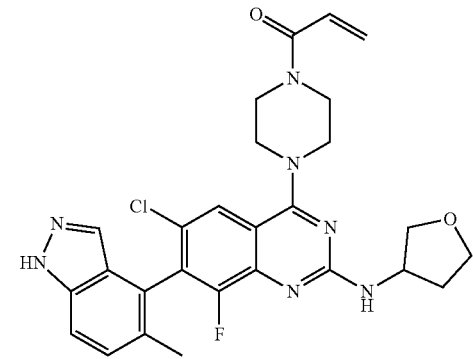 [SMILES: C=CC(=O)N1CCN(c2nc(NC3CCOC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(tetrahydrofuran-3-ylamino)quinazolin-4-yl)piperazin-1-yl)prop-2-en-1-one | AC | 536.3 |

TABLE 1-continued
Representative Compounds
| No. | Structure | Name | Method | [M + H]+ |
|---|---|---|---|---|
| 348 | 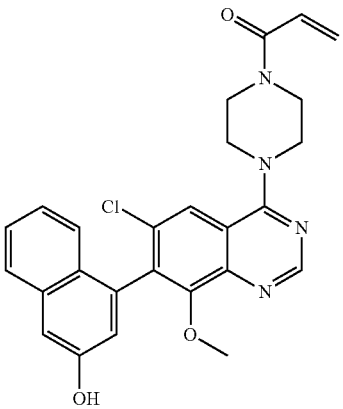 [SMILES: C=CC(=O)N1CCN(c2ncnc3c(OC)c(-c4cc(O)cc5ccccc45)c(Cl)cc23)CC1] | 1-(4-(6-chloro-7-(3-hydroxynaphthalen-1-yl)-8-methoxyquinazolin-4-yl)piperazin-1-yl)prop-2-en-1-one | Z | 475.3 |
| 349 | 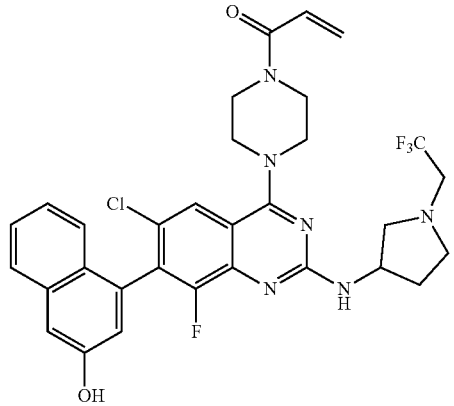 [SMILES: C=CC(=O)N1CCN(c2nc(NC3CCN(CC(F)(F)F)C3)nc3c(F)c(-c4cc(O)cc5ccccc45)c(Cl)cc23)CC1] | 1-(4-(6-chloro-8-fluoro-7-(3-hydroxynaphthalen-1-yl)-2-(1-(2,2,2-trifluoroethyl)pyrrolidin-3-ylamino)quinazolin-4-yl)piperazin-1-yl)prop-2-en-1-one | AC | 629.3 |
| 350 | 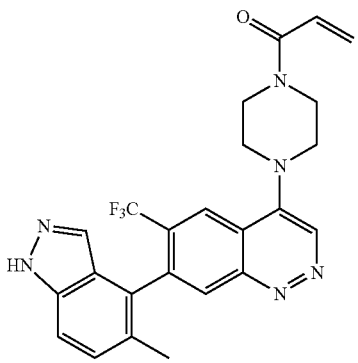 [SMILES: C=CC(=O)N1CCN(c2cnnc3cc(-c4c(C)ccc5[nH]ncc45)c(C(F)(F)F)cc23)CC1] | 1-(4-(7-(5-methyl-1H-indazol-4-yl)-6-(trifluoromethyl)cinnolin-4-yl)piperazin-1-yl)prop-2-en-1-one | X | 467.3 |

TABLE 1-continued

Representative Compounds

| No. | Structure | Name | Method | [M + H]+ |
|---|---|---|---|---|
| 351 | 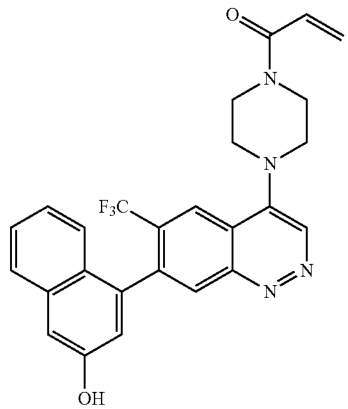 [SMILES: C=CC(=O)N1CCN(c2cnnc3cc(-c4cc(O)cc5ccccc45)c(C(F)(F)F)cc23)CC1] | 1-(4-(7-(3-hydroxynaphthalen-1-yl)-6-(trifluoromethyl)cinnolin-4-yl)piperazin-1-yl)prop-2-en-1-one | X | 479.2 |
| 352 | 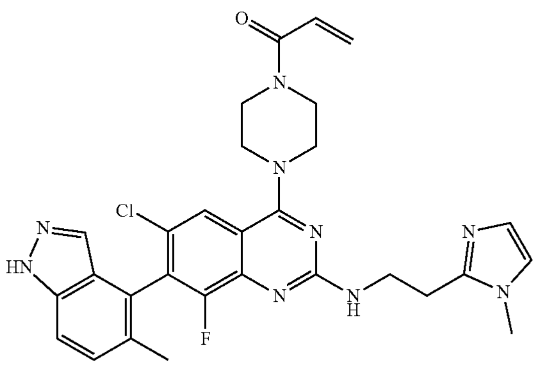 [SMILES: C=CC(=O)N1CCN(c2nc(NCCc3nccn3C)nc3c(F)c(-c4c(C)ccc5[nH]ncc45)c(Cl)cc23)CC1] | 1-(4-(6-chloro-8-fluoro-2-(2-(1-methyl-1H-imidazol-2-yl)ethylamino)-7-(5-methyl-1H-indazol-4-yl)quinazolin-4-yl)piperazin-1-yl)prop-2-en-1-one | F | 575.2 |
| 353 | 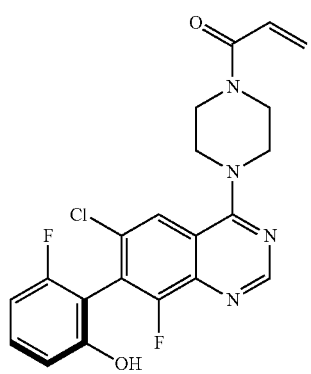 | (S)-1-(4-(6-chloro-8-fluoro-7-(2-fluoro-6-hydroxyphenyl)quinazolin-4-yl)piperazin-1-yl)prop-2-en-1-one | O | 431.2 |
| 354 | 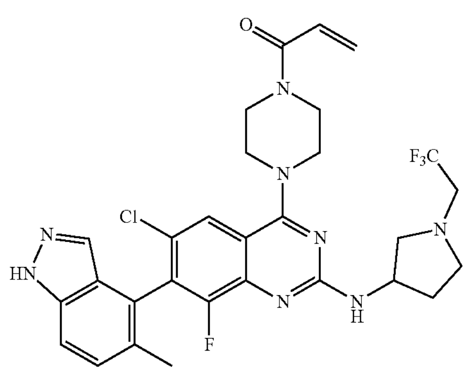 [SMILES: C=CC(=O)N1CCN(c2nc(NC3CCN(CC(F)(F)F)C3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-(2,2,2-trifluoroethyl)pyrrolidin-3-ylamino)quinazolin-4-yl)piperazin-1-yl)prop-2-en-1-one | AC | 617.3 |

TABLE 1-continued

Representative Compounds

| No. | Structure | Name | Method | [M + H]+ |
|---|---|---|---|---|
| 355 | 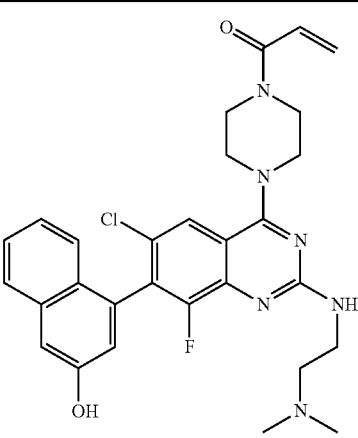 | 1-(4-(6-chloro-2-(2-(dimethylamino)ethylamino)-8-fluoro-7-(3-hydroxynaphthalen-1-yl)quinazolin-4-yl)piperazin-1-yl)prop-2-en-1-one | AC | 549.3 |
| 356 | 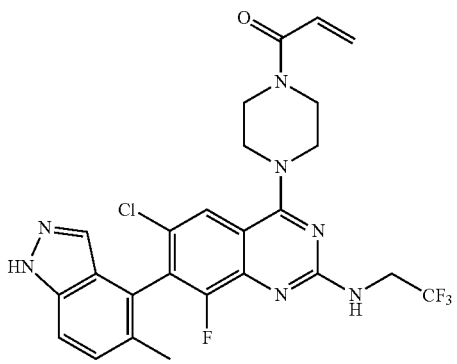 [SMILES: C=CC(=O)N1CCN(c2nc(NCC(F)(F)F)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2,2,2-trifluoroethylamino)quinazolin-4-yl)piperazin-1-yl)prop-2-en-1-one | AC | 548.3 |
| 357 | 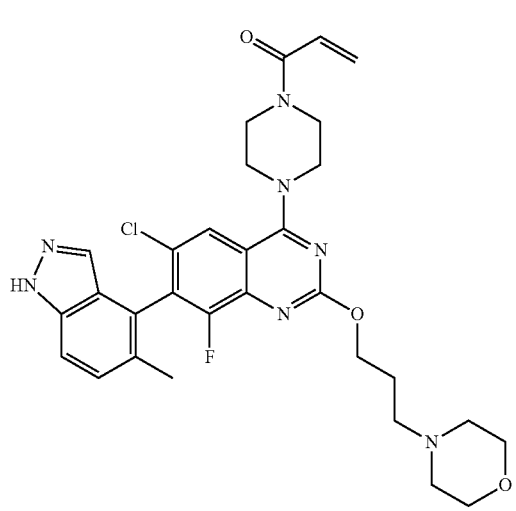 [SMILES: C=CC(=O)N1CCN(c2nc(OCCCN3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(3-morpholinopropoxy)quinazolin-4-yl)piperazin-1-yl)prop-2-en-1-one | F | 594.2 |

TABLE 1-continued

Representative Compounds

| No. | Structure | Name | Method | [M + H]+ |
|---|---|---|---|---|
| 358 | 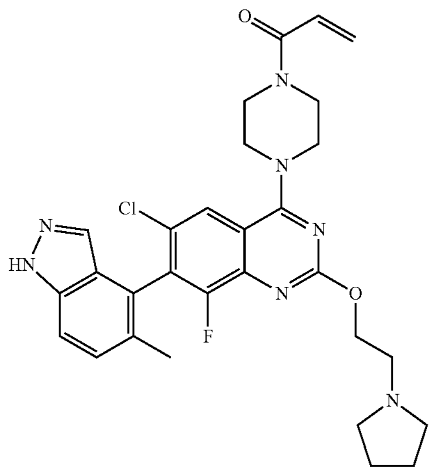 [SMILES: C=CC(=O)N1CCN(c2nc(OCCN3CCCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2-(pyrrolidin-1-yl)ethoxy)quinazolin-4-yl)piperazin-1-yl)prop-2-en-1-one | F | 564.2 |
| 359 | 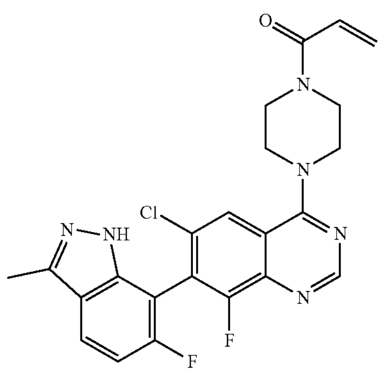 [SMILES: C=CC(=O)N1CCN(c2ncnc3c(F)c(-c4c(F)ccc5c(C)n[nH]c45)c(Cl)cc23)CC1] | 1-(4-(6-chloro-8-fluoro-7-(6-fluoro-3-methyl-1H-indazol-7-yl)quinazolin-4-yl)piperazin-1-yl)prop-2-en-1-one | B | 469.1 |
| 360 | 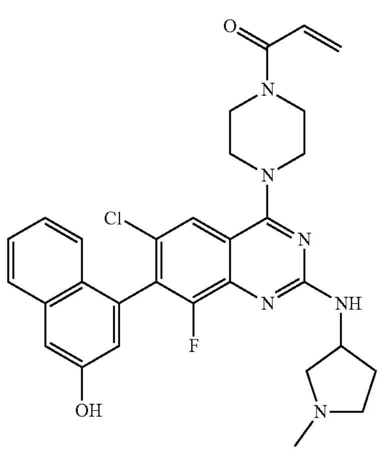 [SMILES: C=CC(=O)N1CCN(c2nc(NC3CCN(C)C3)nc3c(F)c(-c4cc(O)cc5ccccc45)c(Cl)cc23)CC1] | 1-(4-(6-chloro-8-fluoro-7-(3-hydroxynaphthalen-1-yl)-2-(1-methylpyrrolidin-3-ylamino)quinazolin-4-yl)piperazin-1-yl)prop-2-en-1-one | AC | 561.4 |

TABLE 1-continued

Representative Compounds

| No. | Structure | Name | Method | [M + H]+ |
|---|---|---|---|---|
| 361 | 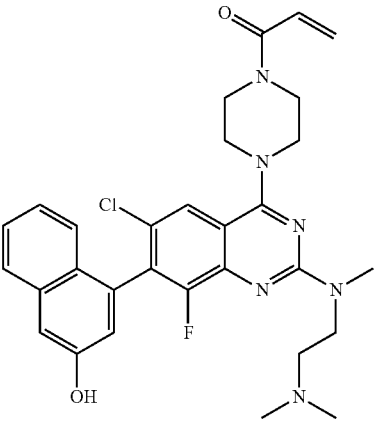 [SMILES: C=CC(=O)N1CCN(c2nc(N(C)CCN(C)C)nc3c(F)c(-c4cc(O)cc5ccccc45)c(Cl)cc23)CC1] | 1-(4-(6-chloro-2-((2-(dimethylamino)ethyl)(methyl)amino)-8-fluoro-7-(3-hydroxynaphthalen-1-yl)quinazolin-4-yl)piperazin-1-yl)prop-2-en-1-one | AC | 563.4 |
| 362 | 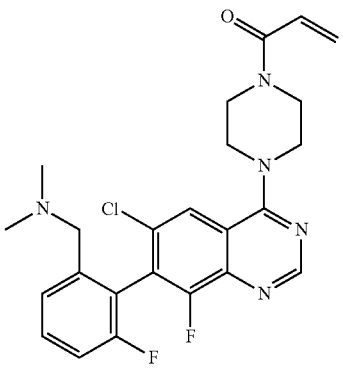 [SMILES: C=CC(=O)N1CCN(c2ncnc3c(F)c(-c4c(F)cccc4CN(C)C)c(Cl)cc23)CC1] | 1-(4-(6-chloro-7-(2-((dimethylamino)methyl)-6-fluorophenyl)-8-fluoroquinazolin-4-yl)piperazin-1-yl)prop-2-en-1-one | O | 472.3 |
| 363 | 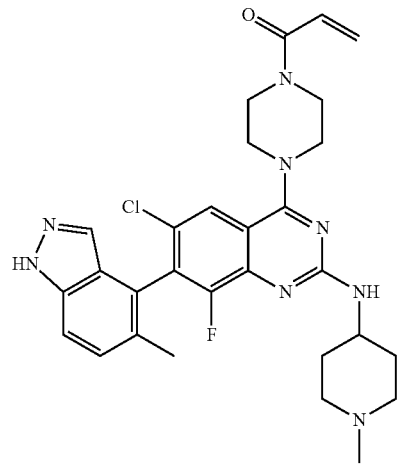 [SMILES: C=CC(=O)N1CCN(c2nc(NC3CCN(C)CC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methylpiperidin-4-ylamino)quinazolin-4-yl)piperazin-1-yl)prop-2-en-1-one | AC | 563.4 |

TABLE 1-continued

Representative Compounds

| No. | Structure | Name | Method | [M + H]+ |
|---|---|---|---|---|
| 364 | 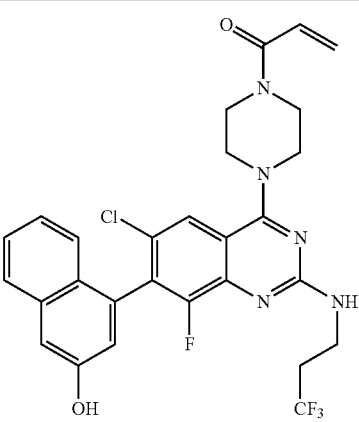 [SMILES: C=CC(=O)N1CCN(c2nc(NCCC(F)(F)F)nc3c(F)c(-c4cc(O)cc5ccccc45)c(Cl)cc23)CC1] | 1-(4-(6-chloro-8-fluoro-7-(3-hydroxynaphthalen-1-yl)-2-(3,3,3-trifluoropropylamino)quiazolin-4-yl)piperazin-1-yl)prop-2-en-1-one | AC | 560.30 |
| 365 | 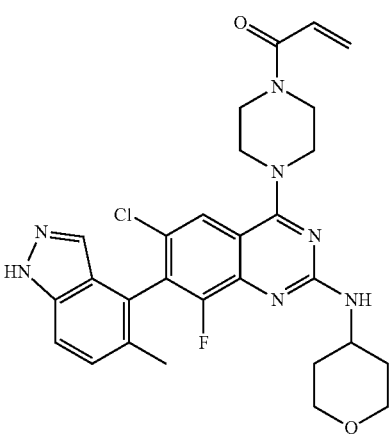 [SMILES: C=CC(=O)N1CCN(c2nc(NC3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(tetrahydro-2H-pyran-4-ylamino)quinazolin-4-yl)piperazin-1-yl)prop-2-en-1-one | AC | 550.30 |
| 366 | 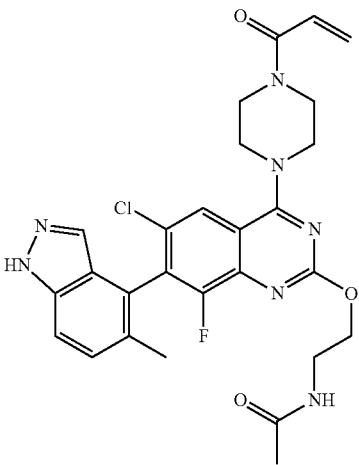 [SMILES: C=CC(=O)N1CCN(c2nc(OCCNC(C)=O)nc3c(F)c(-c4c(C)ccc5[nH]ncc45)c(Cl)cc23)CC1] | N-(2-(4-(4-acryloylpiperazin-1-yl)-6-chloro-8-fluoro-7-(5-methyl-1H-indazol-4-yl)quinazolin-2-yloxy)ethyl)acetamide | AC | 552.35 |

TABLE 1-continued
Representative Compounds
| No. | Structure | Name | Method | [M + H]+ |
|---|---|---|---|---|
| 367 | 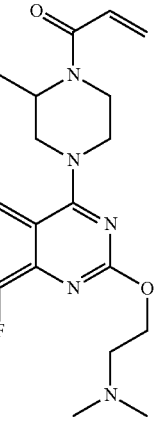 | 1-(4-(6-chloro-2-(2-(dimethylamino)ethoxy)-8-fluoro-7-(5-methyl-1H-indazol-4-yl)quinazolin-4-yl)-2-methylpiperazin-1-yl)prop-2-en-1-one | F | 552.30 |
| 368 | 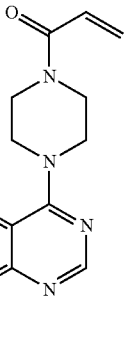 | 1-(4-(6-chloro-8-fluoro-7-(6-fluoro-1H-indazol-7-yl)quinazolin-4-yl)piperazin-1-yl)prop-2-en-1-one | B | 455.1 |
| 369 | 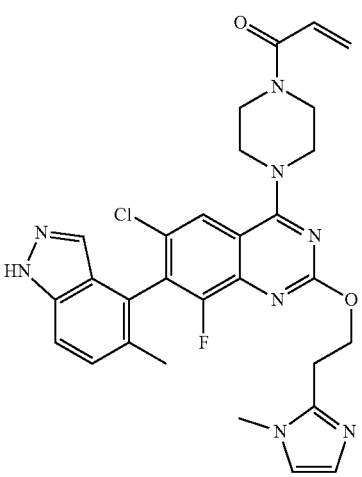 [SMILES: C=CC(=O)N1CCN(c2nc(OCCc3nccn3C)nc3c(F)c(-c4c(C)ccc5[nH]ncc45)c(Cl)cc23)CC1] | 1-(4-(6-chloro-8-fluoro-2-(2-(1-methyl-1H-imidazol-2-yl)ethoxy)-7-(5-methyl-1H-indazol-4-yl)quinazolin-4-yl)piperazin-1-yl)prop-2-en-1-one | F | 575.2 |

TABLE 1-continued

Representative Compounds

| No. | Structure | Name | Method | [M + H]+ |
|---|---|---|---|---|
| 370 | 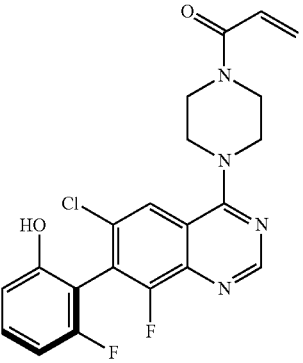 | (R)-1-(4-(6-chloro-8-fluoro-7-(2-fluoro-6-hydroxyphenyl)quinazolin-4-yl)piperazin-1-yl)prop-2-en-1-one | O | 431.2 |
| 371 | 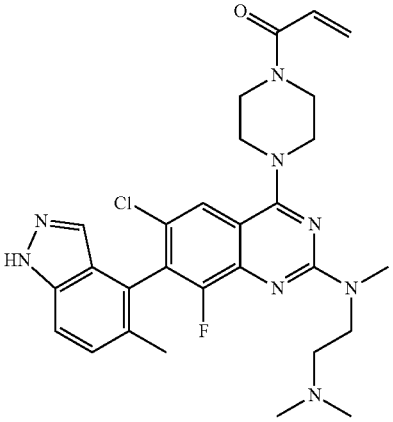 [SMILES: C=CC(=O)N1CCN(c2nc(N(C)CCN(C)C)nc3c(F)c(-c4c(C)ccc5[nH]ncc45)c(Cl)cc23)CC1] | 1-(4-(6-chloro-2-((2-(dimethylamino)ethyl)(methyl)amino)-8-fluoro-7-(5-methyl-1H-indazol-4-yl)quinazolin-4-yl)piperazin-1-yl)prop-2-en-1-one | AC | 551.35 |
| 372 | 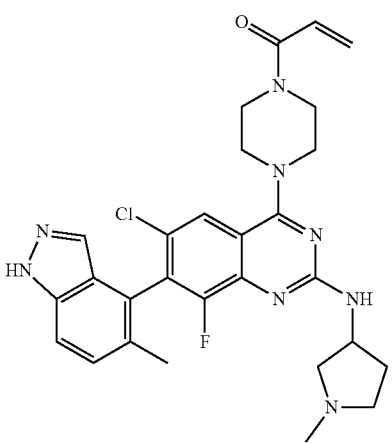 [SMILES: C=CC(=O)N1CCN(c2nc(NC3CCN(C)C3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methylpyrrolidin-3-ylamino)quinazolin-4-yl)piperazin-1-yl)prop-2-en-1-one | AC | 549.30 |

TABLE 1-continued

Representative Compounds

| No. | Structure | Name | Method | [M + H]+ |
|---|---|---|---|---|
| 373 | 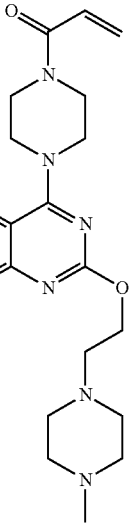 | 1-(4-(6-chloro-8-fluoro-7-(5-methyl-1H-indazol-4-yl)-2-(2-(4-methylpiperazin-1-yl)ethoxy)quinazolin-4-yl)piperazin-1-yl)prop-2-en-1-one | F | 593.30 |
| 374 | 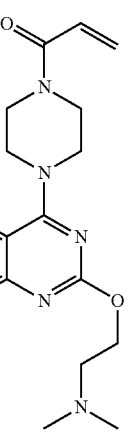 | 1-(4-(6-chloro-2-(2-(dimethylamino)ethoxy)-8-fluoro-7-(3-hydroxynaphthalen-1-yl)quinazolin-4-yl)piperazin-1-yl)prop-2-en-1-one | F | 550.25 |
| 375 | 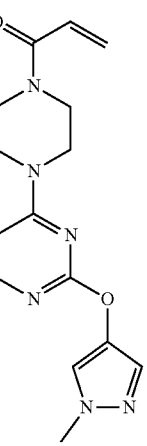 | 1-(4-(6-chloro-8-fluoro-7-(5-methyl-1H-indazol-4-yl)-2-(1-methyl-1H-pyrazol-4-yloxy)quinazolin-4-yl)piperazin-1-yl)prop-2-en-1-one | F | 547.25 |

TABLE 1-continued

Representative Compounds

| No. | Structure | Name | Method | [M + H]+ |
|---|---|---|---|---|
| 376 | 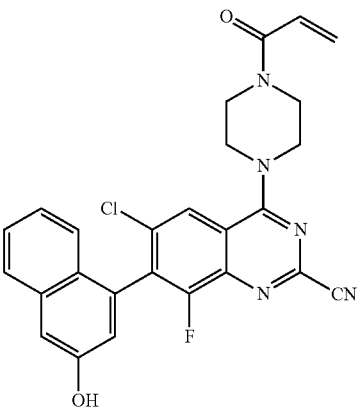 [SMILES: C=CC(=O)N1CCN(c2nc(C#N)nc3c(F)c(-c4cc(O)cc5ccccc45)c(Cl)cc23)CC1] | 4-(4-acryloylpiperazin-1-yl)-6-chloro-8-fluoro-7-(3-hydroxynaphthalen-1-yl)quinazoline-2-carbonitrile | AI | 488.15 |

*[M + Na]+
†[M − H]−
[M]

The compounds in Table 1 were each prepared and analyzed by mass spectrometry and/or $^1$H NMR. Experimental mass spectrometry data is included in Table 1 above. Exemplary synthetic procedures are described in more detail below and in the Examples. General methods by which the compounds may be prepared are provided below and indicated in Table 1 above.

It is understood that in the present description, combinations of substituents and/or variables of the depicted formulae are permissible only if such contributions result in stable compounds.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R″ (where R″ is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art.

Salts of the compounds of the invention can be converted to their free base or acid form by standard techniques.

The following General Reaction Schemes illustrate exemplary methods of making compounds of compounds of structure (I):

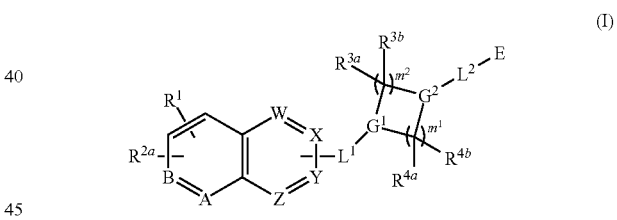

or a pharmaceutically acceptable salt, tautomer or stereoisomer thereof, wherein $R^1$, $R^{2a}$, $R^{3a}$, $R^{3b}$, $R^{4a}$, $R^{4b}$, $G^1$, $G^2$, $L^1$, $L^2$, $m^1$, $m^2$, A, B, W, X, Y, Z and E are as defined above. For ease of illustration, many of the schemes which follow illustrate an "R$^2$" moiety. The R2 moiety is meant to include any one of $R^{2a}$, $R^{2b}$ or $R^{2c}$. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 1

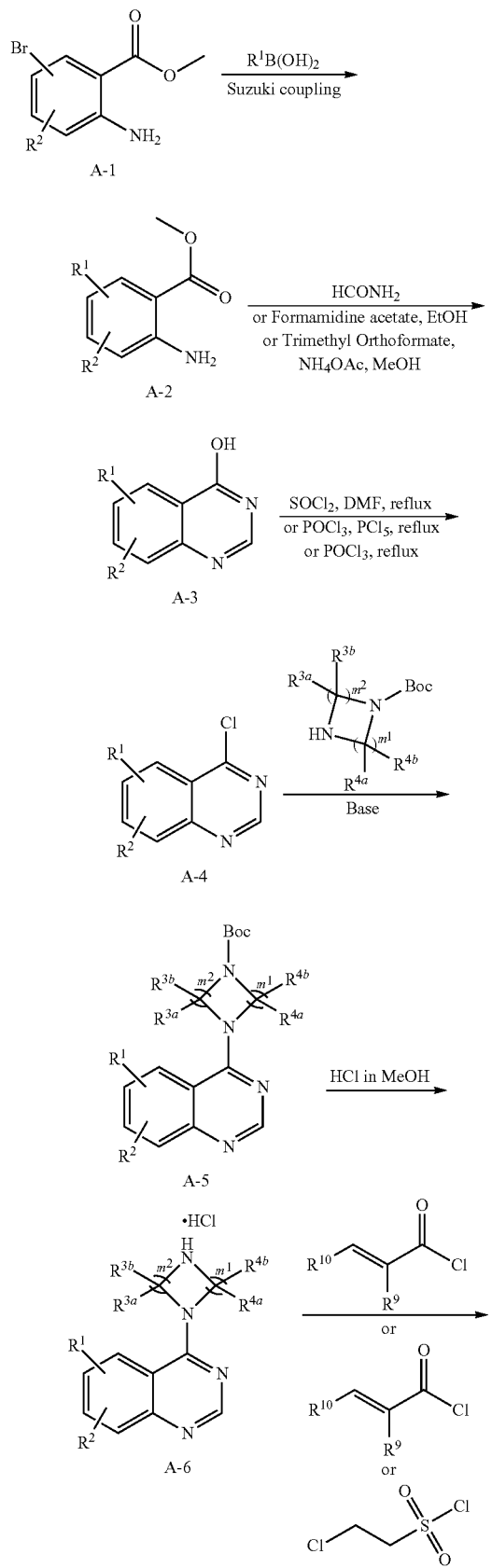

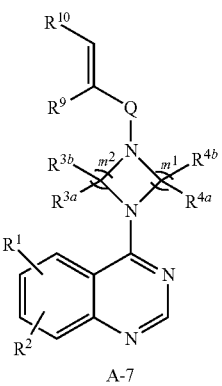

Embodiments of the compound of structure (I) (e.g., compound A-7) can be prepared according to General Reaction Scheme 1 ("Method A"), wherein $R^1$, $R^2$, $R^{3a}$, $R^{3b}R^{4a}$, $R^{4b}$, $R^9$, $R^{10}$, Q, $m^1$ and $m^2$ are as defined herein above. As shown in General Reaction Scheme 1, compounds of structure A-1 can be purchased from commercial sources or prepared according to methods familiar to one of ordinary skill in the art. Reaction of A-1 under Suzuki conditions yields A-2. Reaction of compounds of structure A-2 with formamide or other suitable reagents, such as formamidine acetate or trimethyl orthoformate, yields quinazolines of structure A-3. A-3 is chlorinated under appropriate conditions (e.g., $SOCl_2$, $POCl_3/PCl_5$ or $POCl_3$) to yield chloroqinazoline A-4. Reaction of A-4 with an appropriately protected heterocycle under basic conditions yields A-5. Appropriate protecting groups include butyloxycarbonyl (BOC) as depicted in General reaction Scheme 1, as well as other protecting groups known in the art. Deprotection of A-5 followed by acylation with an acid chloride (or sulfonyl chloride) or acid and appropriate activating reagents yields A-7.

General Reaction Scheme 2

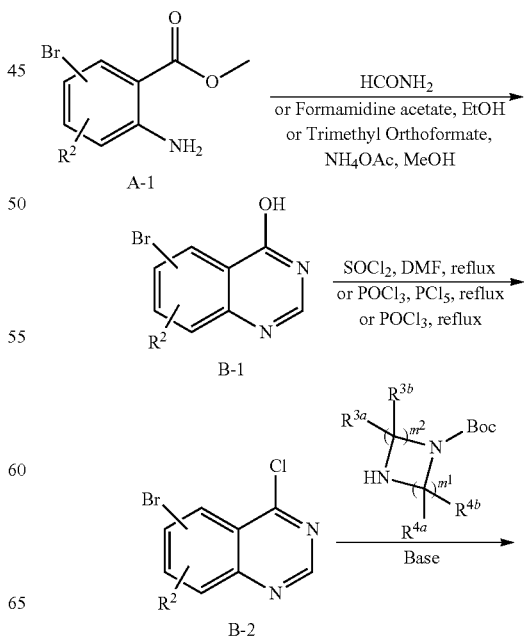

253
-continued

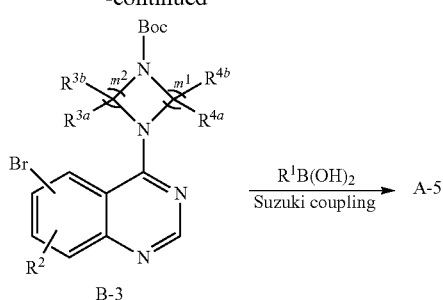
B-3

254
-continued

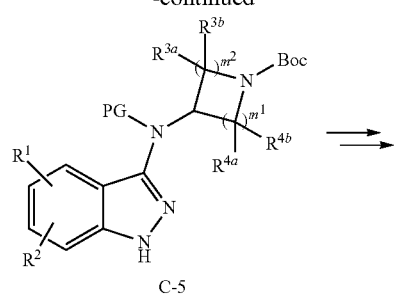
C-5

Alternatively, embodiments of the compound of structure (I) (e.g., compound A-7) can be prepared according to General Reaction Scheme 2 ("Method B"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Compounds of structure A-1 are prepared or purchased as described above. Treatment of A-1 with formamide or other suitable reagents, such as formamidine acetate or trimethyl orthoformate, yields quinazolines of structure B-1. B-1 can then be chlorinated to yield B-2 and reacted with an appropriately protected heterocycle under basic conditions to yield B-3 as described above for Method A. Suzuki coupling then yields A-5 which can be converted to A-7 as described in Method A above.

General Reaction Scheme 3

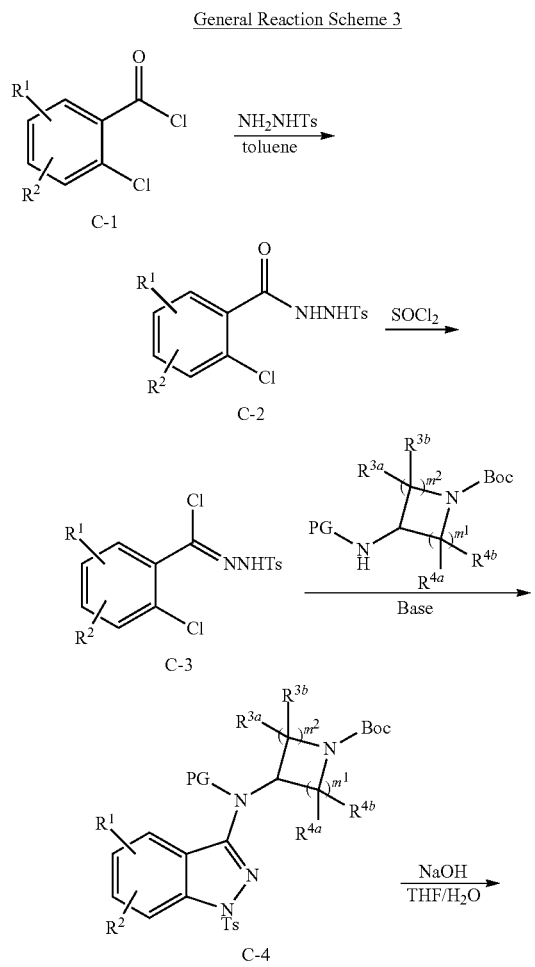

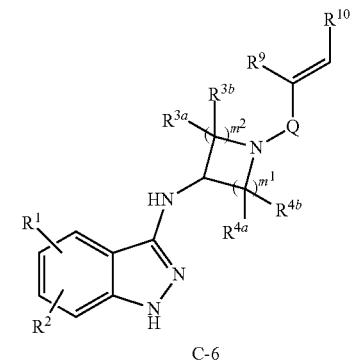
C-6

Other embodiments of the compound of structure (I) (e.g., compound C-6) can be prepared according to General Reaction Scheme 3 ("Method C"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 3, compounds of structure C-1, which can be purchased from commercial sources or prepared according to well-known procedures, are reacted with tosyl hydrazine to yield C-2. Chlorination of C-2 with an appropriate reagent(s), such as thionyl chloride, then yields C-3 which can be reacted under basic conditions with an appropriately protected heterocycle (PG=protecting group or $C_1$-$C_6$alkyl) to yield indazole C-4. The tosyl group is removed from C-4 by treatment with sodium hydroxide in THF/$H_2O$ to yield C-5. Removal of the nitrogen protecting group and acylation or thioacylation as described in Method A then yields the desired compound C-6.

General Reaction Scheme 4

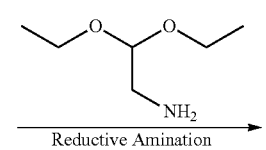
D-1

D-2

255
-continued

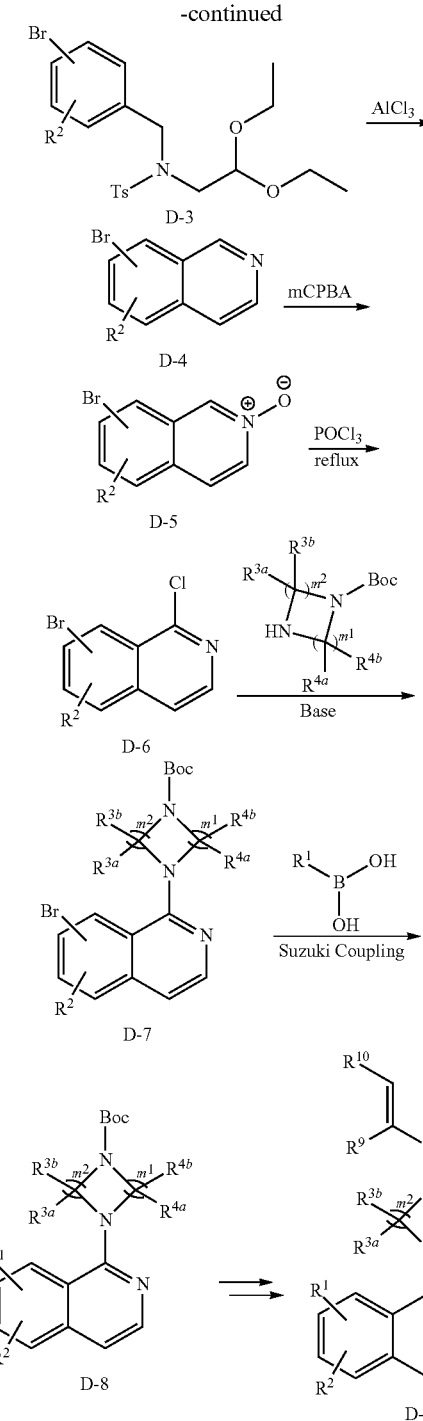

Other embodiments of the compound of structure (I) (e.g., compound D-9) can be prepared according to General Reaction Scheme 4 ("Method D"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 4, benzaldehyde D-1 is treated under reductive amination conditions to yield D-2. Formation of the tosyl-protected amine (D-3) followed by treatment with an appropriate Lewis acid (e.g., AlCl$_3$) yields isoquinoline D-4. Oxidation of D-4 with meta-chloroperbenzoic acid (mCPBA) yields D-5 which can be chlorinated by treatment with an appropriate reagent, such as POCl$_3$.

256

Chloride D-6 is then treated in a manner analogous to that described for Method B to yield D-9.

General Reaction Scheme 5

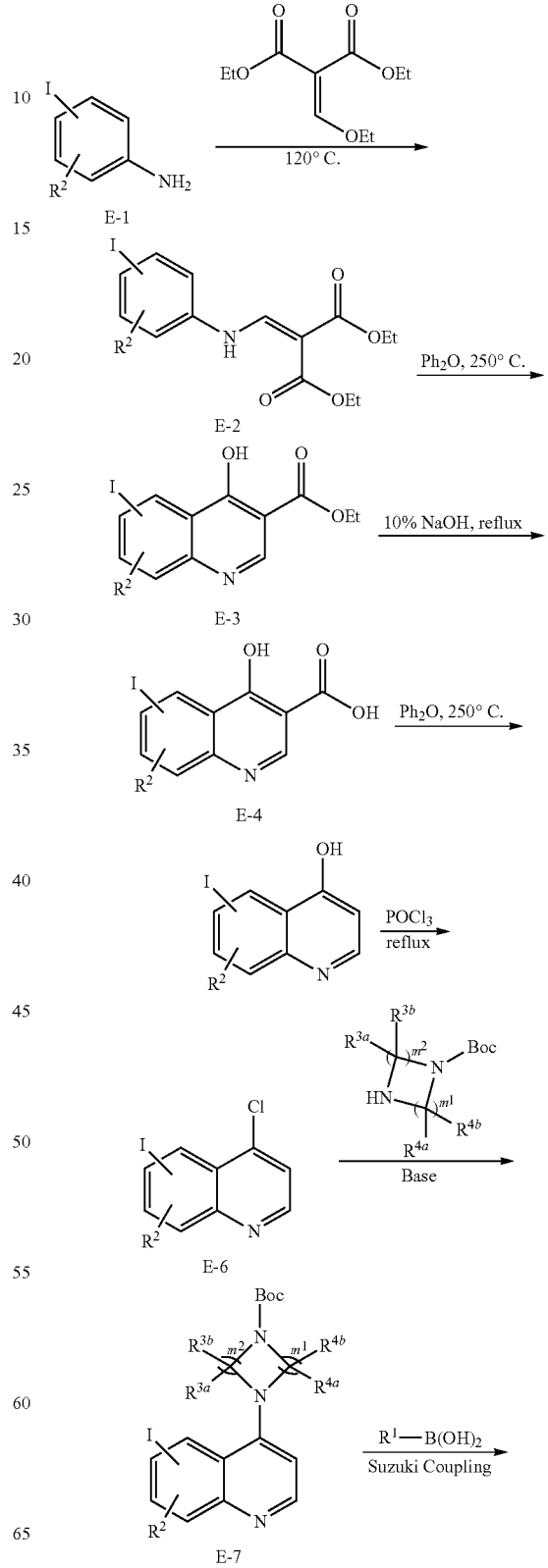

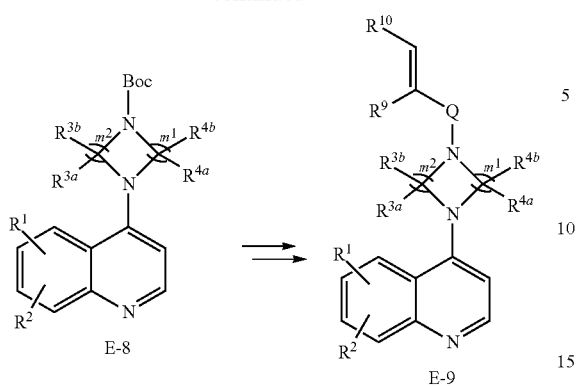

Other embodiments of the compound of structure (I) (e.g., compound E-9) can be prepared according to General Reaction Scheme 5 ("Method E"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 5, aniline E-1, which can be purchased from commercial sources or prepared via well-known procedures, can be reacted with diethyl 2-(ethoxymethylene)malonate to yield E-2. E-2 can then be cyclized by heating in an appropriate high-boiling solvent (e.g., $Ph_2O$) to yield quinolone E-3. Saponification of E-3 followed by decarboxylation yields E-4 and E-5, respectively. E-5 is then treated in a manner analogous to that described for Method B to yield E-9.

General Reaction Scheme 6

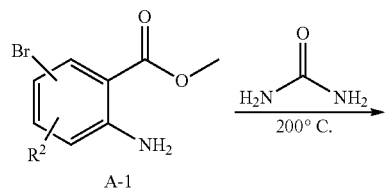

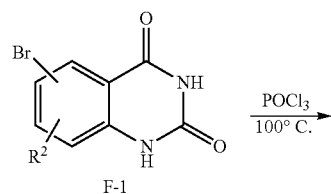

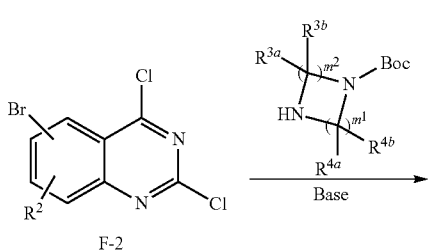

Other embodiments of the compound of structure (I) (e.g., compound F-6) can be prepared according to General Reaction Scheme 6 ("Method F"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 6, A-1 is cyclized to quinazolinedione F-1 by treatment with urea. Chlorination of F-1 by treatment with $POCl_3$ followed by reaction with a protected heterocycle yield F-2 and F-3, respectively. The $R^6$ substituent is installed by $S_NAr$ reaction of G-3 with LG-R6, wherein LG is an appropriate leaving group. For example, where $R^6$ is cyano or alkoxy, LG is sodium or another appropriate action. The general procedures described above with respect to Method B can then be employed to yield F-6.

General Reaction Scheme 7

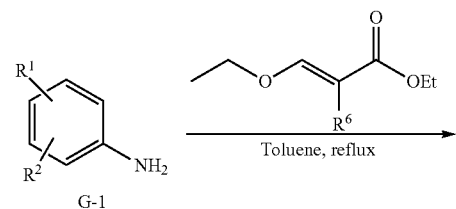

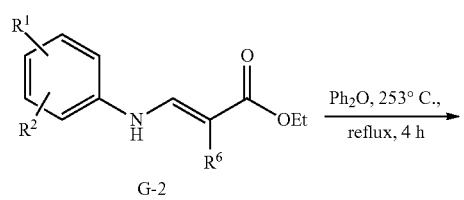

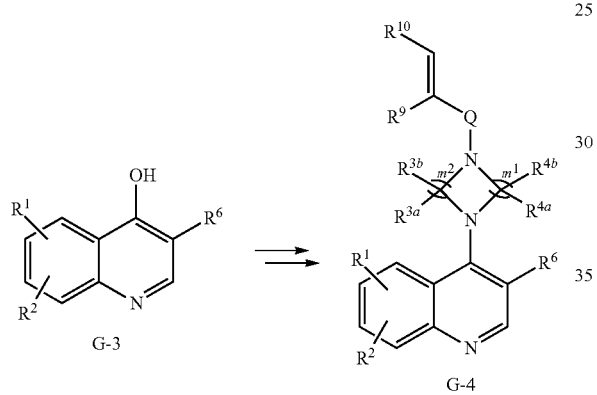

Other embodiments of the compound of structure (I) (e.g., compound G-4) can be prepared according to General Reaction Scheme 7 ("Method G"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 7, aniline E-1 is treated under Suzuki conditions to install the R-1 substituent. G-1 is then heated in toluene with an appropriately substituted unsaturated ester to yield G-2. Cyclization of G-2 to hydroxyquinoline G-3 is accomplished by heating in a high boiling solvent (e.g., Ph₂O) for an appropriate amount of time. Following the general procedures outlined in Method A then yields G-4.

General Reaction Scheme 8

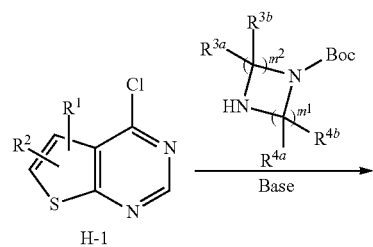

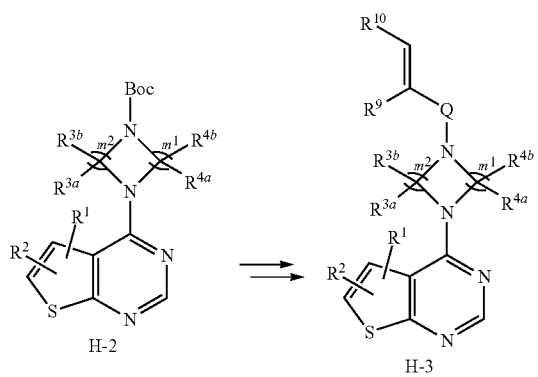

Other embodiments of the compound of structure (I) (e.g., compound H-3) can be prepared according to General Reaction Scheme 8 ("Method H"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 8, thienopyrimidine H-1 can be prepared according to well-known procedures or purchased from commercial sources. H-1 is treated with an appropriately protected heterocycle under basic conditions to yield H-2. Deprotection followed by acylation or thioacylation according to the procedures described above then yields H-3.

General Reaction Scheme 9

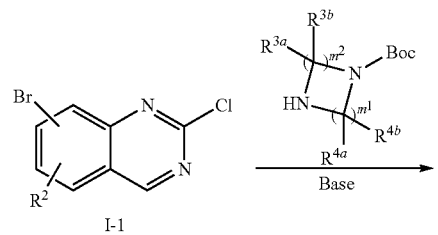

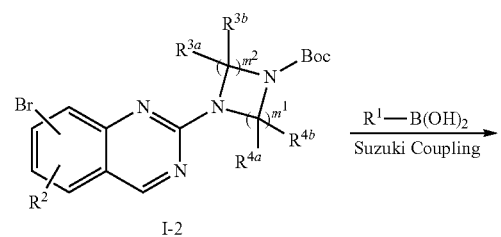

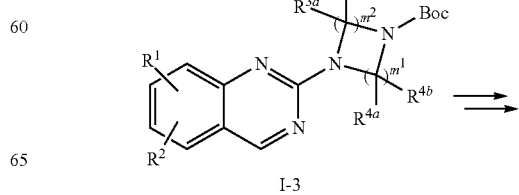

261

-continued

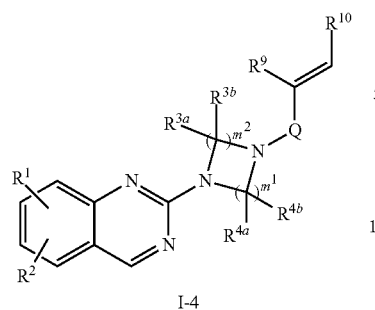

I-4

Other embodiments of the compound of structure (I) (e.g., compound I-4) can be prepared according to General Reaction Scheme 9 ("Method I"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 9, quinazoline I-1 can be prepared according to well-known procedures or purchased from commercial sources. I-1 is treated with an appropriately protected heterocycle under basic conditions to yield I-2. Suzuki reaction of I-2 with an appropriate reagent to install the $R^1$ moiety results in I-3. I-3 is then deprotected and acylated (or thioacylated) according to the procedures described above to yield I-4.

General Reaction Scheme 10

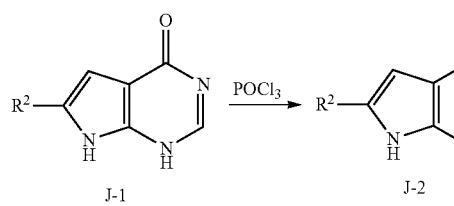

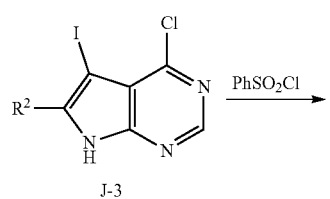

262

-continued

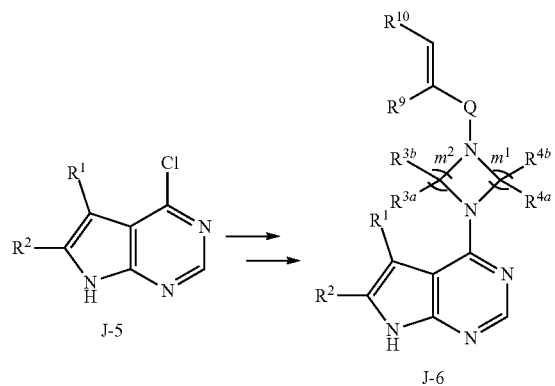

Other embodiments of the compound of structure (I) (e.g., compound J-6) can be prepared according to General Reaction Scheme 10 ("Method J"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 10, pyrrolopyrimidinone J-1 can be prepared according to well-known procedures or purchased from commercial sources. J-1 is chlorinated with an appropriate reagent (e.g., POCl3) to yield J-2 which is then iodinated with an appropriate reagent, such as N-iodosuccinimide (NIS) to yield J-3. Protection of J-3 followed by Suzuki reaction yields J-5. J-5 is then treated according to the procedures described above to yield J-6.

General Reaction Scheme 11

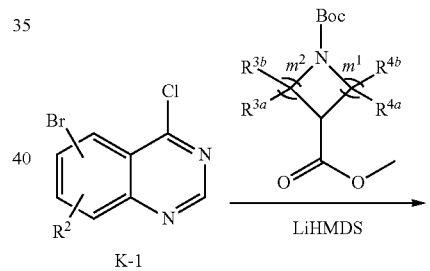

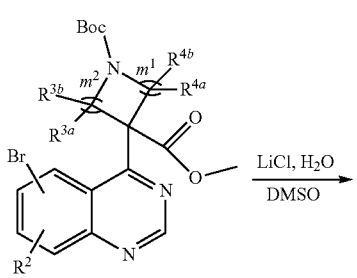

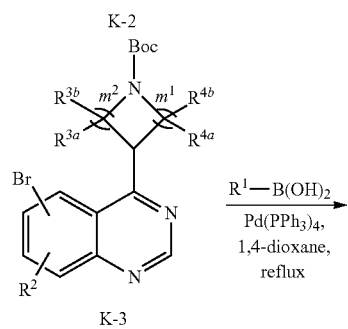

General Reaction Scheme 11 (continued)

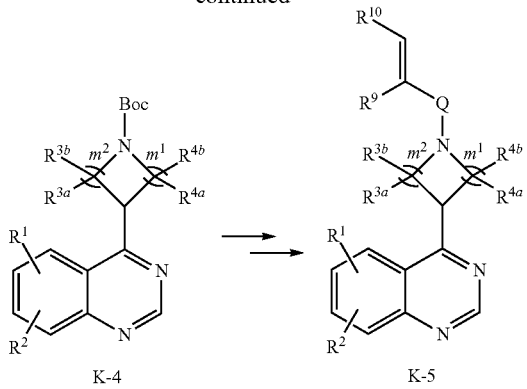

K-4 → K-5

Other embodiments of the compound of structure (I) (e.g., compound K-5) can be prepared according to General Reaction Scheme 11 ("Method K"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 11, quinazoline K-1 can be prepared according to well-known procedures or purchased from commercial sources. K-1 is reacted with an appropriate ester under basic conditions to form the requisite carbon-carbon bond. K-2 is then decarboxylated to yield K-3. Suzuki reaction, deprotection and acylation or thioacylation are then carried out as described in the above schemes to yield K-5.

General Reaction Scheme 12

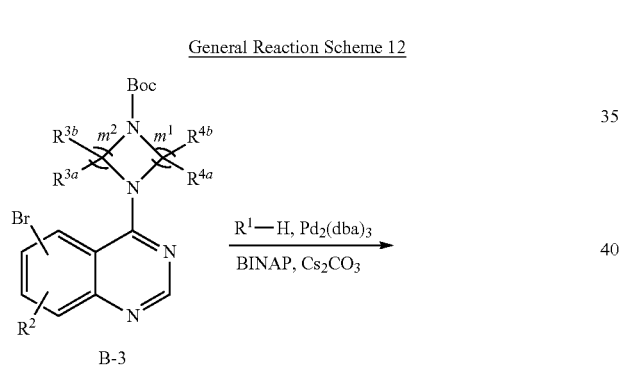

B-3 → L-1

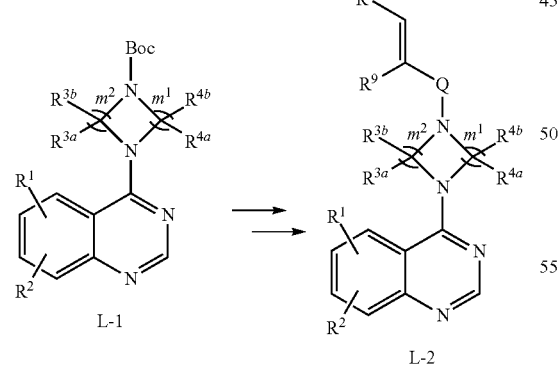

L-1 → L-2

Other embodiments of the compound of structure (I) (e.g., compound L-2) can be prepared according to General Reaction Scheme 12 ("Method L"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Specifically, compounds wherein $R^1$ is a N-heterocycle can be efficiently prepared according to Method L. Referring to General Reaction Scheme 12, compound B-3 is prepared according to Method B and treated under Buchwald conditions (where $R^1$—H is a N-heterocycle or alkylaminyl) to yield L-1. Methods for Buchwald reactions are well-known in the art. L-1 is then converted to L-2 according to the above general procedures.

General Reaction Scheme 13

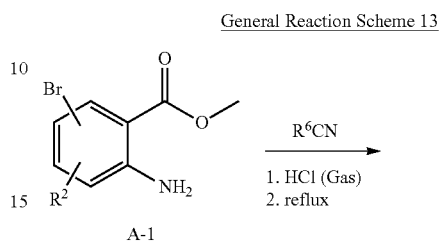

A-1

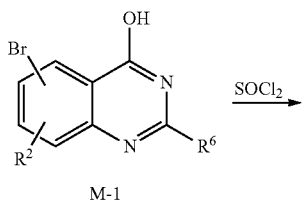

M-1

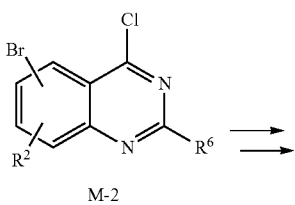

M-2

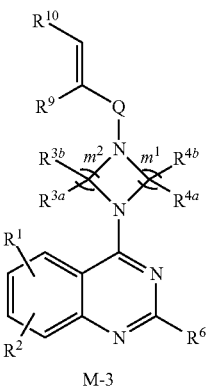

M-3

Other embodiments of the compound of structure (I) (e.g., compound M-3) can be prepared according to General Reaction Scheme 13 ("Method M"), wherein $R^1$, $R^2$, $R^{3a}$, $R^{3b}$, $R^{4a}$, $R^{4b}$, $R^6$, $R^9$, $R^{10}$, Q, $m^1$ and $m^2$ are as defined herein above. Referring to General Reaction Scheme 13, compound A-1 is reacted an appropriate nitrile (R6CN) to form compound M-1. In this regard, $R^6$ may be any of the $R^6$ moieties described herein, for example alkyl. M-1 is chlorinated by reaction with an appropriate reagent such as thionyl chloride. Compound M-3 is then prepared according to the general procedures outlined herein, for example the procedures of General Reaction Scheme 2.

General Reaction Scheme 14

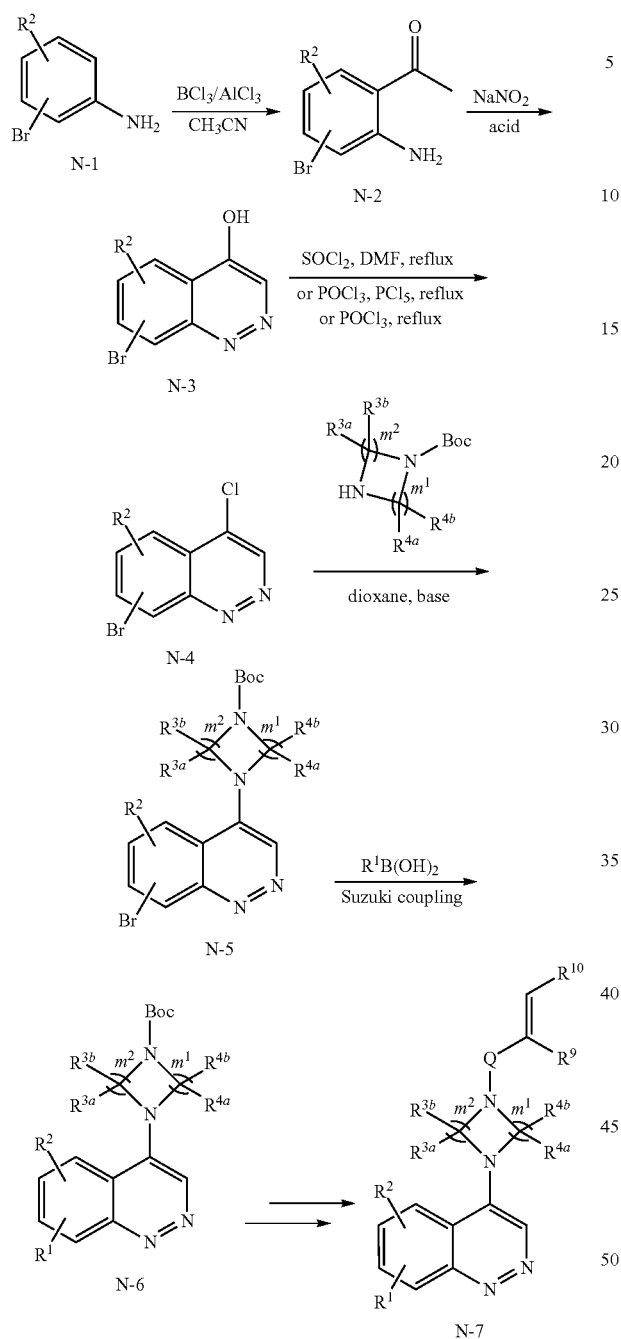

protected heterocycle under basic conditions yields N-5. Appropriate protecting groups include butyloxycarbonyl (BOC) as depicted in General reaction Scheme 1, as well as other protecting groups known in the art. Suzuki reaction of N-5 with an appropriate reagent to install the $R^1$ moiety results in N-6. Deprotection of N-6 followed by acylation with an acid chloride (or sulfonyl chloride) or acid and appropriate activating reagents yields N-7.

General Reaction Scheme 15

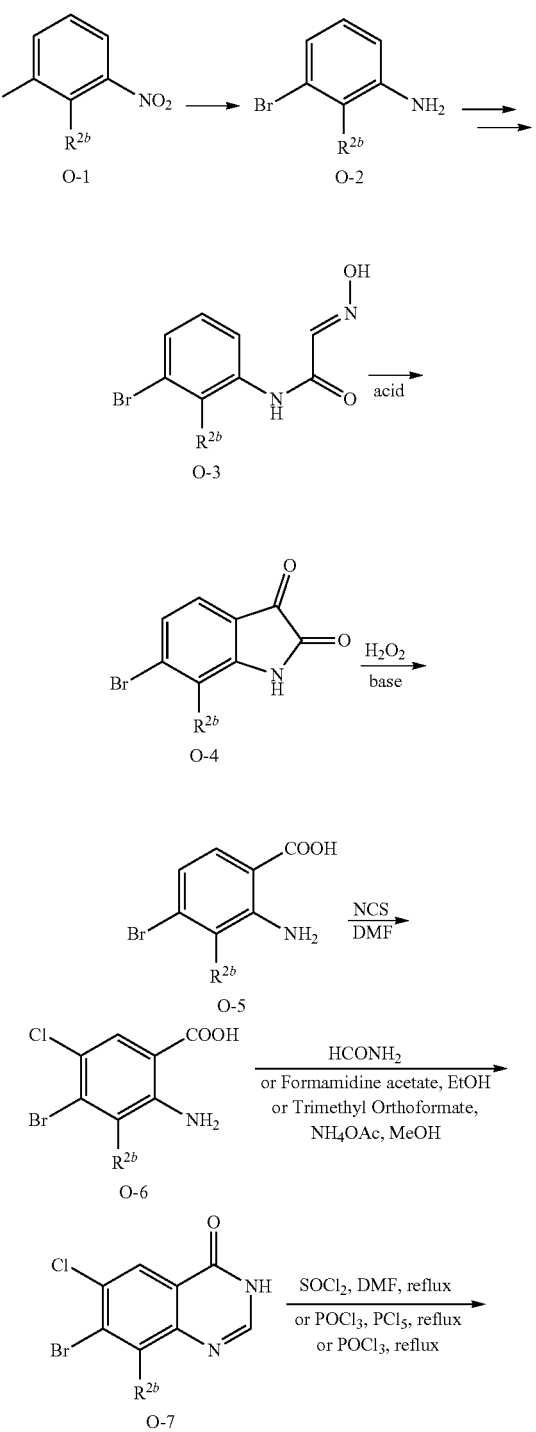

Embodiments of the compound of structure (I) (e.g., compound N-7) can be prepared according to General Reaction Scheme 14 ("Method N"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 14, compounds of structure N-1 can be purchased from commercial sources or prepared according to methods familiar to one of ordinary skill in the art. Compound N-1 is reacted with methylnitrite to form compound N-2. Reaction of N-2 with sodium nitrite under acidic conditions yields cinnolines of structure N-3. N-3 is chlorinated under appropriate conditions (e.g., $SOCl_2$, $POCl_3/PCl_5$ or $POCl_3$) to yield the chlorocinnoline N-4. Reaction of N-4 with an appropriately succinimide to yield O-6. Reaction of O-6 with formamide or other suitable reagents such as formamidine acetate or trimethyl orthoformate yields the quinazolin-4(3H)-one, O-7. O-7 is chlorinated under appropriate conditions (e.g., $SOCl_2$, $POCl_3/PCl_5$ or $POCl_3$) to yield the chloroquinazoline, O-8. Reaction of O-8 with an appropriately protected heterocycle under basic conditions yields O-9. Appropriate protecting groups include butyloxycarbonyl (BOC) as depicted in General reaction Scheme 1, as well as other protecting groups known in the art. Suzuki reaction of O-9 with an appropriate reagent to install the $R^1$ moiety results in O-10. Deprotection of O-10 followed by acylation with an acid chloride (or sulfonyl chloride) or acid and appropriate activating reagents yields O-11.

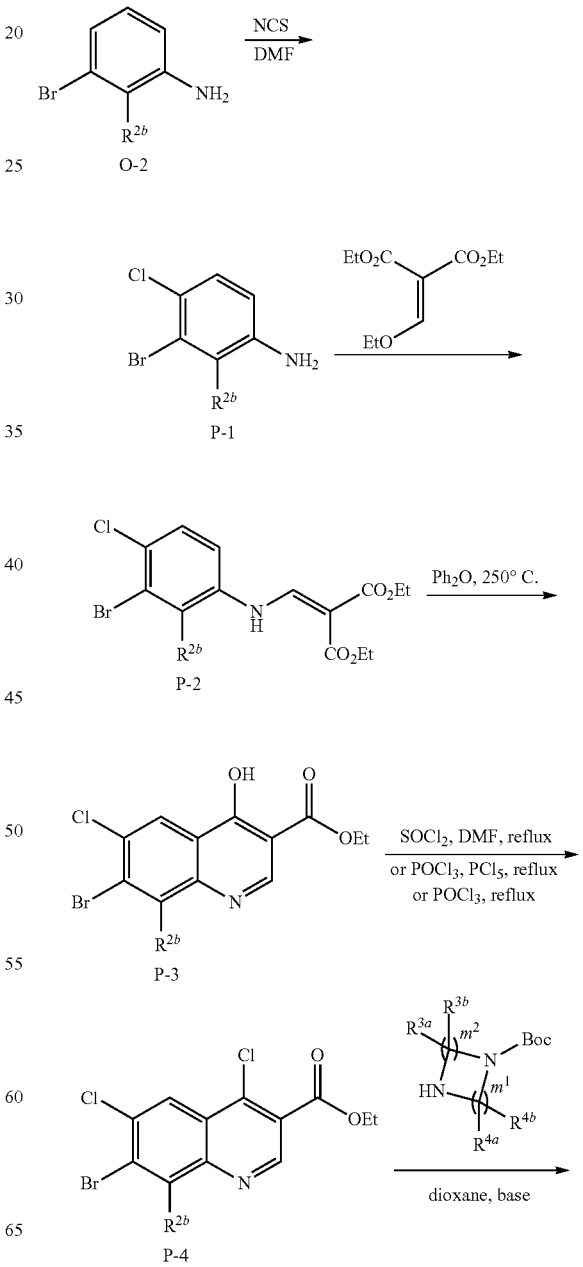

Embodiments of the compound of structure (I) (e.g., compound O-11) can be prepared according to General Reaction Scheme 15 ("Method O"), wherein $R^1$, $R^{2b}$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 15, compounds of structure O-1 can be purchased from commercial sources or prepared according to methods familiar to one of ordinary skill in the art. Compound O-1 is reduced to form compound O-2. Reaction of O-2 with 2,2,2-trichloroethane-1,1-diol under acidic conditions, then hydroxylamine hydrochloride, yields O-3. O-3 is cyclized in the presence of acid to yield O-4. O-4 is reacted in the presence $H_2O_2$ under basic conditions to yield O-5. O-5 is chlorinated using N-chloro-

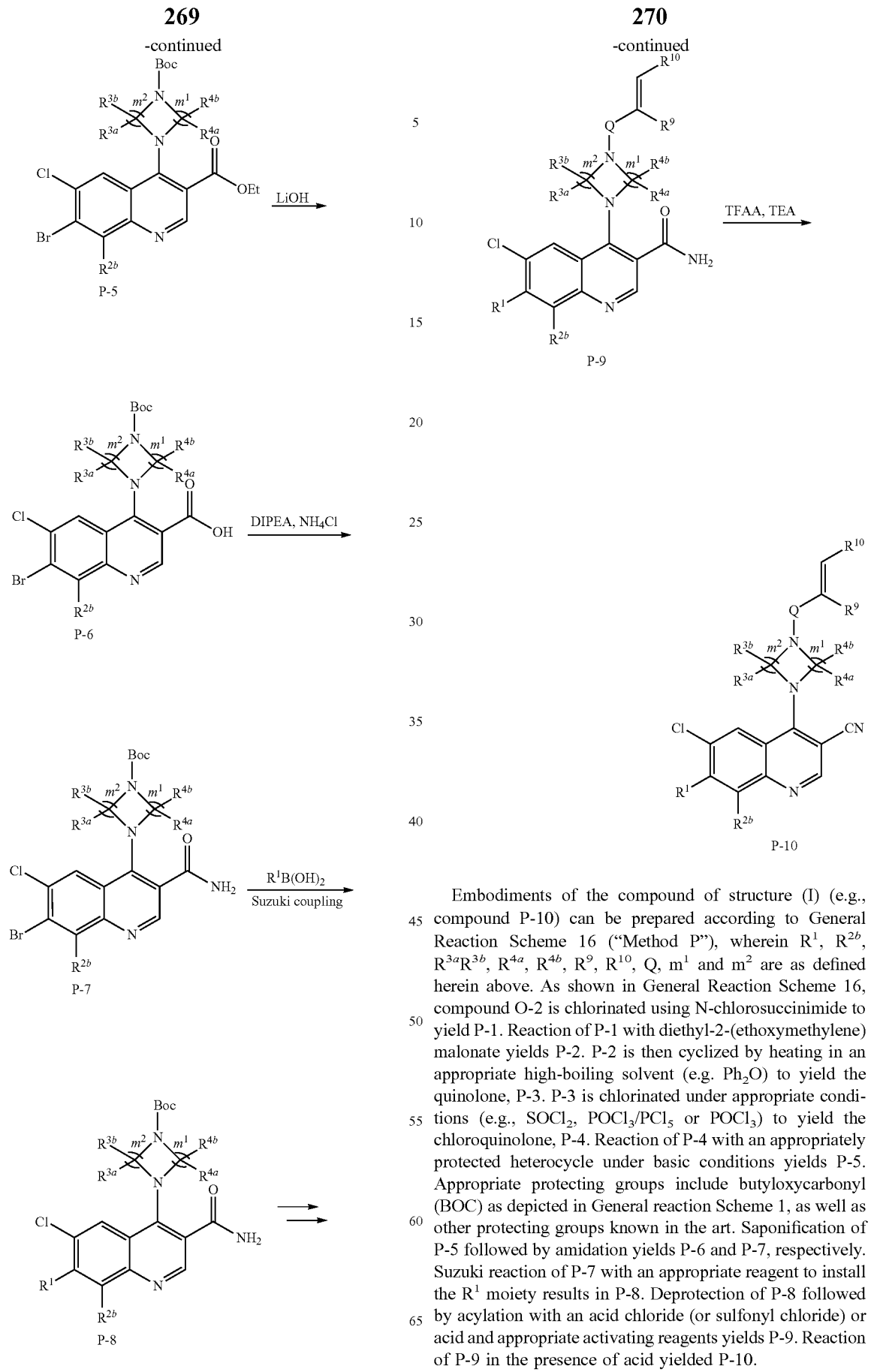

Embodiments of the compound of structure (I) (e.g., compound P-10) can be prepared according to General Reaction Scheme 16 ("Method P"), wherein $R^1$, $R^{2b}$, $R^{3a}R^{3b}$, $R^{4a}$, $R^{4b}$, $R^9$, $R^{10}$, Q, $m^1$ and $m^2$ are as defined herein above. As shown in General Reaction Scheme 16, compound O-2 is chlorinated using N-chlorosuccinimide to yield P-1. Reaction of P-1 with diethyl-2-(ethoxymethylene) malonate yields P-2. P-2 is then cyclized by heating in an appropriate high-boiling solvent (e.g. $Ph_2O$) to yield the quinolone, P-3. P-3 is chlorinated under appropriate conditions (e.g., $SOCl_2$, $POCl_3/PCl_5$ or $POCl_3$) to yield the chloroquinolone, P-4. Reaction of P-4 with an appropriately protected heterocycle under basic conditions yields P-5. Appropriate protecting groups include butyloxycarbonyl (BOC) as depicted in General reaction Scheme 1, as well as other protecting groups known in the art. Saponification of P-5 followed by amidation yields P-6 and P-7, respectively. Suzuki reaction of P-7 with an appropriate reagent to install the $R^1$ moiety results in P-8. Deprotection of P-8 followed by acylation with an acid chloride (or sulfonyl chloride) or acid and appropriate activating reagents yields P-9. Reaction of P-9 in the presence of acid yielded P-10.

General Reaction Scheme 17

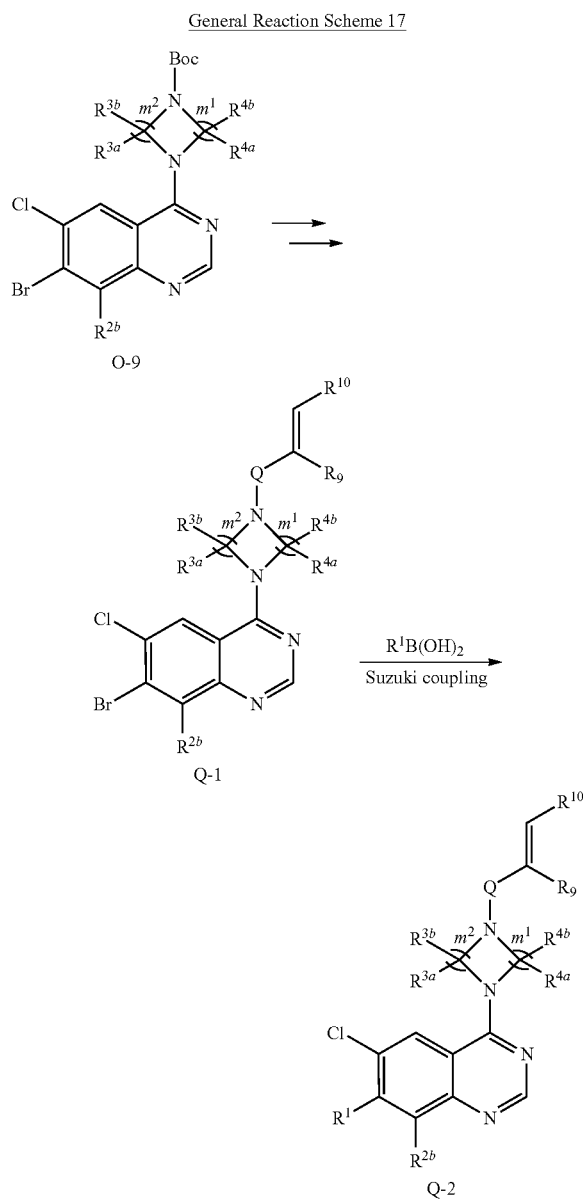

Embodiments of the compound of structure (I) (e.g., compound Q-2) can be prepared according to General Reaction Scheme 16 ("Method Q"), wherein $R^1$, $R^{2b}$, $R^{3a}R^{3b}$, $R^{4a}$, $R^{4b}$, $R^9$, $R^{10}$, Q, $m^1$ and $m^2$ are as defined herein above. As shown in General Reaction Scheme 17, deprotection of compound O-9 followed by acylation with an acid chloride (or sulfonyl chloride) or acid and appropriate activating reagents yields Q-1. Suzuki reaction of Q-1 with an appropriate reagent to install the $R^1$ moiety results in Q-2.

Additional General synthetic methods are provided in the Examples. It will be apparrent to one of ordinary skill in the art that all compounds of structure (I) can be prepared according to one or more of the methods described herein or otherwise known in the art. It will also be apparent that in some instances it will be necessary to use a differenrrently substituted starting material and/or protecting groups to arrive at the desired compound when following the general procedures described herein. Various substituents may also be added at various points in the synthetic scheme to prepare the desired compound.

Further, one skilled in the art will recognize that certain modifications to the above schemes and those provided in the examples are possible to prepare different embodiments of compounds of structure (I). For example, for ease of illustration, most of the general procedures depict preparation of compounds of structure (I) wherein $L^1$ is a bond. However, one of ordinary skill in the art will readily recognize that compounds wherein $L^1$ is $NR^7$ can be prepared by substituting a heterocycle having the following structure (see e.g., Method C):

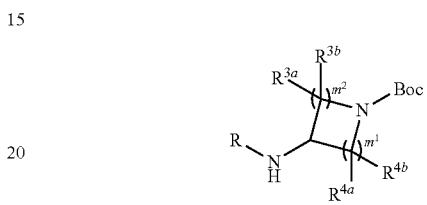

where R is H, a protecting group or $C_1$-$C_6$alkyl.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present invention provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK level; and/or (e) a decrease in binding of RAS complex to downstream signaling molecules including but not limited to Raf Kits and commercially available assays can be utilized for determining one or more of the above.

The invention also provides methods of using the compounds or pharmaceutical compositions of the present invention to treat disease conditions, including but not limited to conditions implicated by G12C KRAS, HRAS or NRAS mutation, G12C HRAS mutation and/or G12C NRAS mutation (e.g., cancer).

In some embodiments, a method for treatment of cancer is provided, the method comprising administering an effective amount of any of the foregoing pharmaceutical compositions comprising a compound of structure (I) to a subject in need thereof. In some embodiments, the cancer is mediated by a KRAS, HRAS or NRAS G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound of structure (I) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymeRASe chain reaction-restriction fragment length polymorphism (PCR-RFLP) assays, polymeRASe chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the invention include subjects that have been diagnosed as having a non-cancerous hyperproliferative disorder such as benign hyperplasia of the skin (e. g., psoriasis), restenosis, or prostate (e. g., benign prostatic hypertrophy (BPH)).

The invention further provides methods of modulating a G12C Mutant KRAS, HRAS or NRAS protein activity by contacting the protein with an effective amount of a compound of the invention. Modulation can be inhibiting or activating protein activity. In some embodiments, the invention provides methods of inhibiting protein activity by contacting the G12C Mutant KRAS, HRAS or NRAS protein with an effective amount of a compound of the invention in solution. In some embodiments, the invention provides methods of inhibiting the G12C Mutant KRAS, HRAS or NRAS protein activity by contacting a cell, tissue, organ that express the protein of interest. In some embodiments, the invention provides methods of inhibiting protein activity in subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting KRAS, HRAS or NRAS G12C activity in a cell by contacting said cell with an amount of a compound of the invention sufficient to inhibit the activity of KRAS, HRAS or NRAS G12C in said cell. In some embodiments, the invention provides methods of inhibiting KRAS, HRAS or NRAS G12C activity in a tissue by contacting said tissue with an amount of a compound of the invention sufficient to inhibit the activity of KRAS, HRAS or NRAS G12C in said tissue. In some embodiments, the invention provides methods of inhibiting KRAS, HRAS or NRAS G12C activity in an organism by contacting said organism with an amount of a compound of the invention sufficient to inhibit the activity of KRAS, HRAS or NRAS G12C in said organism. In some embodiments, the invention provides methods of inhibiting KRAS, HRAS or NRAS G12C activity in an animal by contacting said animal with an amount of a compound of the invention sufficient to inhibit the activity of KRAS, HRAS or NRAS G12C in said animal. In some embodiments, the invention provides methods of inhibiting KRAS, HRAS or NRAS G12C activity in a mammal by contacting said mammal with an amount of a compound of the invention sufficient to inhibit the activity of KRAS, HRAS or NRAS G12C in said mammal. In some embodiments, the invention provides methods of inhibiting KRAS, HRAS or NRAS G12C activity in a human by contacting said human with an amount of a compound of the invention sufficient to inhibit the activity of KRAS, HRAS or NRAS G12C in said human. The present invention provides methods of treating a disease mediated by KRAS, HRAS or NRAS G12C activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, tautomer, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomeRASe inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments are used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesteRASe agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobac-* terium avium complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, tRAStuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

The following examples are provided for exemplary purposes. Other compounds of structure (I) were prepared according to the following general procedures as indicated in Table 1.

Example 1

Synthesis of 1-(4-(7-chloro-6-(2-chlorophenyl)quinazolin-4-yl)piperazin-1-yl)prop-2-en-1-one (1)

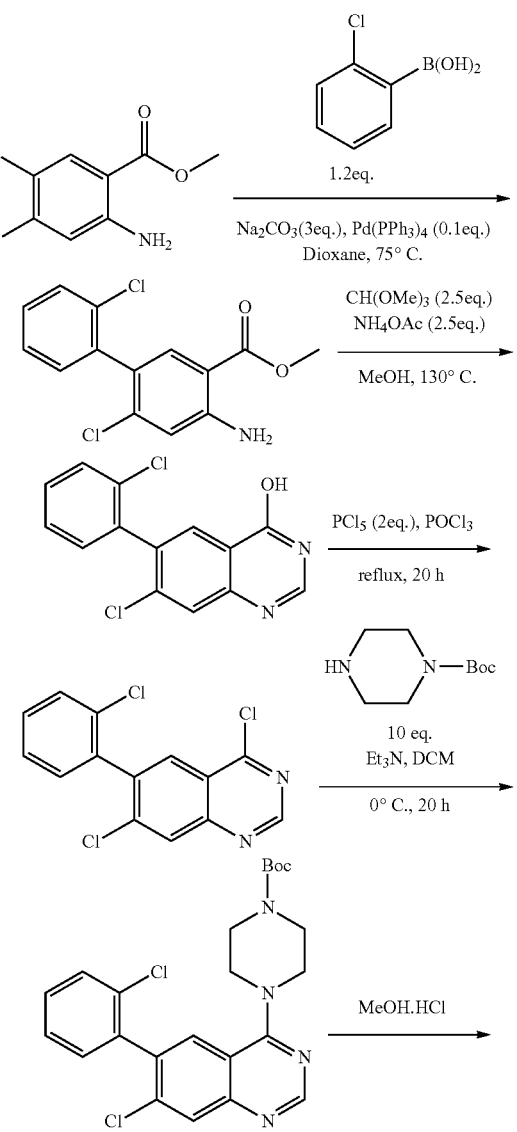

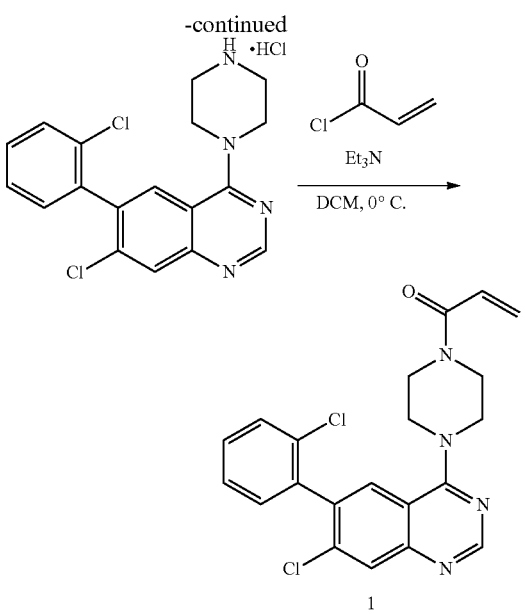

Compound 1 was prepared according to Method A as described below:

Methyl 2-amino-5-(2-chlorophenyl)-4-chlorobenzoate

A mixture of methyl 2-amino-5-bromo-4-chlorobenzoate (1.2 g, 4.54 mmol), 2-chlorophenylboronic acid (0.85 g, 5.44 mmol), $Na_2CO_3$ (1.44 g, 13.61 mmol), and $Pd(PPh_3)_4$ (0.52 g, 0.45 mmol) in 1,4-dioxane (30 mL) and water (6 mL) was stirred at 75° C. under argon for 16 h. The mixture was allowed to cool to room temperature (RT), and concentrated in vacuo. The residue was purified by flash column chromatography on silica gel (ethyl acetate/petroleum=8:1) to afford the desired product (1.22 g, 91% yield) as a yellow solid.

7-Chloro-6-(2-chlorophenyl)quinazolin-4-ol

A mixture of methyl 2-amino-5-(2-chlorophenyl)-4-chlorobenzoate (342 mg, 1.16 mmol), $CH(OMe)_3$ (306 mg, 2.89 mmol), and $NH_4OAc$ (223 mg, 2.89 mmol) in MeOH (1 mL) in a sealed tube was stirred at 130° C. for 4.5 h. The mixture was allowed to cool to RT, and concentrated in vacuo. The residue was purified by flash column chromatography on silica gel eluting with DCM and MeOH (40:1) to yield the desired product (277 mg, 82% yield) as a white solid. ESI-MS m/z: 289.2 [M−H]⁻.

4,7-Dichloro-6-(2-chlorophenyl)quinazoline

A mixture of 7-chloro-6-(2-chlorophenyl)quinazolin-4-ol (277 mg, 0.95 mmol), $PCl_5$ (397 mg, 1.90 mmol) and $POCl_3$ (16 mL) was stirred at reflux for 20 h. The mixture was allowed to cool to RT, and then concentrated in vacuo to yield the crude product (1.19 g) as a dark oil which was used directly in next step without further purification.

tert-Butyl-4-(7-chloro-6-(2-chlorophenyl)quinazolin-4-yl)piperazine-1-carboxylate The above obtained crude 4,7-dichloro-6-(2-chlorophenyl)quinazoline (1.19 g) was added to the mixture of tert-butyl piperazine-1-carboxylate (5 g, 26.9 mmol) and $Et_3N$ (7.76 g, 76.8 mmol) in DCM (200 mL) at 0° C. and the resulting mixture was stirred at the same temperature for 1 h. The mixture was poured into water (500 mL) and brine (100 mL), and then dichloromethane (DCM) (200 mL) was added. The mixture was filtered through filter paper. The organic layer was separated, dried over $Na_2SO_4$ and concentrated in vacuo. The residue was purified by flash column chromatography on silica gel eluting with DCM and MeOH (30:1) to yield the desired product (184 mg, 42% yield, 2 steps) as a light yellow oil. ESI-MS m/z: 459.3 [M+H]⁺.

1-(4-(7-Chloro-6-(2-chlorophenyl)quinazolin-4-yl)piperazin-1-yl)prop-2-en-1-one

A mixture of tertbutyl-4-(7-chloro-6-(2-chlorophenyl)quinazolin-4-yl)piperazine-1-carboxylate (184 mg, 0.40 mmol) and HCl in MeOH (20 mL) was stirred at RT for 1 h. The mixture was concentrated in vacuo to yield the crude product (176 mg) as a yellow solid which was used directly in next step without further purification.

1-(4-(7-Chloro-6-(2-chlorophenyl)quinazolin-4-yl)piperazin-1-yl)prop-2-en-1-one (1)

The above obtained crude 1-(4-(7-chloro-6-(2-chlorophenyl)quinazolin-4-yl)piperazin-1-yl)prop-2-en-1-one (17 6 mg) was dissolved in $Et_3N$ (450 mg, 4.45 mmol) and DCM (30 mL) and cooled to 0° C., acryloyl chloride (44 mg, 0.49 mmol) in DCM (50 mL) was added to the mixture. The resulting mixture was allowed to warm to RT and stirred at RT for 1.5 h. The reaction mixture was quenched with saturated $NaHCO_3$ aqueous solution, and then extracted with ethyl acetate. The organic layer was washed with saturated $NaHCO_3$ solution and brine, dried over $Na_2SO_4$ and concentrated in vacuo. The residue was purified by flash column chromatography on silica gel eluting with DCM and MeOH (30:1) to yield the desired product (82 mg, 50% yield, 2 steps) as a yellow solid. ¹H NMR (400 MHz, DMSO-d6) δ: 8.75 (s, 1H), 8.03 (s, 1H), 7.96 (s, 1H), 7.62-7.49 (m, 4H), 6.81 (dd, J=10.4, 16.4 Hz, 1H), 6.15 (dd, J=16.4, 2.4 Hz, 1H), 5.71 (dd, J=10.4, 2.0 Hz, 1H), 3.87-3.72 (m, 8H). ESI-MS m/z: 413.2 [M+H]⁺.

Example 2

Synthesis of 1-(4-(7-chloro-6-phenylquinazolin-4-yl)piperazin-1-yl)prop-2-en-1-one (18)

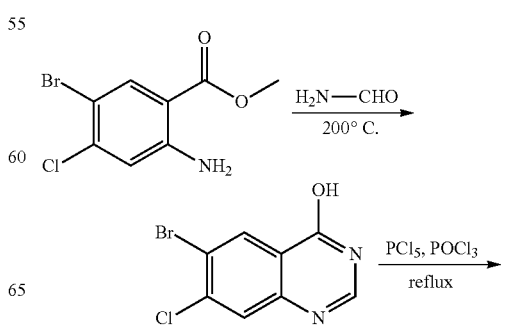

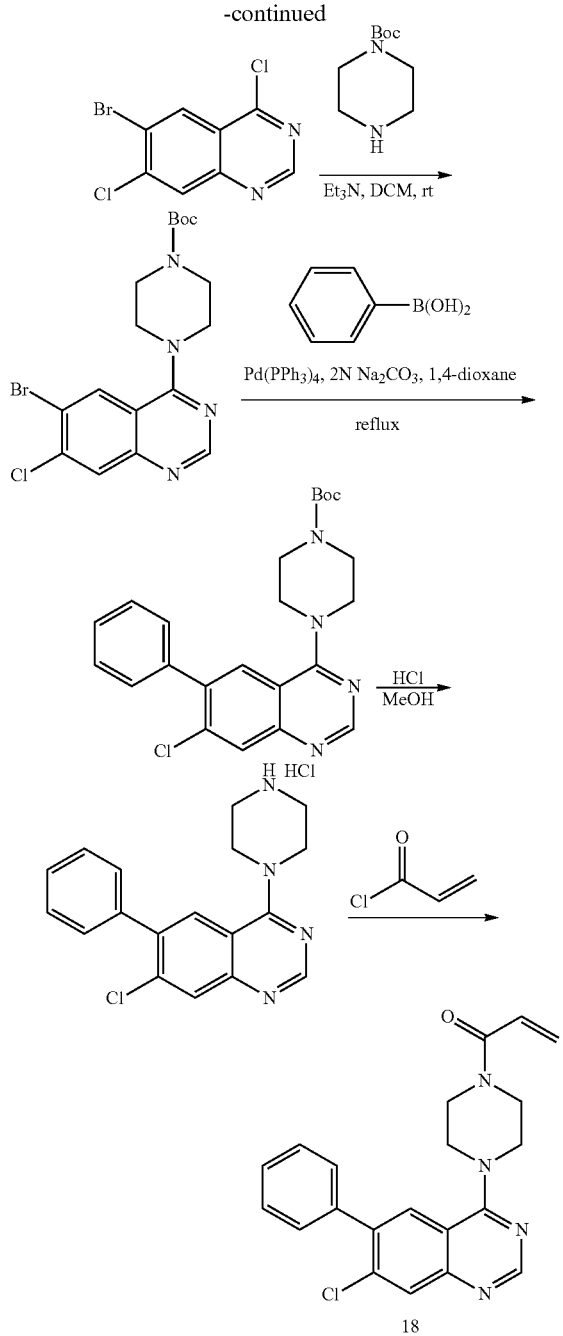

was stirred at reflux for 16 h. The mixture was allowed to cool to RT and then concentrated in vacuo to yield the desired product as a dark oil which was used directly in next step without further purification.

tert-Butyl 4-(6-bromo-7-chloroquinazolin-4-yl)piperazine-1-carboxylate

The above obtained crude 6-bromo-4,7-dichloroquinazoline was added to the mixture of tert-butyl piperazine-1-carboxylate (4.82 g, 25.9 mmol) and Et$_3$N (2.62 g, 25.9 mmol) in DCM (70 mL). The resulting mixture was stirred at RT for 2 h and then was quenched with saturated NaHCO$_3$ aqueous solution. The mixture was extracted with DCM, washed with saturated NaHCO$_3$ aqueous solution and brine, dried over Na$_2$SO$_4$ and concentrated in vacuo. The residue was purified by flash column chromatography on silica gel eluting with ethyl acetate and petroleum ether (4:1) to yield the desired product (631 mg, 57% yield, 2 steps) as a yellow solid. ESI-MS m/z: 429.3 [M+H]$^+$.

tert-Butyl 4-(7-chloro-6-phenylquinazolin-4-yl)piperazine-1-carboxylate

A mixture of tert-butyl 4-(6-bromo-7-chloroquinazolin-4-yl)piperazine-1-carboxylate (200 mg, 0.47 mmol), phenylboronic acid (115 mg, 0.94 mmol), Na$_2$CO$_3$ solution (2.0 M, 0.71 mL, 1.41 mmol), Pd(PPh$_3$)$_4$ (109 g, 0.094 mmol) in 1,4-dioxane (10 mL) was stirred at reflux under argon for 16 h. The mixture was allowed to cool to RT, diluted with ethyl acetate, and then washed with H$_2$O and brine. The organic layer was dried over Na$_2$SO$_4$ and concentrated in vacuo. The residue was purified by flash column chromatography on silica gel eluting with ethyl acetate and petroleum ether (1:4) to yield the desired product (120 mg, 60% yield) as a yellow oil. ESI-MS m/z: 425.4 [M+H]$^+$.

1-(4-(7-Chloro-6-phenylquinazolin-4-yl)piperazin-1-yl)prop-2-en-1-one

The title compound was prepared from tert-butyl 4-(7-chloro-6-phenylquinazolin-4-yl)piperazine-1-carboxylate in two steps following the procedure described in Example 1. $^1$H NMR (400 MHz, CDCl$_3$) δ: 8.74 (s, 1H), 8.15 (s, 1H), 7.83 (s, 1H), 7.50-7.45 (m, 5H), 6.58 (dd, J=16.8, 10.4 Hz, 1H), 6.36 (dd, J=16.4, 1.6 Hz, 1H), 5.77 (dd, J=10.4, 2.0 Hz, 1H), 3.92-3.81 (m, 8H). ESI-MS m/z: 379.3 [M+H]$^+$.

Example 3

Synthesis of 1-(4-(6-chloro-5-(2-chlorophenyl)-1H-indazol-3-ylamino)piperidin-1-yl)prop-2-en-1-one (31)

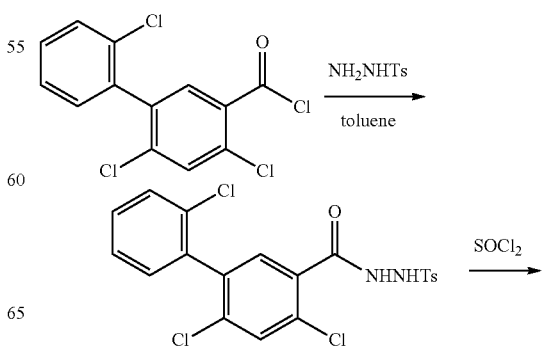

Compound 18 was prepared according to Method B as described below:

6-Bromo-7-chloroquinazolin-4-ol

A mixture of methyl 2-amino-5-bromo-4-chlorobenzoate (1 g, 3.95 mmol) and NH$_2$CHO (20 mL) was stirred at 200° C. for 3 h. The mixture was allowed to cool to RT and quenched with water. The solid precipitate was collected by filtration and dried in vacuo to yield the desired product (669 mg, 66% yield) as a brown solid.

6-Bromo-4,7-dichloroquinazoline

A mixture of 6-bromo-7-chloroquinazolin-4-ol (669 mg, 2.59 mmol), PCl$_5$ (1.6 g, 7.78 mmol) and POCl$_3$ (15 mL)

297

-continued

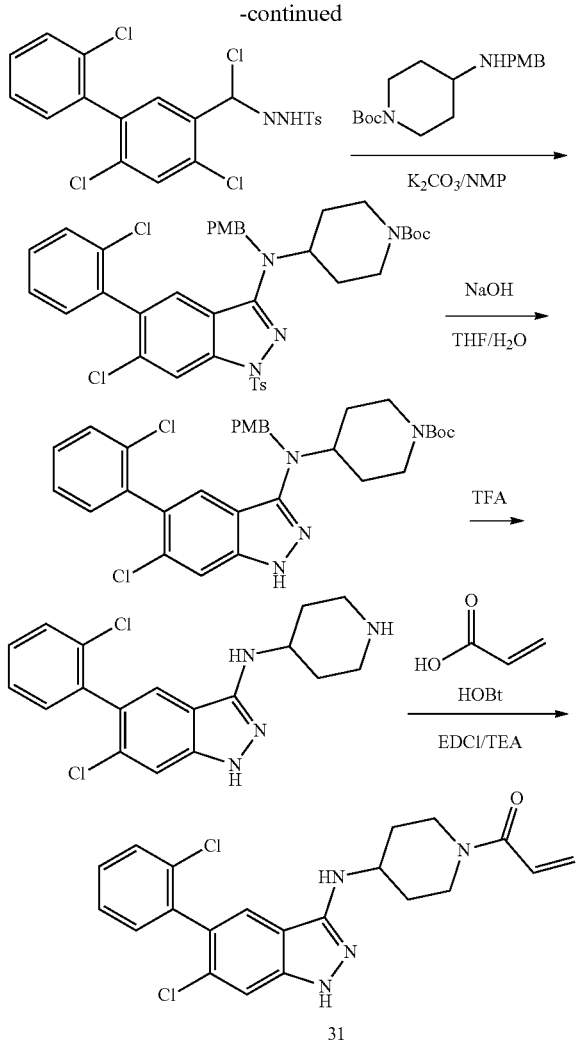

31

Compound 31 was prepared according to Method C as described below:

4-Methyl-N'-(2',4,6-trichlorobiphenylcarbonyl)benzenesulfonohydrazide

To a stirred solution of 2',4,6-trichlorobiphenyl-3-carbonyl chloride (5.5 g) in toluene at RT, NH$_2$NHTs (3.8 g, 20.3 mmol) was added and the resulting mixture was stirred at 75° C. overnight. The mixture was allowed to cool to RT. The solid was collected by filtration and dried in vacuo to afford the desired product (6 g, 75% yield) as a white solid.

2',4,6-Trichloro-'-tosylbiphenyl-3-carbohydrazonoyl chloride

A solution of 4-methyl-'-(2',4,6-trichlorobiphenylcarbonyl)benzenesulfonohydrazide (2.3 g, 4.5 mmol) in SOCl$_2$ (5.8 g, 45 mmol) was stirred at 75° C. for 4 h. The mixture was allowed to cool to RT, and then petroleum ether was added. The resulting mixture was stirred at 0° C. for 1 h. The precipitate was collected by filtration and dried in vacuo to afford the desired product (1.6 g, 67% yield) as a white solid.

298 tert-Butyl 4-((6-chloro-5-(2-chlorophenyl)-1-tosyl-1H-indazol-3-yl)(4-methoxybenzyl)amino) piperidine-1-carboxylate To a stirred solution of 2',4,6-trichloro-'-tosylbiphenyl-3-carbohydrazonoyl chloride (1.6 g, 3.4 mmol) in 100 mL of NMP at RT, tert-butyl 4-(4-methoxybenzylamino)piperidine-1-carboxylate (1.1 g, 3.4 mmol) was added followed by K$_2$CO$_3$ (1.4 g, 10.2 mmol). The reaction mixture was stirred at 40° C. overnight. The mixture was allowed to cool to RT, and partitioned between water and ethyl acetate. The organic layer was dried over anhydrous Na$_2$SO$_4$, filtered and concentrated in vacuo. The residue was purified by flash column chromatography on silica gel (1-20% ethyl acetate/petroleum ether) to afford the desired product (550 mg, 23% yield) as a white solid.

tert-Butyl 4-((6-chloro-5-(2-chlorophenyl)-1H-indazol-3-yl)(4-methoxybenzyl)amino) piperidine-1-carboxylate To a stirred solution of tert-butyl 4-((6-chloro-5-(2-chlorophenyl)-1-tosyl-1H-indazol-3-yl)(4-methoxybenzyl) amino) piperidine-1-carboxylate (550 mg, 0.75 mmol) in THF (20 mL) and water (5 mL) at RT, NaOH (75 mg, 1.87 mmol) was added, and the resulting mixture was stirred at reflux overnight. The reaction mixture was cooled to RT and partitioned between water and ethyl acetate. The organic layer was dried over anhydrous Na$_2$SO$_4$, filtered and concentrated in vacuo. The residue was purified by flash column chromatography on silica gel (1-10% ethyl acetate/petroleum ether) to afford the desired product (100 mg, 23% yield) as a white solid. ESI-MS m/z: 581.5 [M+H]$^+$.

6-Chloro-5-(2-chlorophenyl)-N-(piperidin-4-yl)-1H-indazol-3-amine

A solution of tert-butyl 4-((6-chloro-5-(2-chlorophenyl)-1H-indazol-3-yl)(4-methoxybenzyl)amino) piperidine-1-carboxylate (100 mg, 0.17 mmol) in 5 mL of TFA was stirred at reflux for 2 h. The reaction mixture was allowed to cool to RT and then partitioned between saturated NaHCO$_3$ aqueous solution and ethyl acetate. The organic layer was dried over anhydrous Na$_2$SO$_4$, filtered and concentrated in vacuo to afford the desired product (62 mg) as a yellow solid. The crude product was used directly in the next step without further purification.

1-(4-(6-Chloro-5-(2-chlorophenyl)-1H-indazol-3-ylamino)piperidin-1-yl)prop-2-en-1-one To a stirred solution of acrylic acid (12.4 mg, 0.17 mmol) in 5 mL of DMF at RT, 6-chloro-5-(2-chlorophenyl)-N-(piperidin-4-yl)-1H-indazol-3-amine (62 mg, 0.17 mmol), HOBT (30 mg, 0.22 mmol), EDCI (42 mg, 0.22 mmol), and TEA (52 mg, 0.51 mmol) were added sequentially. The reaction mixture was stirred at RT overnight. The mixture was partitioned between brine and ethyl acetate. The organic layer was dried over anhydrous Na$_2$SO$_4$, filtered and concentrated in vacuo. The residue was purified by prep-HPLC to give the desired product (2 mg, 3% yield) as a white solid. $^1$H NMR (300 MHz, DMSO-d6) δ: 11.67 (s, 1H), 7.73 (s, 1H), 7.56-7.58 (m, 1H), 7.41-7.47 (m, 2H), 7.42 (s, 1H), 7.36-7.39 (m, 1H), 6.80-6.87 (m, 1H), 6.07 (dd, J=2.5, 16.7 Hz, 1H), 6.04 (d, J=7.3 Hz, 1H), 5.65 (dd, J=2.4, 10.4 Hz, 1H), 4.23 (d, J=12.3 Hz, 1H), 3.98 (d, J=13.6 Hz, 1H), 3.76-3.80 (m, 1H), 3.26 (t, J=13.0 Hz, 1H), 2.97 (t, J=10.2 Hz, 1H), 2.06 (m, 2H), 1.38 (m, 2H). ESI-MS m/z: 415.1 [M+H]$^+$.

Example 4

Synthesis of 1-(4-(6-chloro-7-(2-chlorophenyl)isoquinolin-1-yl)piperazin-1-yl)prop-2-en-1-one (24)

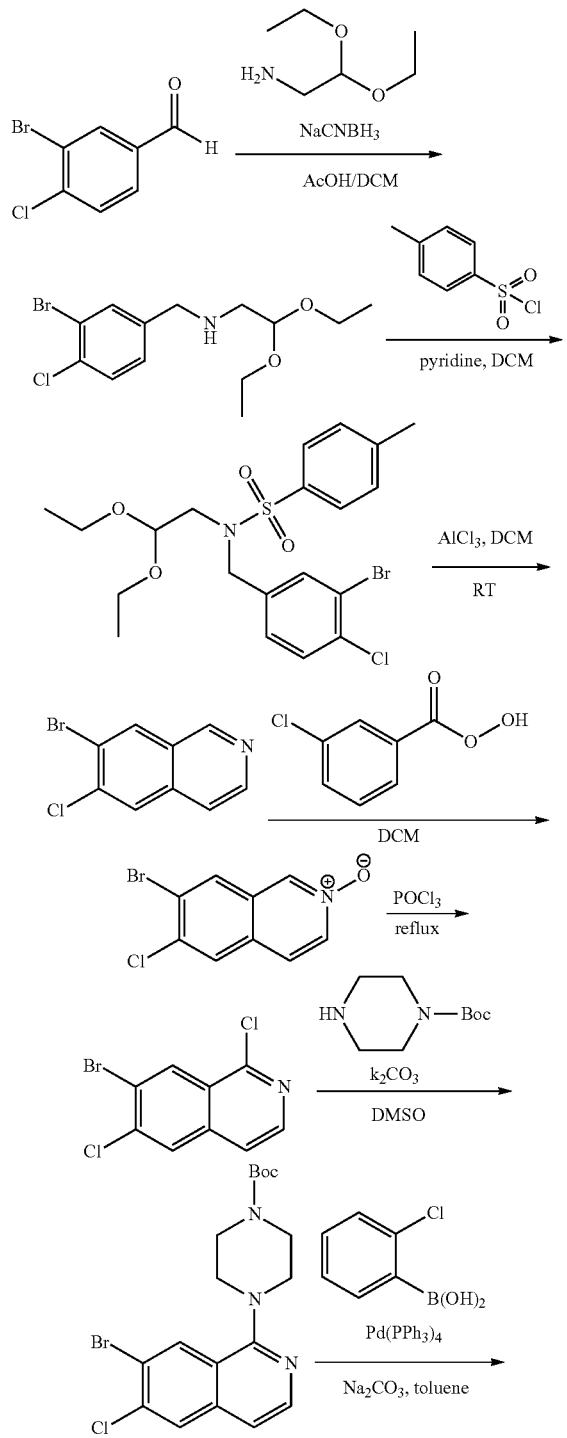

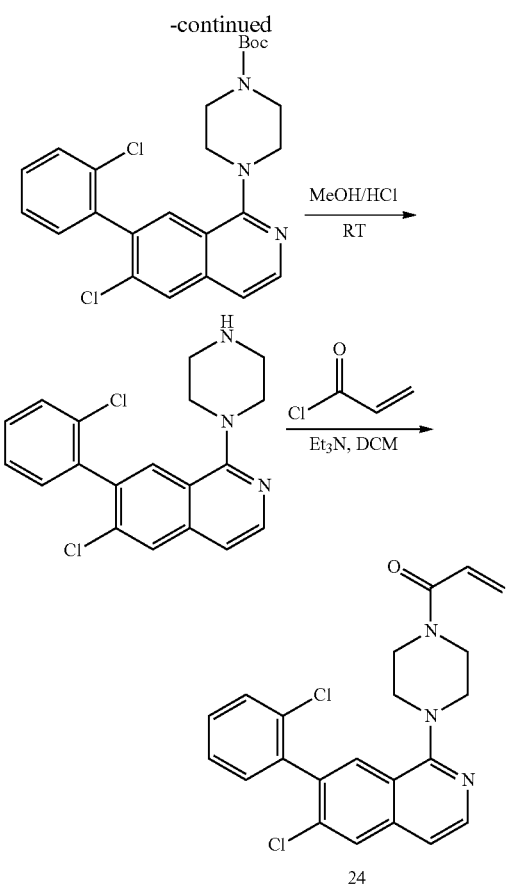

Compound 24 was prepared according to Method D as described below:

N-(3-Bromo-4-chlorobenzyl)-2,2-diethoxyethanamine

To a solution of 3-bromo-4-chlorobenzaldehyde (10.0 g, 45 mmol) and 2,2-diethoxyethanamine (6.68 g, 50 mmol) in 200 mL of DCM at RT, 0.5 mL of AcOH was added and the resulting mixture was stirred at RT for 30 min. To this mixture, NaCNBH$_3$ (8.1 g, 135 mmol) was added in portions and then stirred at RT overnight. The reaction mixture was portioned between water and DCM. The organic layer was washed with water (80 mL×2) and brine, dried over anhydrous Na$_2$SO$_4$, filtered and concentrated in vacuo to afford the desired product (11 g, 72% yield) as an oil. The crude product obtained was used directly in the next step without further purification.

N-(3-Bromo-4-chlorobenzyl)-2,2-diethoxy-N-tosylethanamine

To a solution of N-(3-bromo-4-chlorobenzyl)-2,2-diethoxyethanamine (11 g, 33 mmol) in 100 mL of DCM, pyridine (10 mL) was added and the resulting mixture was cooled to 0° C. To this mixture, a solution of 4-methylbenzene-1-sulfonyl chloride (6.8 g, 36 mmol) in 50 mL of DCM was added dropwise. The reaction mixture was allowed to warm to RT and stirring was continued until conversion was completed. The reaction mixture was washed twice with HCl aqueous solution (2 M), sodium bicarbonate solution and brine. The organic layer was dried over anhydrous Na$_2$SO$_4$, filtered and concentrated in vacuo. The residue was purified by flash column chromatography on silica gel (5-20% ethyl acetate/petroleum ether) to afford the desired product (12.5 g, 78% yield). ESI-MS m/z: 490.2 [M+H]+.

7-Bromo-6-chloroisoquinoline

AlCl₃ (14.9 g) was suspended in DCM at RT, a solution of N-(3-bromo-4-chlorobenzyl)-2,2-diethoxy-N-tosylethanamine (11.0 g, 22.5 mmol) in 75 mL of DCM was added and the resulting mixture was stirred overnight. The mixture was poured into ice water, and extracted with DCM. The combined organic layer was dried over anhydrous Na₂SO₄, filtered and concentrated in vacuo. The residue was purified by flash column chromatography on silica gel (10-40% ethyl acetate/petroleum ether) to afford the desired product (5 g, 92.5% yield) as a white solid. ESI-MS m/z: 242 [M+H]+.

7-Bromo-6-chloroisoquinoline2-oxide

To a solution of 7-bromo-6-chloroisoquinoline (5.5 g, 22.8 mmol) in 100 mL of DCM at RT, was added m-chloroperbenzoic acid (70%, 5.88 g, 34.2 mmol) and the resulting mixture was stirred at RT overnight. The precipitate was filtered off and rinsed with DCM. The filtrate was washed with sodium bicarbonate solution. The layers were separated and the aqueous layer was extracted with DCM. The combined organic layer was dried with anhydrous Na₂SO₄ and concentrated in vacuo to afford the desired product (4.6 g, 79% yield). The crude product was used directly in the next step without further purification. ESI-MS m/z: 258.2 [M+H]+.

1-(4-(6-chloro-7-(2-chlorophenyl)isoquinolin-1-yl)piperazin-1-yl)prop-2-en-1-one The title compound was prepared from 7-Bromo-6-chloroisoquinoline2-oxide in five steps following the procedure described in Example 1. ¹H NMR (400 MHz, DMSO-d6) δ: 8.22-8.21 (m, 2H), 8.00 (s, 1H), 7.65-7.47 (m, 5H), 6.87 (dd, J=16.9, 10.5 Hz, 1H), 6.16 (dd, J=16.7, 1.7 Hz, 1H), 5.72 (dd, J=10.3, 2.1 Hz, 1H), 3.83 (m, 4H), 3.37 (m, 4H). ESI-MS m/z: 412.2 [M+H]+.

Example 5

Synthesis of 1-(4-(7-chloro-6-(2-chlorophenyl)quinolin-4-yl)piperazin-1-yl)prop-2-en-1-one (27)

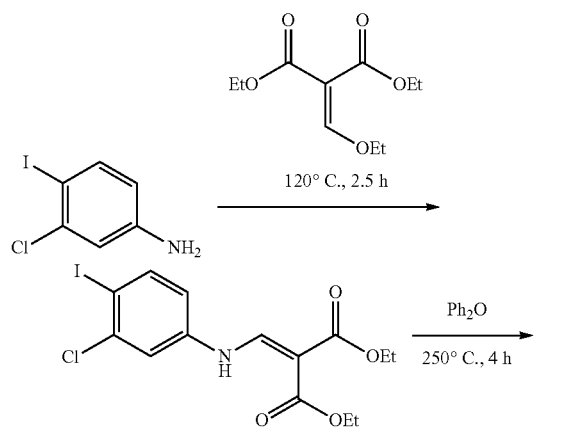

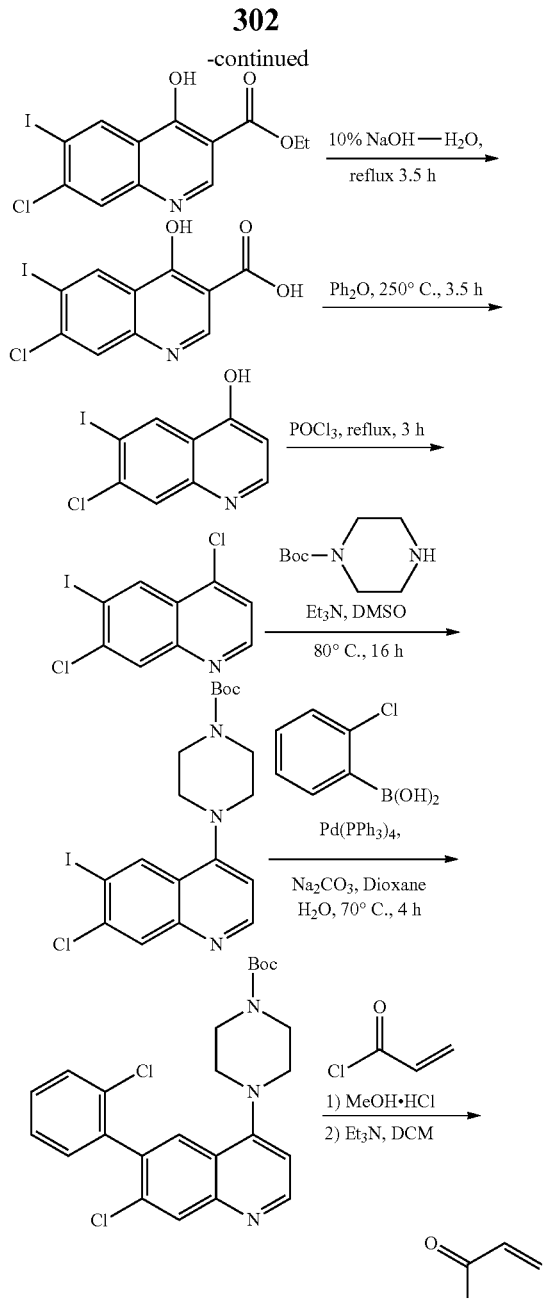

Compound 27 was prepared according to Method E as described below:

Diethyl 2-((3-chloro-4-iodophenylamino)methylene)malonate

3-Chloro-4-iodoaniline (3.0 g, 11.8 mmol) and diethyl 2-(ethoxymethylene)malonate (12.78 g, 59.2 mmol) were mixed in a 100 mL single neck flask, and the resulting mixture was heated to 120° C. and stirred for 2.5 h. The mixture was allowed to cool to RT and purified by flash column chromatography on silica gel (10-20% ethyl acetate/petroleum ether) to afford the desired product (3.93 g) as a white solid. ESI-MS m/z: 422.1 [M−H]−.

Ethyl 7-chloro-4-hydroxy-6-iodoquinoline-3-carboxylate (E)-diethyl 2-(((3-chloro-4-iodophenyl)imino)methyl)malonate (2.0 g, 4.73 mmol) was suspended in 30 mL of Ph$_2$O. The mixture was stirred at 250° C. for 4 h. The mixture was allowed to cool to RT and then 100 mL of petroleum ether was added. The white solid was collected by filtration and rinsed with petroleum ether (100 mL) to afford the desired product (1.20 g) as a white solid.

7-Chloro-4-hydroxy-6-iodoquinoline-3-carboxylic acid

Ethyl 7-chloro-4-hydroxy-6-iodoquinoline-3-carboxylate (1.2 g, 3.18 mmol) was suspended in 10% NaOH aqueous solution (50 mL). The mixture was stirred at reflux for 3.5 h. The white solid was slowly dissolved in NaOH solution. After the mixture turned to a colorless phase, it was kept heating for additional 1 h. The mixture was allowed to cool to RT, and the white solid was separated out. The mixture was acidified with con. HCl to adjust the pH to 2. The white precipitate was collected by filtration and rinsed with petroleum ether to afford the desired product (1.13 g) as a white solid.

7-Chloro-6-iodoquinolin-4-ol

7-Chloro-4-hydroxy-6-iodoquinoline-3-carboxylic acid (1.134 g, 3.25 mmol) was suspended in 40 mL of Ph$_2$O. The mixture was stirred at 250° C. for 3.5 h. The mixture was allowed to cool to RT and 100 mL of petroleum ether was added. The solid was collected by filtration, and rinsed with petroleum ether to afford the desired product (0.92 g) as a white solid.

4,7-Dichloro-6-iodoquinoline

7-Chloro-6-iodoquinolin-4-ol (591 mg, 1.94 mmol) was dissolved in 40 mL of POCl$_3$ and the mixture was stirred at reflux for 3 h. The mixture was allowed to cool to RT and concentrated in vacuo. The residue was poured into a solution of Et$_3$N (2.93 g, 29.03 mmol, 15 eq.) in 40 mL of DCM at 0° C. The mixture was partitioned between ethyl acetate and brine. The organic layer was dried and concentrated in vacuo. The residue was purified by flash column chromatography on silica gel (40% ethyl acetate/petroleum ether) to afford the desired product (895 mg) as a solid. ESI-MS m/z: 323.9 [M+H]+.

tert-Butyl 4-(7-chloro-6-iodoquinolin-4-yl)piperazine-1-carboxylate 4,7-Dichloro-6-iodoquinoline (200 mg, 0.62 mmol) was mixed with tert-butyl piperazine-1-carboxylate (172 mg, 0.93 mmol) and Et$_3$N (250 mg, 2.47 mmol) in 15 mL DMSO. The resulting mixture was stirred at 80° C. under argon for 16 h. The mixture was poured into 250 mL of water and 50 mL of brine, and then extracted with ethyl acetate. The combined organic layer was washed with brine, dried over Na$_2$SO$_4$, and concentrated in vacuo. The residue was purified by flash column chromatography on silica gel (20-30% ethyl acetate/petroleum ether) to afford the desired product (132 mg). ESI-MS m/z: 374.2 [M+H]+.

tert-Butyl 4-(7-chloro-6-(2-chlorophenyl)quinolin-4-yl)piperazine-1-carboxylate tert-Butyl 4-(7-chloro-6-iodoquinolin-4-yl)piperazine-1-carboxylate (130 mg, 0.28 mmol) was mixed with (2-chlorophenyl)boronic acid (109 mg, 0.33 mmol), Pd(PPh$_3$)$_4$ (32 mg, 0.028 mmol) and Na$_2$CO$_3$ (88 mg, 0.83 mmol) in 1,4-dioxane (20 mL) and water (4 mL). The mixture was stirred at 70° C. under argon for 4 h. The mixture was allowed to cool to RT and concentrated in vacuo. The residue was purified by flash column chromatography on silica gel (30-40% ethyl acetate/petroleum ether) to afford the desired (100 mg). ESI-MS m/z: 458.3 [M+H]+.

1-(4-(7-Chloro-6-(2-chlorophenyl)quinolin-4-yl)piperazin-1-yl)prop-2-en-1-one tert-butyl 4-(7-chloro-6-(2-chlorophenyl)quinolin-4-yl)piperazine-1-carboxylate (100 mg, 0.22 mmol) was dissolved in 20% MeOH—HCl solution (20 mL). The mixture was stirred at RT for 1 h. The mixture was concentrated in vacuo to yield a yellow solid salt (124 mg). The yellow salt (124 mg, 0.32 mmol) was dissolved in 30 mL of DCM in the presence of Et$_3$N (191 mg, 1.89 mmol). The mixture was cooled to 0° C. and then a solution of acryloyl chloride (32 mg, 0.35 mmol) in DCM (2 mL) was added dropwise. The mixture was stirred at 0° C. for 30 min. The mixture was concentrated in vacuo and the residue was purified by flash column chromatography on silica gel (50-100% ethyl acetate/petroleum ether) to afford the desired product (35 mg). $^1$H NMR (300 MHz, DMSO-d6) δ: 8.78-8-79 (m, 1H), 8.17 (s, 1H), 7.96 (s, 1H), 7.65-7.51 (m, 4H), 7.10-7.09 (m, 1H), 6.87 (dd, J=16.4, 10.4 Hz, 1H), 6.15 (d, J=16.4 Hz, 1H), 5.71 (d, J=10.4 Hz, 1H), 3.81 (br s, 4H), 3.22 (br s, 4H). ESI-MS m/z: 412.2 [M+H]+.

Example 6

Synthesis of 4-(4-acryloylpiperazin-1-yl)-7-chloro-6-(4-chlorophenyl)quinoline-3-carbonitrile (42)

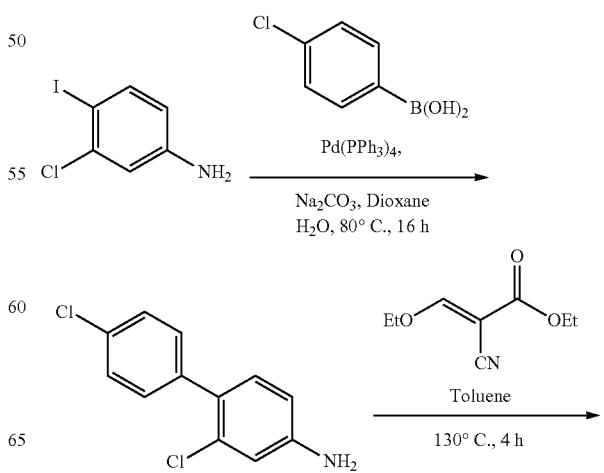

305

-continued

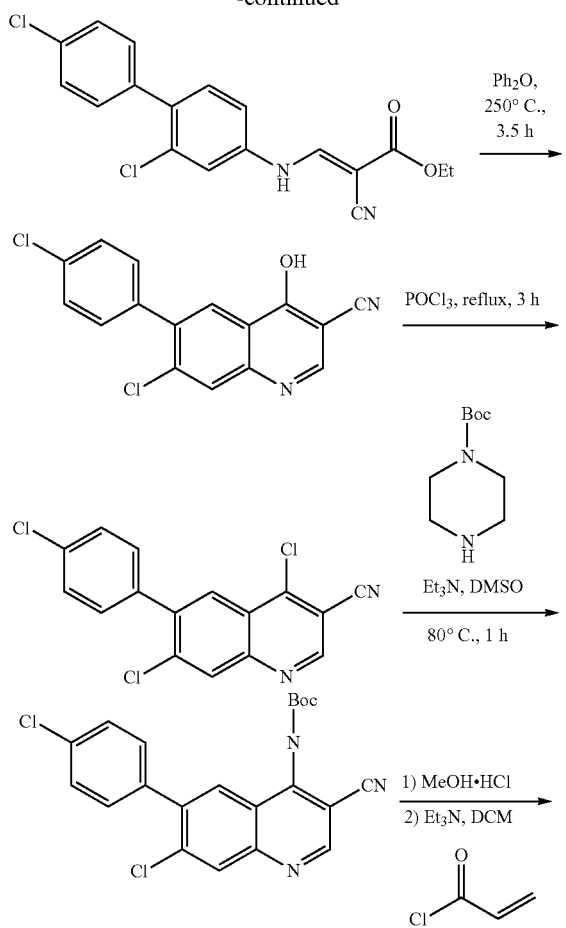

Compound 42 was prepared according to Method G as described below:

3-Chloro-4-(4-chlorophenyl)benzenamine

A mixture of 3-chloro-4-iodobenzenamine (500 mg, 1.97 mmol), 4-chlorophenylboronic acid (324 mg, 2.07 mmol), Na$_2$CO$_3$ (627 mg, 5.92 mmol) and Pd(PPh$_3$)$_4$ (228 mg, 0.20 mmol) in 1,4-dioxane (21 mL) and H$_2$O (4 mL) was stirred at 80° C. under argon for 16 h. The mixture was allowed to cool to RT and concentrated in vacuo. The residue was purified by flash column chromatography on silica gel (ethyl acetate/petroleum ether=5/1) to afford the desired product (424 mg, 91% yield) as a yellow solid.

306

(E)-Ethyl 3-(3-chloro-4-(4-chlorophenyl)-phenylamino)-2-cyanoacrylate

A mixture of 3-chloro-4-(4-chlorophenyl)benzenamine (250 mg, 1.05 mmol) and (E)-ethyl 2-cyano-3-ethoxyacrylate (186 mg, 1.10 mmol) was stirred at 100° C. for 2 h and then at 130° C. for 4 h. The mixture was allowed to cool to RT and concentrated in vacuo. The residue was triturated with ethyl acetate to afford the desired product (219 mg, 55% yield) as a white solid. ESI-MS m/z: 359.1 [M–H]$^-$.

7-chloro-6-(4-chlorophenyl)-4-hydroxyquinoline-3-carbonitrile

A mixture of (E)-Ethyl-3-(3-chloro-4-(4-chlorophenyl)-phenylamino)-2-cyanoacrylate (219 mg, 0.608 mmol) in Ph$_2$O (8 mL) was stirred at 253° C. for 4 h. The mixture was cooled to RT and poured into petroleum ether (20 mL). The precipitate was collected by filtration and washed with petroleum ether (50 mL×2) to yield the desired product (65 mg, 34% yield) as a brown solid.

4-(4-acryloylpiperazin-1-yl)-7-chloro-6-(4-chlorophenyl)quinoline-3-carbonitrile The title compound was prepared from 7-chloro-6-(4-chlorophenyl)quinolin-4-ol in four steps according to the procedure described in Example 1. $^1$H NMR (400 MHz, DMSO-d6) δ: 8.84 (s, 1H), 8.21 (s, 1H), 8.05 (s, 1H), 7.66-7.59 (m, 4H), 6.88 (dd, J=16.8, 10.4 Hz, 1H), 6.17 (dd, J=16.8, 2.0 Hz, 1H), 5.74 (dd, J=10.4, 2.0 Hz, 1H), 3.83-3.74 (m, 8H). ESI-MS m/z: 437.2 [M+H]$^+$.

Example 7

Synthesis of 1-(4-(5-(4-chlorophenyl)thieno[2,3-d]pyrimidin-4-yl)piperazin-1-yl)prop-2-en-1-one (22)

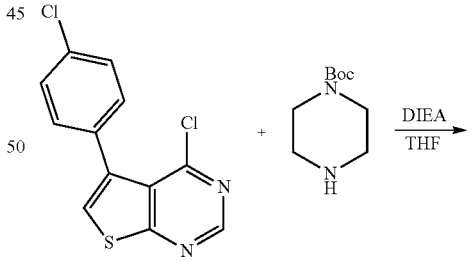

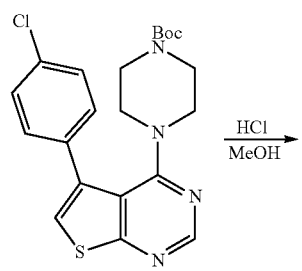

307

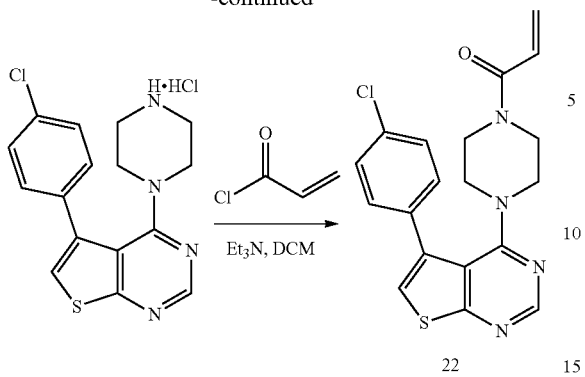

Compound 22 was prepared according to Method H as described below:

tert-Butyl 4-(5-(4-chlorophenyl)thieno[2,3-d]pyrimidin-4-yl)piperazine-1-carboxylate A solution of 4-chloro-5-(4-chlorophenyl)thieno[2,3-d]pyrimidine (180 mg, 0.64 mmol), tert-butyl piperazine-1-carboxylate (119 mg, 0.64 mmol) and diisopropyl amine in THF (6 mL) was stirred at RT overnight. The mixture was partitioned between DCM and water. The organic layer was dried over $Na_2SO_4$, filtered and concentrated in vacuo to afford the desired product which was used directly in the next step without further purification.

5-(4-Chlorophenyl)-4-(piperazin-1-yl)thieno[2,3-d]pyrimidine hydrochloride

To a suspension of tert-butyl 4-(5-(4-chlorophenyl)thieno[2,3-d]pyrimidin-4-yl)piperazine-1-carboxylate obtained from the previous step in 1,4-dioxane (10 mL) and MeOH (5 mL), was added a solution of HCl in 1,4-dioxane (4 M, 1.0 mL). The mixture was stirred at RT overnight. The mixture was concentrated in vacuo and the residue was used directly in the next step without further purification.

1-(4-(5-(4-Chlorophenyl)thieno[2,3-d]pyrimidin-4-yl)piperazin-1-yl)prop-2-en-1-one To a solution of 5-(4-Chlorophenyl)-4-(piperazin-1-yl)thieno[2,3-d]pyrimidine hydrochloride obtained above in DCM (10 mL) at 0° C., $Et_3N$ (0.2 mL) was added followed by acryloyl chloride. The resulting mixture was allowed to warm to RT and stirred for 1 h. The mixture was partitioned between DCM and water. The organic layer was dried over $Na_2SO_4$, filtered and concentrated in vacuo. The residue was purified via Isolera One (silica cartridge, 0-60% ethyl acetate/hexanes) to afford the desired product (27.5 mg). $^1H$ NMR (300 MHz, $CDCl_3$), δ: 8.64 (s, 1H), 7.35-7.48 (m, 4H), 7.30 (s, 1H), 6.42-6.60 (m, 1H), 6.26 (d, J=24 Hz, 1H), 5.69 (d, J=10.5 Hz, 1H), 3.10-3.35 (m, 8H). ESI-MS m/z: 385.0 $[M+H]^+$

308

Example 8

Synthesis of 1-(4-(8-(2-chlorophenyl)quinazolin-2-yl)piperazin-1-yl)prop-2-en-1-one (35)

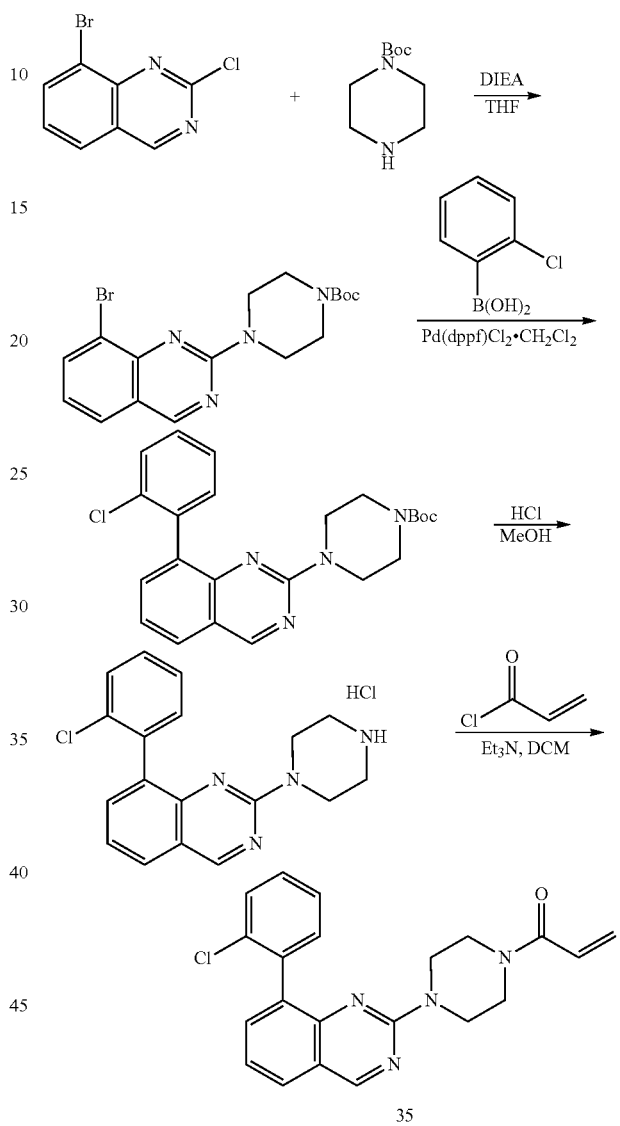

Compound 35 was prepared according to Method I as described below:

tert-Butyl 4-(8-bromoquinazolin-2-yl)piperazine-1-carboxylate

The title compound was prepared from 8-bromo-2-chloroquinazoline according to the procedure described in step 1 in Example 7.

tert-Butyl 4-(8-(2-chlorophenyl)quinazolin-2-yl)piperazine-1-carboxylate

A mixture of tert-Butyl 4-(8-bromoquinazolin-2-yl)piperazine-1-carboxylate (250 mg, 0.64 mmol), 2-chlorophenylbronic acid (110 mg, 1.1 mmol) and $Pd(dppf)Cl_2\cdot CH_2Cl_2$ (50 mg) in a mixture of 1,4-dioxane (6 mL) and sat. NaHCO$_3$ solution (3 mL) was stirred at 100° C. for 1 h. The mixture was allowed to cool to RT, and partitioned between water and ethyl acetate. The organic layer was dried over Na$_2$SO$_4$, filtered and concentrated in vacuo. The residue was purified via Isolera One (silica cartridge, 0-60% ethyl acetate/hexanes) to afford the desired product.

1-(4-(8-(2-Chlorophenyl)quinazolin-2-yl)piperazin-1-yl)prop-2-en-1-one

The title compound was prepared from tert-Butyl 4-(8-(2-chlorophenyl)quinazolin-2-yl)piperazine-1-carboxylate according to the procedure described in steps 2 and 3 in Example 7. $^1$H NMR (300 MHz, CDCl$_3$) δ: 9.07 (s, 1H), 7.74 (dd, J=8.0, 1.6 Hz, 1H), 7.67 (dd, J=6.8, 1.2 Hz, 1H), 7.46-7.56 (m, 1H), 7.39-7.42 (m, 4H), 6.58 (dd, J=16.8, 10.8 Hz, 1H), 6.32 (dd, J=16.8, 2.0 Hz, 1H), 5.71 (dd, J=10.6, 1.9 Hz, 1H), 3.8-3.9 (br., 4H), 3.68-3.78 (br., 2H), 3.55-3.62 (br., 2H). ESI-MS m/z: 379.1 [M+H]$^+$.

Example 9

Synthesis of 1-(4-(5-(2-chlorophenyl)-7H-pyrrolo[2,3-d]pyrimidin-4-yl)piperazin-1-yl)prop-2-en-1-one (28)

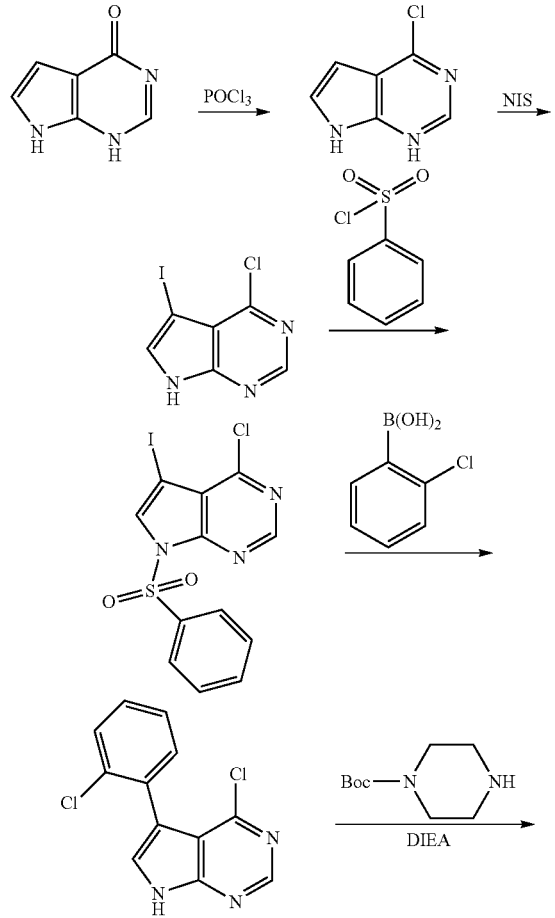

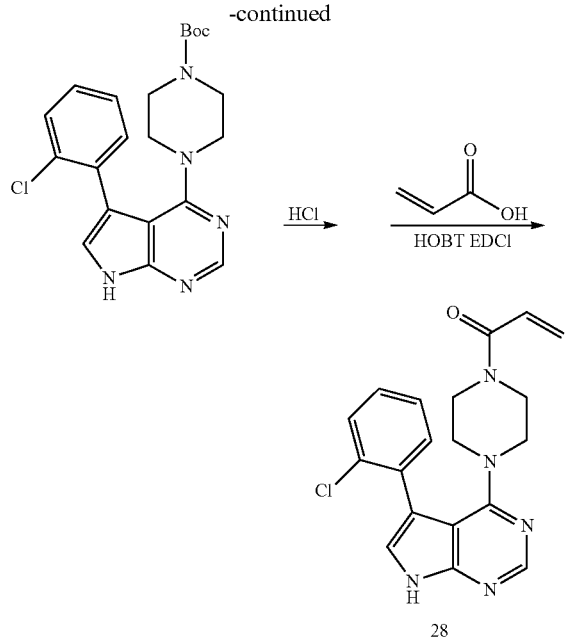

Compound 28 was prepared according to Method J as described below:

4-Chloro-7H-pyrrolo[2,3]pyrimidine

A mixture of 1H-pyrrolo[2,3-d]pyrimidin-4(7H)-one (2.5 g. 18.6 mmol) in 46 mL of POCl$_3$ was stirred at reflux for 5 h. The mixture was allowed to cool to RT and then concentrated in vacuo to remove the excess amount of POCl$_3$. Ice was added to the residue and the mixture was stirred at RT for 10 min. The aqueous layer was extracted with diethyl ether. The organic layer was dried over MgSO$_4$, filtered, and concentrated in vacuo to afford the desired product (1.5 g, 54% yield) as an off-white solid.

4-Chloro-5-iodo-7H-pyrrolo[2,3]pyrimidine

4-Chloro-7H-pyrrolo[2,3-d]pyrimidine (1.8 g 11.9 mmol) and N-iodosuccinamide (3 g, 13.1 mmol) were mixed in a round bottomed flask. The flask was dried under high vacuum for 5 h and then back-filled with argon. To this mixture, dry DMF (100 mL) was added and the resulting mixture was stirred in the dark for 20 h. The reaction was quenched with methanol and concentrated in vacuo. The residue was diluted with 150 mL of DCM and washed with water (200 mL), saturated aqueous sodium sulfite (200 mL), and brine (100 mL). The organic layer was dried over MgSO$_4$, filtered, and concentrated in vacuo. The residue was purified by flash column chromatography on silica gel (50% ethyl acetate/hexanes) to afford the desired product (3.1 g, 95% yield) as a white solid. ESI-MS m/z: 279.5 [M+H]$^+$.

4-Chloro-5-iodo-7benzenesulfonyl-pyrrolo[2,3-d]pyrimidine

To a solution of 4-chloro-5-iodo-7H-pyrrolo[2,3]pyrimidine (280 mg, 1 mmol) in DMF (5 mL) at 0° C., NaH (60%, 52 mg, 1.3 mmol) was added and the resulting mixture was stirred at 0° C. for 30 min. To this mixture, benzenesulfonyl chloride (194 mg, 1.1 mmol) was added. The mixture was then stirred at RT for 2 h. The mixture was partitioned between ethyl acetate and water. The organic layer was dried over MgSO$_4$, filtered, and concentrated in vacuo. The residue was purified by flash column chromatography on silica gel to afford the desired product (300 mg, 71.6% yield).

4-Chloro-5-(2-chlorophenyl)-7H-pyrrolo[2,3-d]pyrimidine

To a solution of 4-chloro-5-iodo-7benzenesulfonyl-pyrrolo[2,3-d]pyrimidine (300 mg, 0.71 mmol) and 2-chlorophenylboronic acid (167 mg, 1.07 mmol) in 1,4-dioxane (15 mL) and water (3 mL), Pd(PPh$_3$)$_4$ (60 mg) and Na$_2$CO$_3$ (227 mg, 2.14 mmol) were added. The mixture was stirred at 80° C. overnight. The mixture was allowed to cool to RT and concentrated in vacuo. The residue was purified by flash column chromatography on silica gel to afford the desired product (120 mg, 63% yield). ESI-MS m/z: 262.2 [M−H]$^-$.

tert-butyl-4-(5-(2-chlorophenyl)-7H-pyrrolo[2,3-d]pyrimidin-4-yl)piperazine-1-carboxylate To a solution of 4-chloro-5-(2-chlorophenyl)-7H-pyrrolo[2,3-d]pyrimidine (120 mg, 0.45 mmol) and tert-butyl piperazine-1-carboxylate (254 mg, 1.36 mmol) in 1,4-dioxane (15 mL), DIEA (293 mg, 2.27 mmol) was added. The mixture was stirred at 100° C. overnight. The mixture was concentrated in vacuo and the residue was purified by flash column chromatography on silica gel to afford the desired product (120 mg, 64% yield).

1-(4-(5-(2-Chlorophenyl)-7H-pyrrolo[2,3-d]pyrimidin-4-yl)piperazin-1-yl)prop-2-en-1-one The title compound was prepared from tert-butyl-4-(5-(2-chlorophenyl)-7H-pyrrolo[2,3-d]pyrimidin-4-yl)piperazine-1-carboxylate in two steps according to the procedure described in Example 1. $^1$H NMR (400 MHz, DMSO-d6) δ: 8.5 (s, 1H), 7.5 (m, 1H), 7.4 (m, 3H), 7.3 (s, 2H), 6.5 (m, 1H), 6.3 (m, 1H), 5.7 (m, 1H), 3.4 (m, 8H). ESI-MS m/z: 368.3 [M+H]$^+$.

Example 10

Synthesis of 1-(4-(2-amino-7-chloro-6-(4-chlorophenyl)quinazolin-4-yl)piperazin-1-yl)prop-2-en-1-one (39) and 1-(4-(7-chloro-6-(4-chlorophenyl)-2-methoxyquinazolin-4-yl)piperazin-1-yl)prop-2-en-1-one (43)

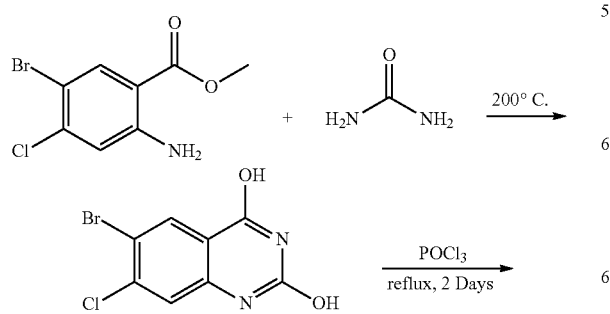

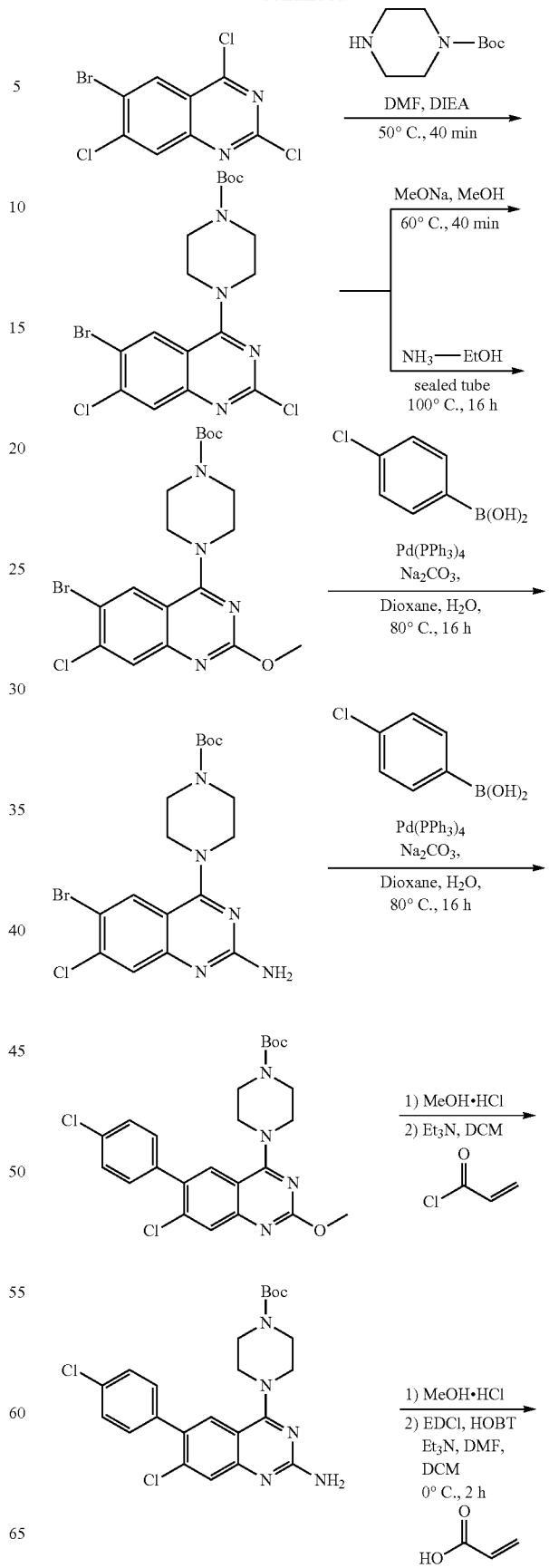

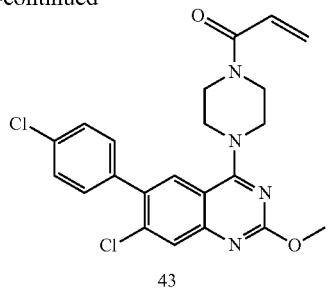

43

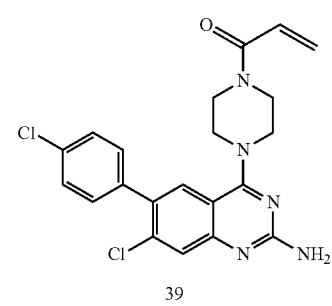

39

Compounds 39 and 43 were prepared according to Method F as described below:

6-Bromo-7-chloroquinazoline-2,4-diol

A mixture of methyl 2-amino-5-bromo-4-chlorobenzoate (3.0 g, 11.34 mmol) and urea (1.36 g, 22.68 mmol, 2 eq.) was stirred at 200° C. for 3 h. The mixture was allowed to cool to RT, triturated with ethyl acetate and dried to afford the desired product (2.39 g) as a brown solid.

6-Bromo-2,4,7-trichloroquinazoline

The mixture of 6-bromo-7-chloroquinazoline-2,4-diol (1.1 g, 6.79 mmol) in 30 mL of $POCl_3$ was stirred at reflux for 2 days. The mixture was allowed to cool to RT and concentrated in vacuo to remove $POCl_3$. The residue was poured into a solution of $Et_3N$ (13.7 g, 20 eq.) in 30 mL of DCM at 0° C. The mixture was partitioned between ethyl acetate and brine. The organic layer was dried over $Na_2SO_4$, filtered and concentrated in vacuo. The residue was purified by flash chromatography on silica gel (5-10% ethyl acetate/petroleum ether) to afford the desired product (474 mg) as a yellow solid.

tert-Butyl-4-(6-bromo-2,7-dichloroquinazolin-4-yl)piperazine-1-carboxylate

To a solution of tert-butyl piperazine-1-carboxylate (123 mg, 0.66 mmol) in DMF (10 mL) at RT, DIEA (94 mg, 0.72 mmol) was added followed by 6-bromo-2,4,7-trichloroquinazoline (206 mg, 0.66 mmol). The resulting mixture was stirred at 50° C. for 40 min. The mixture was allowed to cool to RT and partitioned between water and ethyl acetate. The organic layer was washed with brine, dried over $Na_2SO_4$ and concentrated. The residue was purified by flash column chromatography on silica gel (5% ethyl acetate/petroleum ether) to afford the desired product (222 mg) as a yellow solid. ESI-MS m/z: 463.2 $[M+H]^+$.

tert-Butyl 4-(6-bromo-7-chloro-2-methoxyquinazolin-4-yl)piperazine-1-carboxylate To a solution of NaOMe (26 mg, 0.476 mmol) in MeOH (20 mL), tert-butyl-4-(6-bromo-2,7-dichloroquinazolin-4-yl)piperazine-1-carboxylate (110 mg, 0.238 mmol) was added. The mixture was stirred at 60° C. under argon for 40 min. The mixture was quenched by water (1.0 mL) and then concentrated in vacuo. The residue was purified by flash column chromatography on silica gel (10-20% ethyl acetate/petroleum ether) to afford the desired product (55 mg) as a yellow solid. ESI-MS m/z: 459.2 $[M+H]^+$.

tert-Butyl-4-(7-chloro-6-(4-chlorophenyl)-2-methoxyquinazolin-4-yl)piperazine-1-carboxylate The mixture of tert-butyl 4-(6-bromo-7-chloro-2-methoxyquinazolin-4-yl)piperazine-1-carboxylate (85 mg, 0.19 mmol), (4-chlorophenyl)boronic acid (35 mg, 0.22 mmol), $Pd(PPh_3)_4$ (22 mg, 0.019 mmol), $Na_2CO_3$ (60 mg, 0.56 mmol) in dioxane (20 mL) and water (2 mL) was stirred at 80° C. under argon for 16 h. The mixture was allowed to cool to RT and concentrated in vacuo. The residue was purified by flash column chromatography on silica gel (10-20% ethyl acetate/petroleum ether) followed by Prep-TLC to afford the desired product (100 mg) as a white solid. ESI-MS m/z: 489.4 $[M+H]^+$.

1-(4-(7-Chloro-6-(4-chlorophenyl)-2-methoxyquinazolin-4-yl)piperazin-1-yl)prop-2-en-1-one tert-Butyl-4-(7-chloro-6-(4-chlorophenyl)-2-methoxyquinazolin-4-yl)piperazine-1-carboxylate (100 mg, 0.20 mmol) was dissolved in 20 mL of 20% HCl methanol solution. The mixture was stirred at RT for 1 h and then concentrated in vacuo to yield a yellow solid salt (90 mg).

The above yellow solid (90 mg, 0.21 mmol) was dissolved in 30 mL of DCM with $Et_3N$ (129 mg, 1.27 mmol). The mixture was cooled to 0° C. and then added dropwise to a solution of acryloyl chloride (23 mg, 0.25 mmol) in DCM (2 mL). The resulting mixture was stirred at 0° C. for 30 min. The mixture was poured into $H_2O$ (100 mL), sat. $NaHCO_3$ (50 mL) and brine (50 mL), and then extracted with ethyl acetate. The organic layer was washed with brine, dried over $Na_2SO_4$ and concentrated. The residue was purified by Prep-TLC followed by Prep-HPLC to afford the desired product (8 mg) as a white solid. ESI-MS m/z: 443.2 $[M+H]^+$.

tert-Butyl-4-(2-amino-6-bromo-7-chloroquinazolin-4-yl)piperazine-1-carboxylate

The mixture of tert-butyl 4-(6-bromo-2,7-dichloroquinazolin-4-yl)piperazine-1-carboxylate in sat. $NH_3$-EtOH (4 mL) in a sealed tube was stirred at 100° C. for 16 h. The mixture was allowed to cool to RT and concentrated in vacuo. The residue was purified by flash column chromatography on silica gel (20-30% ethyl acetate/petroleum ether) to afford the desired product (70 mg) as a white solid.

tert-Butyl-4-(2-amino-7-chloro-6-(4-chlorophenyl)quinazolin-4-yl)piperazine-1-carboxylate The mixture of tert-butyl-4-(2-amino-6-bromo-7-chloroquinazolin-4-yl)piperazine-1-carboxylate (70 mg, 0.16 mmol), (4-chlorophenyl)boronic acid (29 mg, 0.19 mmol), $Pd(PPh_3)_4$ (18 mg, 0.019 mmol), and $Na_2CO_3$ (50 mg, 0.48 mmol) in dioxane (20 mL) and water (2 mL) was stirred at 80° C. under argon for 16 h. The mixture was allowed to cool to RT and then concentrated in vacuo. The residue was purified by flash column chromatography on silica gel (10-20% ethyl acetate/petroleum ether) followed by Prep-TLC to afford the desired product (70 mg) as a red solid. ESI-MS m/z: 474.5[M+H]$^+$.

1-(4-(2-Amino-7-chloro-6-(4-chlorophenyl)quinazo-lin-4-yl)piperazin-1-yl)prop-2-en-1-one tert-Butyl-4-(2-amino-7-chloro-6-(4-chlorophenyl)qui-nazolin-4-yl)piperazine-1-carboxylate (70 mg, 0.15 mmol) was dissolved in 20% HCl methanol solution (20 mL) and the resulting mixture was stirred at RT for 1 h. The mixture was concentrated to afford the desired product (70 mg) as a yellow solid salt.

The mixture of above obtained yellow solid (70 mg, 0.21 mmol), acrylic acid (18 mg, 0.25 mmol), EDCI (73 mg, 0.381 mmol) and HOBT (52 mg, 0.381 mmol) in 10 mL of DMF at 0° C., a solution of Et$_3$N (120 mg, 1.2 mmol) in DCM (2 mL) was added dropwise. The resulting mixture was stirred at 0° C. for 30 min and at RT for 1.5 h. The mixture was poured into water (100 mL), sat. NaHCO$_3$ (50 mL) and brine (50 mL), and then extracted with ethyl acetate. The organic layer was washed with brine, dried over Na$_2$SO$_4$ and concentrated in vacuo. The residue was purified by flash column chromatography on silica gel to yield the desired product (5 mg) as a gray solid. ESI-MS m/z: 428.3 [M+H]$^+$.

Example 11

Synthesis of 1-(4-(7-chloro-6-(2-chlorophenyl)qui-nazolin-4-yl)piperidin-1-yl)prop-2-en-1-one (36)

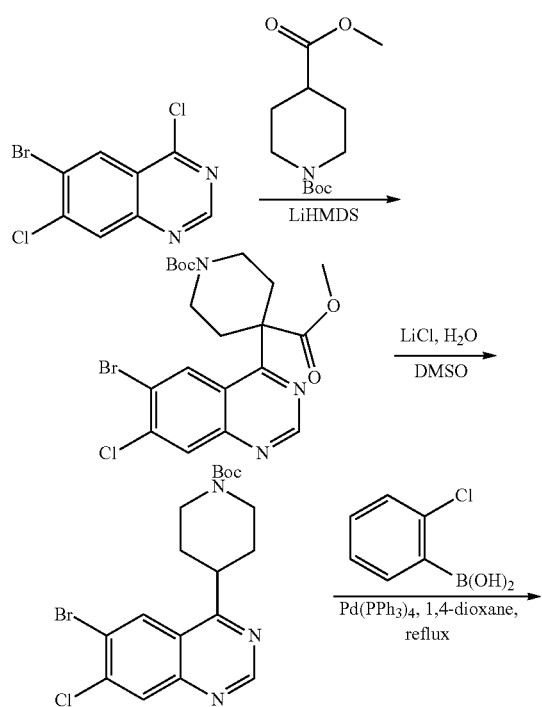

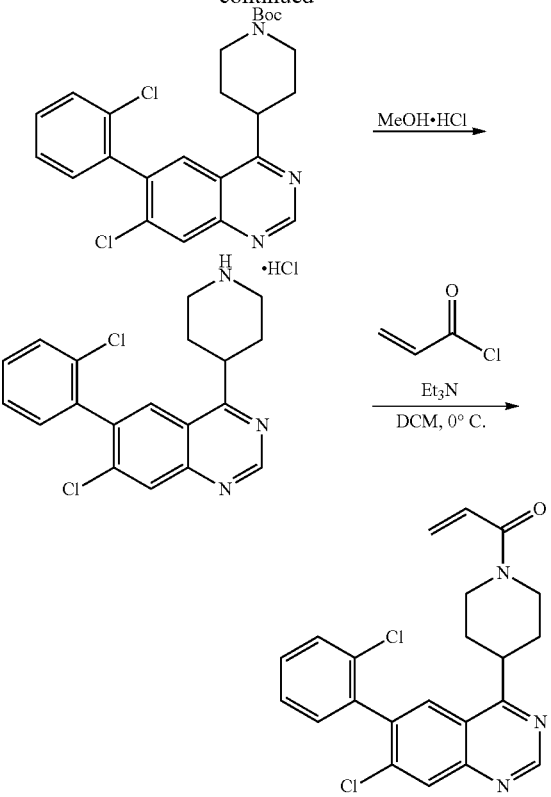

36

Compound 36 was prepared according to Method K as described below:

1-tert-Butyl 4-methyl 4-(6-bromo-7-chloroquinazo-lin-4-yl)piperidine-1,4-dicarboxylate To a stirred solution of tert-butyl methyl piperidine-1,4-dicarboxylate (3.3 g, 13.5 mmol) in anhydrous THF (30 mL) at 0° C. under nitrogen, LiHMDS (15 mL, 15 mmol) was added and the resulting mixture was stirred at 0° C. for 1 h. To this mixture, a solution of 6-bromo-4,7-dichloroquinazo-line (748 mg, 2.7 mmol) in THF (5 mL) was added and the resulting mixture was stirred at room temperature for 4 h. The mixture was quenched with ice-water and partitioned between water and ethyl acetate. The organic layer was dried over anhydrous Na$_2$SO$_4$, filtered and concentrated in vacuo. The residue was purified by flash column chromatography on silica gel (1-10% ethyl acetate/petroleum ether) to afford the desired product (580 mg, 37% yield) as a white solid.

tert-Butyl 4-(6-bromo-7-chloroquinazolin-4-yl)pip-eridine-1-carboxylate

To a solution of 1-tert-butyl 4-methyl 4-(6-bromo-7-chloroquinazolin-4-yl)piperidine-1,4-dicarboxylate (483 mg, 1.2 mmol) in DMSO (10 mL), LiCl (103 mg, 2.4 mmol) and water (65 mg, 3.6 mmol) were added, and the rusting mixture was stirred at 110° C. for 16 h. The mixture was allowed to cool to room temperature and partitioned between water and ethyl acetate. The organic layer was dried over anhydrous Na$_2$SO$_4$, filtered and concentrated in vacuo. The residue was purified by flash column chromatography on silica gel (1-20% ethyl acetate/petroleum ether) to afford the desired product (170 mg, 33% yield) as a white solid.

tert-Butyl 4-(7-chloro-6-(2-chlorophenyl)quinazolin-4-yl)piperidine-1-carboxylate A mixture of tert-butyl 4-(6-bromo-7-chloroquinazolin-4-yl)piperidine-1-carboxylate (230 mg, 0.59 mmol), 2-chlorophenylboronic acid (138 mg, 0.88 mmol), Pd(PPh₃)₄ (69 mg, 0.06 mmol) and Na₂CO₃ (188 mg, 106 mmol) in 1,4-dioxane (10 mL) under argon was stirred at 100° C. for 16 h. The mixture was allowed to cool to room temperature, and partitioned between water and ethyl acetate. The organic layer was dried over anhydrous Na₂SO₄, filtered and concentrated in vacuo. The residue was purified by flash column chromatography on silica gel (1-20% ethyl acetate/petroleum ether) to afford the desired product (160 mg, 65% yield) as a white solid.

1-(4-(7-Chloro-6-(2-chlorophenyl)quinazolin-4-yl)piperidin-1-yl)prop-2-en-1-one (45)

The title compound was prepared from tert-butyl 4-(7-chloro-6-(2-chlorophenyl) quinazolin-4-yl)piperidine-1-carboxylate according to the procedure described in steps 5 and 6 in Example 1. ¹H NMR (400 MHz, DMSO-d6) δ: 9.28 (s, 1H), 8.55 (s, 1H), 8.27 (s, 1H), 7.70 (m, 2H), 7.53-7.68 (m, 2H), 6.82-6.88 (m, 1H), 6.10 (dd, J=2.5, 16.8 Hz, 1H), 5.68 (dd, J=2.3, 10.3 Hz, 1H), 4.55 (d, J=12.2 Hz, 1H), 4.09-4.16 (m, 2H), 3.32 (t, J=12.2 Hz, 1H), 2.89 (t, J=12.1 Hz, 1H), 1.72-1.93 (m, 4H). ESI-MS m/z: 410.35 [M−H]⁻.

Example 12

Synthesis of 7-chloro-6-(4-chlorophenyl)-4-(4-(vinylsulfonyl)piperazin-1-yl)quinazoline (45)

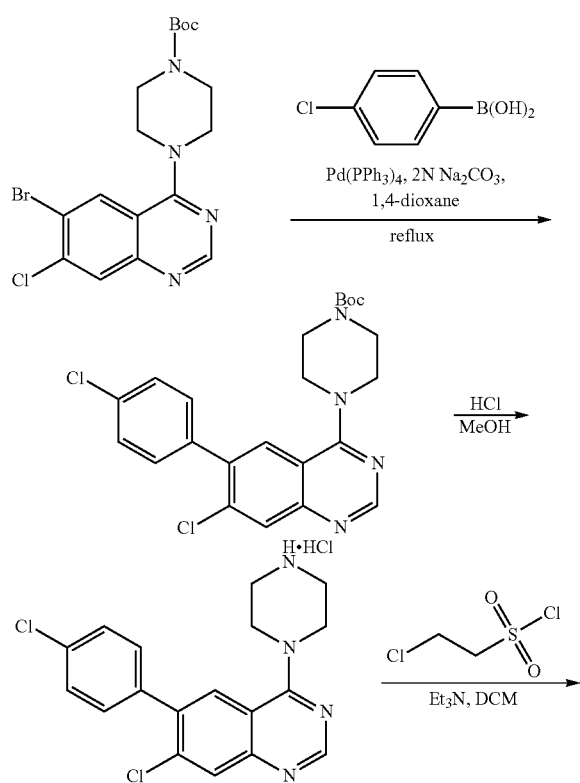

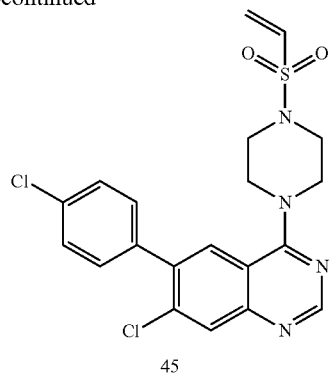

Compound 45 was prepared according to the general procedures of Method A as described below:

tert-Butyl 4-(7-chloro-6-(4-chlorophenyl)quinazolin-4-yl)piperazine-1-carboxylate The title compound was prepared from tert-butyl 4-(6-bromo-7-chloroquinazolin-4-yl)piperazine-1-carboxylate and 4-chlorophenylboronic acid according to the procedure described in step 4 in Example 2.

tert-Butyl 4-(7-chloro-6-(4-chlorophenyl)quinazolin-4-yl)piperazine-1-carboxylate A solution of tert-butyl4-(7-chloro-6-(4-chlorophenyl)quinazolin-4-yl)piperazine-1-carboxylate (500 mg, 1.09 mmol) in HCl/MeOH (10 mL, 28.6 mmol) was stirred at room temperature for 30 min. The mixture was concentrated in vacuo to afford the crude product.

7-Chloro-6-(4-chlorophenyl)-4-(4-(vinylsulfonyl)piperazin-1-yl)quinazoline

The above obtained crude product was dissolved with DCM (15 mL) and cooled to 0° C. To this mixture, 2-chloroethanesulfonyl chloride (213.2 mg, 1.31 mmol) and Et₃N (1.5 mL, 10.9 mmol) were added and the resulting mixture was stirred at 0° C. for 10 min. The mixture was quenched with ice-water and partitioned between water and ethyl acetate. The organic layer was dried over anhydrous Na₂SO₄, filtered and concentrated in vacuo. The residue was purified by prep-HPLC to afford the desired product (3 mg, 0.6% yield). ¹H-NMR (400 M Hz, CDCl₃) δ: 8.78 (s, 1H), 8.08 (s, 1H), 7.75 (s, 1H), 7.49 (d, J=8.4 Hz, 2H), 7.42 (d, J=8.4 Hz, 2H), 6.46 (dd, J=10, 16.8 Hz, 1H), 6.31 (d, J=16.8 Hz, 1H), 6.11 (d, J=9.6 Hz, 1H), 3.91 (t, J=4.8 Hz, 4H), 3.35 (t, J=4.8 Hz, 4H). ESI-MS m/z: 449.25 [M+H]⁺.

Example 13

Synthesis of 1-(4-(7-chloro-6-(4-chlorophenyl)quinazolin-4-yl)-2-(hydroxymethyl)piperazin-1-yl)prop-2-en-1-one (46)

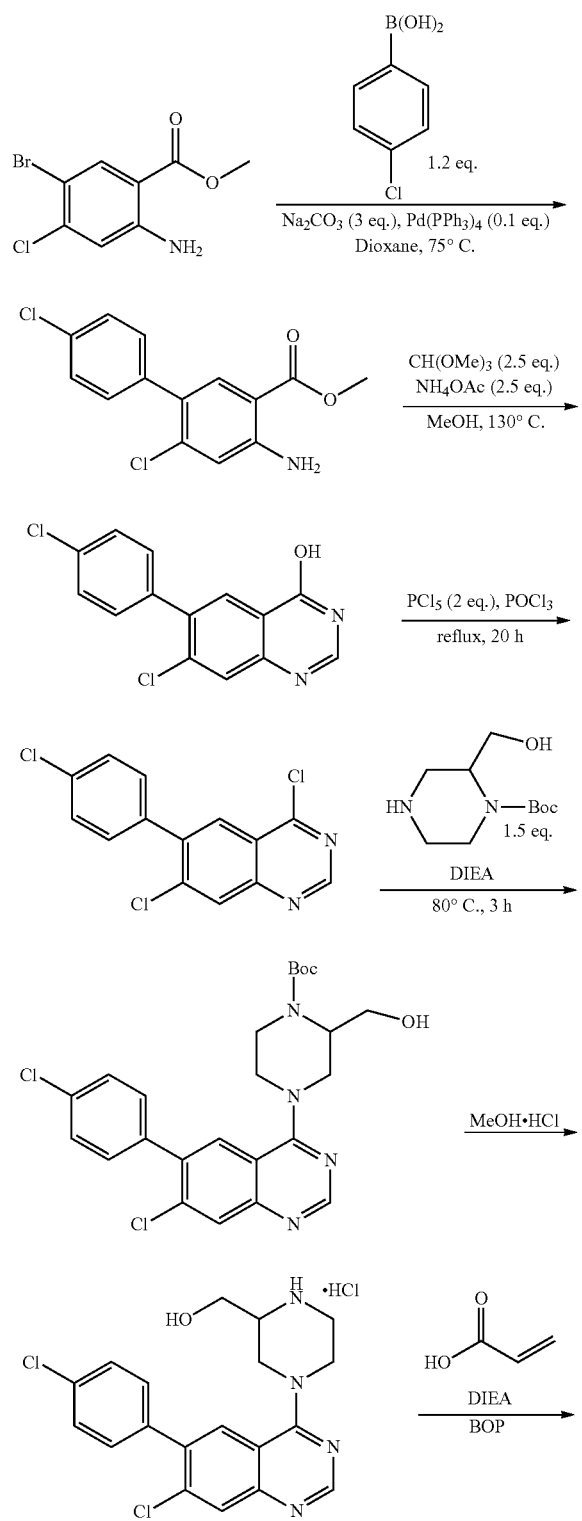

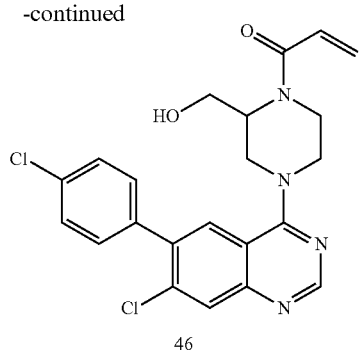

46

Compound 46 was prepared according to the general procedures of Method A as described below:

4,7-Dichloro-6-(4-chlorophenyl)quinazoline

The title compound was prepared from 2-amino-5-bromo-4-chlorobenzoate according to the procedure described in steps 1, 2 and 3 in Example 1.

tert-Butyl 4-(7-chloro-6-(4-chlorophenyl)quinazolin-4-yl)-2-(hydroxymethyl)piperazine-1-carboxylate The above obtained crude 4,7-dichloro-6-(4-chlorophenyl)quinazoline (200 mg, 0.464 mmol) was added to the mixture of tert-butyl 2-(hydroxymethyl)piperazine-1-carboxylate (210 mg, 0.968 mmol) and DIEA (418 mg, 3.24 mmol) in 1,4-dioxane (20 mL) at room temperature and the resulting mixture was stirred at 80° C. for 3 h. The mixture was allowed to cool to room temperature and then concentrated in vacuo. The residue was purified by flash column chromatography on silica gel (DCM/MeOH=30:1) to afford the desired product (110 mg, 35% yield) as a light yellow oil. ESI-MS m/z: 498.9 [M+H]+.

(4-(7-Chloro-6-(4-chlorophenyl)quinazolin-4-yl)piperazin-2-yl)methanol hydrochloride A mixture of 4-(7-chloro-6-(4-chlorophenyl)quinazolin-4-yl)-2-(hydroxymethyl)piperazine-1-carboxylate (110 mg, 0.225 mmol) and HCl in MeOH (10 mL, 28.6 mmol) was stirred at room temperature for 1 h. The mixture was concentrated in vacuo to afford the crude product (106 mg) as a yellow solid which was used directly in next step without further purification.

1-(4-(7-Chloro-6-(4-chlorophenyl)quinazolin-4-yl)-2-(hydroxymethyl)piperazin-1-yl)prop-2-en-1-one To a stirred solution of above obtained yellow solid (106 mg, 0.225 mmol) in DMF (5 mL) at room temperature, acrylic acid (19 mg, 0.27 mmol), BOP (149 mg, 0.338 mmol) and DIEA (203 mg, 1.58 mmol) were added and the resulting mixture was stirred at room temperature for 30 min. The mixture was poured into saturated aqueous NaHCO$_3$ solution (50 mL), and then extracted with ethyl acetate. The organic layer was washed with brine, dried over Na$_2$SO$_4$ and concentrated in vacuo. The residue was purified by flash column chromatography on silica gel (DCM/MeOH=20:1) to afford the desired product (20 mg, 20% yield, 2 steps) as a solid. $^1$H NMR (400 MHz, DMSO-d6) δ: 8.7 (s, 1H), 8.2 (d, J=2.8 Hz, 1H), 8.0 (s, 1H), 7.5 (m, 4H), 6.8 (dd, J=10.4, 16.4 Hz, 1H), 6.1 (d, J=17 Hz, 1H), 5.7 (dd, J=2.4, 10.4 Hz, 1H), 5.0 (m, 1H), 4.3 (m, 2H), 4.2 (m, 2H), 3.6 (m, 3H), 2.5 (s, 2H). ESI-MS m/z: 443.30 [M+H]$^+$.

Example 14

Synthesis of 1-acryloyl-4-(7-chloro-6-(4-chlorophenyl)quinazolin-4-yl)piperazine-2-carbonitrile (47)

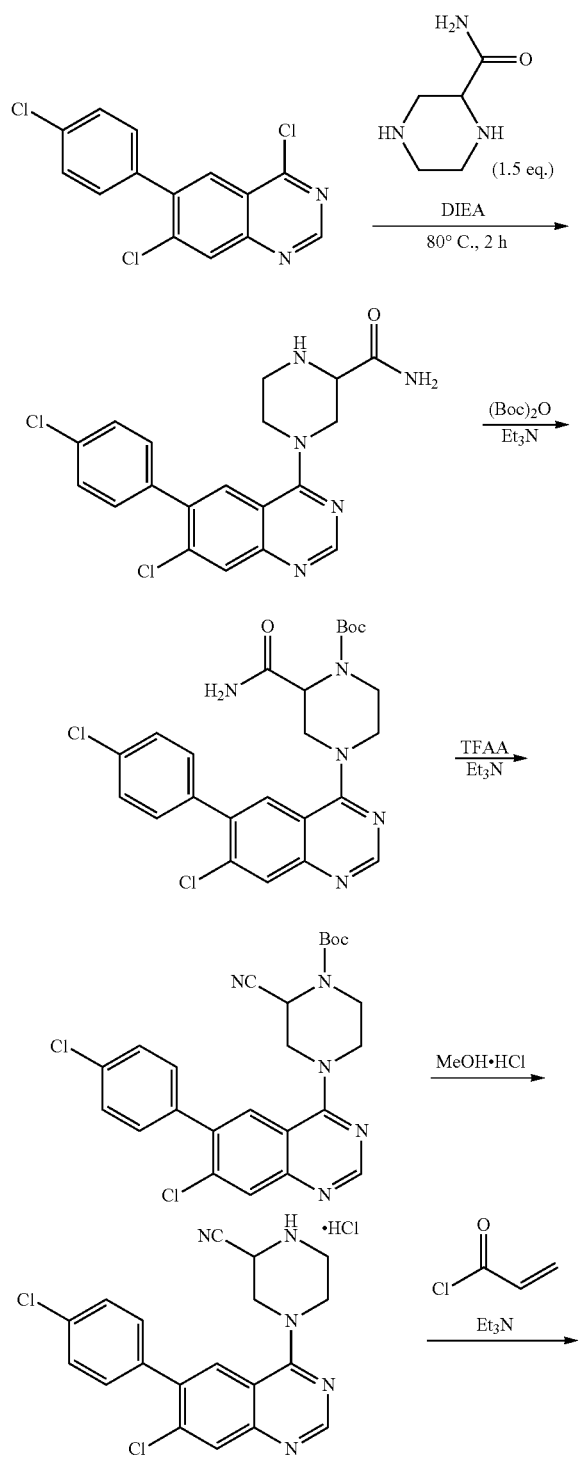

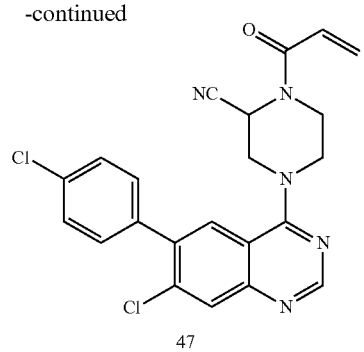

Compound 47 was prepared according to the general procedures of Method A as described below:

4-(7-Chloro-6-(4-chlorophenyl)quinazolin-4-yl)piperazine-2-carboxamide

The crude 4,7-dichloro-6-(4-chlorophenyl)quinazoline (310 mg, 1 mmol) was added to the mixture of piperazine-2-carboxamide (249 mg, 1.5 mmol) and DIEA (645 mg, 5 mmol) in 1,4-dioxane (20 mL) at room temperature and the resulting mixture was stirred at 80° C. for 2 h. The mixture was allowed to cool to room temperature and then concentrated in vacuo. The residue was used in the next step without further purification.
ESI-MS m/z: 402.3 [M+H]$^+$.

tert-Butyl 2-carbamoyl-4-(7-chloro-6-(4-chlorophenyl)quinazolin-4-yl)piperazine-1-carboxylate To a solution of the above obtained crude product 4-(7-chloro-6-(4-chlorophenyl)quinazolin-4-yl)piperazine-2-carboxamide in DCM (20 mL) at room temperature, Et$_3$N (152 mg, 1.5 mmol) and di-tert-butyl dicarbonate (262 mg, 1.2 mmol) were added. The mixture was stirred at room temperature for 3 h. The mixture was concentrated in vacuo and the residue was purified by flash column chromatography on silica gel (DCM/MeOH=30:1) to afford the desired product (60 mg, 12% yield) as a solid. ESI-MS m/z: 502.4 [M+H]$^+$.

tert-Butyl 4-(7-chloro-6-(4-chlorophenyl)quinazolin-4-yl)-2-cyanopiperazine-1-carboxylate To a solution of tert-butyl 2-carbamoyl-4-(7-chloro-6-(4-chlorophenyl)quinazolin-4-yl)piperazine-1-carboxylate (60 mg, 0.12 mmol) and Et$_3$N (48 mg, 0.48 mmol) in DCM (20 mL) at 0° C., TFAA (50 mg, 0.24 mmol) and the resulting mixture was stirred at room temperature for 1 h. The reaction mixture was quenched with saturated NaHCO$_3$ solution, and then extracted with DCM. The organic layer was washed with saturated NaHCO$_3$ solution and brine, dried over Na$_2$SO$_4$ and concentrated in vacuo.
The residue was purified by flash column chromatography on silica gel (DCM/MeOH=50:1) to afford the desired product (50 mg, 86% yield) as a solid. ESI-MS m/z: 484.4 [M+H]$^+$.

1-Acryloyl-4-(7-chloro-6-(4-chlorophenyl)quinazolin-4-yl)piperazine-2-carbonitrile The title compound was prepared from tert-butyl 4-(7-chloro-6-(4-chlorophenyl)quinazolin-4-yl)-2-cyanopiperazine-1-carboxylate according to the procedure described in steps 5 and 6 in Example 1. ¹H NMR (400 MHz, DMSO-d6) δ: 8.7 (s, 1H), 8.1 (s, 1H), 8.0 (d, J=2.0 Hz, 1H), 7.5 (m, 4H), 6.8 (dd, J=10.4, 16.8 Hz, 1H), 6.3 (dd, J=1.6, 16.8 Hz, 1H), 5.8 (dd, J=1.6, 10.4 Hz, 1H), 4.6 (m, 1H), 4.3 (m, 3H), 3.6 (m, 2H), 3.4 (s, 1H). ESI-MS m/z: 438.25 [M+H]⁺.

Example 15

Synthesis of 1-(4-(7-chloro-6-(4-chlorophenyl)-2-methylquinazolin-4-yl)piperazin-1-yl)prop-2-en-1-one (50)

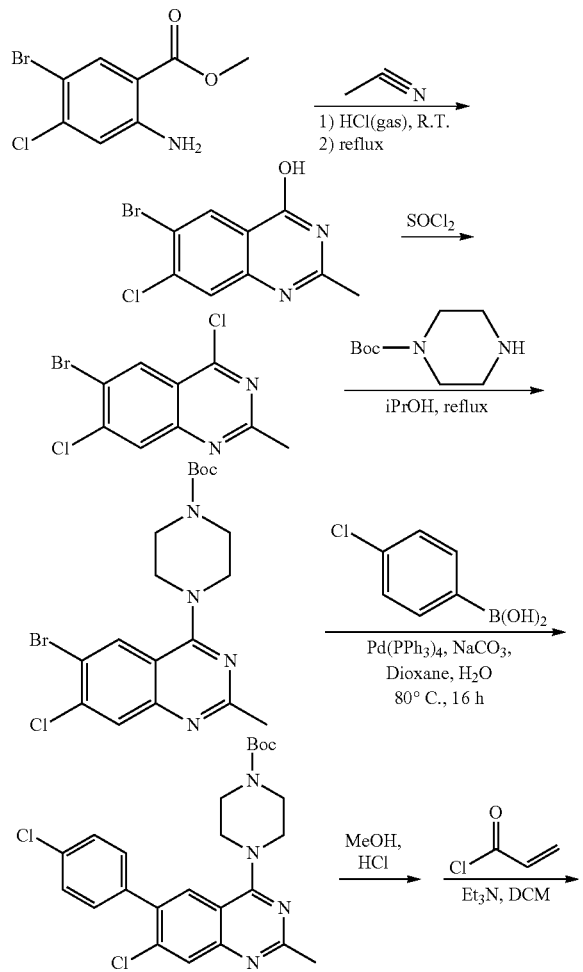

Compound 50 was prepared according to the general procedures of Method M as described below:

6-Bromo-7-chloro-2-methylquinazolin-4-ol

To a solution of methyl 2-amino-5-bromo-4-chlorobenzoate (1.0 g, 3.781 mmol) in MeCN (35 mL) at RT, dry hydrogen chloride was added continuously for 20 min. The resulting mixture was stirred at reflux for 2 h. The mixture was allowed to cool to RT and poured into saturated NaHCO₃ solution. The white solid was filtered, and the filtrate was extracted with ethyl acetate. The filtrate cake and organic layer was combined and dried over Na₂SO₄, concentrated in vacuo to afford the crude product (1.62 g) as a white solid. ESI-MS m/z: 273.3 [M+H]⁺.

6-Bromo-4,7-dichloro-2-methylquinazoline

The mixture of 6-bromo-7-chloro-2-methylquinazolin-4-ol (500 mg, 1.828 mmol) in 30 mL of SOCl₂ was stirred at reflux for 16 h. The mixture was allowed to cool to RT and concentrated in vacuo. The residue was purified through silica chromatography (5-10% ethyl acetate/petroleum ether) to afford the desired product (180 mg, 34% yield) as a yellow solid.

tert-Butyl 4-(6-bromo-7-chloro-2-methylquinazolin-4-yl)piperazine-1-carboxylate

To a solution of tert-butyl piperazine-1-carboxylate (76 mg, 0.410 mmol) in i-PrOH (10 mL) at RT, 6-bromo-4,7-dichloro-2-methylquinazoline (60 mg, 0.205 mmol) was added. The resulting mixture was stirred at reflux for 40 min. The mixture was allowed to cool to RT and partitioned between water and ethyl acetate. The organic layer was washed with saturated NaHCO₃ and brine, dried over Na₂SO₄ and concentrated. The residue was purified by flash column chromatography on silica gel (5% ethyl acetate/petroleum ether) to afford the desired product (53 mg, 59% yield) as a yellow solid.

1-(4-(7-Chloro-6-(4-chlorophenyl)-2-methylquinazolin-4-yl)piperazin-1-yl)prop-2-en-1-one The title compound was prepared from tert-butyl 4-(6-bromo-7-chloro-2-methylquinazolin-4-yl)piperazine-1-carboxylate in three steps according to the procedure described in Example 2. ¹H NMR (400 MHz, DMSO-d6) δ: 7.92 (s, 2H), 7.59 (m, 4H), 6.84-6.77 (dd, J=10.4, 16.8 Hz, 1H), 6.17-6.36 (m, 1H), 5.74-5.71 (m, 1H), 3.85-3.72 (m, 8H), 2.54 (s, 3H). ESI-MS m/z: 428.3 [M+H]⁺.

Example 16

Synthesis of 1-acryloyl-4-(7-chloro-6-(4-chlorophenyl)-2-methylquinazolin-4-yl)piperazine-2-carbonitrile (56)

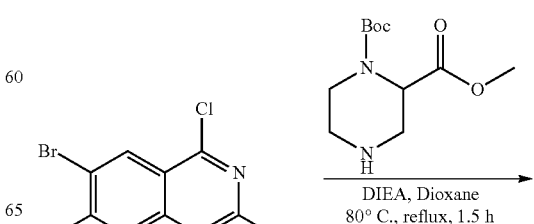

325
-continued

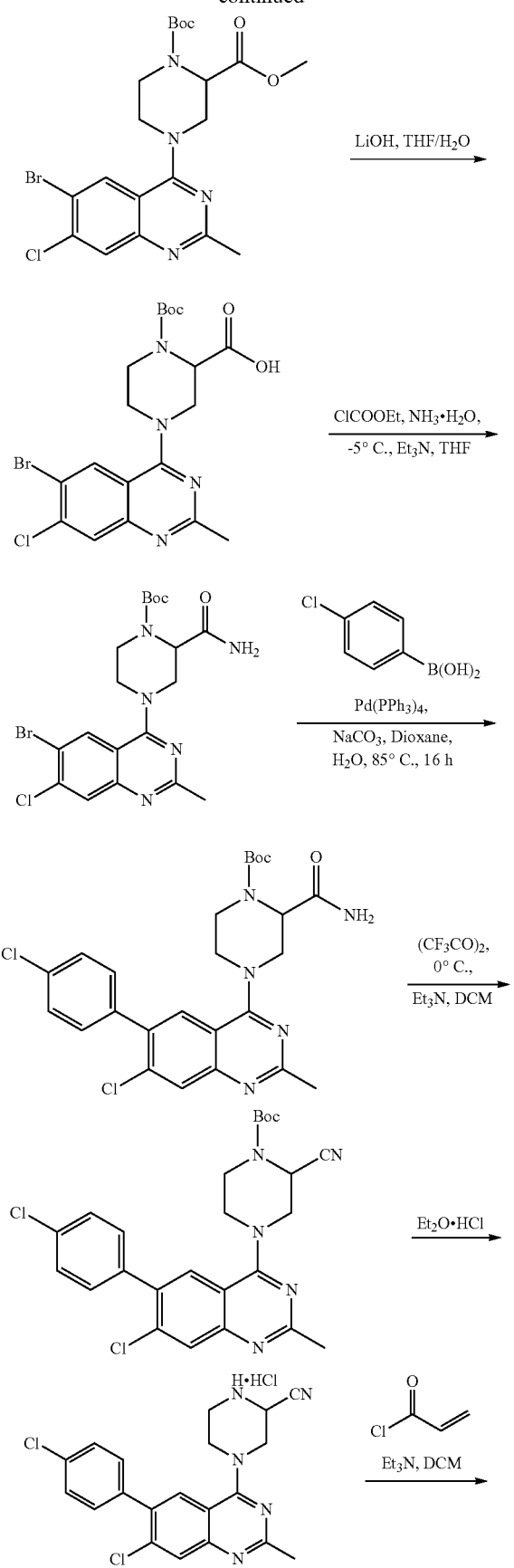

326
-continued

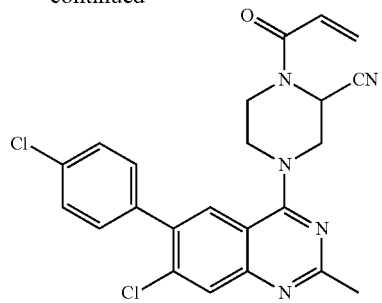

Compound 56 was prepared according to the general procedures of Method M as described below:

1-tert-butyl 2-methyl 4-(6-Bromo-7-chloro-2-methylquinazolin-4-yl)piperazine-1,2-dicarboxylate To a solution of 6-bromo-4,7-dichloro-2-methylquinazoline (435 mg, 1.49 mmol) and 1-tert-butyl 2-methyl piperazine-1,2-dicarboxylate (437 mg, 1.79 mmol) in 1,4-dioxane (30 mL), DIEA (769 mg, 5.96 mmol) was added. The mixture was stirred at 80° C. for 1.5 h. The mixture was allowed to cool to RT and partitioned between water and ethyl acetate. The organic layer was washed with brine, dried over Na$_2$SO$_4$ and concentrated. The residue was purified by flash column chromatography on silica gel (5-50% ethyl acetate/petroleum ether) to afford the desired product (224 mg, 30% yield) as a yellow solid.

4-(6-Bromo-7-chloro-2-methylquinazolin-4-yl)-1-(tert-butoxycarbonyl)piperazine-2-carboxylic acid To a solution of 1-tert-butyl 2-methyl 4-(6-bromo-7-chloro-2-methylquinazolin-4-yl)piperazine-1,2-dicarboxylate (224 mg, 0.448 mmol) in THF (15 mL) and H$_2$O (5 mL), LiOH.H$_2$O (114 mg, 2.690 mmol) was added and the resulting mixture was stirred at RT for 1 h. The mixture was diluted with H$_2$O, acidified with HCl to adjust pH to 4 and then extracted with ethyl acetate. The organic layer was washed with brine, dried over Na$_2$SO$_4$ and concentrated in vacuo to afford the desired product (211 mg, 97% yield) as a yellow solid.

tert-Butyl 4-(6-bromo-7-chloro-2-methylquinazolin-4-yl)-2-carbamoylpiperazine-1-carboxylate To a solution of 4-(6-bromo-7-chloro-2-methylquinazolin-4-yl)-1-(tert-butoxycarbonyl)piperazine-2-carboxylic acid (221 mg, 0.435 mmol) and Et$_3$N (176 mg, 1.738 mmol) in THF (35 mL) at −5° C., ethyl chloroformate (51 mg, 0.465 mmol) was added. The mixture was stirred at −5° C. for 40 min and NH$_3$.H$_2$O (30%, 507 mg, 4.346 mmol) was added. The resulting mixture was kept stirring for 5 min at 0° C. The mixture was partitioned between water and ethyl acetate. The organic layer was washed with brine, dried over Na$_2$SO$_4$ and concentrated. The residue was purified by flash column chromatography on silica gel (3% methanol/dichloromethane) to afford the desired product (179 mg, 85% yield) as a yellow solid. ESI-MS m/z: 484.3 [M+H]$^+$.

tert-Butyl 2-carbamoyl-4-(7-chloro-6-(4-chlorophenyl)-2-methylquinazolin-4-yl)piperazine-1-carboxylate A mixture of tert-butyl 4-(6-bromo-7-chloro-2-methylquinazolin-4-yl)-2-carbamoylpiperazine-1-carboxylate (179 mg, 0.371 mmol), (4-chlorophenyl)boronic acid (67 mg, 0.426 mmol), Pd(PPh$_3$)$_4$ (51 mg, 0.0445 mmol) and Na$_2$CO$_3$ (118 mg, 1.113 mmol) in 1,4-dioxane (25 mL) was stirred at 85° C. for 16 h under argon. The mixture was allowed to cool to RT and concentrated in vacuo. The residue was purified by flash column chromatography on silica gel (3% methanol/dichloromethane) to afford the desired product (181 mg, 95% yield) as a brown solid. ESI-MS m/z: 517.4 [M+H]$^+$.

tert-Butyl 4-(7-chloro-6-(4-chlorophenyl)-2-methylquinazolin-4-yl)-2-cyanopiperazine-1-carboxylate To a solution of tert-butyl 2-carbamoyl-4-(7-chloro-6-(4-chlorophenyl)-2-methylquinazolin-4-yl)piperazine-1-carboxylate (100 mg, 0.194 mmol) and Et$_3$N (78 mg, 0.775 mmol) in DCM (30 mL) at 0° C., TFAA (162 mg, 0.776 mmol) was added and the resulting mixture was stirred at RT for 1 h. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatographyon silica gel (petroleum ether/ethyl acetate=2:1) to afford the desired product (58 mg, 60% yield) as a yellow solid. ESI-MS m/z: 499.4[M+H]$^+$. 1-Acryloyl-4-(7-chloro-6-(4-chlorophenyl)-2-methylquinazolin-4-yl)piperazine-2-carbonitrile tert-Butyl 4-(7-chloro-6-(4-chlorophenyl)-2-methylquinazolin-4-yl)-2-cyanopiperazine-1-carboxylate (100 mg, 0.194 mmol) was dissolved in 20 mL of 20% HCl/Et$_2$O solution. The mixture was stirred at RT for 30 min and then concentrated in vacuo to yield a solid salt (44 mg, 87% yield). The above solid (44 mg, 0.101 mmol) was dissolved in 25 mL of DCM with Et$_3$N (51 mg, 0.505 mmol). The mixture was cooled to 0° C. and then a solution of acryloyl chloride (10 mg, 0.111 mmol) in dichloromethane (2 mL) was added. The resulting mixture was stirred at 0° C. for 40 min. The mixture was extracted with ethyl acetate. The organic layer was washed with saturated NaHCO$_3$ and brine, dried over Na$_2$SO$_4$ and concentrated. The residue was purified with silica chromatography (petroleum ether/ethyl acetate=2:1) to afford the desired product (24 mg, 52% yield) as a white solid. $^1$H NMR (400 MHz, DMSO-d6) δ: 8.01 (d, J=6.4 Hz, 2H), 7.63 (q, J=8.4, 20.4 Hz, 4H), 6.90 (dd, J=10.4, 16.4 Hz, 1H), 6.30 (m, 1H), 5.68 (s, 1H), 4.60 (m, 1H), 4.32 (m, 2H), 3.57 (m, 2H), 2.59 (s, 3H), 3.36 (m, 1H). ESI-MS m/z: 453.3 [M+H]$^+$.

Example 17

Synthesis of 1-(4-(7-chloro-6-(4-chlorophenyl)quinazolin-4-yl)-2-(2-Hydroxyethyl)piperazin-1-yl)prop-2-en-1-one (62)

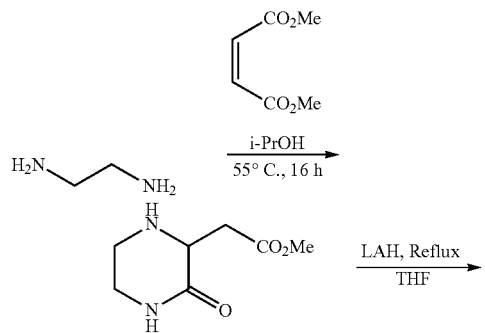

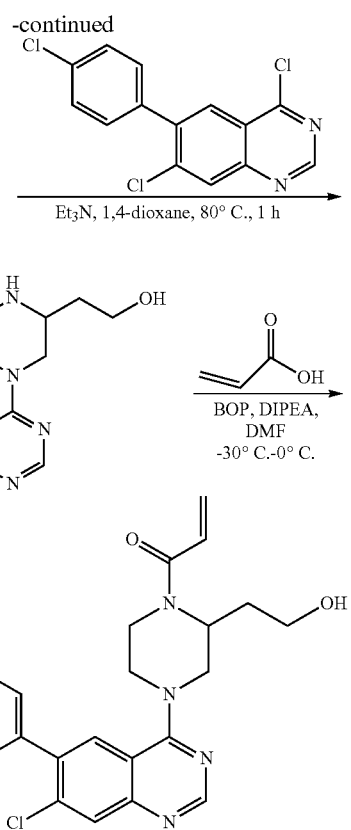

Compound 62 was prepared according to the general procedures of Method A as described below:

Methyl 2-(3-oxopiperazin-2-yl)acetate

To a solution of dimethyl maleate (4.0 g, 27.78 mmol) in propan-2-ol (40 mL) at RT, ethane-1,2-diamine (1.167 g, 27.78 mmol) was added. The resulting mixture was stirred at 55° C. for 16 h and concentrated in vacuo. The residue was washed by a mixture of ethyl acetate/petroleum ether=1:1 to afford the desired product (2.8 g, 59% yield) as a white solid.

2-(Piperazin-2-yl)ethanol

To a solution of methyl 2-(3-oxopiperazin-2-yl)acetate (1.82 g, 10.58 mmol) in THF (150 mL) at 0° C., LiAlH$_4$ (2.01 g, 52.9 mmol) was added. The resulting mixture was stirred at reflux for 16 h. Then the mixture was cooled to RT. It was quenched with 10H$_2$O.Na$_2$SO$_4$ and filtered, washed with ethyl acetate. The filtrated was dried over Na$_2$SO$_4$ and concentrated in vacuo to afford the desired product (674 mg, 49% yield) as a yellow oil.

2-(4-(7-Chloro-6-(4-chlorophenyl)quinazolin-4-yl)piperazin-2-yl)ethanol

A mixture of 4,7-dichloro-6-(4-chlorophenyl)quinazoline (150 mg, 0.48 mmol), 2-(piperazin-2-yl)ethanol (187 mg, 1.44 mmol), Et$_3$N (0.33 mL, 2.4 mmol), in 1,4-dioxane (5 mL) was stirred at 80° C. for 30 min. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:30) to afford the desired product (121 mg, 63% yield) as a colorless oil. ESI-MS m/z: 403.3 [M+H]$^+$.

1-(4-(7-Chloro-6-(4-chlorophenyl)quinazolin-4-yl)-2-(2-hydroxyethyl)piperazin-1-yl)prop-2-en-1-one To a solution of 2-(4-(7-chloro-6-(4-chlorophenyl)quinazolin-4-yl)piperazin-2-yl)ethanol (123 mg, 0.305 mmol), acrylic acid (24 mg, 0.336 mmol), BOP (270 mg, 0.61 mmol) in DMF (5 mL) at −30° C., DIEA (157 mg, 1.22 mmol) was added. The resulting mixture was warmed to 0° C. over 1 h, quenched with saturated NaHCO$_3$ solution, and then extracted with ethyl acetate. The organic layer was washed with saturated NaHCO$_3$ solution and brine, dried over Na$_2$SO$_4$ and concentrated in vacuo. The residue was purified by Pre-HPLC to afford the desired product (16 mg, 12% yield) as a light-yellow oil. $^1$H NMR (400 MHz, DMSO-d6) δ: 8.64 (s, 1H), 8.01 (s, 1H), 7.99 (s, 1H), 7.64-7.57 (m, 4H), 6.89-6.78 (m, 1H), 6.17-6.13 (m, 1H), 5.72 (dd, J=2.4, 10.4 Hz, 1H), 4.72-4.58 (m, 2H), 4.38-4.29 (m, 4H), 4.06-3.99 (m, 1H), 3.67-3.60 (m, 2H), 1.79-1.68 (m, 2H). ESI-MS m/z: 457.4 [M+H]$^+$.

Example 18

Synthesis of 2-(1-acryloyl-4-(7-chloro-6-(4-chlorophenyl)quinazolin-4-yl)piperazin-2-yl)acetonitrile (70)

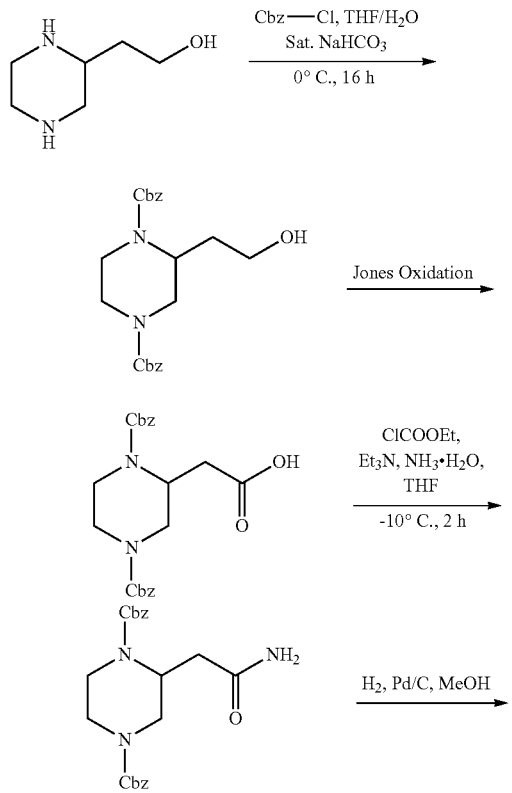

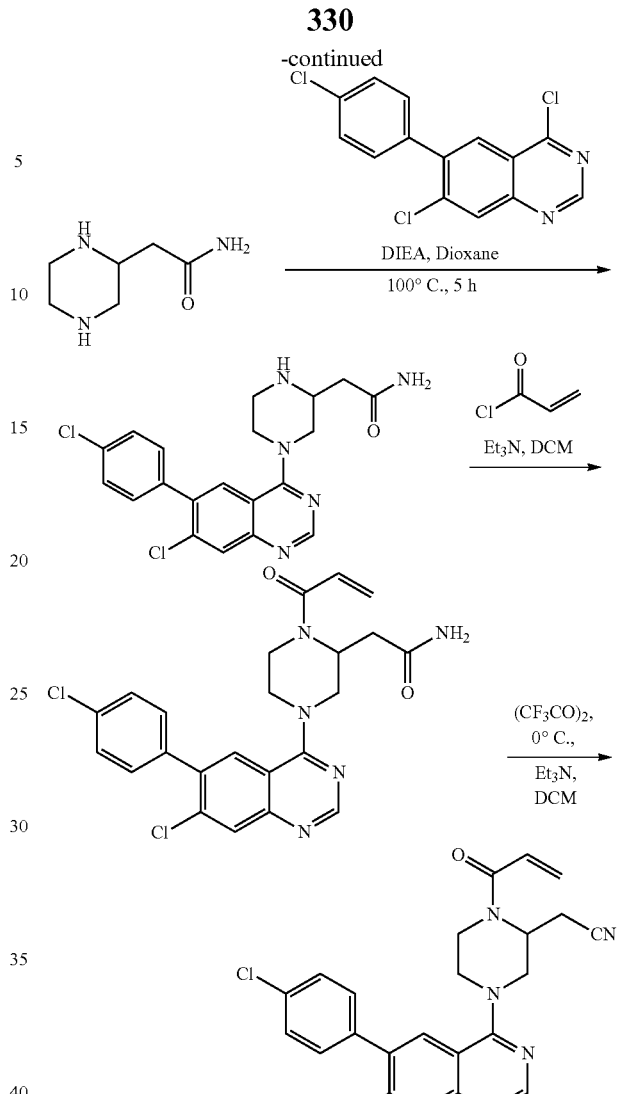

Compound 70 was prepared according to the general procedures of Method A as described below:

Dibenzyl 2-(2-hydroxyethyl)piperazine-1,4-dicarboxylate

To a solution of 2-(piperazin-2-yl)ethanol (2.0 g, 15.4 mmol) in THF (48 mL), H$_2$O (32 mL) and saturated NaHCO$_3$ (32 mL) at 0° C., Cbz-Cl (5.5 g, 32.3 mmol) was added dropwise. The mixture was stirred at 0° C. for 2 h and at RT for 16 h. The mixture was diluted with brine, extracted with dichloromethane. The organic layer was washed with brine, dried over Na$_2$SO$_4$ and concentrated. The residue was purified by flash column chromatography on silica gel (25%-50% ethyl acetate/petroleum ether) to afford the desired product (1.454 g, 23% yield) as a colorless oil. ESI-MS m/z: 399.4 [M+H]$^+$.

2-(1,4-Bis((benzyloxy)carbonyl)piperazin-2-yl)acetic acid

To a solution of dibenzyl 2-(2-hydroxyethyl)piperazine-1,4-dicarboxylate (515 mg, 1.294 mmol) in acetone (30 mL), Jones reagent (1.48 mL, 3.88 mmol, 2.6 M) was added dropwise at 0° C., which was stirred at RT for 1 h. The mixture was quenched with i-PrOH (2 mL) and filtered through celite. The filtrate was extracted with ethyl acetate. The organic layer was washed with brine, dried over $Na_2SO_4$ and concentrated to afford the crude product (545 mg) as a colorless oil. ESI-MS m/z: 413.2 [M+H]$^+$.

Dibenzyl 2-(2-amino-2-oxoethyl)piperazine-1,4-dicarboxylate

To a solution of 2-(1,4-bis((benzyloxy)carbonyl)piperazin-2-yl)acetic acid (545 mg, 1.323 mmol) and $Et_3N$ (535 mg, 5.292 mmol) in THF (20 mL), ethyl chloroformate (154 mg, 1.415 mmol) was added at −10° C. and stirred at this temperature for 40 min. Then the mixture was added $NH_3 \cdot H_2O$ (1.984 g, 15.87 mmol) at −10° C. and stirred for 20 min at −10° C. The mixture was partitioned between water and ethyl acetate. The organic layer was washed with brine, dried over $Na_2SO_4$ and concentrated. The residue was purified by flash column chromatography on silica gel (2% methanol/dichloromethane) to afford the desired product (393 mg, 72% yield) as a colorless oil. ESI-MS m/z: 412.3 [M+H]$^+$.

2-(Piperazin-2-yl)acetamide

A mixture of dibenzyl 2-(2-amino-2-oxoethyl)piperazine-1,4-dicarboxylate (385 mg, 0.937 mmol), Pd/C (10%, 40 mg) and MeOH (30 mL) was stirred at 40° C. for 2.5 h under $H_2$ (1 atm). The mixture was filtered through celite and concentrated to afford the crude product (188 mg) as a colorless oil.

2-(4-(7-Chloro-6-(4-chlorophenyl)quinazolin-4-yl)piperazin-2-yl)acetamide

A mixture of 4,7-dichloro-6-(4-chlorophenyl)quinazoline (313 mg, 1.315 mmol), 2-(piperazin-2-yl)acetamide (188 mg, 1.315 mmol), DIEA (848 mg, 6.575 mmol) and 1,4-dioxane (30 mL) at 100° C. for 5 h. The mixture was allowed to cool to RT and concentrated in vacuo. The residue was purified by flash column chromatography on silica gel (5-20% methanol/dichloromethane) to afford the desired product (78 mg, 14% yield) as a brown solid. ESI-MS m/z: 417.3 [M+H]$^+$.

2-(1-Acryloyl-4-(7-chloro-6-(4-chlorophenyl)quinazolin-4-yl)piperazin-2-yl)acetamide A mixture of 2-(4-(7-chloro-6-(4-chlorophenyl)quinazolin-4-yl)piperazin-2-yl)acetamide (78 mg, 0.1875 mmol), $Et_3N$ (76 mg, 0.750 mmol) and dichloromethane (30 mL) at 0° C., a solution of acryloyl chloride (21 mg, 0.225 mmol) in dichloromethane (2 mL) was added dropwise. The resulting mixture was stirred at 0° C. for 40 min. The mixture was quenched with saturated $NaHCO_3$ and extracted with ethyl acetate. The organic layer was washed with brine, dried over $Na_2SO_4$ and concentrated. The residue was purified with column chromatography on silica gel (2.5-4% methanol in dichloromethane) to afford the desired product (32 mg, 36% yield) as a white solid. $^1$H NMR (400 MHz, DMSO-d6) δ: 8.74 (s, 1H), 8.07 (s, 1H), 7.80 (s, 1H), 7.50-7.42 (dd, J=8.8, 14.4 Hz, 1H), 6.79-6.24 (m, 3H), 5.83 (m, 1H), 5.36-5.14 (m, 2H), 4.72-4.49 (m, 2H, 4.32 (m, 1H), 3.99-3.49 (m, 3H), 3.07-2.44 (m, 3H). ESI-MS m/z: 470.2 [M+H]$^+$.

2-(1-Acryloyl-4-(7-chloro-6-(4-chlorophenyl)quinazolin-4-yl)piperazin-2-yl)acetonitrile To a solution of 2-(1-acryloyl-4-(7-chloro-6-(4-chlorophenyl)quinazolin-4-yl)piperazin-2-yl)acetamide (25 mg, 0.0533 mmol) and $Et_3N$ (27 mg, 0.267 mmol) in DCM (10 mL) at 0° C., TFAA (46 mg, 0.214 mmol) and the resulting mixture was stirred at RT for 20 min. The reaction mixture was quenched with saturated $NaHCO_3$ solution, and then extracted with dichloromethane. The organic layer was washed with saturated $NaHCO_3$ solution and brine, dried over $Na_2SO_4$ and concentrated in vacuo. The residue was purified by flash column chromatographyon silica gel (2.5% methanol in dichloromethane) to afford the desired product (21 mg, 87% yield) as a white solid. $^1$H NMR (400 MHz, DMSO-d6) δ: 8.67 (s, 1H), 8.06 (m, 2H), 7.70 (s, 4H), 6.88 (m, 1H), 6.20 (d, J=10.0 Hz, 1H), 5.76 (s, 1H), 4.97 (m, 1H), 4.30 (m, 4H), 3.75 (m, 2H), 2.99 (m, 2H). ESI-MS m/z: 453.3 [M+H]$^+$.

Example 19

Synthesis of 4-(4-acryloyl-3-cyanopiperazin-1-yl)-7-chloroquinazoline-6-carbonitrile (53)

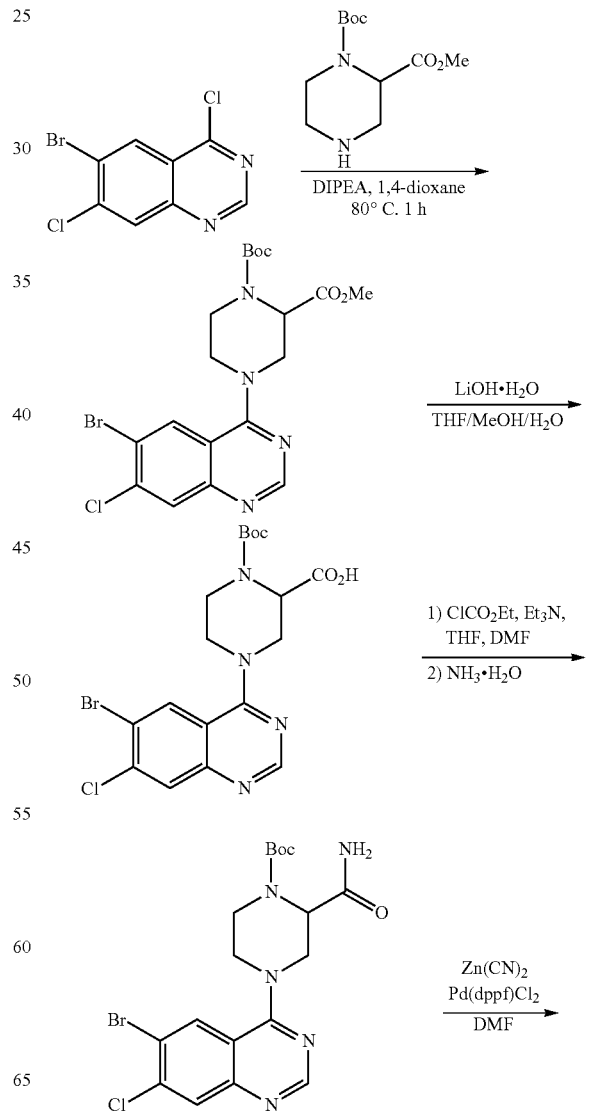

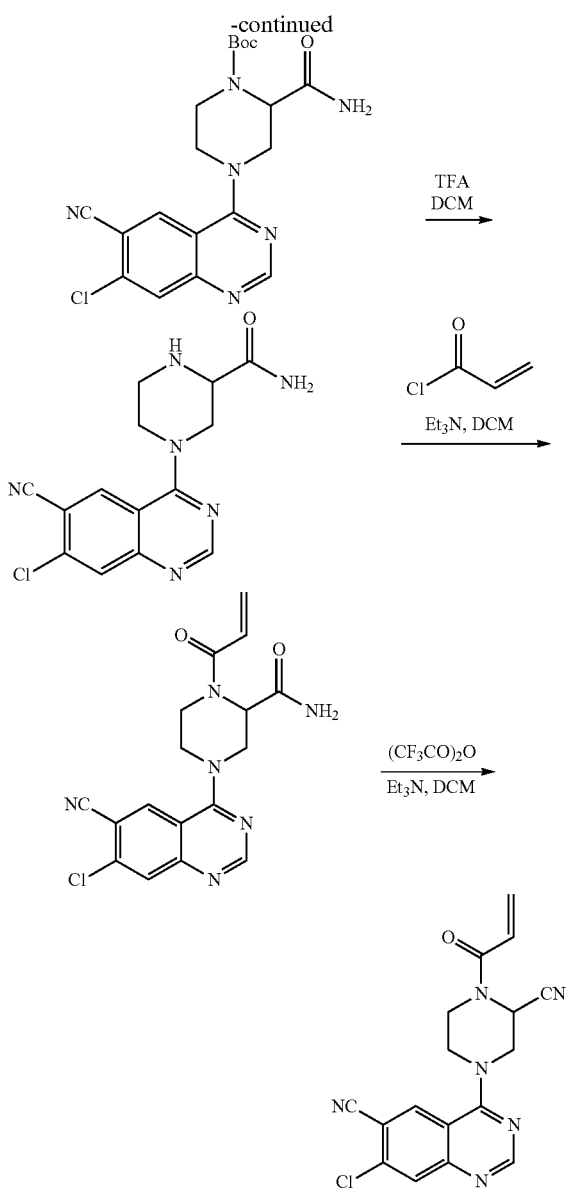

Compound 53 was prepared according to the general procedures of Method B as described below:

1-tert-Butyl 2-methyl 4-(6-bromo-7-chloroquinazolin-4-yl)piperazine-1,2-dicarboxylate A mixture of 6-bromo-4,7-dichloroquinazoline (300 mg, 1.08 mmol), tert-butyl methyl piperazine-1,2-dicarboxylate (395 mg, 1.62 mmol), DIEA (836 mg, 6.48 mmol) in 1,4-dioxane (8 mL) was stirred at 80° C. for 1 h. The mixture was allowed to cool to RT, quenched with saturated NaHCO₃ solution and then extracted with ethyl acetate. The organic layer was washed with brine, dried over Na₂SO₄, filtered and concentrated in vacuo. The residue was purified by flash column chromatography on silica gel (ethyl acetate/petroleum ether=1:5) to afford the desired product (367 mg, 70% yield) as a white solid.

1-(tert-Butoxycarbonyl)-4-(6-bromo-7-chloroquinazolin-4-yl)piperazine-2-carboxylic acid To a solution of 1-tert-butyl 2-methyl 4-(6-bromo-7-chloroquinazolin-4-yl)piperazine-1,2-dicarboxylate (100 mg, 0.206 mmol) in THF (2 mL), MeOH (2 mL) and water (2 mL), LiOH.H₂O (165 mg, 4.12 mmol) was added and the resulting mixture was stirred at RT for 1 h. The mixture was washed with 20% ethyl acetate/petroleum ether. The aqueous layer was acidified with aqueous HCl (1 N) to adjust pH to 5 and extracted with ethyl acetate. The organic layer was dried over MgSO4, filtered, and concentrated in vacuo to afford the desired product (65 mg, 67% yield).

tert-Butyl 4-(6-bromo-7-chloroquinazolin-4-yl)-2-carbamoylpiperazine-1-carboxylate To a mixture of 1-(tert-butoxycarbonyl)-4-(6-bromo-7-chloroquinazolin-4-yl)piperazine-2-carboxylic acid (65 mg, 0.14 mmol), Et₃N (0.11 mL, 0.77 mmol) in THF (4 mL) and DMF (2 mL) at 0° C., ethyl chloroformate (83 mg, 0.77 mmol) was added. The resulting mixture was stirred at 0° C. for 1 h and NH₃.H₂O (1 mL, 15 N) was added. Then the mixture was warmed to RT and stirred for another 1 h. It was quenched with saturated NaHCO₃ solution and then extracted with ethyl acetate. The organic layer was washed with brine, dried over Na₂SO₄, filtered and concentrated in vacuo to afford the crude product (77 mg) as a yellow solid. ESI-MS m/z: 471.4 [M+H]⁺.

tert-Butyl 2-carbamoyl-4-(7-chloro-6-cyanoquinazolin-4-yl)piperazine-1-carboxylate A mixture of tert-butyl 4-(6-bromo-7-chloroquinazolin-4-yl)-2-carbamoylpiperazine-1-carboxylate (200 mg, 0.43 mmol), PdCl₂(dppf) (31 mg, 0.043 mmol), Zn(CN)₂ (80 mg, 0.68 mmol) and DMF (20 mL) was stirred at reflux for 5 h. The mixture was allowed to cool to room temperature, and partitioned between ethyl acetate and water. The organic layer was washed with brine, dried over Na₂SO₄ and concentrated. The residue was purified by flash column chromatography on silica gel (1-2% methanol/dichloromethane) to afford the desired product (140 mg, 79% yield) as a solid. ESI-MS m/z: 417.3 [M+H]⁺.

4-(7-Chloro-6-cyanoquinazolin-4-yl)piperazine-2-carboxamide

A solution of tert-butyl 2-carbamoyl-4-(7-chloro-6-cyanoquinazolin-4-yl)piperazine-1-carboxylate (140 mg, 0.34 mmol) in dichloromethane (20 mL) at RT, TFA (2 mL) was added. The resulting mixture was stirred at RT for 2 h. The mixture was concentrated in vacuo to afford the crude product (100 mg) which was used directly in the next step without further purification.

1-Acryloyl-4-(7-chloro-6-cyanoquinazolin-4-yl)piperazine-2-carboxamide

A mixture of 4-(7-chloro-6-cyanoquinazolin-4-yl)piperazine-2-carboxamide (100 mg, 0.32 mmol), Et₃N (96 mg, 0.96 mmol) in dichloromethane (10 mL) at 0° C., acryloyl chloride (35 mg, 0.384 mmol) was added. The resulting mixture was stirred at RT for 0.5 h, poured into water and then extracted with dichloromethane. The organic layer was washed with brine, dried over Na₂SO₄ and concentrated. The residue was purified by flash column chromatography on silica gel (1-2% methanol/dichloromethane) to afford the desired product (50 mg, 43% yield) as a solid. ESI-MS m/z: 371.3 [M+H]⁺.

4-(4-Acryloyl-3-cyanopiperazin-1-yl)-7-chloroquinazoline-6-carbonitrile

A mixture of 1-acryloyl-4-(7-chloro-6-cyanoquinazolin-4-yl)piperazine-2-carboxamide (50 mg, 0.14 mmol) and Et₃N (82 mg, 0.81 mmol) in DCM (10 mL) at RT, trifluoroacetic anhydride (117.6 mg, 0.56 mmol) was added. The resulting mixture was stirred at RT for 0.5 h and poured into water and then extracted with dichloromethane. The organic layer was washed with brine, dried over Na₂SO₄ and concentrated. The residue was purified by flash column chromatography on silica gel (1-3% methanol/dichloromethane) to afford the desired product (15 mg, 32% yield). ¹H NMR (400 MHz, DMSO-d6) δ: 8.79 (s, 1H), 8.77 (s, 1H), 8.16 (s, 1H), 6.92-6.85 (m, 1H), 6.32-6.28 (m, 1H), 5.91-5.88 (m, 1H), 5.68 (s, 1H), 4.73-4.70 (d, J=14 Hz, 1H), 4.46-4.43 (d, J=13.2 Hz, 1H), 4.25-4.22 (d, J=12.8 Hz, 1H), 3.82-3.74 (m, 2H), 3.59-3.56 (m, 1H). ESI-MS m/z: 353.2 [M+H]⁺.

Example 20

Synthesis of 1-acryloyl-4-(7-chloro-6-cyclopropylquinazolin-4-yl)piperazine-2-carbonitrile (55)

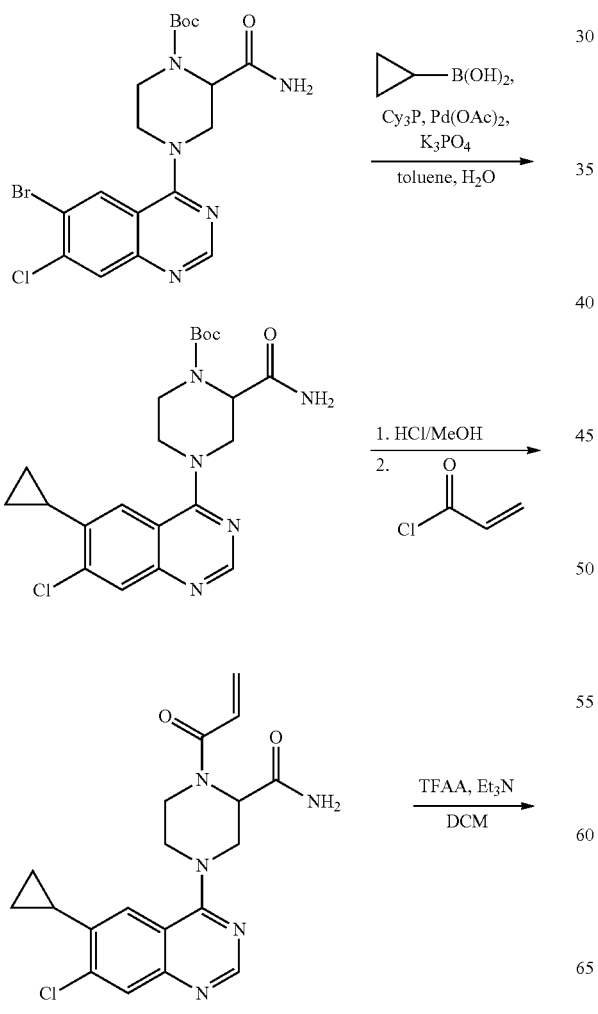

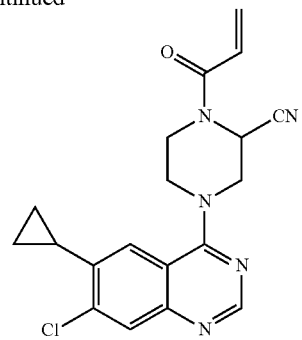

Compound 55 was prepared according to the general procedures of Method B as described below:

tert-Butyl 2-carbamoyl-4-(7-chloro-6-cyclopropylquinazolin-4-yl)piperazine-1-carboxylate A mixture of tert-butyl 4-(6-bromo-7-chloroquinazolin-4-yl)-2-carbamoylpiperazine-1-carboxylate (200 mg, 0.414 mmol), cyclopropylboronic acid (44 mg, 0.51 mmol), K₃PO₄·3H₂O (270 mg, 1.272 mmol), Pd(OAc)₂ (18 mg, 0.08 mmol) and tricyclohexyl phosphine (22 mg, 0.08 mmol) in toluene (10 mL) and water (1 mL) was stirred at reflux under argon for 16 h. The solvent was removed, and the residue was purified by flash column chromatography on silica gel (dichloromethane/methanol=50:1) to afford the desired product (100 mg, 56% yield) as a solid. ESI-MS m/z: 432.4 [M+H]⁺.

Acryloyl-4-(7-chloro-6-cyclopropylquinazolin-4-yl)piperazine-2-carboxamide

The title compound was prepared from tert-butyl 2-carbamoyl-4-(7-chloro-6-cyclopropylquinazolin-4-yl)piperazine-1-carboxylate in two steps following the procedure described in Example 1.

Acryloyl-4-(7-chloro-6-cyclopropylquinazolin-4-yl)piperazine-2-carboxamide

To a solution of 1-acryloyl-4-(7-chloro-6-cyclopropylquinazolin-4-yl)piperazine-2-carboxamide (17 mg, 0.044 mmol) and Et₃N (18 mg, 0.176 mmol) in DCM (5 mL) at 0° C., TFAA (18 mg, 0.088 mmol) was added and the resulting mixture was stirred at RT for 1 h. The reaction mixture was quenched with saturated NaHCO₃ solution, and then extracted with dichloromethane. The organic layer was washed with saturated NaHCO₃ solution and brine, dried over Na₂SO₄ and concentrated in vacuo. The residue was purified by flash column chromatography on silica gel (dichloromethane/methanol=50:1) to afford the desired product (10 mg, 62% yield) as a solid. ¹H NMR (400 MHz, CDCl3) δ: 8.8 (s, 1H), 8.0 (s, 1H), 7.7 (s, 1H), 6.6 (dd, J=10.0, 16.4 Hz, 1H), 6.5 (d, J=16.4 Hz, 1H), 6.0 (dd, J=2.0, 10.4 Hz, 1H), 6.0-5.9 (m, 1H), 4.4 (dd, J=2, 13.2 Hz, 1H), 4.3-4.1 (m, 2H), 3.9-3.8 (m, 1H), 3.3-3.1 (m, 2H), 2.4-2.3 (m, 1H), 1.2-1.1 (m, 2H), 1.0-0.9 (m, 2H). ESI-MS m/z: 368.3 [M+H]⁺.

Example 21

Synthesis of (S)-1-acryloyl-4-(7-chloro-6-(4-chlorophenyl)quinazolin-4-yl)piperazine-2-carboxamide (54)

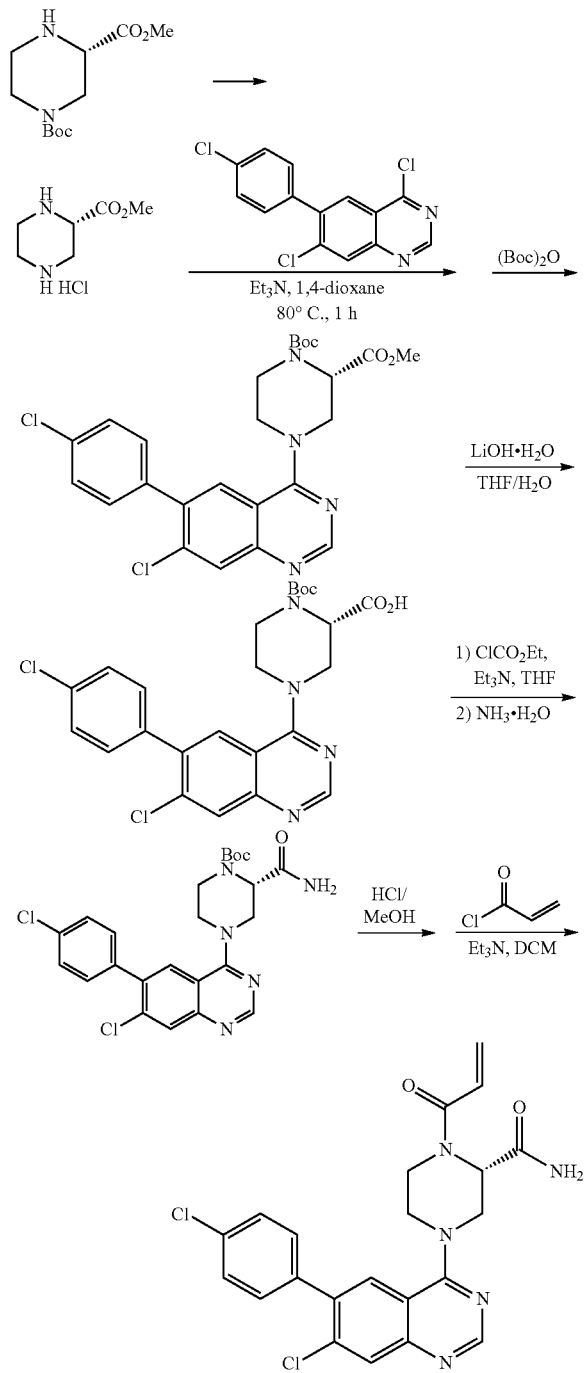

Compound 54 was prepared according to the general procedures of Method A as described below:

(S)-Methyl piperazine-2-carboxylate hydrochloride

A mixture of (S)-tert-butyl methyl piperazine-1,3-dicarboxylate (366 mg, 1.5 mmol) and HCl in MeOH (20 mL, 2.9 M) was stirred at RT for 1 h. The mixture was concentrated in vacuo to yield the crude product (270 mg) as a yellow solid which was used directly in next step without further purification.

(S)-1-tert-Butyl 2-methyl 4-(7-chloro-6-(4-chlorophenyl)quinazolin-4-yl)piperazine-1,2-dicarboxylate To the mixture of above obtained crude (S)-methyl piperazine-2-carboxylate hydrochloride, 4,7-dichloro-6-(4-chlorophenyl)quinazoline (310 mg, 1 mmol), DIEA (1.29 g, 10 mmol) and 1,4-dioxane (20 mL) was stirred for 1 h at 80° C. Then mixture was cooled to RT and di-tert butyl dicarbonate (327 mg, 1.5 mmol) was added. The mixture was stirred for 16 h and quenched with saturated $NaHCO_3$ solution and then extracted with ethyl acetate. The organic layer was washed with brine, dried over $Na_2SO_4$, filtered and concentrated in vacuo. The residue was purified by flash column chromatography on silica gel (methanol/dichloroethane=1:50) to afford the desired product (300 mg, 58% yield, 2 steps) as a solid oil. ESI-MS m/z: 517.5 $[M+H]^+$.

(S)-1-(tert-Butoxycarbonyl)-4-(7-chloro-6-(4-chlorophenyl)quinazolin-4-yl)piperazine-2-carboxylic acid To a solution of (S)-1-tert-butyl 2-methyl 4-(7-chloro-6-(4-chlorophenyl)quinazolin-4-yl)piperazine-1,2-dicarboxylate (300 mg, 0.58 mmol) in mixture of 1:1 tetrahydrofuran and water (20 mL) at RT, $LiOH \cdot H_2O$ (49 mg, 1.16 mmol) were added and the resulting mixture was stirred for 1 h and then acidified with aqueous HCl (1 N) to adjust the pH to 3-5. The mixture was extracted with ethyl acetate. The combined organic layer was washed with brine, dried over anhydrous $Na_2SO_4$, filtered and concentrated in vacuo to afford the crude product (230 mg) which was used directly in the next step without further purification.

(S)-tert-Butyl 2-carbamoyl-4-(7-chloro-6-(4-chlorophenyl)quinazolin-4-yl)piperazine-1-carboxylate To a mixture of (S)-1-(tert-butoxycarbonyl)-4-(7-chloro-6-(4-chlorophenyl)quinazolin-4-yl)piperazine-2-carboxylic acid (230 mg, 0.46 mmol), $Et_3N$ (139 mmg, 1.37 mmol) in THF (5 mL) at 0° C., ethyl chloroformate (148 mg, 1.37 mmol) was added. The resulting mixture was stirred at 0° C. for 1 h, then Ammonium hydroxide (1 mL, 15 N) was added and kept stirring for another 1 h at RT. The mixture was extracted with ethyl acetate dried over anhydrous $Na_2SO_4$, filtered and concentrated in vacuo. The residue was purified by flash column chromatography on silica gel (dichloromethane/methanol=50:1) to afford the desired product (150 mg, 65% yield) as a solid. ESI-MS m/z: 502.4 $[M+H]^+$.

(S)-1-Acryloyl-4-(7-chloro-6-(4-chlorophenyl)quinazolin-4-yl)piperazine-2-carboxamide The title compound was prepared from (S)-tert-butyl 2-carbamoyl-4-(7-chloro-6-(4-chlorophenyl)quinazolin-4-yl)piperazine-1-carboxylate in 2 steps according to the procedure described in Example 1. $^1H$ NMR (400 MHz, DMSO-d6) δ: 8.7 (s, 1H), 8.3 (d, J=8.0 Hz, 1H), 8.0 (s, 1H), 7.8-7.5 (m, 5H), 7.4-7.2 (m, 1H), 6.9-6.6 (m, 1H), 6.2 (d, J=2.4, 17.6 Hz, 1H), 5.8-5.7 (m, 1H), 5.0-4.8 (m, 1H), 4.7 (d, J=13.2 Hz, 1H), 4.2-4.0 (m, 2H), 3.9-3.8 (m, 1H), 3.7-3.5 (m, 1H), 3.5-3.4 (m, 1H). ESI-MS m/z: 456.3 $[M+H]^+$.

Example 22

Synthesis of (S)-1-acryloyl-4-(7-chloro-6-(4-chlorophenyl)quinazolin-4-yl)piperazine-2-carbonitrile (59)

Example 23

Synthesis of (S)-1-(4-(7-chloro-6-(4-chlorophenyl)quinazolin-4-yl)-2-(hydroxymethyl)piperazin-1-yl)prop-2-en-1-one (63)

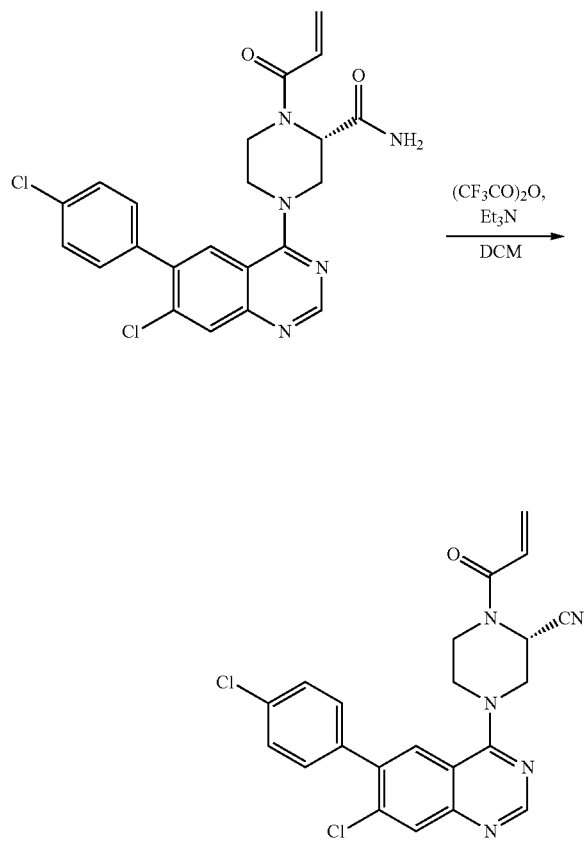

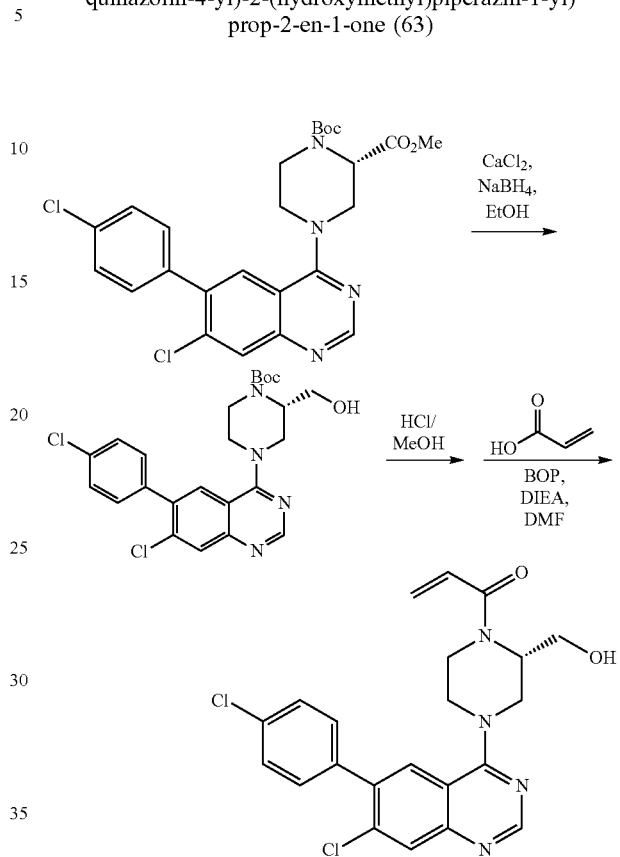

Compound 59 was prepared according to the general procedures of Method A as described below:

(S)-1-Acryloyl-4-(7-chloro-6-(4-chlorophenyl)quinazolin-4-yl)piperazine-2-carbonitrile To a solution of (S)-1-acryloyl-4-(7-chloro-6-(4-chlorophenyl)quinazolin-4-yl)piperazine-2-carboxamide (23 mg, 0.05 mmol) and Et$_3$N (20 mg, 0.2 mmol) in DCM (5 mL) at 0° C., trifluoroacetic anhydride (21 mg, 0.1 mmol) and the resulting mixture was stirred at RT for 1 h. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatographyon on silica gel (dichloromethane/methanol=50:1) to afford the desired product (15 mg, 68% yield) as a solid. $^1$H NMR (400 MHz, DMSO-d6) δ: 8.7 (s, 1H), 8.1 (s, 1H), 8.0 (s, 1H), 7.5 (m, 4H), 6.8 (dd, J=10.4, 16.4 Hz, 1H), 6.3 (dd, J=2.0, 17.2 Hz, 1H), 5.8 (dd, J=2.0, 10.8 Hz, 1H), 5.7 (m, 1H), 4.6 (d, J=14.0 Hz, 3H), 4.3 (m, 2H), 3.6 (m, 2H). ESI-MS m/z: 438.3 [M+H]$^+$.

Compound 63 was prepared according to the general procedures of Method A as described below:

(S)-tert-Butyl 4-(7-chloro-6-(4-chlorophenyl)quinazolin-4-yl)-2-(hydroxymethyl)piperazine-1-carboxylate To a solution of (S)-1-tert-butyl 2-methyl 4-(7-chloro-6-(4-chlorophenyl)quinazolin-4-yl)piperazine-1,2-dicarboxylate (200 mg, 0.387 mmol) in EtOH (10 mL) was added CaCl$_2$ (215 mg, 1.933 mmol) and NaBH$_4$ (74 mg, 1.933 mmol) at 0° C. The mixture was stirred at RT for 16 h. The mixture was filtered, and washed by ethylanol. The mixture was concentrated in vacuo, and the residue was purified by flash column chromatography on silica gel (dichloromethane/methanol=50:1) to afford the desired product (80 mg, 42% yield) as a solid. ESI-MS m/z: 489.4 [M+H]$^+$.

1-((S)-4-(7-Chloro-6-(4-chlorophenyl)quinazolin-4-yl)-2-(hydroxymethyl)piperazin-1-yl)prop-2-en-1-one The title compound was prepared from (S)-tert-butyl 4-(7-chloro-6-(4-chlorophenyl)quinazolin-4-yl)-2-(hydroxymethyl)piperazine-1-carboxylate in two steps according to the procedure described in Example 13. $^1$H NMR (400 MHz, DMSO-d6) δ: 8.7 (s, 1H), 8.3-8.1 (m, 1H), 8.0 (s, 1H), 7.7-7.5 (m, 4H), 6.8 (dd, J=10.4, 16.4 Hz, 1H), 6.1 (d, J=16

Hz, 1H), 5.8 (dd, J=2, 10.4 Hz, 1H), 5.1-4.9 (m, 1H), 4.3-4.1 (m, 4H), 4.2 (m, 2H), 3.7-3.5 (m, 4H). ESI-MS m/z: 443.3 [M+H]⁺.

Example 24

Synthesis of 1-(4-(6-chloro-7-phenylquinazolin-4-yl)piperazin-1-yl)prop-2-en-1-one (67)

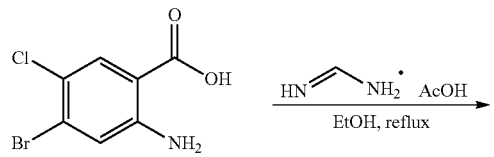

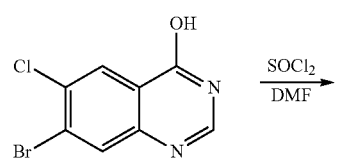

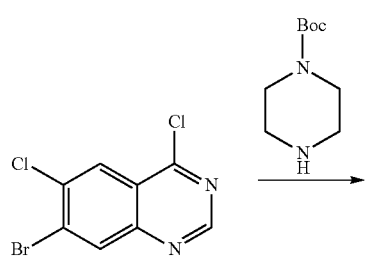

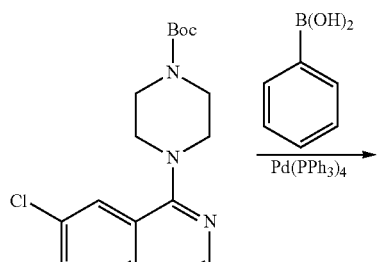

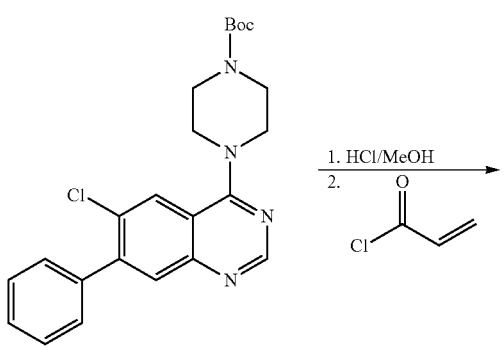

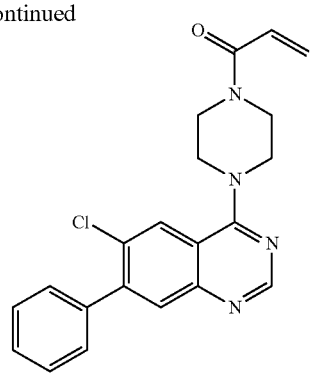

Compound 67 was prepared according to the general procedures of Method B as described below:

7-Bromo-6-chloroquinazolin-4-ol

To a solution of 2-amino-4-bromo-5-chlorobenzoic acid (500 mg, 2 mmol) in EtOH (20 mL) at RT, formamidine acetate (620 mg, 6 mmol) was added. The mixture was reflux for 16 hour. The mixture was concentrated in vacuo, and the residue was washed by saturated NaHCO₃ aqueous solution, and a mixture of ethyl acetate/petroleum ether=1:2. The solid was dried in vacuo to get the product (520 mg, 100% yield) which was used directly in next step without further purification. ESI-MS m/z: 259.0 [M+H]⁺.

7-Bromo-4,6-dichloroquinazoline

To a solution of 7-bromo-6-chloroquinazolin-4-ol (520 mg, 2 mmol) in thionyl chloride (15 mL) was added one drop of DMF. The mixture was reflux for 16 h. The mixture was concentrated in vacuo, the residue was used directly in next step without further purification.

1-(4-(6-Chloro-7-phenylquinazolin-4-yl)piperazin-1-yl)prop-2-en-1-one

The title compound was prepared from 7-bromo-4,6-dichloroquinazoline in four steps according to the procedure described in Example 2. ¹H NMR (400 MHz, DMSO) δ: 8.7 (s, 1H), 8.2 (s, 1H), 7.8 (s, 1H), 7.6-7.4 (m, 5H), 6.85 (dd, J=10.8, 16.8 Hz, 1H), 6.2 (d, J=16.8 Hz, 1H), 5.75 (d, J=10 Hz, 1H), 3.9-3.7 (m, 8H). ESI-MS m/z: 379.3 [M+H]⁺.

Example 25

Synthesis of 1-(4-(7-chloro-6-(4-chlorophenyl)quinazolin-4-yl)-2-((dimethylamino)methyl)piperazin-1-yl)prop-2-en-1-one (60)

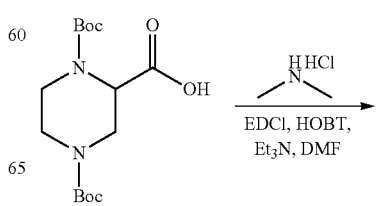

343

-continued

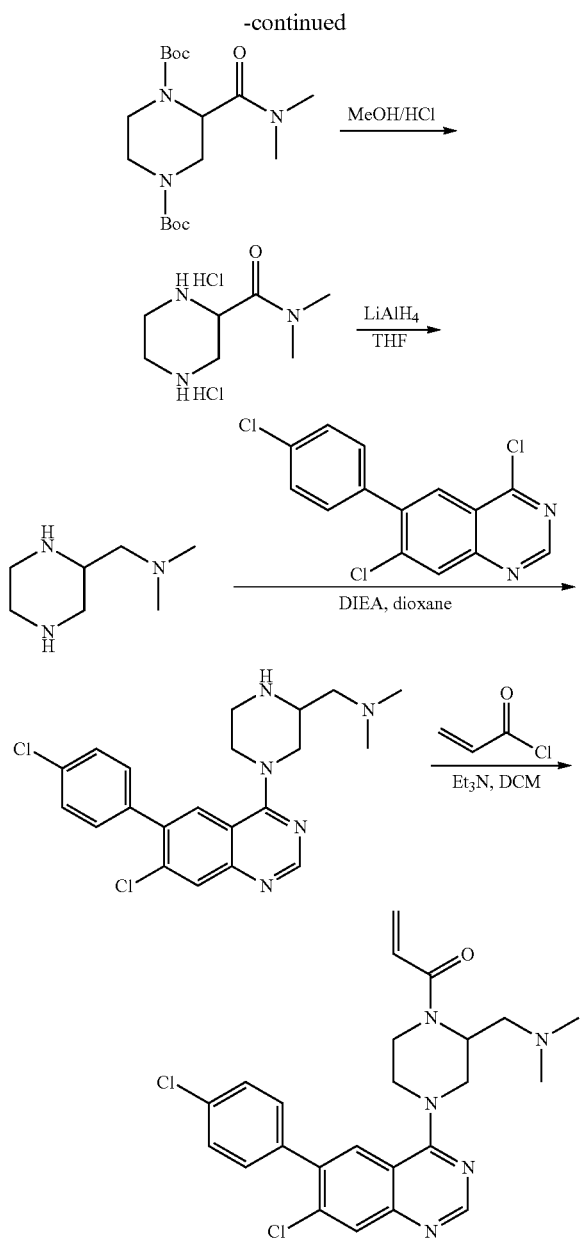

Compound 60 was prepared according to the general procedures of Method A as described below:

di-tert-Butyl
2-(dimethylcarbamoyl)piperazine-1,4-dicarboxylate

A mixture of 1,4-bis(tert-butoxycarbonyl)piperazine-2-carboxylic acid (5 g, 15.13 mmol), dimethylamine hydrochloride (1.3 g, 15.13 mmol), EDCI (4.3 g, 22.7 mmol), HOBt (3.1 g, 22.7 mmol) and DMF (100 mL) at 0° C., Et$_3$N (4.6 g, 45.39 mmol) was added. The mixture was then warmed to RT and kept stirring for 2 h. The reaction mixture was poured into water, extracted with ethyl acetate, the combined organic layer was washed with NaHCO$_3$ solution, brine and dried over Na$_2$SO$_4$ and concentrated. The residue was washed with petroleum ether to afford the desired product (3.64 g, 67% yield).

344

N,N-Dimethylpiperazine-2-carboxamide dihydrochloride

A mixture of the above obtained crude of di-tert-butyl 2-(dimethylcarbamoyl)piperazine-1,4-dicarboxylate, HCl in MeOH (50 mL, 2.9 M) was stirred at RT for 1 h, evaporated the solvent to afford the crude product (2.4 g).

N,N-Dimethyl-1-(piperazin-2-yl)methanamine

A mixture of the above obtained crude of N,N-dimethylpiperazine-2-carboxamide dihydrochloride (2.4 g, 10.43 mmol) and THF (50 mL) at −40° C., LiAlH$_4$ (1.6 g, 41.73 mmol) was added slowly. The mixture was heated to reflux for 3 h and cooled to RT. It was quenched with 10H$_2$O.Na$_2$SO$_4$ and filtered, washed with ethyl acetate. The filtrated was dried over Na$_2$SO$_4$ and concentrated in vacuo to afford the desired product (693 mg, 47% yield).

1-(4-(7-Chloro-6-(4-chlorophenyl)quinazolin-4-yl) piperazin-2-yl)-N,N-dimethylmethanamine A mixture of N,N-dimethyl-1-(piperazin-2-yl)methanamine (200 mg, 0.68 mmol), 4,7-dichloro-6-(4-chlorophenyl)quinazoline (111 mg, 0.77 mmol), DIEA (397 mg, 3.08 mmol) and dioxane (10 mL) was stirred at 80° C. for 30 min. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:20) to afford the desired product (78 mg, 30% yield). ESI-MS m/z: 416.3 [M+H]$^+$.

1-(4-(7-Chloro-6-(4-chlorophenyl)quinazolin-4-yl)-2-((dimethylamino)methyl)piperazin-1-yl)prop-2-en-1-one A mixture of 1-(4-(7-chloro-6-(4-chlorophenyl)quinazolin-4-yl)piperazin-2-yl)-N,N-dimethylmethanamine (78 mg, 0.19 mmol), Et$_3$N (58 mg, 0.57 mmol) and dichloromethane (15 mL) at 0° C., acryloyl chloride (20 mg, 0.22 mmol) was added. The reaction was stirred at RT for 30 min and quenched with water, extracted with dichloromethane. The organic layer was washed with water and brine, anhydrous sodium sulfate, filtered and concentrated in vacuo. The residue was purified by flash column chromatography on silica gel (dichloromethane/methanol=30:1) to afford the desired product (32 mg, 36% yield). $^1$H NMR (400 MHz, DMSO-d6) δ: 8.70 (s, 1H), 8.57-8.56 (bs, 1H), 8.03 (s, 1H), 7.61-7.53 (m, 4H), 6.83-6.80 (m, 1H), 6.17-6.13 (m, 1H), 5.75-5.72 (m, 1H), 4.76-4.74 (m, 0.5H), 4.70-4.57 (m, 1H), 4.36-3.29 (m, 2H), 4.11-4.08 (m, 0.5H), 3.46 (m, 1H), 3.27-3.11 (m, 2H), 2.93-2.84 (m, 1H), 1.99-1.94 (m, 1H), 1.87 (s, 6H). ESI-MS m/z: 470.4 [M+H]$^+$.

Example 26

Synthesis of 1-acryloyl-4-(6-chloroisoquinolin-1-yl) piperazine-2-carbonitrile (61)

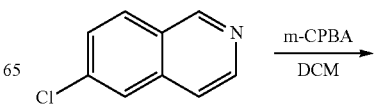

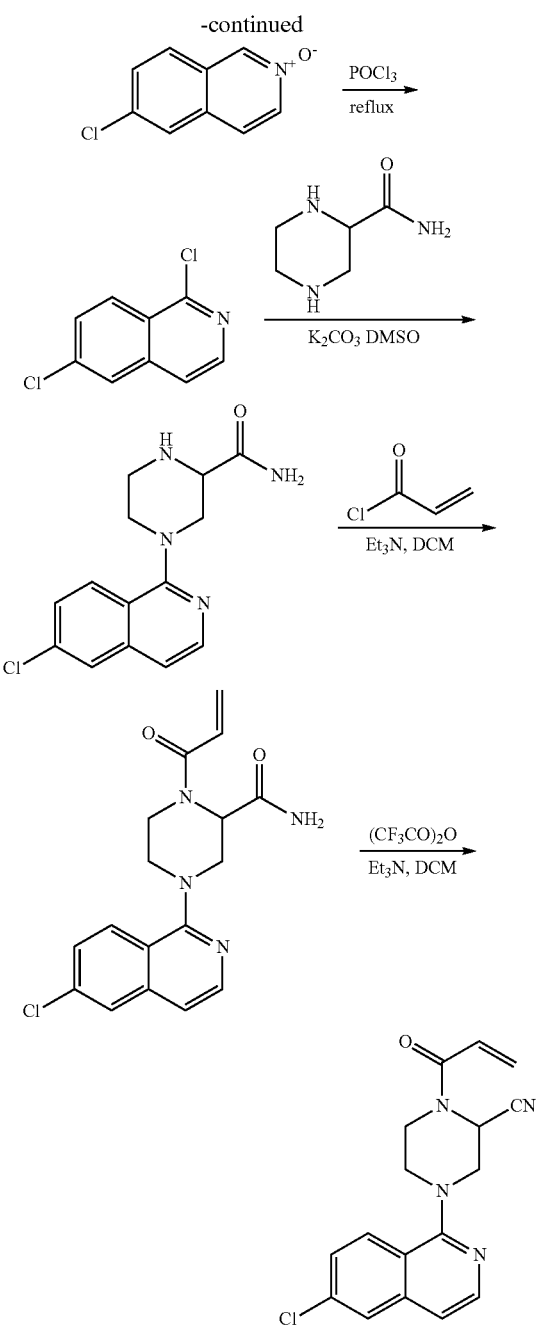

Compound 61 was prepared according to the general procedures of Method D as described below:

6-Chloroisoquinoline 2-oxide

To a stirred solution 6-chloroisoquinoline (1.0 g, 6.1 mmol) in dichloromethane (20 mL) at RT, 3-chlorobenzoperoxoic acid (1.57 g, 9.2 mmol) was added. The reaction mixture was stirred at RT for 2 h. The precipitate was filtered off and washed with dichloromethane, the filtrate was washed twice with NaHCO$_3$ solution. The organic layer was dried with Na$_2$SO$_4$ and concentrated in vacuo to afford the desired product (1.05 g, 96% yield) as a white solid. ESI-MS m/z: 180.2 [M+H]$^+$.

1,6-Dichloroisoquinoline

A mixture of 6-chloroisoquinoline 2-oxide (1.0 g, 5.58 mmol) and POCl$_3$ (10 mL) was heated to reflux for 4 h. After cooled down to RT, the reaction mixture was poured into ice-water, and extracted with dichloromethane. The organic layer was dried over anhydrous Na$_2$SO$_4$, filtered and concentrated in vacuo to afford the desired crude product which was used in the next step without further purification.

4-(6-Chloroisoquinolin-1-yl)piperazine-2-carboxamide

To a stirred solution of 1,6-dichloroisoquinoline (500 mg, 2.56 mmol) in DMSO (5 mL) at RT, piperazine-2-carboxamide (425.6 mg, 2.56 mmol) and K$_2$CO$_3$ (1.05 g, 7.68 mmol). The reaction mixture was heated at 80° C. for 5 h. The reaction mixture was diluted with ethyl acetate and washed with brine. The organic layer was dried over anhydrous Na$_2$SO$_4$, filtered and concentrated in vacuo. The residue was purified by flash column chromatography on silica gel (ethyl acetate/petroleum ether=1:5) to afford the desired product (80 mg, 12% yield). ESI-MS m/z: 291[M+H]$^+$.

Acryloyl-4-(6-chloroisoquinolin-1-yl)piperazine-2-carboxamide

To a mixture of 4-(6-chloroisoquinolin-1-yl)piperazine-2-carboxamide (50 mg, 0.172 mmol), triethylamine (52.1 mg, 0.51 mmol) in dichloromethane (20 mL), acryloyl chloride (15.6 mg, 0.172 mmol) in dichloromethane (1 mL) was added dropwise. The reaction mixture was stirred at RT for 30 min, poured into water, and extracted with dichloromethane. The organic layer was washed with water and brine, dried over Na$_2$SO$_4$ and concentrated in vacuo. The residue was purified by flash column chromatography on silica gel (dichloromethane/methanol=100:1) to afford the desired product (45 mg, 76.3% yield). ESI-MS m/z: 345 [M+H]$^+$.

Acryloyl-4-(6-chloroisoquinolin-1-yl)piperazine-2-carbonitrile

To a mixture of 1-acryloyl-4-(6-chloroisoquinolin-1-yl)piperazine-2-carboxamide (40 mg, 0.116 mmol), triethylamine (46.8 mg, 0.46 mmol) in DCM (5 mL) at 0° C., trifluoroacetic anhydride (50 mg, 0.233 mmol) was added. The reaction mixture was warmed to RT over 1 h, poured into water and extracted with dichloromethane. The organic layer was washed with water and brine, dried over Na$_2$SO$_4$ and concentrated in vacuo. The residue was purified by flash column chromatography on silica gel (dichloromethane/methanol=100:1) to afford the desired product (20 mg, 53% yield). $^1$H NMR (400 MHz, DMSO-d6) δ: 8.25 (m, 1H), 8.22 (m, 1H), 8.11 (s, 1H), 7.71 (m, 1H), 7.52 (m, 1H), 6.96 (dd, J=10.5, 16.9 Hz, 1H), 6.32 (dd, J=1.7, 16.7 Hz, 1H), 5.90 (dd, J=1.7, 16.7 Hz, 1H), 5.79 (m, 1H), 4.34 (m, 1H), 3.99 (m, 1H), 3.79 (m, 1H), 3.66 (m, 1H), 3.16 (m, 1H), 2.97 (m, 1H). ESI-MS m/z: 327 [M+H]$^+$.

Example 27

Synthesis of (E)-4-(7-chloro-6-(4-chlorophenyl) quinazolin-4-yl)-1-(4-(dimethylamino)but-2-enoyl) piperazine-2-carbonitrile (66)

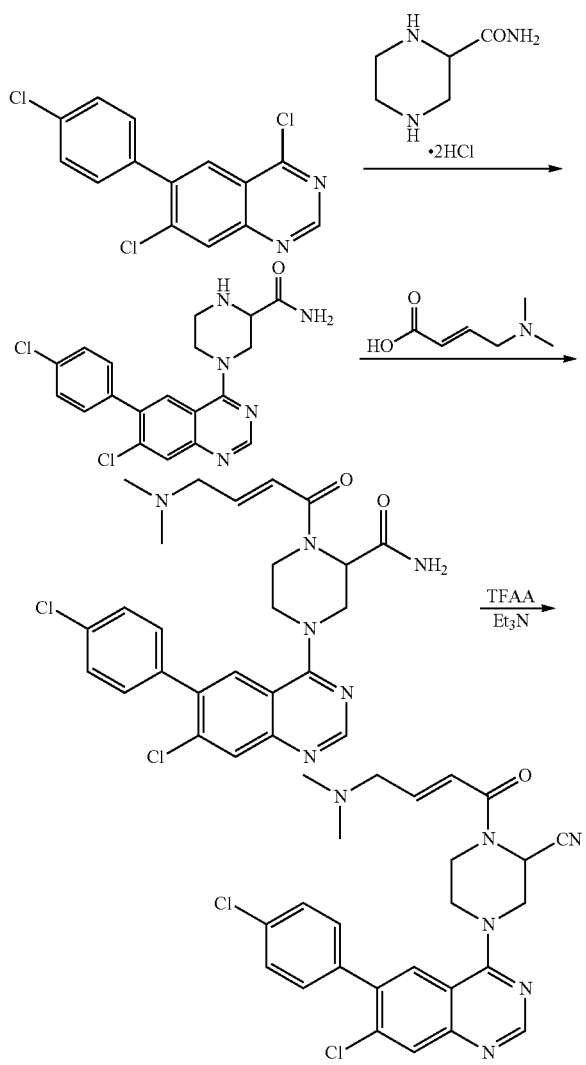

Compound 66 was prepared according to the general procedures of Method A as described below:

4-(7-Chloro-6-(4-chlorophenyl)quinazolin-4-yl)piperazine-2-carboxamide

A mixture of 4,7-dichloro-6-(4-chlorophenyl)quinazoline (769 mg, 2.48 mmol), piperazine-2-carboxamide dihydrochloride (498 mg, 2.48 mmol), DIPEA (3.2 g, 24.8 mmol) and 1,4-dioxane (20 mL) was stirred at 80° C. for 16 h. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:20) to afford the desired product (486 mg, 48.7% yield).

(E)-4-(7-Chloro-6-(4-chlorophenyl)quinazolin-4-yl)-1-(4-(dimethylamino)but-2-enoyl)piperazine-2-carboxamide To a mixture of 4-(7-chloro-6-(4-chlorophenyl)quinazolin-4-yl)piperazine-2-carboxamide (100 mg, 0.26 mmol), BOP (256.6 mg, 0.58 mmol), (E)-4-(dimethylamino)but-2-enoic acid (48 mg, 0.58 mmol) in dichloromethane (10 ml) at RT, DIEA (108.6 mg, 0.78 mmol) was added. The mixture was stirred for 30 min, extracted with ethyl acetate. The organic layer was washed with brine, dried over Na$_2$SO$_4$, filtered and concentrated in vacuo. The residue was purified by flash column chromatography on silica gel (methanol/dichloroethane=1:10) to afford the desired product (50 mg, 39% yield). ESI-MS m/z: 513.3 [M+H]$^+$

(E)-4-(7-Chloro-6-(4-chlorophenyl)quinazolin-4-yl)-1-(4-(dimethylamino)but-2-enoyl)piperazine-2-carbonitrile To a solution of (E)-4-(7-chloro-6-(4-chlorophenyl)quinazolin-4-yl)-1-(4-(dimethylamino)but-2-enoyl)piperazine-2-carboxamide (50 mg, 0.10 mmol) and Et$_3$N (0.05 mL, 0.40 mmol) in DCM (10 mL) at 0° C., TFAA (51 mg, 0.20 mmol) and the resulting mixture was stirred at RT for 1 h. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatography on silica gel (dichloromethane/methanol=20:1) to afford the desired product (14 mg, 29% yield) as a solid. $^1$H NMR (400 MHz, DMSO-d6) δ: 8.76 (s, 1H), 8.08 (d, J=16 Hz, 2H), 7.61 (dd, J=8, 24 Hz, 4H), 6.78-6.72 (m, 2H), 5.67 (s, 1H), 4.62 (d, J=14.4 Hz, 1H), 4.36-4.26 (m, 2H), 3.63 (d, J=12.4 Hz, 1H), 3.21 (s, 2H), 3.03 (d, J=6.4 Hz, 2H), 2.26 (s, 1H). ESI-MS m/z: 495.4 [M+H]$^+$.

Example 28

Synthesis of 1-(4-(7-(2-fluorophenyl)-6-hydroxyquinazolin-4-yl)piperazin-1-yl)prop-2-en-1-one

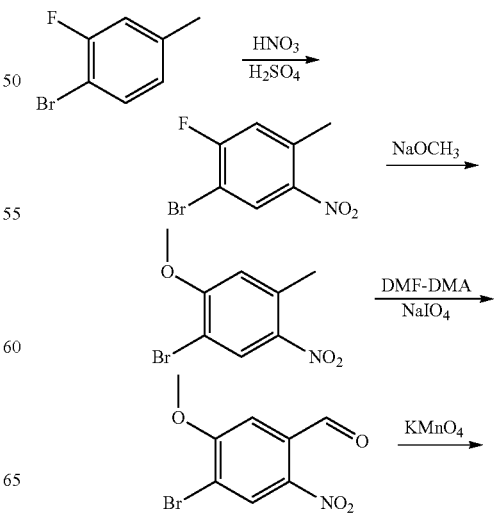

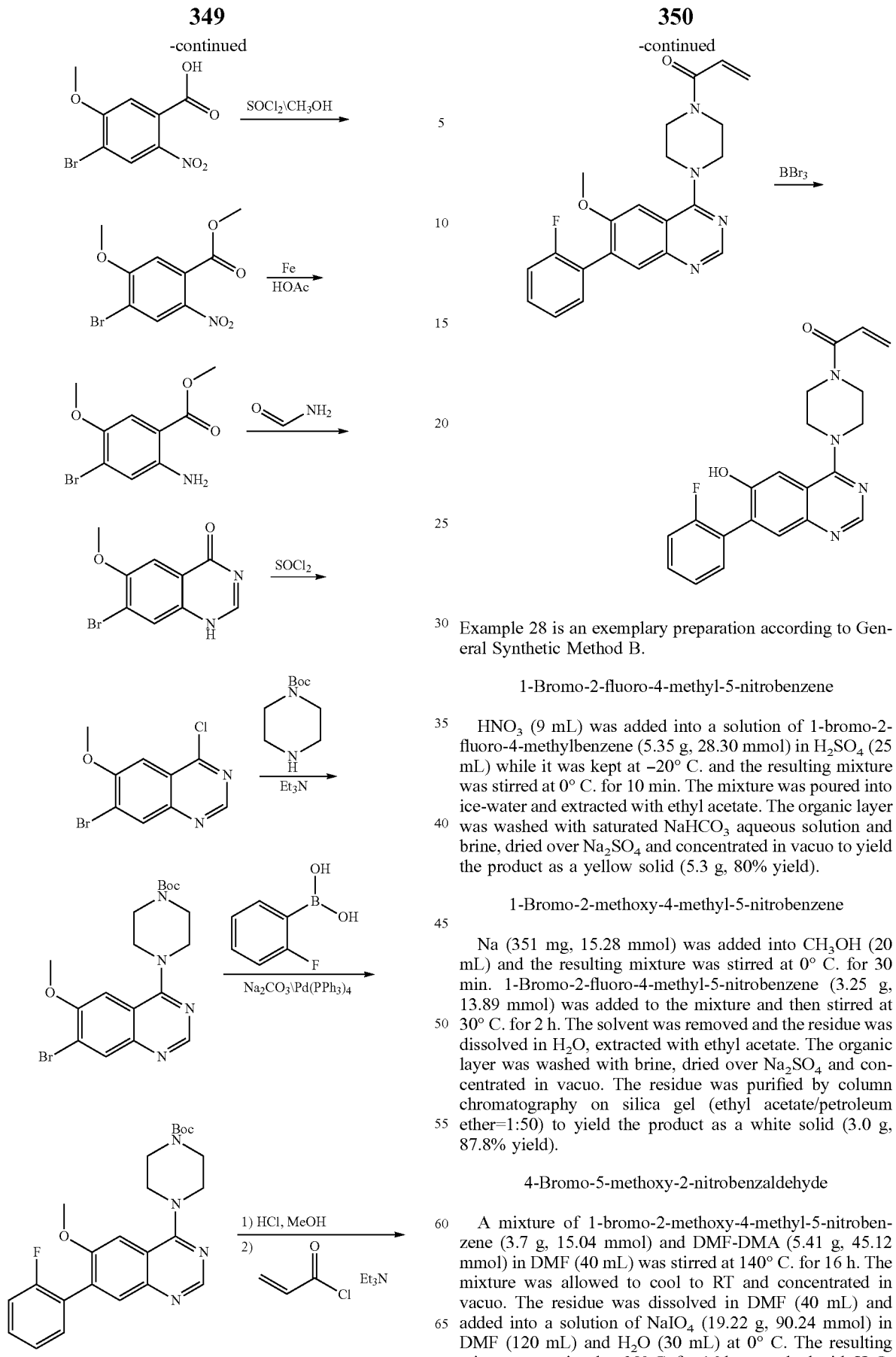

Example 28 is an exemplary preparation according to General Synthetic Method B.

1-Bromo-2-fluoro-4-methyl-5-nitrobenzene

HNO$_3$ (9 mL) was added into a solution of 1-bromo-2-fluoro-4-methylbenzene (5.35 g, 28.30 mmol) in H$_2$SO$_4$ (25 mL) while it was kept at −20° C. and the resulting mixture was stirred at 0° C. for 10 min. The mixture was poured into ice-water and extracted with ethyl acetate. The organic layer was washed with saturated NaHCO$_3$ aqueous solution and brine, dried over Na$_2$SO$_4$ and concentrated in vacuo to yield the product as a yellow solid (5.3 g, 80% yield).

1-Bromo-2-methoxy-4-methyl-5-nitrobenzene

Na (351 mg, 15.28 mmol) was added into CH$_3$OH (20 mL) and the resulting mixture was stirred at 0° C. for 30 min. 1-Bromo-2-fluoro-4-methyl-5-nitrobenzene (3.25 g, 13.89 mmol) was added to the mixture and then stirred at 30° C. for 2 h. The solvent was removed and the residue was dissolved in H$_2$O, extracted with ethyl acetate. The organic layer was washed with brine, dried over Na$_2$SO$_4$ and concentrated in vacuo. The residue was purified by column chromatography on silica gel (ethyl acetate/petroleum ether=1:50) to yield the product as a white solid (3.0 g, 87.8% yield).

4-Bromo-5-methoxy-2-nitrobenzaldehyde

A mixture of 1-bromo-2-methoxy-4-methyl-5-nitrobenzene (3.7 g, 15.04 mmol) and DMF-DMA (5.41 g, 45.12 mmol) in DMF (40 mL) was stirred at 140° C. for 16 h. The mixture was allowed to cool to RT and concentrated in vacuo. The residue was dissolved in DMF (40 mL) and added into a solution of NaIO$_4$ (19.22 g, 90.24 mmol) in DMF (120 mL) and H$_2$O (30 mL) at 0° C. The resulting mixture was stirred at 30° C. for 16 h, quenched with H$_2$O, and then extracted with ethyl acetate. The organic layer was washed with brine, dried over Na$_2$SO$_4$ and concentrated in vacuo, the residue was purified by column chromatography on silica gel (acetate/petroleum ether=1:20) to yield the product as an off-white solid (1.52 g, 38.9% yield).

4-Bromo-5-methoxy-2-nitrobenzoic acid

A mixture of 4-bromo-5-methoxy-2-nitrobenzoic acid (1.52 g, 5.84 mmol) and KMnO$_4$ (5.53 g, 35.04 mmol) in CH$_3$CN (40 mL) was stirred at reflux for 2 h. The mixture was allowed to cool to RT, quenched with H$_2$O, adjusted pH to 3-4 with 1N HCl, and then extracted with ethyl acetate. The organic layer was washed with brine, dried over Na$_2$SO$_4$ and concentrated in vacuo to yield the product as an off-white solid (1.24 g, 77.4% yield).

methyl 4-bromo-5-methoxy-2-nitrobenzoate

A mixture of 4-bromo-5-methoxy-2-nitrobenzoic acid (1.24 g, 4.52 mmol) and SOCl$_2$ (5 mL) in CH$_3$OH (10 mL) was stirred at reflux for 2 h, Then solvent was removed and the residue was dissolved in H$_2$O, extracted with ethyl acetate. The organic layer was washed with brine, dried over Na$_2$SO$_4$ and concentrated to yield the product as an off-white solid (1.3 g, 99% yield).

Methyl 2-amino-4-bromo-5-methoxybenzoate

A mixture of methyl 4-bromo-5-methoxy-2-nitrobenzoate (1.3 g, 4.48 mmol) and Fe (1.25 g, 22.4 mmol) in acetic acid (10 mL) and H$_2$O (10 mL) was stirred at reflux for 16 h. The mixture was allowed to cool to RT and quenched with saturated NaHCO$_3$ aqueous solution. The mixture was extracted with ethyl acetate. The combined organic layer was washed with saturated NaHCO$_3$ aqueous solution and brine, dried over Na$_2$SO$_4$ and concentrated in vacuo. The residue was purified by flash column chromatography on silica gel (ethyl acetate/petroleum ether=1:4) to yield the desired product (1.1 g, 94% yield) as a yellow solid.

7-Bromo-6-methoxyquinazolin-4(1H)-one

The product was made from methyl 2-amino-4-bromo-5-methoxybenzoate in 6 steps followed the procedure described in Example 2. ESI-MS m/z: 393.8 [M+H]$^+$.

1-(4-(7-(2-Fluorophenyl)-6-hydroxyquinazolin-4-yl) piperazin-1-yl)prop-2-en-1-one BBr$_3$ (127 mg, 0.51 mmol) was added into a solution of 1-(4-(7-(2-fluorophenyl)-6-methoxyquinazolin-4-yl)piperazin-1-yl)prop-2-en-1-one (20 mg, 0.051 mmol) in dichloromethane (5 mL) at −78° C. and stirred at 40° C. for 1 h. Then it was cooled to −78° C., quenched with saturated NaHCO$_3$ aqueous solution extracted with dichloromethane. The organic layer was washed with saturated NaHCO$_3$ aqueous solution and brine, dried over Na$_2$SO$_4$ and concentrated in vacuo. The residue was purified by Prep-HPLC to yield the desired product (7 mg, 36% yield) as a yellow solid. $^1$H NMR (400 MHz, DMSO-d6): δ 10.44 (bs, 1H), 8.57 (s, 1H), 7.69 (s, 1H), 7.51-7.46 (m, 3H), 7.33-7.29 (m, 1H), 6.87 (dd, J=10.4, 16.4 Hz, 1H), 6.18 (dd, J=2.0, 16.4 Hz, 1H) 5.75 (dd, J=2.4, 10.4 Hz, 1H), 3.82-3.68 (m, 8H). ESI-MS m/z: 379.3 [M+H]$^+$.

Example 29

Synthesis of 1-(4-(6-chloro-7-(5-methyl-1H-indazol-4-yl)cinnolin-4-yl)piperazin-1-yl)prop-2-en-1-one

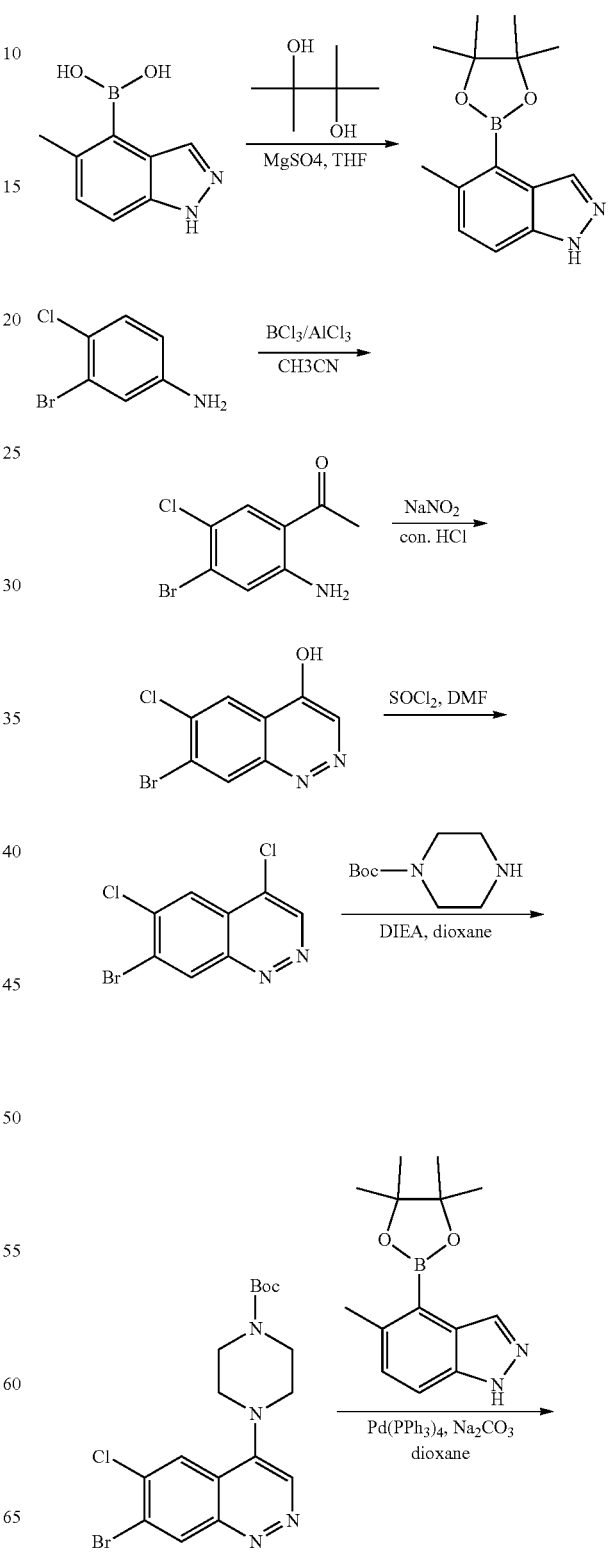

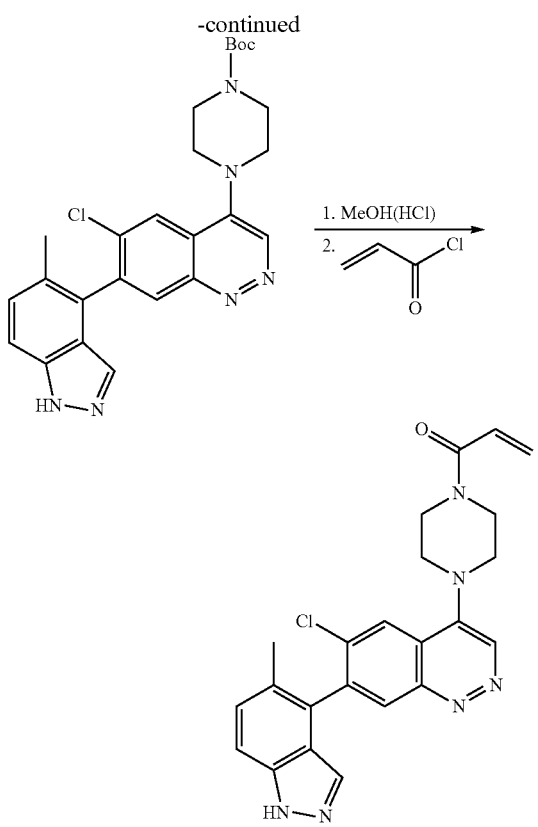

Example 29 provides and exemplary preparation according to General Synthetic Method N 5-Methyl-4-(4,4,5,5-tetramethyl-1,3,2-dioxaborolan-2-yl)-1H-indazole To a solution of 5-methyl-1H-indazol-4-yl-4-boronic acid (300 mg, 1.7 mmol) in THF (20 mL), pinacol (249 mg, 2.1 mmol) and MgSO$_4$ (614 mg, 5.1 mmol) were added, and the resulting mixture was stirred at 45° C. for 3 h. The mixture was filtered and rinsed with brine, dried over Na$_2$SO$_4$ and concentrated in vacuo to afford the desired product (330 mg, 75% yield).

1-(2-Amino-4-bromo-5-chlorophenyl)ethanone

To a stirred solution of BCl$_3$ (51 mL, 51 mmol) in toluene at 0° C., 3-bromo-4-chlorobenzenamine (10 g, 48.4 mmol) in CH$_3$CN (90 mL) was added dropwise over 20 min. To this suspension, AlCl$_3$ (7.1 g, 53.2 mmol) was added in three portions. The mixture was stirred at reflux for 16 h. The mixture was cooled to 0° C., HCl (4 N, 100 mL) was added and the resulting mixture was stirred at reflux for 2 h. The mixture was allowed to cool to RT and extracted with ethyl acetate. The organic layer was washed with 2 N HCl and brine, dried over Na$_2$SO$_4$, and concentrated in vacuo. The residue was purified by flash column chromatography on silica gel (petroleum ether/ethyl acetate=4:1) to afford the desired product (1.6 g, 11% yield).

7-Bromo-6-chlorocinnolin-4(1H)-one

To a mixture of concentrated HCl (20 mL) and 1-(2-amino-4-bromo-5-chlorophenyl)ethanone (1.6 g, 6.44 mmol) at 0° C., sodium nitrite (466 mg, 6.76 mmol) in water (1 mL) was slowly added (over 30 min). The mixture was stirred at 0° C. for 30 min and then stirred at 60° C. for 2 h. The mixture was allowed to cool to RT and poured into water. The solid was collected by filtration to afford the desired product (1.4 g, 84% yield).

7-Bromo-4,6-dichlorocinnoline

Thionyl chloride (10 mL) and DMF (3 drops) was added to 7-bromo-6-chlorocinnolin-4(1H)-one (1.4 g, 5.4 mmol), and the resulting mixture was stirred at reflux for 2 h. The mixture was concentrated in vacuo to afford the crude product (1.5 g) which was used in next step without further purification.

tert-Butyl 4-(7-bromo-6-chlorocinnolin-4-yl)piperazine-1-carboxylate

A mixture of 7-bromo-4,6-dichlorocinnoline (1.5 g, 5.4 mmol), tert-butyl piperazine-1-carboxylate (1.51 g, 8.1 mmol), DIEA (2.1 g, 16.2 mmol) and 1,4-dioxane (20 mL) was stirred at reflux for 16 h. The mixture was allowed to cool to RT, poured into ice water, and extracted with ethyl acetate. The organic layer was washed with brine, dried over Na$_2$SO$_4$ and concentrated. The residue was purified by flash column chromatography on silica gel (petroleum ether/ethyl acetate=1:1) to afford the desired product (1.8 g, 78% yield). ESI-MS m/z: 429.05 [M+H]$^+$.

tert-Butyl 4-(6-chloro-7-(5-methyl-1H-indazol-4-yl)cinnolin-4-yl)piperazine-1-carboxylate To a solution of tert-butyl 4-(7-bromo-6-chlorocinnolin-4-yl)piperazine-1-carboxylate (138 mg, 0.32 mmol) and 5-methyl-4-(4,4,5,5-tetramethyl-1,3,2-dioxaborolan-2-yl)-1H-indazole (250 mg, 0.97 mmol) in 1,4-dioxane (10 mL) and water (2 mL), Pd(PPh$_3$)$_4$ (37 mg, 0.0325 mmol) and Na$_2$CO$_3$ (136 mg, 1.28 mmol) were added. The mixture was stirred at 100° C. for 16 h. The mixture was allowed to cool to RT and concentrated in vacuo. The residue was purified by flash column chromatography on silica gel (dichloromethane/methanol=20:1) to afford the desire product (140 mg, 91% yield).

1-(4-(6-Chloro-7-(5-methyl-1H-indazol-4-yl)cinnolin-4-yl)piperazin-1-yl)prop-2-en-1-one The mixture of 4-(6-chloro-7-(5-methyl-1H-indazol-4-yl)cinnolin-4-yl)piperazine-1-carboxylate (140 mg, 0.29 mmol) in HCl/MeOH (20 mL, 2.8 N) was stirred for 1 h. The mixture was concentrated in vacuo and the residue was dissolved in DCM (5 mL) and Et$_3$N (88 mg, 0.87 mmol). This mixture was cooled to −60° C., acryloyl chloride (26 mg, 0.29 mmol) was added slowly. The reaction mixture was stirred at RT for 1 h. The mixture was partitioned between ethyl acetate and water. The organic layer was washed with brine, dried over Na$_2$SO$_4$ and concentrated in vacuo. The residue was purified by Prep-HPLC to afford the desired product (12 mg, 10% yield) as a white solid. $^1$H NMR (400 MHz, DMSO-d6) δ: 13.18 (s, 1H), 9.08 (s, 1H), 8.34 (m, 2H), 7.57 (m, 2H), 7.39 (d, J=8.4 Hz, 1H), 6.90 (dd, J=10.8, 16.4 Hz, 1H), 6.20 (d, J=16.4 Hz, 1H), 5.77 (d, J=10.4 Hz, 1H), 3.91-3.88 (m, 4H), 3.51 (m, 4H), 2.20 (s, 3H). ESI-MS m/z: 433.1 [M+H]$^+$.

Example 30

Synthesis of 1-(4-(6-chloro-8-fluoro-7-(2-fluoro-6-hydroxyphenyl)quinazolin-4-yl)piperazin-1-yl)prop-2-en-1-one

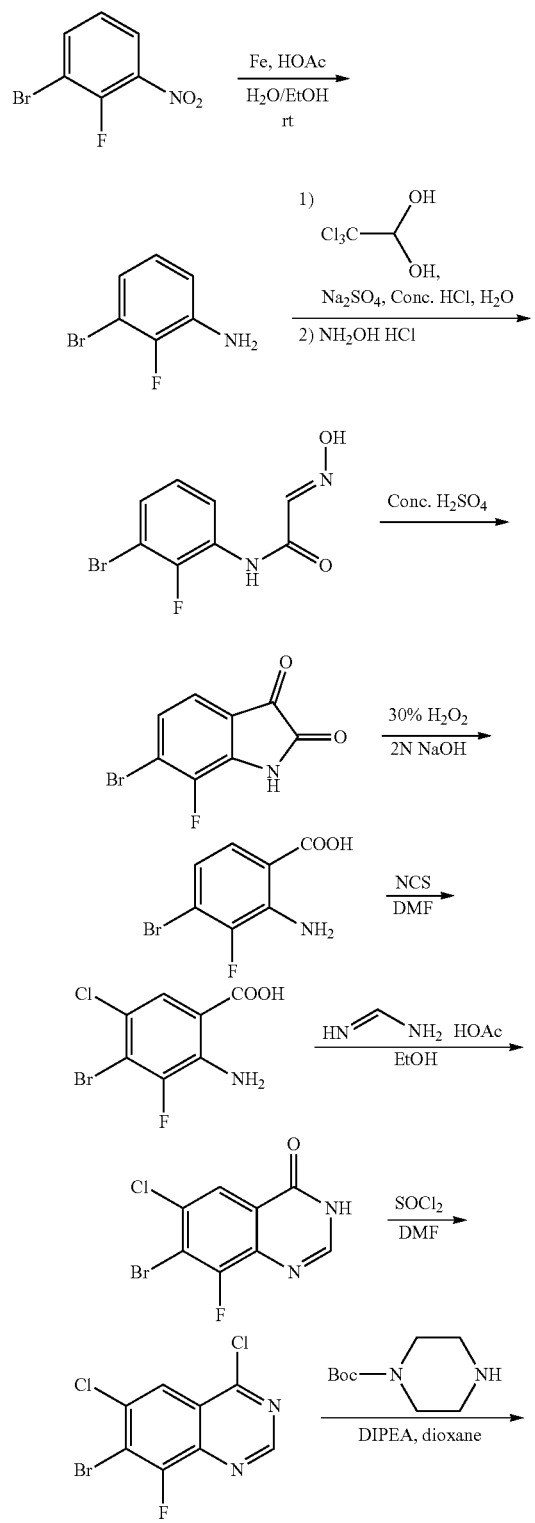

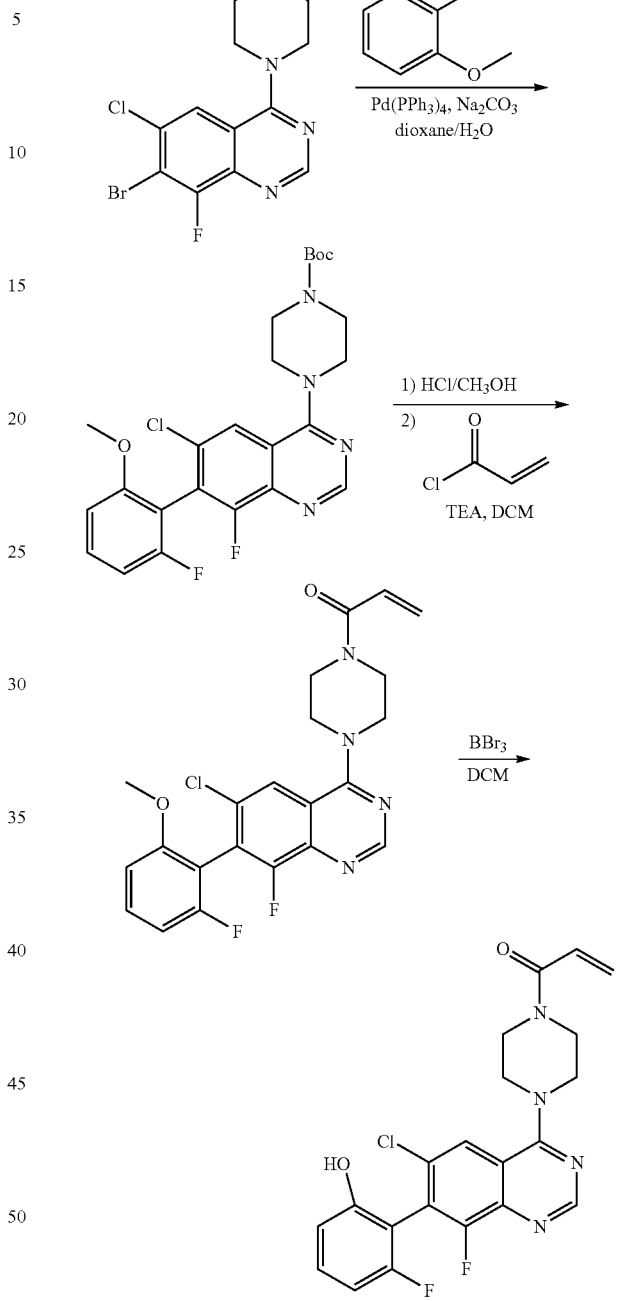

Example 30 provides an exemplary preparation according to General Synthetic Method O

3-Bromo-2-fluorobenzenamine

To a mixture of 1-bromo-2-fluoro-3-nitrobenzene (13.75 g, 62.76 mmol), HOAc (26.36 g, 439 mmol), EtOH (150 mL) and H$_2$O (60 mL) at room temperature, iron powder (9.14 g, 163 mmol) was added portion-wise. The resulting mixture was stirred at room temperature for 16 h and then was neutralized with NaOH (5 N) solution. Then the mixture was extracted with ethyl acetate. The organic layer was washed with brine, dried over Na$_2$SO$_4$ and concentrated in vacuo. The residue was purified by flash column chromatography on silica gel (petroleum ether/ethyl acetate=10:1) to afford the desired product (7.77 g, 65% yield) as a brown oil.

N-(3-Bromo-2-fluorophenyl)-2-(hydroxyimino)acetamide

A mixture of 2,2,2-trichloroethane-1,1-diol (8.09 g, 49.33 mmol) and $Na_2SO_4$ (53 g, 370 mol) was dissolved in water and warmed to 35° C. 3-Bromo-2-fluorobenzenamine (7.77 g, 41.11 mmol) in water was added, followed by 35% aqueous HCl solution (4.6 mL) and hydroxylamine hydrochloride (9.08 g, 131.6 mmol). The resulting mixture was stirred at 90° C. for 16 h and yellow precipitate was formed. The mixture was cooled to room temperature. The solid was collected by filtration, rinsed with water, and dried in the air to afford the desired product (6.5 g, 61% yield).

6-Bromo-7-fluoroindoline-2,3-dione

To the concentrated sulfuric acid (20 mL), N-(3-bromo-2-fluorophenyl)-2-(hydroxyimino)acetamide (1.82 g, 7.03 mmol) was added at 60° C. The temperature was raised to 90° C. and maintained for 3 h. The reaction mixture was cooled to room temperature and poured into ice. The yellow precipitate was collected by filtration and dried to afford the desired product (1.41 g, 82% yield). $^1$H NMR (400 MHz, DMSO-d6) δ: 11.75 (s, 1H), 7.39 (dd, J=5.7, 7.9 Hz, 1H), 7.31 (d, J=8.2 Hz, 1H).

2-Amino-4-bromo-3-fluorobenzoic acid

To a solution of 6-bromo-7-fluoroindoline-2,3-dione (1.41 g, 5.80 mmol) in 2 N NaOH (15 mL), $H_2O_2$ solution (30%, 3 mL) was added at 0° C. and the resulting mixture was stirred at 0° C. for 30 min. After stirring at room temperature for 16 h, the mixture was poured into ice-water, and the solution was acidified with conc. HCl solution. The precipitate was collected by filtration and dried in the air to afford the desired product (1.2 g, 89% yield) as a white solid.

2-Amino-4-bromo-5-chloro-3-fluorobenzoic acid

To a solution of 2-amino-4-bromo-3-fluorobenzoic acid (234 mg, 1.00 mmol) in DMF (10 mL), NCS (134 mg, 1 mmol) was added at room temperature and the resulting mixture was stirred at 70° C. for 16 h. The mixture was poured into ice-water. The precipitate was collected by filtration, rinsed with water and dried to afford the desired product (209 mg, 78% yield) as a white solid. ESI-MS m/z: 269.8 [M+H]$^+$.

7-Bromo-6-chloro-8-fluoroquinazolin-4(3H)-one

To a solution of 2-amino-4-bromo-5-chloro-3-fluorobenzoic acid (1.07 g, 3.98 mmol) in EtOH (15 mL), formamidine acetate (4.92 g, 47.76 mmol) was added at room temperature and the resulting mixture was stirred at reflux for 16 h. The mixture was allowed to cool to room temperature and then concentrated in vacuo. The residue was partitioned between ethyl acetate and water. The organic layer was washed with brine, dried over $Na_2SO_4$ and concentrated in vacuo. The residue was purified by column chromatography on silica gel (dichloromethane/methanol=100:1 to 50:1) to afford the desired product (600 mg, 55% yield) as a white solid. ESI-MS m/z: 278.9 [M+H]$^+$.

7-Bromo-4,6-dichloro-8-fluoroquinazoline

A mixture of 7-bromo-6-chloro-8-fluoroquinazolin-4 (3H)-one (600 mg, 2.16 mmol), $SOCl_2$ (30 mL) and DMF (3 drops) was stirred at reflux for 16 h. The mixture was allowed to cool to room temperature and then concentrated in vacuo to afford the crude product (639 mg), which was used directly in the next step.

tert-Butyl 4-(7-bromo-6-chloro-8-fluoroquinazolin-4-yl)piperazine-1-carboxylate

To a solution of 7-bromo-4,6-dichloro-8-fluoroquinazoline (639 mg, 2.16 mmol) in 1,4-dioxane (20 mL), tert-butyl piperazine-1-carboxylate (1.21 g, 6.48 mmol) and DIPEA (1.39 g, 10.8 mmol) were added at room temperature. The resulting mixture was stirred at 50° C. for 3 h. The mixture was allowed to cool to room temperature and concentrated in vacuo. The residue was partitioned between ethyl acetate and saturated $NaHCO_3$ solution. The organic layer was washed with brine, dried over $Na_2SO_4$ and concentrated in vacuo. The residue was purified by column chromatography on silica gel (dichloromethane/methanol=100:1) to afford the desired product (950 mg, 98% yield) as a yellow solid. ESI-MS m/z: 446.1 [M+H]$^+$.

tert-Butyl4-(6-chloro-8-fluoro-7-(2-fluoro-6-methoxyphenyl)quinazolin-4-yl)piperazine-1-carboxylate A mixture of tert-butyl 4-(7-bromo-6-chloro-8-fluoroquinazolin-4-yl)piperazine-1-carboxylate (45 mg, 0.1 mmol), 2-fluoro-6-methoxyphenylboronic acid (85 mg, 0.5 mmol), $Pd(PPh_3)_4$ (6 mg, 0.05 mmol) and $Na_2CO_3$ (53 mg, 0.5 mmol) in 1,4-dioxane/$H_2O$ (8 mL/2 mL) was stirred at 85° C. under an argon atmosphere for 16 h. The mixture was allowed to cool to room temperature and concentrated in vacuo. The residue was purified by column chromatography on silica gel (dichloromethane/methanol=100:1) to afford the desired product (46 mg, 92% yield) as a yellow solid. ESI-MS m/z: 491.2 [M+H]$^+$.

1-(4-(6-Chloro-8-fluoro-7-(2-fluoro-6-methoxyphenyl)quinazolin-4-yl)piperazin-1-yl)prop-2-en-1-one A mixture of tert-butyl4-(6-chloro-8-fluoro-7-(2-fluoro-6-methoxyphenyl)quinazolin-4-yl)piperazine-1-carboxylate (136 mg, 0.277 mmol) and HCl in MeOH (6 mL, 2.8 N) was stirred at room temperature for 1 h. The mixture was concentrated in vacuo to yield the crude product (118 mg) as a yellow solid which was used directly in the next step.

Acryloyl chloride (30 mg, 0.33 mmol) was added to the mixture of the above obtained crude 6-chloro-8-fluoro-7-(2-fluoro-6-methoxyphenyl)-4-(piperazin-1-yl)quinazoline (118 mg, 0.277 mmol) in $Et_3N$ (140 mg, 1.38 mmol) and dichloromethane (15 mL) at 0° C. The resulting mixture was stirred at 0° C. for 2 h. The mixture was quenched with saturated $NaHCO_3$ solution, and then extracted with ethyl acetate. The organic layer was washed with saturated $NaHCO_3$ solution and brine, dried over $Na_2SO_4$ and concentrated in vacuo. The residue was purified by flash column chromatography on silica gel (dichloromethane/methanol=80:1) to yield the desired product (61 mg, 49% yield) as a solid.

1-(4-(6-Chloro-8-fluoro-7-(2-fluoro-6-hydroxyphenyl)quinazolin-4-yl)piperazin-1-yl)prop-2-en-1-one To a solution of 1-(4-(6-chloro-8-fluoro-7-(2-fluoro-6-methoxyphenyl)quinazolin-4-yl)piperazin-1-yl)prop-2-en-1-one (61 mg, 0.137 mmol) in dichloromethane (10 mL) at −78° C. under nitrogen atmosphere, BBr$_3$ (343 mg, 1.37 mmol) was added and the resulting mixture was stirred at room temperature for 3 h. The mixture was quenched with saturated NaHCO$_3$ solution at −30° C. and then extracted with ethyl acetate. The organic layer was washed with brine, dried over Na$_2$SO$_4$ and concentrated in vacuo. The residue was purified by pre-TLC to afford the desired product (45 mg, 76% yield) as a solid. $^1$H NMR (400 MHz, DMSO-d6) δ:10.30 (s, 1H), 8.70 (s, 1H), 8.04 (s, 1H), 7.34-7.40 (m, 1H), 6.80-6.87 (m, 3H), 6.16-6.20 (m, 1H), 5.73-5.76 (m, 1H), 3.77-3.93 (m, 8H). ESI-MS m/z: 431.1 [M+H]$^+$.

Example 31

Synthesis of 4-(4-acryloylpiperazin-1-yl)-6-chloro-8-fluoro-7-(2-fluoro-6-hydroxyphenyl)quinoline-3-carbonitrile

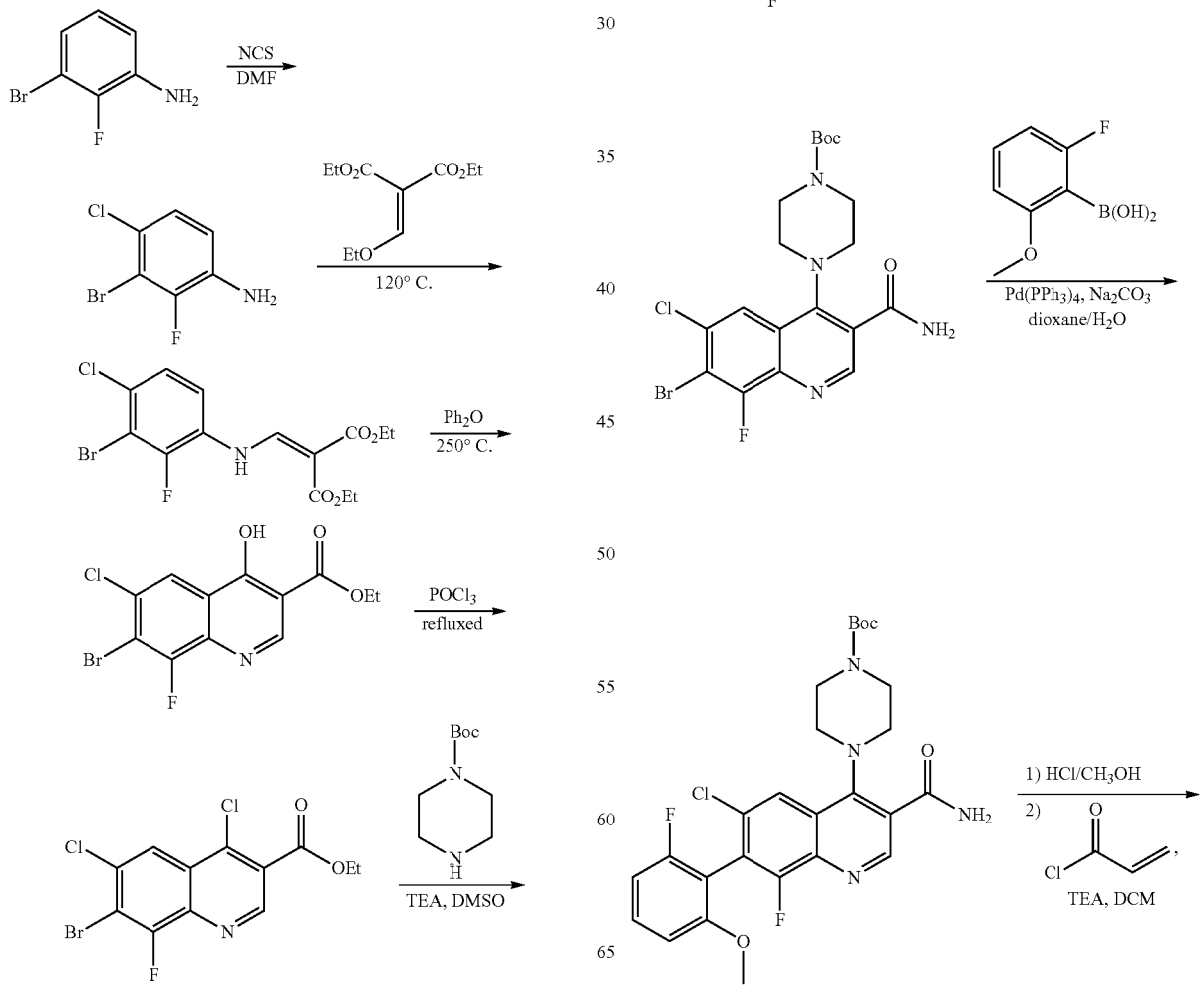

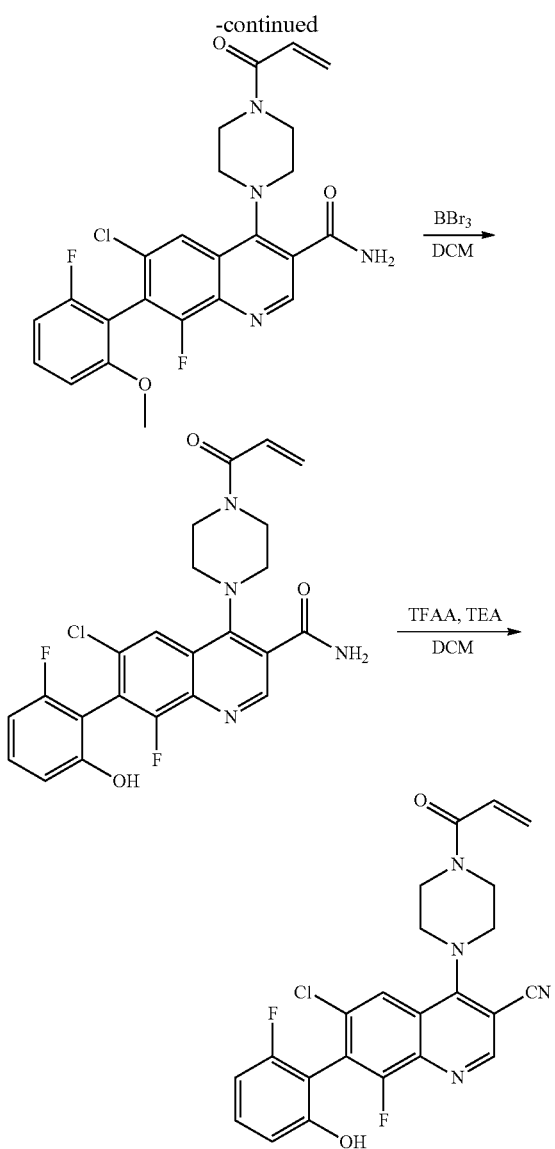

Example 31 provides an exemplary preparation according to General Synthetic Method P 3-Bromo-4-chloro-2-fluorobenzenamine To a solution of 3-bromo-2-fluorobenzenamine (1.9 g, 10 mmol) in DMF (10 mL) at room temperature, NCS (1.4 g, 10.5 mmol) was added and the resulting mixture was stirred at room temperature for 16 h. The mixture was poured into ice-water and extracted with ethyl acetate. The organic layer was washed with brine, dried over $Na_2SO_4$ and concentrated in vacuo. The residue was purified by flash column chromatography on silica gel (petroleum ether/ethyl acetate=30:1) to afford the desired product (1.15 g, 51% yield) as a solid. ESI-MS m/z: 225.9 $[M+H]^+$.

Diethyl 2-((3-bromo-4-chloro-2-fluorophenylamino) methylene)malonate

A mixture of 3-bromo-4-chloro-2-fluorobenzenamine (2.3 g, 10.2 mmol) and diethyl 2-(ethoxymethylene)malonate (2.42 g, 11.22 mmol) was stirred at 120° C. for 3 h. The mixture was allowed to cool to room temperature, and then petroleum ether was added. The mixture was stirred at room temperature for 1 h. The precipitate was collected by filtration and dried to afford the desired product (2.76 g, 68.7% yield) as a solid. ESI-MS m/z: 395.9 $[M+H]^+$.

Ethyl 7-bromo-6-chloro-8-fluoro-4-hydroxyquinoline-3-carboxylate

Diethyl 2-((3-bromo-4-chloro-2-fluorophenylamino) methylene)malonate (2.76 g, 6.99 mmol) was suspended in $Ph_2O$ (20 mL). The mixture was stirred at 250° C. for 2 h. The mixture was allowed to cool to room temperature and then 100 mL of petroleum ether was added. The white solid was collected by filtration and rinsed with petroleum ether (100 mL) to afford the desired product (1.85 g, 76% yield) as a solid. ESI-MS m/z: 349.9 $[M+H]^+$.

Ethyl 7-bromo-4,6-dichloro-8-fluoroquinoline-3-carboxylate

A mixture of ethyl 7-bromo-6-chloro-8-fluoro-4-hydroxyquinoline-3-carboxylate (1.85 g, 5.31 mmol) and $POCl_3$ (10 mL) was stirred at reflux for 4 h. The mixture was allowed to cool to room temperature and concentrated in vacuo to afford the crude product (1.41 g).

Ethyl4-(4-(tert-butoxycarbonyl)piperazin-1-yl)-7-bromo-6-chloro-8-fluoroquinoline-3-carboxylate A mixture of ethyl 7-bromo-4,6-dichloro-8-fluoroquinoline-3-carboxylate (1.41 g, 3.84 mmol), tert-butyl piperazine-1-carboxylate (1.43 g, 7.68 mmol), $Et_3N$ (1.55 g, 15.36 mmol) and DMSO (20 mL) was stirred at 80° C. under an argon atmosphere for 2 h. The mixture was allowed to cool to room temperature and poured into ice-water. The mixture was extracted with ethyl acetate. The combined organic layer was washed with brine, dried over $Na_2SO_4$, and concentrated in vacuo. The residue was purified by flash column chromatography on silica gel (petroleum ether/ethyl acetate=3:1) to afford the desired product (1.96 g, 98% yield) as a solid. ESI-MS m/z: 518.1 $[M+H]^+$.

4-(4-(tert-Butoxycarbonyl)piperazin-1-yl)-7-bromo-6-chloro-8-fluoroquinoline-3-carboxylic acid To a solution of ethyl4-(4-(tert-butoxycarbonyl)piperazin-1-yl)-7-bromo-6-chloro-8-fluoroquinoline-3-carboxylate (517 mg, 1 mmol) in $EtOH/H_2O$ (16 mL/8 mL), $LiOH.H_2O$ (126 mg, 3 mmol) was added. The mixture was stirred at room temperature for 16 h and poured into ice-water. The mixture was acidified with 1N HCl solution and extracted with ethyl acetate. The organic layer was washed with brine, dried over $Na_2SO_4$ and concentrated in vacuo to afford the desired product (489 mg, 100% yield) as a solid. ESI-MS m/z: 489.1 $[M+H]^+$.

tert-Butyl4-(7-bromo-3-carbamoyl-6-chloro-8-fluoroquinolin-4-yl)piperazine-1-carboxylate A mixture of 4-(4-(tert-butoxycarbonyl)piperazin-1-yl)-7-bromo-6-chloro-8-fluoroquinoline-3-carboxylic acid (290 mg, 0.59 mmol), HOBt (121 mg, 0.89 mmol), $NH_4Cl$ (63 mg, 1.18 mmol), DIPEA (306 mg, 2.37 mmol) in DMF (16 ml) at room temperature, BOP (393 mg, 0.89 mmol) was added and the resulting mixture was stirred at room temperature for 16 h. The mixture was poured into ice-water and extracted with ethyl acetate. The organic layer was washed with brine, dried over Na$_2$SO$_4$ and concentrated in vacuo. The residue was purified by flash column chromatography on silica gel (dichloromethane/methanol=15:1) to afford the desired product (160 mg, 55% yield) as a white solid. ESI-MS m/z: 533.2 [M+H]$^+$.

tert-Butyl-4-(3-carbamoyl-6-chloro-8-fluoro-7-(2-fluoro-6-methoxyphenyl)quinolin-4-yl)piperazine-1-carboxylate A mixture of tert-butyl-4-(7-bromo-3-carbamoyl-6-chloro-8-fluoroquinolin-4-yl)piperazine-1-carboxylate (100 mg, 0.21 mmol), 2-fluoro-6-methoxyphenylboronic acid (174 mg, 1.025 mmol), Pd(PPh$_3$)$_4$ (12 mg, 0.01 mmol) and Na$_2$CO$_3$ (109 mg, 1.02 mmol) in 1,4-dioxane/H$_2$O (12 mL/3 mL) was stirred at 100° C. under an argon atmosphere for 16 h. The mixture was allowed to cool to room temperature and concentrated in vacuo. The residue was purified by pre-TLC to afford the desired product (71 mg, 65% yield) as a white solid.

4-(4-Acryloylpiperazin-1-yl)-6-chloro-8-fluoro-7-(2-fluoro-6-methoxyphenyl)quinoline-3-carboxamide A mixture of tert-butyl 4-(3-carbamoyl-6-chloro-8-fluoro-7-(2-fluoro-6-methoxyphenyl)quinolin-4-yl)piperazine-1-carboxylate (71 mg, 0.13 mmol) and HCl in MeOH (8 mL, 2.8 N) was stirred at room temperature for 1 h. The mixture was concentrated in vacuo to afford the crude 6-chloro-8-fluoro-7-(2-fluoro-6-methoxyphenyl)-4-(piperazin-1-yl)quinoline-3-carboxamide hydrochloride.

The above obtained crude compound was dissolved in Et$_3$N (40 mg, 0.40 mmol) and dichloromethane (15 mL) and cooled to 0° C., acryloyl chloride (14 mg, 0.16 mmol) was added to the mixture. The resulting mixture was stirred at 0° C. for 2 h. The reaction mixture was quenched with saturated NaHCO$_3$ aqueous solution, and then extracted with ethyl acetate. The organic layer was washed with saturated NaHCO$_3$ solution and brine, dried over Na$_2$SO$_4$ and concentrated in vacuo. The residue was purified by pre-TLC to afford the desired product (62 mg, 95% yield) as a white solid. ESI-MS m/z: 487.2 [M+H]$^+$.

4-(4-Acryloylpiperazin-1-yl)-6-chloro-8-fluoro-7-(2-fluoro-6-hydroxyphenyl)quinoline-3-carboxamide To a solution of 4-(4-acryloylpiperazin-1-yl)-6-chloro-8-fluoro-7-(2-fluoro-6-methoxyphenyl)quinoline-3-carboxamide (62 mg, 0.13 mmol) in dichloromethane (10 mL) at −78° C. under nitrogen atmosphere, BBr$_3$ (317 mg, 1.27 mmol) was added and the resulting mixture was stirred at room temperature for 3 h. The reaction mixture was quenched with saturated NaHCO$_3$ at −30° C., and the aqueous solution was extracted with ethyl acetate. The organic layer was washed with brine, dried over Na$_2$SO$_4$ and concentrated in vacuo to afford the desired product as a yellow solid (60 mg, 100% yield).

4-(4-Acryloylpiperazin-1-yl)-6-chloro-8-fluoro-7-(2-fluoro-6-hydroxyphenyl)quinoline-3-carbonitrile A mixture of 4-(4-acryloylpiperazin-1-yl)-6-chloro-8-fluoro-7-(2-fluoro-6-hydroxyphenyl)quinoline-3-carboxamide, TEA (64 mg, 0.635 mmol) in dichloromethane (10 mL) at 0° C., TFAA (80 mg, 0.38 mmol) was added. The mixture was stirred at 0° C. for 2 h and then poured into saturated NaHCO$_3$ solution. The mixture was extracted with ethyl acetate. The organic layer was washed with brine, dried over Na$_2$SO$_4$ and concentrated. The residue was purified by pre-TLC to afford the desired product (15 mg, 26% yield) as a white solid. $^1$H NMR (400 MHz, DMSO-d6) δ: 10.33 (s, 1H), 8.89 (s, 1H), 8.08 (d, J=0.4, 1H), 7.35-7.41 (m, 1H), 6.81-6.94 (m, 3H), 6.17-6.22 (m, 1H), 5.74-5.77 (m, 1H), 3.85-3.89 (m, 4H), 3.73 (m, 4H). ESI-MS m/z: 455.2 [M+H]$^+$.

Example 32

Synthesis of 1-(4-(6-chloro-8-fluoro-7-(5-methyl-1H-indazol-4-yl)quinazolin-4-yl)piperazin-1-yl)prop-2-en-1-one

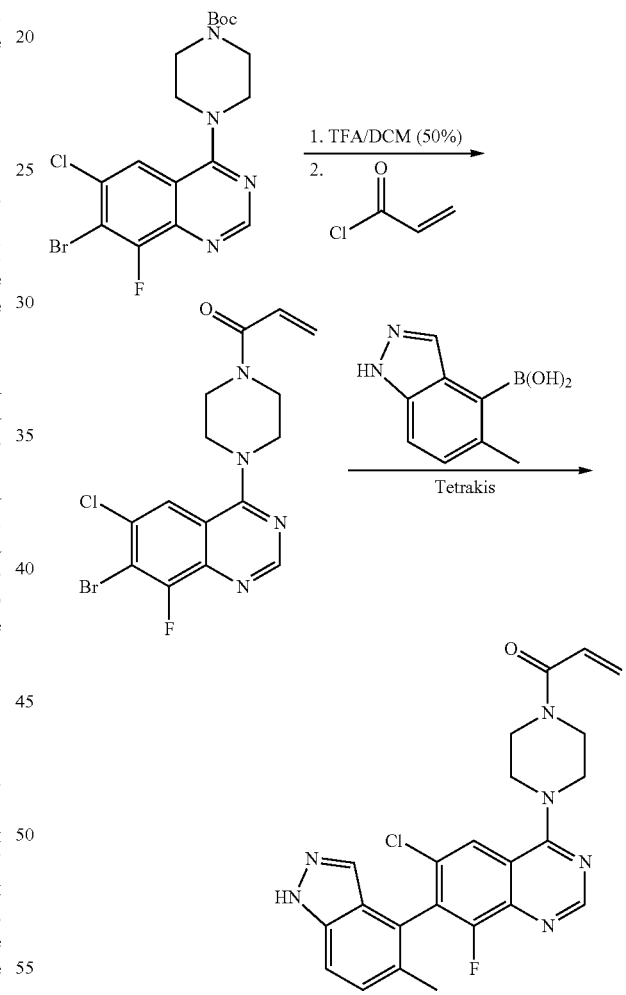

Example 32 provides an exemplary preparation according to General Synthetic Method Q 1-(4-(7-Bromo-6-chloro-8-fluoroquinazolin-4-yl)piperazin-1-yl)prop-2-en-1-one tert-Butyl 4-(7-bromo-6-chloro-8-fluoroquinazolin-4-yl)piperazine-1-carboxylate (300 mg, 0.67 mmol) was dissolved in TFA and DCM (50% TFA, 5 mL) and the resulting mixture was stirred at room temperature for 30 min. The mixture was concentrated in vacuo. The residue was dissolved in DCM and washed with sat. NaH—CO₃ solution. The organic layer was dried over MgSO₄, filtered and concentrated in vacuo. The residue was dissolved in DCM at 0° C., iPr₂NEt (262 mg, 2 mml) was added, followed by acryloyl chloride (122 mg, 1.35 mmol). The mixture was stirred at 0° C. for 30 min. The mixture was concentrated in vacuo, and the residue was purified via Isolera One (MeOH/DCM=0-3%) to afford the desired product (250 mg, 93% yield).

1-(4-(6-Chloro-8-fluoro-7-(5-methyl-1H-indazol-4-yl)quinazolin-4-yl)piperazin-1-yl)prop-2-en-1-one A mixture of 1-(4-(7-bromo-6-chloro-8-fluoroquinazolin-4-yl)piperazin-1-yl)prop-2-en-1-one (30 mg, 0.075 mmol), (5-methyl-1H-indazol-4-yl)boronic acid (20 ng, 0.113 mmol) and Tetrakis (43 mg, 0.038 mmol) in co-solvent of 1,4-dioxane (3 mL) and 1 M Na₂CO₃ (0.5 mL) was heated in microwave reactor at 120° C. for 15 main. The mixture was partitioned between DCM and water. The organic layer was dried over Na₂, SO₄ and concentrated in vacuo. The residue was purified via Isolear One (MeOH/DCM=0-10%) followed by prep-TLC (MeOH/DCM=10%) to afford the desired product (9 mg, 26.6% yield). H NMR (500 MHz, CDCl₃) δ: 8.86 (s, 1H), 9.08 (s, 1H), 7.90 (s, 1H), 7.59 (s, 1H), 7.54 (d, J=8.5 Hz, 1H), 7.40 (d, J=8.5 Hz, 1H), 6.62 (dd, J=10.5, 17 Hz, 1H), 6.40 (dd, J=1.5, 17 Hz, 1H), 5.80 (dd, J=1.5, 10.5 Hz, 1H), 3.78-4.02 (m, 8H), 2.25 (s, 3H). ESI-MS m/z: 451.1 [M+H]⁺.

Example 33

Synthesis of 1-(4-(7-(2-fluorophenyl)-6-(trifluoromethyl)quinazolin-4-yl)piperazin-1-yl)prop-2-en-1-one

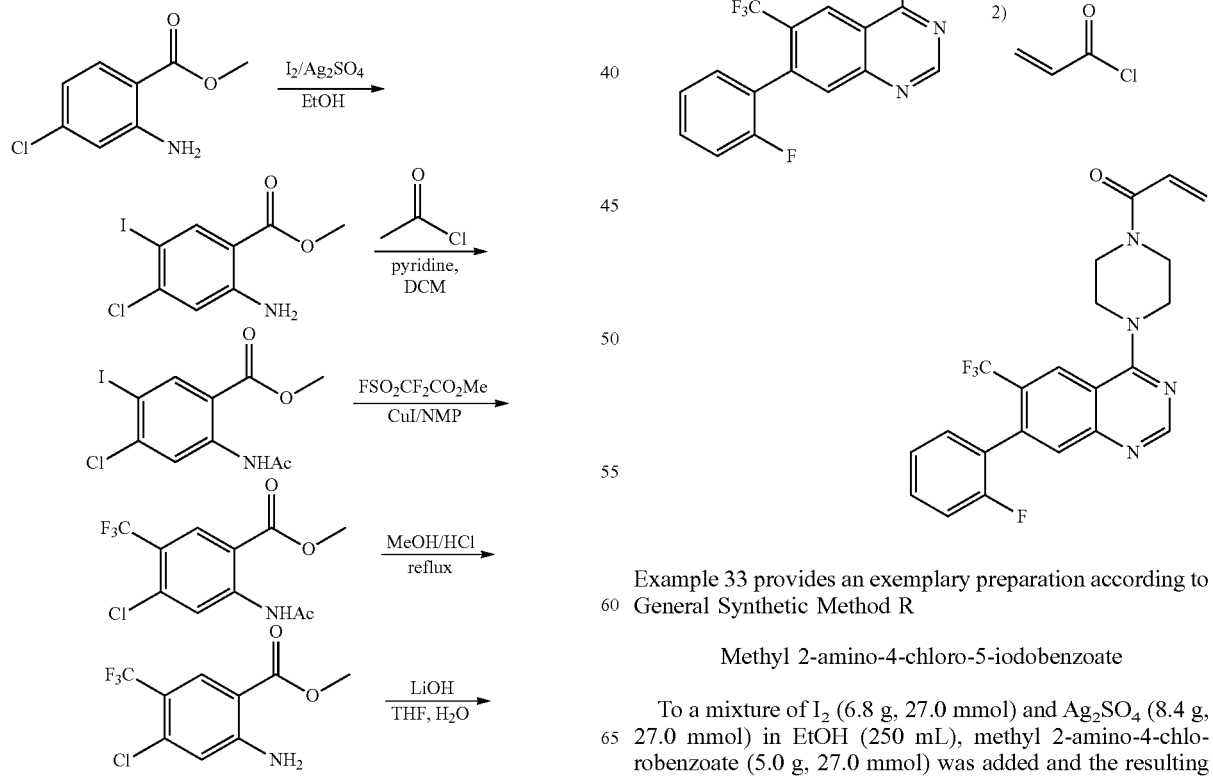

Example 33 provides an exemplary preparation according to General Synthetic Method R Methyl 2-amino-4-chloro-5-iodobenzoate To a mixture of I₂ (6.8 g, 27.0 mmol) and Ag₂SO₄ (8.4 g, 27.0 mmol) in EtOH (250 mL), methyl 2-amino-4-chlorobenzoate (5.0 g, 27.0 mmol) was added and the resulting mixture was stirred at RT for 45 min. The solid was filtered off and washed with dichloromethane, and the filtrate was concentrated in vacuo. The residue was extracted with dichloromethane and washed with brine. The organic layer was dried over $Na_2SO_4$ and concentrated in vacuo to afford the desired product (6.4 g, 76% yield) as a white solid. ESI-MS m/z: 311.9 $[M+H]^+$.

Methyl 2-acetamido-4-chloro-5-iodobenzoate

A mixture of methyl 2-amino-4-chloro-5-iodobenzoate (8.4 g, 0.027 mol), pyridine (6.4 g, 0.081 mol) in dichloromethane (250 mL) at 0° C., acetyl chloride (2.5 g, 0.032 mol) was added. The mixture was stirred at RT for 16 h. The reaction mixture was washed with brine. The organic layer was dried over anhydrous $Na_2SO_4$, filtered and concentrated in vacuo. The residue was purified by flash column chromatography on silica gel (ethyl acetate/petroleum ether=1:5) to afford the desired product (7.6 g, 80% yield). ESI-MS m/z: 353.9 $[M+H]^+$.

Methyl 2-amino-4-chloro-5-(trifluoromethyl)benzoate

To a stirred solution of methyl 2-acetamido-4-chloro-5-iodobenzoate (2.5 g, 7.08 mmol) and methyl 2,2-difluoro-2-(fluorosulfonyl)acetate (2.72 g, 14.2 mmol) in NMP (30 mL) at RT, CuI (0.4 g, 2.12 mmol) was added and the resulting mixture was stirred at 80° C. for 16 h. The mixture was quenched with water and partitioned between water and ethyl acetate. The organic layer was dried over anhydrous $Na_2SO_4$, filtered and concentrated in vacuo. The residue was purified by flash column chromatography on silica gel (ethyl acetate/petroleum ether=1:5) to afford the desired product (1.8 g, 90% yield) as a light yellow oil. ESI-MS m/z: 296.4 $[M+H]^+$.

Methyl 2-amino-4-chloro-5-(trifluoromethyl)benzoate

A mixture of methyl 2-amino-4-chloro-5-(trifluoromethyl)benzoate (800 mg, 2.71 mmol) in HCl/MeOH (2.85 mol/L, 10 mL) was stirred at 80° C. for 1.5 h. The reaction mixture was concentrated in vacuo to afford the desired product which was used in the next step without further purification.

2-Amino-4-chloro-5-(trifluoromethyl)benzoic acid

To a mixture of methyl 2-amino-4-chloro-5-(trifluoromethyl)benzoate (600 mg, 2.55 mmol) in THF (10 mL) and water (2.5 mL) at RT, $LiOH \cdot H_2O$ (408 mg, 10.21 mmol) was added and the resulting mixture was stirred at 80° C. for 3 h. The mixture was diluted with $H_2O$, acidified with HCl to adjust pH to 4 and then extracted with ethyl acetate. The organic layer was washed with brine, dried over $Na_2SO_4$ and concentrated in vacuo to afford the desired product (500 mg, 82% yield) as a solid.

7-Chloro-6-(trifluoromethyl)quinazolin-4-ol

A mixture of 2-amino-4-chloro-5-(trifluoromethyl)benzoic acid (500 mg, 2.09 mmol) and formamidine acetate (430 mg, 4.18 mmol) in 2-ethoxyethanol (15 mL) was stirred at reflux for 16 h. The mixture was concentrated in vacuo and extracted with dichloromethane. The organic layer was washed with brine, dried over $Na_2SO_4$ and concentrated to afford the desired product (500 mg, 96% yield) which was used in the next step without further purifications. ESI-MS m/z: 249.3 $[M+H]^+$.

4,7-Dichloro-6-(trifluoromethyl)quinazoline

To a suspension of 7-chloro-6-(trifluoromethyl)quinazolin-4-ol (500 mg, 0.016 mol) in $SOCl_2$ (20 mL), DMF (one drop) was added and the resulting mixture was stirred at reflux for 3 h. The mixture was concentrated in vacuo to afford the crude product which was used in the next step without further purification tert-Butyl 4-(7-chloro-6-(trifluoromethyl)quinazolin-4-yl)piperazine-1-carboxylate To a solution of 4,7-dichloro-6-(trifluoromethyl)quinazoline (500 mg, 1.88 mmol) and $Et_3N$ (3.33 g, 33 mmol) in dichloromethane (20 mL) at RT, tert-butyl piperazine-1-carboxylate (3.07 g, 16.5 mmol) was added. The resulting mixture was stirred at RT for 16 h. The mixture was washed with saturated $NH_4Cl$ solution and brine, dried over $Na_2SO_4$ and concentrated. The residue was purified by flash column chromatography on silica gel (50% ethyl acetate/petroleum ether) to afford the desired product (650 mg, 83% yield) as a yellow solid. ESI-MS m/z: 417.0 $[M+H]^+$.

tert-Butyl 4-(6-(trifluoromethyl)-7-(2-fluorophenyl) quinazolin-4-yl)piperazine-1-carboxylate The mixture of 4-(7-chloro-6-(trifluoromethyl)quinazolin-4-yl)piperazine-1-carboxylate (200 mg, 0.48 mmol), 2-fluorophenylboronic acid (132.6 mg, 0.96 mmol), $PdCl_2$(dppf) (35 mg, 0.048 mmol), $Na_2CO_3$ (254 mg, 2.4 mmol) in dioxane (20 mL) and water (2 mL) was stirred at 100° C. under argon for 16 h. The mixture was allowed to cool to RT and concentrated in vacuo. The residue was purified by flash column chromatography on silica gel (50% ethyl acetate/petroleum ether) to afford the desired product (100 mg, 44% yield) as a white solid.

1-(4-(6-(Trifluoromethyl)-7-(2-fluorophenyl)quinazolin-4-yl)piperazin-1-yl)prop-2-en-1-one The title compound was prepared from tert-butyl 4-(6-(trifluoromethyl)-7-(2-fluorophenyl)quinazolin-4-yl)piperazine-1-carboxylate according to the procedure described in steps 5 and 6 in Example 1. $^1$H NMR (400 MHz, DMSO-d6) δ: 9.74 (s, 1H), 8.43 (s, 1H), 7.78 (s, 1H), 7.58-7.53 (m, 1H), 7.44-7.32 (m, 3H), 6.87-6.80 (dd, J=11.0, 16.4 Hz, 1H), 6.21 (dd, J=2.4, 16.8 Hz, 1H), 5.77 (dd, J=2.1, 10.0 Hz, 1H), 4.06-4.00 (m, 4H), 3.05-3.77 (m, 4H). ESI-MS m/z: 431.2 $[M+H]^+$.

Example 34

Synthesis of 1-(1-acryloylpiperidin-4-yl)-7-chloro-6-(2,4-difluorophenyl)quinoxalin-2(1H)-one

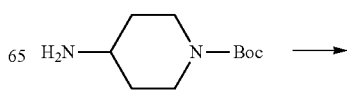

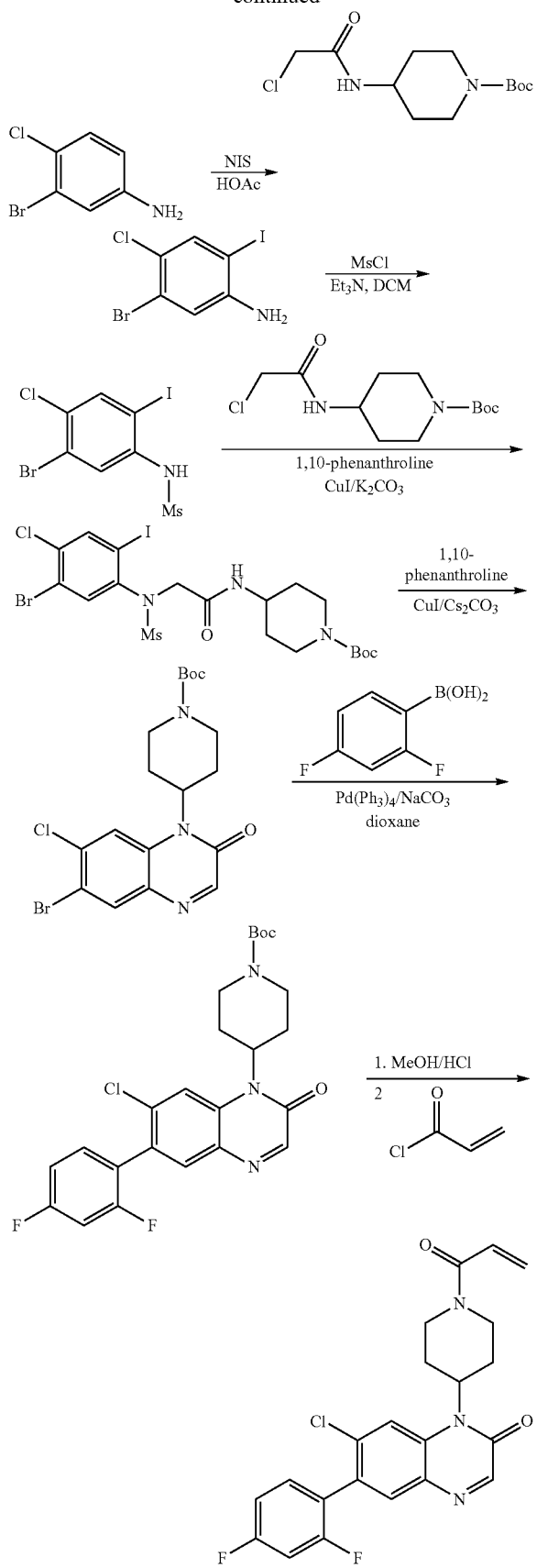

Example 34 provides an exemplary preparation according to General Synthetic Method S tert-Butyl 4-(2-chloroacetamido)piperidine-1-carboxylate To a mixture of tert-butyl 4-aminopiperidine-1-carboxylate (5 g, 25 mmol), Et₃N (4.5 mL, 32.3 mmol) in dichloromethane (50 mL) at 0° C., 2-chloroacetyl chloride (3.4 g, 30 mmol) was added dropwise. The reaction mixture was allowed to warm to RT and stirring was continued until conversion was completed. The reaction mixture was washed with NaHCO₃ aqueous solution and brine. The organic layer was dried over anhydrous Na₂SO₄, filtered and concentrated in vacuo. The residue was purified by flash column chromatography on silica gel (20-50% ethyl acetate/ petroleum ether) to afford the desired product (4 g, 57.8% yield).

5-Bromo-4-chloro-2-iodobenzenamine

A mixture of 3-bromo-4-chlorobenzenamine (15 g, 72.6 mmol) in HOAc (100 mL), NIS (19.6 g, 87.1 mmol) was added and the resulting mixture was stirred at RT for 6 h. The mixture was quenched with water, and extracted with ethyl acetate. The organic layer washed with brine, dried over Na₂SO₄ and concentrated in vacuo. The residue was purified by flash column chromatography on silica gel (5% petroleum ether/ethyl acetate) to afford the desired product (5.2 g, 21.6% yield).

N-(5-Bromo-4-chloro-2-iodophenyl)methanesulfonamide

A mixture of 5-bromo-4-chloro-2-iodobenzenamine (5.2 g, 15.6 mmol), Et₃N (4.7 g, 46.8 mmol) in dichloromethane (60 mL) at 0° C., methanesulfonyl chloride (2.2 g, 18.8 mmol) was added dropwise. The resulting mixture was stirred at RT for 10 h. The mixture was quenched with water, and extracted with dichloromethane. The organic layer was washed with brine, dried over Na₂SO₄ and concentrated in vacuo. The residue was purified by flash column chromatography on silica gel (10% petroleum ether/ethyl acetate) to afford the desired product (5 g, 78.1% yield).

tert-Butyl 4-(2-(N-(5-bromo-4-chloro-2-iodophenyl) methylsulfonamido)acetamido)piperidine-1-carboxylate A mixture of 5-bromo-4-chloro-2-iodo-N-methanesulfonybenzenamine (1.6 g, 3.9 mmol), tert-butyl 4-(2-chloroacetamido)piperidine-1-carboxylate (1.08 g, 3.9 mmol), CuI (74 mg, 0.39 mmol), 1,10-phenanthroline (141 mg, 0.78 mmol), K₂CO₃ (1.1 g, 7.58 mmol) in dioxane (20 mL) was stirred at reflux under argon for 12 h. The mixture was allowed to cool to RT, quenched with water, and then extracted with ethyl acetate. The organic layer was washed with brine, dried over Na₂SO₄ and concentrated in vacuo. The residue was purified by flash column chromatography on silica gel (30% petroleum ether/ethyl acetate) to afford the desired product (1.5 g, 59% yield).

tert-Butyl 4-(6-bromo-7-chloro-2-oxoquinoxalin-1(2H)-yl) piperidine-1-carboxylate A mixture of tert-butyl 4-(2-(N-(5-bromo-4-chloro-2-iodophenyl)methylsulfonamido)acetamido)piperidine-1-carboxylate (1.5 g, 2.31 mmol), CuI (44 mg, 0.231 mmol), 1,10-phenanthroline (83 mg, 0.462 mmol), Cs$_2$CO$_3$ (1.9 g, 5.78 mmol) in dioxane (10 mL) was stirred at reflux under argon for 12 h. The mixture was allowed to cool to RT, quenched with water, and extracted with ethyl acetate. The organic layer was washed with brine, dried over Na$_2$SO$_4$ and concentrated in vacuo. The residue was purified by flash column chromatography on silica gel (30% petroleum ether/ethyl acetate) to afford the desired product (55 mg, 5.4% yield).

1-(1-Acryloylpiperidin-4-yl)-7-chloro-6-(2,4-difluorophenyl)quinoxalin-2(1H)-one The title compound was prepared from tert-butyl4-(6-bromo-7-chloro-2-oxoquinoxalin-1 (2H)-yl)piperidine-1-carboxylate in three steps following the procedure described in Example 2. $^1$H NMR (400 MHz, DMSO-d6) δ: 8.24 (s, 1H), 7.86 (s, 1H), 7.66 (s, 1H), 7.37-7.31 (m, 1H), 7.05-6.95 (m, 2H), 6.71-6.64 (m, 1H), 6.38 (dd, J=2, 16.8 Hz, 1H), 5.74 (dd, J=2.0, 10.8 Hz, 1H), 4.97 (m, 1H), 4.27 (m, 1H), 3.28 (m, 1H), 2.84 (m, 3H), 1.89 (m, 2H), 1.66 (m, 1H) ESI-MS m/z: 430.3 [M+1]$^+$.

Example 35

Synthesis of 1-(4-(4-acryloylpiperazin-1-yl)-6-chloroquinazolin-7-yl)-5-chloropyridin-2(1H)-one

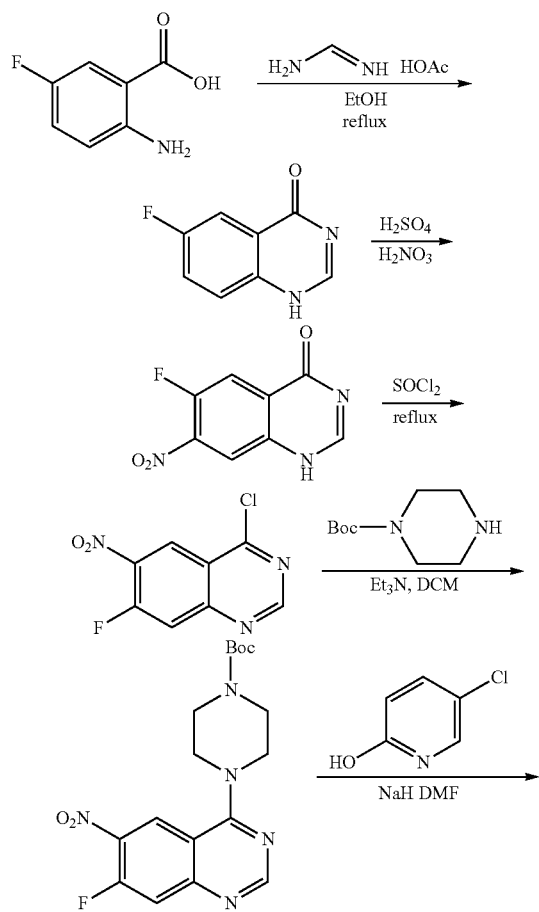

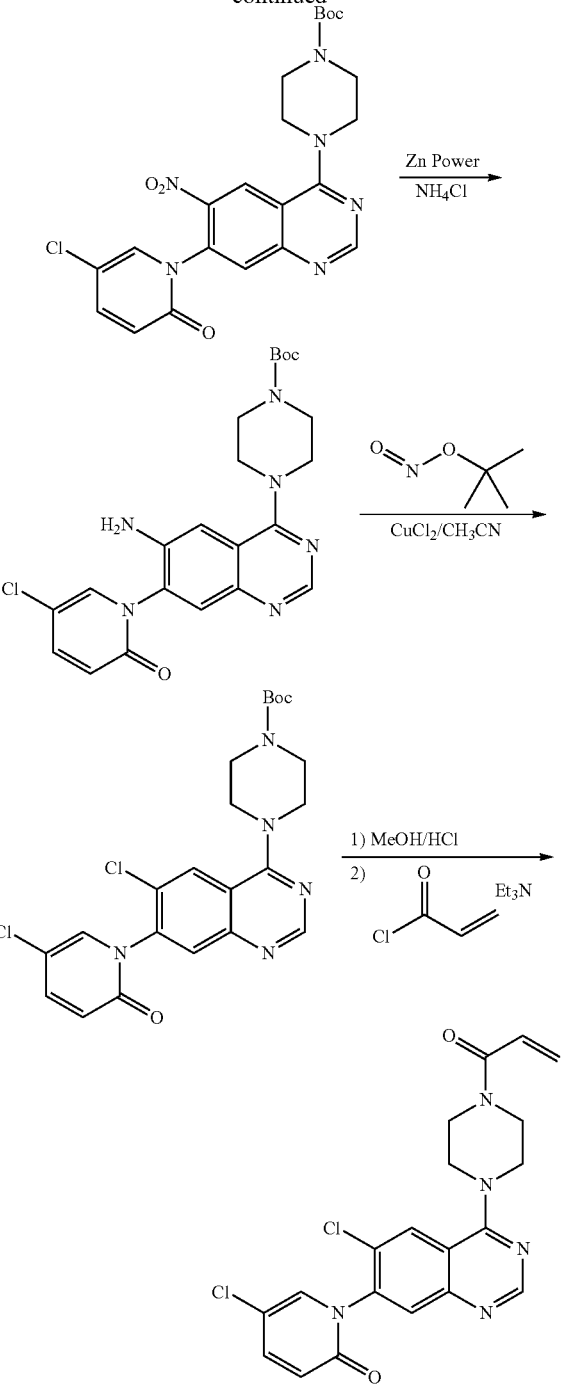

Example 35 provides an exemplary preparation according to General Synthetic Method T 6-Fluoroquinazolin-4(1H)-one A mixture of 2-amino-5-fluorobenzoic acid (8.0 g, 51.6 mmol) and formamidine acetate (10.6 g, 103 mmol) in EtOH (150 mL) was stirred at reflux for 16 h. The mixture was concentrated in vacuo and extracted with dichloromethane. The organic layer was washed with brine, dried over Na$_2$SO$_4$ and concentrated in vacuo to afford the desired product (7.8 g, 92% yield) which was used in the next step without further purification.

6-Fluoro-7-nitroquinazolin-4(1H)-one

6-Fluoroquinazolin-4(1H)-one (4.3 g, 26.2 mmol) was added to a mixture of concentrated $H_2SO_4$ (10 mL) and fuming $HNO_3$ (5 mL) at 0° C. The resulting mixture was stirred at RT for 1 h and then stirred at 110° C. for 2 h. The mixture was cooled to RT and poured into ice-water. The precipitate was collected by filtration and dried to afford the desired product (2.3 g, 42.6% yield) as a yellow solid. ESI-MS m/z: 210.3 $[M+H]^+$.

4-Chloro-7-fluoro-6-nitroquinazoline

A suspension of 6-fluoro-7-nitroquinazolin-4(1H)-one (2.3 g, 0.011 mol) in $SOCl_2$ (10 mL) was stirred at reflux for 3 h. The mixture was allowed to cool to RT, and concentrated in vacuo to afford the crude product (2.5 g) which was used in the next step without further purification.

tert-Butyl 4-(7-fluoro-6-nitroquinazolin-4-yl)piperazine-1-carboxylate

To a solution of 4-chloro-7-fluoro-6-nitroquinazoline (2.5 g, 11.0 mmol) in dichloromethane (50 mL) and $Et_3N$ (3.33 g, 33 mmol) at RT, tert-butyl piperazine-1-carboxylate (3.07 g, 16.5 mmol) was added, and the resulting mixture was stirred at RT for 16 h. The mixture was washed with saturated $NH_4Cl$ solution and brine, dried over $Na_2SO_4$ and concentrated. The residue was purified by flash column chromatography on silica gel (50% ethyl acetate/petroleum ether) to afford the desired product (1.8 g, 44% yield) as a yellow solid. ESI-MS m/z: 378.0 $[M+H]^+$.

tert-Butyl 4-(7-(5-chloro-2-oxopyridin-1(2H)-yl)-6-nitroquinazolin-4-yl)piperazine-1-carboxylate To a solution of 5-chloropyridin-2-ol (213 mg, 1.39 mmol) in DMF (5 mL) at RT, NaH (55.6 mg, 1.39 mmol) was added and the resulting mixture was stirred for 30 min. To this mixture, tert-butyl 4-(7-fluoro-6-nitroquinazolin-4-yl)piperazine-1-carboxylate (350 mg, 0.928 mmol) was added and the resulting mixture was stirred at 50° C. for 1.5 h. The mixture was allowed to cool to RT and partitioned between water and ethyl acetate. The organic layer was washed with brine, dried over $Na_2SO_4$ and concentrated. The residue was purified by flash column chromatography on silica gel (5% ethyl acetate/petroleum ether) to afford the desired product (400 mg, 88% yield) as a yellow solid. ESI-MS m/z: 487.2 $[M+H]^+$.

tert-Butyl 4-(6-amino-7-(5-chloro-2-oxopyridin-1(2H)-yl)quinazolin-4-yl)piperazine-1-carboxylate A mixture of 4-(7-(5-chloro-2-oxopyridin-1(2H)-yl)-6-nitroquinazolin-4-yl)piperazine-1-carboxylate (400 mg, 0.818 mmol), ammonium chloride (520 mg, 9.82 mmol), Zn powder (265.8 mg, 4.09 mmol) in EtOH (20 mL) and water (4 mL) was stirred at 70° C. for 2 h. The mixture was concentrated in vacuo and extracted with dichloromethane. The organic layer was washed with $NaHCO_3$ and brine, dried over $Na_2SO_4$ and concentrated in vacuo. The residue was purified by flash column chromatography on silica gel (30% ethyl acetate/petroleum ether) to afford the desired product (300 mg, 80.4% yield) as a solid. ESI-MS m/z: 457.2 $[M+H]^+$.

tert-Butyl 4-(6-chloro-7-(5-chloro-2-oxopyridin-1(2H)-yl)quinazolin-4-yl)piperazine-1-carboxylate To a mixture of tert-Butyl nitrite (135.5 mg, 1.32 mmol) and cupric chloride (280 mg, 1.65 mmol) in $CH_3CN$ (10 mL), tert-butyl 4-(6-amino-7-(5-chloro-2-oxopyridin-1(2H)-yl)quinazolin-4-yl)piperazine-1-carboxylate (300 mg, 0.658 mmol) in $CH_3CN$ (5 mL) was added and the resulting mixture was stirred at RT for 2 h. The mixture was partitioned between water and ethyl acetate. The organic layer was washed with brine, dried over $Na_2SO_4$ and concentrated. The residue was purified by flash column chromatography on silica gel (50% ethyl acetate/petroleum ether) to afford the desired product (110 mg, 38% yield).

1-(4-(4-Acryloylpiperazin-1-yl)-6-chloroquinazolin-7-yl)-5-chloropyridin-2(1H)-one The title compound was prepared from tert-butyl 4-(6-chloro-7-(5-chloro-2-oxopyridin-1 (2H)-yl)quinazolin-4-yl) piperazine-1-carboxylate according to the procedure described in steps 5 and 6 in Example 1. $^1$HNMR (400 MHz, DMSO-d6) δ: 8.71 (s, 1H), 8.29 (s, 1H), 8.10 (s, 1H), 7.95 (d, 1H), 7.75 (d, 1H), 6.87-6.80 (dd, J=12.0, 12.0 Hz, 1H), 6.46 (dd, J=8.0, 1H), 6.20 (d, J=2.6, 16.8 Hz, 1H), 5.76 (dd, J=2.2, 10.0 Hz, 1H), 3.91-3.77 (m, 8H). ESI-MS m/z: 430.4 $[M+H]^+$.

Example 36

Synthesis of 1-(4-(6-chloro-7-(2-(thiazol-2-yl)phenyl)quinazolin-4-yl)piperazin-1-yl)prop-2-en-1-one

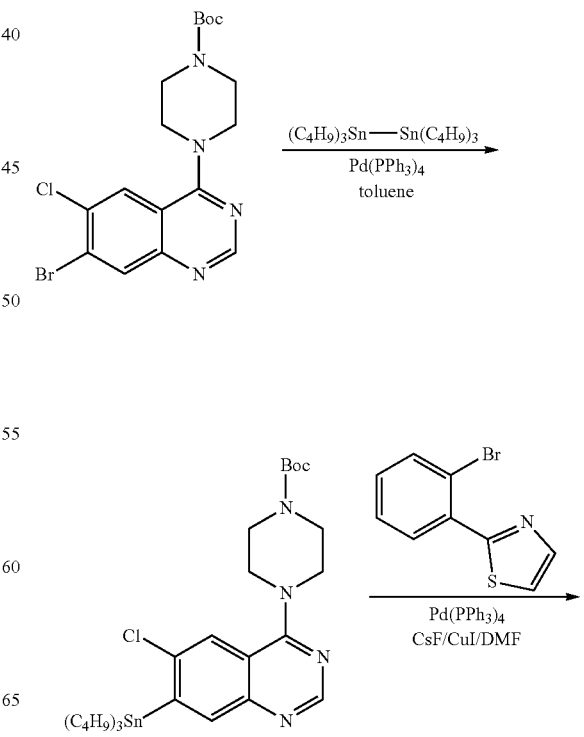

-continued

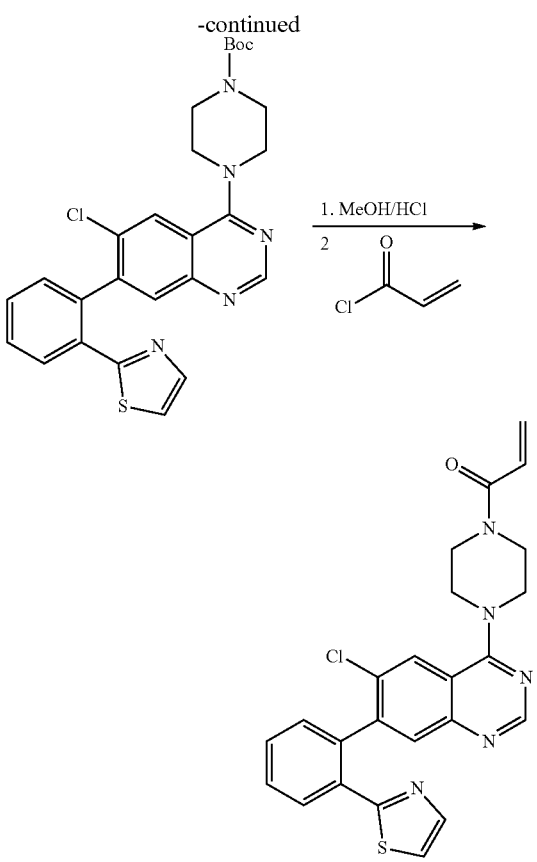

Example 36 provides an exemplary preparation according to General Synthetic Method U tert-Butyl 4-(7-(tributylstannyl)-6-chloroquinazolin-4-yl)piperazine-1-carboxylate A mixture of tert-butyl 4-(7-bromo-6-chloroquinazolin-4-yl)piperazine-1-carboxylate (1.5 g, 3.51 mmol), 1,1,1,2,2,2-hexabutyldistannane (2.6 g, 4.56 mmol), Pd(PPh$_3$)$_4$ (203 mg, 0.18 mmol) in toluene (40 mL) was stirred at reflux under argon for 16 h. The mixture was allowed to cool to RT, quenched with water, and extracted with ethyl acetate. The organic layer was washed with brine, dried over Na$_2$SO$_4$ and concentrated in vacuo. The residue was purified by flash column chromatography on silica gel (40% petroleum ether/ethyl acetate) to afford the desired product (542 mg, 24% yield).

tert-Butyl 4-(6-chloro-7-(2-(thiazol-2-yl)phenyl)quinazolin-4-yl)piperazine-1-carboxylate A mixture of tert-butyl4-(7-(tributylstannyl)-6-chloroquinazolin-4-yl)piperazine-1-carboxylate (150 mg, 0.24 mmol), 2-(2-bromophenyl)thiazole (68 mg, 0.28 mmol), Pd(PPh$_3$)$_4$ (28 mg, 0.024 mmol), CsF (73 mg, 0.48 mmol) and CuI (9 mg, 0.048 mmol) in DMF (10 mL) was stirred at 80° C. under argon for 16 h. Then reaction mixture was allowed to cool to room temperature, quenched with water, extracted with ethyl acetate. The organic layer was washed with brine, dried over Na$_2$SO$_4$ and concentrated in vacuo. The residue was purified by flash column chromatography on silica gel (dichloromethane/methanol=25:1) to afford the desired product (38 mg, 31.1% yield).

1-(4-(6-Chloro-7-(2-(thiazol-2-yl)phenyl)quinazolin-4-yl)piperazin-1-yl)prop-2-en-1-one A mixture of 4-(6-chloro-7-(2-(thiazol-2-yl)phenyl)quinazolin-4-yl)piperazine-1-carboxylate (38 mg, 0.075 mmol) in HCl/MeOH (2.86 M, 5 mL) was stirred at RT for 1 h. The mixture was concentrated in vacuo to afford the crude product. The crude product was dissolved in dichloromethane (5 mL) at RT, acryloyl chloride (8 mg, 0.090 mmol) and Et$_3$N (23 mg, 0.225 mmol) were added and the resulting mixture was stirred at RT for 1 h. The mixture was partitioned between dichloromethane and water. The organic layer was washed brine, dried over MgSO$_4$, filtered and concentrated in vacuo. The residue was purified by flash column chromatography on silica gel (dichloromethane/methanol=20:1) to afford the desired product (8 mg, 23% yield, 2 steps). $^1$H NMR (400 MHz, DMSO-d6) δ: 8.69 (s, 1H), 8.15 (d, J=2.4 Hz, 1H), 8.13 (s, 1H), 7.82 (s, 1H), 7.76 (d, J=3.2 Hz, 1H), 7.67-7.60 (m, 3H), 7.43-7.41 (m, 1H), 6.87-6.81 (m, 1H), 6.18 (dd, J=2.0, 16.8 Hz, 1H), 5.75 (dd, J=2.0, 10.0 Hz, 1H), 3.92-3.78 (m, 8H). ESI-MS m/z: 462.3 [M+1]$^+$.

Example 37

Synthesis of 1-(4-(6,8-dichloro-7-(2-(fluorophenyl)quinazolin-4-yl)piperazin-1-yl)prop-2-en-1-one

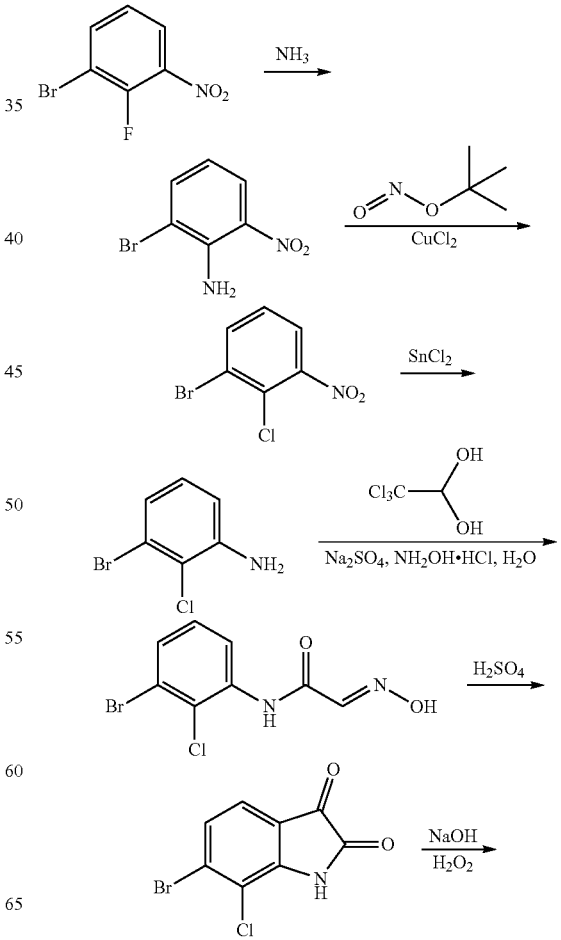

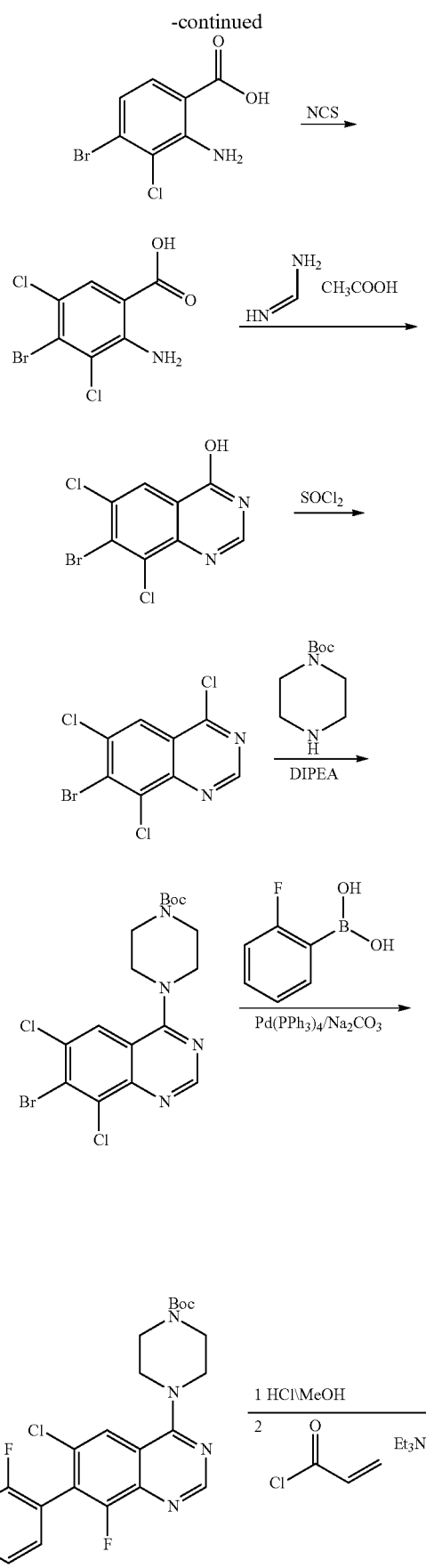

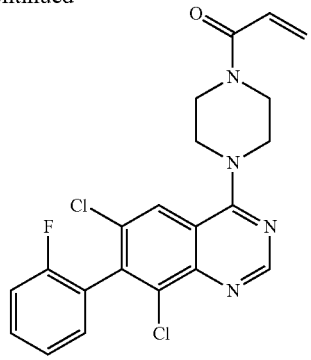

Example 37 provides an exemplary preparation according to General Synthetic Method V

2-Bromo-6-nitroaniline

A mixture of 1-bromo-2-fluoro-3-nitrobenzene (6.0 g, 27.27 mmol) and $NH_3$ in $CH_3OH$ (7 M, 20 mL) was stirred in a sealed tube at 100° C. for 16 h. The solvent was removed and the residue was dissolved in $H_2O$, and then extracted with ethyl acetate. The organic layer was washed with brine, dried over $Na_2SO_4$ and concentrated. The residue was purified by column chromatography on silica gel (ethyl acetate/petroleum ether=1:100) to afford the product as a yellow solid (5.4 g, 91.3% yield).

1-Bromo-2-chloro-3-nitrobenzene

A mixture of 2-bromo-6-nitroaniline (3.0 g, 13.84 mmol), tert-butyl nitrite (2.85 g 27.68 mmol) and $CuCl_2$ (3.7 g, 27.68 mmol) in $CH_3CN$ (60 mL) was stirred at 60° C. under argon for 1 h. The mixture was allowed to cool to RT, quenched with $H_2O$, and extracted with ethyl acetate. The organic layer was washed with brine, dried over $Na_2SO_4$ and concentrated. The residue was purified by column chromatography on silica gel (ethyl acetate/petroleum ether=1:100) to yield the product as an off-white solid (2.7 g, 82.7% yield).

3-Bromo-2-chloroaniline

A mixture of 1-bromo-2-chloro-3-nitrobenzene (2.7 g, 11.44 mmol) and $SnCl_2$ (12.97 g, 57.20 mmol) in $CH_3CH_2OH$ (60 mL) was stirred at reflux for 3 h. The mixture was allowed to cool to RT, quenched with $H_2O$, and extracted with ethyl acetate. The organic layer was washed with brine, dried over $Na_2SO_4$ and concentrated. The residue was purified by column chromatography on silica gel (ethyl acetate/petroleum ether=1:50) to yield the product as an off-white solid (1.3 g, 55.2% yield).

1-(4-(6,8-Dichloro-7-(2-fluorophenyl)quinazolin-4-yl)piperazin-1-yl)prop-2-en-1-one The title compound was prepared from 3-bromo-2-chloroaniline according to the procedure described in Example 30. $^1$H NMR (400 MHz, DMSO-d6) δ: 8.76 (s, 1H), 8.20 (s, 1H), 7.61-7.57 (m, 1H), 7.45-7.40 (m, 3H), 6.83 (dd, J=10.4, 16.8, 1H), 6.18 (dd, J=2.4, 16.8, 1H), 5.75 (dd, J=2.4, 10.4, 1H), 3.93-3.76 (m, 8H). ESI-MS m/z: 430.1 [M+H]$^+$.

Example 38
Synthesis of 1-(4-(8-fluoro-7-(2-fluorophenyl)-6-(trifluoromethyl)quinazolin-4-yl)piperazin-1-yl)prop-2-en-1-one
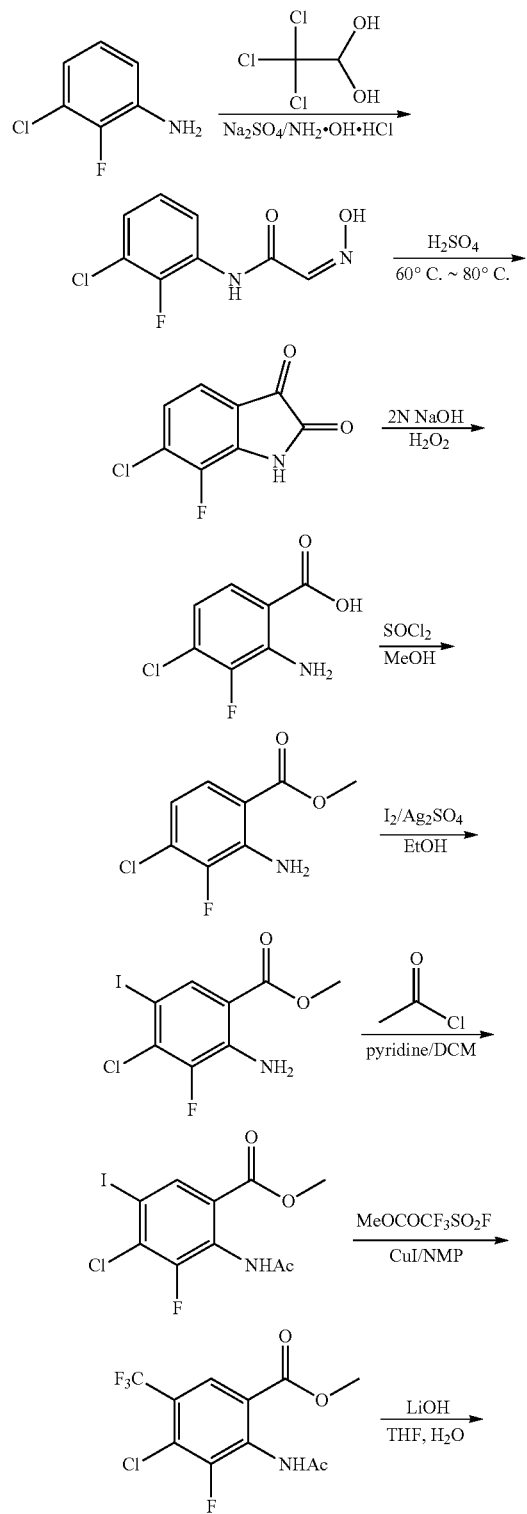
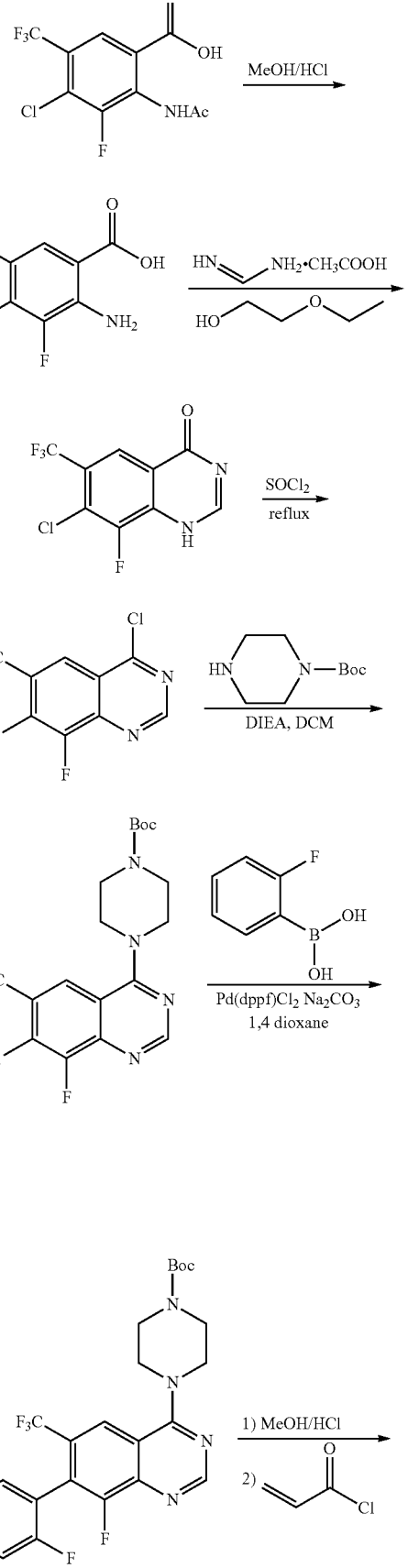

-continued

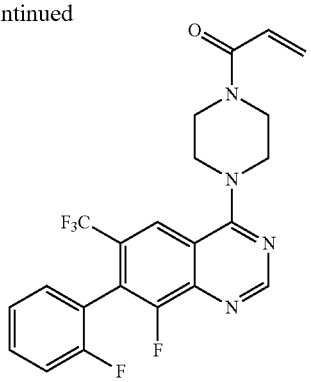

Example 38 provides an exemplary preparation according to General Synthetic Method W 2-Amino-4-chloro-3-fluorobenzoic acid The title compound was prepared from 3-chloro-2-fluorobenzenamine according to the procedure described in Example 30.

Methyl 2-amino-4-chloro-3-fluorobenzoate

To a solution of 2-amino-4-chloro-3-fluorobenzoic acid (7.0 g, 35.0 mmol) in MeOH (100 mL) at 0° C., thionyl chloride (8.37 g, 70 mmol) was added dropwise. The mixture was warmed stirred at RT for 30 min, and then stirred at reflux for 16 h. The mixture was concentrated in vacuo. The residue was extracted with dichloromethane and washed with brine. The organic layer was dried over $Na_2SO_4$ and concentrated in vacuo. The residue was purified by flash column chromatography on silica gel (10% ethyl acetate/ petroleum ether) to afford the desired product (4.0 g, 56% yield) as a white solid.

1-(4-(8-Fluoro-6-(trifluoromethyl)-7-(2-fluorophenyl)quinazolin-4-yl)piperazin-1-yl)prop-2-en-1-one The title compound was prepared from methyl 2-amino-4-chloro-3-fluorobenzoate according to the procedure described in Example 32. $^1$HNMR (400 MHz, DMSO-d6) δ: 8.78 (s, 1H), 8.32 (s, 1H), 7.61 (m, 1H), 7.49-7.37 (m, 3H), 6.87-6.80 (dd, J=11.0, 16.4 Hz, 1H), 6.21-6.16 (dd, J=2.4, 16.8 Hz, 1H), 5.775.73 (dd, J=2.1, 10.0 Hz, 1H), 4.06-4.00 (m, 4H), 3.85-3.72 (m, 4H). ESI-MS m/z: 449.2 [M+H]$^+$ Example 39

Synthesis of 1-(4-(7-(2-fluoro-6-hydroxyphenyl)-6-(trifluoromethyl)cinnolin-4-yl)piperazin-1-yl)prop-2-en-1-one

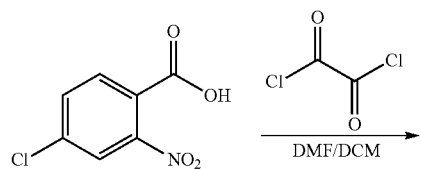

-continued

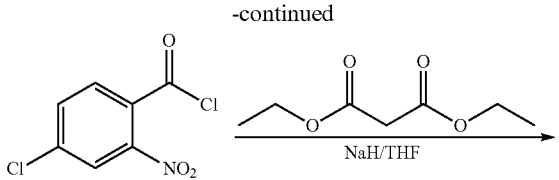

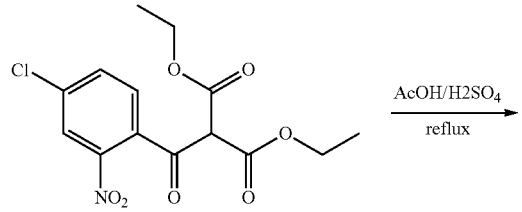

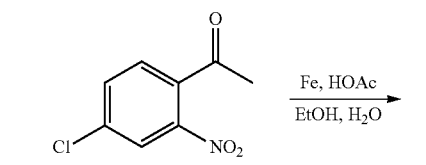

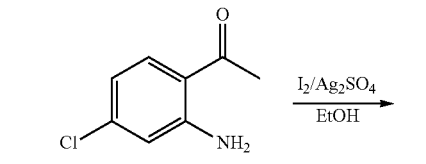

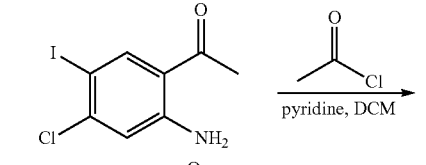

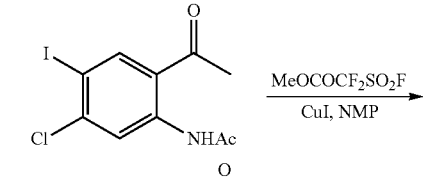

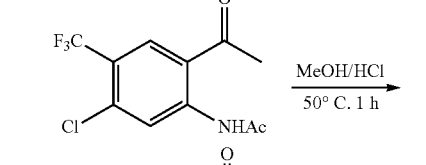

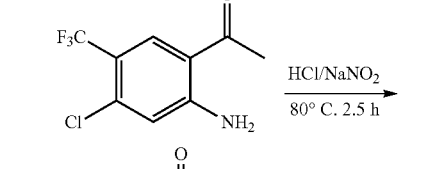

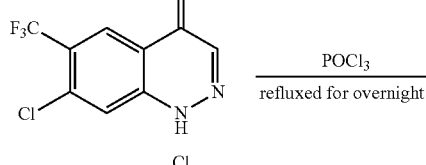

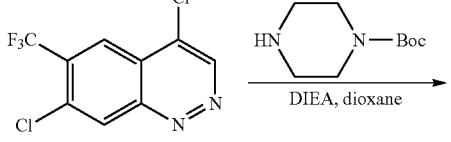

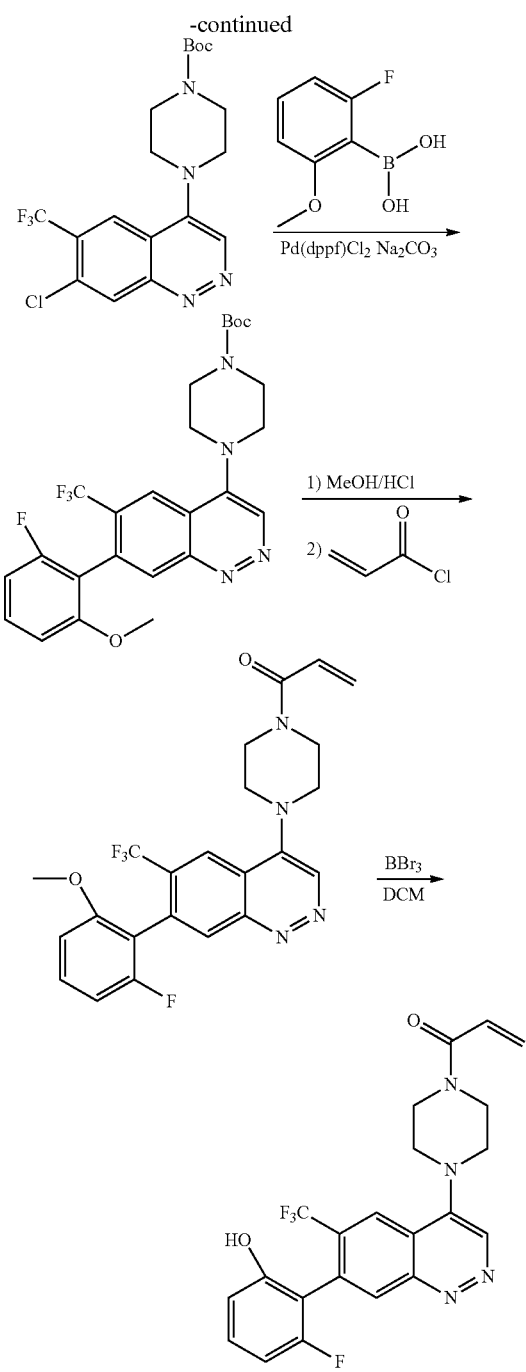

Example 39 provides an exemplary preparation according to General Synthetic Method X 1-(4-Chloro-2-nitrophenyl)ethanone To a stirred solution of 4-chloro-2-nitrobenzoic acid (15.0 g, 75 mmol) in THF (250 mL) at 0° C., oxalyl chloride (13 mL, 150 mmol) was added followed by DMF (2 drops). The mixture was stirred at 0° C. for 10 min and then stirred at reflux 2 h. The mixture was concentrated in vacuo to dryness to afford 4-chloro-2-nitrobenzoyl chloride. To a solution of diethyl malonate (12.0 g, 75 mmol) in THF (250 mL), NaH (3.6 g, 90 mmol) was added in portions and the resulting mixture was stirred at RT for 20 min. A solution of 4-chloro-2-nitrobenzoyl chloride in THF (100 mL) was added dropwise to the reaction mixture at 0° C. The resulting mixture was stirred at RT for 30 min and then stirred at 80° C. for 2 h. The mixture was quenched with water and partitioned between water and ethyl acetate. The organic layer was dried over anhydrous $Na_2SO_4$, filtered and concentrated in vacuo. The residue was dissolved in AcOH (25 mL) and 20% $H_2SO_4$ (25 mL) and the resulting mixture was stirred at 80° C. for 6 h. The mixture was extracted with ethyl acetate, washed with brine, water and $NaHCO_3$ solution. The organic layer was dried over $Na_2SO_4$ and concentrated in vacuo. The residue was purified by flash column chromatography on silica gel (ethyl acetate/petroleum ether=1:5) to afford the desired product (5.0 g, 33% yield) as a light yellow solid.

1-(2-Amino-4-chlorophenyl)ethanone

A mixture of methyl 1-(4-chloro-2-nitrophenyl)ethanone (5.0 g, 25 mmol) and Fe (5.6 g, 100 mmol) in $CH_3COOH$ (50 mL) and $H_2O$ (50 mL) was stirred at reflux for 16 h. The mixture was allowed to cool to RT and quenched with saturated $NaHCO_3$ aqueous solution. The mixture was extracted with ethyl acetate. The organic layer was washed with saturated $NaHCO_3$ aqueous solution and brine, dried over $Na_2SO_4$ and concentrated in vacuo. The residue was purified by flash column chromatography on silica gel (ethyl acetate/petroleum ether=1:4) to afford the desired product (3.8 g, 89% yield) as a yellow solid.

1-(2-Amino-4-chloro-5-iodophenyl)ethanone

To a mixture of $I_2$ (4.5 g, 17.7 mmol) and $Ag_2SO_4$ (5.5 g, 17.7 mmol) in EtOH (100 mL), 1-(2-amino-4-chlorophenyl)ethanone (3.0 g, 17.7 mmol) was added and the resulting mixture was stirred at RT for 45 min. The solid was filtered off and washed with dichloromethane, and the filtrate was concentrated in vacuo. The residue was extracted with dichloromethane. The organic layer was washed with brine, dried over $Na_2SO_4$ and concentrated in vacuo to afford the desired product (2.0 g, 38% yield) as a white solid. ESI-MS m/z: 295.3 $[M+H]^+$.

N-(2-Acetyl-5-chloro-4-iodophenyl)acetamide

To a stirred solution of methyl 2-amino-4-chloro-3-fluoro-5-iodobenzoate (2.0 g, 6.8 mmol) and pyridine (1.6 g, 20.3 mmol) in DCM (50 mL) at 0° C., acetyl chloride (634 mg, 8.14 mmol) was added. The mixture was stirred at RT for 16 h. The reaction mixture was washed with brine. The organic layer was dried over anhydrous $Na_2SO_4$, filtered and concentrated in vacuo. The residue was purified by flash column chromatography on silica gel (ethyl acetate/petroleum ether=1:5) to afford the desired product (1.4 g, 61% yield). ESI-MS m/z: 338.4 $[M+H]^+$.

N-(2-Acetyl-5-chloro-4-(trifluoromethyl)phenyl)acetamide

To a stirred solution of N-(2-acetyl-5-chloro-4-iodophenyl)acetamide (1.4 g, 4.2 mmol) and methyl 2,2-difluoro-2-(fluorosulfonyl)acetate (1.6 g, 8.3 mmol) in NMP (20 mL) at RT, CuI (235 mg, 1.24 mmol) was added and the resulting mixture was stirred at 90° C. for 16 h. The mixture was quenched with water and partitioned between water and ethyl acetate. The organic layer was dried over anhydrous $Na_2SO_4$, filtered and concentrated in vacuo. The residue was purified by flash column chromatography on silica gel (ethyl acetate/petroleum ether=1:5) to afford the desired product (1.0 g, 87% yield) as oil. ESI-MS m/z: 280.1 [M+H]+.

1-(2-Amino-4-chloro-5-(trifluoromethyl)phenyl) ethanone

The mixture of 2-acetamido-4-chloro-3-fluoro-5-(trifluoromethyl)benzoic acid (1.0 g, 3.58 mmol) in HCl/MeOH (2.85 M, 10 mL) was stirred at 60° C. for 1.5 h. The reaction mixture was concentrated in vacuo to afford the desired product (900 mg) which was used in the next step without further purification.

7-Chloro-6-(trifluoromethyl)cinnolin-4(1H)-one

Concentrated HCl (10 mL) was added to 1-(2-amino-4-chloro-5-(trifluoromethyl)phenyl)ethanone (900 mg, 3.58 mmol). After the mixture was cooled to 0° C., a solution of sodium nitrite (259 mg, 3.76 mmol) in water (2 mL) was added over 30 min. The mixture was stirred at 0° C. for 30 min and then stirred at 60° C. for 2 h. The mixture was cooled and poured into water. The solid was collected by filtration afford the desired the crude product (680 mg, 77% yield).

1-(4-(7-(2-Fluoro-6-hydroxyphenyl)-6-(trifluoromethyl)cinnolin-4-yl)piperazin-1-yl)prop-2-en-1-one The title compound was prepared from 7-chloro-6-(trifluoromethyl)cinnolin-4(1H)-one according to the procedure described in Example 29. $^1$HNMR (400 MHz, CDCl$_3$) δ: 9.06 (s, 1H), 8.47 (s, 1H), 8.45 (s, 1H), 6.84 (m, 1H), 6.69-6.62 (dd, J=14.0, 12.0 Hz, 1H), 6.44 (dd, J=2.6, 14.5 Hz, 1H), 5.85 (dd, J=2.2, 10.0 Hz, 1H), 5.38 (m, 1H), 4.05-3.96 (m, 4H), 3.54-3.52 (m, 4H). ESI-MS m/z: 447.2 [M+H]+.

Example 40

Synthesis of 1-(4-(7-(2,4-difluorophenyl)-8-fluoro-6-methylquinazolin-4-yl)piperazin-1-yl)prop-2-en-1-one

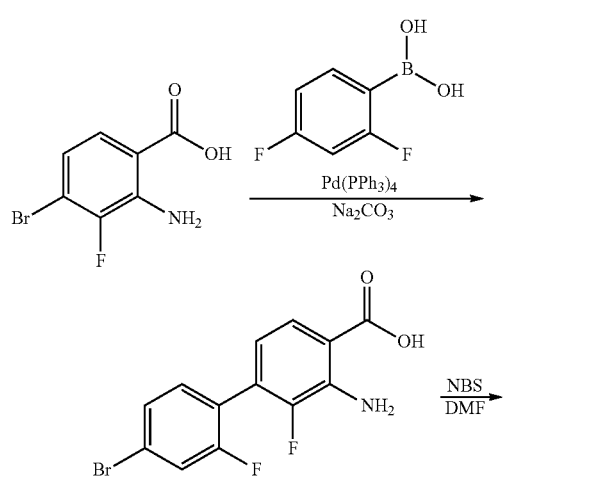

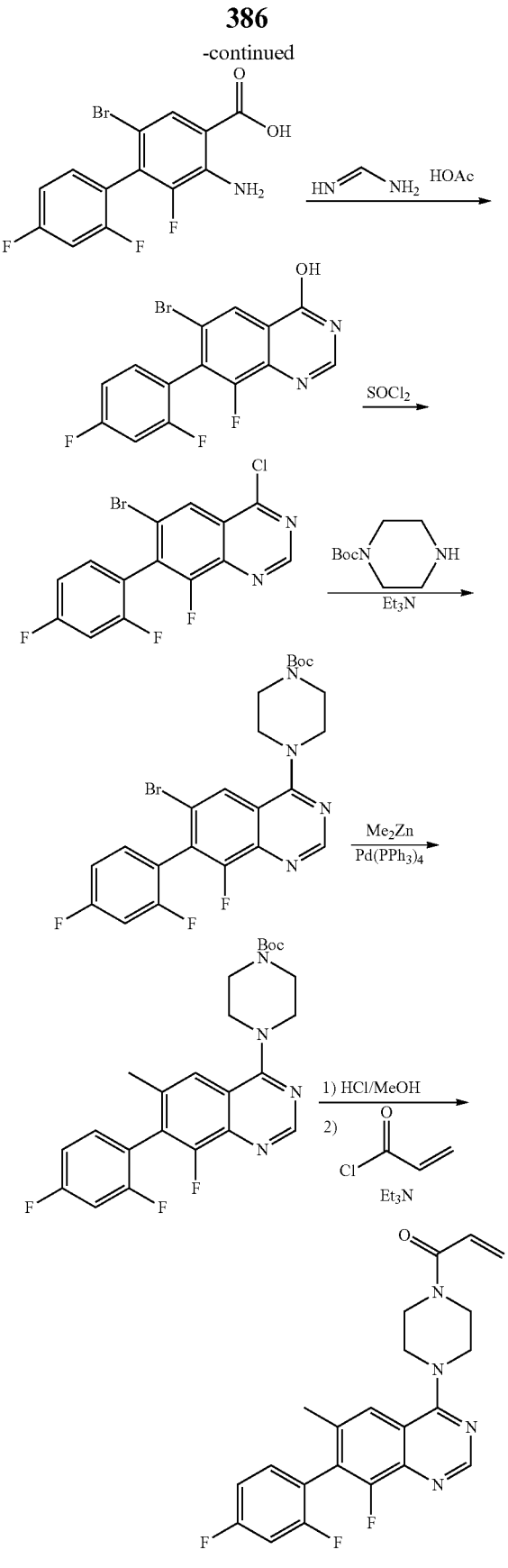

Example 40 provides an exemplary preparation according to General Synthetic Method AJ

3-Amino-2,2',4'-trifluoro-[1,1'-biphenyl]-4-carboxylic acid

A mixture of 2-amino-4-bromo-3-fluorobenzoic acid (400 mg, 1.71 mmol), (2,4-difluorophenyl)boronic acid (405 mg, 1.5 mmol), Pd(PPh₃)₄ (197 mg, 0.171 mmol) and Na₂CO₃ (725 mg, 6.84 mmol) in 1,4-dioxane/H₂O (10 mL/2 mL) was stirred at 100° C. under argon for 16 h. The mixture was allowed to cool to RT and concentrated in vacuo. The residue was purified by flash column chromatography on silica gel (dichloromethane/methanol=20:1) to yield the desired product (374 mg, 81.9% yield) as an off-white solid. ESI-MS m/z: 268.1 [M+H]⁺.

3-Amino-6-bromo-2,2',4'-trifluoro-[1,1'-biphenyl]-4-carboxylic acid

A mixture of 3-amino-2,2',4'-trifluoro-[1,1'-biphenyl]-4-carboxylic acid (374 mg, 1.4 mmol) and NBS (249 mg, 1.4 mmol) in DMF (4 mL) was stirred at RT for 2 h. The reaction mixture was quenched with H₂O, and then extracted with ethyl acetate. The organic layer was washed with brine, dried over Na₂SO₄ and concentrated in vacuo. The residue was purified by flash column chromatography on silica gel (Petroleum ether/ethyl acetate=2:1) to yield the desired product (330 mg, 67.9% yield) as a gray solid. ESI-MS m/z: 345.9 [M+H]⁺.

6-Bromo-7-(2,4-difluorophenyl)-8-fluoroquinazolin-4-ol

A mixture of 3-amino-6-bromo-2,2',4'-trifluoro-[1,1'-biphenyl]-4-carboxylic acid (330 mg, 0.95 mmol) and formimidamide acetate (790 mg, 7.6 mmol) was stirred at reflux for 16 h. The mixture was allowed to cool to RT, and quenched with water. The solid precipitate was collected by filtration and rinsed with a mixture of petroleum ether-ethyl acetate-MeOH (100:10:5) and dried in vacuo to yield the crude product (320 mg, 94.8% yield) as a brown solid. ESI-MS m/z: 354.9 [M+H]⁺.

6-Bromo-4-chloro-7-(2,4-difluorophenyl)-8-fluoroquinazoline

A mixture of 6-bromo-7-(2,4-difluorophenyl)-8-fluoroquinazolin-4-ol (320 mg, 0.901 mmol), SOCl₂ (3 mL) and DMF (cat.) was stirred at reflux for 1 h. The mixture was allowed to cool to RT and then concentrated in vacuo to yield the desired product as a brown solid which was used directly in next step without further purification tert-Butyl-4-(6-bromo-7-(2,4-difluorophenyl)-8-fluoroquinazolin-4-yl)piperazine-1-carboxylate The above obtained crude 6-bromo-4-chloro-7-(2,4-difluorophenyl)-8-fluoroquinazoline was added to the mixture of tert-butyl piperazine-1-carboxylate (344 mg, 1.80 mmol) and DIPEA (585 mg, 4.50 mmol) in dioxane (10 mL). The resulting mixture was stirred at reflux for 16 h and then was quenched with saturated NaHCO₃ aqueous solution. The mixture was extracted with dichloromethane. The organic layer was washed with saturated NaHCO₃ aqueous solution and brine, dried over Na₂SO₄ and concentrated in vacuo. The residue was purified by flash column chromatography on silica gel (ethyl acetate/petroleum ether=2:1) to yield the desired product (410 mg, 87% yield, 2 steps) as an off-white solid. ESI-MS m/z: 523.1 [M+H]⁺.

tert-Butyl-4-(7-(2,4-difluorophenyl)-8-fluoro-6-methylquinazolin-4-yl)piperazine-1-carboxylate To a solution of tert-butyl-4-(6-bromo-7-(2,4-difluorophenyl)-8-fluoroquinazolin-4-yl)piperazine-1-carboxylate (200 mg, 0.382 mmol) and Pd(PPh₃)₄ (44 mg, 0.0382 mmol) in THF (4 mL) at RT under nitrogen atmosphere, dimethylzinc (1.147 mL, 1.147 mmol, 1.0 M in THF) was added. The resulting mixture was stirred at RT for 30 min and then stirred at 50° C. overnight. The mixture was allowed to cool to RT, quenched with saturated NH₄Cl aqueous solution, and extracted with ethyl acetate. The organic layer was washed with saturated NaHCO₃ solution and brine, dried over Na₂SO₄ and concentrated in vacuo. The residue was purified by Prep-HPLC to yield the desired product (90 mg, 51.3% yield) as an off-white solid. ESI-MS m/z: 459.2 [M+H]⁺.

1-(4-(7-(2,4-Difluorophenyl)-8-fluoro-6-methylquinazolin-4-yl)piperazin-1-yl)prop-2-en-1-one The title compound was prepared from tert-butyl-4-(7-(2,4-difluorophenyl)-8-fluoro-6-methylquinazolin-4-yl)piperazine-1-carboxylate in two steps according to the procedure described in Example 2. ¹H NMR (400 MHz, DMSO-d6) δ: 8.67 (s, 1H), 7.83 (s, 1H), 7.57-7.47 (m, 2H), 7.32-7.29 (m, 1H), 6.84 (dd, J=10.4, 16.8, 1H), 6.18 (dd, J=2.4, 16.8, 1H), 5.75 (dd, J=2.0, 10.4, 1H), 3.87-3.77 (m, 8H), 2.26 (s, 3H). ESI-MS m/z: 413.2 [M+H]⁺.

Example 41

Synthesis of 1-(4-(7-(2,4-difluorophenyl)-6,8-difluoroquinazolin-4-yl)piperazin-1-yl)prop-2-en-1-one

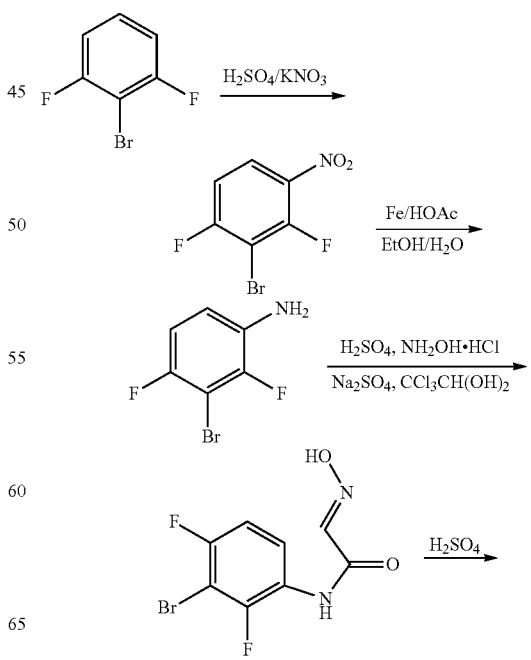

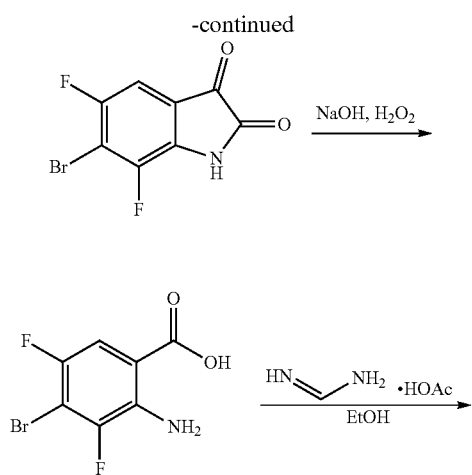

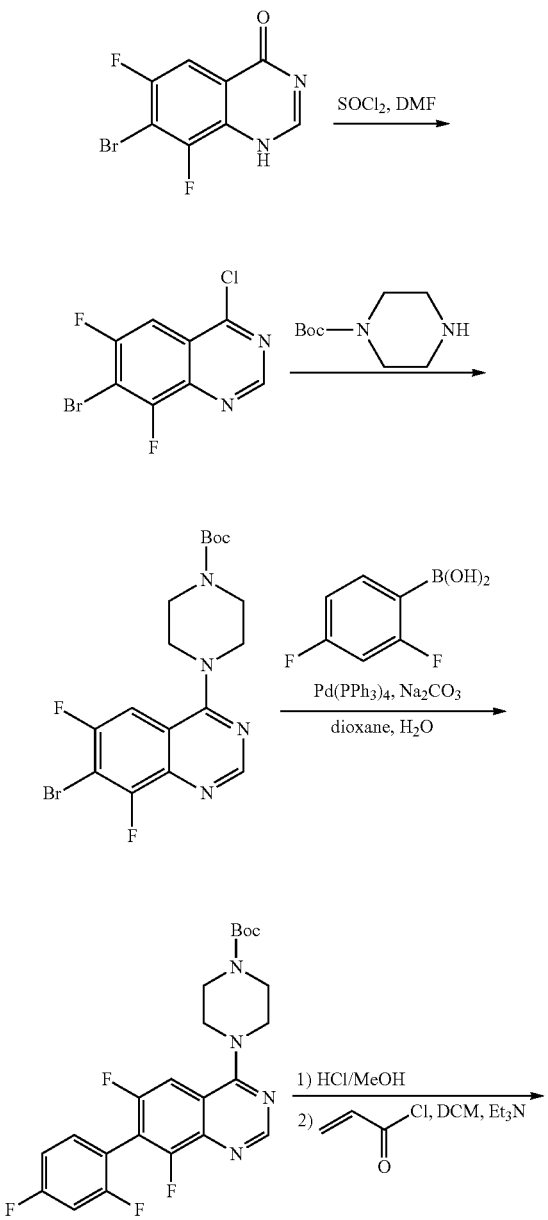

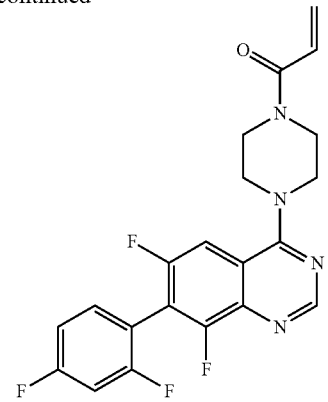

Example 41 provides an exemplary preparation according to General Synthetic Method Y 2-Bromo-1,3-difluoro-4-nitrobenzene KNO$_3$ (5.20 g, 51.80 mmol) was added into a solution of 2-bromo-1,3-difluorobenzene (5.0 g, 26.0 mmol) in H$_2$SO$_4$ (30 mL) at) 0° C. and stirred at 25° C. for 18 h. The mixture was poured into ice-water and extracted with ethyl acetate. The organic layer was washed with saturated NaHCO$_3$ aqueous solution and brine, dried over Na$_2$SO$_4$ and concentrated to yield the product as a yellow solid (5.0 g, 81% yield).

3-Bromo-2,4-difluoroaniline

To a mixture of 2-bromo-1,3-difluoro-4-nitrobenzene (5 g, 21.01 mmol), AcOH (5.70 g, 94.53 mmol), EtOH (100 mL) and H$_2$O (60 mL) at RT, iron powder (5.30 g, 94.53 mmol) was added in portions and the resulting mixture was stirred at RT for 16 h. The mixture was neutralized with NaOH (5 N) solution and then extracted with ethyl acetate. The organic layer was washed with brine, dried over Na$_2$SO$_4$ and concentrated in vacuo. The residue was purified by flash column chromatography on silica gel (petroleum) to afford the desired product (1.60 g, 37% yield) as a brown oil.

N-(3-Bromo-2,4-difluorophenyl)-2-(hydroxyimino) acetamide

To a mixture of 3-bromo-2,4-difluoroaniline (1.60 g, 7.69 mmol), Na$_2$SO$_4$ (9.8 g, 68.77 mmol), 2,2,2-trichloroethane-1,1-diol (1 g, 5.82 mmol) and hydroxylamine hydrochloride (1.1 g, 15.87 mmol), the concentrated sulfuric acid (4 mL) was added. The resulting mixture was stirred at 130° C. for 2 h and yellow precipitate was formed. The mixture was cooled to RT. The solid was collected by filtration, rinsed with water, and dried in the air to afford the desired product (1.3 g, 61% yield).

1-(4-(6,8-Difluoro-7-(2,4-difluorophenyl)quinazolin-4-yl)piperazin-1-yl)prop-2-en-1-one The title compound was prepared from N-(3-bromo-2,4-difluorophenyl)-2-(hydroxyimino)acetamide according to the procedure described in Example 30. $^1$H NMR (400 MHz, CDCl$_3$) δ: 8.83 (s, 1H), 7.49-7.44 (m, 2H), 7.09-7.00 (m, 2H), 6.63 (dd, J=10.5, 16.9 Hz, 1H), 6.39 (dd, J=1.3, 16.8 Hz, 1H), 5.80 (dd, J=1.4, 10.4 Hz, 1H), 3.91-3.86 (m, 8H). ESI-MS m/z: 417.2 [M+H]$^+$.

Example 42

Synthesis of 1-(4-(6-chloro-7-(2,4-difluorophenyl)-8-hydroxyquinazolin-4-yl)piperazin-1-yl)prop-2-en-1-one

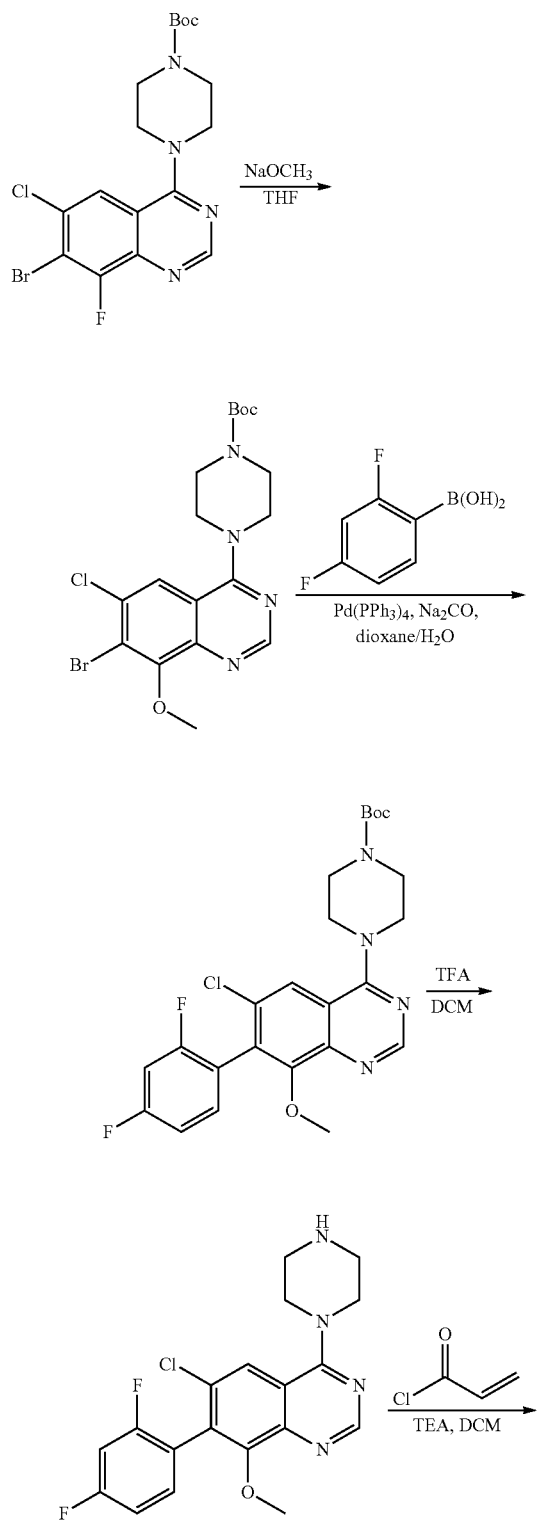

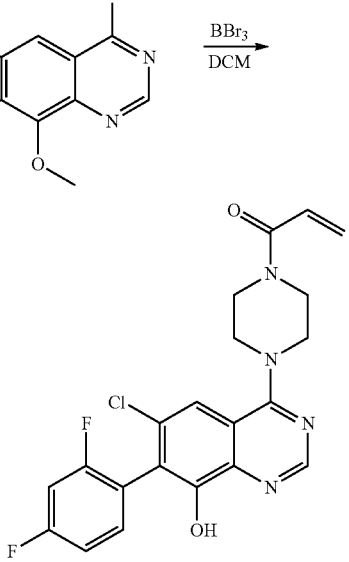

Example 42 provides an exemplary preparation according to General Synthetic Method Z tert-Butyl4-(7-bromo-6-chloro-8-methoxyquinazolin-4-yl)piperazine-1-carboxylate To a solution of tert-butyl 4-(7-bromo-6-chloro-8-fluoroquinazolin-4-yl)piperazine-1-carboxylate (45 mg, 0.10 mmol) in THF (8 mL) at RT, $CH_3ONa$ (17 mg, 0.15 mmol) was added and the resulting mixture was stirred for 16 h. The mixture was poured into ice-water, and extracted with ethyl acetate. The organic layer was washed with brine, dried over $Na_2SO_4$ and concentrated in vacuo. The residue was purified by Prep-TLC to afford the desired product as a white solid (32 mg, 70% yield). ESI-MS m/z: 459.1 [M+H]$^+$.

tert-Butyl4-(6-chloro-7-(2,4-difluorophenyl)-8-methoxyquinazolin-4-yl)piperazine-1-carboxylate A mixture of tert-butyl4-(7-bromo-6-chloro-8-methoxyquinazolin-4-yl)piperazine-1-carboxylate (65 mg, 0.14 mmol), 2,4-difluorophenylboronic acid (25 mg, 0.15 mmol), Pd(PPh$_3$)$_4$ (16 mg, 0.014 mmol) and $Na_2CO_3$ (45 mg, 0.42 mmol) in 1,4-dioxane/H$_2$O (8 mL/2 mL) was stirred at 100° C. under argon for 16 h. The mixture was allowed to cool to RT and concentrated in vacuo. The residue was purified by column chromatography on silica gel (1% methanol/dichloromethane) to afford the desired product (17 mg, 25% yield) as a white solid. ESI-MS m/z: 491.2 [M+H]$^+$.

6-Chloro-7-(2,4-difluorophenyl)-8-methoxy-4-(piperazin-1-yl)quinazoline

To a solution of tert-butyl4-(6-chloro-7-(2,4-difluorophenyl)-8-methoxyquinazolin-4-yl)piperazine-1-carboxylate (22 mg, 0.044 mmol) in dichloromethane (5 mL) at RT, TFA (1 mL) was added and the resulting mixture was stirred at RT for 1 h. The mixture was concentrated in vacuo. The resultant was quenched with NaHCO$_3$ solution, and the aqueous solution was extracted with ethyl acetate. The organic layer was washed with brine, dried over Na$_2$SO$_4$ and concentrated in vacuo to afford the desired product as a white solid (17 mg, 100% yield).

1-(4-(6-Chloro-7-(2,4-difluorophenyl)-8-methoxy-quinazolin-4-yl)piperazin-1-yl)prop-2-en-1-one To a solution of the above obtained crude 6-chloro-7-(2,4-difluorophenyl)-8-methoxy-4-(piperazin-1-yl)quinazoline (17 mg, 0.0448 mmol) in dichloromethane (10 mL) and Et$_3$N (14 mg, 0.134 mmol) at 0° C., acryloyl chloride (5 mg, 0.05 mmol) was added and the resulting mixture was stirred at 0° C. for 2 h. The mixture was quenched with saturated NaHCO$_3$ aqueous solution, and then extracted with ethyl acetate. The organic layer was washed with saturated NaHCO$_3$ solution and brine, dried over Na$_2$SO$_4$ and concentrated in vacuo. The residue was purified by Prep-TLC to yield the desired product (9 mg, 47% yield) as a white solid. $^1$H NMR (400 MHz, CDCl$_3$) δ: 8.82 (s, 1H), 7.77 (s, 1H), 7.29-7.33 (m, 1H), 6.97-7.06 (m, 2H), 6.61-6.67 (m, 1H), 6.37-6.42 (m, 1H), 5.79-5.82 (m, 1H), 3.96 (s, 3H), 3.82-3.92 (m, 8H). ESI-MS m/z: 445.2 [M+H]$^+$.

1-(4-(6-Chloro-7-(2,4-difluorophenyl)-8-hydroxy-quinazolin-4-yl)piperazin-1-yl)prop-2-en-1-one To a solution of 1-(4-(6-chloro-7-(2,4-difluorophenyl)-8-methoxyquinazolin-4-yl)piperazin-1-yl)prop-2-en-1-one (53 mg, 0.119 mmol) in dichloromethane (10 mL) at −78° C. under nitrogen, BBr$_3$ (298 mg, 1.19 mmol) was added and the resulting mixture was stirred from at −78° C. to RT for 3 h. The mixture was cooled to −30° C., and NaHCO$_3$ solution was added. The aqueous solution was extracted with ethyl acetate. The organic layer was washed with brine, dried over Na$_2$SO$_4$ and concentrated in vacuo. The residue was purified by prep-TLC to afford the desired product as a white solid (17 mg, 33% yield). $^1$H NMR (400 MHz, DMSO-d6) δ: 8.70 (s, 1H), 7.61 (s, 1H), 7.37-7.46 (m, 2H), 7.20-7.24 (m, 1H), 6.80-6.87 (m, 1H), 6.15-6.20 (m, 1H), 5.72-5.76 (m, 1H), 3.76-3.86 (m, 8H). ESI-MS m/z: 431.1 [M+H]$^+$.

Example 43

Synthesis of 1-(4-(6-chloro-7-(2-fluoro-6-hydroxyphenyl)-5-(trifluoromethyl)quinazolin-4-yl)piperazin-1-yl)prop-2-en-1-one

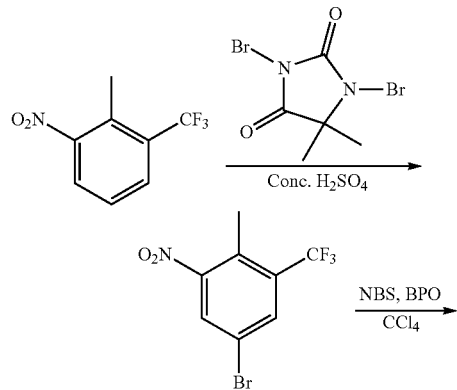

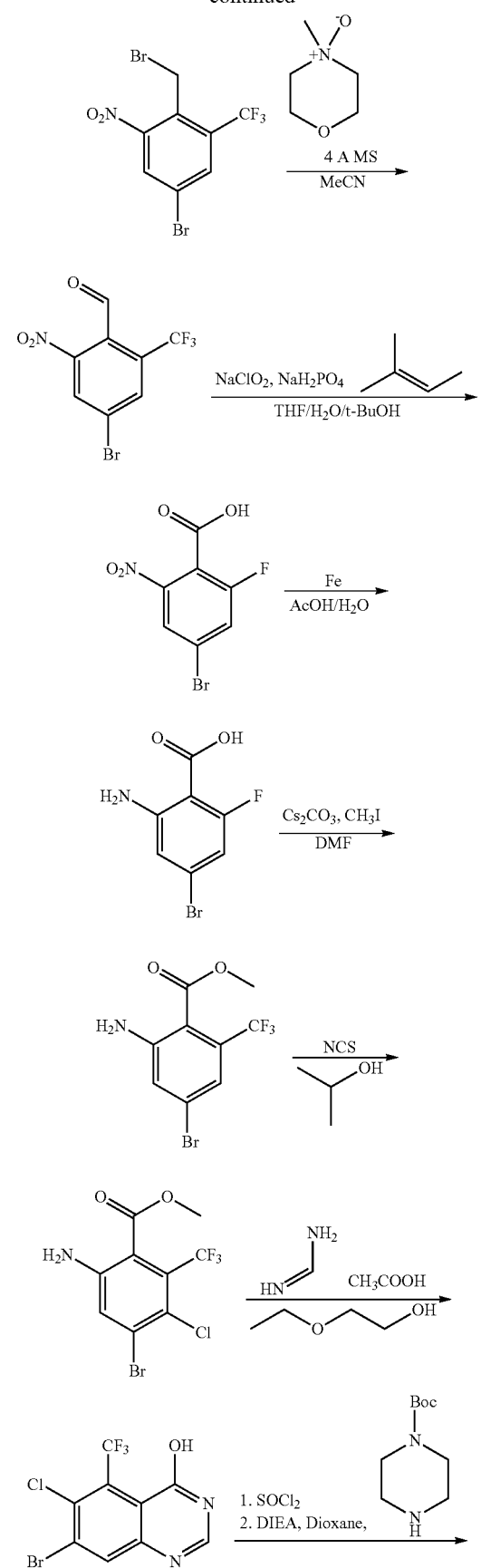

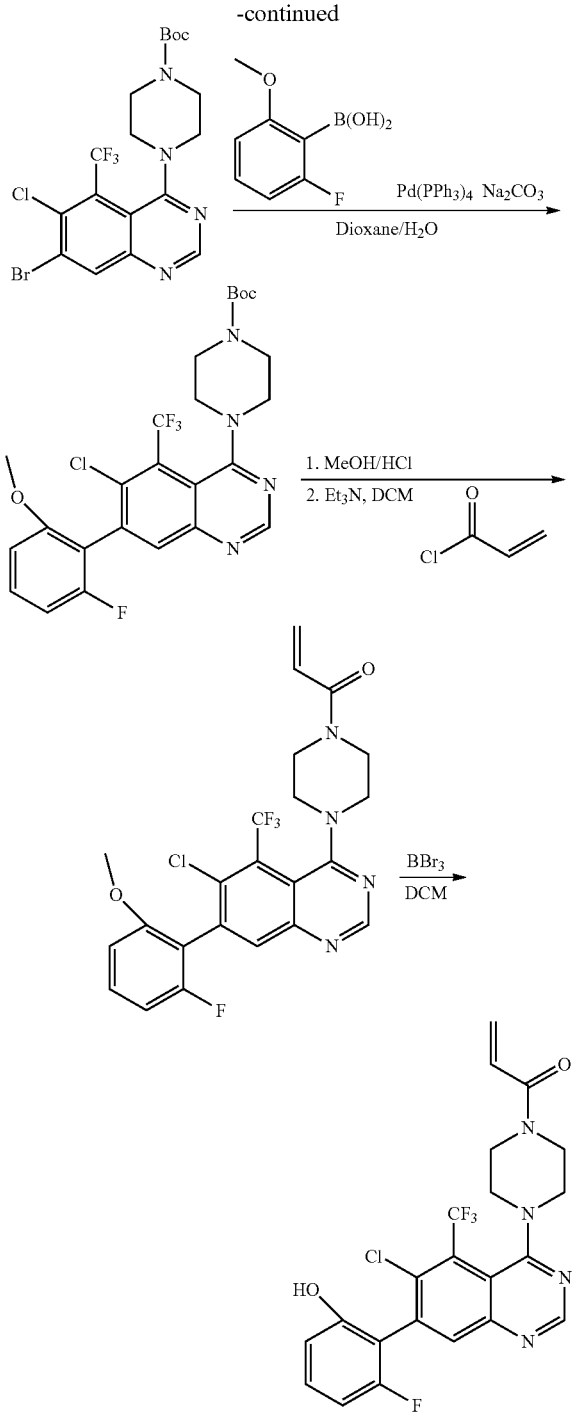

Example 43 provides an exemplary preparation according to General Synthetic Method AA 5-Bromo-2-methyl-1-nitro-3-(trifluoromethyl)benzene 2-Methyl-1-nitro-3-(trifluoromethyl)benzene (1 g, 4.87 mmol) was dissolved in concentrated sulfuric acid (15 mL), 1,3-dibromo-5,5-dimethylimidazolidine-2,4-dione (836 mg, 2.92 mmol) was added in portions and the resulting mixture was stirred at RT for 2 h. The reaction mixture was poured into ice water, stirred for 10 min, and then extracted with ethyl acetate. The combined organic layer was washed with water, saturated $NaHCO_3$ solution and brine, dried over $Na_2SO_4$, and concentrated in vacuo to afford the crude product (1.1 g).

5-Bromo-2-(bromomethyl)-1-nitro-3-(trifluoromethyl)benzene

NBS (12.6 g, 70.61 mmol) was added into a solution of 5-bromo-2-methyl-1-nitro-3-(trifluoromethyl)benzene (19 g, 67.25 mmol) and BPO (1.63 g, 6.73 mmol) in $CCl_4$ (200 mL). The mixture was stirred at reflux under argon for 18 h. The resulting mixture was concentrated and the residue was purified by column chromatography eluting with petroleum ether to yield the product (14 g, 58% yield).

4-Bromo-2-nitro-6-(trifluoromethyl)benzaldehyde

To a mixture of 5-bromo-2-(bromomethyl)-1-nitro-3-(trifluoromethyl)benzene (14 g, 38.88 mmol) and 4 Å molecular sieves (25 g) in MeCN (120 mL) at RT, N-methylmorpholine N-oxide (9.2 g, 82.14 mmol) was added and the resulting mixture was stirred under argon for 1.5 h. The mixture was diluted with ethyl acetate and filtered. The filtrate was washed with $H_2O$, 1 N HCl and brine, dried over $Na_2SO_4$ and concentrated in vacuo to give the desired product (4.1 g, 37% yield) which was used in the next step without further purification.

4-Bromo-2-fluoro-6-nitrobenzoic acid

To a solution of 4-bromo-2-nitro-6-(trifluoromethyl)benzaldehyde (4.1 g, 13.75 mmol) in a mixture of THF, $H_2O$ and t-BuOH at −5° C., $NaClO_2$ (4.97 g, 55.03 mmol) and $NaH_2PO_4$ (6.6 g, 55.03 mmol) were added. The mixture was treated with 2-methylbut-2-ene (6.75 g, 96.25 mmol) dropwise. The reaction was stirred at 0° C. for 1.5 h and concentrated in vacuo. The residue was diluted with water, acidified with 2 N HCl to pH 4-5 and then extracted with ethyl acetate. The organic layer was washed with water and brine, dried over $Na_2SO_4$, and concentrated to afford crude product (4.4 g) which used in next step directly.

2-Amino-4-bromo-6-(trifluoromethyl)benzoic acid

To a solution of 4-bromo-2-fluoro-6-nitrobenzoic acid (4.4 g, 12.9 mmol) in a mixture of AcOH (40 mL) and H2O (20 mL), Fe (3.6 g, 64.5 mmol) was added and the resulting mixture was stirred at RT for 2 h. The mixture was poured into water, and extracted with EtOAc. The organic layer was washed with water and brine, dried over $Na_2SO_4$, and concentrated in vacuo to afford the target product (3.1 g) without further purification.

Methyl 2-amino-4-bromo-6-(trifluoromethyl)benzoate $Cs_2CO_3$ (4.82 g, 14.79 mmol) was added into a solution of 2-amino-4-bromo-6-(trifluoromethyl)benzoic acid (2.8 g, 9.86 mmol) in DMF (30 mL), and the resulting mixture was stirred at RT for 40 min. To this mixture, $CH_3I$ (1.4 g, 9.86 mmol) was added dropwise and stirring was continued at RT for 16 h. The mixture was poured into water and extracted with ethyl acetate. The organic layer was washed with water and brine, dried over $Na_2SO_4$ and concentrated in vacuo. The residue was purified by flash column chromatography on silica gel (ethyl acetate/petroleum ether=1:10) to yield the desired product (2.9 g, 97% yield) as a yellow solid.

Methyl 6-amino-4-bromo-3-chloro-2-(trifluoromethyl)benzoate

To a solution of methyl 2-amino-4-bromo-6-(trifluoromethyl)benzoate (2.8 g, 9.39 mmol) in isopropyl alcohol (45 mL) at RT, NCS (1.51 g, 11.28 mmol) was added in portions and the resulting mixture was stirred at reflux for 16 h. The mixture was allowed to coo, to RT and the residue was purified by flash column chromatography on silica (ethyl acetate/petroleum ether=1:20) to afford the desired product (860 mg, 27% yield).

1-(4-(6-Chloro-7-(2-fluoro-6-hydroxyphenyl)-5-(trifluoromethyl)quinazolin-4-yl)piperazin-1-yl)prop-2-en-1-one The title compound was prepared from methyl 6-amino-4-bromo-3-chloro-2-(trifluoromethyl)benzoate according to the procedure described in Example 30. $^1$H NMR (400 MHz, DMSO-d6) δ:10.29 (s, 1H), 8.50 (s, 1H), 7.93 (s, 1H), 7.35-7.33 (m, 1H), 6.91-6.89 (m, 1H), 6.83-6.76 (m, 1H), 6.17-6.12 (dd, J=2.0, 16.8 Hz, 1H), 5.74-5.70 (dd, J=2.4, 10.4 Hz, 1H), 3.88 (s, 4H), 3.66-3.64 (m, 2H), 3.46 (m, 2H). ESI-MS m/z: 481.3 [M+H]$^+$.

Example 44

Synthesis of 4-(4-acryloylpiperazin-1-yl)-6-chloro-7-(5-methyl-1H-indazol-4-yl)quinolin-2(1H)-one

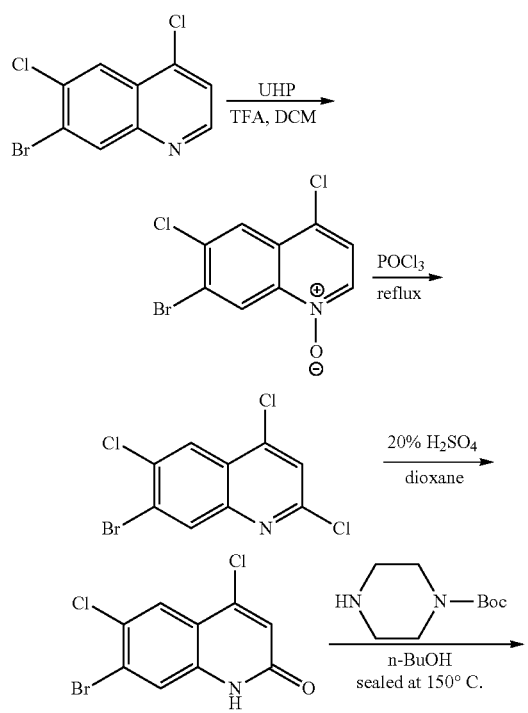

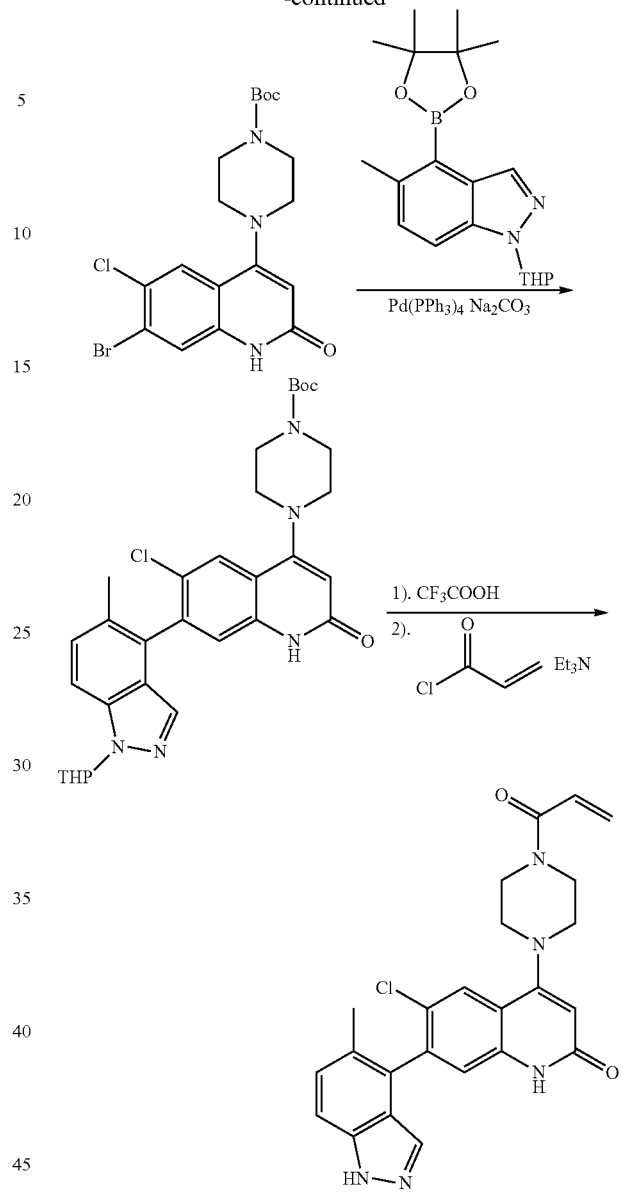

Example 44 provides an exemplary preparation according to General Synthetic Method AB 7-Bromo-4,6-dichloroquinoline N-oxide To a stirred solution of 7-bromo-4,6-dichloroquinoline (500 mg, 1.82 mmol) in DC under argon, UHP (359 mg, 3.82 mmol) was added. The mixture was cooled to 0° C., and TFA (415 mg, 3.64 mmol) was added. The resulting mixture was stirred at RT for 16 h. The mixture was washed with brine, dried over anhydrous Na$_2$SO$_4$, filtered and concentrated in vacuo to afford the desired product (450 mg, 85% yield). ESI-MS m/z: 292.3 [M+H]$^+$.

7-Bromo-2,4,6-trichloroquinoline

The mixture of 7-bromo-2,4,6-trichloroquinolin N-oxide (450 mg, 1.55 mmol) in POCl$_3$ (20 mL) was stirred at reflux for 1 h. The mixture was concentrated to dryness and the residue was partitioned between water and ethyl acetate. The organic layer was dried over anhydrous Na₂SO₄, filtered and concentrated in vacuo. The residue was purified by flash column chromatography on silica gel (ethyl acetate/petroleum ether=1:5) to afford the desired product (400 mg, 84% yield) as solid. ESI-MS m/z: 310.1 [M+H]⁺.

7-Bromo-4,6-dichloroquinolin-2(1H)-one

The mixture of 7-bromo-2,4,6-trichloroquinolin (400 mg, 1.29 mmol) in 20% H₂SO₄ (10 mL) and dioxane (10 mL) was stirred at 140° C. for 8 h. The mixture was quenched with water and extracted with ethyl acetate. The organic layer was dried over anhydrous Na₂SO₄, filtered and concentrated in vacuo to afford the desired product (250 mg, 66% yield) as solid. ESI-MS m/z: 292.1 [M+H]⁺.

tert-Butyl 4-(7-bromo-6-chloro-1,2-dihydro-2-oxo-quinolin-4-yl)piperazine-1-carboxylate A mixture of 7-bromo-4,6-dichloroquinolin-2(1H)-one (250 mg, 0.856 mmol) and tert-butyl piperazine-1-carboxylate (796 mg, 4.28 mmol) in n-BuOH (10 mL) was stirred at 150° C. in a sealed tube for 24 h. The mixture was quenched with water and extracted with ethyl acetate. The organic layer was dried over anhydrous Na₂SO₄, filtered and concentrated in vacuo. The residue was purified by flash column chromatography on silica gel (dichloromethane/MeOH=30:1) to afford the desired product (180 mg, 47% yield) as solid. ESI-MS m/z: 442.1 [M+H]⁺.

4-(4-Acryloylpiperazin-1-yl)-6-chloro-7-(5-methyl-1H-indazol-4-yl)quinolin-2(1H)-one The title compound was prepared from tert-butyl 4-(7-bromo-6-chloro-1,2-dihydro-2-oxoquinolin-4-yl)piperazine-1-carboxylate according to the procedure described in Examples 2. ¹H NMR (400 MHz, DMSO-d6) δ: 13.15 (s, 1H), 11.60 (s, 1H), 7.86 (s, 1H), 7.55 (m, 1H), 7.52 (s, 1H), 7.35 (m, 1H), 7.25 (s, 1H), 6.90-6.84 (dd, J=12.0, 16.4 Hz, 1H), 6.20-6.15 (dd, J=2.4, 16.8 Hz, 1H), 6.02 (s, 1H), 5.77-5.74 (dd, J=2.1, 10.0 Hz, 1H), 3.86-3.83 (m, 4H), 3.13 (m, 4H), 2.17 (s, 3H). ESI-MS m/z: 450.2 [M+H]⁺.

Example 45

Synthesis of 1-(4-(6-chloro-2-(2-(dimethylamino)ethylamino)-8-fluoro-7-(5-methyl-1H-indazol-4-yl)quinazolin-4-yl)piperazin-1-yl)prop-2-en-1-one

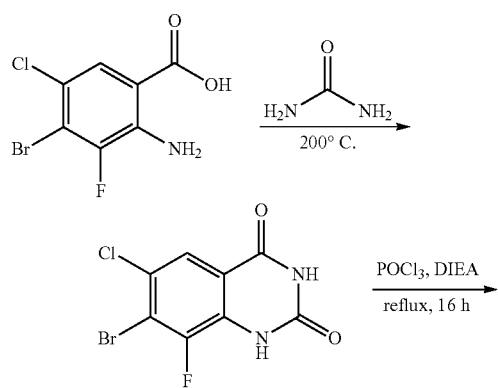

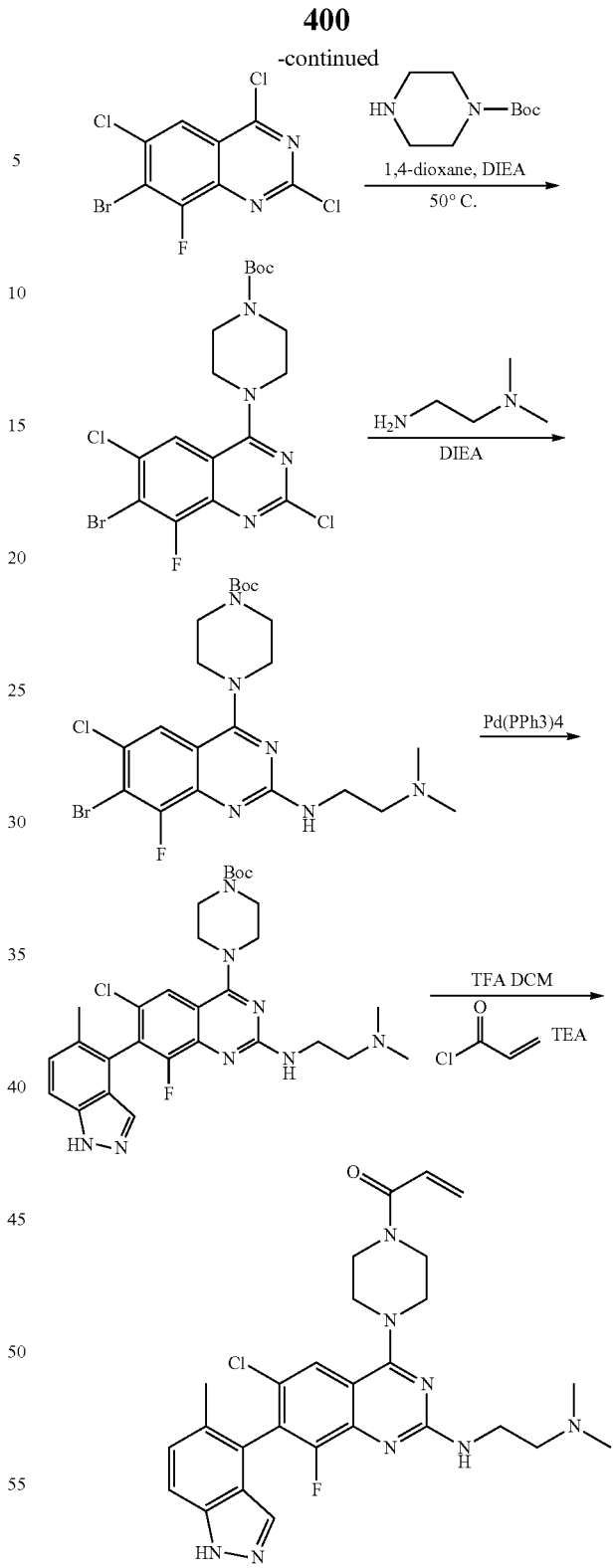

Example 44 provides an exemplary preparation according to General Synthetic Method AC

7-Bromo-6-chloro-8-fluoroquinazoline-2,4(1H,3H)-dione

A mixture of methyl 2-amino-4-bromo-5-chloro-3-fluorobenzoic acid (10.0 g, 39.9 mmol) and urea (12 g, 199.6 mmol) was stirred at 200° C. for 3 h. The mixture was allowed to cool to RT, triturated with ethyl acetate and dried to afford the crude product (13 g) as a brown solid.

7-Bromo-2,4,6-trichloro-8-fluoroquinazoline

The mixture of 7-bromo-6-chloro-8-fluoroquinazoline-2,4(1H,3H)-dione (13 g, 44.5 mmol) in POCl$_3$ (200 mL) and DIPEA (20 mL) was stirred at reflux for 16 h. The mixture was allowed to cool to RT and concentrated in vacuo to remove POCl$_3$. The residue was purified by flash chromatography on silica gel (5% ethyl acetate/petroleum ether) and then washed by HCl (1M) to afford the product (10.4 g, 74% yield) as a yellow solid.

4-(7-Bromo-2,6-dichloro-8-fluoroquinazolin-4-yl) piperazine-1-carboxylate

To a solution of 7-bromo-2,4,6-trichloro-8-fluoroquinazoline (10.4 g, 33.3 mmol) and DIEA (29 mL, 167 mmol) in 1,4-dioxane (100 mL) at RT, tert-butyl piperazine-1-carboxylate (6.2 g, 33.3 mmol) was added. The resulting mixture was stirred at 50° C. for 20 min. The mixture was allowed to cool to RT and partitioned between water and ethyl acetate. The organic layer was washed with brine, dried over Na$_2$SO$_4$ and concentrated. The residue was purified by flash column chromatography on silica gel (MeOH/dichloromethane=1:200) to afford the desired product (6 g, 40% yield) as a yellow solid. ESI-MS m/z: 447.2 [M+H]$^+$.

tert-Butyl 4-(2-(2-(dimethylamino)ethylamino)-7-bromo-6-chloro-8-fluoroquinazolin-4-yl)piperazine-1-carboxylate To a stirred solution of tert-butyl 4-(7-bromo-2,6-dichloro-8-fluoroquinazolin-4-yl) piperazine-1-carboxylate (300 mg, 0.63 mmol) in propan-2-ol (10 mL), DIEA (243 mg, 1.88 mmol) and N$^1$,N$^1$-dimethylethane-1,2-diamine (166 mg, 1.88 mmol) were added and the resulting mixture was stirred at 95° C. overnight. The mixture was allowed to cool to RT, and partitioned between water and ethyl acetate. The organic layer was dried over anhydrous Na$_2$SO$_4$, filtered and concentrated in vacuo. The residue was purified by flash column chromatography on silica gel (1-5% MeOH/dichoromethane) to afford the desired product (230 mg, 69% yield) as a white solid. ESI-MS m/z: 531.3 [M+H]$^+$.

1-(4-(2-(2-(Dimethylamino)ethylamino)-6-chloro-8-fluoro-7-(5-methyl-1H-indazol-4-yl)quinazolin-4-yl)piperazin-1-yl)prop-2-en-1-one The title compound was prepared from tert-butyl 4-(2-(2-(dimethylamino)ethylamino)-6-chloro-8-fluoro-7-(5-methyl-1H-indazol-4-yl)quinazolin-4-yl)piperazine-1-carboxylate in three steps following the procedure described in Example 2.

$^1$H NMR (400 MHz, DMSO-d6) δ: 13.16 (s, 1H), 7.81 (s, 1H), 7.56-7.58 (m, 2H), 7.37-7.39 (m, 1H), 6.96-7.32 (m, 1H), 6.82-6.89 (m, 1H), 6.17 (dd, J=2.2, 16.5 Hz, 1H), 5.74 (dd, J=2.1, 10.3 Hz, 1H), 3.72-3.84 (m, 8H), 3.45 (m, 2H), 2.42-2.45 (m, 2H), 2.17-2.21 (m, 9H). ESI-MS m/z: 537.4 [M+H]$^+$.

Example 46

Synthesis of 1-(4-(6-chloro-2-((dimethylamino)methyl)-8-fluoro-7-(5-methyl-1H-indazol-4-yl)quinazolin-4-yl)piperazin-1-yl)prop-2-en-1-one

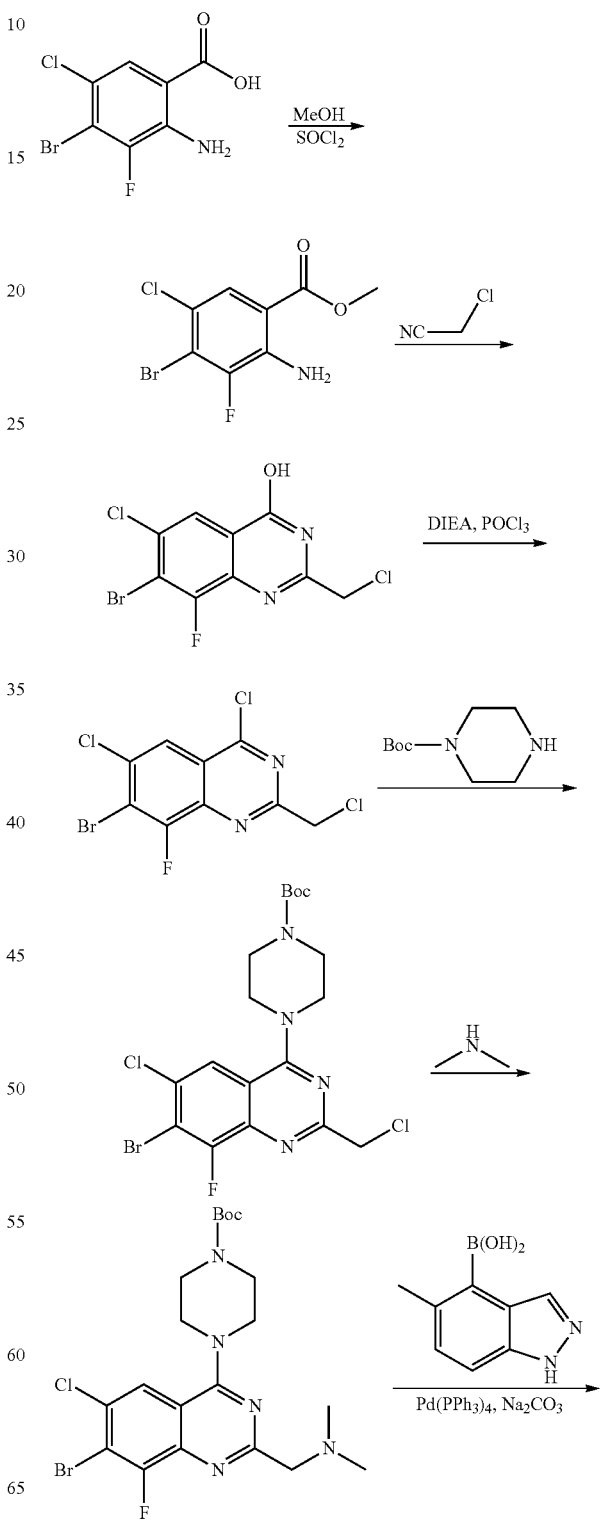

-continued

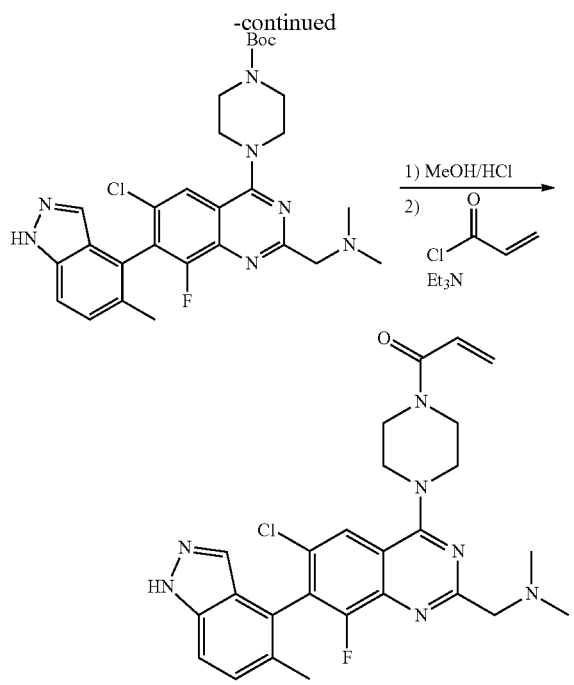

Example 46 provides an exemplary preparation according to General Synthetic Method AD Methyl 2-amino-4-bromo-5-chloro-3-fluorobenzoate A mixture of 2-amino-4-bromo-5-chloro-3-fluorobenzoic acid (1.0 g, 3.746 mmol) in CH$_3$OH (30 mL), SOCl$_2$ (4.457 g, 37.46 mmol) was added dropwise and the resulting mixture was stirred at 100° C. for 16 h. The solvent was removed and the residue was dissolved in ethyl acetate. The organic layer was washed with saturated NaHCO$_3$ aqueous solution and brine, dried over Na$_2$SO$_4$ and concentrated. The residue was purified by column chromatography (ethyl acetate/petroleum ether=1:10) to afford the product as a pink solid (848 mg, 81% yield).

7-Bromo-6-chloro-2-(chloromethyl)-8-fluoroquinazolin-4-ol

A mixture of methyl 2-amino-4-bromo-5-chloro-3-fluorobenzoate (500 mg, 1.779 mmol) and 2-chloroacetonitrile (667 mg, 8.895 mmol) in dioxane (30 mL) was bubbled with HCl gas at RT for 1 h, and the resulting mixture was stirred at 80° C. for 16 h. The mixture was allowed to cool to RT and then Et$_2$O (20 mL) was added to it. After stirring for 1 h, the mixture was filtered and the white solid was collected. The white solid was dissolved in ethyl acetate and washed with saturated NaHCO$_3$ aqueous solution and brine. The organic layer was dried over Na$_2$SO$_4$ and concentrated in vacuo to afford the product as a white solid (605 mg, 104% yield).

7-Bromo-4,6-dichloro-2-(chloromethyl)-8-fluoroquinazoline

A mixture of 7-bromo-6-chloro-2-(chloromethyl)-8-fluoroquinazolin-4-ol (300 mg, 0.925 mmol) and DIEA (3 mL) in POCl$_3$ (30 mL) was stirred at 130° C. for 16 h.

The mixture was concentrated in vacuo and azeotroped with toluene. The residue was purified by column chromatography on silica gel (ethyl acetate/petroleum ether=1:6) to afford the product as an orange color solid (320 mg, 100% yield).

tert-Butyl-4-(7-bromo-6-chloro-2-(chloromethyl)-8-fluoroquinazolin-4-yl)piperazine-1-carboxylate A mixture of 7-bromo-4,6-dichloro-2-(chloromethyl)-8-fluoroquinazoline (320 mg, 0.936 mmol) and tert-butyl piperazine-1-carboxylate (260 mg, 1.397 mmol) in i-PrOH (30 mL) was stirred at 75° C. for 1 h. The mixture was concentrated in vacuo. The residue was dissolved in ethyl acetate, washed with saturated NaHCO$_3$ aqueous solution and brine, dried over Na$_2$SO$_4$ and concentrated. The residue was purified by column chromatography on silica gel (ethyl acetate/petroleum ether=1:4) to afford the product as a yellow solid (422 mg, 92% yield). ESI-MS m/z: 495.2 [M+H]$^+$.

tert-Butyl-4-(7-bromo-6-chloro-2-((dimethylamino)methyl)-8-fluoroquinazolin-4-yl)piperazine-1-carboxylate A mixture of 7-bromo-4,6-dichloro-2-(chloromethyl)-8-fluoroquinazoline (422 mg, 0.857 mmol) and dimethylamine (2.0 M in THF, 4.7 mL) was stirred at 80° C. for 16 h. The mixture was diluted with ethyl acetate, washed with saturated NaHCO$_3$ aqueous solution and brine, dried over Na$_2$SO$_4$ and concentrated. The residue was purified by column chromatography on silica gel (dichloromethane/MeOH=30:1) to afford the product as an orange color thick oil (437 mg, 100% yield). ESI-MS m/z: 504.2 [M+H]$^+$.

1-(4-(6-Chloro-2-((dimethylamino)methyl)-8-fluoro-7-(5-methyl-1H-indazol-4-yl)quinazolin-4-yl)piperazin-1-yl)prop-2-en-1-one The title compound was prepared from tert-butyl-4-(7-bromo-6-chloro-2-((dimethylamino)methyl)-8-fluoroquinazolin-4-yl)piperazine-1-carboxylate in three steps cording to the procedure described in Example 2. $^1$H NMR (400 MHz, DMSO-d6) δ: 13.24 (s, 1H), 8.15 (s, 1H), 7.62 (m, 2H), 7.42 (m, 1H), 6.88 (dd, J=10.4 Hz, J$_2$=16.8 Hz, 1H), 6.22 (dd, J=2.4 Hz, J$_2$=17.2 Hz, 1H), 5.78 (dd, J=2.4 Hz, J$_2$=10.4 Hz, 1H), 4.33 (s, 2H), 4.05 (m, 8H), 2.82 (s, 6H), 2.17 (s, 3H). ESI-MS m/z: 508.2[M+H]$^+$.

Example 47

Synthesis of 1-(4-(6-chloro-5-fluoro-7-(2-fluoro-6-hydroxyphenyl)quinazolin-4-yl)piperazin-1-yl)prop-2-en-1-one

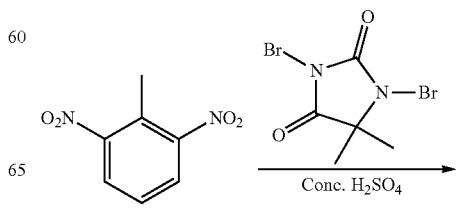

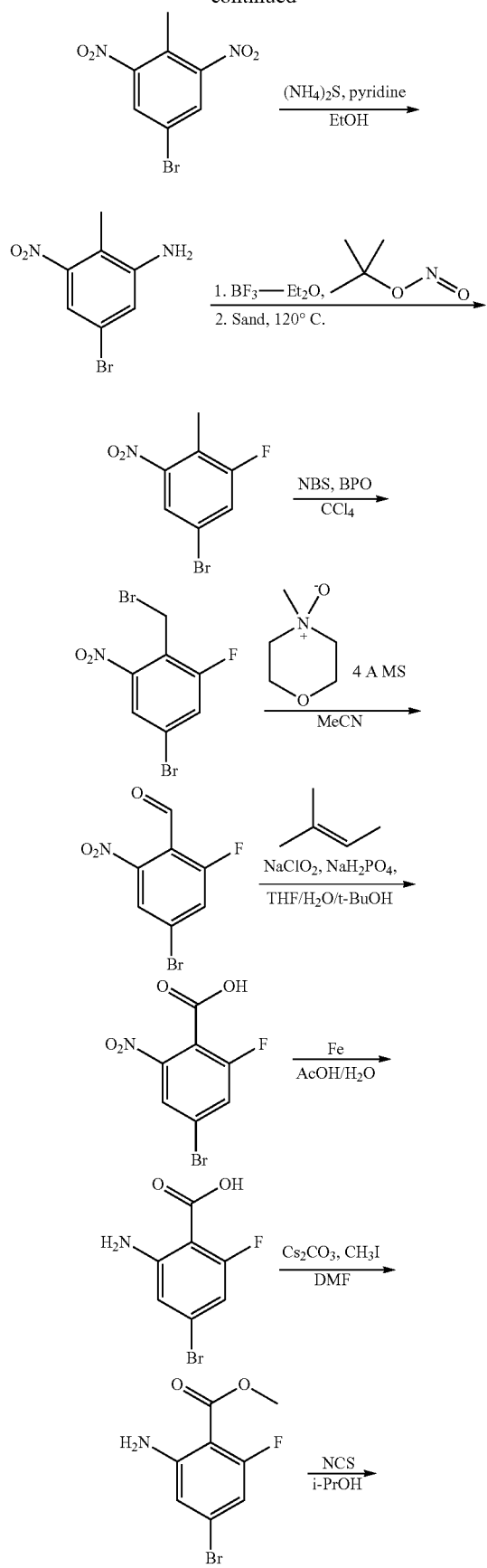
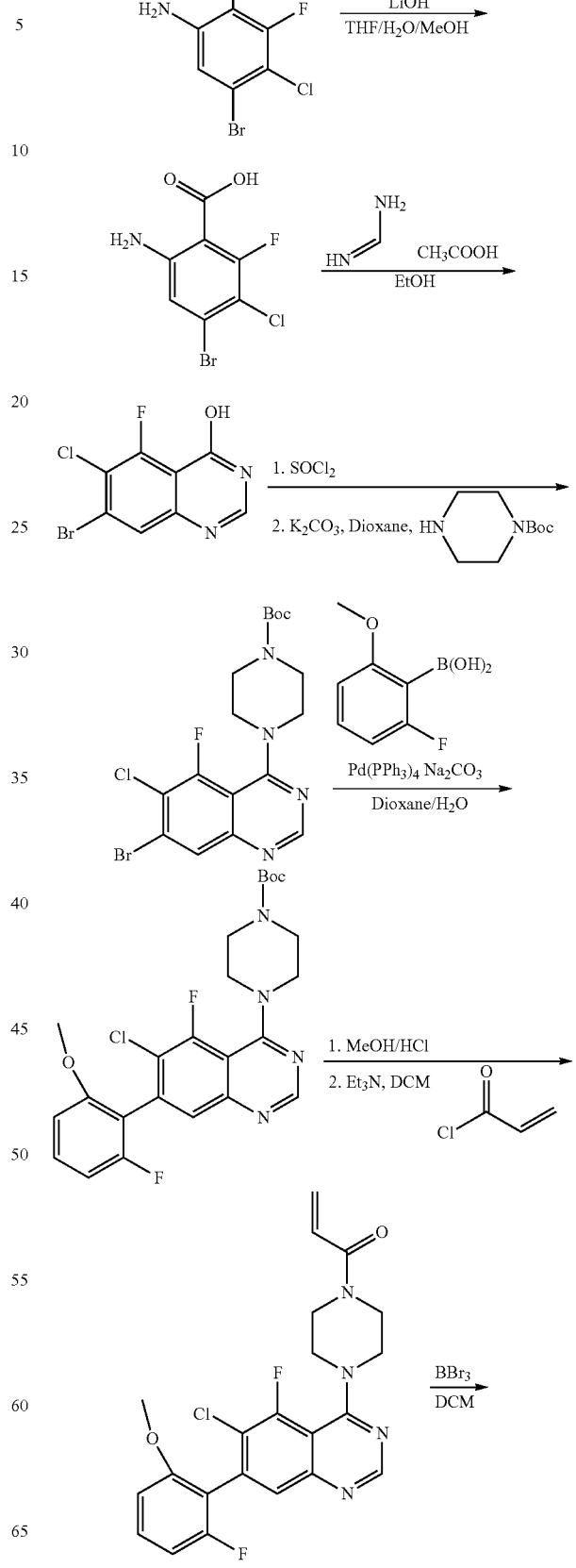

-continued

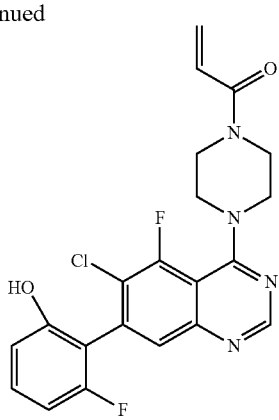

Example 47 provides an exemplary preparation according to General Synthetic Method AE 5-Bromo-2-methyl-1,3-dinitrobenzene To a solution of 2-methyl-1,3-dinitrobenzene (10 g, 54.91 mmol) in concentrated sulfuric acid (150 mL), 1,3-dibromo-5,5-dimethylimidazolidine-2,4-dione (9.42 g, 32.94 mmol) was added and the resulting mixture was stirred at RT for 2 h. The mixture was poured into ice-water, stirred for 10 min, and then extracted with ethyl acetate. The combined organic layer was washed with water, saturated NaHCO$_3$ solution and brine, dried over Na$_2$SO$_4$, concentrated to afford the crude product (15 g).

5-Bromo-2-methyl-3-nitroaniline

To a mixture of 5-bromo-2-methyl-1,3-dinitrobenzene (11.2 g, 42.91 mmol) and pyridine (15.6 g, 197.47 mmol) in EtOH (230 mL), (NH$_4$)$_2$S (39 g, 22% in water) was added dropwise over 1 h. The mixture was concentrated in vacuo. The residue was diluted with water and stirred at 0° C. for 10 min. The solid was collected by filtration, rinsed with water, and dried under vacuum to afford 10.5 g crude product.

5-Bromo-1-fluoro-2-methyl-3-nitrobenzene

To a mixture of 5-bromo-2-methyl-3-nitroaniline (9.5 g, 41.12 mmol) and BF$_3$-Et$_2$O (8.7 g, 61.67 mmol) in THF (30 mL) and dichloromethane (60 mL) at −10 OC, tert-butyl nitrite (5.1 g, 49.34 mmol) was added dropwise and the resulting mixture was stirred at 0° C. for 1.5 h. The mixture was diluted with dichloromethane (200 mL) and stirred for 5 min. The solid was collected by filtration and dried in vacuo. The crude product was mixed with sand and heated to 120° C. for 40 min. The mixture was allowed to cool to RT, and then rinsed with dichloromethane. The organic layer was concentrated in vacuo and the residue was purified by column chromatography on silica gel (petroleum ether) to yield the product (3.6 g, 37.5% yield).

5-Bromo-2-(bromomethyl)-1-fluoro-3-nitrobenzene

To a solution of 5-bromo-1-fluoro-2-methyl-3-nitrobenzene (11.2 g, 47.86 mmol) and BPO (1.2 g, 4.79 mmol) in CCl$_4$ (150 mL), NBS (10.2 g, 57.43 mmol) was added and the resulting mixture was stirred at reflux under argon for 18 h. The mixture was concentrated in vacuo and the residue was purified by column chromatography on silica gel (petroleum ether) to yield the product (11.7 g, 78% yield).

4-Bromo-2-fluoro-6-nitrobenzaldehyde

To a mixture of 5-bromo-2-(bromomethyl)-1-fluoro-3-nitrobenzene (10 g, 41.28 mmol) and 4 Å molecular sieves (25 g) in MeCN (120 mL) at RT, N-methylmorpholine N-oxide (9.2 g, 82.14 mmol) was added and the resulting mixture was stirred under argon for 1.5 h. The mixture was diluted with ethyl acetate and filtered. The filtrate was washed with H$_2$O, 1 N HCl and brine. The organic layer was dried over Na$_2$SO$_4$ and concentrated in vacuo to afford the product (6.82 g, 67%) which was used in the next step without further purification.

4-Bromo-2-fluoro-6-nitrobenzoic acid

To a solution of 4-bromo-2-fluoro-6-nitrobenzaldehyde (4 g, 16.13 mmol) in THF-H$_2$O-t-BuOH at −5° C., NaClO$_2$ (5.83 g, 64.51 mmol) and NaH$_2$PO$_4$ (7.74 g, 64.51 mmol) were added followed by addition of 2-methylbut-2-ene (7.92 g, 112.91 mmol) dropwise. The mixture was stirred at 0° C. for 1.5 h and concentrated in vacuo. The residue was diluted with water and acidified with 2 N HCl to pH 4-5. The mixture was extracted with ethyl acetate. The organic layer was washed with water and brine, dried over Na$_2$SO$_4$, and concentrated in vacuo to afford the crude product (4.8 g) which was used in the next step directly.

2-Amino-4-bromo-6-fluorobenzoic acid

To a solution of 4-bromo-2-fluoro-6-nitrobenzoic acid (4.8 g, 18.18 mmol) in AcOH (40 mL) and H$_2$O (20 mL), Fe (5.1 g, 90.9 mmol) was added and the resulting mixture was stirred at RT for 2 h. The mixture was poured into water, and extracted with ethyl acetate. The organic layer was washed with water and brine, dried over Na$_2$SO$_4$, and concentrated in vacuo to afford the crude product (2.75 g) which was used in the next step without further purification.

Methyl 2-amino-4-bromo-6-fluorobenzoate

To a solution of 2-amino-4-bromo-6-fluorobenzoic acid (2.75 g, 11.75 mmol) in DMF (40 mL), Cs$_2$CO$_3$ (5.74 g, 17.63 mmol) was added and the resulting mixture was stirred at RT for 40 min. To this mixture, CH$_3$I (1.75 g, 12.33 mmol) was added dropwise and the resulting mixture was stirred at RT for 16 h. The mixture was poured into water and extracted with ethyl acetate. The organic layer was washed with water and brine, dried Na$_2$SO$_4$, and concentrated in vacuo. The residue was purified by flash column chromatography on silica gel (ethyl acetate/petroleum ether=1:15) to yield the desired product (2.32 g, 80% yield) as a yellow solid.

Methyl 6-amino-4-bromo-3-chloro-2-fluorobenzoate

To a solution of methyl 2-amino-4-bromo-6-fluorobenzoate (3.8 g, 15.48 mmol) in isopropyl alcohol (45 mL) at RT, NCS (2.2 g, 16.25 mmol) was added in portions and the resulting mixture was stirred at reflux for 4 h. The mixture was concentrated in vacuo and the residue was purified by flash column chromatography on silica gel (ethyl acetate/petroleum ether=1:30) to yield the desired product (1.68 g, 38% yield).

6-Amino-4-bromo-3-chloro-2-fluorobenzoic acid

To a solution of methyl 6-amino-4-bromo-3-chloro-2-fluorobenzoate (200 mg, 0.71 mmol) in a mixture of THF (5 mL), H$_2$O (2 mL) and MeOH (1 mL), LiOH.H$_2$O (297 mg, 7.08 mmol) was added. The resulting mixture was stirred at RT for 2 h. The mixture was concentrated in vacuo. The residue was diluted with water and acidified with 2 N HCl to pH 4-5. The mixture was extracted with ethyl acetate. The organic layer was washed with water and brine, dried over Na$_2$SO$_4$, and concentrated in vacuo to afford the desired product (189 mg, 100% yield).

1-(4-(6-Chloro-5-fluoro-7-(2-fluoro-6-hydroxyphenyl)quinazolin-4-yl)piperazin-1-yl)prop-2-en-1-one The title compound was prepared from 6-amino-4-bromo-3-chloro-2-fluorobenzoic acid according to the procedure described in Example 30. $^1$H NMR (400 MHz, DMSO-d6) δ: 10.22 (s, 1H), 8.66 (s, 1H), 7.65 (s, 1H), 7.31-7.37 (m, 1H), 6.88-6.79 (m, 3H), 6.19-6.14 (dd, J=2.0, 16.8 Hz, 1H), 5.75-5.72 (dd, J=2.4, 10.4 Hz, 1H), 3.78-3.70 (m, 8H). ESI-MS m/z: 431.4 [M+H]$^+$.

Example 48

Synthesis of 1-(4-(6-chloro-7,8'-biquinazolin-4-yl)piperazin-1-yl)prop-2-en-1-one

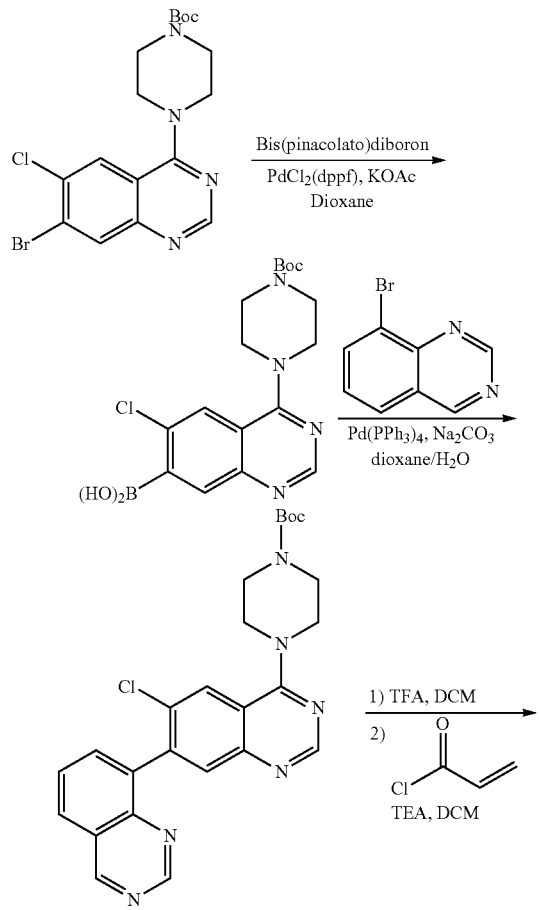

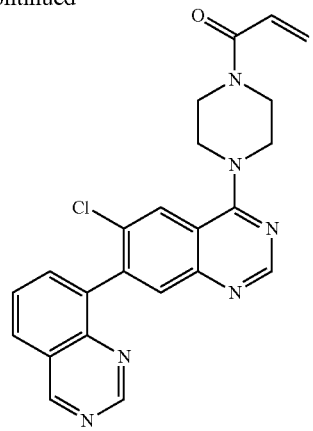

Example 48 provides an exemplary preparation according to General Synthetic Method AF

(4-(4-(tert-Butoxycarbonyl)piperazin-1-yl)-6-chloroquinazolin-7-yl)boronic acid The mixture of tert-butyl 4-(7-bromo-6-chloroquinazolin-4-yl)piperazine-1-carboxylate (1.45 g, 1.0 eq), bis(pinacolato)diboron (2.02 g, 2.3 eq.), and potassium acetate (1.66 g, 5.0 eq) in dioxane was degassed via nitrogen gas. After adding PdCl$_2$(dppf) (306 mg, 0.11 eq.), the reaction mixture was degassed again via nitrogen gas. The resulting mixture was stirred at 120° C. for 2 h. The mixture was allowed to cool to RT, diluted with EtOAc, washed with water, dried over Na$_2$SO$_4$ and concentrated in vacuo. The residue was purified by column chromatography on silica gel to afford the desired product in 43% yield.

tert-Butyl 4-(6-chloro-[7,8'-biquinazolin]-4-yl)piperazine-1-carboxylate

To a solution of (4-(4-(tert-butoxycarbonyl)piperazin-1-yl)-6-chloroquinazolin-7-yl)boronic acid (108 mg, 1.0 eq.) in dioxane (4 mL) in the sealed tube, 8-bromoquinazoline (79 mg, 1.3 eq.), PdCl$_2$(dppf) (26 mg, 0.1 eq.) and aqueous Na$_2$CO$_3$ (1M, 2 mL) we added. The resulting mixture was stirred at 120° C. for 5 min in the Microwave Reactor. After cooling down, it was filtered and partitioned between EtOAc and water. The organic layer was dried over Na$_2$SO$_4$ and concentrated in vacuo. The residue was used directly in the next step.

1-(4-(6-chloro-[7,8'-biquinazolin]-4-yl)piperazin-1-yl)prop-2-en-1-one

TFA (1 mL) was added into above obtained tert-butyl 4-(6-chloro-[7,8'-biquinazolin]-4-yl)piperazine-1-carboxylate (131 mg, 1.0 eq.) in DCM (10 mL). The reaction mixture was stirred at RT for 1 h. The mixture was concentrated in vacuo. To a solution of above obtained crude compound in Et$_3$N (0.5 mL, 13.0 eq) and dichloromethane (10 mL), acryloyl chloride (0.062 mL, 2.8 eq.) was added and the resulting mixture was stirred at RT for 1.5 h. The mixture was concentrated in vacuo to remove the DCM. The residue was dissolved in EtOAC. It was washed with water, dried over Na$_2$SO$_4$ and concentrated in vacuo. After column purification, the desired product was obtained in 44% yield over three steps from (4-(4-(tert-butoxycarbonyl)piperazin- 1-yl)-6-chloroquinazolin-7-yl)boronic acid. ¹H NMR (500 MHz, DMSO-d6) δ: 9.73 (s, 1H), 9.26 (s, 1H), 8.700 (s, 1H), 8.32 (dd, J=8, 1.5 Hz, 1H), 8.20 (s, 1H), 8.09 (dd, J=7, 1.5 Hz, 1H), 7.92 (t, J=8 Hz, 1H), 7.891 (s, 1H), 6.84 (dd, J=17, 10.5 Hz, 1H), 6.18 (dd, J=17, 2.5 Hz, 1H), 5.75 (dd, J=10.5, 2.5 Hz, 1H), 3.92-3.79 (m, 8H). ESI-MS m/z: 431.1 [M+H]⁺.

Example 49

Synthesis of 1-(4-(6-chloro-8-fluoro-7-(5-methyl-1H-indazol-4-yl)-2-(thiazol-5-yl)quinazolin-4-yl)piperazin-1-yl)prop-2-en-1-one

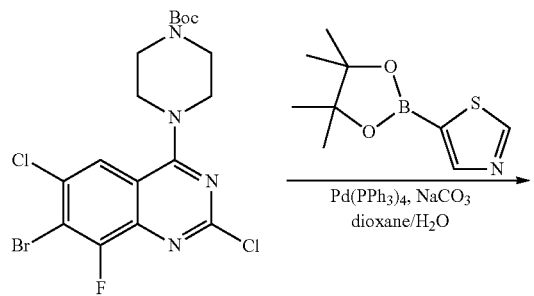

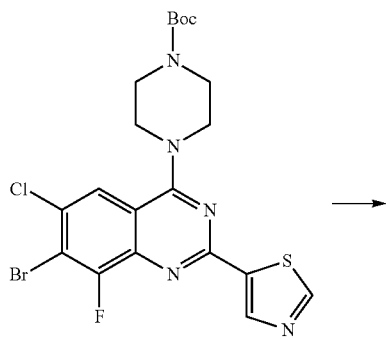

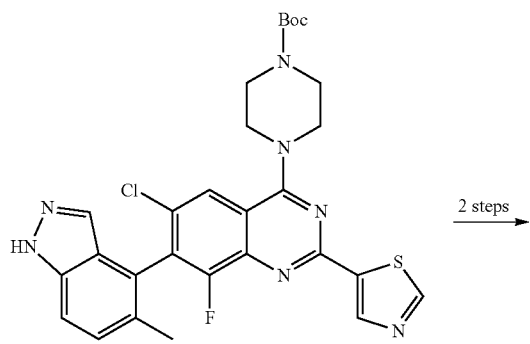

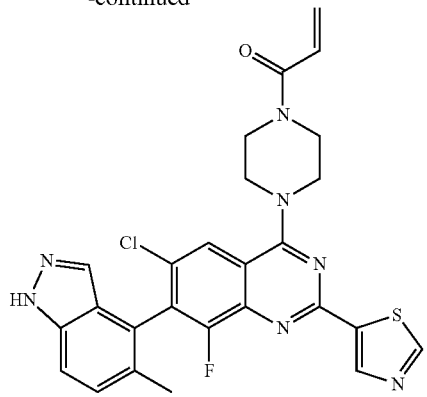

Example 49 provides an exemplary preparation according to General Synthetic Method AG tert-Butyl 4-(6-chloro-8-fluoro-7-(5-methyl-1H-indazol-4-yl)-2-(thiazol-5-yl)quinazolin-4-yl)piperazine-1-carboxylate 5-(4,4,5,5-Tetramethyl-1,3,2-dioxaborolan-2-yl)-1,3-thiazole (67 mg, 1.1 eq.) and tetrakis (158 mg, 0.5 eq.) were added into tert-butyl 4-(7-bromo-2,6-dichloro-8-fluoroquinazolin-4-yl)piperazine-1-carboxylate (133 mg, 1.0 eq.) in dioxane (6 mL) and aqueous $Na_2CO_3$ (1 M, 3 mL) in the sealed tube. The reaction mixture was stirred at 120° C. in the Microwave Reactor for 15 min. After cooling down, into this mixture (5-methyl-1H-indazol-4-yl)boronic acid (267 mg, 5.1 eq.), tetrakis (164 mg, 0.5 eq.), 4 mL of dioxane, and 2 mL of aqueous $Na_2CO_3$ (1M) were added. The resulting mixture was stirred at 120° C. in the Microwave Reactor for 45 min. After cooling down, it was filtered and partitioned between EtOAc and water. The organic layer was dried over $Na_2SO_4$, and concentrated in vacuo. The residue was purified by flash column chromatography on silica gel (dichloromethane/methanol=10:1) to afford the desired product (88 mg, 55% yield) as a solid. ESI-MS m/z: 580 [M+H]⁺.

1-(4-(6-Chloro-8-fluoro-7-(5-methyl-1H-indazol-4-yl)-2-(thiazol-5-yl)quinazolin-4-yl)piperazin-1-yl)prop-2-en-1-one The title compound was prepared from tert-butyl 4-(6-chloro-8-fluoro-7-(5-methyl-1H-indazol-4-yl)-2-(thiazol-5-yl)quinazolin-4-yl)piperazine-1-carboxylate in two steps according to the procedure described in Example 46. ¹H NMR (500 MHz, DMSO-d6) δ: 13.19 (s, 1H), 9.22 (s, 1H), 8.70 (s, 1H), 8.12 (s, 1H), 7.60 (d, J=8.5 Hz, 1H), 7.59 (s, 1H), 7.41 (d, J=8.5 Hz, 1H), 6.84 (dd, J=17, 10.5 Hz, 1H), 6.18 (dd, J=17, 2.5 Hz, 1H), 5.76 (dd, J=10.5, 2.5 Hz, 1H), 4.06-3.82 (m, 8H), 2.18 (s, 3H). ESI-MS m/z: 534.1 [M+H]⁺.

413
Example 50

Synthesis of 1-(4-(6-chloro-8-fluoro-7-(3-fluoro-5-methyl-1H-indazol-4-yl)quinazolin-4-yl)piperazin-1-yl)prop-2-en-1-one

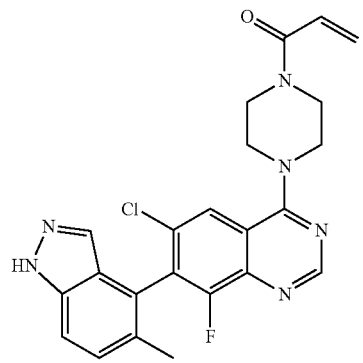

Selectfluor
CH₃CN
→

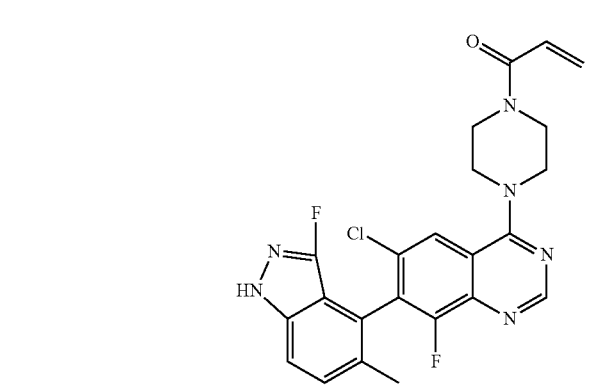

Example 50 provides an exemplary preparation according to General Synthetic Method AH 1-(4-(6-chloro-8-fluoro-7-(3-fluoro-5-methyl-1H-indazol-4-yl)quinazolin-4-yl)piperazin-1-yl)prop-2-en-1-one A mixture of 1-(4-(6-chloro-8-fluoro-7-(5-methyl-1H-indazol-4-yl)quinazolin-4-yl)piperazin-1-yl)prop-2-en-1-one (45.1 mg, 0.1 mmol) and Selectfluor (53 mg, 0.15 mmol) in acetonitrile (5 mL) was stirred at 120° C. for 2 h. The mixture was allowed to cool to RT and partitioned between DCM and water. The organic layer was dried over Na₂SO₄ and concentrated in vacuo. The residue was purified by column chromatography on silica gel via Isolera One (MeOH/DCM=0-5%) to afford the desired product (4.4 mg). ¹H NMR (500 MHz, CDCl₃) δ: 1H NMR (CDCl₃): 8.84 (s, 1H), 7.88 (s, 1H), 7.40-7.46 (m, 2H), 6.63 (dd, J=8.4, 13.2 Hz, 1H), 6.40 (d, J=13.6 Hz, 1H), 5.78 (d, J=8.4 Hz, 1H), 3.75-4.01 (m, 8H), 2.24 (s, 1H). ESI-MS m/z: 469.1 [M+H]⁺.

414
Example 51

Synthesis of 4-(4-acryloylpiperazin-1-yl)-6-chloro-8-fluoro-7-(3-hydroxynaphthalen-1-yl)quinazoline-2-carbonitrile

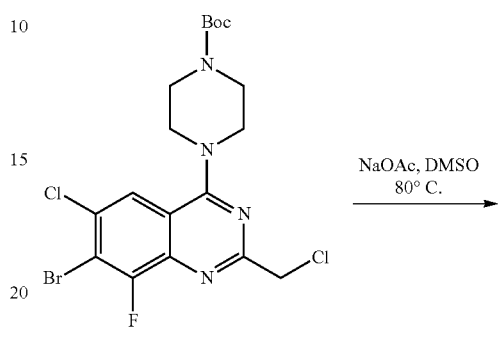

NaOAc, DMSO
80° C.
→

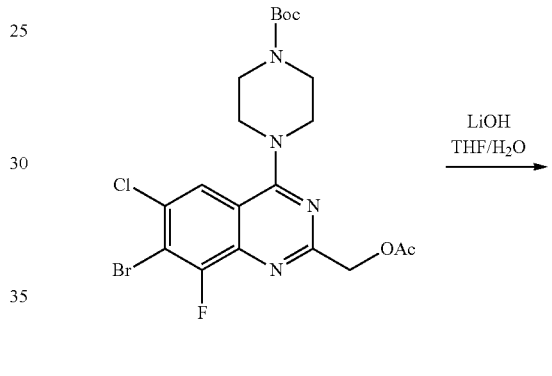

LiOH
THF/H₂O
→

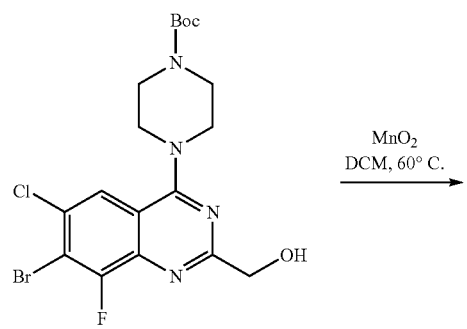

MnO₂
DCM, 60° C.
→

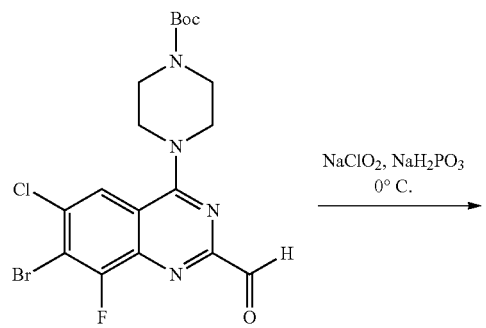

NaClO₂, NaH₂PO₃
0° C.
→

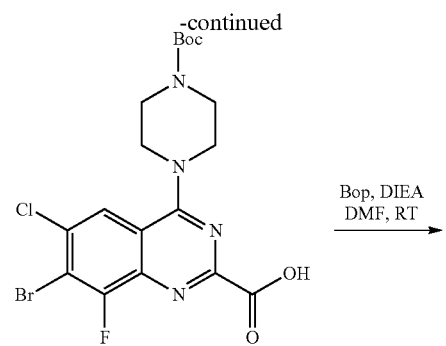

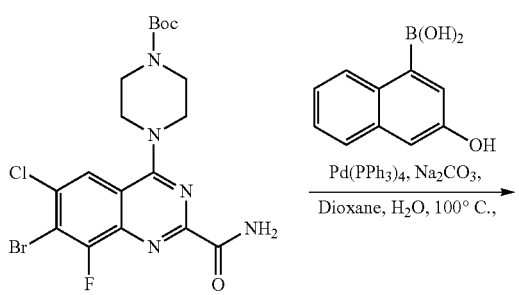

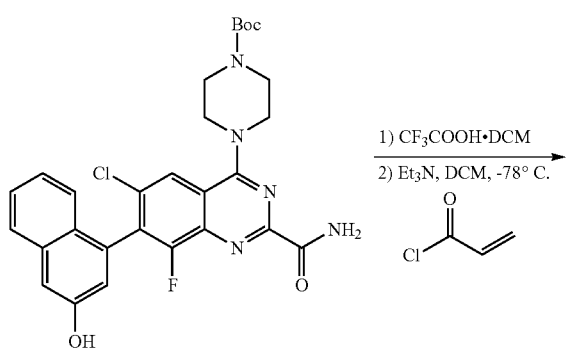

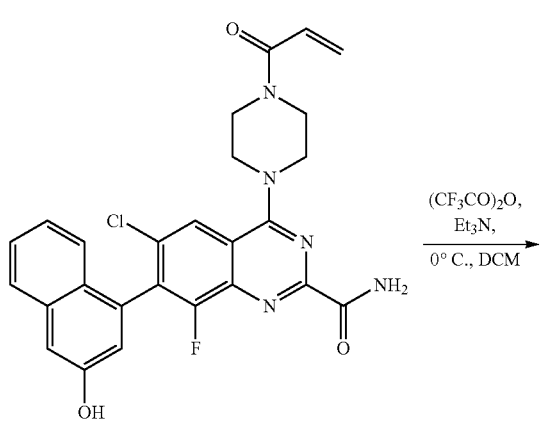

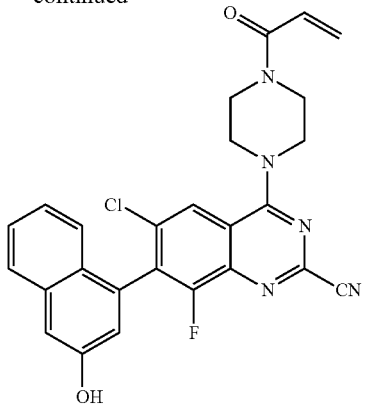

tert-Butyl 4-(2-(acetoxymethyl)-7-bromo-6-chloro-8-fluoroquinazolin-4-yl)piperazine-1-carboxylate A mixture of tert-butyl 4-(7-bromo-6-chloro-2-(chloromethyl)-8-fluoroquinazolin-4-yl)piperazine-1-carboxylate (288 mg, 0.59 mmol) in DMSO (10 mL), NaOAc (143 mg, 1.75 mmol) was added and the resulting mixture was stirred at 80° C. for 2 h. The mixture was partitioned between ethyl acetate and water. The organic layer was washed with sat. NaHCO$_3$ and brine, dried over Na$_2$SO$_4$ and concentrated in vacuo. The residue was purified by column chromatography on silica gel (ethyl acetate/petroleum ether=1:2) to afford the product (306 mg, 100% yield). ESI-MS m/z: 519.2 [M+H]$^+$.

tert-Butyl 4-(7-bromo-6-chloro-8-fluoro-2-(hydroxymethyl)quinazolin-4-yl)piperazine-1-carboxylate A mixture of tert-butyl 4-(2-(acetoxymethyl)-7-bromo-6-chloro-8-fluoroquinazolin-4-yl)piperazine-1-carboxylate (306 mg, 0.59 mmol), LiOH.H$_2$O (99 mg, 2.64 mmol) in THF (30 mL) and H$_2$O (10 mL) was stirred at RT for 1 h. The mixture was extracted with ethyl acetate. The organic layer was washed with brine, dried over Na$_2$SO$_4$ and concentrated in vacuo to afford the product (286 mg, 100% yield). ESI-MS m/z: 477.2 [M+H]$^+$.

tert-Butyl 4-(7-bromo-6-chloro-8-fluoro-2-formylquinazolin-4-yl)piperazine-1-carboxylate A mixture of tert-butyl 4-(7-bromo-6-chloro-8-fluoro-2-(hydroxymethyl) quinazolin-4-yl)piperazine-1-carboxylate (286 mg, 0.60 mmol) and MnO$_2$ (523 mg, 6.01 mmol) in dichloromethane (30 mL) was stirred at 60° C. for 16 h. The mixture was purified by column chromatography on silica gel (ethyl acetate/petroleum ether=1:1) to afford the product as an orange color solid (212 mg, 74.5% yield). ESI-MS m/z: 505.2 [M+H]$^+$.

7-Bromo-4-(4-(tert-butoxycarbonyl)piperazin-1-yl)-6-chloro-8-fluoroquinazoline-2-carboxylic acid To a mixture of tert-butyl 4-(7-bromo-6-chloro-8-fluoro-2-formylquinazolin-4-yl) piperazine-1-carboxylate (212 mg, 0.45 mmol) in THF (10 mL), t-BuOH (10 mL), DCM (5 mL) and H$_2$O (10 mL) at 0° C., NaH$_2$PO$_4$ (215 mg, 1.79 mmol) and NaClO$_2$ (162 mg, 1.79 mmol) were added and resulting mixture was stirred at 0° C. for 1 h. To this mixture, 2-methylbut-2-ene (219 mg, 3.13 mmol) was added and stirring was continued for 1 h. The mixture was concentrated in vacuo and the residue was diluted with 1M HCl (30 mL) and extracted with ethyl acetate. The organic layer was washed with brine, dried over $Na_2SO_4$ and concentrated in vacuo to afford the crude product as a yellow solid (257 mg) which was used in the next step directly withought purification. ESI-MS m/z: 489.1 $[M+H]^+$.

tert-Butyl 4-(7-bromo-2-carbamoyl-6-chloro-8-fluoroquinazolin-4-yl)piperazine-1-carboxylate To a mixture of 7-bromo-4-(4-(tert-butoxycarbonyl)piperazin-1-yl)-6-chloro-8-fluoroquinazoline-2-carboxylic acid (257 mg, 0.53 mmol), $NH_4Cl$ (112 mg, 2.10 mmol), BOP (464 mg, 1.05 mmol) in DMF (10 mL) at RT, DIEA (271 mg, 2.10 mmol) in DCM (5 mL) was added dropwise. The mixture was stirred for 1 h. The mixture was extracted with ethyl acetate, washed with sat.$NaHCO_3$ and brine. The organic layer was dried over $Na_2SO_4$ and concentrated in vacuo. The residue was purified by column chromatography on silica gel (dichloromethane/MeOH=40:1) to afford the product as a yellow solid (163 mg, 63.5% yield). ESI-MS m/z: 490.1 $[M+H]^+$.

tert-Butyl 4-(2-carbamoyl-6-chloro-8-fluoro-7-(3-hydroxynaphthalen-1-yl)quinazolin-4-yl)piperazine-1-carboxylate A mixture of tert-butyl 4-(7-bromo-2-carbamoyl-6-chloro-8-fluoroquinazolin-4-yl) piperazine-1-carboxylate (80 mg, 0.16 mmol), (3-hydroxynaphthalen-1-yl)boronic acid (34 mg, 0.18 mmol), $Na_2CO_3$ (86 mg, 0.82 mmol), $Pd(PPh_3)_4$ (19 mg, 0.016 mmol) in dioxane (15 mL) and $H_2O$ (5 mL) was stirred at 100° C. for 16 h. The mixture was partitioned between ethyl acetate and water. The organic layer was washed with sat.$NaHCO_3$ and brine, dried over $Na_2SO_4$ and concentrated in vacuo. The residue was purified by column chromatography on silica gel (dichloromethane/ MeOH=30:1) to afford the product as a yellow solid (35 mg, 40.2% yield). ESI-MS m/z: 552.2 $[M+H]^+$.

4-(4-Acryloylpiperazin-1-yl)-6-chloro-8-fluoro-7-(3-hydroxynaphthalen-1-yl)quinazoline-2-carboxamide A mixture of tert-butyl-4-(2-carbamoyl-6-chloro-8-fluoro-7-(3-hydroxynaphthalen-1-yl)quinazolin-4-yl)piperazine-1-carboxylate (35 mg, 0.066 mmol) in dichloromethane (10 mL) and $CF_3COOH$ (2 mL) was stirred at R.T. for 0.5 h. The mixture was concentrated in vacuo. The residue was dissolved in dichloromethane (20 mL) and $Et_3N$ (32 mg, 0.317 mmol). The mixture was stirred at −78° C. and acryloyl chloride (5.4 mg, 0.063 mmol) in dichloromethane (0.8 mL) was added dropwise. The mixture was stirred at −78° C. for 5 min and quenched with sat.$NaHCO_3$. The mixture was extracted with dichloromethane. The organic layer was dried over $Na_2SO_4$ and concentrated in vacuo. The residue was purified by column chromatography on silica gel (dichloromethane/MeOH=40:1 to 15:1) to afford the product as a white solid (33 mg). ESI-MS m/z: 506.2 $[M+H]^+$.

4-(4-Acryloylpiperazin-1-yl)-6-chloro-7-(3-hydroxynaphthalen-1-yl)quinazoline-2-carbonitrile To a stirred mixture of 4-(4-acryloylpiperazin-1-yl)-6-chloro-7-(3-hydroxynaphthalen-1-yl) quinazoline-2-carbox-amide (33 mg, 0.065 mmol) and $Et_3N$ (33 mg, 0.326 mmol) in dichloromethane (20 mL) at RT, $(CF_3CO)_2O$ (68 mg, 0.326 mmol) was added and the resulting mixture was stirred for 0.5 h. The mixture was quenched with sat.$NaHCO_3$ and extracted with dichloromethane. The organic layer was washed with brine, dried over $Na_2SO_4$ and concentrated in vacuo. The residue was purified by column chromatography on silica gel (dichloromethane/MeOH=40:1) to afford the product as a white solid (6 mg, 18.8% yield). $^1$H NMR (400 MHz, DMSO-d6) δ: 10.11 (s, 1H), 8.21 (s, 1H), 7.84 (m, 2H), 7.48-7.10 (m, 5H), 6.86 (dd, J=10.4 Hz, J=16.8 Hz, 1H), 6.22 (dd, J=2.0 Hz, J=16.4 Hz, 1H), 5.78 (dd, J=2.4 Hz, J=10.8 Hz, 1H), 4.10 (m, 4H), 3.89 (m, 4H). ESI-MS m/z: 488.2 $[M+H]^+$.

Example 52

Synthesis of 1-(4-(6-chloro-8-fluoro-7-(2-hydroxynaphthalen-1-yl)quinazolin-4-yl)piperazin-1-yl)prop-2-en-1-one

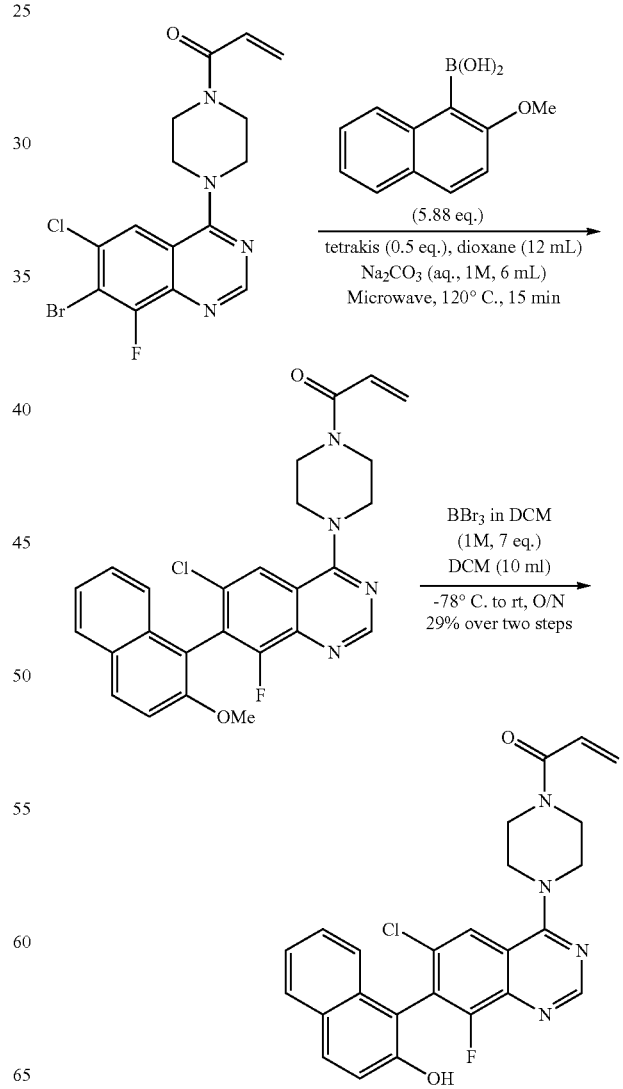

1-(4-(6-Chloro-8-fluoro-7-(2-methoxynaphthalen-1-yl)quinazolin-4-yl)piperazin-1-yl)prop-2-en-1-one (2-Methoxynaphthalen-1-yl)boronic acid (904 mg, 98%, 5.88 eq.) and tetrakis (431 mg, 0.5 eq.) were added into a mixture of 1-(4-(7-bromo-6-chloro-8-fluoroquinazolin-4-yl)piperazin-1-yl)prop-2-en-1-one (297 mg, 1.0 eq.) in 1,4-dioxane (12 mL) and aqueous $Na_2CO_3$ (1M, 6 mL) in the sealed tube. The reaction mixture was heated at 120° C. in the Microwave Reactor for 15 min. After cooling down, it was filtered. The filtrate was diluted with ethyl acetate, and washed with water. The separated organic layer was dried over $Na_2SO_4$, and concentrated in vacuo. The residue was used directly in the next step.

1-(4-(6-Chloro-8-fluoro-7-(2-hydroxynaphthalen-1-yl)quinazolin-4-yl)piperazin-1-yl)prop-2-en-1-one To a solution of above obtained 1-(4-(6-chloro-8-fluoro-7-(2-methoxynaphthalen-1-yl)quinazolin-4-yl)piperazin-1-yl)prop-2-en-1-one in dichloromethane (10 mL) at −78° C., $BBr_3$ in DCM (1M, 4.7 ml, 7 eq.) was added dropwise and the resulting mixture was stirred from −78° C. to room temperature overnight. The reaction was quenched with saturated aqueous $NaHCO_3$ solution at 0° C. The mixture was partitioned between dichloromethane and water. The organic layer was dried with $Na_2SO_4$ and concentrated in vacuo. The residue was purified by flash column chromatography on silica gel (MeOH/DCM=1-10%) to afford the desired product (100 mg, 29% yield in 2 steps) as a white solid. $^1$H NMR (500 MHz, DMSO-d6) δ: 9.98 (s, 1H), 8.71 (s, 1H), 8.9 (s, 1H), 7.95 (d, J=9 Hz, 1H), 7.90 (d, J=9.0 Hz, 1H), 7.34 (m, 3H), 7.11 (d, J=8.0 Hz, 1H), 6.84 (dd, J=17, 10.5 Hz, 1H), 6.18 (dd, J=17, 2.5 Hz, 1H), 6.18 (dd, J=10.5, 2.5 Hz, 1H), 3.96-3.79 (m, 8H). ESI-MS m/z: 463.1 $[M+H]^+$.

Example 53

Biochemical Assay of the Compounds

Test compounds were prepared as 10 mM stock solutions in DMSO (Fisher cat # BP-231-100). KRAS G12C 1-169, his-tagged protein, GDP-loaded was diluted to 2 µm in buffer (20 mM Hepes, 150 mM NaCl, 1 mM $MgCl_2$). Compounds were tested for activity as follows:

Compounds were diluted to 50× final test concentration in DMSO in 96-well storage plates. Compound stock solutions were vortexed before use and observed carefully for any sign of precipitation. Dilutions were as follow:

For 100 µM final compound concentration, compounds were diluted to 5000 µM (5 µl 10 mM compound stock+5 µl DMSO and mixed well by pipetting.

For 30 µM final compound concentration, compounds were diluted to 1500 µM (3 µl 10 mM compound stock+17 µl DMSO) and mixed well by pipetting.

For 10 µM final compound concentration, compounds were diluted to 500 µM (2 µl 10 mM compound stock+38 µl DMSO) and mixed well by pipetting.

49 µl of the stock protein solution was added to each well of a 96-well PCR plate (Fisher cat #1423027). 1 µl of the diluted 50× compounds were added to appropriate wells in the PCR plate using 12-channel pipettor. Reactions were mixed carefully and thoroughly by pipetting up/down with a 200 µl multi-channel pipettor. The plate was sealed well with aluminum plate seal, and stored in drawer at room temperature for 30 min, 2 hour or 24 hrs. 51 µl of 2% formic acid (Fisher cat # A117) in DI $H_2O$ was then added to each well followed by mixing with a pipette. The plate was then resealed with aluminum seal and stored on dry ice until analyzed as described below.

The above described assays were analyzed by mass spectrometry according to the following procedure:

The MS instrument is set to positive polarity, 2 GHz resolution, and low mass (1700) mode and allowed to equilibrate for 30 minutes. The instrument is then calibrated, switched to acquisition mode and the appropriate method loaded.

After another 30 minute equilibration time, a blank batch (i.e., buffer) is run to ensure equipment is operating properly. The samples are thawed at 37° C. for 10 minutes, briefly centrifuged, and transfer to the bench top. Wells A1 and H12 are spiked with 1 uL 500 uM internal standard peptide, and the plates centrifuged at 2000×g for 5 minutes. The method is then run and masses of each individual well recorded.

The masses (for which integration data is desired) for each well are pasted into the platemap and exported from the analysis. Masses for the internal standards are exported as well. The data at 50 ppm is extracted for the +19 charge state, and identity of well A1 is assigned using the internal standard spike and integrated. Peak data is exported as a TOF list and the above steps are repeated individually, for the +20, 21, 22, 23, 24, and 25 charge states.

Other in vitro analyses are as follows:

Inhibition of Cell Growth:

The ability of the subject compounds to inhibit RAS-mediated cell growth is assessed and demonstrated as follows. Cells expressing a wildtype or a mutant RAS are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s is determined by analyzing 8 point compound dose responses at half-log intervals decreasing from 100 µM.

Inhibition of RAS-Mediated Signaling Transduction:

The ability of the compounds disclosed herein in inhibiting RAS-mediated signaling is assessed and demonstrated as follows. Cells expressing wild type or a mutant RAS (such as G12C, G12V, or G12A) are treated with or without (control cells) a subject compound. Inhibition of RAS signaling by one or more subject compounds is demonstrated by a decrease in the steady-state level of phosphorylated MEK, and/or Raf binding in cells treated with the one or more of the subject compounds as compared to the control cells.

Inhibition of RAS-mediated signaling transduction:

The ability of the compounds disclosed herein in inhibiting RAS-mediated signaling is assessed and demonstrated as follows. Cells expressing wild type or a mutant RAS (such as G12C, G12V, or G12A) are treated with or without (control cells) a subject compound. Inhibition of RAS signaling by one or more subject compounds is demonstrated by percentage binding of compound to the G12C mutated RAS protein in cells treated with the one or more of the subject compounds as compared to the control cells.

Inhibition of RAS-Mediated Signaling Transduction:

The ability of the compounds disclosed herein in inhibiting RAS-mediated signaling is assessed and demonstrated as follows. Cells expressing wild type or a mutant RAS (such as G12C, G12V, or G12A) are treated with or without (control cells) a subject compound. Inhibition of RAS signaling by one or more subject compounds is demonstrated by a decrease in binding of RAS complex to downstream signaling molecules (for example Raf) in cells treated with the one or more of the subject compounds as compared to the control cells.

Each of the compounds in Table 1 were tested according to the above methods and found to covalently bind to KRAS G12C to the extent of at least about 5% (i.e., at least about 5% of the protein present in the well was found to be covalently bound to test compound).

TABLE 2

Activity of Representative Compounds*

| No. | Binding % | No. | Binding % | No. | Binding % | No. | Binding % |
|---|---|---|---|---|---|---|---|
| 1 | +++ | 2 | + | 3 | + | 4 | ++++ |
| 5 | +++ | 6 | +++ | 7 | ++++ | 8 | ++ |
| 9 | +++ | 10 | ++ | 11 | ++++ | 12 | + |
| 13 | ++ | 14 | ++ | 15 | +++ | 16 | ++ |
| 17 | + | 18 | ++ | 19 | ++ | 20 | + |
| 21 | +++ | 22 | + | 23 | ++ | 24 | + |
| 25 | ++ | 26 | ++ | 27 | ++ | 28 | + |
| 29 | + | 30 | + | 31 | + | 32 | + |
| 33 | ++ | 34 | +++ | 35 | + | 36 | + |
| 37 | ++ | 38 | ++ | 39 | + | 40 | +++ |
| 41 | + | 42 | +++ | 43 | +++ | 44 | +++ |
| 45 | + | 46 | ++++ | 47 | ++++ | 48 | ++++ |
| 49 | ++++ | 50 | + | 51 | ++++ | 52 | ++++ |
| 53 | ++++ | 54 | ++ | 55 | ++++ | 56 | ++++ |
| 57 | + | 58 | +++ | 59 | ++++ | 60 | + |
| 61 | + | 62 | + | 63 | + | 64 | ++ |
| 65 | + | 66 | ++++ | 67 | +++ | 68 | + |
| 69 | + | 70 | +++ | 71 | + | 72 | ++ |
| 73 | ++ | 74 | +++ | 75 | + | 76 | + |
| 77 | +++ | 78 | + | 79 | + | 80 | + |
| 81 | +++ | 82 | + | 83 | ++ | 84 | ++ |
| 85 | +++ | 86 | + | 87 | + | 88 | + |
| 89 | + | 90 | + | 91 | ++ | 92 | + |
| 93 | + | 94 | ++ | 95 | ++ | 96 | + |
| 97 | ++ | 98 | + | 99 | +++ | 100 | +++ |
| 101 | +++ | 102 | +++ | 103 | ++ | 104 | +++ |
| 105 | + | 106 | ++++ | 107 | ++++ | 108 | ++ |
| 109 | ++++ | 110 | +++ | 111 | +++ | 112 | +++ |
| 113 | +++ | 114 | +++ | 115 | +++ | 116 | ++ |
| 117 | +++ | 118 | +++ | 119 | +++ | 120 | +++ |
| 121 | ++++ | 122 | ++ | 123 | ++++ | 124 | +++ |
| 125 | ++++ | 126 | ++++ | 127 | ++++ | 128 | +++ |
| 129 | + | 130 | + | 131 | + | 132 | +++ |
| 133 | ++ | 134 | ++ | 135 | + | 136 | ++ |
| 137 | + | 138 | ++++ | 139 | ++++ | 140 | +++ |
| 141 | + | 142 | + | 143 | +++ | 144 | + |
| 145 | ++++ | 146 | ++++ | 147 | ++ | 148 | +++ |
| 149 | + | 150 | ++++ | 151 | + | 152 | +++ |
| 153 | ++++ | 154 | ++ | 155 | ++ | 156 | ++ |
| 157 | + | 158 | ++++ | 159 | +++ | 160 | + |
| 161 | ++ | 162 | + | 163 | + | 164 | + |
| 165 | N/A | 166 | + | 167 | + | 168 | ++ |
| 169 | +++ | 170 | + | 171 | +++ | 172 | +++ |
| 173 | ++++ | 174 | ++ | 175 | +++ | 176 | +++ |
| 177 | + | 178 | + | 179 | + | 180 | + |
| 181 | + | 182 | +++ | 183 | +++ | 184 | ++++ |
| 185 | ++ | 186 | +++ | 187 | +++ | 188 | +++ |
| 189 | ++ | 190 | + | 191 | +++ | 192 | ++ |
| 193 | ++ | 194 | ++++ | 195 | ++++ | 196 | ++++ |
| 197 | ++ | 198 | ++++ | 199 | N/A | 200 | ++ |
| 201 | +++ | 202 | +++ | 203 | ++++ | 204 | +++ |
| 205 | + | 206 | +++ | 207 | ++++ | 208 | ++++ |
| 209 | ++++ | 210 | ++++ | 211 | + | 212 | ++++ |
| 213 | ++ | 214 | + | 215 | ++ | 216 | + |
| 217 | +++ | 218 | +++ | 219 | + | 220 | +++ |
| 221 | ++ | 222 | +++ | 223 | + | 224 | +++ |
| 225 | ++ | 226 | + | 227 | ++++ | 228 | + |
| 229 | ++ | 230 | + | 231 | +++ | 232 | + |
| 233 | +++ | 234 | ++++ | 235 | +++ | 236 | +++ |
| 237 | ++++ | 238 | +++ | 239 | +++ | 240 | +++ |
| 241 | + | 242 | ++++ | 243 | ++++ | 244 | + |
| 245 | + | 246 | ++++ | 247 | +++ | 248 | N/A |
| 249 | + | 250 | ++ | 251 | ++++ | 252 | ++++ |
| 253 | ++++ | 254 | +++ | 255 | +++ | 256 | +++ |
| 257 | ++++ | 258 | ++ | 259 | +++ | 260 | ++ |
| 261 | + | 262 | + | 263 | + | 264 | ++ |
| 265 | + | 266 | +++ | 267 | + | 268 | +++ |
| 269 | +++ | 270 | +++ | 271 | +++ | 272 | ++++ |
| 273 | ++++ | 274 | ++++ | 275 | ++ | 276 | + |
| 277 | + | 278 | ++ | 279 | +++ | 280 | +++ |
| 281 | ++ | 282 | +++ | 283 | ++ | 284 | ++++ |
| 285 | +++ | 286 | + | 287 | ++ | 288 | ++ |
| 289 | +++ | 290 | +++ | 291 | ++++ | 292 | + |
| 293 | ++++ | 294 | ++++ | 295 | + | 296 | + |
| 297 | + | 298 | ++ | 299 | + | 300 | ++ |
| 301 | ++ | 302 | +++ | 303 | ++ | 304 | ++ |
| 305 | ++ | 306 | ++ | 307 | ++ | 308 | +++ |
| 309 | +++ | 310 | ++++ | 311 | +++ | 312 | ++++ |
| 313 | +++ | 314 | ++++ | 315 | + | 316 | ++ |
| 317 | N/A | 318 | + | 319 | ++ | 320 | ++ |
| 321 | + | 322 | +++ | 323 | +++ | 324 | + |
| 325 | ++ | 326 | + | 327 | ++ | 328 | + |
| 329 | ++ | 330 | ++ | 331 | ++ | 332 | ++ |
| 333 | + | 334 | ++++ | 335 | ++++ | 336 | +++ |
| 337 | + | 338 | ++ | 339 | ++++ | 340 | ++++ |
| 341 | ++++ | 342 | ++++ | 343 | +++ | 344 | +++ |
| 345 | ++++ | 346 | ++++ | 347 | ++++ | 348 | ++++ |
| 349 | +++ | 350 | ++++ | 351 | ++++ | 352 | ++++ |
| 353 | ++++ | 354 | ++++ | 355 | ++++ | 356 | +++ |
| 357 | ++++ | 358 | ++++ | 359 | ++++ | 360 | ++++ |
| 361 | ++++ | 362 | ++ | 363 | ++++ | 364 | ++++ |
| 365 | ++++ | 366 | ++++ | 367 | ++++ | 368 | ++++ |
| 369 | ++++ | 370 | + | 371 | ++ | 372 | +++ |
| 373 | +++ | 374 | +++ | 375 | +++ | 376 | N/A |

*Binding for compounds 1-47 was measured at 24 h; binding for compounds 48-246 was measured at 2 h; binding for compounds 247-375 was measured at 30 min.

N/A = results pending

+ indicates binding activity from 5% to 25%

++ indicates binding activity greater than 25% and up to 50%

+++ indicates binding activity greater than 50% and up to 75%

++++ indicates binding activity greater than 75%

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:
1. A compound having the following structure (I'b):

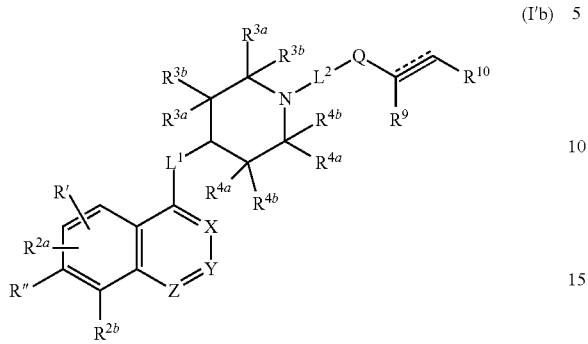

or a pharmaceutically acceptable salt, tautomer, or stereoisomer thereof,
wherein:
==== is a double bond;
≡≡≡ is a double or triple bond;
Q is —C(=$NR^{8'}$)—, —C(=O)—, —$NR^8$C(=O)—, —$NR^8$S(=O)$_2$—, or —S(=O)$_2$—;
X is $CR^6$;
Y is N;
Z is N;
$L^1$ is a bond;
$L^2$ is a bond or alkylene;
(i) R' is $R^1$; and
R" is $R^{2c}$; or
(ii) R' is H; and
R" is $R^1$;
$R^1$ is heterocyclyl, aryl, or heteroaryl;
$R^{2a}$ is H, halo, $C_1$-$C_6$ alkyl, $C_1$-$C_6$ haloalkyl, OH, $OC_1$-$C_6$ alkyl, $C_3$-$C_8$ cycloalkyl, aryl, or heteroaryl;
$R^{2b}$ is H, halo, $C_1$-$C_6$ alkyl, $C_1$-$C_6$ haloalkyl, OH, $OC_1$-$C_6$ alkyl, $C_3$-$C_8$ cycloalkyl, aryl, or heteroaryl;
$R^{2c}$ is H, halo, $C_1$-$C_6$ alkyl, $C_1$-$C_6$ haloalkyl, OH, $OC_1$-$C_6$ alkyl, $C_3$-$C_8$ cycloalkyl, aryl, or heteroaryl;
each $R^{3a}$ is independently H, halo, CN, $C_1$-$C_6$ alkyl, cyanoalkyl, aminylcarbonylalkyl, carboxyalkyl, aminylalkyl, alkylaminylalkyl, hydroxyalkyl, aminylcarbonyl, C(O)OH, $NH_2$, OH, or $C_2$-$C_6$ alkynyl;
each $R^{3b}$ is independently H, halo, CN, $C_1$-$C_6$ alkyl, cyanoalkyl, aminylcarbonylalkyl, carboxyalkyl, aminylalkyl, alkylaminylalkyl, hydroxyalkyl, aminylcarbonyl, C(O)OH, $NH_2$, OH, or $C_2$-$C_6$ alkynyl;
each $R^{4a}$ is independently H, halo, CN, $C_1$-$C_6$ alkyl, cyanoalkyl, aminylcarbonylalkyl, carboxyalkyl, aminylalkyl, alkylaminylalkyl, hydroxyalkyl, aminylcarbonyl, C(O)OH, $NH_2$, OH, or $C_2$-$C_6$ alkynyl;
each $R^{4b}$ is independently H, halo, CN, $C_1$-$C_6$ alkyl, cyanoalkyl, aminylcarbonylalkyl, carboxyalkyl, aminylalkyl, alkylaminylalkyl, hydroxyalkyl, aminylcarbonyl, C(O)OH, $NH_2$, OH, or $C_2$-$C_6$ alkynyl;
$R^6$ is H, CN, $C_1$-$C_6$ alkyl, cyanoalkyl, amidinylalkyl, guanidinylalkyl, aminylalkyl, aminylcarbonyl, $CO_2NR^aR^b$, $NH_2$, alkylaminyl, haloalkylaminyl, amidinylalkylaminyl, guanidinylalkylaminyl, aminylalkylaminyl, hydroxyalkylaminyl, heterocyclylalkylaminyl, arylalkylaminyl, heteroarylalkylaminyl, heterocyclylaminyl, arylaminyl, heteroarylaminyl, $OC_1$-$C_6$ alkyl, alkylaminylalkoxy, alkylcarbonylaminylalkoxy, amidinylalkoxy, guanidinylalkoxy, aminylalkoxy, heterocyclylalkyloxy, arylalkyloxy, heteroarylalkyloxy, heterocyclyloxy, aryloxy, heteroaryloxy, aminylsulfonyl, heterocyclyl, aryl, or heteroaryl;

$R^a$ is H or $C_1$-$C_6$ alkyl;
$R^b$ is H or $C_1$-$C_6$ alkyl; or
$R^a$ and $R^b$, together with the nitrogen atom to which they are attached, form a heterocyclyl;
$R^8$ is H, $C_1$-$C_6$ alkyl, or hydroxyalkyl; and
$R^{8'}$ is H, CN, $C_1$-$C_6$ alkyl, or OH;
wherein each alkylene, $C_1$-$C_6$ alkyl, $C_1$-$C_6$ haloalkyl, cyanoalkyl, amidinylalkyl, aminylcarbonylalkyl, carboxyalkyl, guanidinylalkyl, aminylalkyl, alkylaminylalkyl, hydroxyalkyl, $C_2$-$C_6$ alkynyl, aminylcarbonyl, alkoxycarbonyl, alkylaminyl, haloalkylaminyl, amidinylalkylaminyl, guanidinylalkylaminyl, aminylalkylaminyl, hydroxyalkylaminyl, heterocyclylalkylaminyl, arylalkylaminyl, heteroarylalkylaminyl, heterocyclylaminyl, arylaminyl, heteroarylaminyl, $OC_1$-$C_6$ alkyl, alkylaminylalkoxy, alkylcarbonylaminylalkoxy, amidinylalkoxy, guanidinylalkoxy, aminylalkoxy, heterocyclylalkyloxy, arylalkyloxy, heteroarylalkyloxy, heterocyclyloxy, aryloxy, heteroaryloxy, aminylsulfonyl, $C_3$-$C_8$ cycloalkyl, heterocyclyl, aryl, and heteroaryl is optionally substituted with one or more substituents independently selected from the group consisting of halo, CN, $NO_2$, $C_1$-$C_{12}$ alkyl, $C_1$-$C_{12}$ haloalkyl, cyano$C_1$-$C_6$ alkyl, aminylcarbonyl$C_1$-$C_6$ alkyl, $C_1$-$C_6$ hydroxyalkyl, $C_1$-$C_6$ alkoxyalkyl, $C_1$-$C_6$ haloalkoxyalkyl, $C_3$-$C_8$ cycloalkylalkyl, heterocyclylalkyl, aralkyl, heteroarylalkyl, $C_2$-$C_6$ alkynyl, imino, aminylcarbonyl, $C_1$-$C_6$ alkylaminylcarbonyl, $C_3$-$C_8$ cycloalkylaminylcarbonyl, aminyl, $C_1$-$C_6$ alkylaminyl, $C_1$-$C_6$ alkylcarbonylaminyl, $C_2$-$C_6$ alkenylcarbonylaminyl, OH, $OC_1$-$C_6$ alkyl, $OC_1$-$C_6$ haloalkyl, =O, $C_1$-$C_6$ thioalkyl, aminylsulfonyl, =S, $C_1$-$C_6$ alkylcycloalkyl, $C_3$-$C_8$ cycloalkyl, cyano$C_3$-$C_8$ cycloalkyl, aminylcarbonyl$C_3$-$C_8$ cycloalkyl, $C_3$-$C_8$ fused cycloalkyl, $C_1$-$C_6$ alkylheterocycloalkyl, heterocyclyl, aryl, and heteroaryl;
provided that:
(i) when ≡≡≡ is a double bond, then $R^9$ and $R^{10}$ are each independently H, CN, $C_1$-$C_6$ alkyl, aminylalkyl, alkylaminylalkyl, hydroxyalkyl, C(O)OH, alkoxycarbonyl, or heteroaryl; or
(ii) when ≡≡≡ is a double bond, then $R_9$ and $R_{10}$, together with the carbon atoms to which they are attached, form a carbocyclyl or heterocyclyl; and
(iii) when ≡≡≡ is a triple bond, then $R^9$ is absent and $R^{10}$ is H, $C_1$-$C_6$ alkyl, aminylalkyl, alkylaminylalkyl, or hydroxyalkyl.

2. The compound of claim 1, wherein the compound has structure (I'f):

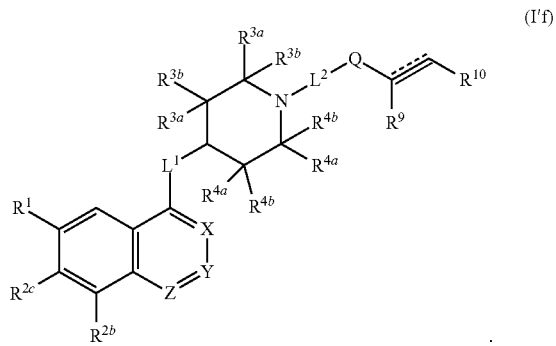

or a pharmaceutically acceptable salt, tautomer, or stereoisomer thereof.

3. The compound of claim 1, wherein the compound has structure (I'j):

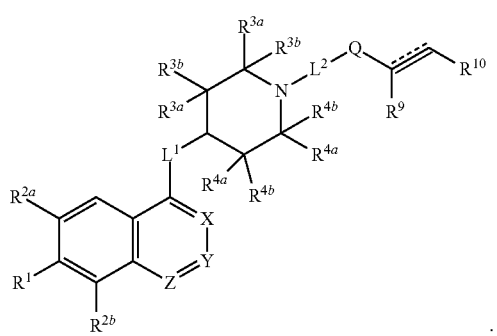

or a pharmaceutically acceptable salt, tautomer, or stereoisomer thereof.

4. The compound of claim 1, or a pharmaceutically acceptable salt, tautomer, or stereoisomer thereof, wherein Q is —C(=O)—.

5. The compound of claim 1, or a pharmaceutically acceptable salt, tautomer, or stereoisomer thereof, wherein $L^2$ is a bond.

6. The compound of claim 1, or a pharmaceutically acceptable salt, tautomer, or stereoisomer thereof, wherein $R^1$ is optionally substituted aryl.

7. The compound of claim 6, or a pharmaceutically acceptable salt, tautomer, or stereoisomer thereof, wherein $R^1$ is optionally substituted phenyl.

8. The compound of claim 6, or a pharmaceutically acceptable salt, tautomer, or stereoisomer thereof, wherein $R^1$ is substituted with one or more independently selected substituents.

9. The compound of claim 8, or a pharmaceutically acceptable salt, tautomer, or stereoisomer thereof, wherein the one or more substituents are independently selected from the group consisting of halo, CN, $C_1$-$C_6$ alkyl, $C_1$-$C_6$ haloalkyl, cyano$C_1$-$C_6$ alkyl, aminylcarbonyl$C_1$-$C_6$ alkyl, $C_1$-$C_6$ hydroxyalkyl, $C_1$-$C_6$ alkoxyalkyl, $C_3$-$C_8$ cycloalkylalkyl, $C_2$-$C_6$ alkynyl, aminylcarbonyl, $C_1$-$C_6$ alkylaminylcarbonyl, $C_3$-$C_8$ cycloalkylaminylcarbonyl, $C_1$-$C_6$ alkylaminyl, $C_1$-$C_6$ alkylcarbonylaminyl, OH, O$C_1$-$C_6$ alkyl, O$C_1$-$C_6$ haloalkyl, aminylsulfonyl, $C_1$-$C_6$ alkylcycloalkyl, $C_3$-$C_8$ cycloalkyl, cyano$C_3$-$C_8$ cycloalkyl, aminylcarbonyl$C_3$-$C_8$ cycloalkyl, $C_3$-$C_8$ fused cycloalkyl, and heteroaryl.

10. The compound of claim 9, or a pharmaceutically acceptable salt, tautomer, or stereoisomer thereof, wherein the one or more substituents are independently selected from the group consisting of fluoro, chloro, bromo, CN, methyl, ethyl, isopropyl, difluoromethyl, trifluoromethyl, hydroxymethyl, methoxymethyl, aminylcarbonyl, OH, methoxy, and cyclopropyl.

11. The compound of claim 6, or a pharmaceutically acceptable salt, tautomer, or stereoisomer thereof, wherein $R^1$ is:

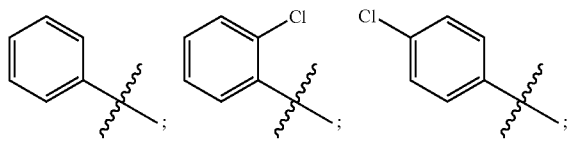

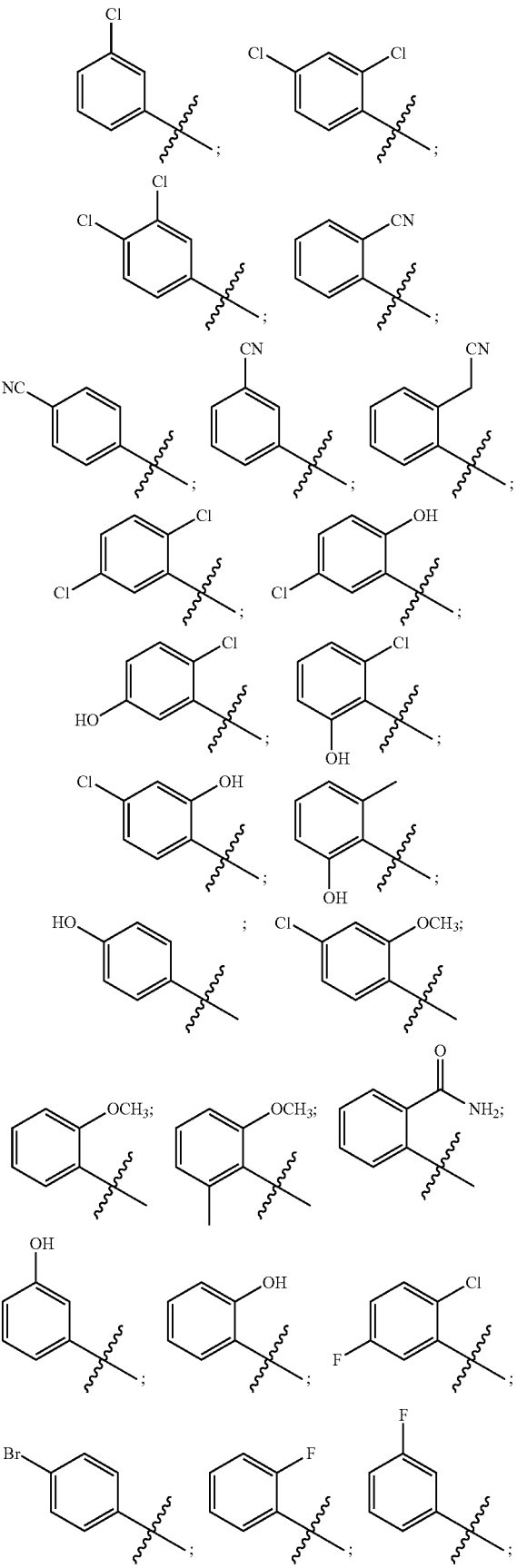

427
-continued
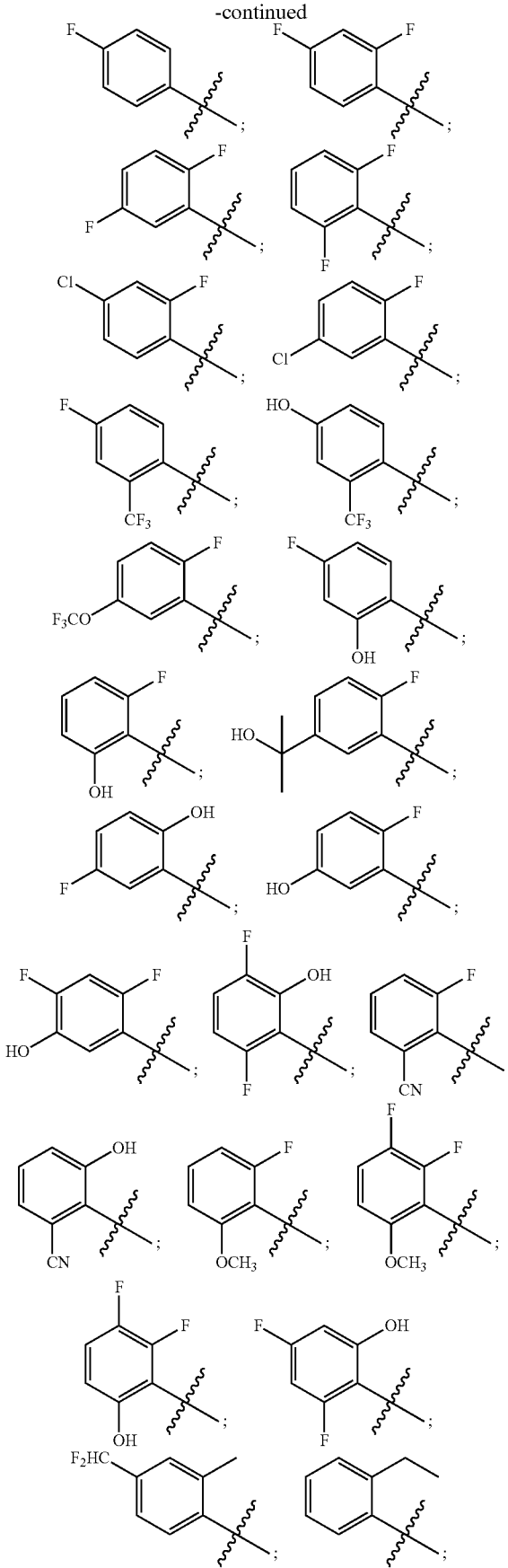
428
-continued
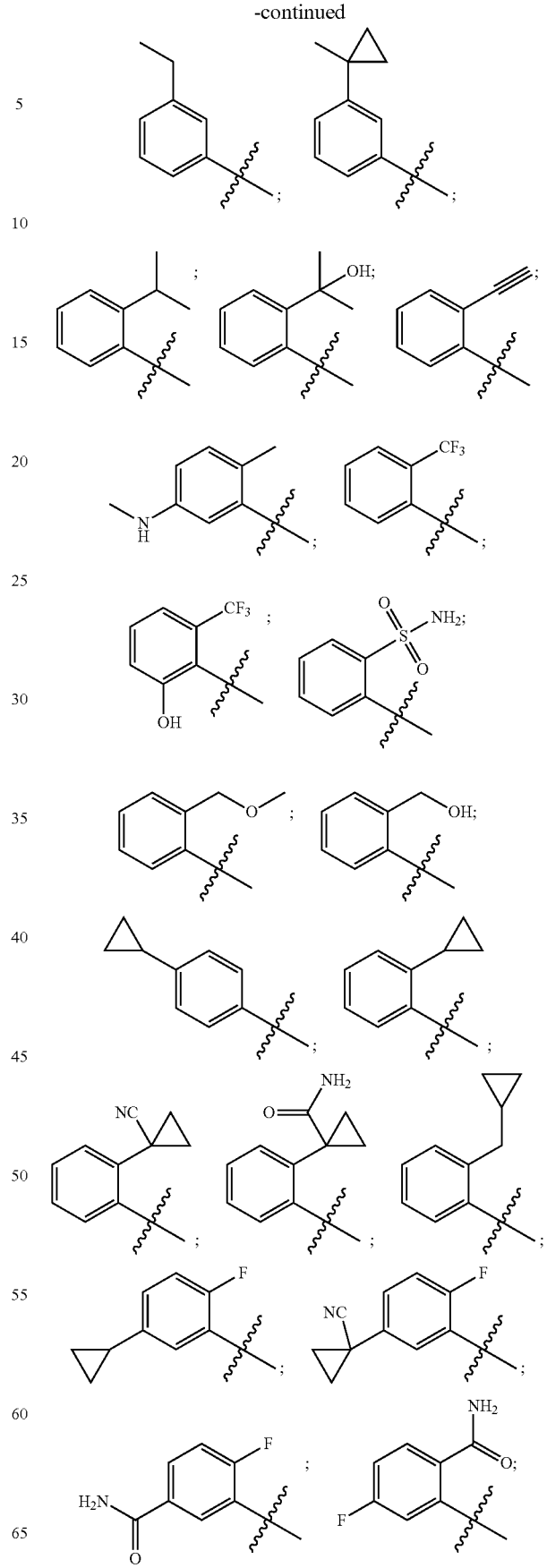

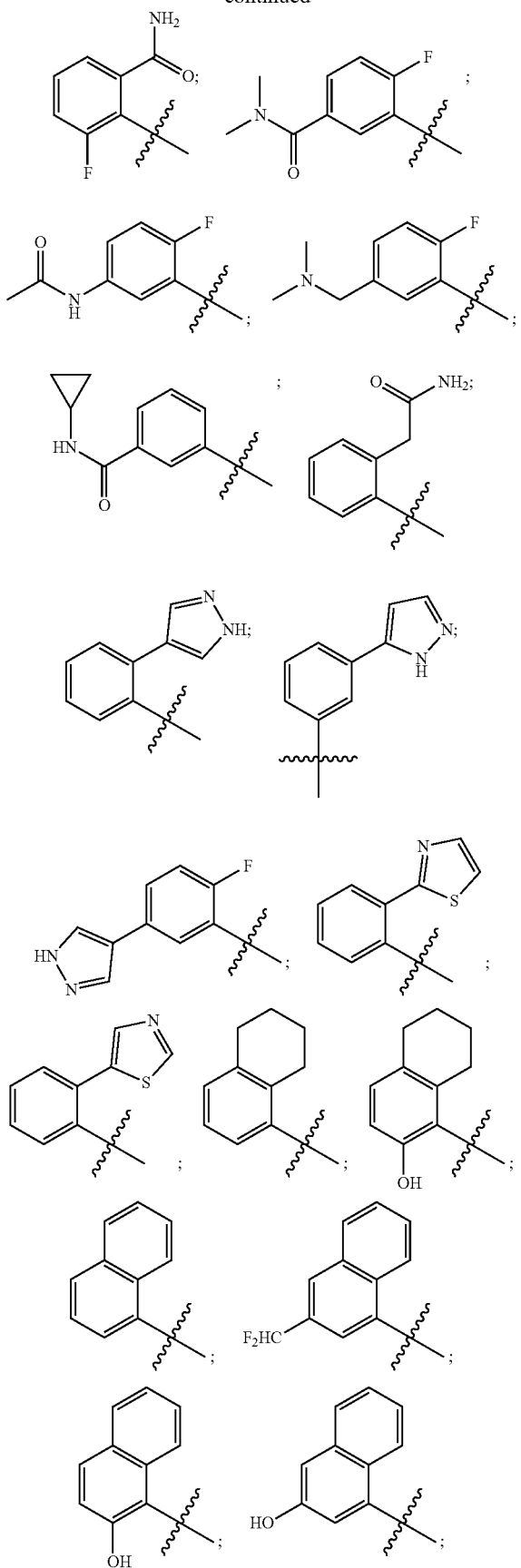
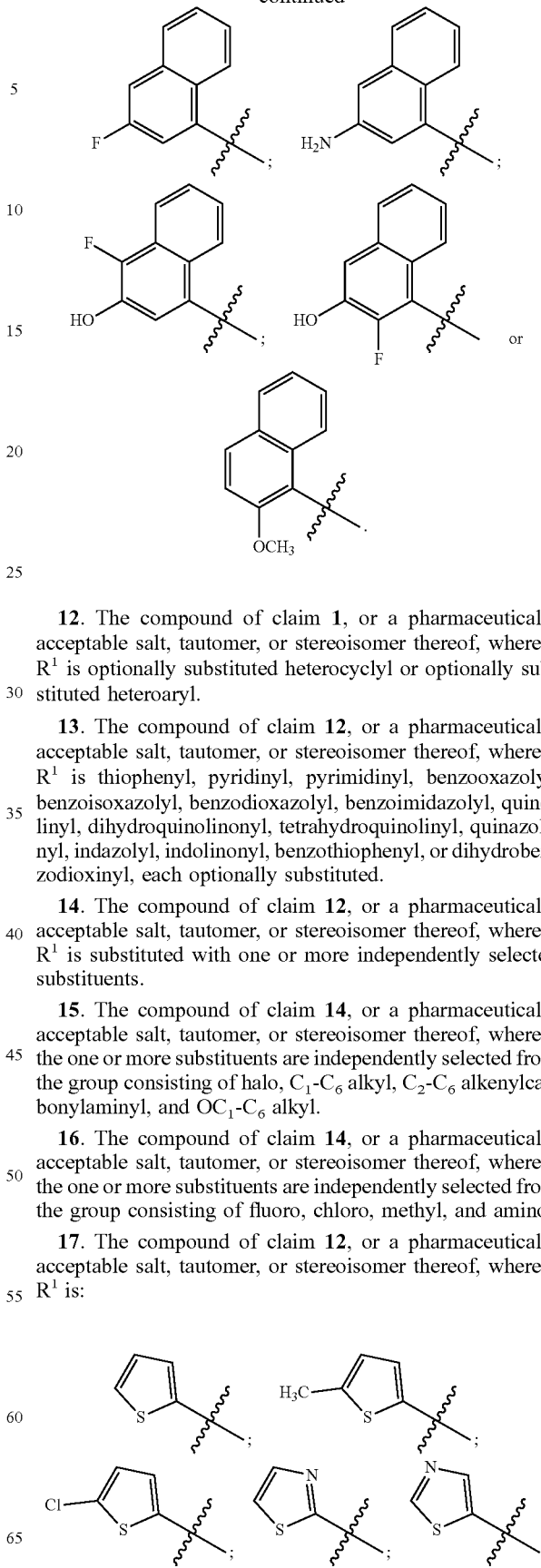

12. The compound of claim 1, or a pharmaceutically acceptable salt, tautomer, or stereoisomer thereof, wherein $R^1$ is optionally substituted heterocyclyl or optionally substituted heteroaryl.

13. The compound of claim 12, or a pharmaceutically acceptable salt, tautomer, or stereoisomer thereof, wherein $R^1$ is thiophenyl, pyridinyl, pyrimidinyl, benzooxazolyl, benzoisoxazolyl, benzodioxazolyl, benzoimidazolyl, quinolinyl, dihydroquinolinonyl, tetrahydroquinolinyl, quinazolinyl, indazolyl, indolinonyl, benzothiophenyl, or dihydrobenzodioxinyl, each optionally substituted.

14. The compound of claim 12, or a pharmaceutically acceptable salt, tautomer, or stereoisomer thereof, wherein $R^1$ is substituted with one or more independently selected substituents.

15. The compound of claim 14, or a pharmaceutically acceptable salt, tautomer, or stereoisomer thereof, wherein the one or more substituents are independently selected from the group consisting of halo, $C_1$-$C_6$ alkyl, $C_2$-$C_6$ alkenylcarbonylaminyl, and $OC_1$-$C_6$ alkyl.

16. The compound of claim 14, or a pharmaceutically acceptable salt, tautomer, or stereoisomer thereof, wherein the one or more substituents are independently selected from the group consisting of fluoro, chloro, methyl, and amino.

17. The compound of claim 12, or a pharmaceutically acceptable salt, tautomer, or stereoisomer thereof, wherein $R^1$ is:

431
-continued
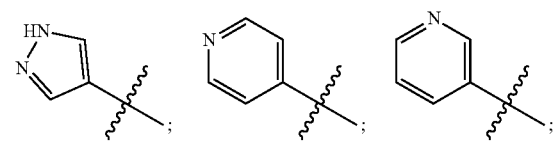
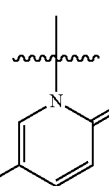
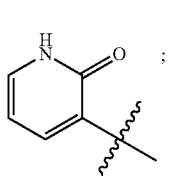
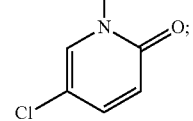
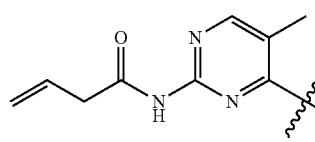
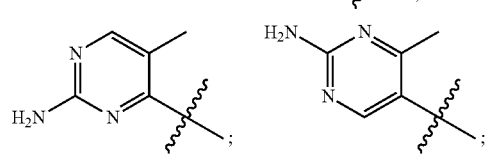
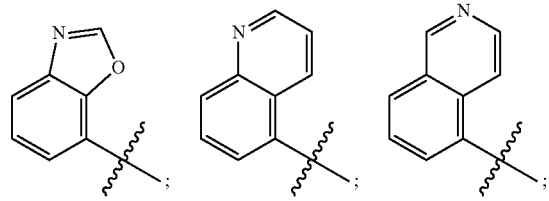
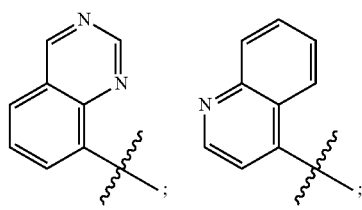
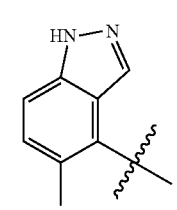
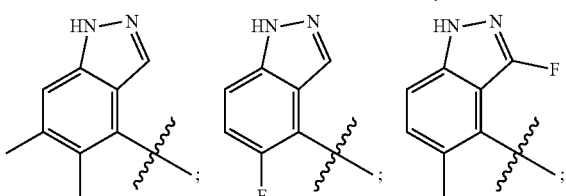
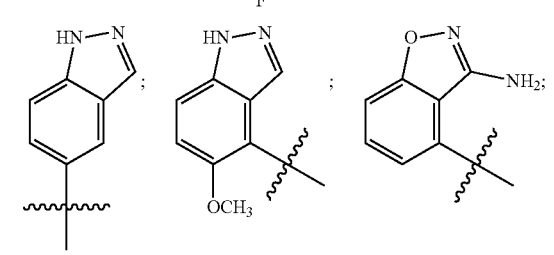
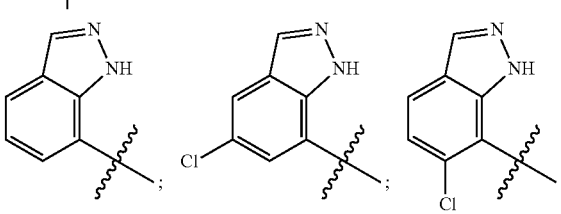
432
-continued
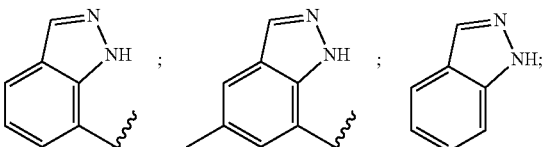
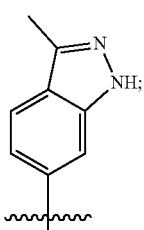
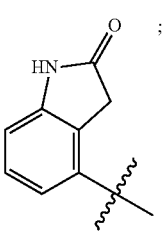
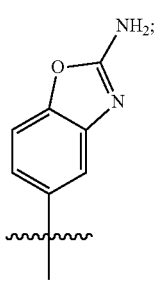
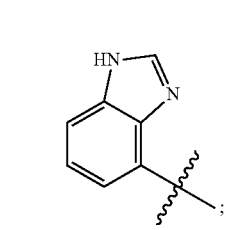
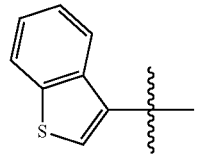
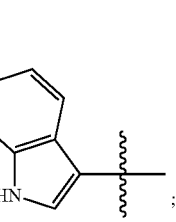
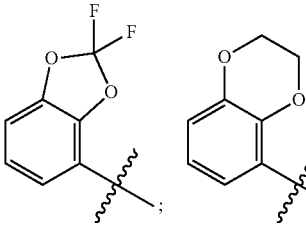
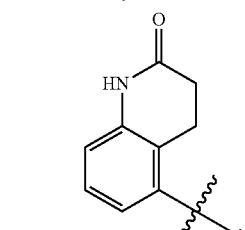
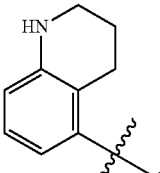
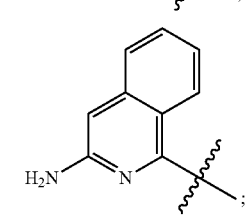
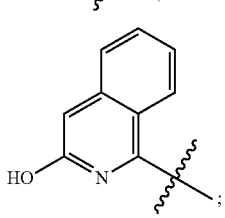
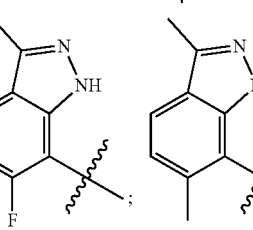
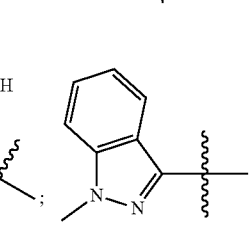 or -continued

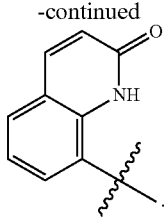

18. The compound of claim 1, or a pharmaceutically acceptable salt, tautomer, or stereoisomer thereof, wherein $R^{2a}$ is halo.

19. The compound of claim 18, or a pharmaceutically acceptable salt, tautomer, or stereoisomer thereof, wherein $R^{2a}$ is fluoro or chloro.

20. The compound of claim 1, or a pharmaceutically acceptable salt, tautomer, or stereoisomer thereof, wherein $R^{2b}$ is halo.

21. The compound of claim 20, or a pharmaceutically acceptable salt, tautomer, or stereoisomer thereof, wherein $R^{2b}$ is fluoro or chloro.

22. The compound of claim 1, or a pharmaceutically acceptable salt, tautomer, or stereoisomer thereof, wherein:
    each $R^{3a}$ is independently H;
    each $R^{3b}$ is independently H;
    each $R^{4a}$ is independently H; and
    each $R^{4b}$ is independently H.

23. The compound of claim 1, or a pharmaceutically acceptable salt, tautomer, or stereoisomer thereof, wherein $R^6$ is H.

24. The compound of claim 1, or a pharmaceutically acceptable salt, tautomer, or stereoisomer thereof, wherein at least one of $R^9$ or $R^{10}$ is H.

25. The compound of claim 24, or a pharmaceutically acceptable salt, tautomer, or stereoisomer thereof, wherein $R^9$ and $R^{10}$ are each independently H.

26. The compound of claim 1, or a pharmaceutically acceptable salt, tautomer, or stereoisomer thereof, wherein

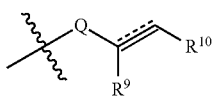

is:

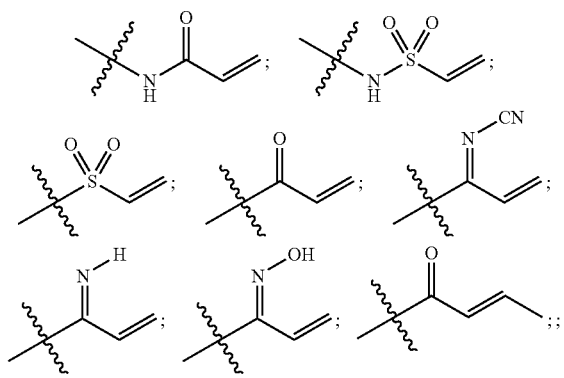

-continued

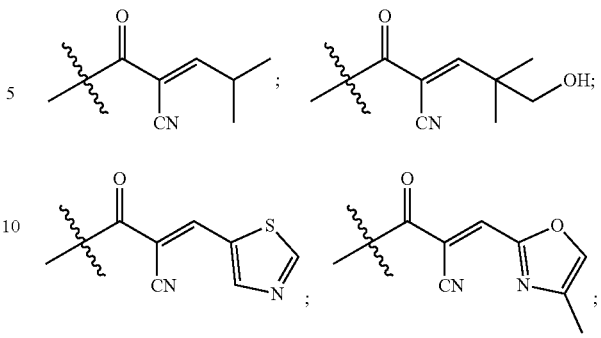

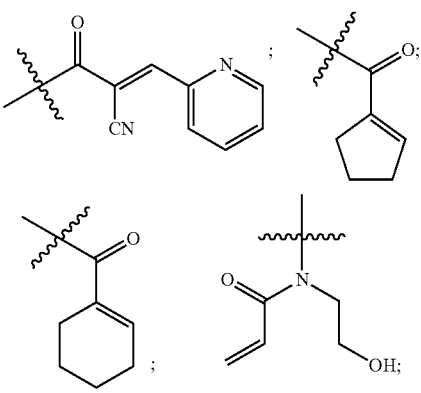

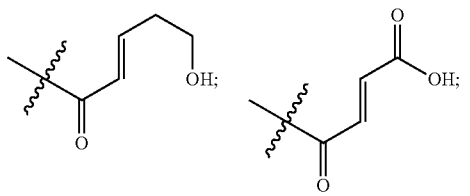

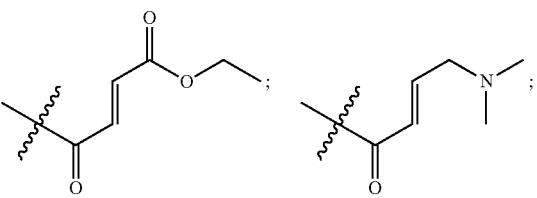

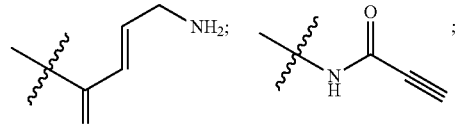

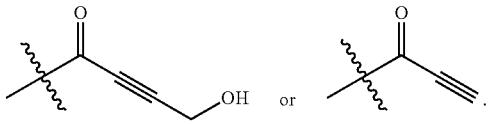

27. The compound of claim 1, or a pharmaceutically acceptable salt, tautomer, or stereoisomer thereof, wherein

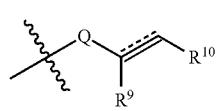

is —C(=O)—CH=CH$_2$.

28. The compound of claim 1, wherein the compound is selected from the group consisting of:
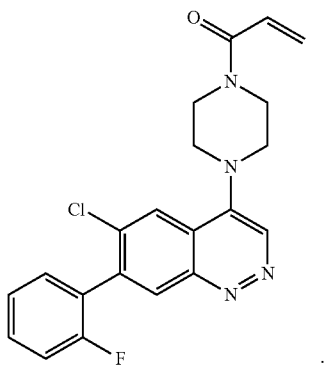
;
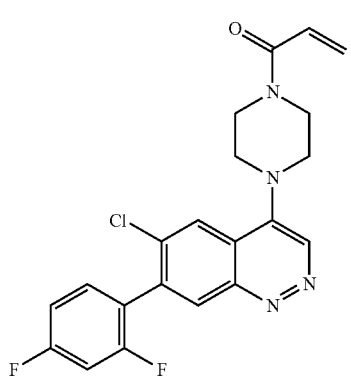
;
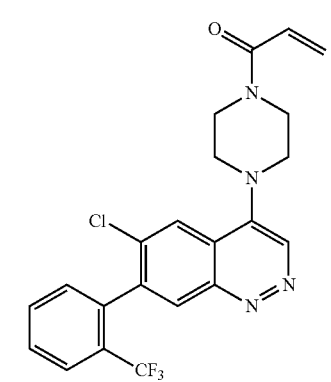
;
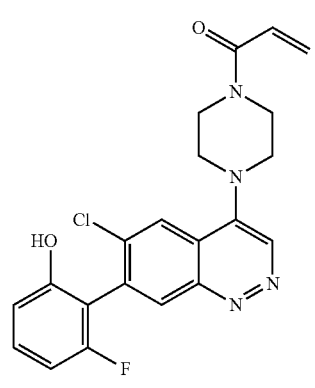
;
-continued
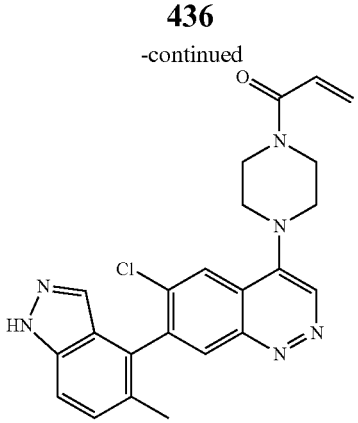
;
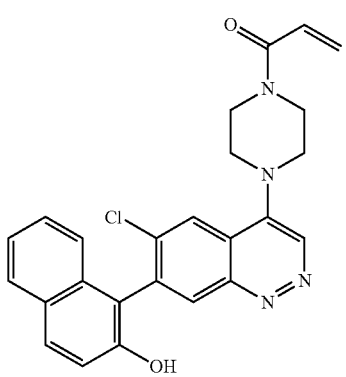
;
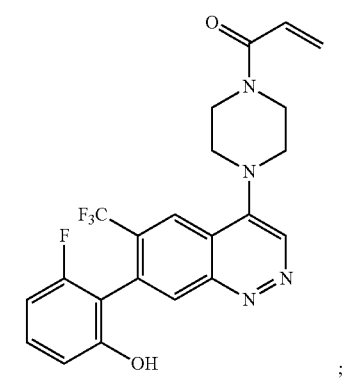
;
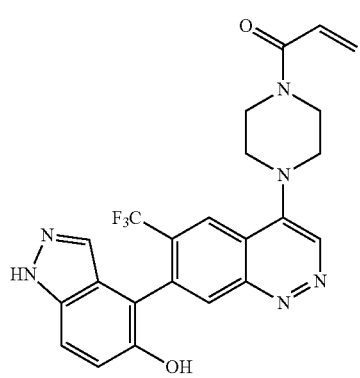
or -continued
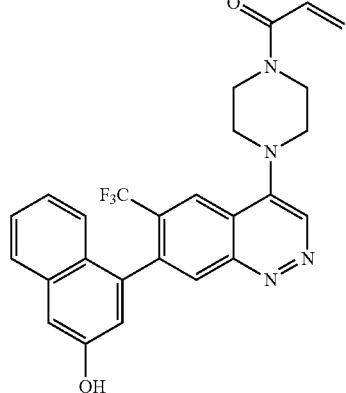
or a pharmaceutically acceptable salt, tautomer, or stereoisomer thereof.
29. A pharmaceutical composition comprising a compound of claim 1, or a pharmaceutically acceptable salt, tautomer, or stereoisomer thereof, and a pharmaceutically acceptable carrier.
* * * * *